US006962980B2

(12) United States Patent
Mitcham et al.

(10) Patent No.: US 6,962,980 B2
(45) Date of Patent: Nov. 8, 2005

(54) COMPOSITIONS AND METHODS FOR THE THERAPY AND DIAGNOSIS OF OVARIAN CANCER

(75) Inventors: Jennifer L. Mitcham, Redmond, WA (US); Gordon E. King, Shoreline, WA (US); Paul A. Algate, Issaquah, WA (US)

(73) Assignee: Corixa Corporation, Seattle, WA (US)

(*) Notice: Subject to any disclaimer, the term of this patent is extended or adjusted under 35 U.S.C. 154(b) by 367 days.

(21) Appl. No.: 09/827,271

(22) Filed: Apr. 4, 2001

(65) Prior Publication Data

US 2003/0165504 A1 Sep. 4, 2003

Related U.S. Application Data

(63) Continuation-in-part of application No. 09/667,857, filed on Sep. 20, 2000, now Pat. No. 6,699,664, which is a continuation-in-part of application No. 09/636,801, filed on Aug. 10, 2000, now abandoned, which is a continuation-in-part of application No. 09/617,747, filed on Jul. 17, 2000, now abandoned, which is a continuation-in-part of application No. 09/404,879, filed on Sep. 24, 1999, now Pat. No. 6,468,546, which is a continuation-in-part of application No. 09/338,933, filed on Jun. 23, 1999, now Pat. No. 6,488,931, which is a continuation-in-part of application No. 09/216,003, filed on Dec. 17, 1998, now Pat. No. 6,670,463, and a continuation-in-part of application No. 09/215,681, filed on Dec. 17, 1998, now Pat. No. 6,528,253.

(51) Int. Cl.[7] .......................... C07K 16/00; C12P 21/08
(52) U.S. Cl. .............................. 530/387.1; 530/387.7; 530/388.1
(58) Field of Search ..................... 530/387.1, 387.7, 530/388.1; 435/7, 230

(56) References Cited

U.S. PATENT DOCUMENTS 6,468,546 B1 * 10/2002 Mitcham et al. ......... 424/277.1

FOREIGN PATENT DOCUMENTS

| WO | WO 99/25877 | 5/1999 | |
| WO | WO 9963088 A2 * | 12/1999 | ........... C12N/15/12 |
| WO | WO9963088 * | 12/1999 | ........... C12N/15/12 |
| WO | WO 00/12758 | 3/2000 | |
| WO | WO 00/36107 | 6/2000 | |
| WO | WO 00/55629 | 9/2000 | |
| WO | EP 1033401 A2 | 9/2000 | |
| WO | WO 00/73454 | 12/2000 | |
| WO | WO 00/76531 | 12/2000 | |
| WO | WO 01/16318 | 3/2001 | |
| WO | WO 01/18542 | 3/2001 | |
| WO | WO 01/40269 | 6/2001 | |
| WO | WO 01/57272 | 8/2001 | |
| WO | WO 01/94641 | 12/2001 | |
| WO | WO 02/02587 | 1/2002 | |
| WO | WO 02/02624 | 1/2002 | |
| WO | WO 02/10187 | 2/2002 | |
| WO | WO 02/16429 | 2/2002 | |
| WO | WO 02/16581 | 2/2002 | |

OTHER PUBLICATIONS

Hovig, E. et al., "CA 125: The End of the Beginning," *Tumor Biology* 22: 345–347, 2001.
O'Brien, T.J. et al., "The CA 125 Gene: A Newly Discovered Extension of the Glycosylated N–Terminal Domain Doubles the Size of This Extracellular Superstructure," *Tumor Biology* 23:154–169, 2002.
O'Brien, T.J. et al., "The CA 125 Gene: An Extracellular Superstructure Dominated by Repeat Sequences," *Tumor Biology* 22: 348–366, 2001.
Schummer, M. et al., "Comparative hybridization of an array of 21 500 ovarian cDNAs for the discovery of genes overexpressed in ovarian carcinomas," *Gene* 238: 375–385, 1999.
Whitehouse, C. et al., "NBR1 interacts with fasciculation and elongation protein zeta–1 (FEZ1) and calcium and integrin binding protein (CIB) and shows developmentally restricted expression in the neural tube," *Eur. J. Biochem.* 269: 538–545, 2002.
Yin and Lloyd, "Molecular Cloning of the CA125 Ovarian Cancer Antigen. Identification as a new mucin, MUC16," *Journal of Biological Chemistry* 276 (29): 27371–27375, Jul. 20, 2001.
Yin, B.W.T. et al., "Ovarian cancer antigen CA125 is encoded by the MUC16 mucin gene," *International Journal of Cancer* 98: 737–740, 2002.
Bookman et al., "Biological therapy of ovarian cancer: Current directions," *Seminars in Oncology,* 25 (3):381–396, 1998.
Gillespie et al., "Mage, Bage, and Gage: Tumour antigen expression in benign and malignant ovarian tissue," *British Journal of Cancer,* 78 (6):816–821, Sep. 1998.
Heller et al., "Discovery and analysis of inflammatory disease–related genes using cDNA microarrays," *Proc. Natl. Acad. Sci. USA* 94: 2150–2155, Mar. 1997.
Ishikawa et al., "Prediction of the coding sequence of unidentified human genes. The complete sequence of 100 new cDNA clones from brain which can code for large proteins in vitro," *DNA Res.,* 5:169–176, 1998.
Jin et al., "Human T cell leukemia virus type 1 oncoprotein tax targets the human mitotic checkpoint protein MAD1," *Cell* 93: 81–91, Apr. 3, 1998.

(Continued)

*Primary Examiner*—Gary Nickol
*Assistant Examiner*—Brandon Fetterolf
(74) *Attorney, Agent, or Firm*—Seed IP Law Group PLLC

(57) ABSTRACT

Compositions and methods for the therapy and diagnosis of cancer, such as ovarian cancer, are disclosed. Compositions may comprise one or more ovarian carcinoma proteins, immunogenic portions thereof, polynucleotides that encode such portions or antibodies or immune system cells specific for such proteins. Such compositions may be used, for example, for the prevention and treatment of diseases such as ovarian cancer. Methods are further provided for identifying tumor antigens that are secreted from ovarian carcinomas and/or other tumors. Polypeptides and polynucleotides as provided herein may further be used for the diagnosis and monitoring of ovarian cancer.

3 Claims, 101 Drawing Sheets

OTHER PUBLICATIONS

Köhler et al., "Immunotherapy of Ovarian Carcinoma with the Monoclonal Anti–Idiotype Antibody ACA125—Results of the Phase LB Study," *Gebrutshilfe und Fraenheilkunde,* 58 (4):180–186, Apr. 1998 + (English Abstract).

Ma et al., "Use of encapsulated single chain antibodies for induction of anti–idiotypic humoral and cellular immune responses," *Journal of Pharmaceutical Sciences,* 87 (11):1375–1378, Nov. 1998.

Parker et al., "Scheme for ranking potential HLA–A2 binding peptides based on independent binding of individual peptide side–chains," *The Journal of Immunology* 152 (1):163–175, Jan. 1, 1994.

Peoples et al., "Ovarian cancer–associated lymphocyte recognition of folate binding protein peptides," *Annals of Surgical Oncology,* 5 (8):743–750, Dec. 1998.

Schena et al., "Parallel human genome analysis: Microarray–based expression monitoring of 1000 genes," *Proc. Natl. Acad. Sci.* 93: 10614–10619, Oct. 1996.

Frankel, A.E. et al., "Targeted Toxins," *Clinical Cancer Research* 6: 326–334, Feb. 2000.

GenBank Accession No. AA075632, Dec. 23, 1997. Available at www.ncbi.nlm.nih.gov/entrz .

GenBank Accession No. AA404225, Aug. 8, 1997. Available at www.ncbi.nlm.nih.gov/entrz .

GenBank Accession No. NM_024626, Sep. 3, 2004. Available at www.ncbi.nlm.nih.gov/entrz .

GenBank Accession No. NP_078902, Sep. 3, 2004. Available at www.ncbi.nlm.nih.gov/entrz .

GenBank Accession No. XM_018334, Oct. 16, 2001. Available at www.ncbi.nlm.nih.gov/entrz .

GenBank Accession No. XP_018334, Oct. 16, 2001. Available at www.ncbi.nlm.nih.gov/entrz .

\* cited by examiner

11729.1 contg

TTAGAGAGGCACAGAAGGAAGAAGAGTTAAAAGCAGCAAAGCCGGGTTTTTTTGTTTTGTTTTGTTTTGTTTT
GTTTTGAGATGGAGTCTCACTCTGTTGCCCAAGCTGGAGTACAACGGCATGATCTCAGCTCGCTGCAACCT
CCGCCTCCCACGTTCAAGTGATTCTCCTGCCTCAGCCTCCCAAGTAGCTGGGATTACAGGCGCCCGCCAC
CACGCTCAGCTAATTTTTTTTGTATTTTTAGTAGAGACAGGGTTTCACCAGGTTGGCCAGGCTGCTCTTGAA
CTCCTGACCTCAGGTGATCCACCCGCCTCGGCCTCCCAAAGTGCTGGGATTACAGGCGTGAGCCACCACG
CCCGGCCCCCAAAGCTGTTTCTTTTGTCTTTAGCGTAAAGCTCTCCTGCCATGCAGTATCTACATAACTGAC
GTGACTGCCAGCAAGCTCAGTCACTCCGTGGTC

11729-45.21.21.cons1

TAGGATGTGTTGGACCCTCTGTGTCAAAAAAAACCTCACAAAGAATCCCCTGCTCATTACAGAAGAAGATGC
ATTTAAAATATGGGTTATTTTCAACTTTTTATCTGAGGACAAGTATCCATTAATTATTGTGTCAGAAGAGATTG
AATACCTGCTTAAGAAGCTTACAGAAGCTATGGGAGGAGGTTGGCAGCAAGAACAATTTGAACATTATAAAA
TCAACTTTGATGACAGTAAAAATGGCCTTTCTGCATGGGAACTTATTGAGCTTATTGGAAATGGACAGTTTA
GCAAAGGCATGGACCGGCAGACTGTGTCTATGGCAATTAATGAAGTCTTTAATGAACTTATATTAGATGTGT
TAAAGCAGGGTTACATGATGAAAAAGGGCCACAGACGGAAAAACTGGACTGAAAGATGGTTTGTACTAAAA
CCCAACATAATTTCTTACTATGTGAGTGAGGATCTGAAGGATAAGAAAGGAGACATTCTCTTGGATGAAAAT
TGCTGTGTAGAGTCCTTGCCTGACAAAGATGGAAA

11729-45.21.21.cons2

TTAGAGAGGCACAGAAGGAAGAAGAGTTAAAAGCAGCAAAGCCGGGTTTTTTTGTTTTGTTTTGTTTTGTTTT
GTTTTGAGATGGAGTCTCACTCTGTTGCCCAAGCTGGAGTACAACGGCATGATCTCAGCTCGCTGCAACCT
CCGCCTCCCACGTTCAAGTGATTCTCCTGCCTCAGCCTCCCAAGTAGCTGGGATTACAGGCGCCCGCCAC
CACGCTCAGCTAATTTTTTTTGTATTTTTAGTAGAGACAGGGTTTCACCAGGTTGGCCAGGCTGCTCTTGAA
CTCCTGACCTCAGGTGATCCACCCGCCTCGGCCTCCCAAAGTGCTGGGATTACAGGCGTGAGCCACCACG
CCCGGCCCCCAAAGCTGTTTCTTTTGTCTTTAGCGTAAAGCTCTCCTGCCATGCAGTATCTACATAACTGAC
GTGACTGCCAGCAAGCTCAGTCACTCCGTGGTC

11731.1contig

TCTTTTTCTTTCGATTTCCTTCAATTTGTCACGTTTGATTTTATGAAGTTGTTCAAGGGCTAACTGCTGTGTAT
TATAGCTTTCTCTGAGTTCCTTCAGCTGATTGTTAAATGAATCCATTTCTGAGAGCTTAGATGCAGTTTCTTTT
TCAAGAGCATCTAATTGTTCTTTAAGTCTTTGGCATAATTCTTCCTTTTCTGATGACTTTTTATGAAGTAAACT
GATCCCTGAATCAGGTGTGTTACTGAGCTGCATGTTTTTAATTCTTTCGTTTAATAGCTGCTTCTCAGGGACC
AGATAGATAAGCTTATTTTGATATTCCTTAAGCTCTTGTTGAAGTTGTTTGATTTCCATAATTTCCAGGTCACA
CTGTTTATCCAAAACTTCTAGCTCAGTCTTTTGTGTTTGCTTTCTGATTTGGACATCTTGTAGTCTGCCTGAG
ATCTGCTGATGXTTTCCATTCACTGCTTCCAGTTCCAGGTGGAGACTTTXCTTTCTGGAGCTCAGCCTGACA
ATGCCTTCTTGXTCCCT

*Fig. 1A*

11731.2contig

```
AGCCAGATGGCTGAGAGCTGCAAGAAGAAGTCAGGATCATGATGGCTCAGTTTCCCACAGCGATGAATGG
AGGGCCAAATATGTGGGCTATTACATCTGAAGAACGTACTAAGCATGATAAACAGTTTGATAACCTCAAACC
TTCAGGAGGTTACATAACAGGTGATCAAGCCCGTACTTTTTTCCTACAGTCAGGTCTGCCGGCCCCGGTTTT
AGCTGAAATATGGGCCTTATCAGATCTGAACAAGGATGGGAAGATGGACCAGCAAGAGTTCTCTATAGCTA
TGAAACTCATCAAGTTAAAGTTGCAGGGCCAACAGCTGCCTGTAGTCCTCCCTCCTATCATGAAACAACCCC
CTATGTTCTCTCCACTAATCTCTGCTCGTTTTGGGATGGGAAGCATGCCCAATCTGTCCATTCATCAGCCAT
TGCCTCCAGTTGCACCTATAGCAACACCCTTGTCTTCTGCTACTTCAGGGACCAGTATTCCTCCCCTAATGA
TGCCTGCTCCCCTAGTGCCTTCTGTTAGTA
```

11734.1contig

```
AATAGATTTAATGCAGAGTGTCAACTTCAATTGATTGATAGTGGCTGCCTAGAGTGCTGTGTTGAGTAGGTT
TCTGAGGATGCACCCTGGCTTGAAGAGAAAGACTGGCAGGATTAACAATATCTAAAATCTCACTTGTAGGA
GAAACCACAGGCACCAGAGCTGCCACTGGTGCTGGCACCAGCTCCACCAAGGCCAGCGAAGAGCCCAAAT
GTGAGAGTGGCGGTCAGGCTGGCACCAGCACTGAAGCCACCACTGGTGCTGGCACTGGCACTGGCACTG
TTATTGGTACTGGTACTGGCACCAGTGCTGGCACTGCCACTCTCTTGGGCTTTGGCTTTAGCTTCTGCTCC
CGCCTGGATCCGGGCTTTGGCCCAGGGTCCGATATCAGCTTCGTCCCAGTTGCAGGGCCCGGCAGCATTC
TCCGAGCCGAGCCCAATGCCCATTCGAGCTCTAATCTCGGCCCTAGCCTTGGCTTCAGCTGCAGCCTCAG
CTGCAGCCTTCAAATCCGCTTCCATCGCCTCTCGGTAC
```

11734.2contig

```
GCCAAGAAAGCCCGAAAGGTGAAGCATCTGGATGGGGAAGAGGATGGCAGCAGTGATCAGAGTCAGGCTT
CTGGAACCACAGGTGGCCGAAGGGTCTCAAAGGCCCTAATGGCCTCAATGGCCCGCAGGGCTTCAAGGG
GTCCCATAGCCTTTTGGGCCCGCAGGGCATCAAGGACTCGGTTGGCTGCTTGGGCCCGGAGAGCCTTGCT
CTCCCTGAGATCACCTAAAGCCCGTAGGGGCAAGGCTCGCCGTAGAGCTGCCAAGCTCCAGTCATCCCAA
GAGCCTGAAGCACCACCACCTCGGGATGTGGCCCTTTTGCAAGGGAGGGCAAATGATTTGGTGAAGTACC
TTTTGGCTAAAGACCAGACGAAGATTCCCATCAAGCGCTCGGACATGCTGAAGGACATCATCAAAGAATAC
ACTGATGTGTACCCCGAAATCATTGAACGAGCAGGCTATTCCTTGGAGAAGGTATTTGGGATTCAATTGAAG
GAAATTGATAAGAATGACCACTTGTACATTCTTCTCAGC
```

11736.1contg

```
GAGGTCTCACTATGTTGCCCAGGCTGTTCTTGAACTCCTGGGATCAAGCAATCCACCCATGTTGGTCTCCA
AAAGTGCTGGGATCATAGGCGTGAGCCACCTCACCCAGCCACCAATTTTCAATCAGGAAGACTTTTTCCTTC
TTCAAGAAGTGAAGGGTTTCCAGAGTATAGCTACACTATTGCTTGCCTGAGGGTGACTACAAAATTGCTTGC
TAAAAGGTTAGGATGGGTAAAGAATTAGATTTTCTGAATGCAAAAATAAAATGTGAACTAATGAACTTTAGGT
AATACATATTCATAAAATAATTATTCACATATTTCCTGATTTATCACAGAAATAATGTATGAAATGCTTTGAGTT
TCTTGGAGTAAACTCCATTACTCATCCCAAGAAACCATATTATAAGTATCACTGATAATAAGAACAACAGGAC
CTTGTCATAAATTCTGGATAAGAGAAATAGTCTCTGGGTGTTTGXTCTTAATTGATAAAATTTACTTGTCCATC
TTTTAGTTCAGAATCACAAAA
```

*Fig. 1B*

11736.2contig

AAGCGGAAATGAGAAAGGAGGGAAAATCATGTGGTATTGAGCGGAAAACTGCTGGATGACAGGGCTCAGT
CCTGTTGGAGAACTCTGGGTGGTGCTGTAGAACAGGGCCACTCACAGTGGGGTGCACAGACCAGCACGG
CTCTGTGACCTGTTTGTTACAGGTCCATGATGAGGTAAACAATACACTGAGTATAAGGGTTGGTTTAGAAAC
TCTTACAGCAATTTGACAAAGTAATCTTCTGTGCAGTGAATCTAAGAAAAAAATTGGGGCTGTATTTGTATGT
TCCTTTTTTTCATTTCATGTTCTGAGTTACCTATTTTTATTGCATTTTACAAAAGCATCCTTCCATGAAGGACC
GGAAGTTAAAAACAAAGCAGGTCCTTTATCACAGCACTGTCGTAGAACACAGTTCAGAGTTATCCACCCAAG
GAGCCAGGGAGCTGGGCTAAACCAAAGAATTTTGCTTTTGGTTAATCATCAGGTACTTGAGTTGGAATTGTT
TTAATCCCATCATTACCAGGCTGGAXGTG

11739-1&2

CCGCGGCTCCTGTCCAGACCCTGACCCTCCCTCCCAAGGCTCAACCGTCCCCCAACAACCGCCAGCCTTG
TACTGATGTCGGCTGCGAGAGCCTGTGCTTAAGTAAGAATCAGGCCTTATTGGAGACATTCAAGCAAAGGT
TGGACAACTACTTTTCCAGAACAGAAAGGAAACTCATGCATCAGAAAAGGTGACTAATAAAGGTACCAGAAG
AATATGGCTGCACAAATACCAGAATCTGATCAGATAAAACAGTTTAAGGAATTTCTGGGGACCTACAATAAA
CTTACAGAGACCTGCTTTTTGGACTGTGTTAGAGACTTCACAACAAGAGAAGTAAAACCTGAAGAGACCACC
TGTTCAGAACATTGCTTACAGAAATATTTAAAAATGACACAAAGAATATCCATGAGATTTCAGGAATATCATA
TTCAGCAGAATGAAGCCCTGGCAGCCAAAGCAGGACTCCTTGGCCAACCACGATAGAGAAGTCCTGATGG
ATGAACTTTTGATGAAAGATTGCCAACAGCTGCTTTATTGGAAATGAGGACTCATCTGATAGAATCCCCTGA
AAGCAGTAGCCACCATGTTCAACCATCTGTCATGACTGTTTGGCAAATGGAAACCGCTGGAGAAACAAAATT
GCTATTTACCAGGAATAATCACAATAGAAGGTCTTATTGTTCAGTGAAATAATAAGATGCAACATTTGTTGAG
GCCTTATGATTCAGCAGCTTGGTCACTTGATTAGAAAAATAAACCATTGTTTCTTCAATTGTGACTGTTAATTT
TAAAGCAACTTATGTGTTCGATCATGTATGAGATAGAAAAATTTTTATTACTCAAAGTAAAATAAATGGA

11740.1.contig

GAAAAAAAATATAAAACACACTTTTGCGAAAACGGTGGCCCTAAAAGAGGAAAAGAATTTCACCAATATAAAT
CCAATTTTATGAAAACTGACAATTTAATCCAAGAATCACTTTTGTAAATGAAGCTAGCAAGTGATGATATGAT
AAAATAAACGTGGAGGAAATAAAAACACAAGACTTGGCATAAGATATATCCACTTTTGATATTAAACTTGTGA
AGCATATTCTTCGACAAATTGTGAAAGCGTTCCTGATCTTGCTTGTTCTCCATTTCAAATAAGGAGGCATATC
ACATCCCAAGAGTAACAGAAAAAGAAAAAAGACATTTTTGCATTTTGAGATGAACCAAAGACACAAAACAAA
ACGAACAAAGTGTCATGTCTAATTCTAGCCTCTGAAATAAACCTTGAACATCTCCTACAAGGCACCGTGATT
TTTGTAATTCTAACCTGAAGAAATGTGATGACTTTTGTGGACATGAAAATCAGATGAGAAAACTGTGGTCTTT
CCAAAGCCTGAACTCCCCTGAAAACCTTTGCA

*Fig. 1C*

11766.1.contig

```
CTGGGATCATTTCTCTTGATGTCATAAAAGACTCTTCTTCTTCCTCTTCATCCTCTTCTTCATCCTCTTCTGTA
CAGTGCTGCCGGGTACAACGGCTATCTTTGTCTTTATCCTGAGATGAAGATGATGCTTCTGTTTCTCCTACC
ATAACTGAAGAAATTTCGCTGGAAGTCGTTTGACTGGCTGTTTCTCTGACTTCACCTTCTTTGTCAAACCTGA
GTCTTTTTACCTCATGCCCCTCAGCTTCCACAGCATCTTCATCTGGATGTTTATTTTTCAAAGGGCTCACTGA
GGAAACTTCTGATTCAGAGGTCGAAGAGTCACTGTGATTTTTCTCCTCATTTTGCTGCAAATTTGCCTCTTTG
CTGTCTGTGCTCTCAGGCAACCCATTTGTTGTCATGGGGGCTGACAAAGAAACCTTTGGTCGATTAAGTGG
CCTGGGTGTCCCAGGCCCATTTATATTAGACCTCTCAGTATAGCTTGGTGAATTTCCAGGAAACATAACACC
ATTCATTCGATTTAAACTATTGGAATTGGTTTT
```

11766.2.contig

```
GAGGGTTGGTGGTAGCGGCTTGGGGAGGTGCTCGCTCTGTCGGTCTTGCTCTCTCGCACGCTTCCCCCGG
CTCCCTTCGTTTCCCCCCCCGGTCGCCTGCGTGCCGGAGTGTGTGCGAGGGAGGGGGAGGGCGTCGG
GGGGGTGGGGGGAGGCGTTCCGGTCCCCAAGAGACCCGCGGAGGGAGGCGGAGGCTGTGAGGGACTCC
GGGAAGCCATGGACGTCGAGAGGCTCCAGGAGGCGCTGAAAGATTTTGAGAAGAGGGGGAAAAAGGAAG
TTTGTCCTGTCCTGGATCAGTTTCTTTGTCATGTAGCCAAGACTGGAGAAACAATGATTCAGTGGTCCCAAT
TTAAAGGCTATTTTATTTTCAAACTGGAGAAAGTGATGGATGATTTCAGAACTTCAGCTCCTGAGCCAAGAG
GTCCTCCCAACCCTAATGTCGA
```

11773.2.contig

```
AAGCAGGCGGCTCCCGCGCTCGCAGGGCCGTGCCACCTGCCCGCCCGCCCGCTCGCTCGCTCGCCCGC
CGCGCCGCGCTGCCGACCGCCAGCATGCTGCCGAGAGTGGGCTGCCCCGCGCTGCCGXTGCCG
```

11775-1&2

```
ATCTCTTGTATGCCAAATATTTAATATAAATCTTTGAAACAAGTTCAGATGAAATAAAAATCAAAGTTTGCAAA
AACGTGAAGATTAACTTAATTGTCAAATATTCCTCATTGCCCCAAATCAGTATTTTTTTTATTTCTATGCAAAA
GTATGCCTTCAAACTGCTTAAATGATATATGATATGATACACAAACCAGTTTTCAAATAGTAAAGCCAGTCAT
CTTGCAATTGTAAGAAATAGGTAAAAGATTATAAGACACCTTACACACACACACACACACACACGTGTGC
ACGCCAATGACAAAAAACAATTTGGCCTCTCCTAAAATAAGAACATGAAGACCCTTAATTGCTGCCAGGAGG
GAACACTGTGTCACCCCTCCCTACAATCCAGGTAGTTTCCTTTAATCCAATAGCAAATCTGGGCATATTTGA
GAGGAGTGATTCTGACAGCCACGTTGAAATCCTGTGGGGAACCATTCATGTCCACCCACTGGTGCCCTGAA
AAAATGCCAATAATTTTTCGCTCCCACTTCTGCTGCTGtCTCTTCCACATCCTCACATAGACCCCAGACCCGC
TGGCCCCTGGCTGGGCATCGCATTGCTGGTAGAGCAAGTCATAGGTCTCGTCTTTGACGTCACAGAAGCG
ATACACCAAATTGCCTGGTCGGTCATTGTCATAACCAGAGA
```

*Fig. 1D*

11777.1&2.cons

CAGACGGGGTTTCACTATGTTGGCTAGGCTGGTCTTGAACTCCTGACTTCAGGTGATCTGCCTGCCTTGGC
CTCCCAAAGTGCTGGGATTACAGGCATAAGCCACTGCGCCCGGCTGATCTGATGGTTTCATAAGGCTTTTC
CCCCTTTTGCTCAGCACTTCTCCTTCCTGCCGCCATGTGAAGAAGGACATGTTTGCTTCCCCTTCCACCACG
ATTGTAAGTTGTTTCCTGAGGCCTCCCCGGCCATGCTGAACTGTGAGTCAATTAAACCTCTTTCCTTTATAAA
TTATCCAGTTTTGGGTATGTCTTTATTAGTAGAATGAGAACAGACTAATACAACCCTTAAAGGAGACTGACG
GAGAGGATTCTTCCTGGATCCCAGCACTTCCTCTGAATGCTACTGACATTCTTCTTGAGGACTTTAAACTGG
GAGATAGAAAACAGATTCCATGGCTCAGCAGCCTGAGAGCAGGGAGGGAGCCAAGCTATAGATGACATGG
GCAGCCTCCCCTGAGGCCAGGTGTGGCCGAACCTGGGCAGTGCTGCcACCCACCCCACCAGGGCCAAGT
CCTGTCCTTGGAGAGCCAAGCCTCAATCACTGCTAGCCTCAAGTGTCCCCAAGCCACAGTGGCTAGGGGG
ACTCAGGGAACAGTTCCCAGTCTGCCCTACTTCTCTTACCTTTACCCCTCATACCTCCAAAGTAGACCATGT
TCATGAGGTCCAAAGG

11779.2.contig

AAGCGAGGAAGCCACTGCGGCTCCTGGCTGAAAAGCGGCGCCAGGCTCGGGAACAGAGGGAACGCGAAG
AACAGGAGCGGAAGCTGCAGGCTGAAAGGGACAAGCGAATGCGAGAGGAGCAGCTGGCCCGGGAGGCT
GAAGCCCGGGCTGAACGTGAGGCCGAGGCGCGGAGACGGGAGGAGCAGGAGGCTCGAGAGAAGGCGCA
GGCTGAGCAGGAGGAGCAGGAGCGACTGCAGAAGCAGAAAGAGGAAGCCGAAGCCCGGTCCCGGGAAG
AAGCTGAGCGCCAGCGCCAGGAGCGGGAAAAGCACTTTCAGAAGGAGGAACAGGAGAGACAAGAGCGAA
GAAAGCGGCTGGAGGAGATAATGAAGAGGACTCGGAAATCAGAAGCCGCCGAAACCAAGAAGCAGGATGC
AAAGGAGACCGCAGCTAACAATTCCGGCCCAGACCCTTGTGAAAGCTGTAGAGACTCGGCCCTCTGGGCT
TCCAGAAAGGATTCTATTGCAGAAAGGAAGGAGCTXGGCCCCCCAXGGA

11781 & 37.cons

CTCTGTGGAAAACTGATGAGGAATGAATTTACCATTACCCATGTTCTCATCCCCAAGCAAAGTGCTGGGTCT
GATTACTGCAACACAGAGAACGAAGAAGAACTTTTCCTCATACAGGATCAGCAGGGCCTCATCACACTGGG
CTGGATTCATACTCACCCCACACAGACCGCGTTTCTCTCCAGTGTCGACCTACACACTCACTGCTCTTACCA
GATGATGTTGCCAGAGTCAGTAGCCATTGTTTGCTCCCCAAGTTCCAGGAAACTGGATTCTTTAAACTAAC
TGACCATGGACTAGAGGAGATTTCTTCCTGTCGCCAGAAAGGATTTCATCCACACAGCAAGGATCCACCTC
TGTTCTGTAGCTGCAGCCACGTGACTGTTGTGGACAGAGCAGTGACCATCACAGACCTTCGATGAGCGTTT
GAGTCCAACACCTTCCAAGAACAACAAAACCATATCAGTGTACTGTAGCCCCTTAATTTAAGCTTTCTAGAAA
GCTTTGGAAGTTTTTGTAGATAGTAGAAAGGGGGGCATCACXTGAGAAAGAGCTGATTTTGTATTTCAGGTT
TGAAAAGAAATAACTGAACATATTTTTAGGCAAGTCAGAAAGAGAACATGGTCACCCAAAAGCAACTGTAA
CTCAGAAATTAAGTTACTCAGAAATTAAGTAGCTCAGAAATTAAGAAAGAATGGTATAATGAACCCCCATATA
CCCTTCCTTCTGGATTCACCAATTGTTAACATTTTTTTCCTCTCAGCTATCCTTCTAATTTCTCTCTAATTTCA
ATTTGTTTATATTTACCTCTGGGCTCAATAAGGGCATCTGTGCAGAAATTTGGAAGCCATTTAGAAAATCTTT
TGGATTTTCCTGTGGTTTATGGCAATATGAATGGAGCTTATTACTGGGGTGAGGGACAGCTTACTCCATTTG
ACCAGATTGTTTGGCTAACACATCCCGAAGAATGATTTTGTCAGGAATTATTGTTATTTAATAAATATTTCAG
GATATTTTTCCTCTACAATAAAGTAACAAT

CTCTGTGGAAAACTGATGAGGAATGAATTTACCATTACCCATGTTCTCATCCCCAAGCAAAGTGCTGGGTCT
GATTACTGCAACACAGAGAACGAAGAAGAACTTTTCCTCATACAGGATCAGCAGGGCCTCATCACACTGGG
CTGGATTCATACTCACCCCACACAGACCGCGTTTCTCTCCAGTGTCGACCTACACACTCACTGCTCTTACCA
GATGATGTTGCCAGAGTCAGTAGCCATTGTTTGCTCCCCCAAGTTCCAGGAAACTGGATTCTTTAAACTAAC
TGACCATGGACTAGAGGAGATTTCTTCCTGTCGCCAGAAAGGATTTCATCCACACAGCAAGGATCCACCTC
TGTTCTGTAGCTGCAGCCACGTGACTGTTGTGGACAGAGCAGTGACCATCACAGACCTTCGATGAGCGTTT
GAGTCCAACACCTTCCAAGAACAACAAAACCATATCAGTGTACTGTAGCCCCTTAATTTAAGCTTTCTAGAAA
GCTTTGGAAGTTTTTGTAGATAGTAGAAAGGGGGGCATCACCTGAGAAAGAGCTGATTTTGTATTTCAGGTT
TGAAAAGAAATAACTGAACATATTTTTTAGGCAAGTCAGAAAGAGAACATGGTCACCCAAAAGCAACTGTAA
CTCAGAAATTAAGTTACTCAGAAATTAAGTAGCTCAGAAATTAAGAAAGAATGGTATAATGAACCCCCATATA
CCCTTCCTTCTGGATTCACCAATTGTTAACATTTTTTTCCTCTCAGCTATCCTTCTAATTTCTCTCTAATTTCA
ATTTGTTTATATTTACCTCTGGGCTCAATAAGGGCATCTGTGCAGAAATTTGGAAGCCATTTAGAAAATCTTT
TGGATTTTCCTGTGGTTTATGGCAATATGAATGGAGCTTATTACTGGGGTGAGGGACAGCTTACTCCATTTG
ACCAGATTGTTTGGCTAACACATCCCGAAGAATGATTTTGTCAGGAATTATTGTTATTTAATAAATATTTCAG
GATATTTTTCCTCTACAATAAAGTAACAATTA

11784-1 & 2

GGACGACAAGGCCATGGCGATATCGGATCCGAATTCAAGCCTTTGGAATTAAATAAACCTGGAACAGGGAA
GGTGAAAGTTGGAGTGAGATGTCTTCCATATCTATACCTTTGTGCACAGTTGAATGGGAACTGTTTGGGTTT
AGGGCATCTTAGAGTTGATTGATGGAAAAAGCAGACAGGAACTGGTGGGAGGTCAAGTGGGGAAGTTGGT
GAATGTGGAATAACTTACCTTTGTGCTCCACTTAAACCAGATGTGTTGCAGCTTTCCTGACATGCAAGGATC
TACTTTAATTCCACACTCTCATTAATAAATTGAATAAAAGGGAATGTTTTGGCACCTGATATAATCTGCCAGG
CTATGTGACAGTAGGAAGGAATGGTTTCCCCTAACAAGCCCAATGCACTGGTCTGACTTTATAAATTATTTA
ATAAAATGAACTATTATC

11785.2.contig

GGCAGTGACATTCACCATCATGGGAACCACCTTCCCTTTTCTTCAGGATTCTCTGTAGTGGAAGAGAGCAC
CCAGTGTTGGGCTGAAAACATCTGAAAGTAGGGAGAAGAACCTAAAATAATCAGTATCTCAGAGGGCTCTA
AGGTGCCAAGAAGTCTCACTGGACATTTAAGTGCCAACAAAGGCATACTTTCGGAATCGCCAAGTCAAAAC
TTTCTAACTTCTGTCTCTCTCAGAGACAAGTGAGACTCAAGAGTCTACTGCTTTAGTGGCAACTACAGAAAA
CTGGTGTTACCCAGAAAAACAGGAGCAATTAGAAATGGTTCCAATATTTCAAAGCTCCGCAAACAGGATGTG
CTTTCCTTTGCCCATTTAGGGTTTCTTCTCTTTCCTTTCTCTTTATTAACCACT

*Fig. 1F*

11718-1&2 cons

TGCGCTGAAAACAACGGCCTCCTTTACTGTTAAAATGCAGCCACAGGTGCTTAGCCGTGGGCATCTCAACC
ACCAGCCTCTGTGGGGGGCAGGTGGGCGTCCCTGTGGGCCTCTGGGCCCACGTCCAGCCTCTGTCCTCT
GCCTTCCGTTCTTCGACAGTGTTCCCGGCATCCCTGGTCACTTGGTACTTGGCGTGGGCCTCCTGTGCTGC
TCCAGCAGCTCCTCCAGGXGGTCGGCCCGCTTCACCGCAGCCTCATGTTGTGTCCGGAGGCTGCTCACGG
CCTCCTCCTTCCTCGCGAGGGCTGTCTTCACCCTCCGGXGCACCTCCTCCAGCTCCAGCTGCTGGCGGGC
CTGCAGCGTGGCCAGCTCGGCCTTGGCCTGCCGCGTCTCCTCCTCARAGGCTGCCAGCCGGTCCTCGAA
CTCCTGGCGGATCACCTGGGCCAGGTTGCTGCGCTCGCTAGAAAGCTGCTCGTTCACCGCCTGCGCATCC
TCCAGCGCCCGCTCCTTCTGCCGCACAAGGCCCTGCAGACGCAGATTCTCGCCCTCGGCcTCCCCAAGCT
GGCCCTTCAGCTCCGAGCACCGCTCCTGAAGCTTCCGCTCCGACTGCTCCAGCTCGGAGAGCTCGGCCTC
GTACTTGTCCCGTAAGCGCTTGATGCGGCTCTCGGCAGCCTTCTCACTCTCCTCCTTGGCCAGCGCCATGT
CGGCCTCCAGCCGGTGAATGACCAGCTCAATCTCCTTGTCCCGGCCTTTCCGGATTTCTTCCCTCAGCTCC
TGTTCCCGGTTCAGCAGCCACGCCTCCTCCTTCCTGGTGCGGCCGGCCTCCCACGCCTGCCTCTCCAGCT
CCAGCTGCTGCTTCAGGGTATTCAGCTCCATCTGGCGGGCCTGCAGCGTGGCCA

13690.4

CAACTTATTACTTGAAATTATAATATAGCCTGTCCGTTTGCTGTTTCCAGGCTGTGATATATTTTCCTAGTGG
TTTGACTTTAAAAATAAATAAGGTTTAATTTTCTCCCC

13693.1

TGCAAGTCACGGGAGTTTATTTATTTAATTTTTTTCCCCAGATGGAGACTCTGTCGCCCAGGCTGGAGTGCA
ATGGTGTGATCTTGGCTCACTGCAACCTCCACCTCCTGGGTTCAAGCGATTCTCCTGCCACAGCCTCCCGA
GTAGCTGGGATTACAGGTGCCCGCCACCACACCCAGCTAATTTTTATATTTTTAGTAAAGACAGGGTTTCCC
CATGTTGGCCAGGCTGGTCTTGAACTTCTGACCTCAGGTGATCCACCTGCCTCGGCCTCCCAAAGTGTTGG
GATTACAGGCGTGAGCTACCCGTGCCTGGCCAGCCACTGGAGTTTAAAGGACAGTCATGTTGGCTCCAGC
CTAAGGCGGCATTTTCCCCCATCAGAAAGCCCGCGGCTCCTGTACCTCAAAATAGGGCACCTGTAAAGTCA
GTCAGTGAAGTCTCTGCTCTAACTGGCCACCCGGGGCCATTGGCNTCTGACACAGCCTTGCCAGGANGCC
TGCATCTGCAAAAGAAAAGTTCACTTCCTTTCCG

13694.1

CAGAGAATCTKAGAAAGATGTCGCGTTTTCTTTTAATGAATGAGAGAAGCCCATTTGTATCCCTGAATCATTG
AGAAAAGGCGGCGGTGGCGACAGCGGCGACCTAGGGATCGATCTGGAGGGACTTGGGGAGCGTGCAGA
GACCTCTAGCTCGAGCGCGAGGGACCTCCCGCCGGGATGCCTGGGGAGCAGATGGACCCTACTGGAAGT
CAGTTGGATTCAGATTTCTCTCAGCAAGATACTCCTTGCCTGATAATTGAAGATTCTCAGCCTGAAAGCCAG
GTTCTAGAGGATGATTCTGGTTCTCACTTCAGTATGCTATCTCGACACCTTCCTAATCTCCAGACGCACAAA
GAAAATCCTGTGTTGGATGTTGNGTCCAATCCTTGAACAAACAGCTGGAGAAGAACGAGGAGACCGGTAAT
AGTGGGTTCAATGAACATTTGAAAGAAAACCAGGTTGCAGACCCTG

GACTGTCCTGAACAAGGGACCTCTGACCAGAGAGCTGCAGGAGATGCAGAGTGGTGGCAGGAGTGGAAG
CCAAAGAACACCCACCTTCCTCCCTTGAAGGAGTAGAGCAACCATCAGAAGATACTGTTTTATTGCTCTGGT
CAAACAAGTCTTCCTGAGTTGACAAAACCTCAGGCTCTGGTGACTTCTGAATCTGCAGTCCACTTTCCATAA
GTTCTTGTGCAGACAACTGTTCTTTTGCTTCCATAGCAGCAACAGATGCTTTGGGGCTAAAAGGCATGTCCT
CTGACCTTGCAGGTGGTGGATTTTGCTCTTTTACAACATGTACATCCTTACTGGGCTGTGCTGTCACAGGGA
TGTCCTTGCTGGACTGTTCTGCTATGGGGATATCTTCGTTGGACTGTTCTTCATGCTTAATTGCAGTATTAG
CATCCACATCAGACAGCCTGGTATAACCAGAGTTGGTGGTTACTGATTGTAGCTGCTCTTTGTCCACTTCAT
ATGGCACAAGTATTTTCCTCAACATCCTGGCTCTGGGAAG 13695.1

GAAATGTATATTTAATCATTCTCTTGAACGATCAGAACTCTRAAATCAGTTTTCTATAACARCATGTAATACAG
TCACCGTGGCTCCAAGGTCCAGGAAGGCAGTGGTTAACACATGAAGAGTGTGGGAAGGGGGCTGGAAACA
AAGTATTCTTTTCCTTCAAAGCTTCATTCCTCAAGGCCTCAATTCAAGCAGTCATTGTCCTTGCTTTCAAAAG
TCTGTGTGTGCTTCATGGAAGGTATATGTTTGTTGCCTTAATTTGAATTGTGGCCAGGAAGGGTCTGGAGAT
CTAAATTCAGAGTAAGAAAACCTGAGCTAGAACTCAGGCATTTCTCTTACAGAACTTGGCTTGCAGGGTAGA
ATGAAGGGAAAGAAACTTAGAAGCTCAACAAGCTGAAGATAATCCCATCAGGCATTTCCCATAGGCCTTGCA
ACTCTGTTCACTGAGAGATGTTATCCTG 13695.2

AGTCTGGAGTGAGCAAACAAGAGCAAGAAACAARRAGAAGCCAAAAGCAGAAGGCTCCAATATGAACAAGA
TAAATCTATCTTCAAAGACATATTAGAAGTTGGGAAAATAATTCATGTGAACTAGACAAGTGTGTTAAGAGTG
ATAAGTAAAATGCACGTGGAGACAAGTGCATCCCCAGATCTCAGGGACCTCCCCCTGCCTGTCACCTGGG
GAGTGAGAGGACAGGATAGTGCATGTTCTTTGTCTCTGAATTTTTAGTTATATGTGCTGTAATGTTGCTCTGA
GGAAGCCCCTGGAAAGTCTATCCCAACATATCCACATCTTATATTCCACAAATTAAGCTGTAGTATGTACCC
TAAGACGCTGCTAATTGACTGCCACTTCGCAACTCAGGGGCGGCTGCATTTTAGTAATGGGTCAAATGATT
CACTTTTTATGATGCTTCCCAAGGTGCCTTGGCTTCTCTTCCCAACTGACAAATGCCCAAGTTGAGAAAAAT
GATCATAATTTTAGCATAAACCGAGCAATCGGCGACCCC 13697.1

TAGCTGTCTTCCTCACTCTTATGGCAATGACCCCATATCTTAATGGATTAAGATAATGAAAGTGTATTTCTTA
CACTCTGTATCTATCACCAGAAGCTGAGGTGATAGCCCGCTTGTCATTGTCATCCATATTCTGGGACTCAGG
CGGGAACTTTCTGGAATATTGCCAGGGAGCATGGCAGAGGGGCACAGTGCATTCTGGGGGAATGCACATT
GGCTCAGCCTGGGTAATGAGTGATATACATTACCTCTGTTCACAACTCATTGCCCAGCACCAGTCACAAGG
CCCCACCAAATACCAGAGCCCAAGAAATGTAGTCCTGTTGATATGGTTTTGCTGTGTCCCAACCCAAATCTC
ATCTTGAATTGTAAGCTCCCATAATTCCCATGTGTTGTGGGAGGGACCTGGTG

ATCATGAGGATGTTACCAAAGGGATGGTACTAAACCATTTGTATTCGTCTGTTTTCACACTGCTTTGAAGATA
CTACCTGAGACTGGGTAATTTATAAACAAAAGAGATTTAATTGACTCACAGTTCTGCATGGCTGAAGAGGCC
TCAGGAAACTTACAGTCATGGTGGAAGGCAAAGGAGGAGCAAGGCATGTCTTACATGTCAGTAGGAGAGA
GAGCGAGAGCAGGAGAACCTGCCACTTATAAACCATTCAGATCTCATAACTCCCTATCATGAGAAAAACATG
GAGGAAACCACCCTCATGATCCAATCACCTCCCGCCAGGTCCCTCCCTCGACACGTGGGGATTATAATTCA
GGATTAGAGGGACACAGAGACAAACCATATCATCATTCATGAGAAATCCACCCTCATAGTCCAATCAGCTCC
TACCAGGCCCCACCTCCAACACTGGGGATTGCAATTCAACATGAGATTTGGATGGGGACACAGATTCAAAC
CATATCATAC

13699.1&2

CATGGCCTTTCTCCTTAGAGGCCAGAGGTGCTGCCCTGGCTGGGAGTGAAGCTCCAGGCACTACCAGCTT
TCCTGATTTTCCCGTTTGGTCCATGTGAAGAGCTACCACGAGCCCCAGCCTCACAGTGTCCACTCAAGGGC
AGCTTGGTCCTCTTGTCCTGCAGAGGCAGGCTGGTGTGACCCTGGGAACTTGACCCGGGAACAACAGGTG
GCCCAGAGTGAGTGTGGCCTGGCCCCTCAACCTAGTGTCCGTCCTCCTCTCTCCTGGAGCCAGTCTTGAG
TTTAAAGGCATTAAGTGTTAGATACAAGCTCCTTGTGGCTGGAAAAACACCCCTCTGCTGATAAAGCTCAGG
GGGCACTGAGGAAGCAGAGGCCCCTTGGGGGTGCCCTCCTGAAGAGAGCGTCAGGCCATCAGCTCTGTC
CCTCTGGTGCTCCCACGTCTGTTCCTCACCCTCCATCTCTGGGAGCAGCTGCACCTGACTGGCCACGCGG
GGGCAGTGGAGGCACAGGCTCAGGGTGGCCGGGCTACCTGGCACCCATGGCTTACAAAGTAGAGTTGG
CCCAGTTTCCTTCCACCTGAGGGGAGCACTCTGACTCCTAACAGTCTTCCTTGCCCTGCCATCATCTGGGG
TGGCTGGCTGTCAAGAAAGGCCGGGCATGCTTTCTAAACACAGCCACAGGAGGCTTGTAGGGCATCTTCC
AGGTGGGGAAACAGTCTTAGATAAGTAAGGTGACTTGCCTAAGGCCTCCCAGCACCCTTGATCTTGGAGTC
TCACAGCAGACTGCATGTSAACAACTGGAACCGAAAACATGCCTCAGTATAAAA

13703.3

CCAGAACCTCCTTCTCTTTGGAGAATGGGGAGGCCTCTTGGAGACACAGAGGGTTTCACCTTGGATGACCT
CTAGAGAAATTGCCCAAGAAGCCCACCTTCTGGTCCCAACCTGCAGACCCCACAGCAGTCAGTTGGTCAG
GCCCTGCTGTAGAAGGTCACTTGGCTCCATTGCCTGCTTCCAACCAATGGGCAGGAGAGAAGGCCTTTATT
TCTCGCCCACCCATTCTCCTGTACCAGCACCTCCGTTTTCAGTCAGYGTTGTCCAGCAACGGTACCGTTTAC
ACAGTCA

13705.1

TGCATGTAGTTTTATTTATGTGTTTTSGTCTGGAAAACCAAGTGTCCCAGCAGCATGACTGAACATCACTCAC
TTCCCCTACTTGATCTACAAGGCCAACGCCGAGAGCCCAGACCAGGATTCCAAACACACTGCACGAGAATA
TTGTGGATCCGCTGTCAGGTAAGTGTCCGTCACTGACCCARACGCTGTTACGTGGCACATGACTGTACAGT
GCCACGTAACAGCACTGTACTTTTCTCCCATGAACAGTTACCTGCCATGTATCTACATGATTCAGAACATTTT
GAACAGTTAATTCTGACACTTGAATAATCCCATCAAAAACCGTAAAATCACTTTGATGTTTGTAACGACAACA
TAGCATCACTTTACGACAGAATCATCTGGAAAAACAGAACAACGAATACATACATCTTAAAAAATGCTGGGG
TGGGCCAGGCACAGCTTCACGCCTGTAATCCCAGCACTTTGGGAGGCTTAAGCGGGTG

TGGGGCGGAAAGAAGCCAAGGCCAAGGAGCTGGTGCGGCAGCTGCAGCTGGAGGCCGAGGAGCAGAGG
AAGCAGAAGAAGCGGCAGAGTGTGTCGGGCCTGCACAGATACCTTCACTTGCTGGATGGAAATGAAAATTA
CCCGTGTCTTGTGGATGCAGACGGTGATGTGATTTCCTTCCCACCAATAACCAACAGTGAGAAGACAAAGG
TTAAGAAAACGACTTCTGATTTGTTTTTGGAAGTAACAAGTGCCACCAGTCTGCAGATTTGCAAGGATGTCA
TGGATGCCCTCATTCTGAAAATGGCAAGAAATGAAAAAGTACACTTTAGAAAATAAAGAGGAAGGATCACTC
TCAGATACTGAAGCCGATGCAGTCTCTGGACAACTTCCAGATCCCACAACGAATCCCAGTGCTGGAAAGGA
CGGGCCCTTCCTTCTGGTGGTGGAACANGTCCCGGTGGTGGATCTTGGAANGGAACCTGAANGTGGTGTA
CCCCGTCCAAGGCCGACCTTGGCCAC

13707.4

TCCCGCGCTCGCAGGGCNCGTGCCACCTGCCYGTCCGCCCGCTCGCTCGCTCGCCCGCCGCGCCGCGC
TGCCGACCGYCAGCATGCTGCCGAGAGTGGGCTGCCCCGCGCTGCCGCTGCCGCCGCCGCCGCTGCTG
CCGCTGCTGCCGCTGCTGCTGCTGC

13708.1&2

GGCGGGTAGGCATGGAACTGAGAAGAACGAAGAAGCTTTCAGACTACGTGGGGAAGAATGAAAAAACCAA
AATTATCGCCAAGATTCAGCAAAGGGGACAGGGAGCTCCAGCCCGAGAGCCTATTATTAGCAGTGAGGAG
CAGAAGCAGCTGATGCTGTACTATCACAGAAGACAAGAGGAGCTCAAGAGATTGGAAGAAAATGATGATGA
TGCCTATTTAAACTCACCATGGGCGGATAACACTGCTTTGAAAAGACATTTTCATGGAGTGAAAGACATAAA
GTGGAGACCAAGATGAAGTTCACCAGCTGATGACACTTCCAAAGAGATTAGCTCACCT

13709.1

TCTGAAGGTTAAATGTTTCATCTAAATAGGGATAATGRTAAACACCTATAGCATAGAGTTGTTTGAGATTAAA
TGAGATAATACATGTAAAATTATGTGCCTGGCATACAGCAAGATTGTTGTTGTTGATGATGATGATGATG
ATGATAATATTTTTCTATCCCCAGTGCACAACTGCTTGAACCTATTAGATAATCAATACATGTTTCTTGAACTG
AGATCAATTTCCCCATGTTGTCTGACTGATGAAGCCCTACATTTTCTTCTAGAGGAGATGACATTTGAGCAA
GATCTTAAAGAAAATCAGATGCCTTCACCTGACCACTGCTTGGTGATCCCATGGCACTTTGTACATCTCTCC
ATTAGCTCTCATCTCACCAGCCCATCATTATTGTATGTGCTGCCTTCTGAAGCTTGCAGCTGGCTACCATCM
GGTAGAATAAAAATCATCCTTTCATAAAATAGTGACCCTCCTTTTTTATTTGCATTTCCCAAAGCCAAGCACC
GTGGGANGGTAG

```
TATGAAGAAGGGAAAAGAAGATAATTTGTGAAAGAAATGGGTCCAGTTACTAGTCTTTGAAAAGGGTCAGTC
TGTAGCTCTTCTTAATGAGAATAGGCAGCTTTCAGTTGCTCAGGGTCAGATTTCCTTAGTGGTGTATCTAAT
CACAGGAAACATCTGTGGTTCCCTCCAGTCTCTTTCTGGGGGACTTGGGCCCACTTCTCATTTCATTTAATT
AGAGGAAATAGAACTCAAAGTACAATTTACTGTTGTTTAACAATGCCACAAAGACATGGTTGGGAGCTATTT
CTTGATTTGTGTAAAATGCTGTTTTTGTGTGCTCATAATGGTTCCAAAAATTGGGTGCTGGCCAAAGAGAGA
TACTGTTACAGAAGCCAGCAAGAAGACCTCTGTTCATTCACACCCCCGGGGATATCAGGAATTGACTCCAG
TGTGTGCAAATCCAGTTTGGCCTATCTTCT
```

13712.1&2

```
TGAGGGACTGATTGGTTTGCTCTCTGCTATTCAATTCCCCAAGCCCACTTGTTCCTGCAGCGTCCTCCTTCT
CATTCCCTTTAGTTGTACCCTCTCTTTCATCTGAGACCTTTCCTTCTTGATGTCGCCTTTTCTTCTTCTTGCTT
TTTCTGATGTTCTGCTCAGCATGTTCTGGGTGCTTCTCATCTGCATCATTCCTTTCAGATGCTGTAGCTTCTT
CCTCCTCTTTCTGCCTCCTTTTCTTTTTCTTTTTTTTGGGGGGCTTGCTCTCTGACTGCAGTTGAGGGGCCC
CAGGGTCCTGGCCTTTGAGACGAGCCAGGAAGGCCTGCTCCTGGGCCTCTAGGCGAGCAAGCTTGGCCTT
CATTGTGATCCCAAGACGGGCAGCCTTGTGTGCTGTTCGCCCCTCACAGGCTTGGAGCAGCATCTCATCAG
TCAGAATCTTTGGGGACTTGGACCCCTGGTTGTCGTCATCACTGCAGCTCTCCAAGTCTTTGTTTGGCTTCT
CTCCACCTGAAGTCAATGTAGCCATCTTCACAAACTTCTGATACAGCAAGTTGGGCTTGGGATGATTATAAC
GGGTGGTCTCCTTAGAAAGGCTCCTTATCTGTACTCCATCCTGCCCAGTTTCCACTACCAAGTTGGCCGCA
GTCTTGTTGAAGAGCTCATTCCACCAGTGGTTTGTGAACTCCTTGGCAGGGTCATGTCCTACCCCATGAGT
GTCTTGCTTCAGYGTCACCCTGAGAGCCTGAGTGATACCATTCTCCTTCCG
```

13714.1&2

```
GACAACATGAAATAAATCCTAGAGGACAAAATTAAACTCAATAGAGTGTAGTCTAGTTAAAAACTCGAAAAAT
GAGCAAGTCTGGTGGGAGTGGAGGAAGGGCTATACTATAAATCCAAGTGGGCCTCCTGATCTTAACAAGCC
ATGCTCATTATACACATCTCTGAACTGGACATACCACCTTTACGCAGGAAACAGGGCTTGGAACTTCTAAGG
GAAATTAACATGCACCACCCACATCTAACCTACCTGCCGGGTAGGTACCATCCCTGCTTCGCTGAAATCAG
TGCTC
```

13716.1&2

```
TTGGAATTAAATAAACCTGGAACAGGGAAGGTGAAAGTTGGAGTGAGATGTCTTCCATATCTATACCTTTGT
GCACAGTTGAATGGGAACTGTTTGGGTTTAGGGCATCTTAGAGTTGATTGATGGAAAAAGCAGACAGGAAC
TGGTGGGAGGTCAAGTGGGGAAGTTGGTGAATGTGGAATAACTTACCTTTGTGCTCCACTTAAACCAGATG
TGTTGCAGCTTTCCTGACATGCAAGGATCTACTTTAATTCCACACTCTCATTAATAAATTGAATAAAAGGGAA
TGTTTTGGCACCTGATATAATCTGCCAGGCTATGTGACAGTAGGAAGGAATGGTTTCCCCTAACAAGCCCAA
TGCACTGGTCTGACTTTATAAATTATTTAATAAAATGAACTATTATC
```

AAACTGGACCTGCAACAGGGACATGAATTTACTGCARGGTCTGAGCAAGCTCAGCCCCTCTACCTCAGGGC
CCCACAGCCATGACTACCTCCCCCAGGAGCGGGAGGGTGAAGGGGGCCTGTCTCTGCAAGTGGAGCCAG
AGTGGAGGAATGAGCTCTGAAGACACAGCACCCAGCCTTCTCGCACCAGCCAAGCCTTAACTGCCTGCCT
GACCCTGAACCAGAACCCAGCTGAACTGCCCCTCCAAGGGACAGGAAGGCTGGGGGAGGGAGTTTACAA
CCCAAGCCATTCCACCCCCTCCCCTGCTGGGGAGAATGACACATCAAGCTGCTAACAATTGGGGGAAGGG
GAAGGAAGAAAACTCTGAAAACAAAATCTTGT

13722.3

CATGCGTTTCACCACTGTTGGCCAGGCTGGTCTCGAACTCCTGGCCTCAAGCAATCCACCCGCCTCAGCCT
CCAAAAGTGCTGGGATTACAGATGTGAGCCATGGCACCATGCCAAAAGGCTATATTCCTGGCTCTGTGTTT
CCGAGACTGCTTTTAATCCCAACTTCTCTACATTTAGATTAAAAAATATTTTATTCATGGTCAATCTGGAACAT
AATTACTGCATCTTAAGTTTCCACTGATGTATATAGAAGGCTAAAGGCACAATTTTTATCAAATCTAGTAGAG
TAACCAAACATAAAATCATTAATTACTTTCAACTTAATAACTAATTGACATTCCTCAAAAGAGCTGTTTTCAAT
CCTGATAGGTTCTTTATTTTTTCAAAATATATTTGCCATGGGATGCTAATTTGCAATAAGGCGCATAATGAGA
ATACCCCAAACTGGA

13722.4

GTTGGACCCCCAGGGACTGGAAAGACACTTCTTGCCCGAGCTGTGGCGGGAGAAGCTGATGTTCCTTTTTA
TTATGCTTCTGGATCCGAATTTGATGAGATGTTTGTGGGTGTGGGAGCCAGCCGTATCAGAAATCTTTTTAG
GGAAGCAAAGGCGAATGCTCCTTGTGTTATATTTATTGATGAATTAGATTCTGTTGGTGGGAAGAGAATTGA
ATCTCCAATGCATCCATATTCAAGGCAGACCATAAATCAACTTCTTGCTGAAATGGATGGTTTTAAACCCAAT
GAAGGAGTTATCATAATAGGAGCCACAAACTTCCCAGAGGCATTAGATAATGCCTTAATACCGTCCTGGTCG
TTTTGACATGCAAGTTACAGTTCCAAGGCCAGATGTAAAAGGTCGAACAGAAATTTTGAAATGGTATCTCAA
TAAAATAAAGTTTGATCAATCCCGTTGATCCAGAAATTATAGCCTCGAGGTACTGGTGGCTTTTCCGGAAGC
AGAGTTGGGAGAATCTT

13724-13698-13748

GCCTACAACATCCAGAAAGAGTCTACCCTGCACCTGGTGCTSCGTCTCAGAGGTGGGATGCAGATCTTCGT
GAAGACCCTGACTGGTAAGACCATCACTCTCGAAGTGGAGCCGAGTGACACCATYGAGAACGTCAAAGCA
AAGATCCARGACAAGGAAGGCRTYCCTCCTGACCAGCAGAGGTTGATCTTTGCCGGAAAGCAGCTGGAAG
ATGGDCGCACCCTGTCTGACTACAACATCCAGAAAGAGTCYACCCTGCACCTGGTGCTCCGTCTCAGAGGT
GGGATGCARATCTTCGTGAAGACCCTGACTGGTAAGACCATCACCCTCGAGGTGGAGCCCAGTGACACCA
TCGAGAATGTCAAGGCAAAGATCCAAGATAAGGAAGGCATCCCTCCTGATCAGCAGAGGTTGATCTTTGCT
GGGAAACAGCTGGAAGATGGACGCACCCTGTCTGACTACAACATCCAGAAAGAGTCCACTCTGCACTTGGT
CCTGCGCTTGAGGGGGGGTGTCTAAGTTTCCCCTTTTAAGGTTTCMACAAATTTCATTGCACTTTCCTTTCA
ATAAAGTTGTTGCATTCCC

```
GAACTGGGCCCTGAGCCCAAGTCATGCCTTGTGTCCGCATCTGCCGTGTCACCTCTGTKCCTGCCCCTCAC
CCCTCCCTCCTGGTCTTCTGAGCCAGCACCATCTCCAAATAGCCTATTCCTTCCTGCAAATCACACACACAT
GCGGGCCACACATACCTGCTGCCCTGGAGATGGGGAAGTAGGAGAGATGAATAGAGGCCCATACATTGTA
CAGAAGGAGGGGCAGGTGCAGATAAAAGCAGCAGACCCAGCGGCAGCTGAGGTGCATGGAGCACGGTTG
GGGCCGGCATTGGGCTGAGCACCTGATGGGCCTCATCTCGTGAATCCTCGAGGCAGCGCCACAGCAGAG
GAGTTAAGTGGCACCTGGGCCGAGCAGAGCAGGAGACTGAGGGTCAGAGTGGAGGCTAAGCTGCCCTGG
AACTCCTCAATCTTGCCTGCCCCCTAGTATGAAGCCCCCTTCCTGCCCCTACAATTCCTGA
```

13732.1

```
ATGGATCTTACTTTGCCACCCAGGTTGGAGTGCAGTGCTGCAATCTTGGCTCACTGCAGCCTTAACCTCCC
AGGCTCAAGCTATCCTCCTGCCAAAGCCTTCCACATAGCTGGGACTACAGGTACACNGCCACCACACCCAG
CTAAAATTTTTGTATTTTTTGTAGAGACGGGATCTCGCCACGTTGCCCAGGCTGGTCCCATCCTGACCTCAA
GCAGATCTGCCCACCTCAGCCCCCCAACGTGCTAGGATTACAGGCGTGAGCCACCGCACCCAGCCTTTGT
TTTGCTTTTAATGGAATCACCAGTTCCCCTCCGTGTCTCAGCAGCAGCTGTGAGAAATGCTTTGCATCTGTG
ACCTTTATGAAGGGGAACTTCCATGCTGAATGAGGGTAGGATTACATGCTCCTGTTTCCCGGGGGTCAAGA
AAGCCTCAGACTCCAGCATGATAAGCAGGGTGAG
```

13732.2

```
ATAGGGGCTTTAAGGAGGGAATTCAGGTTCAATGAGGTCGTAAGGCCAGGGCTCTTATCCAGTAAGACTGG
GGTCCTTAGATGAGAAAGAGACACCCGAGGTCCTTCTCTCTGCCGTGTGAGGATGCATCAAGAAGGCGGC
CGTCTGCAAGCGAAGGAGAGGCCGCACCAGAAACCGACACCTTCATCTTGGACTTGCAGCCTCTAGAACT
GAGAAAATAACTGTCTGTTGGTTAAGCCACCCAGTTTGTAGTATTCTCTTATGGCTTCCTAAGCAGACTAAC
AAACAAACACCCAAAATTAACTGATGGCTTCGCTGTCTTCTGTAAAAATTGCTATGAGAGAACTTTTCACTCA
CTGTTTTGCAGTTTCTCCCTCAGTCCCTGGTTCTTTCTTCTCACATAATCCCAATTTCAATTTATAGTTCATGG
CCCAGGCAGAGTCATTCATCACGGCATCTCCTGAGCTAAACCAGCACCTGCTCTGCTCACTTCTTGACTGG
CTGCTCATCATCAGCCCTCTTGCAGAGATTTCATTTCCTCCCGTGCCAGGTACTTCACGCACCAAGCTCA
```

```
GGATAATGAAGTTGTTTTATTTAGCTTGGACAAAAAGGCATATTCCTCTATTTTCTTATACAACAAATATCCCC
AAAATAAAGCAAGCATATATATCTTGAATGTGTAATAATCCAGTGATAAACAAGAGCAGTACTTTAAAAGAAA
AAAAAATATGTATTTCTGTCAGGTTAAAATGAGAATCAAAACCATTTACTCTGCTAACTCATTATTTTTTGCTT
TCTTTTTGGTTAAGAGAGGCAATGCAATACACTGAAAAAGGTTTTTATCTTATCTGGCATTGGAATTAGACAT
ATTCAAACCCCAGCCCCCATTTCCAAACTTTAAGACCACAAACAAGTAATTTACTTTTCTGAACATTGGTTTT
TTCTGGAAAATGGGAATTATAAAATAGACTTTGCAGACTCTTATGAGATTAAATAAGATAATGTATGAAATTCT
TTCTTCTTTTTTACTTCTTTTTCCTTTTTGAGATGGAGTCTCACCCCGTCACCCAGGCTGGAGTACAGTG
```

13735.2

```
CCACTGCACTCCAGCCTGGGTGACGGAGTGAGACTCTGTCTCAAAAAAACAAACAAACAAACAAACAAAAA
ACTGAAAAGGAAATAGAGTTCCTCTTTCCTCATATATGAATATATTATTTCAACAGATTGTTGATCACCTACCA
TATGCTTGGTATTGTTCTAATTGCTGGGGATACAGCAAGAGGTTCTGCAGAACTTCATGGAGCATGAAAGTA
AATAAACAAAGTTAATTTCAAGGCCAGGCATGGTTGCTCACACCTTTAGTCCCAGCACTTTGGGAGGCTGA
GGCAGGTGGATCACTTGGGCCCAGGAGTTCAAGGCTGCAGTGAGCCAAGATTGTGCCACTACTCTCCAGG
CTGGGCAACAGAGCAAGACCCTGTCTCAGGGGGAACAAAAAGTTAATTTCAGATTTTGTTAAGTGCTGTAAA
GGAAGTAAATAGGTTGATATTCAAGAGAGCACCTGAAGGCCAGGCGTGGTGGCTCACGCCTGTGGTCTAA
CGCTTTGGGAAGCCCGAGCGGGCGGATCACAAGGTCAGGAGAATTTTGGCCAGGCATGGTG
```

13736.1

```
AGAATCCATTTATTGGGTTTTAAACTAGTTACACAACTGAAATCAGTTTGGCACTACTTTATACAGGGATTAC
GCCTGTGTATGCCGACACTTAAATACTGTACCAGGACCACTGCTGTGCTTAGGTCTGTATTCAGTCATTCAG
CATGTAGATACTAAAAATATACTGTAGTGTTCCTTTAAGGAAGACTGTACAGGGTGTGTTGCAAGATGACAT
TCACCAATTTGTGAATTATTTCAACCCAGAAGATACCTTTCACTCTATAAACTTGTCATAGGCAAACATGTGG
TGTTAGCATTGAGAGATGCACACAAAAATGTTACATAAAAGTTCAGACATTCTAATGATAAGTGAACTGAAAA
AAAAAAAAAACCCCACATCTCAATTTTTGTAACAAGATAAAGAAAATAATTTAAAAACACAAAAAATGGCATTCA
GTGGGTACAAAGCC
```

13737.1&2

```
CAAATATTTAATATAAATCTTTGAAACAAGTTCAGAKGAAATAAAAATCAAAGTTTGCAAAAACGTGAAGATTA
ACTTAATTGTCAAATATTCCTCATTGCCCCAAATCAGTATTTTTTTTATTTCTATGCAAAAGTATGCCTTCAAA
CTGCTTAAATGATATATGATATGATACACAAACCAGTTTTCAAATAGTAAAGCCAGTCATCTTGCAATTGTAA
GAAATAGGTAAAAGATTATAAGACACCTTACACACACACACACACACACACACACGTGTGCACcGCCAAT
GACAAAAAACAATTTGGCCTCTCCTAAAATAAGAACATGAAGACCCTTAATTGCTGCCAGGAGGGAACACTG
TGTCACCCCTCCCTACAATCCAGGTAGTTTCCTTTAATCCAATAGCAAATCTGGGCATATTTGAGAGGAGTG
ATTCTGACAGCCACSGTTGAAATCCTGTGGGGAACCATTCATGTCCACCCACTGGTGCCCTGAAAAAATGC
CAATAATTTTTCGCTCCCACTTCTGCTGCTGTCTCTTCCACATCCTCACATAGACCCCAGACCCGCTGGCCC
CTGGCTGGGCATCGCATTGCTGGTAGAGCAAGTCATAGGTCTCGTCTTTGACGTCACAGAAGCGATACACC
AAATTGCCTGGTCGGTCATTGTCATAACCAG
```

TTTGACTTTAGTAGGGGTCTGAACTATTTATTTTACTTTGCCMGTAATATTTARACCYTATATATCTTTCATTA
TGCCATCTTATCTTCTAATGBCAAGGGAACAGWTGCTAAMCTGGCTTCTGCATTWATCACATTAAAAATGGC
TTTCTTGGAAAATCTTCTTGATATGAATAAAGGATCTTTTAVAGCCATCATTTAAAGCMGGNTTCTCTCCAAC
ACGAGTCTGCTSASGGGGGGKGAGCTGTGAACTCTGGCTGAAGGCTTTCCCATACACACTGCAATGACMT
GGTTTCTGACCAGBGTGAGTTA

13738.2

AGAGAAGCCCCATAAATGCAATCAGTGTGGGAAGGCCTTCAGTCAGAGCTCAAGCCTTTTCCTCCATCATC
GGGTTCATACTGGAGAGAAACCCTATGTATGTAATGAATGCGGCAGAGCCTTTGGTTTTAACTCTCATCTTA
CTGAACACGTAAGGATTCACACAGGAGAAAAACCCTATGTTTGTAATGAGTGCGGCAAAGCCTTTCGTCGG
AGTTCCACTCTTGTTCAGCATCGAAGAGTTCACACTGGGGAGAAGCCCTACCAGTGCGTTGAATGTGGGAA
AGCTTTCAGCCAGAGCTCCCAGCTCACCCTACATCAGCCGAGTTCACACTGGAGAGAAGCCCTATGACTGT
GGTGACTGTGGGAAGGCCTTCAGCCGGAGGTCAACCCTCATTCAGCATCAGAAAGTTCACAGCGGAGAGA
CTCGTAAGTGCAGAAAACATGGTCCAGCCTTTGTTCATGGCTCCAGCCTCACAGCAGATGGACAGATTCCC
ACTGGAGAGAAGCACGGCAGAACCTTTAACCATGGTGCAAATCTCATTCTGCGCTGGACAGTTC

13739.1&2

GAGACAGGGTCTCACTTTGTCACCCAGGCTGGAATGCAGTGGTGCGATCTTACGTAGCTCACTGCAGCCCT
GACCTCCTGGACTCAAACAATTCTCCTGCCTCAGCCCTGCAAGTAGCTGGGACTGTGGGTGCATGCCACCA
TGCCTGGCTAACTTTTGTAGTTTTTGTAAAGATGGGGTTTTGCCATGTTGCACATGCTGGTCTTGAACTCCT
GAGCTCAAACGATCTGCCCACCTCGGCCTCCCAGAATGTTGGGATTACAGGGGTAAACCACCACGCCTGG
CCCCATTAGGGTATTCTTAGCATCCACTTGCTCACTGAGATTAATCATAAGAGATGATAAGCACTGGAAGAA
AAAAATTTTTACTAGGCTTTGGATATTTTTTTCCTTTTTCAGCTTTATACAGAGGATTGGATCTTTAGTTTTCCT
TTAACTGATAATAAAACATTGAAAGGAAATAAGTTTACCTGAGATTCACAGAGATAACCGGCATCACTCCCTT
GCTCAATTCCAGTCTTTACCACATCAATTATTTTCAGAGGTGCAGGATAAAGGCCTTTAGTCTGCTTTCGCA
CTTTTTCTTCCACTTTTTTGTAAACCTGTTGCCTGACAAATGGAATTGACAGCGTATGCCATGACTATTCCAT
TTGTCAGGCATACGCTGTCAATTTTTCCACCAATCCCTTGTCTCTCTTTGGAGAGATCTTCTTATCAGCTAGT
CCTTTGGCAAAAGTAATTGCAACTTCTTCTAGGTATTCTATTGTCCGTTCCACTGGTGGAACCCCTGGGACC
AGGACTAAAACCTCCAG

13741.1

ATCTCATATATATATTTCTTCCTGACTTTATTTGCTTGCTTCTGNCACGCATTTAAAATATCACAGAGACCAAA
ATAGAGCGGCTTTCTGGTGGAACGCATGGCAGTCACAGGACAAAATACAAAACTAGGGGGCTCTGTCTTCT
CATACATCATACAATTTTCAAGTATTTTTTTTATGTACAAAGAGCTACTCTATCTGAAAAAAAATTAAAAAATAA
ATGAGACAAGATAGTTTATGCATCCTAGGAAGAAAGAATGGGAAGAAAGAACGGGGCAGTTGGGTACAGAT
TCCTGTCCCCTGTTCCCAGGGACCACTACCTTCCTGCCACTGAGTTCCCCCACAGCCTCACCCATCATGTC
ACAGGGCAAGTGCCAGGGTAGGTGGGGACCAGTGGAGACAGGAACCAGCAACATACTTTGGCCTGGAAG
ATAAGGAGAAAGTCTCAGAAACACACTGGTGGGAAGCAATCCCACGGCCGTGCCCCANGAGCTTCCCAC
CTGCTGCTGGCTCCCTGGGTGGCTTTGGGAACAGCTTGGGCAGGCCCTTTTGGGTGGGGNCCAACTGGG
CCTTTGGGCCCGTGTGGAAAG

AAACATTGAGATGGAATGATAGGGTTTCCCAGAATCAGGTCCATATTTTAACTAAATGAAAATTATGATTTAT
AGCCTTCTCAAATACCTGCCATACTTGATATCTCAACCAGAGCTAATTTTACCTCTTTACAAATTAAATAAGC
AAGTAACTGGATCCACAATTTATAATACCTGTCAATTTTTTCTGTATTAAACCTCTATCATAGTTTAAGCCTAT
TAGGGTACTTAATCCTTACAAATAAACAGGTTTAAAATCACCTCAATAGGCAACTGCCCTTCTGGTTTTCTTC
TTTGACTAAACAATCTGAATGCTTAAGATTTTCCACTTTGGGTGCTAGCAGTACACAGTGTTACACTCTGTAT
TCCAGACTTCTTAAATTATAGAAAAAGGAATGTACACTTTTTGTATTCTTTCTGAGCAGGGCCGGGAGGCAA
CATCATCTACCATGGTAGGGACTTGTATGCATGGACTACTTTA

14351.1

ACTCTGTCGCCCAGGCTGGAGCCCABTGGMGCGATCTCGACTCCCTGCAAGCTMCGCCTCACAGGWTCA
TGCCATTCTCCTGCCTCAGCATCTGGAGTAGCTGGGACTACAGGCGCCAGCCACCATGCCCAGCTAATTTT
T

14351.2

ACCTTAAAGACATAGGAGAATTTATACTGGGAGAGAAAGCTTACAAATGTAAGGTTTCTGACAAGACTTGGG
AGTGATTCACACCTGGAACAACATACTGGACTTCACACTGGABAGAAACCTTACAAGTGTAATGAGTGTGGC
AAAGCCTTTGGCAAGCAGTCAACACTTATTCACCATCAGGCAATTCA

14354.2

AGTCAGGATCATGATGGCTCAGTTTCCCACAGCGATGAATGGAGGGCCAAATATGTGGGCTATTACATCTG
AAGAACGTACTAAGCATGATAAACAGTTTGATAACCTCAAACCTTCAGGAGGTTACATAACAGGTGATCAAG
CCCGTACTTTTTTCCTACAGTCAGGTCTGCCGGCCCCGGTTTTAGCTGAAATATGGGCCTTATCAGATCTGA
ACAAGGATGGGAAGATGGACCAGCAAGAGTTCTCTATAGCTATGAAACTCATCAAGTTAAAGTTGCAGGGC
CAACAGCTGCCTGTAGTCCTCCCTCCTATCATGAAACAACCCCCTATGTTCTCTCCACTAATCTCTGCTCGT
TTTGGGATGGGAAGCATGCCCAATCTGTCCATTCATCAGCCATTGCCTCCAGTTGCACCTATAGCAACACC
CTTGTCTTCTGCTACTTCAGGGACCAGTATTCCTCCCTAATGATGCCTGCT

14354.1

CTTTCGATTTCCTTCAATTTGTCACGTTTGATTTTATGAAGTTGTTCAAGGGCTAACTGCTGTGTATTATAGCT
TTCTCTGAGTTCCTTCAGCTGATTGTTAAATGAATCCATTTCTGAGAGCTTAGATGCAGTTTCTTTTTCAAGA
GCATCTAATTGTTCTTTAAGTCTTTGGCATAATTCTTCCTTTTCTGATGACTTTCTATGAAGTAAACTGATCCC
TGAATCAGGTGTGTTACTGAGCTGCATGTTTTTAATTCTTTCGTTTAATAGCTGCTTCTCAGGGACCAGATAG
ATAAGCTTATTTTGATATTCCTTAAGCTCTTGGTGAAGTTGTTCGATTTCCATAATTTCCAGGTCACACTGGT
TATCCCAAACTTCT

TGGAGGTGAAACGGAGGCAAGAAAGGGGGCTACCTCAGGAGCGAGGGACAAAGGGGGCGTGAGGCACC
TAGGCCGCGGCACCCCGGCGACAGGAAGCCGTCCTGAACCGGGCTACCGGGTAGGGGAAGGGCCCGCG
TAGTCCTCGCAGGGCCCCAGAGCTGGAGTCGGCTCCACAGCCCCGGGCCGTCGGCTTCTCACTTCCTGG
ACCTCCCCGGCGCCCGGGCCTGAGGACTGGCTCGGCGGAGGGAGAAGAGGAAACAGACTTGAGCAGCTC
CCCGTTGTCTCGCAACTCCACTGCCGAGGAACTCTCATTTCTTCCCTCGCTCCTTCACCCCCCACCTCATGT
AGAAAGGTGCTGAAGCGTCCGGAGGGAAGAAGAACCTGGGCTACCGTCCTGGCCTTCCCMCCCCCTTCC
CGGGGCGCTTTGGTGGGCGTGGAGTTGGGGTTGGGGGGGTGGGTGGGGGTTCTTTTTTGGAGTGCTGGG
GAACTTTTTTCCCTTCTTCAGGTCAGGGGAAAGGGAATGCCCAATTCAGAGAGACATGGGGGCAAGAAGGA
CGGGAGTGGAGGAGCTTCTGGAACTTTGCAGCCGTCATCGGGAGGCGGCAGCTCTAACAGCAGAGAGCG
TCACCGCTTGGTATCGAAGCACAAGCGGCATAAGTCCAAACACTCCAAAGACATGGGGTTGGTGACCCCC
GAAGCAGCATCCCTGGGCACAGTTATCAAACCTTTGGTGGAGTATGATGATATCAGCTCTGATTCCGACAC
CTTCTCCGATGACATGGCCTTCAAACTAGACCGAAGGGAGAACGACGAACGTCGTGGATCAGATCGGAGC
GACCGCCTGCACAAACATCGTCACCACCAGCACAGGCGTTCCCGGGACTTACTAAAAGCTAAACAGACCG

16432-1

GACATGTTTGCCTGCAGGGGACCAGAGACAATGGGATTAGCCAGTGCTCACTGTTCTTTATGCTTCCAGAG
AGGATGGGGACAGCTCTCAGGTCAGAATCCAGGCTGAGAAGGCCATGCTGGTTGGGGGCCCCCGGAAGC
ACGGTCCGGATCCTCCCTGGCATCAGCGTAGACCCGCTGCTCAGGCTTGGGGTACCAAACTCATGCTCTG
TACTGTTTTGGCCCCATGCGGTGAGAGGAAAACCTAGAAAAAGATTGGTCGTGCTAAGGAATCAGCTGCCC
CCTCATCCTCCGCATCCAATGCTGGTGACAACATATTCCCTCTCCCAGGACACAGACTCGGTGACTCCACA
CTGGGCTGAGTGGCCTCTGGAGGCTCGTGGCCTAAGGCAGGGCTCCGTAAGGCTGATCGGCTGAACTGG
GTGGGGTGAGGGTTTCTGACCCTTCGCTTCCCATCCCATAACCGCTGTCAATGAGCTCACACTGTGGTCA

16432-2

GATGGCATGGTCGTTGCTAATGTGCCTGCTGGGATGGAGCACTTCCTCCTGTGAGCCCAGGGGACCCGCC
TGTCCCTGGAGCTTGGGGCAAGGAGGGAAGAGTGATACCAGGAAGGTGGGGCTGCAGCCAGGGGCCAGA
GTCAGTTCAGGGAGTGGTCCTCGGCCCTCAAAGCTCCTCCGGGGACTGCTCAGGAGTGATGGTGCCCTGG
AGTTTGCCCCAACTTCCCTGGCCACCCTGGAAGGTGCCTGGCTGCTCCAGGCCTCTAGGCTGGGCTGATG
GGTTTCTCCAGGACACAAGTATCATTAAAGCCACCCTCTCCTCAGCTTGTCAGGCCGCACATGTGGGACAG
GCTGTGCTCACAACCCCCTCGCCTGCCCTGCCCTCCATCAGGAGGAGCCAGTGGAACCTTCGGAAAGCTC
CCAGCATCTCAGCAGCCCTCAAAAGTCGTCCTGGGGCAAGCTCTGGTTCTCCTGACTGGAGGTCATCTGG
GCTTGGCCTGCTCTCTCTCGC

17184.3

TAAAAAAGTGTAACAAAGGTTTATTTAGACTTTCTTCATGCCCCCAGATCCAGGATGTCTATGTAAACCGTTA
TCTTACAAAGAAAGCACAATATTTGGTATAAACTAAGTCAGTGACTTGCTTAACTGAAATAGCGTCCATCCAA
AAGTGGGTTTAAGGTAAAACTACCTGACGATATTGGCGGGGATCCTGCAGTTTGGACTGCTTGCCGGGTTT
GTCCAGGGTTCCGGGTCTGTTCTTGGCACTCATGGGGACAGGCATCCTGCTCGTCTGTGGGGCCCCGCTG
GAGCCCTTACGTGAAGCTGAAGGTATCGACCSTAGGGGGCTCTAGGGCAGTGGGACCTTCATCCGGAACT
AACAAGGGTCGGGGAGAGGCCTCTTGGGCTATGTGGG

CAAGCGTTCCTTTATGGATGTAAATTCAAACAGTCATGCTGAGCCATCCCGGGCTGACAGTCACGTTWAAG
ACACTAGGTCGGGCGCCACAGTGCCACCCAAGGAGAAGAAGAATTTGGAATTTTTCCATGAAGATGTACGG
AAATCTGATGTTGAATATGAAAATGGCCCCCAAATGGAATTCCAAAAGGTTACCACAGGGGCTGTAAGACCT
AGTGACCCTCCTAAGTGGGAAAGAGGAATGGAGAATAGTATTTCTGATGCATCAAGAACATCAGAATATAAA
ACTGAGATCATAATGAAGGAAAATTCCATATCCAATATGAGTTTACTCAGAGACAGTAGAAACTATTCCCAG
G

17185.1

TAGGAATAACAAATGTTTATTCAGAAATGGATAAGTAATACATAATCACCCTTCATCTCTTAATGCCCCTTCC
TCTCCTTCTGCACAGGAGACACAGATGGGTAACATAGAGGCATGGGAAGTGGAGGAGGACACAGGACTAG
CCCACCACCTTCTCTTCCCGGTCTCCCAAGATGACTGCTTATAGAGTGGAGGAGGCAAACAGGTCCCCTCA
ATGTACCAGATGGTCACCTATAGCACCAGCTCCAGATGGCCACGTGGTTGCAGCTGGACTCAATGAAACTC
TGTGACAACCAGAAGATACCTGCTTTGGGATGAGAGGGAGGATAAAGCCATGCAGGGAGGATATTTACCAT
CCCTACCCTAAGCACAGTGCAAGCAGTGAGCCCCCGGCTCCCAGTACCTGAAAAACCAAGGCCTACTGNC
TTTTGGATGCTCTCTTGGGCCACG

17188.2

AAGCCTCCTGCCCTGGAAATCTGGAGCCCCTTGGAGCTGAGCTGGACGGGGCAGGGAGGGGCTGAGAGG
CAAGACCGTCTCCCTCCTGCTGCAGCTGCTTCCCCAGCAGCCACTGCTGGGCACAGCAGAAACGCCAGCA
GAGAAAATGGGAGCCGAGAGTCCTTAGCCCTGGAGCTGAGGCTGCCTCTGGGCTGACCCGCTGGCTGTA
CGTGGCCAGAACTGGGGTTGGCATCTGGCATCCATTTGAGGCCAGGGTGGAGGAAAGGGAGGCCAACAG
AGGAAAACCTATTCCTGCTGTGACAACACAGCCCTTGTCCCACGCAGCCTAAGTGCAGGGAGCGTGATGAA
GTCAGGCAGCCAGTCGGGGAGGACGAGGTAACTCAGCAGCAATGTCACCTTGTAGCCTATGCGCTCAATG
GCCCGGAGGGGCAGCAACCCCCCGCACACGTCAGCCAACAGCAGTGCCTCTGCAGGCACCAAGAGAGCG
ATGATGGACTTGAGCGCCGTGTTC

17190.1

GTTTGGCAGAAGACATGTTTAATAACATTTTCATATTTAAAAAAATACAGCAACAATTCTCTATCTGTCCACCAT
CTTGCCTTGCCCTTCCTGGGGCTGAGGCAGACAAAGGAAAGGTAATGAGGTTAGGGCCCCCAGGCGGGCT
AAGTGCTATTGGCCTGCTCCTGCTCAAAGAGAGCCATAGCCAGCTGGGCACGGCCCCCTAGCCCCTCCAG
GTTGCTGAGGCGGCAGCGGTGGTAGAGTTCTTCACTGAGCCGTGGGCTGCAGTCTCGCAGGGAGAACTTC
TGCACCAGCCCTGGCTCTACGGCCCGAAAGAGGTGGAGCCCTGAGAACCGGAGGAAAACATCCATCACCT
CCAGCCCCTCCAGGGCTTCCTCCTCTTCCTGGCCTGCCAGTTCACCTGCCAGCCGGGCTCGGGCCGCCA
GGTAGTCAGCGTTGTAGAAGCAGCCCTCCGCAGAAGCCTGCCGGTCAAATCTCCCCGCTATAGGAGCCCC
CCGGGAGGGGTCAGCACC

```
CAAGTTGAACGTCAGGCTTGGCAGAGGTGGAGTGTAGATGAAAACAAAGGTGTGATTATGAAGAGGATGTG
AGTCCTTTGGGTGTAGGAGAGAAAGGCTGTTGAGCTTCTATTTCAAGATACTTTTACCTGTGCAAAAAGCAC
ATTTTCCACCTCCTTCTCATGGCATTTGTGTAAGGTGAGTATGATTCCTATTCCATCTGCATTTTAGAGGTGA
AGAATAACGTACAAGGGATTCAGTGATTAGCAAGGGACCCCTCACTAAGTGTTGATGGAGTTAGGACAGAG
CTCAGCTGTTTGAATCTCAGAGCCCAGGCAGCTGGAGCTGGGTAGGATCCTGGAGCTGGCACTAATGTGA
GGTGCATTCCCTCCAACCCAGGCTCAGATCCGGAACCTGACCGTGCTGACCCCCGAAGGGGAGGCAGGG
CTGAGCTGGCCCGTTGGGCTCCCTGCTCCTTTCACACCACACTCTCGCTTTGAGGTGCTGGGCTGGGACT
ACTTCACAGAGCAGC
```

17191.2&89.2

```
TGGCCTGGGCAGGATTGGGAGAGAGGTAGCTACCCGGATGCAGTCCTTTGGGATGAAGACTATAGGGTAT
GACCCCATCATTTCCCCAGAGGTCTCGGCCTCCTTTGGTGTTCAGCAGCTGCCCCTGGAGGAGATCTGGC
CTCTCTGTGATTTCATCACTGTGCACACTCCTCTCCTGCCCTCCACGACAGGCTTGCTGAATGACAACACCT
TTGCCCAGTGCAAGAAGGGGGTGCGTGTGGTGAACTGTGCCCGTGGAGGGATCGTGGACGAAGGCGCCC
TGCTCCGGGCCCTGCAGTCTGGCCAGTGTGCCGGGGCTGCACTGGACGTGTTTACGGAAGAGCCGCCAC
GGGACCGGGCCTTGGTGGACCATGAGAATGTCATCAGCTGTCCCCACCTGGGTGCCAGCACCAAGGAGG
CTCAGAGCCGCTGTGGGGAGGAAATTGCTGTTCAGTTCGTGGACATGGTGAAGGGGAAATCTCTCACGGG
GGTTGTGAATGCCCAGGCCCTT
```

Fig. 1S

```
AGCCAGATGGCTGAGAGCTGCAAGAAGAAGTCAGGATCATGATGGCTCAGTTTCCCACAGCGATGAATGG
AGGGCCAAATATGTGGGCTATTACATCTGAAGAACGTACTAAGCATGATAAACAGTTTGATAACCTCAAACC
TTCAGGAGGTTACATAACAGGTGATCAAGCCCGTACTTTTTTCCTACAGTCAGGTCTGCCGGCCCCGGTTTT
AGCTGAAATATGGGCCTTATCAGATCTGAACAAGGATGGGAAGATGGACCAGCAAGAGTTCTCTATAGCTA
TGAAACTCATCAAGTTAAAGTTGCAGGGCCAACAGCTGCCTGTAGTCCTCCCTCCTATCATGAAACAACCCC
CTATGTTCTCTCCACTAATCTCTGCTCGTTTTGGGATGGGAAGCATGCCCAATCTGTCCATTCATCAGCCAT
TGCCTCCAGTTGCACCTATAGCAACACCCTTGTCTTCTGCTACTTCAGGGACCAGTATTCCTCCCCTAATGA
TGCCTGCTCCCCTAGTGCCTTCTGTTAGTACATCCTCATTACCAAATGGAACTGCCAGTCTCATTCAGCCTT
TATCCATTCCTTATTCTTCTTCAACATTGCCTCATGCATCATCTTACAGCCTGATGATGGGAGGATTTGGTGG
TGCTAGTATCCAGAAGGCCCAGTCTCTGATTGATTTAGGATCTAGTAGCTCAACTTCCTCAACTGCTTCCCT
CTCAGGGAACTCACCTAAGACAGGGACCTCAGAGTGGGCAGTTCCTCAGCCTTCAAGATTAAAGTATCGGC
AAAAATTTAATAGTCTAGACAAAGGCATGAGCGGATACCTCTCAGGTTTTCAAGCTAGAAATGCCCTTCTTC
AGTCAAATCTCTCTCAAACTCAGCTAGCTACTATTTGGACTCTGGCTGACATCGATGGTGACGGACAGTTGA
AAGCTGAAGAATTTATTCTGGCGATGCACCTCACTGACATGGCCAAAGCTGGACAGCCACTACCACTGACG
TTGCCTCCCGAGCTTGTCCCTCCATCTTTCAGAGGGGGAAAGCAAGTTGATTCTGTTAATGGAACTCTGCCT
TCATATCAGAAAACACAAGAAGAAGAGCCTCAGAAGAAACTGCCAGTTACTTTTGAGGACAAACGGAAAGC
CAACTATGAACGAGGAAACATGGAGCTGGAGAAGCGACGCCAAGTGTTGATGGAGCAGCAGCAGAGGGA
GGCTGAACGCAAAGCCCAGAAAGAGAAGGAAGAGTGGGAGCGGAAACAGAGAGAACTGCAAGAGCAAGA
ATGGAAGAAGCAGCTGGAGTTGGAGAAACGCTTGGAGAAACAGAGAGAGCTGGAGAGACAGCGGGAGGA
AGAGAGGAGAAAGGAGATAGAAAGACGAGAGGCAGCAAAACAGGAGCTTGAGAGACAACGCCGTTTAGAA
TGGGAAAGACTCCGTCGGCAGGAGCTGCTCAGTCAGAAGACCAGGGAACAAGAAGACATTGTCAGGCTGA
GCTCCAGAAAGAAAAGTCTCCACCTGGAACTGGAAGCAGTGAATGGAAAACATCAGCAGATCTCAGGCAGA
CTACAAGATGTCCAAATCAGAAAGCAAACACAAAAGACTGAGCTAGAAGTTTTGGATAAACAGTGTGACCTG
GAAATTATGGAAATCAAACAACTTCAACAAGAGCTTAAGGAATATCAAAATAAGCTTATCTATCTGGTCCCTG
AGAAGCAGCTATTAAACGAAAGAATTAAAAACATGCAGCTCAGTAACACACCTGATTCAGGGATCAGTTTAC
TTCATAAAAAGTCATCAGAAAAGGAAGAATTATGCCAAAGACTTAAAGAACAATTAGATGCTCTTGAAAAAGA
AACTGCATCTAAGCTCTCAGAAATGGATTCATTTAACAATCAGCTGAAGGAACTCAGAGAAAGCTATAATAC
ACAGCAGTTAGCCCTTGAACAACTTCATAAAAATCAAACGTGACAAATTGAAGGAAATCGAAAGAAAAAGATT
AGAGCAAAAAAAAAAAAAA
```

Fig. 2A

```
ATGGCAGTGACATTCACCATCATGGGAACCACCTTCCCTTTTCTTCAGGATTCTCTGTAGTGGAAGAGAGCA
CCCAGTGTTGGGCTGAAAACATCTGAAAGTAGGGAGAAGAACCTAAAATAATCAGTATCTCAGAGGGCTCT
AAGGTGCCAAGAAGTCTCACTGGACATTTAAGTGCCAACAAAGGCATACTTTCGGAATCGCCAAGTCAAAA
CTTTCTAACTTCTGTCTCTCTCAGAGACAAGTGAGACTCAAGAGTCTACTGCTTTAGTGGCAACTACAGAAA
ACTGGTGTTACCCAGAAAAACAGGAGCAATTAGAAATGGTTCCAATATTTCAAAGCTCCGCAAACAGGATGT
GCTTTCCTTTGCCCATTTAGGGTTTCTTCTCTTTCCTTTCTCTTTATTAACCACTA
```

Fig. 2B

```
ATATCTAGAAGTCTGGAGTGAGCAAACAAGAGCAAGAAACAAAAAGAAGCCAAAAGCAGAAGGCTCCAATA
TGAACAAGATAAATCTATCTTCAAAGACATATTAGAAGTTGGGAAAATAATTCATGTGAACTAGACAAGTGTG
TTAAGAGTGATAAGTAAAATGCACGTGGAGACAAGTGCATCCCCAGATCTCAGGGACCTCCCCCTGCCTGT
CACCTGGGGAGTGAGAGGACAGGATAGTGCATGTTCTTTGTCTCTGAATTTTTAGTTATATGTGCTGTAATG
TTGCTCTGAGGAAGCCCCTGGAAAGTCTATCCCAACATATCCACATCTTATATTCCACAAATTAAGCTGTAG
TATGTACCCTAAGACGCTGCTAATTGACTGCCACTTCGCAACTCAGGGGCGGCTGCATTTTAGTAATGGGT
CAAATGATTCACTTTTTATGATGCTTCCAAAGGTGCCTTGGCTTCTCTTCCCAACTGACAAATGCCAAAGTTG
AGAAAAATGATCATAATTTTAGCATAAACAGAGCAGTCGGCGACACCGATTTTATAAATAAACTGAGCACCTT
CTTTTTAAACAAACAAATGCGGGTTTATTTCTCAGATGATGTTCATCCGTGAATGGTCCAGGGAAGGACCTT
TCACCTTGACTATATGGCATTATGTCATCACAAGCTCTGAGGCTTCTCCTTTCCATCCTGCGTGGACAGCTA
AGACCTCAGTTTTCAATAGCATCTAGAGCAGTGGGACTCAGCTGGGGTGATTTCGCCCCCCATCTCCGGGG
GAATGTCTGAAGACAATTTTGTTACCTCAATGAGGGAGTGGAGGAGGATACAGTGCTACTACCAACTAGTG
GATAAAGGCCAGGGATGCTGCTCAACCTCCTACCATGTACAGGACGTCTCCCCATTACAACTACCCAATCC
GAAGTGTCAACTGTGTCAGGACTAAGAAACCCTGGTTTTGAGTAGAAAAGGGCCTGGAAAGAGGGGAGCC
AACAAATCTGTCTGCTTCCTCACATTAGTCATTGGCAAATAAGCATTCTGTCTCTTTGGCTGCTGCCTCAGC
ACAGAGAGCCAGAACTCTATCGGGCACCAGGATAACATCTCTCAGTGAACAGAGTTGACAAGGCCTATGGG
AAATGCCTGATGGGATTATCTTCAGCTTGTTGAGCTTCTAAGTTTCTTTCCCTTCATTCTACCCTGCAAGCCA
AGTTCTGTAAGAGAAATGCCTGAGTTCTAGCTCAGGTTTTCTTACTCTGAATTTAGATCTCCAGACCCTTCCT
GGCCACAATTCAAATTAAGGCAACAAACATATACCTTCCATGAAGCACACACAGACTTTTGAAAGCAAGGAC
AATGACTGCTTGAATTGAGGCCTTGAGGAATGAAGCTTTGAAGGAAAAGAATACTTTGTTTCCAGCCCCCTT
CCCACACTCTTCATGTGTTAACCACTGCCTTCCTGGACCTTGGAGCCACGGTGACTGTATTACATGTTGTTA
TAGAAAACTGATTTTAGAGTTCTGATCGTTCAAGAGAATGATTAAATATACATTTCCTA
```

*Fig. 2C*

| Diff (Exp) | Probe1 | Exp | Probe2 | GEM Element | Plate/Well | Probe1 | S/B | A% | Probe2 | S/B | A% |
|---|---|---|---|---|---|---|---|---|---|---|---|
| +1.7 | 364A Ovary T (mets) | | 272A Dendritic cells | 4224O606 (420) | 421G0198 (C:11) | 2393 | 13.7 | 50 | 1430 | 2.0 | 50 |
| -1.1 | 335A Ovary N | | S7 Ovary N | 4222O626 (420) | 421G0196 (C:11) | 355 | 2.7 | 54 | 362 | 1.8 | 54 |
| +1.8 | 261A Ovary T | | S10 Skeletal muscle N | 4223O621 (420) | 421G0196 (C:11) | 1238 | 6.9 | 51 | 707 | 1.9 | 51 |
| -8.1 | 284A Ovary T | | S2 Pancreas N | 422N0629 (420) | 421G0196 (C:11) | 8590 | 44.0 | 62 | 1190 | 2.3 | 62 |
| -1.2 | 386A Ovary T | | S40 PBMC (activated) | 422I0605 (420) | 421G0196 (C:11) | 516 | 3.8 | 50 | 618 | 2.0 | 50 |
| +4.7 | 265A Ovary T | | CT5 Heart N | 422O0624 (420) | 421G0196 (C:11) | 2305 | 14.6 | 53 | 489 | 2.2 | 53 |
| -1.4 | S25 Ovary T | | CT4 Bone Marrow N | 422H0619 (420) | 421G0196 (C:11) | 531 | 3.5 | 53 | 743 | 2.0 | 53 |
| | 363A Ovary T (mets) | | I1 Colon N | 422B0609 (420) | 421G0196 (C:11) | 1842 | 10.6 | 39 | 671 | 2.0 | 39 |
| -1.9 | S22 Ovary T | | CT9 Kidney N | 4229O627 (420) | 421G0196 (C:11) | 453 | 3.3 | 68 | 657 | 3.2 | 68 |
| -3.2 | 9485 OT 5-P (SCID) | | 9485 OT 5-P (SCID) | 422Y0602 (420) | 421G0196 (C:11) | 1892 | 12.6 | 57 | 594 | 2.3 | 57 |
| +1.5 | 262A Ovary T | | 334A Large Intestine N | 422A0622 (420) | 421G0196 (C:11) | 1496 | 7.5 | 55 | 965 | 2.2 | 55 |
| -1.1 | S115 Ovary T (mets) | | CT10 Small Intestine N | 477C0604 (420) | 421G0196 (C:11) | 509 | 3.4 | 51 | 573 | 2.0 | 51 |
| +1.1 | 288A Ovary T | | CT12 Lung N | 422V0625 (420) | 421G0196 (C:11) | 700 | 4.5 | 54 | 651 | 2.1 | 54 |
| -2.1 | 201A Ovary T | | S6 Stomach N | 422V0620 (420) | 421G0196 (C:11) | 625 | 4.6 | 46 | 1335 | 3.6 | 46 |
| +7.8 | S23 Ovary T | | S56 Spinal Cord N | 422G0628 (420) | 421G0196 (C:11) | 3896 | 22.0 | 50 | 502 | 2.2 | 50 |
| +1.8 | 205A Ovary T | | 270A Liver N | 422Q0606 (420) | 421G0196 (C:11) | 2251 | 14.1 | 46 | 1256 | 2.0 | 46 |
| -1.9 | 9334 Ovary T (SCID) | | I2 Skin N | 422R0601 (420) | 421G0196 (C:11) | 552 | 3.4 | 72 | 1029 | 2.3 | 72 |
| +5.6 | 385A Ovary T | | S91 Fetal tissue | 422X0607 (420) | 421G0196 (C:11) | 8128 | 35.6 | 50 | 1449 | 2.0 | 50 |
| -3.5 | 263A Ovary T | | S73 Breast N | 422H0623 (420) | 421G0196 (C:11) | 439 | 3.2 | 61 | 1531 | 3.4 | 61 |
| -3.3 | 362A Ovary T | | CT19 Brain N | 422Q0610 (420) | 421G0196 (C:11) | 387 | 3.2 | 50 | 1278 | 2.1 | 50 |
| +4.8 | 266A Ovary T | | S27 Ovary N | 4225O603 (420) | 421G0196 (C:11) | 4242 | 22.0 | 58 | 883 | 2.0 | 58 |

Fig. 3

```
TCGAGCGGCCGCCCGGGCAGGTCCTTCAGACTTGGACTGTGTCACACTGCCAGGCTTCCAGGGCTCCAAC
TTGCAGACGGCCTGTTGTGGGACAGTCTCTGTAATCGCGAAAGCAACCATGGAAGACCTGGGGGAAAACA
CCATGGTTTTATCCACCCTGAGATCTTTGAACAACTTCATCTCTCAGCGTGCGGAGGGAGGCTCTGGACTG
GATATTTCTACCTCGGCCGCGACCACGCT
```

Fig. 4

```
TAGCGYGGTCGCGGCCGAGGYCTGCTTYTCTGTCCAGCCCAGGGCCTGTGGGGTCAGGGCGGTGGGTGC
AGATGGCATCCACTCCGGTGGCTTCCCCATCTTTCTCTGGCCTGAGCAAGGTCAGCCTGCAGCCAGAGTA
CAGAGGGCCAACACTGGTGTTCTTGAACAAGGGCCTTAGCAGGCCCTGAAGGRCCCTCTCTGTAGTGTTG
AACTTCCTGGAGCCAGGCCACATGTTCTCCTCATACCGCAGGYTAGYGATGGTGAAGTTGAGGGTGAAATA
GTATTMANGRAGATGGCTGGCARACCTGCCCGGGCGGCCGCTCSAAATCC
```

Fig. 5

```
AGCGTGGTCGCGGCCGAGGTGTCCTTCAGGGTCTGCTTATGCCCTTGTTCAAGAACACCAGTGTCAGCTCT
CTGTACTCTGGTTGCAGACTGACCTTGCTCAGGCCTGAGAAGGATGGGGCAGCCACCAGAGTGGATGCTG
TCTGCACCCATCGTCCTGACCCCAAAAGCCCTGGACTGGACAGAGAGCGGCTGTACTGGAAGCTGAGCCA
GCTGACCCACGGCATCACTGAGCTGGGCCCCTACACCCTGGACAGGGACAGTCTCTATGTCAATGGTTTC
ACCCATCGGAGCTCTGTACCCACCACCAGCACCGGGGTGGTCAGCGAGGAGCCATTCAACCTGCCCGGG
CGGCCGCTCGA
```

TTGGGGNTTTMGAGCGGCCGCCCGGGCAGGTACCGGGGTGGTCAGCGAGGAGCCATTCACACTGAACTT
CACCATCAACAACCTGCGGTATGAGGAGAACATGCAGCACCCTGGCTCCAGGAAGTTCAACACCACGGAG
AGGGTCCTTCAGGGCCTGCTCAGGTCCCTGTTCAAGAGCACCAGTGTTGGCCCTCTGTACTCTGGCTGCA
GACTGACTTTGCTCAGACTTGAGAAACATGGGGCAGCCACTGGAGTGGACGCCATCTGCACCCTCCGCCT
TGATCCCACTGGTCCTGGACTGGACAGAGAGCGGCTATACTGGGAGCTGAGCCAGTCCTCTGGCGGNGAC
NCCNCTT

Fig. 7B

AGCGTGGTCGCGGCCGAGGTCCAGTCGCAGCATGCTCTTTCTCCTGCCCACTGGCACAGTGAGGAAGATC
TCTGCTGTCAGTGAGAAGGCTGTCATCCACTGAGATGGCAGTCAAAAGTGCATTTAATACACCTAACGTATC
GAACATCATAGCTTGGCCCAGGTTATCTCATATGTGCTCAGAACACTTACAATAGCCTGCAGACCTGCCCG
GGCGGCCGCTCGA

*Fig. 7A and 7B*

```
TGTGGTGTTGAACTTCCTGGAGNCAGGGTGACCCATGTCCTCCCCATACTGCAGGTTGGTGATGGTGAAGT
TGAGGGTGAATGGTACCAGGAGAGGGCCAGCAGCCATAATTGTSGRGCKGSMGMSSGAGGMWGGWGTY
YCWGAGGTTCYRARRTCCACTGTGGAGGTCCCAGGAGTGCTGGTGGTGGGCACAGAGSTCYGATGGGTG
AAACCATTGACATAGAGACTGTTCCTGTCCAGGGTGTAGGGGCCCAGCTCTTYRATGYCATTGGYCAGTTK
GCTYAGCTCCCAGTACAGCCRCTCTCKGYYGMGWCCAGSGCTTTTGGGGTCAAGATGATGGATGCAGATG
GCATCCACTCCAGTGGCTGCTCCATCCTTCTCGGACCTGAGAGAGGTCAGTCTGCAGCCAGAGTACAGAG
GGCCAACACTGGTGTTCTTTGAATA
```

*Fig. 8*

```
TCGAGCGGCCGCCCGGGCAGGTCAGGAAGCACATTGGTCTTAGAGCCACTGCCTCCTGGATTCCACCTGT
GCTGCGGACATCTCCAGGGAGTGCAGAAGGGAAGCAGGTCAAACTGCTCAGATCAGTCAGACTGGCTGTT
CTCAGTTCTCACCTGAGCAAGGTCAGTCTGCAGCCAGAGTACAGAGGGCCAACACTGGTGTTCTTGAACAA
GGGCTTGAGCAGACCCTGCAGAACCCTCTTCCGTGGTGTTGAACTTCCTGGAAACCAGGGTGTTGCATGTT
TTTCCTCATAATGCAAGGTTGGTGATGG
```

*Fig. 9*

| Gene Name | Bal Exp | Probe 1 Name | P1 | P2 | Probe 2 Name | GEM ID | Probe1 Value | Probe2 Value | Probe1 B/B | Probe1 A% | Probe2 B/B | Probe2 A% |
|---|---|---|---|---|---|---|---|---|---|---|---|---|
| 42100188 (D3) | +7.0 | 205A Ovary T | | | 270A Liver N | 422Q0606 | 8620 | 1240 | 57.7 | 65 | 2.2 | 65 |
| 42100188 (D3) | +5.9 | S23 Ovary T | | | S56 Spinal Cord N | 422G0628 | 5894 | 1002 | 35.3 | 89 | 3.9 | 89 |
| 42100188 (D3) | +5.7 | 385A Ovary T | | | S91 Fetal tissue | 422X0607 | 12151 | 2121 | 54.3 | 73 | 2.8 | 73 |
| 42100188 (D3) | +5.1 | 426A Ovary T (met) | | | 415A Aorta N | 422X0611 | 7487 | 1480 | 53.0 | 73 | 9.7 | 73 |
| 42100188 (D3) | +3.5 | 263A Ovary T | | | S73 Breast N | 422I0623 | 7302 | 2116 | 39.2 | 84 | 4.5 | 84 |
| 42100188 (D3) | +3.3 | 383A Ovary T (met) | | | I1 Colon N | 422B0609 | 3714 | 1113 | 20.4 | 83 | 2.6 | 83 |
| 42100188 (D3) | +3.0 | 9334 Ovary T (SCID) | | | I2 Skin N | 422R0601 | 2435 | 814 | 12.1 | 75 | 2.1 | 75 |
| 42100188 (D3) | +2.6 | 384A Ovary T (met) | | | 272A Dendritic cell | 422240608 | 4578 | 1754 | 25.0 | 69 | 2.3 | 69 |
| 42100188 (D3) | +2.2 | 264A Ovary T | | | S2 Pancreas N | 422N0629 | 7904 | 3596 | 38.5 | 81 | 5.6 | 81 |
| 42100188 (D3) | +2.0 | 386A Ovary T | | | S40 PBMC (activa) | 422I0605 | 2191 | 1081 | 14.0 | 90 | 2.9 | 90 |
| 42100188 (D3) | +2.0 | S115 Ovary T (mets) | | | CT10 Small intestin | 422C0604 | 1979 | 971 | 10.4 | 80 | 2.7 | 80 |
| 42100188 (D3) | +2.0 | 265A Ovary T | | | CT5 Heart N | 422O0624 | 1911 | 964 | 13.9 | 93 | 3.4 | 93 |
| 42100188 (D3) | +2.0 | 335A Ovary T | | | S7 Ovary N | 422O0626 | 1666 | 817 | 9.8 | 100 | 3.0 | 100 |
| 42100188 (D3) | -1.9 | 428A Ovary T (met) | | | 243A Esophagus N | 422400612 | 1827 | 9480 | 13.4 | 97 | 9.5 | 97 |
| 42100188 (D3) | +1.6 | 261A Ovary T | | | S10 Skeletal muscl | 422350621 | 5914 | 3653 | 30.4 | 86 | 6.0 | 86 |
| 42100188 (D3) | +1.6 | 266A Ovary T | | | S27 Ovary N | 422SI603 | 2039 | 1274 | 11.9 | 50 | 2.6 | 50 |
| 42100188 (D3) | +1.6 | S22 Ovary T | | | CT9 Kidney N | 422H0627 | 1736 | 1072 | 11.0 | 92 | 4.0 | 92 |
| 42100188 (D3) | +1.4 | 9485 OT 1-P (SCID) | | | 9485 OT 5-P (SCID) | 422Y0602 | 4204 | 3074 | 23.0 | 93 | 7.7 | 93 |
| 42100188 (D3) | +1.4 | 262A Ovary T | | | 334A Large Intestin | 422A0622 | 3002 | 2101 | 16.6 | 89 | 4.0 | 89 |
| 42100188 (D3) | +1.3 | S25 Ovary T | | | CT4 Bone Marrow | 422H0619 | 1643 | 2084 | 9.6 | 90 | 3.1 | 90 |
| 42100188 (D3) | +1.2 | 429A Ovary T (met) | | | 364A Ovary N | 422I0614 | 2521 | 2084 | 22.0 | 65 | 23.9 | 65 |
| 42100188 (D3) | +1.2 | 382A Ovary T | | | CT19 Brain N | 422Q0610 | 2072 | 1663 | 10.9 | 88 | 2.3 | 88 |
| 42100188 (D3) | +1.2 | 288A Ovary T | | | CT12 Lung N | 422V0625 | 1840 | 1473 | 10.7 | 87 | 3.8 | 87 |
| 42100188 (D3) | +1.1 | 201A Ovary T | | | SG Stomach N | 422W0620 | 1329 | 1204 | 9.1 | 90 | 3.5 | 90 |

Fig. 10

| Gene Name | Bal Probe 1 Exp | Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421B0181 (C3) | +18.9 | 385A Ovary T | | | S91 Fetal tissue | 422X0607 | 26711 | 1424 | 103.3 | 54 | 2.0 | 54 |
| 421B0181 (C3) | +11.5 | S23 Ovary T | | | S56 Spinal Cord N | 422G0628 | 13559 | 1179 | 65.3 | 68 | 3.9 | 68 |
| 421B0181 (C3) | +11.1 | 426A Ovary T (mets) | | | 415A Aorta N | 422X0611 | 14125 | 1273 | 67.3 | 61 | 5.6 | 61 |
| 421B0181 (C3) | +10.8 | 205A Ovary T | | | 270A Liver N | 422Q0606 | 16121 | 1488 | 93.1 | 43 | 2.3 | 43 |
| 421B0181 (C3) | +5.1 | 263A Ovary T | | | S73 Breast N | 422H0623 | 11326 | 2235 | 58.2 | 68 | 4.4 | 68 |
| 421B0181 (C3) | +4.6 | 384A Ovary T (mets) | | | 272A Dendritic cells | 422O0608 | 6583 | 1424 | 24.5 | 40 | 2.1 | 40 |
| 421B0181 (C3) | +4.4 | 264A Ovary T | | | S2 Pancreas N | 422N0629 | 9865 | 2245 | 40.9 | 64 | 3.6 | 64 |
| 421B0181 (C3) | +4.4 | 429A Ovary T (mets) | | | 364A Ovary N | 422I0614 | 2803 | 638 | 22.6 | 60 | 7.4 | 60 |
| 421B0181 (C3) | +4.2 | 261A Ovary T | | | S10 Skeletal muscle N | 422300621 | 8271 | 1949 | 39.5 | 68 | 3.6 | 68 |
| 421B0181 (C3) | +3.8 | S115 Ovary T (mets) | | | CT10 Small Intestine N | 422C0604 | 2281 | 607 | 11.6 | 60 | 2.1 | 60 |
| 421B0181 (C3) | +2.5 | 265A Ovary T (mets) | | | CT5 Heart N | 422O0624 | 3192 | 1293 | 19.2 | 68 | 4.0 | 68 |
| 421B0181 (C3) | -2.3 | S22 Ovary T | | | CT9 Kidney N | 422X0627 | 565 | 1276 | 3.6 | 70 | 3.9 | 70 |
| 421B0181 (C3) | +2.2 | 266A Ovary T | | | S27 Ovary N | 422S0603 | 2774 | 1260 | 14.3 | 46 | 2.7 | 46 |
| 421B0181 (C3) | +2.1 | 9334 Ovary T (SCID) | | | I2 Skin N | 422R0601 | 1774 | 837 | 8.4 | 56 | 2.1 | 56 |
| 421B0181 (C3) | +1.9 | 9485 OT 1-P (SCID) | | | 9485 OT 5-P (SCID) | 422Y0602 | 6967 | 3726 | 41.5 | 70 | 9.2 | 70 |
| 421B0181 (C3) | +1.6 | 382A Ovary T | | | CT19 Brain N | 422Q0610 | 2313 | 1471 | 6.2 | 50 | 1.9 | 50 |
| 421B0181 (C3) | +1.6 | 288A Ovary T | | | CT12 Lung N | 422Y0625 | 1657 | 1054 | 9.7 | 69 | 2.9 | 69 |
| 421B0181 (C3) | -1.5 | S25 Ovary T | | | CT4 Bone Marrow N | 422H0619 | 848 | 1243 | 4.5 | 65 | 2.7 | 65 |
| 421B0181 (C3) | +1.4 | 262A Ovary T | | | 334A Large Intestine | 422A0622 | 3171 | 2214 | 16.8 | 69 | 3.8 | 69 |
| 421B0181 (C3) | +1.2 | 386A Ovary T | | | S40 PBMC (activated) | 422J0605 | 630 | 544 | 4.2 | 53 | 1.9 | 53 |
| 421B0181 (C3) | -1.2 | 335A Ovary T | | | S7 Ovary N | 422O0626 | 592 | 730 | 3.7 | 75 | 2.6 | 75 |
| 421B0181 (C3) | -1.0 | 201A Ovary T | | | S6 Stomach N | 422W0620 | 1197 | 1237 | 7.8 | 65 | 3.5 | 65 |
| 421B0181 (C3) | -1.0 | 428A Ovary T (mets) | | | 243A Esophagus N | 422J0612 | 783 | 797 | 4.5 | 95 | 2.4 | 95 |
| 421B0181 (C3) | -1.0 | 383A Ovary T (mets) | | | I1 Colon N | 422B0609 | 3470 | 862 | 18.9 | 24 | 1.7 | 24 |

Fig. 11

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 42110182 (H7) | +16.7 | 426A Ovary T (mets) | | | 415A Aorta N | 422X0611 | 7706 | 462 | 46.3 | 75 | 3.5 | 75 |
| 42110182 (H7) | +10.7 | 205A Ovary T | | | 270A Liver N | 422Q0606 | 10171 | 950 | 61.2 | 41 | 1.8 | 41 |
| 42110182 (H7) | +9.9 | 385A Ovary T | | | S91 Fetal tissue | 422X0607 | 14415 | 1459 | 69.1 | 48 | 2.2 | 48 |
| 42110182 (H7) | +8.8 | S23 Ovary T | | | S56 Spinal Cord N | 422G0628 | 7781 | 880 | 47.3 | 73 | 3.4 | 77 |
| 42110182 (H7) | +6.4 | 383A Ovary T (mets) | | | I1 Colon N | 422B0609 | 4807 | 748 | 27.6 | 47 | 2.2 | 47 |
| 42110182 (H7) | +5.1 | 263A Ovary T | | | S73 Breast N | 422H0623 | 9815 | 1909 | 57.1 | 74 | 4.2 | 74 |
| 42110182 (H7) | +4.9 | 429A Ovary T (mets) | | | 364A Ovary N | 422I0614 | 2661 | 543 | 20.3 | 61 | 6.7 | 61 |
| 42110182 (H7) | +3.5 | 264A Ovary T | | | S2 Pancreas N | 422N0629 | 7934 | 2274 | 38.8 | 71 | 3.9 | 71 |
| 42110182 (H7) | -2.9 | S25 Ovary T | | | CT4 Bone Marrow | 422H0619 | 480 | 1375 | 3.5 | 80 | 3.0 | 80 |
| 42110182 (H7) | +2.8 | 261A Ovary T | | | S10 Skeletal muscle | 422J0621 | 8993 | 3245 | 34.6 | 69 | 5.1 | 69 |
| 42110182 (H7) | +2.5 | S115 Ovary T (SCID) | | | CT10 Small intestine | 422C0604 | 1864 | 738 | 8.1 | 67 | 2.2 | 67 |
| 42110182 (H7) | +2.3 | 9334 Ovary T (SCID) | | | I2 Skin N | 422R0601 | 2552 | 1113 | 12.7 | 41 | 2.6 | 41 |
| 42110182 (H7) | -2.3 | S22 Ovary T | | | CT9 Kidney N | 422O0627 | 386 | 889 | 3.2 | 69 | 3.4 | 69 |
| 42110182 (H7) | +2.2 | 384A Ovary T (mets) | | | 272A Dendritic cell | 422J0608 | 3516 | 1867 | 18.7 | 55 | 2.2 | 55 |
| 42110182 (H7) | -2.2 | 382A Ovary T | | | CT19 Brain N | 422Q0610 | 608 | 1320 | 4.2 | 60 | 1.3 | 60 |
| 42110182 (H7) | +1.9 | 265A Ovary T | | | GT5 Heart N | 422O0624 | 2063 | 1080 | 13.6 | 87 | 3.5 | 87 |
| 42110182 (H7) | +1.8 | 266A Ovary T | | | S27 Ovary N | 422S0603 | 1550 | 847 | 7.0 | 58 | 2.1 | 58 |
| 42110182 (H7) | +1.5 | 262A Ovary T | | | 334A Large Intestine | 422A0622 | 2559 | 1651 | 13.2 | 73 | 3.2 | 73 |
| 42110182 (H7) | -1.4 | 386A Ovary T | | | S40 PBMC (activated) | 422J0605 | 534 | 738 | 3.9 | 62 | 2.2 | 62 |
| 42110182 (H7) | -1.3 | 287A Ovary T | | | CT12 Lung N | 422V0625 | 893 | 1120 | 5.3 | 66 | 3.1 | 66 |
| 42110182 (H7) | -1.3 | 315A Ovary T | | | S7 Ovary N | 422O0626 | 440 | 567 | 3.3 | 60 | 2.2 | 60 |
| 42110182 (H7) | +1.2 | 9485 OT 1-P (SCID) | | | 9485 OT 5-P (SCID) | 422Y0602 | 4188 | 3529 | 21.6 | 66 | 9.5 | 66 |
| 42110182 (H7) | +1.1 | 428A Ovary T (mets) | | | 243A Esophagus N | 422d0612 | 725 | 689 | 6.2 | 65 | 2.8 | 65 |
| 42110182 (H7) | -1.0 | 201A Ovary T | | | S6 Stomach N | 422W0620 | 1018 | 1018 | 2.4 | 62 | 3.2 | 62 |

*Fig. 12*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421V0189 [D1] | +33.2 | 426A Ovary T (met) | | | 415A Aorta N | 422X0611 | 8072 | 243 | 55.2 | 67 | 2.4 | 67 |
| 421V0189 [D1] | +13.7 | S23 Ovary T | | | S56 Spinal Cord N | 422O0628 | 7367 | 537 | 42.6 | 69 | 2.5 | 69 |
| 421V0189 [D1] | +12.6 | 429A Ovary T (met) | | | 364A Ovary N | 422I0614 | 2850 | 227 | 21.7 | 64 | 3.5 | 64 |
| 421V0189 [D1] | +8.0 | 385A Ovary T | | | S91 Fetal tissue | 422X0607 | 1171 | 1469 | 54.0 | 58 | 2.2 | 58 |
| 421V0189 [D1] | +7.3 | 263A Ovary T | | | S73 Breast N | 422H0623 | 6949 | 952 | 37.8 | 69 | 2.6 | 69 |
| 421V0189 [D1] | -5.8 | S25 Ovary T | | | CT4 Bone Marrow | 422H0619 | 208 | 1210 | 2.1 | 44 | 2.9 | 44 |
| 421V0189 [D1] | +5.0 | 205A Ovary T | | | 270A Liver N | 422Q0606 | 8676 | 1737 | 52.3 | 57 | 2.6 | 57 |
| 421V0189 [D1] | +4.5 | 383A Ovary T (met) | | | I1 Colon N | 422B0609 | 3149 | 707 | 17.4 | 57 | 2.0 | 57 |
| 421V0189 [D1] | +4.4 | 261A Ovary T | | | S10 Skeletal muscle | 422J0621 | 6332 | 1443 | 29.1 | 77 | 2.9 | 77 |
| 421V0189 [D1] | +4.2 | 264A Ovary T | | | S2 Pancreas N | 422N0629 | 7612 | 1809 | 38.1 | 79 | 3.3 | 79 |
| 421V0189 [D1] | -3.2 | 382A Ovary T | | | CT19 Brain N | 422Q0610 | 468 | 1508 | 3.4 | 60 | 2.3 | 60 |
| 421V0189 [D1] | +2.9 | 9334 Ovary T (SCID) | | | I2 Skin N | 422R0601 | 2500 | 860 | 12.3 | 51 | 2.1 | 51 |
| 421V0189 [D1] | +2.5 | S115 Ovary T (mets) | | | CT10 Small intestine | 422C0604 | 1424 | 569 | 6.7 | 61 | 2.1 | 61 |
| 421V0189 [D1] | +2.4 | 265A Ovary T | | | CT5 Heart N | 422O0624 | 1742 | 723 | 11.8 | 70 | 2.8 | 70 |
| 421V0189 [D1] | +2.3 | 384A Ovary T (met) | | | 272A Dendritic cell | 422I0608 | 3083 | 1342 | 17.0 | 62 | 2.0 | 62 |
| 421V0189 [D1] | +1.9 | 266A Ovary T | | | S27 Ovary N | 422I0603 | 1370 | 732 | 8.0 | 47 | 2.0 | 47 |
| 421V0189 [D1] | -1.9 | 386A Ovary T | | | S40 PBMC (activated) | 422I0605 | 307 | 580 | 2.6 | 41 | 2.0 | 41 |
| 421V0189 [D1] | +1.7 | 262A Ovary T | | | 344A Large Intestine | 422A0622 | 2097 | 1202 | 11.2 | 86 | 2.7 | 86 |
| 421V0189 [D1] | -1.3 | 335A Ovary T | | | S7 Ovary N | 422O0626 | 373 | 470 | 2.9 | 47 | 2.0 | 47 |
| 421V0189 [D1] | -1.1 | 288A Ovary T | | | CT12 Lung N | 422V0625 | 969 | 1094 | 5.6 | 72 | 2.9 | 72 |
| 421V0189 [D1] | +1.1 | 201A Ovary T | | | S6 Stomach N | 422W0620 | 750 | 672 | 5.6 | 62 | 2.4 | 62 |
| 421V0189 [D1] | +1.1 | 428A Ovary T (met) | | | 243A Esophagus N | 422A0612 | 498 | 446 | 4.2 | 73 | 2.1 | 73 |
| 421V0189 [D1] | -1.0 | 9485 OT 5-P (SCID) | | | 9485 OT 5-P (SCID) | 422Y0602 | 3117 | 3174 | 16.7 | 91 | 8.2 | 91 |
| 421V0189 [D1] | | S22 Ovary T | | | CT9 Kidney N | 422O0627 | 224 | 409 | 2.3 | 48 | 2.3 | 48 |

Fig. 13

| Gene Name | Bal Exp | Probe 1 Name | P1 | | P2 | Probe 2 Name | GEN ID | Probe1 Value | Probe2 Value | Probe1 S/B | Probe1 A% | Probe2 S/B | Probe2 A% |
|---|---|---|---|---|---|---|---|---|---|---|---|---|---|
| 421H0187 [E11] | +20.2 | 426A Ovary T (met) | | | | 415A Aorta N | 422X0611 | 5441 | 270 | 36.3 | 50 | 2.3 | 50 |
| 421H0187 [E11] | +10.0 | S23 Ovary T | | | | S56 Spinal Cord N | 422S0628 | 5318 | 533 | 27.1 | 56 | 2.3 | 56 |
| 421H0187 [E11] | +8.3 | 429A Ovary T (met) | | | | 361A Ovary N | 422J0614 | 1252 | 150 | 10.1 | 58 | 2.5 | 58 |
| 421H0187 [E11] | +5.7 | 385A Ovary T | | | | S91 Fetal tissue | 422X0607 | 9507 | 1668 | 35.8 | 45 | 2.1 | 45 |
| 421H0187 [E11] | +4.4 | 205A Ovary T | | | | 270A Liver N | 422Q0606 | 5456 | 1235 | 31.1 | 50 | 2.0 | 50 |
| 421H0187 [E11] | +4.2 | 265A Ovary T | | | | CT5 Heart N | 422Q0624 | 1834 | 438 | 11.9 | 48 | 2.0 | 48 |
| 421H0187 [E11] | -4.1 | 382A Ovary T | | | | CT19 Brain N | 422Q0610 | 309 | 1259 | 2.6 | 48 | 2.0 | 48 |
| 421H0187 [E11] | +3.6 | 261A Ovary T | | | | S10 Skeletal muscl | 422H0621 | 3733 | 1036 | 17.7 | 55 | 2.3 | 55 |
| 421H0187 [E11] | +3.4 | 263A Ovary T | | | | S73 Breast N | 422H0623 | 4163 | 1239 | 23.0 | 62 | 3.0 | 62 |
| 421H0187 [E11] | +2.5 | S115 Ovary T (met) | | | | CT10 Small intestin | 422C0604 | 1565 | 627 | 8.8 | 47 | 2.1 | 47 |
| 421H0187 [E11] | +2.1 | 264A Ovary T | | | | S2 Pancreas N | 422N0629 | 3455 | 1630 | 14.9 | 60 | 3.0 | 60 |
| 421H0187 [E11] | +2.1 | 384A Ovary T (met) | | | | 272A Dendritic cell | 422J0608 | 2667 | 1270 | 13.4 | 44 | 1.9 | 44 |
| 421H0187 [E11] | -2.1 | S22 Ovary T | | | | CT9 Kidney N | 4229J0627 | 291 | 605 | 2.4 | 51 | 2.5 | 51 |
| 421H0187 [E11] | -1.7 | 386A Ovary T | | | | S40 PBMC (activat | 422J0605 | 410 | 687 | 3.2 | 47 | 2.0 | 47 |
| 421H0187 [E11] | +1.6 | 9334 Ovary T (SCID) | | | | I2 Skin N | 422R0601 | 1622 | 984 | 7.9 | 44 | 2.2 | 44 |
| 421H0187 [E11] | +1.5 | 262A Ovary T | | | | 334A Large Intestin | 422A0622 | 1892 | 1245 | 10.1 | 50 | 2.6 | 50 |
| 421H0187 [E11] | -1.5 | 288A Ovary T | | | | CT12 Lung N | 422V0625 | 604 | 908 | 4.1 | 62 | 2.6 | 62 |
| 421H0187 [E11] | -1.4 | 428A Ovary T (met) | | | | 243A Esophagus N | 422Z0612 | 236 | 325 | 2.7 | 78 | 1.9 | 78 |
| 421H0187 [E11] | -1.3 | 335A Ovary T | | | | S7 Ovary N | 422Z0626 | 382 | 501 | 2.9 | 58 | 2.0 | 58 |
| 421H0187 [E11] | -1.2 | 201A Ovary T | | | | S6 Stomach N | 422W0620 | 558 | 677 | 4.2 | 58 | 2.3 | 58 |
| 421H0187 [E11] | +1.0 | 9485 OT 1-P (SCID) | | | | 9485 OT 5-P (SCID) | 422Y0602 | 2582 | 2493 | 15.1 | 57 | 6.3 | 57 |
| 421H0187 [E11] | | 383A Ovary T (met) | | | | 11 Colon N | 422B0609 | 2261 | 562 | 12.5 | 38 | 1.7 | 38 |
| 421H0187 [E11] | | 266A Ovary T | | | | S27 Ovary N | 422S0603 | 1739 | 965 | 9.7 | 36 | 2.2 | 36 |
| 421H0187 [E11] | | S25 Ovary T | | | | CT4 Bone Marrow | 422H0619 | 283 | 845 | 2.2 | 44 | 2.2 | 44 |

ACGGTTTCAATGGACACTTTTATTGTTTACTTAATGGATCATCAATTTTGTCTCACTACCTACAAATGGAATTT
CATCTTGTTTCCATGCTGAGTAGTGAAACAGTGACAAAGCTAATCATAATAACCTACATCAAAAGAGAACTAA
GCTAACACTGCTCACTTTCTTTTTAACAGGCAAAATATAAATATATGCACTCTAXAATGCACAATGGTTTAGT
CACTAAAAAATTCAAATGGGATCTTGAAGAATGTATGCAAATCCAGGGTGCAGTGAAGATGAGCTGAGATG
CTGTGCAACTGTTTAAGGGTTCCTGGCACTGCATCTCTTGGCCACTAGCTGAATCTTGACATGGAAGGTTTT
AGCTAATGCCAAGTGGAGATGCAGAAAATGCTAAGTTGACTTAGGGGCTGTGCACAGGAACTAAAAGGCAG
GAAAGTACTAAATATTGCTGAGAGCATCCACCCCAGGAAGGACTTTACCTTCCAGGAGCTCCAAACTGGCA
CCACCCCCAGTGCTCACATGGCTGACTTTATCCTCCGTGTTCCATTTGGCACAGCAAGTGGCAGTG 11721-2

AAGGCTGGTGGGTTTTTGATCCTGCTGGAGAACCTCCGCTTTCATGTGGAGGAAGAAGGGAAGGGAAAAG
ATGCTTCTGGGAACAAGGTTAAAGCCGAGCCAGCCAAAATAGAAGCTTTCCGAGCTTCACTTTCCAAGCTA
GGGGATGTCTATGTCAATGATGCTTTTGGCACTGCTCACAGAGCCCACAGCTCCATGGTAGGAGTCAATCT
GCCACAGAAGGCTGGTGGGTTTTTGATGAAGAAGGAGCTGAACTACTTTGCAAAGGCCTTGGAGAGCCCA
GAGCGACCCTTCCTGGCCATCCTGGGCGGAGCTAAAGTTGCAGACAAGATCCAGCTCATCAATAATATGCT
GGACAAAGTCAATGAGATGATTATTGGTGGTGGAATGGCTTTTACCTTCCTTAAGGTGCTCAACAACATGGA
GATTGGCACTTCTCTGTTTGATGAAGAGGGAGCCAAGATTGTCAAAGACCTAATGTCCAAAGCTGAGAAGA
ATGGTGTGAAGATTACCTTGCCTGTTGACTTTGTCACTGCTGACAAGTTTGATGA 11724-1

TTTGTTCCTTACATTTTTCTAAAGAGTTACTTAAATCAGTCAACTGGTCTTTGAGACTCTTAAGTTCTGATTCC
AACTTAGCTAATTCATTCTGAGAACTGTGGTATAGGTGGCGTGTCTCTTCTAGCTGGGACAAAAGTTCTTTG
TTTTCCCCCTGTAGAGTATCACAGACCTTCTGCTGAAGCTGGACCTCTGTCTGGGCCTTGGACTCCCAAAT
CTGCTTGTCATGTTCAAGCCTGGAAATGTTAATCTTTAATTCTTCCATATGGATGGACATCTGTCTAAGTTGA
TCCTTTAGAACACTGCAATTATCTTCTTTGAGTCTAATTTCTTCTTCTTTGCTTTGAATCGCATCACTAAACTT
CCTCTCCCATTTCTTAGCTTCATCTATCACCCTGTCACGATCATCCTGGAGGGAAGACATGCTCTTAGTAAA
GGCTGCAAGCTGGGTCACAGTACTGTCCAAGTTTTCCTGAAGTTGCTGAACTTCCTTGTCTTTCTTGTTCAA
AGTAACCTGAATCTCTCCAATTGTCTCTTCCAAGTGGACTTTTTCTCTGCGCAAAGCATCCAG 11724-2

TCATTGCCTGTGATGGCATCTGGAATGTGATGAGCAGCCAGGAAGTTGTAGATTTCATTCAATCAAAGGATT
CAGCATGTGGTGGAAGCTGTGAGGCAAGAGAAACAAGAACTGTATGGCAAGTTAAGAAGCACAGAGGCAA
ACAAGAAGGAGACAGAAAAGCAGTTGCAGGAAGCTGAGCAAGAAATGGAGGAAATGAAAGAAAAGATGAG
AAAGTTTGCTAAATCTAAACAGCAGAAAATCCTAGAGCTGGAAGAAGAGAATGACCGGCTTAGGGCAGAGG
TGCACCCTGCAGGAGATACAGCTAAAGAGTGTATGGAAACACTTCTTTCTTCCAATGCCAGCATGAAGGAA
GAACTTGAAAGGGTCAAAATGGAGTATGAAACCCTTTCTAAGAAGTTTCAGTCTTTAATGTCTGAGAAAGAC
TCTCTAAGTGAAGAGGTTCAAGATTTAAAGCATCAGATAGAAGGTAATGTATCTAAACAAGCTAACCTAGAG
GCCACCGAGAAACATGATAACCAAACGAATGTCACTGAAGAGGGAACACAGTCTATACCAGGT

AAGCCAATAATCACCATTTATTACTTAATATATGCCAACCACTGTACTTGGCAGTTCACAAATTCTCACCGTT
ACAACAACCCCATGAGGTATTTATTCCCATTCTATAGATAGGGAAACCACAGCTCAAGTAAGTTAGGAAACT
GAGCCAAGTATACACAGAATACGAAGTGGCAAAACTAGAAGGAAAGACTGACACTGCTATCTGCTGGCCTC
CAGTGTCCTGGCTCTTTTCACACGGGtCAATGTCTCCAGCGCTGCTGCTGCTGCTGCATTACCATGCCCTC
ATTGTTTTTCTTCCTCTGGTGTTCAACTGCATCCTTCAAAGAATCTAACTCATTCCAGAGACCACTTATTTCTT
TCTCTCTTTCTGAAATTACTTTTAATAATTCTTCATGAGGGGGAAAAGAAGATGCCTGTTGGTAGTTTTGTTG
TTTAAGCTGCTCAATTTGGGACTTAAACAATTTGTTTTCATCTTGTACATCCTGTAACAGCTGTGTTTTGCTA
GAAAGATCACTCTCCCTCTCTTTTAGCATGGCTTCTAACCTCTTCAATTCATTTTCCTTTTCTTTCAACACAAT
CTCAAGTTCTTCAAACTGTGATGCAGAAGAGGCCTCTTTCAAGTTATGTTGTGCTACTTCCTGAACATGTGC
TTTTAAAGATTCATTTTCTTCTTGAAGATCCTGTAACCACTTCCCTGTATTGGCTAGGTCTTTCTCTTTCTCTT
CCAAAACAGCCTTCATGGTATTCATCTGTTCCTCTTTTCCTTTTAATAAGTTCAGGAGCTTCAGAAC

11726-1&2

CAAGCTTTTTTTTTTTTTTTAAAAAGTGTTAGCATTAATGTTTTATTGTCACGCAGATGGCAACTGGGTTTATG
TCTTCATATTTTATATTTTTGTAAATTAAAAAAATTACAAGTTTTAAATAGCCAATGGCTGGTTATATTTTCAGA
AAACATGATTAGACTAATTCATTAATGGTGGCTTCAAGCTTTTCCTTATTGGCTCCAGAAAATTCACCCACCT
TTTGTCCCTTCTTAAAAAACTGGAATGTTGGCATGCATTTGACTTCACACTCTGAAGCAACATCCTGACAGTC
ATCCACATCTACTTCAAGGAATATCACGTTGGAATACTTTTCAGAGAGGGAATGAAAGAAAGGCTTGATCAT
TTTGCAAGGCCCACACCACGTGGCTGAGAAGTCAACTACTACAAGTTTATCACCTGCAGCGTCCAAGGCTT
CCTGAAAAGCAGTCTTGCTCTCGATCTGCTTCACCATCTTGGCTGCTGGAGTCTGACGAGCGGCTGTAAGG
ACCGATGGAAATGGATCCAAAGCACCAAACAGAGCTTCAAGACTCGCTGCTTGGCTTGAATTCGGATCCGA
TATCGCCATGGCCT

11727-1&2

AAGTGTTAGCATTAATGTTTTATTGTCACGCAGATGGCAACTGGGTTTATGTCTTCATATTTTATATTTTTGTA
AATTAAAAAAATTMCAAGTTTTAAATAGCCAATGGCTGGTTATATTTTCAGAAAACATGATTAGACTAATTCAT
TAATGGTGGCTTCAAGCTTTTCCTTATTGGCTCCAGAAAATTCACCCACCTTTTGTCCCTTCTTAAAAAACTG
GAATGTTGGCATGCATTTGACTTCACACTCTGAAGCAACATCCTGACAGTCATCCACATCTACTTCAAGGAA
TATCACGTTGGAATACTTTTCAGAGAGGGAATGAAAGAAAGGCTTGATCATTTTGCAAGGCCCACACCACGT
GGCTGAGAAGTCAACTACTACAAGTTTATCACCTGCAGCGTCCAAGGCTTCCTGAAAAGCAGTCTTGCTCT
CGATCTGCTTCACCATCTTGGCTGCTGGAGTCTGACGAGCGGCTGTAAGGACCGATGGAAATGGATCCAAA
GCACCAAACAGAGCTTCAAGACTCGCTGCTTGGCATGAATTCGGATCCGA

TACAAACTTTATTGAAACGCACACGCGCACACACACAAACACCCCTGTGGATAGGGAAAAGCACCTGGCCA
CAGGGTCCACTGAAACGGGGAGGGGATGGCAGCTTGTAATGTGGCTTTTGCCACAACCCCCTTCTGACAG
GGAAGGCCTTAGATTGAGGCCCCACCTCCCATGGTGATGGGGAGCTCAGAATGGGGTCCAGGGAGAATTT
GGTTAGGGGGAGGTGCTAGGGAGGCATGAGCAGAGGGCACCCTCCGAGTGGGGTCCCGAGGGCTGCAG
AGTCTTCAGTACTGTCCCTCACAGCAGCTGTCTCAAGGCTGGGTCCCTCAAAGGGGCGTCCCAGCGCGGG
GCCTCCCTGCGCAAACACTTGGTACCCCTGGCTGCGCAGCGGAAGCCAGCAGGACAGCAGTGGCGCCGA
TCAGCACAACAGACGCCCTGGCGGTAGGGACAGCAGGCCCAGCCCTGTCGGTTGTCTCGGCAGCAGGTC
TGGTTATCATGGCAGAAGTGTCCTTCCCACACTTCACGTCCTTCACACCCACGTGAXGGCTACXGGCCAGG
AAG

11728.2.40.19.19

CCCGTGGGTGCCATCCACGGAGTTGTTACCTGATCTTTGGAAGCAGGATCGCCCGTCTGCACTGCAGTGG
AAGCCCCGTGGGCAGCAGTGATGGCCATCCCCGCATGCCACGGCCTCTGGGAAGGGGCAGCAACTGGAA
GTCCCTGAGACGGTAAAGATGCAGGAGTGGCCGGCAGAGCAGTGGGCATCAACCTGGCAGGGGCCACCC
AGATGCCTGCTCAGTGTTGTGGGCCATTTGTCCAGAAGGGGACGGCAGCAGCTGTAGCTGGCTCCTCCGG
GGTCCAGGCAGCAGGCCACAGGGCAGAACTGACCATCTGGGCACCGCGTTCCAGCCACCAGCCCTGCTG
TTAAGGCCACCCAGCTCACCAGGGTCCACATGGTCTGCCTGCGTCCGACTCCGCGGTCCTTGGGCCCTGA
TGGTTCTACCTGCTGTGAGCTGCCCAGTGGGAAGTATGGCTGCTGCCAATGCCCAACGCCACCTGCTGCT
CCGATCACCTGCACTGCTGCCCCAAGACACTGTGTGTGACCTGATCCAGAGTAAGTGCCTCTCCAAGGAGA
ACG

11730-1

GAATCACCTTTCTGGTTTAGCTAGTACTTTGTACAGAACAATGAGGTTTCCCACAGCGGAGTCTCCCTGGGC
TCTGTTTGGCTCTCGGTAAGGCAGGCCTACACCTTTTCCTCTCCTCTATGGAGAGGGGAATATGCATTAAG
GTGAAAAGTCACCTTCCAAAAGTGAGAAAGGGATTCGATTGCTGCTTCAGGACTGTGGAATTATTTGGAATG
TTTTACAAATGGTTGCTACAAAACAACAAAAAAGGTAATTACAAAATGTGTACATCACAACATGCTTTTTAAA
GACATTATGCATTGTGCTCACATTCCCTTAAATGTTGTTTCCAAAGGTGCTCAGCCTCTAGCCCAGCTGGAT
TCTCCGGGAAGAGGCAGAGACAGTTTGGCGAAAAAGACACAGGGAAGGAGGGGGTGGTGAAAGGAGAAA
GCAGCCTTCCAGTTAAAGATCAGCCCTCAGTTAAAGGTCAGCTTCCCGCAXGCTGGCCTCAXGCGGAGTCT
GGGTCAGAGGGAGGAGCAGCAGCAGGGTGGGACTGGGGCGT

11730-2

AACCGGAGCGCGAGCAGTAGCTGGGTGGGCACCATGGCTGGGATCACCACCATCGAGGCGGTGAAGCGC
AAGATCCAGGTTCTGCAGCAGCAGGCAGATGATGCAGAGGAGCGAGCTGAGCGCCTCCAGCGAGAAGTT
GAGGGAGAAAGGCGGGCCCGGGAACAGGCTGAGGCTGAGGTGGCCTCCTTGAACCGTAGGATCCAGCTG
GTTGAAGAAGAGCTGGACCGTGCTCAGGAGCGCCTGGCCACTGCCCTGCAAAAGCTGGAAGAAGCTGAAA
AAGCTGCTGATGAGAGTGAGAGAGGTATGAAGGTTATTGAAAACCGGGCCTTAAAAGATGAAGAAAAGATG
GAACTCCAGGAAATCCAACTCAAAGAAGCTAAGCACATTGCAGAAGAGGCAGATAGGAAGTATGAAGAGGT
GGCTCGTAAGTTGGTGATCATTGAAGGAGACTTGGAACGCACAGAGGAACGAGCTGAGCTGGCAGAGTCC
CGTTGCCGAGAGATGGATGAGCAGATTAGACTGATGGACCAGAACCTGAAGTGTCTGAGTGC

*Fig. 15C*

11732.1contig

GAGAACTTGGCCTTTATTGTGGGCCCAGGAGGGCACAAAGGTCAGGAGGCCCAAGGGAGGGATCTGGTTT
TCTGGATAGCCAGGTCATAGCATGGGTATCAGTAGGAATCCGCTGTAGCTGCACAGGCCTCACTTGCTGCA
GTTCCGGGGAGAACACCTGCACTGCATGGCGTTGATGACCTCGTGGTACACGACAGAGCCATTGGTGCAG
TGCAAGGGCACGCGCATGGGCTCCGTCCTCGAGGGCAGGCAGCAGGAGCATTGCTCCTGCACATCCTCG
ATGTCAATGGAGTACACAGCTTTGCTGGCACACTTTCCCTGGCAGTAATGAATGTCCACTTCCTCTTGGGAC
TTACAATCTCCCACTTTGATGTACTGCACCTTGGCTGTGATGTCTTTGCAATCAGGCTCCTCACATGTGTCA
CAGCAGGTGCCTGGAATTTTCACGATTTTGCCTCCTTCAGCCAGACACTTGTGTTCATCAAATGGTGGGCA
GCCCGTGACCCTCTTCTCCCAGATGTACTCTCCTCT

11732.2contig

GCCTGGACCTTGCCGGATCAGTGCCACACAGTGACTTGCTTGGCAAATGGCCAGACCTTGCTGCAGAGTC
ATCGTGTCAATTGTGACCATGGACCCCGGCCTTCATGTGCCAACAGCCAGTCTCCTGTTCGGGTGGAGGA
GACGTGTGGCTGCCGCTGGACCTGCCCTTGTGTGTGCACGGGCAGTTCCACTCGGCACATCGTCACCTTC
GATGGGCAGAATTTCAAGCTTACTGGTAGCTGCTCCTATGTCATCTTTCAAAACAAGGAGCAGGACCTGGA
AGTGCTCCTCCACAATGGGGCCTGCAGCCCCGGGGCAAAACAAGCCTGCATGAAGTCCATTGAGATTAAG
CATGCTGGCGTCTCTGCTGAGCTGCACAGTAACATGGAGATGGCAGTGGATGGGAGACTGGTCCTTGCCC
CGTACGTTGGTGAAAACATGGAAGTCAGCATCTACGGCGCTATCATGTATGAAGTCAGGTTTACCCATCTTG
GCCACATCCTCACATACACCGCCXCAAAACAACGAGTT

11735-1-2

AGATCAACCTCTGCTGGTCAGGAGGAATGCCTTCCTTGTCTTGGATCTTTGCTTTGACGTTCTCGATAGTRW
CAaCTKKRYTSRAMSKMAAGKGYRATGRWMTTKSYWGWRASYKTMWWMRSGRARAYTTaGaCAYCCCMC
CTCWgAGaCGSAGKACCARGTGCAgAgGTGGACTCTTTCTGGATGTTGTAGTCAGACAGGGTGCGTCCATC
TTCCAGCTGTTTCCCAGCAAAGATCAACCTCTGCTGATCAGGAGGGATGCCTTCCTTATCTTGGATCTTTGC
CTTGACATTCTCGATGGTGTCACTGGGCTCCACCTCGAGGGTGATGGTCTTACCAGTCAGGGTCTTCACGA
AGATYTGCATCCCACCTCTGAGACGGAGCACCAGGTGCAGGGTRGACTCTTTCTGGATGTTGTAGTCAGAC
AGGGTGCGYCCATCTTCCAGCTGcTTTCCSaGCAAAGATCAACCTCTGCTGGTCAGGAGGRATGCCTTCCT
TGTCYTGGATCTTTGCYTTGACRTTCTCRATGGTGTCACTCGGCTCCACTTCGAGAGTGATGGTCTTACCAG
TCAGGGTCTTCACGAAGATCTGCATCCCACCTCTAA

11740.2.contig

AAGTCACAAACAGACAAAGATTATTACCAGCTGCAAGCTATATTAGAAGCTGAACGAAGAGACAGAGGTCAT
GATTCTGAGATGATTGGAGACCTTCAAGCTCGAATTACATCTTTACAAGAGGAGGTGAAGCATCTCAAACAT
AATCTCGAAAAAGTGGAAGGAGAAAGAAAAGAGGCTCAAGACATGCTTAATCACTCAGAAAAGGAAAAGAA
TAATTTAGAGATAGATTTAAACTACAAACTTAAATCATTACAACAACGGTTAGAACAAGAGGTAAATGAACAC
AAAGTAACCAAAGCTCGTTTAACTGACAAACATCAATCTATTGAAGAGGCAAAGTCTGTGGCAATGTGTGAG
ATGGAAAAAAAGCTGAAAGAAGAAAGAGAAGCTCGAGAGAAGGCTGAAAATCGGGTTGTTCAGATTGAGAA
ACAGTGTTCCATGCTAGACGTTGATCTGAAGCAATCTCAGCAGAAACTAGAACATTTGACTGGAAATAAAGA
AAGGATGGAGGATGAAGTTAAGAATCTA

*Fig. 15D*

11765.2&64.2.contig

CGCCTCCACCATGTCCATCAGGGTGACCCAGAAGTCCTACAAGGTGTCCACCTCTGGCCCCCGGGCCTTC
AGCAGCCGCTCCTACACGAGTGGGCCCGGTTCCCGCATCAGCTCCTCGAGCTTCTCCCGAGTGGGCAGCA
GCAACTTTCGCGGTGGCCTGGGCGGCGGCTATGGTGGGGCCAGCGGCATGGGAGGCATCACCGCAGTTA
CGGTCAACCAGAGCCTGCTGAGCCCCCTTGTCCTGGAGGTGGACCCCAACATCCAGGCCGTGCGCACCC
AGGAGAAGGAGCAGATCAAGACCCTCAACAACAAGTTTGCCTCCTTCATAGACAAGGTACGGTTCCTGGAG
CAGCAGAACAAGATGCTGGAGACCAAGTGGAGCCTCCTGCAGCAGCAGAAGACGGCTCGAAGCAACATGG
ACAACATGTTCGAGAGCTACATCAACARCCTTAGGCGGCAGCTGGAGACTCTGGGCCAGGAGAAGCTGAA
GCTGGAGGCGGAGCTTGGCAACATGCAGGGGCTGGTGGAGGACTTCAAGAACAAGTATGAGGATGAGATC
AATAAGCGTACAGAGATGGAGAACGAATTTGTCCTCATCAAGAAGGATGTGGATGAAGCTTACATGAACAA
GGTAGAGCTGGAGTCTCGCCTGGAAGGGCTGACCGACGAGATCAACTTCCTCAGGCAGCTGTATGAAGAG
GAGATCCGGGAGCTGCAGTCCCAGATCTCGGACACATCTGTGGTGCTGTCCATGGACAACAGCCGCTCCC
TGGACATGGACAGCATCATTGCTGAGGTCAAGGCACAGTACGAGGATATTGCCAACCGCAGCCGGGCTGA
GGCTGAGAGCATGTACCAGGTCAAGTATGAGGAGCTGCAGAGCCTGGCTGGGAAGCACGGGGATGACCT
GCGGCGCACAAAGACTGAGATCTCTGAGATGAACCCGGAACATCAGCCCGGCTXCAGGCTGAGATTGAGG
GCCTCAAAGGCCAGAXGGCTTXCCTGGAXGXCCGCCAT

11767.2.contig

CCCGGAGCCAGCCAACGAGCGGAAAATGGCAGACAATTTTTCGCTCCATGATGCGTTATCTGGGTCTGGAA
ACCCAAACCCTCAAGGATGGCCTGGCGCATGGGGGAACCAGCCTGCTGGGGCAGGGGGCTACCCAGGG
GCTTCCTATCCTGGGGCCTACCCCGGGCAGGCACCCCCAGGGGCTTATCCTGGACAGGCACCTCCAGGC
GCCTACCCTGGAGCACCTGGAGCTTATCCCGGAGCACCTGCACCTGGAGTCTACCCAGGGCCACCCAGC
GGCCCTGGGGCCTACCCATCTTCTGGACAGCCAAGTGCCACCGGAGCCTACCCTGCCACTGGCCCCTATG
GCGCCCCTGCTGGGCCACTGATTGTGCCTTATAACCTGCCTTTGCCTGGGGGAGTGGTGCCTCGCATGCT
GATAACAATTCTGGGCACGGTGAAGCCCAATGCAAACAGAATTGCTTTAGATTTCCAAAGAGGGAATGATGT
TGCCTTCCACTTTAACCCACGCTTCAATGAGAACAACAGGAGAGTCATTGGTTGCAATACAAAGCTGGATAA

11768-1&2

GGGAATGCAACAACTTTATTGAAAGGAAAGTGCAATGAAATTTGTTGAAACCTTAAAAGGGGAAACTTAGAC
ACCCCCCCTCRAgCGMAGkACCARGTGCARAgGTGGACTCTTTCTGGATGTTGTAGTCAGACAGGGTRCG
WCCATCTTCCAGCTGTTTYCCRGCAAAGATCAACCTCTGCTGATCAGGAGGRATGCCTTCCTTATCTTGGA
TCTTTGCCTTGACATTCTCGATGGTGTCACTGGGCTCCACCTCGAGGGTGATGGTCTTACCAGTCAGGGTC
TTCACGAAGATYTGCATCCCACCTCTGAGACGGAGCACCAGGTGCAGGGTRGACTCTTTCTGGATGTTGTA
GTCAGACAGGGTGCGYCCATCTTCCAGCTGcTTTCCSaGCAAAGATCAACCTCTGCTGGTCAGGAGGRATG
CCTTCCTTGTCYTGGATCTTTGCYTTGACRTTCTCAATGGTGTCACTCGGCTCCACTTCGAGAGTGATGGTC
TTACCAGTCAGGGTCTTCACGAAGATCTGCATCCCACCTCTAAGACGGAGCACCAGGTGCAGGGTGGACT
CTTTCTGGATGgTTGTAGTCAGACAGGGTGCGTCCATCTTCCAGCTGTTTCCCAGCAAAGATCAACCT

AGGTTGATCTTTGCTGGGAAACAGCTGGAAGATGGACGCACCCTGTCTGACTACAAcCATCCAGAAAGAGT
CCACCCTGCACCTGGTGCTCCGTCTTAGAGGTGGGATGCAGATCTTCGTGAAGACCCTGACTGGTAAGAC
CATCACTCTCGAAGTGGAGCCGAGTGACACCATTGAGAAYGTCAARGCAAAGATCCARGACAAGGAAGGC
ATYCCTCCTGACCAGCAGAGGTTGATCTTTGCtSGGAAAgCAGCTGGAAGATGGRCGCACCCTGTCTGACTA
CAACATCCAGAAAGAGTCYACCCTGCACCTGGTGCTCCGTCTCAGAGGTGGGATGCARATCTTCGTGAAGA
CCCTGACTGGTAAGACCATCACCCTCGAGGTGGAGCCCAGTGACACCATCGAGAATGTCAAGGCAAAGAT
CCAAGATAAGGAAGGCATCCCTCCTGATCAGCAGAGGTTGATCTTTGCTGGGAAACAGCTGGAAGATGGAC
GCACCCTGTCTGACTACAACATCCAGAAAGAGTCCACcTYTGCACYTGGTMCTBCGtCTYaGAGGKGGGRTG
caaaTCTWMGTKWagaCaCtCaCTKKYAAGRYYaTCAMCMWtgAKKTCgAKYSCASTKWCaCTWTCRAKAAMGT
YRWWGCAWagaTCCMAGACAAGGAAGGCATTCCTCCTGACCAGCAGAGGTTGATCT

11769.1.contig

ATGGAGTCTCACTCTGTCGACCAGGCTGGAGCGCTGTGGTGCGATATCGGCTCACTGCAGTCTCCACTTC
CTGGGTTCAAGCGATCCTCCTGCCTCAGCCTCCCGAGTAGCTGGGACTACAGGCAGGCGTCACCATAATTT
TTGTATTTTTAGTAGAGACATGGTTTCGCCATGTTGGCTGGGCTGGTCTCGAACTCCTGACCTCAAGTGATC
TGTCCTGGCCTCCCAAAGTGTTGGGATTACAGGCGAAAGCCAACGCTCCCGGCCAGGGAACAACTTTAGA
ATGAAGGAAATATGCAAAAGAACATCACATCAAGGATCAATTAATTACCATCTATTAATTACTATATGTGGGT
AATTATGACTATTTCCCAAGCATTCTACGTTGACTGCTTGAGAAGATGTTTGTCCTGCATGGTGGAGAGTGG
AGAAGGGCCAGGATTCTTAGGTT

11769.2.contig

AGCGCGGTCTTCCGGCGCGAGAAAGCTGAAGGTGATGTGGCCGCCCTCAACCGACGCATCCAGCTCGTT
GAGGAGGAGTTGGACAGGGCTCAGGAACGACTGGCCACGGCCCTGCAGAAGCTGGAGGAGGCAGAAAAA
GCTGCAGATGAGAGTGAGAGAGGAATGAAGGTGATAGAAAACCGGGCCATGAAGGATGAGGAGAAGATGG
AGATTCAGGAGATGCAGCTCAAAGAGGCCAAGCACATTGCGGAAGAGGCTGACCGCAAATACGAGGAGGT
AGCTCGTAAGCTGGTCATCCTGGAGGGTGAGCTGGAGAGGGCAGAGGAGCGTGCGGAGGTGTCTGAACT
AAAATGTGGTGACCTGGAAGAAGAACTCAAGAATGTTACTAACAATCTGAAATCTCTGGAGGCTGCATCTGA
AAAGTATTCTGAAAAGGAGGACAAATATGAAGAAGAAATTAAACTTCTGTCTGACAAACTGAAAGAGGCTGA
GACCCGTGCTGAATTTGCAGAGAGAACGGTTGCAAAACTGGAAAAGACAATTGATGACCTGGAAGAGAAAC
TTGCCCAGC

11770.1.contig

GTGCACAGGTCCCATTTATTGTAGAAAATAATAATAATTACAGTGATGAATAGCTCTTCTTAAATTACAAAAC
AGAAACCACAAAGAAGGAAGAGGAAAAACCCCAGGACTTCCAAGGGTGAAGCTGTCCCCTCCTCCCTGCC
ACCCTCCCAGGCTCATTAGTGTCCTTGGAAGGGGCAGAGGACTCAGAGGGGATCAGTCTCCAGGGGCCCT
GGGCTGAAGCGGGTGAGGCAGAGAGTCCTGAGGCCACAGAGCTGGGCAACCTGAGCCGCCTCTCTGGCC
CCCTCCCCCACCACTGCCCAAACCTGTTTACAGCACCTTCGCCCCTCCCCTCTAAACCCGTCCATCCACTC
TGCACTTCCCAGGCAGGTGGGTGGGCCAGGCCTCAGCCATACTCCTGGGCGCGGGTTTCGGTGAGCAAG
GCACAGTCCCAGAGGTGATATCAAGGCCT

*Fig. 15F*

11770.2.contig

GCAAGGAACTGGTCTGCTCACACTTGCTGGCTTGCGCATCAGGACTGGCTTTATCTCCTGACTCACGGTGC
AAAGGTGCACTCTGCGAACGTTAAGTCCGTCCCCAGCGCTTGGAATCCTACGGCCCCCACAGCCGGATCC
CCTCAGCCTTCCAGGTCCTCAACTCCCGTGGACGCTGAACAATGGCCTCCATGGGGCTACAGGTAATGGG
CATCGCGCTGGCCGTCCTGGGCTGGCTGGCCGTCATGCTGTGCTGCGCGCTGCCCATGTGGCGCGTGAC
GGCCTTCATCGGCAGCAACATTGTCACCTCGCAGACCATCTGGGAGGGCCTATGGATGAACTGCGTGGTG
CAGAGCACCGGCCAGATGCAGTGCAAGGTGTACGACTCGCTGCTGGCACTGCCGCAGGACCTGCAGGCG
GCCCGCGCCCTCGTCATCATCA

11773.1.contig

TGCAAAAGGGACACAGGGGTTCAAAAATAAAAATTTCTCTTCCCCCTCCCCAAACCTGTACCCCAGCTCCC
CGACCACAACCCCCTTCCTCCCCCGGGGAAAGCAAGAAGGAGCAGGTGTGGCATCTGCAGCTGGGAAGA
GAGAGGCCGGGGAGGTGCCGAGCTCGGTGCTGGTCTCTTTCCAAATATAAATACXTGTGTCAGAACTGGA
AAATCCTCCAGCACCCACCACCCAAGCACTCTCCGTTTTCTGCCGGTGTTTGGAGAGGGGCGGGGGGCAG
GGGCGCCAGGCACCGGCTGGCTGCGGTCTACTGCATCCGCTGGGTGTGCACCCCGCGAGCCTCCTGCTG
CTCATTGTAGAAGAGATGACACTCGGGGTCCCCCCGGATGGTGGGGGCTCCCTGGATCAGCTTCCCGGTG
TTGGGGTTCACACACCAGCACTCCCCACGCTGCCCGTTCAGAGACATCTTGCACTGTTTGAGGTTGTACAG
GCCATGCTTGTCACAGTTG

11778.1.contig

GGGTTGGAGGGACTGGTTCTTTATTTCAAAAAGACACTTGTCAATATTCAGTATCAAAACAGTTGCACTATTG
ATTTCTCTTTCTCCCAATCGGCCCCAAAGAGACCACATAAAAGGAGAGTACATTTTAAGCCAATAAGCTGCA
GGATGTACACCTAACAGACCTCCTAGAAACCTTACCAGAAAATGGGGACTGGGTAGGGAAGGAAACTTAAA
AGATCAACAAACTGCCAGCCCACGGACTGCAGAGGCTGTCACAGCCAGATGGGGTGGCCAGGGTGCCAC
AAACCCAAAGCAAAGTTTCAAAATAATATAAAATTTAAAAAGTTTTGTACATAAGCTATTCAAGATTTCTCCAG
CACTGACTGATACAAAGCACAATTGAGATGGCACTTCTAGAGACAGCAGCTTCAAACCCAGAAAAGGGTGA
TGAGATGAGTTTCACATGGCTAAATCAGTGGCAAAAACACAGTCTTCTTTCTTTCTTTCTTTCAAGGAGGCA
GGAAAGCAATTAAGTGGTCACCTCAACATAAGGGGGACATGATCCATTCTGTAAGCAGTTGTGAAGGGG

11778-2&30-2

CAGGAACCGGAGCGCGAGCAGTAGCTGGGTGGGCACCATGGCTGGGATCACCACCATCGAGGCGGTGAA
GCGCAAGATCCAGGTTCTGCAGCAGCAGGCAGATGATGCAGAGGAGCGAGCTGAGCGCCTCCAGCGAGA
AGTTGAGGGAGAAAGGCGGGCCCGGGAACAGGCTGAGGCTGAGGTGGCCTCCTTGAACCGTAGGATCCA
GCTGGTTGAAGAAGAGCTGGACCGTGCTCAGGAGCGCCTGGCCACTGCCCTGCAAAAGCTGGAAGAAGCT
GAAAAAGCTGCTGATGAGAGTGAGAGAGGTATGAAGGTTATTGAAAACCGGGCCTTAAAAGATGAAGAAAA
GATGGAACTCCAGGAAATCCAACTCAAAGAAGCTAAGCACATTGCAGAAGAGGCAGATAGGAAGTATGAAG
AGGTGGCTCGTAAGTTGGTGATCATTGAAGGAGACTTGGAACGCACAGAGGAACGAGCTGAGCTGGCAGA
GTCCCGTTGCCGAGAGATGGATGAGCAGATTAGACTGATGGACCAGAACCTGAAGTGTCTGAGTGC

*Fig. 15G*

11782.1.contig

ATCTACGTCATCAATCAGGCTGGAGACACCATGTTCAATCGAGCTAAGCTGCTCAATATTGGCTTTCAAGAG
GCCTTGAAGGACTATGATTACAACTGCTTTGTGTTCAGTGATGTGGACCTCATTCCGATGGACGACCGTAAT
GCCTACAGGTGTTTTTCGCAGCCACGGCACATTTCTGTTGCAATGGACAAGTTCGGGTTTAGCCTGCCATA
TGTTCAGTATTTTGGAGGTGTCTCTGCTCTCAGTAAACAACAGTTTCTTGCCATCAATGGATTCCCTAATAAT
TATTGGGGTTGGGGAGGAGAAGATGACGACATTTTTAACAGATTAGTTCATAAAGGCATGTCTATATCACGT
CCAAATGCTGTAGTAGGGAGGTGTCGAATGATCCGGCATTCAAGAGACAAGAAAAATGAGCCCAATCCTCA
GAGGTTTGACCGGATCGCACATACAAAGGAAACGATGCGCTTCGATGGTTTGAACTCACTTACCTACAAGG
TGTTGGATGTCAGAGATACCCGTTATATACCCAAATCAC

11782.2.contig

CTAGACCTCTAATTAAAAGGCACAATCATGCTGGAGAATGAACAGTCTGACCCCGAGGGCCACAGCGAATT
TTAGGGAAGGAGGCAAAGAGGTGAGAAGGGAAAGGAAAGAAGGAAGGAAGGAGAACAATAAGAACTGGA
GACGTTGGGTGGGTCAGGGAGTGTGGTGGAGGCTCGGAGAGATGGTAAACAAACCTGACTGCTATGAGTT
TTCAACCCCATAGTCTAGGGCCATGAGGGCGTCAGTTCTTGGTGGCTGAGGGTCCTTCCACCCAGCCCAC
CTGGGGGAGTGGAGTGGGGAGTTCTGCCAGGTAAGCAGATGTTGTCTCCCAAGTTCCTGACCCAGATGTC
TGGCAGGATAACGCTGACCTGTTCCCTCAACAAGGGACCTGAAAGTAATTTTGCTCTTTAC

11783-1 & 2

CCGAATTCAAGCGTCAACGATCCYTCCCTTACCATCAAATCAATTGGCCACCAATGGTACTGAACCTACGAG
TACACCGACTACgGGCGGACTAATCTTCAACTCCTACATACTTCCCCCATTATTCCTAGAACCAGGCGACCT
GCGACTCCTTGACGTTGACAATCGAGTAGTACTCCCGATTGAAGCCCCCATTCGTATAATAATTACATCACA
AGACGTCTTGCACTCATGAGCTGTCCCCACATTAGGCTTAAAAACAGATGCAATTCCCGGACGTCTAAGCC
AAACCACTTTCACCGCTACACGACCGGGGGTATACTACGGTCAATGCTCTGAAATCTGTGGAGCAAACCAC
AGTTTCATGCCCATCGTCCTAGAATTAATTCCCCTAAAAATCTTTGAAATAGGGCCCGTATTTACCCTATAGC
ACCCCCTCTACCCCCTCTAG

11786.1.contig

GCTCTTCACACTTTTATTGTTAATTCTCTTCACATGGCAGATACAGAGCTGTCGTCTTGAAGACCACCACTGA
CCAGGAAATGCCACTTTTACAAAATCATCCCCCCTTTTCATGATTGGAACAGTTTTCCTGACCGTCTGGGAG
CGTTGAAGGGTGACCAGCACATTTGCACATGCAAAAAAGGAGTGACCCCAAGGCCTCAACCACACTTCCCA
GAGCTCACCATGGGCTGCAGGTGACTTGCCAGGTTTGGGGTTCGTGAGCTTTCCTTGCTGCTGCGGTGGG
GAGGCCCTCAAGAACTGAGAGGCCGGGGTATGCTTCATGAGTGTTAACATTTACGGGACAAAAGCGCATCA
TTAGGATAAGGAACAGCCACAGCACTTCATGCTTGTGAGGGTTAGCTGTAGGAGCGGGTGAAAGGATTCCA
GTTTATGAAAATTTAAAGCAAACAACGGTTTTTAGCTGGGTGGGAAACAGGAAAACTGTGATGTCGGCCAAT
GACCACCATTTTTCTGCCCATGTGAAGGTCCCCATGAAACC

*Fig. 15H*

11786.2.contig

CAAGCGCTTGGCGTTTGGACCCAGTTCAGTGAGGTTCTTGGGTTTTGTGCCTTTGGGGATTTTGGTTTGAC
CCAGGGGTCAGCCTTAGGAAGGTCTTCAGGAGGAGGCCGAGTTCCCCTTCAGTACCACCCCTCTCTCCCC
ACTTTCCCTCTCCCGGCAACATCTCTGGGAATCAACAGCATATTGACACGTTGGAGCCGAGCCTGAACATG
CCCCTCGGCCCCAGCACATGGAAAACCCCCTTCCTTGCCTAAGGTGTCTGAGTTTCTGGCTCTTGAGGCAT
TTCCAGACTTGAAATTCTCATCAGTCCATTGCTCTTGAGTCTTTGCAGAGAACCTCAGATCAGGTGCACCTG
GGAGAAAGACTTTGTCCCCACTTACAGATCTATCTCCTCCCTTGGGAAGGGCAGGGAATGGGGACGGTGT
ATGGAGGGGAAGGGATCTCCTGCGCCCTTCATTGCCACACTTGGTGGGACCATGAACATCTTTAGTGTCTG
AGCTTCTCAAATTACTGCAATAGGA

13691.1&2

AGCGTCAAATCAGAATGGAAAAGACTCAAAACCATCATCAACACCAAGATCAAAAGGACAAGRATCCTTCAAG
AAACAGGAAAAAACTCCTAAAACACCAAAAGGACCTAGTTCTGTAGAAGACATTAAAGCAAAAATGCAAGCAA
GTATAGAAAAAGGTGGTTCTCTTCCCAAAGTGGAAGCCAAATTCATCAATTATGTGAAGAATTGCTTCCGGAT
GACTGACCAAGAGGCTATTCAAGATCTCTGGCAGTGGAGGAAGTCTCTTTAAGAAAATAGTTTAAACAATTTG
TTAAAAAATTTTCCGTCTTATTTCATTTCTGTAACAGTTGATATCTGGCTGTCCTTTTTATAATGCAGAGTGAGA
ACTTTCCCTACCGTGTTTGATAAATGTTGTCCAGGTTCTATTGCCAAGAATGTGTTGTCCAAAATGCCTGTTTA
GTTTTTTAAAGATGGAACTCCACCCTTTGCTTGGTTTTAAGTATGTATGGAATGTTATGATAGGACATAGTAGTA
GCGGTGGTCAGACATGGAAATGGTGGGSMGACAAAAATATACATGTGAAATAA

13692.1&2

TCCGAATTCCAAGCGAATTATGGACAAACGATTCCTTTTAGAGGATTACTTTTTTCAATTTCGGTTTTAGTAAT
CTAGGCTTTGCCTGTAAAGAATACAACGATGGATTTTAAATACTGTTTGTGGAATGTGTTTAAAGGATTGATT
CTAGAACCTTTGTATATTTGATAGTATTTCTAACTTTCATTTCTTTACTGTTTGCAGTTAATGTTCATGTTCTGC
TATGCAATCGTTTATATGCACGTTTCTTTAATTTTTTTAGATTTTCCTGGATGTATAGTTTAAACAACAAAAAG
TCTATTTAAAACTGTAGCAGTAGTTTACAGTTCTAGCAAAGAGGAAAGTTGTGGGGTTAAACTTTGTATTTTC
TTTCTTATAGAGGCTTCTAAAAAGGTATTTTTATATGTTCTTTTTAACAAATATTGTGTACAACCTTTAAAACAT
CAATGTTTGGATCAAAACAAGACCCAGCTTATTTTCTGC

13693.2

TGTGGTGGCGCGGGCTGAGGTGGAGGCCCAGGACTCTGACCCTGCCCCTGCCTTCAGCAAGGCCCCCGG
CAGCGCCGGCCACTACGAACTGCCGTGGGTTGAAAAATATAGGCCAGTAAAGCTGAATGAAATTGTCGGG
AATGAAGACACCGTGAGCAGGCTAGAGGTCTTTGCAAGGGAAGGAAATGTGCCCAACATCATCATTGCGG
GCCCTCCAGGAACCGGCAAGACCACAAGCATTCTGTGCTTGGCCCGGGCCCTGCTGGGCCCAGCACTCAA
AGATGCCATGTTGGAACTCAATGCTTCAAATGACAGGGGCATTGACGTTGTGAGGAATAAAATTAAAATGTT
TGCTCAACAAAAAGTCACTCTTCCCAAAGGCCGACATAAGATCATCATTCTGGATGAAGCAGACAGCATGAC
CGACGGAGCCCAGCAAGCCTTGAGGAGAACCATGGAAATCTACTCTAAAACCACTCGTTCGCCCTTGCTTG
TAATGCTTCGGATAAGATCATCGAGCC

CTTTGCAAAGCTTTTATTTCATGTCTGCGGCATGGAATCCACCTGCACATGGCATCTTAGCTGTGAAGGAGA
AAGCAGTGCACGAGAAGGAATGAGTGGGCGGAACCAACGGCCTCCACAAGCTGCCTTCCAGCAGCCTGC
CAAGGCCATGGCAGAGAGAGACTGCAAACAAACACAAGCAAACAGAGTCTCTTCACAGCTGGAGTCTGAAA
GCTCATAGTGGCATGTGTGAATCTGACAAAATTAAAAGTGTGCATAGTCCATTACATGCATAAAACACTAATA
ATAATCCTGTTTACACGTGACTGCAGCAGGCAGGTCCAGCTCCACCACTGCCCTCCTGCCACATCACATCA
AGTGCCATGGTTTAGAGGGTTTTTCATATGTAATTCTTTTATTCTGTAAAAGGTAACAAAATATACAGAACAA
AACTTTCCCTTTTTAAAACTAATGTTACAAATCTGTATTATCACTTGGATATAAATAGTATATAAGCTGATC

13700.1

CAAGGGATATATGTTGAGGGTACRGRGTGACACTGAACAGATCACAAAGCACGAGAAACATTAGTTCTCTC
CCTCCCCAGCGTCTCCTTCGTCTCCCTGGTTTTCCGATGTCCACAGAGTGAGATTGTCCCTAAGTAACTGC
ATGATCAGAGTGCTGKCTTTATAAGACTCTTCATTCAGCGTATCCAATTCAGCAATTGCTTCATCAAATGCCG
TTTTTGCCAGGCTACAGGCCTTTTCAGGAGAGTTTAGAATCTCATAGTAAAAGACTGAGAAATTTAGTGCCA
GACCAAGACGAATTGGGTGTGTAGGCTGCATTNCTTTCTTACTAATTTCAAATGCTTCCTGGTAAGCCTGCT
GGGAGTTCGACACAAGTGGTTTGTTTGTTGCTCCAGATGCCACTTCAGAAAGATACCTAAAATAATCTCCTT
TCATTTTCAAAGTAGAACAC

13700.2

TCCGGAGCCGGGGTAGTCGCCGCCGCCGCCGCCGGTGCAGCCACTGCAGGCACCGCTGCCGCCGCCTG
AGTAGTGGGCTTAGGAAGGAAGAGGTCATCTCGCTCGGAGCTTCGCTCGGAAGGGTCTTTGTTCCCTGCA
GCCCTCCACGGGAATGACAATGGATAAAAGTGAGCTGGTACAGAAAGCCAAACTCGCTGAGCAGGCTGA
GCGATATGATGATATGGCTGCAGCCATGAAGGCAGTCACAGAACAGGGGCATGAACTCTCCAACGAAGAG
AGAAATCTGCTCTCTGTTGCCTACAAGAATGTGGTAAGGCCGCCCGCCGCTCTTCCTGGCGTGTCATCTCC
AGCATTGAGCAGAAAACAGAGAGGAATGAGAAGAAGCAGCAGATGGGCAAAGAGTACCGTGAGAAGATAG
AGGCAGAACTGCAGGACATCTGCAATGATGTTCTGGAGCTTGTTGGACAAATATCTTATTCCAATGCTACAC
AACCCAGAAA

13701.1

AAAAAGCAGCARGTTCAACACAAAATAGAAATCTCAAATGTAGGATAGAACAAAACCAAGTGTGTGAGGGG
GGAAGCAACAGCAAAAGGAAGAAATGAGATGTTGCAAAAAAGATGGAGGAGGGTTCCCCTCTCCTCTGGG
GACTGACTCAAACACTGATGTGGCAGTATACACCATTCCAGAGTCAGGGGTGTTCATTCTTTTTTGGGAGTA
AGAAAAGGTGGGGATTAAGAAGACGTTTCTGGAGGCTTAGGGACCAAGGCTGGTCTCTTTCCCCCCTCCCA
ACCCCCTTGATCCCTTTCTCTGATCAGGGGAAAGGAGCTCGAATGAGGGAGGTAGAGTTGGAAAGGGAAA
GGATTCCACTTGACAGAATGGGACAGACTCCTTCCCA

TGGCAATAGCACAGCCATCCAGGAGCTCTTCARGCGCATCTCGGAGCAGTTCACTGCCATGTTCCGCCGG
AAGGCCTTCCTCCACTGGTACACAGGCGAGGGCATGGACGAGATGGAGTTCACCGAGGCTGAGAGCAACA
TGAACGACCTCGTCTCTGAGTATCAAGCAGTACCAGGATGCCACCGCAGAAGAGGAGGAGGATTTCGGTG
AGGAGGCCGAAGAGGAGGCCTAAGGCAGAGCCCCCATCACCTCAGGCTTCTCAGTTCCCTTAGCCGTCTT
ACTCAACTGCCCCTTTCCTCTCCCTCAGAATTTGTGTTTGCTGCCTCTATCTTGTTTTTTGTTTTTTCTTCTGG
GGGGGTCTAGAACAGTGCCTGGCACATAGTAGGCGCTCAATAAATACTTGGTTGNTGAATGTCTCCT

13702.2

AGCTGGCGCTAGGGCTCGGTTGTGAAATACAGCGTRGTCAGCCCTTGCGCTCAGTGTAGAAACCCACGCC
TGTAAGGTCGGTCTTCGTCCATCTGCTTTTTTCTGAAATACACTAAGAGCAGCCACAAAACTGTAACCTCAA
GGAAACCATAAAGCTTGGAGTGCCTTAATTTTTAACCAGTTTCCAATAAAACGGTTTACTACCT

13704.2-13740.2

GGAGATGAAGATGAGGAAGCTGAGTCAGCTACGGGCARGCGGGCAGCTGAAGATGATGAGGATGACGAT
GTCGATACCAAGAAGCAGAAGACCGACGAGGATGACTAGACAGCAAAAAAGGAAAAGTTAAA

13706.1

GATGAAAATTAAATACTTAAATTAATCAAAAGGCACTACGATACCACCTAAAACCTACTGCCTCAGTGGCAGT
AKGCTAAKGAAGATCAAGCTACAGSACATYATCTAATATGAATGTTAGCAATTACATAKCARGAAGCATGTTT
GCTTTCCAGAAGACTATGGNACAATGGTCATTWGGGCCCAAGAGGATATTTGGCCNGGAAAGGATCAAGA
TAGATNAANGTAAAG

13706.2

GAGTAGCAACGCAAAGCGCTTGGTATTGAGTCTGTGGGSGACTTCGGTTCCGGTCTCTGCAGCAGCCGTG
ATCGCTTAGTGGAGTGCTTAGGGTAGTTGGCCAGGATGCCGAATATCAAAATCTTCAGCAGGCAGCTCCCA
CCAGGACTTATCTCASAAAATTGCTGACCGCCTGGGCCTGGAGCTAGGCAAGGTGGTGACTAAGAAATTCA
GCAACCAGGAGACCTGTGTGGAAATTGGTGAAAGTGTACCGTGGAGAGGATGTCTACATTGTTCAGAGTGG
NTGTGGCGAAATCAATGACAATTTAATGGAGCTTTTGATCATGATTAATGCCTGCAAGATTGCTTCAGCCAG
CCGGGTTACTGCAGTCATCCCATGCTTCCCTTATGCCCCGGCAGGATAAGAAAGATNAGAGCCGGGCCGC
CAATCTCAGCCAAGCTTGGTGCAAATATGCTATCTGTAGCAGTGCAGATCATATTATCACCATGGACCTACA
TGCTTCTCAAATTCANGGCTTTTT

ATGCAAAAGGGGACACAGGGGGTTCAAAAATAAAAATTTCTCTTCCCCCTCCCCAAACCTGTACCCCAGCT
CCCCGACCACAACCCCCTTCCTCCCCCGGGGAAAGCAAGAAGGAGCAGGTGTGGCATCTGCAGCTGGGA
AGAGAGAGGCCGGGGAGGTGCCGAGCTCGGTGCTGGTCTCTTTCCAAATATAAATACGTGTGTCAGAACT
GGAAAATCCTCCAGCACCCACCCACCCAAGCACTCTCCGTTTTCTGCCGGTGTTTGGAGAGGGGCGGNGGG
CAGGGGCGCCAGGCACCGGCTGGCTGCGGTCTACTGCATCCGCTGGGTGTGCACCCCGCGA

13710.2

AGGTTGGAGAAGGTCATGCAGGTGCAGATTGTCCAGGSKCAGCCACAGGGTCAAGCCCAACAGGCCCAGA
GTGGCACTGGACAGACCATGCAGGTGATGCAGCAGATCATCACTAACACAGGAGAGATCCAGCAGATCCC
GGTGCAGCTGAATGCCGGCCAGCTGCAGTATATCCGCTTAGCCCAGCCTGTATCAGGCACTCAAGTTGTG
CAGGGACAGATCCAGACACTTGCCACCAATGCTCAACAGATTACACAGACAGAGGTCCAGCAAGGACAGC
AGCAGTTCAAGCCAGTTCACAAGATGGACAGCAGCTCTACCAGATCCAGCAAGTCACCATGCCTGCGGGC
CANGACCTCGCCAGCCCATGTTCATCCAGTCAAGCCAACCAGCCCTTCNACGGGCAGGCCCCCCAGGTGA
CCGGCGACTGAAGGGCCTGAGCTGGCAAGGCCAANGACACCCAACACAATTTTTGCCATACAGCCCCCAG
GCAATGGGCACAGCCTTTCTTCCCAGAGGAC

13710-1

TGAGATTTATTGCATTTCATGCAGCTTGAAGTCCATGCAAAGGRGACTAGCACAGTTTTTAATGCATTTAAAA
AATAAAAGGGAGGTGGGCAGCAAACACACAAAGTCCTAGTTTCCTGGGTCCCTGGGAGAAAAGAGTGTGG
CAATGAATCCACCCACTCTCCACAGGGAATAAATCTGTCTCTTAAATGCAAAGAATGTTTCCATGGCCTCTG
GATGCAAATACACAGAGCTCTGGGGTCAGAGCAAGGGATGGGGAGAGGACCACGAGTGAAAAAGCAGCTA
CACACATTCACCTAATTCCATCTGAGGGCAAGAACAACGTGGCAAGTCTTGGGGGTAGCAGCTGTT

13711.1

TCCAGACATGCTCCTGTCCTAGGCGGGGAGCAGGAACCAGACCTGCTATGGGAAGCAGAAAGAGTTAAGG
GAAGGTTTCCTTTCATTCCTGTTCCTTCTCTTTTGCTTTTGAACAGTTTTTAAATATACTAATAGCTAAGTCAT
TTGCCAGCCAGGTCCCGGTGAACAGTAGAGAACAAGGAGCTTGCTAAGAATTAATTTTGCTGTTTTTCACCC
CATTCAAACAGAGCTGCCCTGTTCCCTGATGGAGTTCCATTCCTGCCAGGGCACGGCTGAGTAACACGAAG
CCATTCAAGAAAGGCGGGTGTGAAATCACTGCCACCCCATGGACAGACCCCTCACTCTTCCTTCTTAGCCG
CAGCGCTACTTAATAAATATATTTATACTTTGAAATTATGATAACCGATTTTTCCCATGCGGCATCCTAAGGG
CACTTGCCAGCTCTTATCCGGACAGTCAAGCACTGTTGTTGGACAACAGATAAAGGAAAAGAAAAAGAAGA
AAACAACCGCAACTTCTGT

TGAGACGGACCACTGGCCTGGTCCCCCCTCATKTGCTGTCGTAGGACCTGACATGAAACGCAGATCTAGT
GGCAGAGAGGAAGATGATGAGGAACTTCTGAGACGTCGGCAGCTTCAAGAAGAGCAATTAATGAAGCTTAA
CTCAGGCCTGGGACAGTTGATCTTGAAAGAAGAGATGGAGAAAGAGAGCCGGGAAAGGTCATCTCTGTTA
GCCAGTCGCTACGATTCTCCCATCAACTCAGCTTCACATATTCCATCATCTAAAACTGCATCTCTCCCTGGC
TATGGAAGAAATGGGCTTCACCGGCCTGTTTCTACCGACTTCGCTCAGTATAACAGCTATGGGGATGTCAG
CGGGGGAGTGCGAGATTACCAGACACTTCCAGATGGCCACATGCCTGCAATGAGAATGGACCGAGGAGTG
TCTATGCCCAACATGTTGGAACCAAAGATATTTCCATATGAAATGCTCATGGTGACCAACAGAGGGCCGAAA
CCAAATCTCAGAGAGGTGGACAGAA

13713.1&2

TCACTTTATTTTTCTTGTATAAAAACCCTATGTTGTAGCCACAGCTGGAGCCTGAGTCCGCTGCACGGAGAC
TCTGGTGTGGGTCTTGACGAGGTGGTCAGTGAACTCCTGATAGGGAGACTTGGTGAATACAGTCTCCTTCC
AGAGGTCGGGGGTCAGGTAGCTGTAGGTCTTAGAAATGGCATCAAAGGTGGCCTTGGCGAAGTTGCCCAG
GGTGGCAGTGCAGCCCCGGGCTGAGGTGTAGCAGTCATCGATACCAGCCATCATGAG

13715.4

CTGGAATATAGACCCGTGATCGACAAAACTTTGAACGAGGCTGACTGTGCCACCGTCCCGCCAGCCATTCG
CTCCTACTGATGAGACAAGATGTGGTGATGACAGAATCAGCTTTTGTAATTATGTATAATAGCTCATGCATGT
GTCCATGTCATAACTGTCTTCATACGCTTCTGCACTCTGGGGAAGAAGGAGTACATTGAAGGGAGATTGGC
ACCTAGTGGCTGGGAGCTTGCCAGGAACCCAGTGGCCAGGGAGCGTGGCACTTACCTTTGTCCCTTGCTT
CATTCTTGTGAGATGATAAAACTGGGCACAGCTCTTAAATAAAATATAAATGAACA

13717.1&2

TGAATGGGGAGGAGCTGACCCAGGAAATGGAGCTTGNGGAGACCAGGCCTGCAGGGGATGGAACCTTCC
AGAAGTGGGCATCTGTGGTGGTGCCTCTTGGGAAGGAGCAGAAGTACACATGCCATGTGGAACATGAGGG
GCTGCCTGAGCCCCTCACCCTGAGATGGGGCAAGGAGGAGCCTCCTTCATCCACCAAGACTAACACAGTA
ATCATTGCTGTTCCGGTTGTCCTTGGAGCTGTGGTCATCCTTGGAGCTGTGATGGCTTTTGTGATGAAGAG
GAGGAGAAACACAGGTGGAAAAGGAGGGGACTATGCTCTGGCTCCAGGCTCCCAGAGCTCTGATATGTCT
CTCCCAGATTGTAAAGTGTGAAGACAGCTGCCTGGTGTGGACTTGGTGACAGACAATGTCTTCACACATCT
CCTGTGACATCCAGAGACCTCAGTTCTCTTTAGTCAAGTGTCTGATGTTCCCTGTGAGTCTGCGGGCTCAAA
GTGAAGAACTGTGGAGCCCAGTCCACCCCTGCACACCAGGACCCTATCCCTGCACTGCCCTGTGTTCCCTT
CCACAGCCAACCTTGCTGCTCCAGCCAAACATTGGTGGACATCTGCAGCCTGTCAGCTCCATGCTACCCTG
ACCTTCAACTCCTCACTTCCACACTGAGAATAATAATTTGAATGTGGGTGGCTGGAGAGATGGCTCAGCGC
TGACTGCTCTTCCAAAGGTCCTGAGTTCAAATCCCAGCAACCACATGGTGGCTCACAACCATCTGTAATGG
GATCTAATACCCTCTTCTGCAGTGTCTGAAGACASCTACAGTGTACTTACATATAATAATAAATAAG

```
GGCCGGGCGCGCGCGCCCCCGCCACACGCACGCCGGGCGTGCCAGTTTATAAAGGGAGAGAGCAAGCA
GCGAGTCTTGAAGCTCTGTTTGGTGCTTTGGATCCATTTCCATCGGTCCTTACAGCCGCTCGTCAGACTCC
AGCAGCCAAGATGGTGAAGCAGATCGAGAGCAAGACTGCTTTTCAGGAAGCCTTGGACGCTGCAGGTGAT
AAACTTGTAGTAGTTGACTTCTCAGCCACGTGGTGTGGGCCTTGCAAAATGATCAAGCCTTTCTTTCATTCC
CTCTCTGAAAAGTATTCCAACGTGATATTCCTTGAAGTAGATGTGGATGACTGTCAGGATGTTGCTTCAGAG
TGTGAAGTCAAATGCATGCCAACATTCCAGTTTTTTAAGAAGGGACAAAAGGTGGGTGAATTTTCTGGAGCC
AATAAGGAAAAGCTTGAAGCCACCATTAATGAATTAGTCTAATCATGTTTTCTGAAAATATAACCAGCCATTG
GCTATTTAAAACTTGTAATTTTTTTAATTTACAAAAAATATAAAATATGAAGACATAAACCCMGTTGCCATCTGC
GTGACAATAAAACATTAATGCTAACACTT
```

13721.1

```
TCACATAAGAAATTTAAGCAAGTTACRCTATCTTAAAAAACACAACGAATGCATTTTAATAGAGAAACCCTTC
CCTCCCTCCACCTCCCTCCCCCACCCTCCTCATGAATTAAGAATCTAAGAGAAGAAGTAACCATAAAACCAA
GTTTTGTGGAATCCATCATCCAGAGTGCTTACATGGTGATTAGGTTAATATTGCCTTCTTACAAAATTTCTAT
TTTAAAAAAAATTATAACCTTGATTGCTTATTACAAAAAAATTCAGTACAAAAGTTCAATATATTGAAAAATGCT
TTTCCCCTCCCTCACAGCACCGTTTTATATATAGCAGAGAATAATGAAGAGATTGCTAGTCTAGATGGGGCA
ATCTTCAAATTACACCAAGACGCACAGTGGTTTATTTACCCTCCCCTTCTCATAAG
```

13721.2

```
GGAAAGGATTCAAGAATTAGAGGACTTGCTTGCTRRAGAAAAAGACAACTCTCGTCGCATGCTGACAGACA
AAGAGAGAGAGATGGCGGAAATAAGGGATCAAATGCAGCAACAGCTGAATGACTATGAACAGCTTCTTGAT
GTAAAGTTAGCCCTGGACATGGAAATCAGTGCTTACAGGAAACTCTTAGAAGGCGAAGAAGAGAGGTTGAA
GCTGTCTCCAAGCCCTTCTTCCCGTGTGACAGTATCCCGAGCATCCTCAAGTCGTAGTGTACCGTACAACT
AGAGGAAAGCGGAAGAGGGTTGATGTGGAAGAATCAGAGGCGAAGTAGTAGTGTTAGCATCTCTCATTCC
GCCTCAACCACTGGAAATGTTTGCATCGAAGAAATTGATGTTGATGGGAAATTTATCCCGCTTGAAGAACAC
TTCTGAACAGGATCAACCAATGGGAAGGCTTGGGAGATGATCAGAAAAATTGGAGACACATCAGTCAGTTA
TAAATATACCTCAA
```

13723.1

```
CATGGGTTTCACCAGGTTGGCCAGGCTGCTCTTGAACTSCTGACCTCAGGTGATCCACCCGCCTCGGCCT
CCCAAAGTGCTGGGATTACAGGCGTGAGCCACCACGCCCGGCCCCCAAAGCTGTTTCTTTTGTCTTTAGCG
TAAAGCTCTCCTGCCATGCAGTATCTACATAACTGACGTGACTGCCAGCAAGCTCAGTCACTCCGTGGTCTT
TTTCTCTTTCCAGTTCTTCTCTCTCTCTTCAAGTTCTGCCTCAGTGAAAGCTGCAGGTCCCCAGTTAAGTGAT
CAGGTGAGGGTTCTTTGAACCTGGTTCTATCAGTCGAATTAATCCTTCATGATGG
```

GATGTGTTGGACCCTCTGTGTCAAAAAAAACCTCACAAAGAATCCCCTGCTCATTACAGAAGAAGATGCATT
TAAAATATGGGTTATTTTCAACTTTTTATCTGAGGACAAGTATCCATTAATTATTGTGTCAGAAGAGATTGAAT
ACCTGCTTAAGAAGCTTACAGAAGCTATGGGAGGAGGTTGGCAGCAAGAACAATTTGAACATTATAAAATCA
ACTTTGATGACAGTAAAAATGGCCTTTCTGCATGGGAACTTATTGAGCTTATTGGAAATGGACAGTTTAGCA
AAGGCATGGACCGGCAGACTGTGTCTATGGCAATTAATGAAGTCTTTAATGAACTTATATTAGATGTGTTAA
AGCAGGGTTACATGATGAAAAAGGGCCACAGACGGAAAAACTGGACTGAAAGATGGTTTGTACTAAAACCC
AACATAATTTCTTACTATGTGAGTGAGGATCTGAAGGATAAGAAAGGAGACATTCTCTTGGATGAAAATTGC
TGTGTAGAAGTCCTTGCCTGACAAAAGATGGAAAGAAATGCCTTTT

13725.1

GACTGGTTCTTTATTTCAAAAAGACACTTGTCAATATTCAGTRTCAAAACAGTTGCACTATTGATTTCTCTTTC
TCCCAATCGGCCCCAAAGAGACCACATAAAAGGAGAGTACATTTTAAGCCAATAAGCTGCAGGATGTACAC
CTAACAGACCTCCTAGAAACCTTACCAGAAAATGGGGACTGGGTAGGGAAGGAAACTTAAAAGATCAACAA
ACTGCCAGCCCACGGACTGCAGAGGCTGTCACAGCCAGATGGGGTGGCCAGGGTGCCACAAACCCAAAG
CAAAGTTTCAAAATAATATAAAATTTAAAAAGTTTTGTACATAAGCTATTCAAGATTTCTCCAGCACTGACTGA
TACAAAGCACAATTGAGATGGCACTTCTAGAGACAGCAGCTTCAAACCCAGAAAAGGGTGATGAGATGAAG
TTTCACATGGCTAAATCAGTGGCAAAAACACAGTCTTCTTTCTTTCTTTCTTTCAAGGANGCAGGAAAGCAAT
TAAGTGGTCACCTTAACATAAGGGGGAC

13725.2

TGGGTGGGCACCATGGCTGGGATCACCACCATCGAGGCGGTGAAGCGCAAGATCCAGGTTCTGCAGCAG
CAGGCAGATGATGCAGAGGAGCGAGCTGAGCGCCTCCAGCGAGAAGTTGAGGGAGAAAGGCGGGCCCG
GGAACAGGCTGAGGCTGAGGTGGCCTCCTTGAACCGTAGGATCCAGCTGGTTGAAGAAGAGCTGGACCGT
GCTCAGGAGCGCCTGGCCACTGCCCTGCAAAAGCTGGAAGAAGCTGAAAAAGCTGCTGATGAGAGTGAGA
GAGGTATGAAGGTTATTGAAAACCGGGCCTTAAAAGATGAAGAAAAGATGGAACTCCAGGAAATCCAACTC
AAAGAAGCTAAGCACATTGCAGAAGAGGCAGATAGGAAGTATGAAGAGGTGGCTCGTAAGTTGGTGATCAT
TGAAGGAGACTTGGAACCGCACAGAAGGAACGAGCTTGAGCTTGGCAAAAGTCCCGTTGCCCAGAGATGG
GATGAACCAGATTAGACTGATGGACCANAACC

13726.1&2

AGGGGCNGCGGGTGCGTGGGCCACTGGGTGACCGACTTAGCCTGGCCAGACTCTCAGCACCTGGAAGCG
CCCCGAGAGTGACAGCGTGAGGCTGGGAGGGAGGACTTGGCTTGAGCTTGTTAAACTCTGCTCTGAGCCT
CCTTGTCGCCTGCATTTAGATGGCTCCCGCAAAGAAGGGTGGCGAGAAGAAAAAGGGCCGTTCTGCCATC
AACGAAGTGGTAACCCGAGAATACACCATCAACATTCACAAGCGCATCCATGGAGTGGGCTTCAAGAAGCG
TGCACCTCGGGCACTCAAAGAGATTCGGAAATTTGCCATGAAGGAGATGGGAACTCCAGATGTGCGCATTG
ACACCAGGCTCAACAAAGCTGTCTGGGCCAAAGGAATAAGGAATGTGCCATACCGAATCCGGTGTGCGGC
TGTCCAGAAAACGTAATGAGGATGAAGATTCACCAAATAAGCTATATACTTTGGTTACCTATGTACCTGTTAC
CACTTTCAAAAATCTACAGACAGTCAATGTGGATGAGAACTAATCGCTGATCGTCAGATCAAATAAAGTTATA
AAAT

TCGGGAGCCACACTTGGCCCTCTTCCTCTCCAAAGSGCCAGAACCTCCTTCTCTTTGGAGAATGGGGAGGC
CTCTTGGAGACACAGAGGGTTTCACCTTGGATGACCTCTAGAGAAATTGCCCAAGAAGCCCACCTTCTGGT
CCCAACCTGCAGACCCCACAGCAGTCAGTTGGTCAGGCCCTGCTGTAGAAGGTCACTTGGCTCCATTGCC
TGCTTCCAACCAATGGGCAGGAGAGAAGGCCTTTATTTCTCGCCCACCCATTCCTCCTGTACCAGCACCTC
CGTTTTCAGTCAGTGTTGTCCAGCAACGGTACCGTTTACACAGTCACCTCAGACACACCATTTCACCTCCCT
TGCCAAGCTGTTAGCCTTAGAGTGATTGCAGTGAACACTGTTTACACACCGTGAATCCATTCCCATCAGTCC
ATTCCAGTTGGCACCAGCCTGAACCATTTGGTACCTGGTGTTAACTGGAGTCCTGTTTACAAGGTGGAGTC
GGGGCTTGCTGACTTCTCTTCATTTGAGGGCAC

13727.2

ACCTAGACAGAAGGTGGGTGAGGGAGGACTGGTAGGAGGCTGAGGCAATTCCTTGGTAGTTTGTCCTGAA
ACCCTACTGGAGAAGTCAGCATGAGGCACCTACTGAGAGAAGTGCCCAGAAACTGCTGACTGCATCTGTTA
AGAGTTAACAGTAAAGAGGTAGAAGTGTGTTTCTGAATCAGAGTGGAAGCGTCTCAAGGGTCCCACAGTGG
AGGTCCCTGAGCTACCTCCCTTCCGTGAGTGGGAAGAGTGAAGCCCATGAAGAACTGAGATGAAGCAAGG
ATGGGGTTCCTGGGCTCCAGGCAAGGGCTGTGCTCTCTGCAGCAGGGAGCCCCACGAGTCAGAAGAAAA
GAACTAATCATTTGTTGCAAGAAACCTTGCCCGGATACTAGCGGAAAACTGGAGGCGGNGGTGGGGGCAC
AGGAAAGTGGAAGTGATTTGATGGAGAGCAGAGAAGCCTATGCACAGTGGCCGAGTCCACTTGTAAAGTG

13728.1&2

TTCAAGCAATTGTAACAAGTATATGTAGATTAGAGTGAGCAAAATCATATACAATTTTCATTTCCAGTTGCTAT
TTTCCAAATTGTTCTGTAATGTCGTTAAAATTACTTAAAAATTAACAAAGCCAAAAATTATATTTATGACAAGA
AAGCCATCCCTACATTAATCTTACTTTTCCACTCACCGGCCCATCTCCTTCCTCTTTTTCCTAACTATGCCAT
TAAAACTGTTCTACTGGGCCGGGCGTGTGGCTCATGCCTGTAATCCCAGCATTTTGGGAGGCCAAGGCAG
GCGGATCATGAGGTCAAGAGATTGAGACCATCCTGGCCAACATGGTGAAACCCCGCCTCGACTAAGAATAC
AAAAATTAGCTGGGCATGGTGGCGCATGCCTGTAGTCTCAGCTACTCGGGAGGCTGAGGCAGAAGAATCG
CTTGAACCCGGGAGGCAGAGGATGCAGTGAGCCCCGATCGCGCCACTGCACTCTAGCCTGGGCGACAGA
CTGAGACTCTGCTC

13731.1&2

TGTGCCAGTCTACAGGCCTATCAGCAGCGACTCCTTCAGCAACAGATGGGGTCCCCTGTTCAGCCCAACC
CCATGAGCCCCCAGCAGCATATGCTCCCAAATCAGGCCCAGTCCCCACACCTACAAGGCCAGCAGATCCC
TAATTCTCTCTCCAATCAAGTGCGCTCTCCCCAGCCTGTCCCTTCTCCACGGCCACAGTCCCAGCCCCCC
ACTCCAGTCCTTCCCCAAGGATGCAGCCTCAGCCTTCTCCACACCACGTTTCCCCACAGACAAGTTCCCCA
CATCCTGGACTGGTAGTTGCCCAGGCCAACCCCATGGAACAAGGGCATTTTGCCAGCC

TGTAAAAACTTGTTTTTAATTTTGTATAAAATAAAGGTGGTCCATGCCCACGGGGGCTGTAGGAAATCCAAG
CAGACCAGCTGGGGTGGGGGGATGTAGCCTACCTCGGGGGACTGTCTGTCCTCAAAACGGGCTGAGAAG
GCCCGTCAGGGGCCCAGGTCCCACAGAGAGGCCTGGGATACTCCCCCAACCCGAGGGGCAGACTGGGCA
GTGGGGAGCCCCCATCGTGCCCCAGAGGTGGCCACAGGCTGAAGGAGGGGCCTGAGGCACCGCAGCCT
GCAACCCCCAGGGCTGCAGTCCACTAACTTTTTACAGAATAAAAGGAACATGGGGATGGGGAAAAAAGCAC
CAGGTCAGGCAGGGCCCGAGGGCCCCAGATCCCAGGAGGGCCAGGACTCAGGATGCCAGCACCACCCTA
GCAGCTCCCACAGCTCCTGGCACAGGAGGCCGCCACGGATTGGCACAGGCCGCTGCTGGCCATCACGCC
ACATTTGGAGAACTTGTCCCGACAGAGGTCAGCTCGGAGGAGCTCCTCGTGGGCACACACTGTACGAACA
CAGATCTCCTTGTTAATGACGTACACACGGCGGAGGCTGCGGGGACAGGGCACGGGAGGTCTCAGCCCC
ACTT

13736.2

ATGGCTGCTGGATTTAGGTGGTAATAGGGGCTGTGGGCCATAAATCTGAAGCCTTGAGAACCTTGGGTCTG
GAGAGCCATGAAGAGGGAAGGAAAAGAGGGCAAGTCCTGAACCTAACCAATGACCTGATGGATTGCTCGA
CCAAGACACAGAAGTGAAGTCTGTGTCTGTGCACTTCCCACAGACTGGAGTTTTTGGTGCTGAATAGAGCC
AGTTGCTAAAAAATTGGGGGTTTGGTGAAGAAATCTGATTGTTGTGTGTATTCAATGTGTGATTTTAAAAATA
AACAGCAACAACAATAAAAACCCTGACTGGCTGTTTTTTCCCTGTATTCTTTACAACTATTTTTTGACCCTCT
GAAAATTATTATACTTCACCTAAATGGAAGACTGCTGTGTTTGTGGAAATTTTGTAATTTTTTAATTTATTTTAT
TCTCTCTCCTTTTTATTTTGCCTGCAGAATCCGTTGAGAGACTAATAAGGCTTAATATTTAATTGATTTGTTTA
ATATGTATATAAAT

13744.2-13696.2

GGCATGCGAGCGCACTCGGCGGACGCAAGGGCGGCGGGGAGCACACGGAGCACTGCAGGCGCCGGGTT
GGGACAGCGTCTTCGCTGCTGCTGGATAGTCGTGTTTTCGGGGATCGAGGATACTCACCAGAAACCGAAA
ATGCCGAAACCAATCAATGTCCGAGTTACCACCATGGATGCAGAGCTGGAGTTTGCAATCCAGCCAAATAC
AACTGGAAAACAGCTTTTTGATCAGGTGGTAAAGACTATCGGCCTCCGGGAAGTGTGGTACTTTGGCCTCC
ACTATGTGGATAATAAAGGATTTCCTACCTGGCTGAAGCTGGATAAGAAGGTGTCTGCCCAGGAGGTCAGG
AAGGAGAATCCCCTCCAGTTCAAGTTCCGGGCCAAaGTTCTACCCTGAAGATGTGGCTGAGGAGCTCATCC
AGGACATCACCCAGAAACTTTTCTTCCTTCAAGTGAAGGAAGGAATCCTTAGCGATGAGATCTACTGCCCCC
CTTGARACTGCCGTGCTCTTGGGGTCCTACGCTTGTGCATGCCAAGTTTGGGGACTACCACCAAGAAG

13746.1&2-13720.1&2

GAAGGAGTCGGGATACTCAGCATTGATGCACCCCAATTTCAAAGCGGCATTCTTCGGCAGGTCTCTGGGAC
AATCTCTAGGGTCACTACCTGGAAACTCGTTAGGGTACAACTGAATGCTGAAAGGAAAGAACACCTGCAGA
ACCGGACAGAAATTCACCCCGGCGATCAGCTGATTGATCTCGGTCGACCAGAAGTCATGGCTAAAGATGAC
GAGGACGTTGTCAATTCCCTGGGCTTTTCGAAGTGAGTCCAGCAGCAGTCTGAGGTATTCGGGCCGGTTAT
GCACCTGGACCACCAGCACCAGCTCCCGGGGGCCCAGGTGCCAGCCTTATCTACATTCCTCAGGGTCTG
ATCAAAGTTCAGCTGGTACACCAGGGACCGGTACCGCAGCGTCAGGTTGTCCGCTCGGGCTGGGGGACC
GCCGGGACCAGGGAAGCCGCCGACACGTTGGAGACCCTGCGGATGCCCACAGCCACAGAGGGGTGGTC
CCCACCGCGGCCGCCGGCACCCCGCGCGGGTTCGGCGTCCAGCAACGGTGGGGCGAGGGCCTCGTTCT
TCCTTTGTCGCCCATTGCTGCTCCAGAGGACGAAGCCGCAGGCGGCCACCACGAGCGTCAGGATTAGCAC
CTTCCGTTTGTAGATGCGGAACCTCATGGTCTCCAGGGCCGGGAGCGCAGCTACAGCTCGAGCGTCGGCG
CCGCCGCTAGGAGCCGCGGCTCGGCTTCGTCTCCGTCCTCTCCATTCAGCACCACGGGTCCCGGAAAAAG
CTCAGCCSCGGTCCCAACCGCACCCTAGCTTCGTTACCTGCGCCTCGCTTG

CAGATTTTTATTTGCAGTCGTCACTGGGGCCGTTTCTTGCTGCTTATTTGTCTGCTAGCCTGCTCTTCCAGC
TGCATGGCCAGGCGCAAGGCCTTGATGACATCTCGCAGGGCTGAGAAATGCTTGGCTTGCTGGGCCAGAG
CAGATTCCGCTTTGTTCACAAAGGTCTCCAGGTCATAGTCTGGCTGCTCGGTCATCTCAGAGAGCTCAAGC
CAGTCTGGTCCTTGCTGTATGATCTCCTTGAGCTCTTCCATAGCCTTCTCCTCCAGCTCCCTGATCTGAGTC
ATGGCTTCGTTAAAGCTGGACATCTGGGAAGACAGTTCCTCCTCTTCCTTGGATAAATTGCCTGGAATCAGC
GCCCCGTTAGAGCAGGCTTCCATCTCTTCTGTTTCCATTTGAATCAACTGCTCTCCACTGGGCCCACTGTG
GGGGCTCAGCTCCTTGACCCTGCTGCATATCTTAAGGGTGTTTAAAGGATATTCACAGGAGCTTATGCCTG
GT 14347.2

CTCCTCTTGGTACATGAACCCAAGTTGAAAGTGGACTTAACAAAGTATCTGGAGAACCAAGCATTCTGCTTT
GACTTTGCATTTGATGAAACAGCTTCGAATGAAGTTGTCTACAGGTTCACAGCAAGGCCACTGGTACAGACA
ATCTTTGAAGGTGGAAAAGCAACTTGTTTTGCATATGGCCAGACAGGAAGTGGCAAGACACATACTATGGG
CGGAGACCTCTCTGGGAAAGCCCAGAATGCATCCAAAGGGATCTATGCCATGGCCTTCCGGGACGTCTTC
TTCTGAAGAATCAACCCTGCTACCGGAAGTTGGGCCTGGAAGTCTATGTGACATTCTTCGAGATCTACAATG
GGAAGCTGTTTGACCTGCTCAACAAGAAGGCCAAGCTTGCGCGTGCTGGAAGACGGCAAGCAACAGGTGC
AAGTGGTGGGGGCTTGCAGGAACATCTGGNTAACTCTGCTTGATGATGGCANTCAAGATGATCGACATGG
GCAGCGCCTGCAGA 14348.2&14350.1&2

TCCCGAATTCAAGCGACAAATTGGAWAGTGAAATGGAAGATGCCTATCATGAACATCAGGCAAATCTTTTG
CGCCAAGATCTGATGAGACGACAGGAAGAATTAAGACGCATGGAAGAACTTCACAATCAAGAAATGCAGAA
ACGTAAAGAAATGCAATTGAGGCAAGAGGAGGAACGACGTAGAAGAGAGGAAGAGATGATGATTCGTCAA
CGTGAGATGGAAGAACAAATGAGGCGCCAAAGAGAGGAAAGTTACAGCCGAATGGGCTACATGGATCCAC
GGGAAAGAGACATGCGAATGGGTGGCGGAGGAGCAATGAACATGGGAGATCCCTATGGTTCAGGAGGCC
AGAAATTTCCACCTCTAGGAGGTGGTGGTGGCATAGGTTATGAAGCTAATCCTGGCGTTCCACCAGCAACC
ATGAGTGGTTCCATGATGGGAAGTGACATGCGTACTGAGCGCTTTGGGCAGGGAGGTGCGGGGCCTGTG
GGTGGACAGGGTCCTAGAGGAATGGGGCCTGGAACTCCAGCAGGATATGGTAGAGGGAGAGAAGAGTAC
GAAGGC 14349.1&2

TTCGTGAAGACCCTGACTGGTAAGACCATCACTCTCGAAGTGGAGCCCGAGTGACACCATTGAGAATGTCA
AGGCAAAGATCCAAGACAAGGAAGGCATCCCTCCTGACCAGCAKAGGTTGATCTTTGCTGGGAAACAGCTG
GAAGATGGACGCACCCTGTCTGACTACAACATCCAGAAAGAGTCCACCCTGCACCTGGTGCTCCGTCTCAG
AGGTGGGATGCAAATCTTCGTGAAGACCCTGACTGGTAAGACCATCACCCTCGAGGTGGAGCCCAGTGAC
ACCATCGAGAATGTCAAGGCAAAGATCCAAGATAAGGAAGGCATCCCTCCTGATCAGCAGAGGTTGATCTT
TGCTGGGAAACAGCTGGAAGATGGACGCACCCTGTCTGACTACAACATCCAGAAAGAGTCCACTCTGCACT
TGGTCCTGCGCTTGAGGGGGGGTGTCTAAGTTTCCCCTTTTAAGGTTTCAACAAATTTCATTGCACTTTCCT
TTCAATAAAGTTGTTGCATTC

GCGCGGGTGCGTGGGCCACTGGGTGACCGACTTAGCCTGGCCAGACTCTCAGCACCTGGAAGCGCCCCG
AGAGTGACAGCGTGAGGCTGGGAGGGAGGACTTGGCTTGAGCTTGTTAAACTCTGCTCTGAGCCTCCTTG
TCGCCTGCATTTAGATGGCTCCCGCAAAGAAGGGTGGCGAGAAGAAAAAGGGCCGTTCTGCCATCAACGA
AGTGGTAACCCGAGAATACACCATCAACATTCACAAGCGCATCCATGGAGTGGGCTTCAAGAAGCGTGCAC
CTCGGGCACTCAAAGAGATTCGGAAATTTGCCATGAAGGAGATGGGAACTCCAGATGTGCGCATTGACACC
AGGCTCAACAAAGCTGTCTGGGCCAAAGGAATAAGGAATGTGCCATACCGAATCCGTGTGCGGCTGTCCA
GAAAACGTAATGAGGATGAAGATTCACCAAATAAGCTATATACTTTGGTTACCTATGTACCTGTTACCACTTT
CAAAAATCTACAGACAGTCAATGTGGATGAGAACTAATCGCTGATCGT

14353.1

AATTCTTTATTTAAATCAACAAACTCATCTTCCTCAAGCCCCAGACCATGGTAGGCAGCCCTCCCTCTCCAT
CCCCTCACCCCACCCCTTAGCCACAGTGAAGGGAATGGAAAATGAGAAGCCACGAGGGCCCCTGCCAGG
GAAGGCTGCCCCAGATGTGTGGTGAGCACAGTCAGTGCAGCTGTGGCTGGGGCAGCAGCTGCCACAGGC
TCCTCCCTATAAATTAAGTTCCTGCAGCCACAGCTGTGGGAGAAGCATACTTGTAGAAGCAAGGCCAGTCC
AGCATCAGAAGGCAGAGGCAGCATCAGTGACTCCCAGCCATGGAATGAACGGAGGACACAGAGCTCAGAG
ACAGAACAGGCCAGGGGGAAGAAGGAGAGACAGAATAGGCCAGGGCATGGCGGTGAGGGA

14353.2

TGATGAATCTGGGTGGGCTGGCAGTAGCCCGAGATGATGGGCTCTTCTCTGGGGATCCCAACTGGTTCCC
TAAGAAATCCAAGGAGAATCCTCGGAACTTCTCGGATAACCAGCTGCAAGAGGGCAAGAACGTGATCGGGT
TACAGATGGGCACCAACCGCGGGGCGTCTCANGCAGGCATGACTGGCTACGGGATGCCACGCCAGATCC
TCTGATCCCACCCCAGGCCTTGCCCCTGCCCTCCCACGAATGGTTAATATATATGTAGATATATATTTTAGC
AGTGACATTCCCAGAGAGCCCCAGAGCTCTCAAGCTCCTTTCTGTCAGGGTGGGGGGTTCAAGCCTGTCC
TGTCACCTCTGAAGTGCCTGCTGGCATCCTCTCCCCCATGCTTACTAATACATTCCCTTCCCCATAGCC

17182.1&2

AGCGGAGCTCCCTCCCCTGGTGGCTACAACCCACACACGCCAGGCTCAGGCATCGAGCAGAACTCCAGC
GACTGGGTAACCACTGACATTCAGGTGAAGGTGCGGGACACCTACCTGGATACACAGGTGGTGGGACAGA
CAGGTGTCATCCGCAGTGTCACGGGGGGCATGTGCTCTGTGTACCTGAAGGACAGTGAGAAGGTTGTCAG
CATTTCCAGTGAGCACCTGGAGCCTATCACCCCCACCAAGAACAACAAGGTGAAAGTGATCCTGGGCGAG
GATCGGGAAGCCACGGGCGTCCTACTGAGCATTGATGGTGAGGATGGCATTGTCCGTATGGACCTTGATG
AGCAGCTCAAGATCCTCAACCTCCGCTTCCTGGGGAAGCTCCTGGAAGCCTGAAGCAGGCAGGGCCGGTG
GACTTCGTCGGATGAAGAGTGATCCTCCTTCCTTCCCTGGCCCTTGGCTGTGACACAAGATCCTCCTGCAG
GGCTAGGCGGATTGTTCTGGATTTCCTTTTGTTTTTCCTTTTAGGTTTCCATCTTTTCCCTCCCTGGTGCTCA
TTGGAATCTGAGTAGAGTCTGGGGGAGGGTCCCCACCTTCCTGTACCTCCTCCCCACAGCTTGCTTTTGTT
GTACCGTCTTTCAATAAAAAGAAGCTGTTTGGTCTA

GGTTCACAGCACTGCTGCTTGTGTGTTGCCGGCCAGGAATTCCAGGCTCACAAGGCTATCTTAGCAGCTCG
TTCTCCGGTTTTTAGTGCCATGTTTGAACATGAAATGGAGGAGAGCAAAAAGAATCGAGTTGAAATCAATGA
TGTGGAGCCTGAAGTTTTTAAGGAAATGATGTGCTTCATTTACACGGGGAAGGCTCCAAACCTCGACAAAAT
GGCTGATGATTTGCTGGCAGCTGCTGACAAGTATGCCCTGGAGCGCTTAAAGGTCATGTGTGAGGATGCC
CTCTGCAGTAACCTGTCCGTGGAGAACGCTGCAGAAATTCTCATCCTGGCCGACCTCCACAGTGCAGATCA
GTTGAAAACTCAGGCAGTGGATTTCATCAACTATCATGCTTCGGATGTCTTGGAGACCTCTTGGG

17186.1&2

TCGTAGCCATTTTTCTGCTTCTTTGGAGAATGACGCCACACTGACTGCTCATTGTCGTTGGTTCCATGCCAA
TTGGTGAAATAGAACCTCATCCGGTAGTGGAGCCGGAGGGACATCTTGTCATCAACGGTGATGGTGCGATT
TGGAGCATACCAGAGCTTGGTGTTCTCGCCATACAGGGCAAAGAGGTTGTGACAAAGAGGAGAGATACGG
CATGCCTGTGCAGCCCTGATGCACAGTTCCTCTGCTGTGTACTCTCCACTGCCCAGCCGGAGGGGCTCCC
TGTCCGACAGATAGAAGATCACTTCCACCCCTGGCTTG

17187.1&2

TGGCACACTGCTCTTAAGAAACTATGAWGATCTGAGATTTTTTTGTGTATGTTTTTGACTCTTTTGAGTGGTA
ATCATATGTGTCTTTATAGATGTACATACCTCCTTGCACAAATGGAGGGGAATTCATTTTCATCACTGGGAGT
GTCCTTAGTGTATAAAAACCATGCTGGTATATGGCTTCAAGTTGTAAAAATGAAAGTGACTTTAAAAGAAAAT
AGGGGATGGTCCAGGATCTCCACTGATAAGACTGTTTTTAAGTAACTTAAGGACCTTTGGGTCTACAAGTAT
ATGTGAAAAAAATGAGACTTACTGGGTGAGGAAATTCATTGTTTAAAGATGGTCGTGTGTGTGTGTGTGT
GTGTGTGTTGTGTTGTGTTTTGTTTTTAAGGGAGGGAATTTATTATTTACCGTTGCTTGAAATTACTGKGTA
AATATATGTYTGATAATGATTTGCTYTTTGVCMACTAAAATTAGGVCTGTATAAGTWCTARATGCMTCCCTG
GGKGTTGATYTTCCMAGATATTGATGATAMCCCTTAAAATTGTAACCYGCCTTTTTCCCTTTGCTYTCMATTA
AAGTCTATTCMAAAG

17191.1&89.1

GGGGGTAGGCTCTTTATTAGACGGTTATTGCTGTACTACAGGGTCAGAGTGCAGTGTAAGCAGTGTCAGAG
GCCCGCGTTCAGCCCAAGAATGTGGATTTTCTCTCCCTATTGATCACAGTGGGTGGGTTTCTTCAGAAAAG
CCCCAGAGGCAGGGACCAGTGAGCTCCAAGGTTAGAAGTGGAACTGGAAGGCTTCAGTCACATGCTGCTT
CCACGCTTCCAGGCTGGGCAGCAAGGAGGAGATGCCCATGACGTGCCAGGTCTCCCCATCTGACACCAGT
GAAGTCTGGTAGGACAGCAGCCGCACGCCTGCCTCTGCCAGGAGGCCAATCATGGTAGGCAGCATTGCAG
GGTCAGAGGTCTGAGTCCGGAATAGGAGCAGGGGCAGGTCCCTGCGGAGAGGCACTTCTGGCCTGAAGA
CAGCTCCATTGAGCCCCTGCAGTACAGGYGTAGTGCCTTGGACCAAGCCCACAGCCTGGTAAGGGGCGCC
TGCCAGGGCCACGGCCAGGAGGCA

TAATTTCTTAGTCGTTTGGAATCCTTAAGCATGCAAAAGCTTTGAACAGAAGGGTTCACAAAGGAACCAGGG
TTGTCTTATGGCATCCAGTTAAGCCAGAGCTGGGAATGCCTCTGGGTCATCCACATCAGGAGCAGAAGCAC
TTGACTTGTCGGTCCTGCTGCCACGGTTTGGGCGCCCACCACGCCCACGTCCACCTCGTCCTCCCCTGCC
GCCACGTCCTGGGCGGCCAAGGTCTCCAAAATTGATCTCCAGCTGAGACGTTATATCATTTGCTGGCTTCC
GGAAATGATGGTCCATAACCGAATCTTCAGCATGAGCCTCTTCACTCTTTGATTTATGAAGAACAAATCCCTT
CTTCCACTGCCCATCAGCACCTTCATTTGGTTTTCGGATATTAAATTCTACTTTTGCCCGGTCCTTATTTTGA
ATAGCCTTCCACTCATCCAAAGTCATCTCTTTTGGACCCTCCTCTTTTACCTCTTCAACTTCATTCTCCTTATT
TTCAGTGTCTGCCACTGGATGATGTTCTTCACCTTCAGGTGTTTCCTCAGTCACATTTGATTGATCCAAGTCA
GTTAATTCGTCTTTGACAGTTCCCCAGTTGTGAGATCCGCTACCTCCACGTTTGTCCTCGTGCTTCAGGCCA
GATCTATCACTTCCACTATGCCTATCAAATTCACGTTTGCCACGAGAATCAAATCCATCTCCTCGGCCCATT
CCACGTCCACGGCCCCCTCGACCTCTTCCAAGACCACCACGACCTCGAATAGGTCGGTCAATAATCGGTCT
ATCAACTGAAAATTCGCCTCCTTCACCCTTTTCTTCAAGTGGCTTTTCGAATCTTCGTTCACGAGGTGGTCG
CCTTTCTGGTCTTCTATCAATTATTTTCCCTTCACCCTGAAGTTGTTGATCAGGTCTTCTTCCAACTCGTGC

17193

AAGCGGATGGACCTGAGTCAGCCGAATCCTAGCCCCTTCCCTTGGGCCTGCTGTGGTGCTCGACATCAGT
GACAGACGGAAGCAGCAGACCATCAAGGCTACGGGAGGCCCGGGGCGCTTGCGAAGATGAAGTTTGGCT
GCCTCTCCTTCCGGCAGCCTTATGCTGGCTTTGTCTTAAATGGAATCAAGACTGTGGAGACGCGCTGGCGT
CCTCTGCTGAGCAGCCAGCGGAACTGTACCATCGCCGTCCACATTGCTCACAGGGACTGGGAAGGCGATG
CCTGTCGGGAGCTGCTGGTGGAGAGACTCGGGATGACTCCTGCTCAGATTCAGGCCTTGCTCAGGAAAGG
GGAAAAGTTTGGTCGAGGAGTGATAGCGGGACTCGTTGACATTGGGGAAACTTTGCAATGCCCCGAAGAC
TTAACTCCCGATGAGGTTGTGGAACTAGAAAATCAAGCTGCACTGACCAACCTGAAGCAGAAGTACCTGAC
TGTGATTTCAAACCCCAGGTGGTTACTGGAGCCCATACCTAGGAAAGGAGGCAAGGATGTATTCCAGGTAG
ACATCCCAGAGCACCTGATCCCTTTGGGGCATGAAGTGTGACAAGTGTGGGCTCCTGAAAGGAATGTTCCR
GAGAAACCAGCTAAATCATGGCACCTTCAATTTGCCATCGTGACGCAGACCTGTATAAATTAGGTTAAAGAT
GAATTTCCACTGCTTTGGAGAGTCCCACCCACTAAGCACTGTGCATGTAAACAGGTTCCTTTGCTCAGATGA
AGGAAGTAGGGGGTGGGGCTTTCCTTGTGTGATGCCTCCTTAGGCACACAGGCAATGTCTCAAGTACTTTG
ACCTTAGGGTAGAAGGCAAAGCTGCCAGTAAATGTCTCAGCATTGCTGCTAATTTTGGTCCTGCTAGTTTCT
GGATTGTACAAATAAATGTGTTGTAGATGA

*Fig. 15U*

16443.1.edit

TCGAGCGGCCGCCCGGGCAGGTGTCGGAGTCCAGCACGGGAGGCGTGGTCTTGTAGTTGTTCTCCGGCT
GCCCATTGCTCTCCCACTCCACGGCGATGTCGCTGGGATAGAAGCCTTTGACCAGGCAGGTCAGGCTGAC
CTGGTTCTTGGTCATCTCCTCCCGGGATGGGGGCAGGGTGTACACCTGTGGTTCTCGGGGCTGCCCTTTG
GCTTTGGAGATGGTTTTCTCGATGGGGGCTGGGAGGGCTTTGTTGGAGACCTTGCACTTGTACTCCTTGCC
ATTCAACCAGTCCTGGTGCANGACGGTGAGGACGCTNACCACACGGTACGNGCTGGTGTACTGCTCCTCC
CGCGGCTTTGTCTTGGCATTATGCACCTCCACGCCGTCCACGTACCAATTGAACTTGACCTCAGGGTCTTC
GTGGCTCACGTCCACCACCACGCATGTAACCTCAAANCTCGGNCGCGANCACGC

16443.2.edit

AGCGTGGTCGCGGCCGAGGTCTGAGGTTACATGCGTGGTGGTGGACGTGAGCCACGAAGACCCTGAGGT
CAAGTTCAACTGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAGCC
CCGAGAACCACAGGTGTACACCCTGCCCCCATCCCGGGAGGAGATGACCAAGAACCAGGTCAGCCTGACC
TGCCTGGTCAAAGGCTTCTATCCCAGCGACATCGCCCGTGGAGTGGGAGAGCAATGGGCAGCCGGAGAA
CAACTACAAGACCACGCCTCCCGTGCTGGACTCCGACACCTGCCGGGCGGCCGCTCGA

16444.2.edit

AGCGTGGTTNCGGCCGAGGTCCCAACCAAGGCTGCANCCTGGATGCCATCAAAGTCTTCTGCAACATGGA
GACTGGTGAGACCTGCGTGTACCCCACTCAGCCCAGTGTGGCCCAGAAGAACTGGTACATCAGCAAGAAC
CCCAAGGACAAGAGGCATGTCTGGTTCGGCGAGAGCATGACCGATGGATTCCAGTTCGAGTATGGCGGCC
AGGGCTCCGACCCTGCCGATGTGGACCTGCCCGGCGGNCGCTCGA

16445.1.edit

AGCGTGGTCGCGGCCGAGGTCAAGAACCCCGCCCGCACCTGCCGTGACCTCAAGATGTGCCACTCTGACT
GGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGCCCAGAAGAACTGGTACATCAGCA
AGAACCCCAAGGACAAGAGGCATGTCTGGTTCGGCGAGAGCATGACCGATGGATTCCAGTTCGAGTATGG
CGGCCAGGGCTCCGACCCTGCCGATGTGGACCTGCCCGGGCGGCCGCTCGA

*Fig. 15V*

16445.2.edit

TCGAGCGGTCGCCCGGGCAGGTCCACATCGGCAGGGTCGGAGCCCTGGCCGCCATACTCGAACTGGAAT
CCATCGGNCATGCTCTCGCCGAACCAGACATGCCTCTTGNCCTTGGGGTTCTTGCTGATGTACCAGNTCTT
CTGGGCCACACTGGGCTGAGTGGGGTACACGCAGGTCTCACCANTCTCCATGTTGCANAAGACTTTGATG
GCATCCAGGTTGCAGCCTTGGTTGGGGTCAATCCAGTACTCTCCACTCTTCCAGACAGAGTGGCACATCTT
GAGGTCACGGCAGGTGCGGGCGGGGTTCTTGACCTCGGTCGCGACCACGCT

16446.1.edit

TCGAGCGGCCGCCCGGGCAGGTCCTCCTCAGAGCGGTAGCTGTTCTTATTGCCCCGGCAGCCTCCATAGA
TNAAGTTATTGCANGAGTTCCTCTCCACGTCAAAGTACCAGCGTGGGAAGGATGCACGGCAAGGCCCAGT
GACTGCGTTGGCGGTGCAGTATTCTTCATAGTTGAACATATCGCTGGAGTGGACTTCAGAATCCTGCCTTCT
GGGAGCACTTGGGACAGAGGAATCCGCTGCATTCCTGCTGGTGGACCTCGGCCGCGACCACGCT

16446.2.edit

AGCGTGGTCGCGGCCGAGGTCCACCAGCAGGAATGCAGCGGATTCCTCTGTCCCAAGTGCTCCCAGAAG
GCAGGATTCTGAAGACCACTCCAGCGATATGTTCAACTATGAAGAATACTGCACCGCCAACGCAGTCACTG
GGCCTTGCCGTGCATCCTTCCCACGCTGGTACTTTGACGTGGAGAGGAACTCCTGCAATAACTTCATCTAT
GGAGGCTGCCGGGGCAATAAGAACAGCTACCGCTCTGAGGAGGACCTGCCCGGGCGGCCGCTCGA

16447.1.edit

TCGAGCGGCCGCCCGGGCAGGTCCACATCGGCAGGGTCGGAGCCCTGGCCGCCATACTCGAACTGGAAT
CCATCGGTCATGCTCTCGCCGAACCAGACATGCCTCTTGTCCTTGGGGTTCTTGCTGATGTACCAGTTCTT
CTGGGCCACACTGGGCTGAGTGGGGTACACGCAGGTCTCACCAGTCTCCATGTTGCAGAAGACTTTGATG
GCATCCAGGTTGCAGCCTTGGTTGGGGTCAATCCAGTACTCTCCACTCTTCCAGCCAGAATGGCACATCTT
GAGGTCACGGCANGTGCGGGCGGGGTTCTTGACCTCGGCCGCGACCACGCT

*Fig. 15W*

16447.2.edit

AGCGTGGTCGCGGCCGAGGTCAAGAAACCCCGCCCGCACCTGCCGTGACCTCAAGATGTGCCACTCTGG
CTGGAAGAGTGGAGAGTACTGGATTGACCCCAACCAAGGCTGCAACCTGGATGCCATCAAAGTCTTCTGCA
ACATGGAGACTGGTGAGACCTGCGTGTACCCCACTCAGCCCAGTGTGGCCCAGAAGAACTGGTACATCAG
CAAGAACCCCAAGGACAAGAGGCATGTCTGGCTCGGCGAGAGCATGACCGATGGATTCCAGTTCGAGTAT
GGCGGCCAGGGCTCCGACCCTGCCGATGTGGACCTGCCCGGGCGGCCGCTCGA

16449.1.edit

AGCGTGGTCGCGGCCGAGGTCCTGTCAGAGTGGCACTGGTAGAAGNTCCAGGAACCCTGAACTGTAAGG
GTTCTTCATCAGTGCCAACAGGATGACATGAAATGATGTACTCAGAAGTGTCCTGNAATGGGGCCCATGAN
ATGGTTGNCTGAGAGAGAGCTTCTTGTCCTACATTCGGCGGGTATGGTCTTGGCCTATGCCTTATGGGGGT
GGCCGTTGNGGGCGGTGNGGTCCGCCTAAAACCATGTTCCTCAAAGATCATTTGTTGCCCAACACTGGGTT
GCTGACCANAAGTGCCAGGAAGCTGAATACCATTTCCAGTGTCATACCCAGGGTGGGTGACGAAAGGGGT
CTTTTGAACTGTGGAAGGAACATCCAAGATCTCTGNTCCATGAAGATTGGGGTGTGGAAGGGTTACCAGTT
GGGGAAGCTCGCTGTCTTTTTCCTTCCAATCANGGGCTCGCTCTTCTGAATATTCTTCAGGGCAATGACATA
AATTGTATATTCGGTTCCCGGTTCCAGGCCAG

16450.1.edit

TCGAGCGGCCGCCCGGGCAGGTCCACCACACCCAATTCCTTGCTGGTATCATGGCAGCCGCCACGTGCCA
GGATTACCGGCTACATCATCAAGTATGAGAAGCCTGGGTCTCCTCCCAGAGAAGTGGTCCCTCGGCCCCG
CCCTGGTGTCACAGAGGCTACTATTACTGGCCTGGAACCGGGAACCGAATATACAATTTATGTCATTGCCC
TGAAGAATAATCAGAAGAGCGAGCCCCTGATTGGAAGGAAAAAGACAGACGAGCTTCCCCAACTGGTAACC
CTTCCACACCCCAATCTTCATGGACCAGAGATCTTGGATGTTCCTTCCACAGTTCAAAAGACCCCTTTCGTC
ACCCACCCTGGGTATGACACTGGAAATGGTATTCAGCTTCCTGGCACTTCTGGTCAGCAACCCAGTGTTGG
GCAACAAATGATCTTTGANGAACATGGNTTTAGGCGGACCACACCGGCCACAACGGGCACCCCCATAAGG
CATAGGCCAAGAACATACCCGNCGAATGTAGGACAAGAAGCTCTNTCTCANACAANCATCTCATGGGCCCC
ATTCCANGACACTTCTGAGTACATCANTTCATGGCATCCTGGTGGCACTGATAAAAACCCTTACAGTTA

16450.2.edit

AGCGTGGTCGCGGGCGAGGTCCTGTCAGAGTGGCACTGGTAGAAGTTCCAGGAACCCTGAACTGTAAGG
GTTCTTCATCAGTGCCAACAGGATGACATGAAATGATGTACTCAGAAGTGTCCTGGAATGGGGCCCATGAG
ATGGTTGTCTGAGAGAGAGCTTCTTGTCCTACATTCGGCGGGTATGGTCTTGGCCTATGCCTTATGGGGGT
GGCCGTTGTGGGCGGTGTGGTCCGCCTAAAACCATGTTCCTCAAAGATCATTTGTTGCCCAACACTGGGTT
GCTGACCAGAAGTGCCAGGAAGCTGAATACCATTTCCAGTGTCATACCCAGGGTGGGTGACGAAAGGGGT
CTTTTGAACTGTGGAAGGAACATCCAAGATCTCTGGTCCATGAAGATTGGGGTGTGGAAGGGTTACCAGTT
GGGGAAGCTCGTCTGTCTTTTTCCTTCCAATCANGGGCTCGCTCTTCTGATTATTCTTCAGGGCAATGACAT
AAATTGTATATTCGGNTCCCGGGTNCAGCCAATAATAATAACCCTCTGTGACACCANGGCGGGGCCGAAGG
ANCACT

*Fig. 15X*

16451.1.edit

```
AGCGTGGTCGCGGCCGAGGTCCTCACCAGAGGTACCACCTACAACATCATAGTGGAGGCACTGAAAGACC
AGCAGAGGCATAAGGTTCGGGAAGAGGTTGTTACCGTGGGCAACTCTGTCAACGAAGGCTTGAACCAACC
TACGGATGACTCGTGCTTTGACCCCTACACAGTTTCCCATTATGCCGTTGGAGATGAGTGGGAACGAATGT
CTGAATCAGGCTTTAAACTGTTGTGCCAGTGCTTANGCTTTGGAAGTGGTCATTTCAGATGTGATTCATCTA
GATGGTGCCATGACAATGGTGTGAACTACAAGATTGGAGAGAAGTGGGACCGTCAGGGAGAAAATGGACC
TGCCCGGGCGGCCGCTCGA
```

16451.2.edit

```
TCGAGCGGCCGCCCGGGCAGGTCCATTTTCTCCCTGACGGTCCCACTTCTCTCCAATCTTGTAGTTCACAC
CATTGTCATGGCACCATCTAGATGAATCACATCTGAAATGACCACTTCCAAAGCCTAAGCACTGGCACAACA
GTTTAAAGCCTGATTCAGACATTCGTTCCCACTCATCTCCAACGGCATAATGGGAAACTGTGTAGGGGTCAA
AGCACGAGTCATCCGTAGGTTGGTTCAAGCCTTCGNTGACAGAGTTGCCCACGGTAACAACCTCTTCCCGA
ACCTTATGCCTCTGCTGGTCTTTCAGTGCCTCCACTATGATGTTGTAGGTGGTACCTCTGGTGAGGACCTC
GGCCGCGACCACGCT
```

16452.1.edit

```
AGCGTGGCCGCGGCCGAGGTCCATTGGCTGGAACGGCATCAACTTGGAAGCCAGTGATCGTCTCAGCCTT
GGTTCTCCAGCTAATGGTGATGGNGGTCTCAGTAGCATCTGTCACACGAGCCCTTCTTGGTGGGCTGACAT
TCTCCAGAGTGGTGACAACACCCTGAGCTGGTCTGCTTGTCAAAGTGTCCTTAAGAGCATAGACACTCACT
TCATATTTGGCGNCCACCATAAGTCCTGATACAACCACGGAATGACCTGTCAGGAAC
```

16452.2.edit

```
TCGAGCGGCCGCCCGGGCAGGTCCTCAGACCGGGTTCTGAGTACACAGTCAGTGTGGTTGCCTTGCACGA
TGATATGGAGAGCCAGCCCCTGATTGGAACCCAGTCCACAGCTATTCCTGCACCAACTGACCTGAAGTTCA
CTCAGGTCACACCCACAAGCCTGAGCGCCCAGTGGACACCACCCAATGTTCAGCTCACTGGATATCGAGT
GCGGGTGACCCCCAAGGAGAAGACCGGACCAATGAAAGAAATCAACCTTGCTCCTGACAGCTCATCCGTG
GTTGTATCAGGACTTATGGCGGCCACCAAATATGAAGTGAGTGTCTATGCTCTTAAGGACACTTTGACAAGC
AGACCAGCTCAGGGTGTTGTCACCACTCTGGAGAATGTCAGCCCACCAAGAAGGGCTCGTGTGACAGATG
CTACTGAGACCACCATCACCATTAGCTGGAGAACCAAGACTGAGACGATCACTGGCTTCCAAGTTGATGCC
GTTCCAGCCAATGGACCTCGGCCGCGACCACGCTT
```

*Fig. 15Y*

16453.1.edit

AGCGTGGTCGCGGCCGAGGTCTGGCCGAACTGCCAGTGTACAGGGAAGATGTACATGTTATAGNTCTTCT
CGAAGTCCCGGGCCAGCAGCTCCACGGGGTGGTCTCCTGCCTCCAGGCGCTTCTCATTCTCATGGATCTT
CTTCACCCGCAGCTTCTGCTTCTCAGTCAGAAGGTTGTTGTCCTCATCCCTCTCATACAGGGTGACCAGGA
CGTTCTTGAGCCAGTCCCGCATGCGCAGGGGGAATTCGGTCAGCTCAGAGTCCAGGCAAGGGGGGATGT
ATTTGCAAGGCCCGATGTAGTCCAAGTGGAGCTTGTGGCCCTTCTTGGTGCCCTCCAAGGTGCACTTTGTG
GCAAAGAAGTGGCAGGAAGAGTCGAAGGTCTTGTTGTCATTGCTGCACACCTTCTCAAACTCGCCAATGGG
GGCTGGGCAGACCTGCCCGGGCGGCCGCTCGA

16453.2.edit

TCGAGCGGCCGCCCGGGCAGGTCTGCCCAGCCCCCATTGGCGAGTTTGAGAAGGNGTGCAGCAATGACA
ACAAGACCTTCGACTCTTCCTGCCACTTCTTTGCCACAAAGTGCACCCTGGAGGGCACCAAGAAGGGCCAC
AAGCTCCACCTGGACTACATCGGGCCTTGCAAATACATCCCCCCTTGCCTGGACTCTGAGCTGACCGAATT
CCCCCTGCGCATGCGGGACTGGCTCAAGAACGTCCTGGTCACCCTGTATGAGAGGGATGAGGACAACAAC
CTTCTGACTGAGAAGCANAAGCTGCGGGTGAAGAANATCCATGAGAATGANAAGCGCCTGNAGGCANGAG
ACCACCCCGTGGAGCTGCTGGCCCGGGACTTCGAGAAGAACTATAACATGTACATCTTCCCTGTACACTGG
CAGTTCGGCCAGACCTCGGCCGCGACCACGCT

16454.1.edit

AGCGTGGNTGCGGACGACGCCCACAAAGCCATTGTATGTAGTTTTANTTCAGCTGCAAANAATACCNCCAG
CATCCACCTTACTAACCAGCATATGCAGACA

16454.2.edit

TCGAGCGGTCGCCCGGGCAGGTCTGGGCGGATAGCACCGGGCATATTTTGGAATGGATGAGGTCTGGCA
CCCTGAGCAGCCCAGCGAGGACTTGGTCTTAGTTGAGCAATTTGGCTAGGAGGATAGTATGCAGCACGGT
TCTGAGTCTGTGGGATAGCTGCCATGAAGNAACCTGAAGGAGGCGCTGGCTGGTANGGGTTGATTACAGG
GCTGGGAACAGCTCGTACACTTGCCATTCTCTGCATATACTGGNTAGTGAGGCGAGCCTGGCGCTCTTCTT
TGCGCTGAGCTAAAGCTACATACAATGGCTTTGNGGACCTCGGCCGCGACCACGCTT

*Fig. 15Z*

16455.1.edit

TCGAGCGGCCGCCCGGGCAGGTCCATTTTCTCCCTGACGGTCCCACTTCTCTCCAATCTTGTAGTTCACAC
CATTGTCATGACACCATCTAGATGAATCACATCTGAAATGACCACTTCCAAAGCCTAAGCACTGGCACAACA
GTTTAAAGCCTGATTCAGACATTCGTTCCCACTCATCTCCAACGGCATAATGGGAAACTGTGTAGGGGTCAA
AGCACGAGTCATCCGTAGGTTGGTTCAAGCCTTCGTTGACAGAAGTTGCCCACGGTAACAACCTCTTCCCG
AACCTTATGCCTCTGCTGGTCTTTCAAGTGCCTCCACTATGATGTTGTAGGTGGCACCTCTGGTGAGGACC
TCGGCCGCGACCACGCT

16455.2.edit

AGCGTGGTTTGCGGCCGAGGTCCTCACCANAGGTGCCACCTACAACATCATAGTGGAGGCACTGAAAGAC
CAGCAGAGGCATAAGGTTCGGGAAGAGGTTGTTACCGTGGGCAACTCTGTCAACGAAGGCTTGAACCAAC
CTACGGATGACTCGTGCTTTGACCCCTACACAGNTTCCCATTATGCCGTTGGAGATGAGTGGGAACGAATG
TCTGAATCAGGCTTTAAACTGTTGTGCCAGTGCTTANGCTTTGGAAGTGGTCATTTCAGATGTGATTCATCT
ANATGGTGTCATGACAATGGTGNGAACTACAAGATTGGAGAGAAGTGGNACCGTCAGGGGANAAAATGGA
CCTGCCCGGGCGGCNCGCTCGA

16456.1.edit

AGCGTGGTCGCGGCCGAGGTCTGGCTTNCTGCTCANGTGATTATCCTGAACCATCCAGGCCAAATAAGCG
CCGGCTATGCCCCTGNATTGGATTGCCACACGGCTCACATTGCATGCAAGTTTGCTGAGCTGAAGGAAAAG
ATTGATC

16456.2.edit

TCGAGCGGCCGCCCGGGCAGGTCCAATTGAAACAAACAGTTCTGAGACCGTTCTTCCACCACTGATTAAGA
GTGGGGNGGCGGGTATTAGGGATAATATTCATTTAGCCTTCTGAGCTTTCTGGGCAGACTTGGTGACCTTG
CCAGCTCCAGCAGCCTTCTGGTCCACTGCTTTGATGACACCCACCGCAACTGTCTGTCTCATATCACGAAC
AGCAAAGCGACCCAAAGGTGGATAGTCTGAGAAGCTCTCAACACACATGGGCTTGCCAGGAACCATATCAA
CAATGGGCAGCATCACCAGACTTCAAGAATTTAAGGGCCATCTTCCAGCTTTTTACCAGAACGGCGATCAAT
CTTTTCCTTCAGCTCAGCAAACTTGCATGCAATGTGAGCCG

*Fig. 15AA*

16459.1.edit

```
TCGAGCGGCCGCCCGGGCAGGTCCAGAGGGCTGTGCTGAAGTTTGCTGCTGCCACTGGAGCCACTCCAA
TTGCTGGCCGCTTCACTCCTGGAACCTTCACTAACCAGATCCAGGCAGCCTTCCGGGAGCCACGGCTTCTT
GTGGNTACTGACCCCAGGGCTGACCACCAGCCTCTCACGGAGGCATCTTATGTTAACCTACCTACCATTGC
GCTGTGTAACACAGATTCTCCTCTGCGCTATGTGGACATTGCCATCCCATGCAACAACAAGGGAGCTCACT
CAGNGGGGTTTGATGTGGTGGATGCTGGCTCGGGAAGTTCTGCGCATGCGTGGCACCATTTCCCGTGAAC
ACCCATGGGANGNCATGCCTGATCTGGACTTCTACAGAGATCCTGAAGAGATTGAAAAAGAAGAACAGGCT
GNTTGCTGANAAAGCAAGTGACCAAGGANGAAATTTCANGGGTGAAANGGACTGCTCCCGCTCCTGAATTC
ACTGCTACTCAACCTGANGNTGCAGACTGGTCTTGAAGGNGNACANGGGCCCTCTGGGCCTATTTAAGCA
NCTTCGGTCGCGAACACGNT
```

16459.2.edit

```
AGCGTGNGTCGCGGCCGAGGTGCTGAATAGGCACAGAGGGCACCTGTACACCTTCAGACCAGTCTGCAAC
CTCAGGCTGAGTAGCAGTGAACTCAGGAGCGGGAGCAGTCCATTCACCCTGAAATTCCTCCTTGGNCACT
GCCTTCTCAGCAGCAGCCTGCTCTTCTTTTTCAATCTCTTCAGGATCTCTGTAGAAGTACAGATCAGGCATG
ACCTCCCATGGGTGTTCACGGGAAATGGTGCCACGCATGCGCAGAACTTCCCGAGCCAGCATCCACCACA
TCAAACCCACTGAGTGAGCTCCCTTGTTGTTGCATGGGATGGGCAATGTCCACATAGCGCAGAGGAGAATC
TGTGTTACACAGCGCAATGGTAGGTAGGTTAACATAAGATGCCTCCGCGAGAAGCTGGTGGTCAGCCCTG
GGGTCAAGTAACCACAAGAAGCCGTGGCTCCCGGAAGGCTGCCTGGATCTGGTTAGTGAAGGNTCCAGGA
GTGAAGCGGCCAACAATTGGAGTGGCTTCAGTGGCAAGCAGCAAACTTCAGCACAAGCCCTCTGGACCTG
CCCGGCGGCCGCTCGA
```

16460.1.edit

```
TCGAGCGGCCGCCCGGGCAGGTCCATTTTCTCCCTGACGGNCCCACTTCTCTCCAATCTTGTAGTTCACAC
CATTGTCATGGCACCATCTAGATGAATCACATCTGAAATGACCACTTCCAAAGCCTAAGCACTGGCACAACA
GTTTAAAGCCTGATTCAGACATTCGTTCCCACTCATCTCCAACGGCATAATGGGAAACTGTGTAGGGGTCAA
AGCACGAGTCATCCGTAGGTTGGTTCAAGCCTTCGTTGACAGAGTTGCCCACGGTAACAACCTCNTCCCCG
AACCTTATGCCTCTGCTGGGCTTTCAGNGCCTCCACTATGATGNTGTAGGGGGGCACCTCTGGNGANGAC
CTCGGCCGCGACCACGCT
```

16460.2.edit

```
AGCGTGGTCGCGGCCGAGGTCCTCACCAGAGGTGCCACCTACAACATCATAGTGGAGGCACTGAAAGACC
AGCAGAGGCATAAGGCTCGGGAAGAGGTTGTTACCGTGGGCAACTCTGTCAACGAAGGCTTGAACCAACC
TACGGATGACTCGTGCTTTGACCCCTACACAGTTTCCCATTATGCCGTTGGAGATGAGTGGGAACGAATGT
CTGAATCAGGCTTTAAACTGTTGTGCCAGTGCTTANGCTTTGGAAGTGGGTCATTTCAGATGTGATTCATCT
AGATGGTGCCATGACAATGGNGNGAACTACAAGATTGGAGAGAAGTGGNACCGNCAGGGAGAAAATGGAC
CTGCCCGGGCGGCCGCTCGA
```

*Fig. 15BB*

16461.1.edit

```
AGCGTGGTCGCGGCCGAGGTCCACATCGGCAGGGTCGGAGCCCTGGCCGCCATACTCGAACTGGAATCC
ATCGGTCATGCTCTCGCCGAACCAGACATGCCTCTTGTCCTTGGGGTTCTTGCTGATGTACCAGTTCTTCTG
GGCCACACTGGGCTGAGTGGGGTACACGCAGGTCTCACCAGTCTCCATGTTGCAGAAGACTTTGATGGCA
TCCAGGNTGCAACCTTGGTTGGGGTCAATCCAGTACTCTCCACTCTTCCAGCCAGAGTGGCACATCTTGAG
GTCACGGCAGGTGCGGNCGGGGGNTTTTGCGGCTGCCCTCTGGNCTTCGGNTGTNCTCNATCTGCTGGC
TCA
```

16461.2.edit

```
TCGAGCGGCCGCCCGGGCAGGTCTCGCGGTCGCACTGGTGATGCTGGTCCTGTTGGTCCCCCCGGCCCT
CCTGGACCTCCTGGCCCCCCTGGTCCTCCCAGCGCTGGTTTCGACTTCAGCTTCCTGCCCCAGCCACCTC
AAGAGAAGGCTCACGATGGTGGCCGCTACTACCGGGCTGATGATGCCAATGTGGTTCGTGACCGTGACCT
CGAGGTGGACACCACCCTCAAGAGCCTGAGCCAGCAGATCGAGAACATCCGGAGCCCAGAGGGCAGNCG
CAAGAACCCCGCCCGCACCTGCCGTGACCTCAAGATGTGCCACTCTGACTGGAAGAGTGGAGAGTACTGG
ATTGACCCCAACCAAGCTGCAACCTGGATGCCATCAAAGTCTTCTGCAACATGGAGACTGGTGAGACCTGC
GTGTACCCCACTCAGCCCAGTGTGGCCCAAAAGAACTGGTACATCAGCAAGAACCCCAAGGACAAGAAGC
ATGTCTGGTTCGGCGAGAACATGACCGATGGATTCCAGTTCGAGTATGGCGGGCAGGGCTCCGACCCTGC
CGATGGGGACCTTGGCCGCGAACACGCT
```

16463.1.edit

```
AGCGTGGNNGCGGCCGAGGTATAAATATCCAGNCCATATCCTCCCTCCACACGCTGANAGATGAAGCTGT
NCAAAGATCTCAGGGTGGANAAAACCAT
```

16463.2.edit

```
TCGAGCGGCCGCCCGGGCAGGTCCTTCAGACTTGGACTGTGTCACACTGCCAGGCTTCCAGGGCTCCAAC
TTGCAGACGGCCTGTTGTGGGACAGTCTCTGTAATCGCGAAAGCAACCATGGAAGACCTGGGGGAAAACA
CCATGGTTTTATCCACCCTGAGATCTTTGAACAACTTCATCTCTCAGCGTGCGGAGGGAGGCTCTGGACTG
GATATTTCTACCTCGGCCGCGACCACGCT
```

*Fig. 15CC*

16464.1.edit

CGAGCGGGCGACCGGGCAGGTNCAGACTCCAATCCANANAACCATCAAGCCAGATGTCAGAAGCTACACC
ATCACAGGTTTACAACCAGGCACTGACTACAAGANCTACCTGCACACCTTGAATGACAATGCTCGGAGCTC
CCCTGTGGTCATCGACGCCTCCACTGCCATTGATGCACCATCCAACCTGCGTTTCCTGGCCACCACACCCA
ATTCCTTGCTGGTATCATGGCAGCCGCCACGTGCCAGGATTACCGGTACATCATCNAGTATGANAAGCCTG
GGCCTCCTCCCAGAGAAGNGGTCCCTCGGCCCCGCCCTGNTGTCCCANAGGNTACTATTACTGNGCCNGC
AACCGGCAACCGATATCNATTTTGNCATTGGCCTTCAACAATAATTA

16464.2.edit

AGCGTGGTTCGCGGCCGANGTCCTGTCAGAGTGGCACTGGTAGAAGTTCCAGGAACCCTGAACTGTAAGG
GTTCTTCATCAGNGCCAACAGGATGACATGAAATGATGTACTCAGAAGTGTCCTGGAATGGGGCCCATGAG
ATGGTTGTCTGAGAGAGAGCTTCTTGNCCTGTCTTTTTCCTTCCAATCAGGGGCTCGCTCTTCTGATTATTC
TTCAGGGCAATGACATAAATTGTATATTCGGGTCCCGGNTCCAGGCCAGTAATAGTANCCTCTGTGACACC
AGGGCGGNGCCGAGGGACCACTTCTCTGGGAGGAGACCCAGGCTTCTCATACTTGATGATGTAACCGGTA
ATCCTGGCACGTGGCGGCTGCCATGATACCAGCAAGGAATTGGGGTGTGGTGGCCAGGAAACGCAGGTT
GGATGGNGCATCAATGGCAGTGGAGGCCGTCGATGACCACAGGGGGAGCTCCGACATTGTCATTCAAGGT
G

16465.1.edit

AGCGTGGNCGCGGCCGAGGTGCAGCGCGGGCTGTGCCACCTTCTGCTCTCTGCCCAACGATAAGGAGGG
TNCCTGCCCCCAGGAGAACATTAACTNTCCCCAGCTCGGCCTCTGCCGG

16465.2.edit

TCGAGCGGCCGCCCGGGCAGGTTTTTTTTGCTGAAAGTGGNTACTTTATTGGNTGGGAAAGGGAGAAGCT
GTGGTCAGCCCAAGAGGGAATACAGAGNCCCGAAAAAGGGGAGGGCAGGTGGGCTGGAACCAGACGCAG
GGCCAGGCAGAAACTTTCTCTCCTCACTGCTCAGCCTGGTGGTGGCTGGAGCTCANAAATTGGGAGTGAC
ACAGGACACCTTCCCACAGCCATTGCGGCGGCATTTCATCTGGCCAGGACACTGGCTGTCCACCTGGCAC
TGGTCCCGACAGAAGCCCGAGCTGGGGAAAGTTAATGTTCACCTGGGGGCAGGAACCCTCCTTATCATTG
NGCAGAGAGCAGAAGGTGGCACAGCCCGCGCTGCACCTCGGCCGCGACCACGCT

16466.2.edit

TCGAGCGGCCGCCCGGGCAGGTCCACCATAAGTCCTGATACAACCACGGATGAGCTGTCAGGAGCAAGGT
TGATTTCTTTCATTGGTCCGGNCTTCTCCTTGGGGGNCACCCGCACTCGATATCCAGTGAGCTGAACATTG
GGTGGCGTCCACTGGGCGCTCAGGCT

16467.2.edit

TCGAGCGGTTCGCCCGGGCAGGTCCACCACACCCAATTCCTTGCTGGTATCATGGCAGCCGCCACGTGCC
AGGATTACCGGCTACATCATCAAGTATGAGAAGCCTGGGTCTCCTCCCAGAGAAGCGGTCCCTCGGCCCC
GCCCTGGTGTCACAGAGGCTACTATTACTGGCCTGGAACCGGGAACCGAATATACAATTTATGTCATTGNC
CTGAAGAATAATCANNAANAGCGANCCCCTGATTGGAAGGA

*Fig. 15DD*

01_16469.edit
AGCGTGGTCGCGGCCGAGGTTGTACAAGCTTTTTTTTTTTTTTTTTTTTTTTTTTTTTTTTTTTTTTTTTTTTT
TTTTTTTTTTTTTTTT

02_16469.edit
TCGAGCGGNCGCCCGGGCAGGTCTGCCAACACCAAGATTGGCCCCCGCCGCATCCACACAGTCCGTGTG
CGGGGAGGTAACAAGAAATACCGTGCCCTGAGGTTGGACGTGGGGAATTTCTCCTGGGGCTCAGAGTGTT
GTACTCGTAAAACAAGGATCATCGATGTTGTCTACAATGCATCTAATAACGAGCTGGTTCGTACCAAGACCC
TGGTGAAGAATTGCATCGTGCTCATCGACAGCACACCGTACCGACAGTGGTACGAGTCCCACTATGCGCTG
CCCCTGGGCCGCAAGAAGGGAGCCAAGCTGACTCCTGAGGAAGAAGAGATTTTAAACAAAAAACGATCTAA
NAAAAAAAAAACAAT

03_16470.edit
AGCGTGGTCGCGGCCGAGGTGAAATGGTATTCAGCTTCCTGGCACTTCTGGTCAGCAACCCAGTGTTGGG
CAACAAATGATCTTTGAGGAACATGGTTTTAGGCGGACCACACCGCCCACAACGGCCACCCCCATAAGGCA
TAGGCCAAGACCATACCCGCCGAATGTAGGACAAGAAGCTCTCTCTCAGACAACCATCTCATGGGCCCCAT
TCCAGGACACTTCTGAGTACATCATTTCATGTCATCCTGTTGGCACTGATGAAGAACCCTTACAGTTCAGGG
TTCCTGGAACTTCTACCAGTGCCACTCTGACAGGACCTGCCCGGGCGGCCGCTCGA

04_16470.edit
TCGAGCGGCCGCCCGGGCAGGTCCTGTCAGAGTGGCACTGGTAGAAGTTCCAGGAACCCTGAACTGTAAG
GGTTCTTCATCAGTGCCAACAGGATGACATGAAATGATGTACTCAGAAGTGTCCTGGAATGGGGCCCATGA
GATGGTTGTCTGAGAGAGAGCTTCTTGTCCTACATTCGGCGGGTATGGTCTTGGCCTATGCCTTATGGGGG
TGGCCGTTGTGGGCGGTGTGGTCCGCCTAAAACCATGTTCCTCAAAGATCATTTGTTGCCCAACACTGGGT
TGCTGACCAGAAGTGCCAGGAAGCTGAATACCATTTCACCTCGGCCGCGACCACGCTA

05_16471.edit
TCGAGCGGCCGCCCGGGCAGGTCTCCCTTCTTGCGGCCCAGGGGCAGCGCATAGTGGGACTCGTACCAC
TGTCGGTACGGTGTGCTGTCGATGAGCACGATGCAATTCTTCACCAGGGTCTTGGTACGAACCAGCTCGTT
ATTAGATGCATTGTAGACAACATCGATGATCCTTGTTTTACGAGTACAACACTCTGAGCCCCAGGAGAAATT
CCCCACGTCCAACCTCAGGGCACGGTATTTCTTGTTACCTCCCCGCACACGGACTGTGTGGATGCGGCGG
GGGCCAAGCTGACTCCTGAGGAAGAAGAGATTTTAAACAAAAAACGATCTAAAAAAATTCAGAAGAAATATG
ATGAAAGGAAAAAGAATGCCAAAATCAGCAGTCTCCTGGAGGAGCAGTTCCAGCAGGGCAAGCTTCTTGCG
TGCATCGCTTCAAGGCCGGGACAGTGTGACCGAGCAGATGGCTATGTGCTAGAGGGCAAAGAAGTGGAGT
TCTATCTTAAGAAAATCAGGGCCCAGAATGGTGNGTCTTCAACTAATCCAAAGGGGAGTTTCAGACCAGTG
CAATCAGCAAAAACATTGATACTGNTGGCCAAATTTATTGGTGCAGGGCTTGCACANTANGANNGGCTGGG
TCTTGGGGCTTGGATTGGNACAAGCTTTGGCAGCCTTTTCTTTGGTTTTGCCAAAAACCTTTTGNTGAAGAN
GANACCTNGGGCGGACCCCTTAACCGATTCCACNCCNGGNGGCGTTCTANGGNCCCNCTTG

*Fig. 15EE*

06_16471.edit

AGCGTGGTCGCGGCCGAGGTCTGCTGCTTCAGCGAAGGGTTTCTGGCATAACCAATGATAAGGCTGCCAA
AGACTGTTCCAATACCAGCACCAGAACCAGCCACTCCTACTGTTGCAGCACCTGCACCAATAAATTTGGCA
GCAGTATCAATGTCTCTGCTGATTGCACTGGTCTGAAACTCCCTTTGGATTAGCTGAGACACACCATTCTGG
GCCCTGATTTTCCTAAGATAGAACTCCAACTCTTTGCCCTCTAGCACATAGCCATCTGCTCGGTCACACTGT
CCCGGCCTTGAAGCGATGCACGCAAGAAGCTTGCCCTGCTGGAACTGCTCCTCCAGGAGACTGCTGATTT
TGGCATTCTTTTTCCTTTCATCATATTTCTTCTGAATTTTTTTAGATCGTTTTTTGTTTAAAATCTCTTCTTCCT
CAGGAGTCAGCTTGGCCCCCGCCGCATCCACACAGTCCGTGTGCGGGGAGGTAACAAGAAATACCGTGCC
CTGAGGTTGGACGTGGGGAATTTCTCCTGGGGCTCAGAGTGGTGTACTCGTAAAACAAGGATCATCGATG
GTGNCTACAATGCATCTAATAACGAGCTGGGTCGGACCCAAAGAACCTGGNGAANAAATGGATCGNCTCAT
CGACAGGACACCGTACCCGACAGGGGNACGANTCCCACTATGCGCTTGCCCCTGGGCCGCAANAAAGGA
AAACTGCCCGGGCGGCCNTCGAAAGCCCAATTNTGGAAAAAATCCATCACACTGGGNGGCCNGTCGAGCA
TGCATNTANAGGGGCCCATTCCCCCTNANN

07_16472.edit

TCGAGCGGCCGCCCGGGCAGGTCCCCAACCAAGGCTGCAACCTGGATGCCATCAAAGTCTTCTGCAACAT
GGAGACTGGTGAGACCTGCGTGTACCCCACTCAGCCCAGTGTGGCCCAGAAGAACTGGTACATCAGCAAG
AACCCCAAGGACAAGAGGCATGTCTGGTTCGGCGAGAGCATGACCGATGGATTCCAGTTCGAGTATGGCG
GCCAGGGCTCCGACCCTGCCGATGTGGACCTCGGCCGCGACCACGCT

08_16472.edit

AGCGTGGTCGCGGCCGAGGTCCACATCGGCAGGGTCGGAGCCCTGGCCGCCATACTCGAACTGGAATCC
ATCGGTCATGCTCTCGCCGAACCAGACATGCCTCTTGTCCTTGGGGTTCTTGCTGATGTACCAGTTCTTCTG
GGCCACACTGGGCTGAGTGGGGTACACGCAGGTCTCACCAGTCTCCATGTTGCAGAAGACTTTGATGGCA
TCCAGGTTGCAGCCTTGGTTGGGGACCTGCCCGGGCGGCCGCTCGA

09_16473.edit

TCGAGCGGCCGCCCGGGCAGGTCCACCACACCCAATTCCTTGCTGGTATCATGGCAGCCGCCACGTGCCA
GGATTACCGGCTACATCATCAAGTATGAGAAGCCTGGGTCTCCTCCCAGAGAAGTGGTCCCTCGGCCCCG
CCCTGGTGTCACAGAGGCTACTATTACTGGCCTGGAACCGGGAACCGAATATACAATTTATGTCATTGCCC
TGAAGAATAATCAGAAGAGCGAGCCCCTGATTGGAAGGAAAAAGACAGACGAGCTTCCCCAACTGGTAACC
CTTCCACACCCCAATCTTCATGGACCAGAGATCTTGGATGTTCCTTCCACAGTTCAAAAGACCCCTTTCGTC
ACCCACCCTGGGTATGACACTGGAAATGGTATTCAGCTTCCTGGCACTTCTGGTCAGCAACCCAGTGTTGG
GCAACAAATGATCTTTGAGGAACATGGNTTTAGGCGGACCACACCGCCCACAACGGCCACCCCATAAGG
CATAGGCCAAGACCATACCCGCCGAATGTAGGACAAGAAGCTNTNTNTCANACACCATNTNATGGGCCCCA
TTCCAGGACACTTCTGAGTACATCATTTATGNCATCTGTGGCACTTGATGAAAACCCTTACAGTTCAGGGTT
CTGGAACTTTTACCAGGCCTNTTACAGGACTNGGCCGGACNCCTTAAGCCNATTNCACCCTGGGGCGTTCT
ANGGTCCCACTCGNNCACTGGNGAAAATGGCTACTGTN

*Fig. 15FF*

11_16474.edit

AGCGTGGTCGCGGCCGAGGTCCACTAGAGGTCTGTGTGCCATTGCCCAGGCAGAGTCTCTGCGTTACAAA
CTCCTAGGAGGGCTTGCTGTGCGGAGGGCCTGCTATGGTGTGCTGCGGTTCATCATGGAGAGTGGGGCC
AAAGGCTGCGAGGTTGTGGTGTCTGNGAAACTCCNAGGACANGAGGGCTAAATTCCATGAAGTTTGTGGAT
GGCCTGATGATCCACAATCGGAGACCCTGTTAACTACTACCGTCTNACCNCCTGCTGTNCNCCCCCNTTTC
TGCTNAANACATNGGGNTNNTNCTTGNCCNTCCTTGGGTNGAANATNNAATNGCCTNCCCNTTCNTANCNC
TACTNGNTCCANANTTGGCCTTTAAANAATCCNCCTTGCCTTNNNCACTGTTCANNTNTTTNNTCGTAAACC
CTATNANTTNNATTANATNNTNNNNNNCTCACCCCCCTCNTCATTNANCCNATANGCTNNNAANTCCTTNAN
NCCTCCCNCCCNNTNCNCTCNTACTNANTNCTTCTNNCCCATTACNNAGCTCTTTCNTTTAANATAATGNNG
CCNNGCTCTNCATNTCTACNATNTGNNNAATNCCCCCNCCCCCNANCGNNTTTTTGACCTNNNAACCTCCT
TTCCTCTTCCCTNCNNAAATTNCNNANTTCCNCNTTCCNNCNTTTCGGNTNNTCCCATNCTTTCCANNNCTT
CANTCTANCNCNCTNCAACTTATTTTCCTNTCATCCCTTNTTCTTTACANNCCCCCTNNTCTACTCNNCNNTT
NCATTANATTTGAAACTNCCACNNCTANTTNCCTCNCTCTACNNTTTTATTTTNCGNTCNCTCTACNTAATAN
TTTAATNANTTNTCN

12_16474.edit

TCGAGCGGCCGCCCGGGCAGGTCTGCCAAGGAGACCCTGTTATGCTGTGGGGACTGGCTGGGGCATGGC
AGGCGGCTCTGGCTTCCCACCCTTCTGTTCTGAGATGGGGGTGGTGGGCAGTATCTCATCTTTGGGTTCCA
CAATGCTCACGTGGTCAGGCAGGGGCTTCTTAGGGCCAATCTTACCAGTTGGGTCCCAGGGCAGCATGAT
CTTCACCTTGATGCCCAGCACACCCTGTCTGAGCAACACGTGGCGCACAAGCAGTGTCAACGTAGTAAGTT
AACAGGGTCTCCGCTGTGGATCATCAGGCCATCCACAAACTTCATGGATTTAGCCCTCTGTCCTCGGAGTT
TCCCAGACACCACAACCTCGCAGCCTTTGGCCCCACTCTCCATGATGAACCGCAGCACACCATAGCAGGC
CCTCCGCACAAGCAAGCCCTCCTAAGAATTTGTAACGCANANACTCTGCTGGCAATGGCACACAAACCTCT
AGTGGACCTCGGNCGCGACCACGC

13_16475.edit

TCGAGCGGCCGCCCGGGCAGGTCTGGTCCAGGATAGCCTGCGAGTCCTCCTACTGCTACTCCAGACTTGA
CATCATATGAATCATACTGGGGAGAATAGTTCTGAGGACCAGTAGGGCATGATTCACAGATTCCAGGGGGG
CCAGGAGAACCAGGGGACCCTGGTTGTCCTGGAATACCAGGGTCACCATTTCTCCCAGGAATACCAGGAG
GGCCTGGATCTCCCTTGGGGCCTTGAGGTCCTTGACCATTAGGAGGGCGAGTAGGAGCAGTTGGAGGCTG
TGGGCAAACTGCACAACATTCTCCAAATGGAATTTCTGGGTTGGGGCAGTCTAATTCTTGATCCGTCACATA
TTATGTCATCGCAGAGAACGGATCCTGAGTCACAGACACATATTTGGCATGGTTCTGGCTTCCAGACATCTC
TATCCGNCATAGGACTGACCAAGATGGGAACATCCTCCTTCAACAAGCTTNCTGTTGTGCCAAAAATAATAG
TGGGATGAAGCAGACCGAGAAGTANCCAGCTCCCCTTTTTGCACAAAGCNTCATCATGTCTAAATATCAGA
CATGAGACTTCTTTGGGCAAAAAAGGAGAAAAAGAAAAAGCAGTTCAAAGTANCCNCCATCAAGTTGGTTCC
TTGCCCNTTCAGCACCCGGGCCCCGTTATAAAACACCTNGGGCCGGACCCCCCTT

*Fig. 15GG*

14_16475.edit

```
AGCGTGGTCGCGGCCGAGGTGTTTTATGACGGGCCCGGTGCTGAAGGGCAGGGAACAACTTGATGGTGC
TACTTTGAACTGCTTTTCTTTTCTCCTTTTTGCACAAAGAGTCTCATGTCTGATATTTAGACATGATGAGCTTT
GTGCAAAAGGGGAGCTGGCTACTTCTCGCTCTGCTTCATCCCACTATTATTTTGGCACAACAGGAAGCTGTT
GAAGGAGGATGTTCCCATCTTGGTCAGTCCTATGCGGATAGAGATGTCTGGAAGCCAGAACCATGCCAAAT
ATGTGTCTGTGACTCAGGATCCGTTCTCTGCGATGACATAATATGTGACGATCAAGAATTAGACTGCCCCAA
CCCAGAAATTCCATTTGGAGAATGTTGTGCAGTTTGCCCACAGCCTCCAACTGCTCCTACTCGCCCTCCTAA
TGGTCAAGGACCTCAAGGCCCCAAGGGAGATCCAGGCCCTCCTGGTATTCCTGGGAGAAATGGTGACCCT
GGTATTCCAGGACAACCAGGGTCCCCTGGTTCTCCTGGCCCCCCTGGAATCNGGNGAATCATGCCCTACT
GGTCCTCAAACTATTCTCCCANATGATTCATATGATGTCAAGTCTGGGATAGCNAGTANGGANGGACTCGC
AGGCTATTCTGGACCANACCTGCCGGGGGGGCGTTCGAAAGCCCGAATCTGCANANNTNCNTTCACACTG
GCGGCCGTCGAGCTGCTTTAAAAGGGCCATTCCNCCTTTAGNGNGGGGGANTACAATTACTNGGCGGCGT
TTTANANCGCGNGNCTGGGAAAT
```

15_16476.edit

```
AGCGTGGTCGCGGCCGAGGTCCACATCGGCAGGGTCGGAGCCCTGGCCGCCATACTCGAACTGGAATCC
ATCGGTCATGCTCTCGCCGAACCAGACATGCCTCTTGTCCTTGGGGTTCTTGCTGATGTACCAGTTCTTCTG
GGCCACACTGGGCTGAGTGGGGTACACGCAGGTCTCACCAGTCTCCATGTTGCAGAAGACTTTGATGGCA
TCCAGGTTGCAGCCTTGGTTGGGGTCAATCCAGTACTCTCCACTCTTCCAGTCAGAGTGGCACATCTTGAG
GTCACGGCAGGTGCGGGCGGGGTTCTTGCGGCTGCCCTCTGGGCTCCGGATGTTCTCGATCTGCTGGCT
CAGGCTCTTGAGGGTGGTGTCCACCTCGAGGTCACGGTCACGAACCACATTGGCATCATCAGCCCGGTAG
TAGCGGCCACCATCGTGAGCCTTCTCTTGANGTGGCTGGGGCAGGAACTGAAGTCGAAACCAGCGCTGGG
AGGACCAGGGGGACCAANAGGTCCAGGAAGGGCCCGGGGGGGACCAACAGGACCAGCATCACCAAGTG
CGACCCGCGAGAACCTGCCCGGCCGNCCGCTCGAA
```

16_16476.edit

```
TCGAGCGNNCGCCCGGGCAGGTCTCGCGGTCGCACTGGTGATGCTGGTCCTGTTGGTCCCCCCGGCCCT
CCTGGACCTCCTGGTCCCCCTGGTCCTCCCAGCGCTGGTTCGACTTCAGCTTCCTGCCCCAGCCACCTC
AAGAGAAGGCTCACGATGGTGGCCGCTACTACCGGGCTGATGATGCCAATGTGGTTCGTGACCGTGACCT
CGAGGTGGACACCACCCTCAAGAGCCTGAGCCAGCAGATCGAGAACATCCGGAGCCCAGAGGGCAGCCG
CAAGAACCCCGCCCGCACCTGCCGTGACCTCAAGATGTGCCACTCTGACTGGAAGAGTGGAGAGTACTGG
ATTGACCCCAACCAAGGCTGCAACCTGGATGCCATCAAAGTCTTCTGCAACATGGAGACTGGTGAGACCTG
CGTGTACCCCACTCAGCCCAGTGTGGCCCAGAAGAACTGGTACATCAGCAAGAACCCCAAGGACAAGAGG
CATGTCTGGTTCGGCGAGAGCATGACCGATGGATTCCAGTTCGAGTATGGCGGCCAGGGCTCCCACCCTG
CCGATGTGGACCTCCGGCCGCGACCACCCTT
```

*Fig. 15HH*

17_16477.edit

TNGAGCGGCCGCCCGGGCAGGNTGNNAACGCTGGTCCTGCTGGTCCTCCTGGCAAGGCTGGTGAAGATG
GTCACCCTGGAAAACCCGGACGACCTGGTGAGAGAGGAGTTGTTGGACCACAGGGTGCTCGTGGTTTCCC
TGGAACTCCTGGACTTCCTGGCTTCAAAGGCATTAGGGGACACAATGGTCTGGATGGATTGAAGGGACAG
CCCGGTGCTCCTGGTGTGAAGGGTGAACCTGGTGCCCCTGGTGAAAATGGAACTCCAGGTCAAACAGGAG
CCCGTGGGCTTCCTGGTGAGAGAGGACCGTGTTGGTGCCCCTGGCCCANACCTCGGCCGCGACCACGCT
AAGCCCGAATTTCCAGCACACTGGNGGCCGTTACTANTGGATCCGAGCTCGGTACCAAGCTTGGCGTAATC
ATGGTCATAGCTGTTTCCTGNGTGAAATTGTTATCCGCTCACAATTTCACACANCATACGAAGCCGGAAAGC
ATAAAGTGTAAAGCCTTGGGGTGCTAATGAGTGAGCTAACTCNCATTAAATTGCGTTGCGCTCACTGCCCG
CTTTTCCANNNGGGAAACCNTGGCNTGCCNGCTTGCNTTAANTGAAATCCGCCNACCCCCGGGGAAAAG
NCGGTTTGCNGTATTGGGGCNCTTTTTCCCTTTCCTCGGNTTACTTGANTTANTGGGCTTTGGNCGNTTCG
GGTTGNGGCGANCNGGTTCAACNTCACNCCAAAGGNGGNAANACGGTTTTCCCANAATCCGGGGGNTANC
CCAANGNAAAACATNNGNCNAANGGGCT

18_16477.edit

AGCGTGGTTNGCGGCCGAGGTCTGGGCCAGGGGCACCAACACGTCCTCTCTCACCAGGAAGCCCACGGG
CTCCTGTTTGACCTGGAGTTCCATTTTCACCAGGGGCACCAGGTTCACCCTTCACACCAGGAGCACCGGGC
TGTCCCTTCAATCCATNCAGACCATTGTGNCCCCTAATGCCTTTGAAGCCAGGAAGTCCAGGAGTTCCAGG
GAAACCACCGAGCACCCTGTGGTCCAACAACTCCTCTCACCAGGTCGTCCGGGTTTTCCAGGGTGACC
ATCTTCACCAGCCTTGCCAGGAGGACCAGCAGGACCAGCGTTACCAACCTGCCCGGGCGGCCGCTCGA

21_16479.edit

TCGAGCGGCCGCCCGGGCAGGTCCATTTTCTCCCTGACGGTCCCACTTCTCTCCAATCTTGTAGTTCACAC
CATTGTCATGGCACCATCTAGATGAATCACATCTGAAATGACCACTTCCAAAGCCTAAGCACTGGCACAACA
GTTTAAAGCCTGATTCAGACATTCGTTCCCACTCATCTCCAACGGCATAATGGGAAACTGTGTAGGGGTCAA
AGCACGAGTCATCCGTAGGTTGGTTCAAGCCTTCGTTGACAGAGTTGCCCACGGTAACAACCTCTTCCCGA
ACCTTATGCCTCTGCTGGTCTTTCAGTGCCTCCACTATGATGTTGTAGGTGGCACCTCTGGTGAGGACCTC
GGCCGCGACCACGCT

22_16479.edit

AGCGTGGTCGCGGCCGAGGTCCTCACCAGAGGTGCCACCTACAACATCATAGTGGAGGCACTGAAAGACC
AGCAGAGGCATAAGGTTCGGGAAGAGGTTGTTACCGTGGGCAACTCTGTCAACGAAGGCTTGAACCAACC
TACGGATGACTCGTGCTTTGACCCCACACAGTTTCCCATTATGCCGTTGGAGATGAGTGGGAACGAATGT
CTGAATCAGGCTTTAAACTGTTGTGCCAGTGCTTAGGCTTTGGAAGTGGTCATTTCAAGATGTGATTCATCT
AGATGGTGCCATGACAATGGTGTGAACTACAAGATTGGAGAGAAGTGGGACCGTCAGGGAGAAAATGGAC
CTGCCCGGGCCGGCCGCTCGA

*Fig. 15II*

24_16480.edit

TCGAGCGNNCGCCCGGGCAGGTCCAGTAGTGCCTTCGGGACTGGGTTCACCCCCAGGTCTGCGGCAGTT
GTCACAGCGCCAGCCCCGCTGGCCTCCAAAGCATGTGCAGGAGCAAATGGCACCGAGATATTCCTTCTGC
CACTGTTCTCCTACGTGGTATGTCTTCCCATCATCGTAACACGTTGCCTCATGAGGGTCACACTTGAATTCT
CCTTTTCCGTTCCCAAGACATGTGCAGCTCATTTGGCTGGCTCTATAGTTTGGGGAAAGTTTGTTGAAACTG
TGCCACTGACCTTTACTTCCTCCTTCTCTACTGGAGCTTTCGTACCTTCCACTTCTGCTGTTGGTAAAATGGT
GGATCTTCTATCAATTTCATTGACAGTACCCACTTCTCCCAAACATCCAGGGAAATAGTGATTTCAGAGCGA
TTAGGAGAACCAAATTATGGGGCAGAAATAAGGGGCTTTTCCACAGGTTTTCCTTTGGAGGAAGATTTCAGT
GGTGACTTTAAAAGAATACTCAACAGTGTCTTCATCCCCATAGCAAAAGAAGAAACNGTAAATGATGGAANG
CTTCTGGAGATGCCNNCATTTAAGGGACNCCCAGAACTTCACCATCTACAGGACCTACTTCAGTTTACANNA
AGNCACATANTCTGACTCANAAAAGGACCCAAGTAGCNCCATGGNCAGCACTTTNAGCCTTTCCCCTGGGGA
AAANNTTACNTTCTTAAAANCCTNGGCCNNGACCCCCTTAAGNCCAAATTNTGGAAAANTTCCNTNCNNCTGG
GGGGCNGTTCNACATGCNTTTNAAGGGCCCAATTNCCCCNT

25_16481.edit

TCGAGCGGCCGCCCGGGCAGGTGTCGGAGTCCAGCACGGGAGGCGTGGTCTTGTAGTTGTTCTCCGGCT
GCCCATTGCTCTCCCACTCCACGGCGATGTCGCTGGGATAGAAGCCTTTGACCAGGCAGGTCAGGCTGAC
CTGGTTCTTGGTCATCTCCTCCCGGGATGGGGGCAGGGTGTACACCTGTGGTTCTCGGGGCTGCCCTTTG
GCTTTGGAGATGGTTTTCTCGATGGGGGCTGGGAGGGCTTTGTTGGAGACCTTGCACTTGTACTCCTTGCC
ATTCAGCCAGTCCTGGTGCAGGACGGTGAGGACGCTGACCACACGGTACGTGCTGTTGTACTGCTCCTCC
CGCGGCTTTGTCTTGGCATTATGCACCTCCACGCCGTCCACGTACCAGTTGAACTTGACCTCAGGGTCTTC
GTGGCTCACGTCCACCACCACGCATGTAACCTCAGACCTCGGCCGCGACCACGCT

26_16481.edit

AGCGTGGTCGCGGCCGAGGTCTGAGGTTACATGCGTGGTGGTGGACGTGAGCCACGAAGACCCTGAGGT
CAAGTTCAACTGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGCAAGGAGTACA
AGTGCAAGGTCTCCAACAAAGCCCTCCCAGCCCCCATCGAGAAAACCATCTCCAAAGCCAAAGGGCAAGC
CCCGAGAACCACAGGTGTACACCCTGCCCCCATCCCGGGAGGAGATGACCAAGAACCAGGTCAGCCTGAC
CTGCCTGGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACACCTGCCCGGGCGGCCGCTCGA

27_16482.edit

TCGAGCGGCCGCCCGGGCAGGTTGAATGGCTCCTCGCTGACCACCCCGGTGCTGGTGGTGGGTACAGAG
CTCCGATGGGTGAAACCATTGACATAGAGACTGTCCCTGTCCAGGGTGTAGGGGCCCAGCTCAGTGATGC
CGTGGGTCAGCTGGCTCAGCTTCCAGTACAGCCGCTCTCTGTCCAGTCCAGGGCTTTTGGGGTCAGGACG
ATGGGTGCAGACAGCATCCACTCTGGTGGCTGCCCCATCCTTCTCAGGCCTGAGCAAGGTCAGTCTGCAA
CCAGAGTACAGAGAGCTGACACTGGTGTTCTTGAACAAGGGCATAAGCAGACCCTGAAGGACACCTCGGC
CGCGACCACGCT

*Fig. 15JJ*

28_16482.edit

AGCGTGGTCGCGGCCGAGGTGTCCTTCAGGGTCTGCTTATGCCCTTGTTCAAGAACACCAGTGTCAGCTCT
CTGTACTCTGGTTGCAGACTGACCTTGCTCAGGCCTGAGAAGGATGGGGCAGCCACCAGAGTGGATGCTG
TCTGCACCCATCGTCCTGACCCCAAAAGCCCTGGACTGGACAGAGAGCGGCTGTACTGGAAGCTGAGCCA
GCTGACCCACGGCATCACTGAGCTGGGCCCCTACACCCTGGACAGGGACAGTCTCTATGTCAATGGTTTC
ACCCATCGGAGCTCTGTACCCACCACCAGCACCGGGGTGGTCAGCGAGGAGCCATTCAACCTGCCCGGG
CGGCCGCTCGA

29_16483.edit

AGCGTGGTCGCGGCCGAGGTCCTGTCAGAGTGGCACTGGTAGAAGTTCCAGGAACCCTGAACTGTAAGGG
TTCTTCATCAGTGCCAACAGGATGACATGAAATGATGTACTCAGAAGTGTCCTGGAATGGGGCCCATGAGA
TGGTTGTCTGAGAGAGAGCTTCTTGTCCTACATTCGGCGGGTATGGTCTTGGCCTATGCCTTATGGGGGTG
GCCGTTGTGGGCGGTGTGGTCCGCCTAAAACCATGTTCCTCAAAGATCATTTGTTGCCCAACACTGGGTTG
CTGACCAGAAGTGCCAGGAAGCTGAATACCATTTCCAGTGTCATACCCAGGGTGGGTGACGAAAGGGGTC
TTTTGAACTGTGGAAGGAACATCCAAGATCTCTGGTCCATGAAGATTGGGGTGTGGAAGGGTTACCAGTTG
GGGAAGCTCGTCTGTCTTTTTCCTTCCAATCAGGGGCTCGCTCTTCTGATTATTCTTCAGGGCAATGACATA
AATTGTATATTCGGTCCCGGTTCCAGGCCAGTAATAGTAGCCTCTGTGACACCAGGGCGGGGCCGAGGGA
CCCTTCTNTTGGAAGAGACCAGCTTCTCATACTTGATGATGAGNCCGGTAATCCTGGCACGTGGNGGTTGC
ATGATNCCACCAAGGAAATNGGNGGGGGNGGACCTGCCCGGCGGCCGTTCNAAAGCCCAATTCCACACA
CTTGGNGGCCGTACTATGGATCCCACTCNGTCCAACTTGGNGGAATATGGCATAACTTTT

31_16484.edit

TCGAGCGGCCGCCCGGGCAGGTCCTTGACCTTTTCAGCAAGTGGGAAGGTGTAATCCGTCTCCACAGACA
AGGCCAGGACTCGTTTGTACCCGTTGATGATAGAATGGGGTACTGATGCAACAGTTGGGTAGCCAATCTGC
AGACAGACACTGGCAACATTGCGGACACCCTCCAGGAAGCGAGAATGCAGAGTTTCCTCTGTGATATCAAG
CACTTCAGGGTTGTAGATGCTGCCATTGTCGAACACCTGCTGGATGACCAGCCCAAAGGAGAAGGGGGAG
ATGTTGAGCATGTTCAGCAGCGTGGCTTCGCTGGCTCCCACTTTGTCTCCAGTCTTGATCAGACCTCGGCC
GCGACCACGCT

37_16487.edit

AGCGTGGTCGCGGCCGAGGTCTGTCCTACAGTCCTCAGGACTCTACTCCCTCAGCAGCGTGGTGACCGTG
CCCTCCAGCAACTTCGGCACCCAGACCTACACCTGCAACGTAGATCACAAGCCCAGCAACACCAAGGTGG
ACAAGAGAGTTGAGCCCAAATCTTGTGACAAAACTCACACATGCCCACCGTGCCCAGCACCTGAACTCCTG
GGGGGACCGTCAGTCTTCCTCTTCCCCCGCATCCCCCTTCCAAACCTGCCCGGGCGGCCGCTCG

*Fig. 15KK*

38_16487.edit
CGAGCGGCCGCCCGGGCAGGTTTGGAAGGGGGATGCGGGGGAAGAGGAAGACTGACGGTCCCCCCAGG
AGTTCAGGTGCTGGGCACGGTGGGCATGTGTGAGTTTTGTCACAAGATTTGGGCTCAACTCTCTTGTCCAC
CTTGGTGTTGCTGGGCTTGTGATCTACGTTGCAGGTGTAGGTCTGGGTGCCGAAGTTGCTGGAGGGCACG
GTCACCACGCTGCTGAGGGAGTAGAGTCCTGAGGACTGTAGGACAGACCTCGGCCGCGACCACGCT

39_16488.edit
NGGNNGGTCCGGNCNGNCAGGACCACTCNTCTTCGAAATA

41_16489.edit
AGCGTGGTCGCGGCCGAGGTCCTCACTTGCCTCCTGCAAAGCACCGATAGCTGCGCTCTGGAAGCGCAGA
TCTGTTTTAAAGTCCTGAGCAATTTCTCGCACCAGACGCTGGAAGGGAAGTTTGCGAATCAGAAGTTCAGT
GGACTTCTGATAACGTCTAATTTCACGGAGCGCCACAGTACCAGGACCTGCCCGGGCGGCCGCTCGA

42_16489.edit
TCGAGCGGCCGCCCGGGCAGGTCCTGGTACTGNGGCGCTCCGTGAAATTAGACGTTATCAGAAGTCCACT
GAACTTCTGATTCGCAAACTTCCCTTCCAGCGTCTGGTGCGAGAAATTGCTCAGGACTTTAAAACAGATCTG
CGCTTCCAGAGCGCAGCTATCGGTGCTTTGCAGGAGGCAAGTGAGGACCTCGGCCGCGACCACGCT

45_16491.edit
TCGAGCGGCCGCCCGGGCAGGTCCACATCGGCAGGGTCGGAGCCCTGGCCGCCATACTCGAACTGGAAT
CCATCGGTCATGCTCTCGCCGAACCAGACATGCCTCTTGTCCTTGGGGTTCTTGCTGATGTACCAGTTCTT
CTGGGCCACACTGGGCTGAGTGGGGTACACGCAGGTCTCACCAGTCTCCATGTTGCAGAAGACTTTGATG
GCATCCAGGTTGCAGCCTTGGTTGGGGTCAATCCAGTACTCTCCACTCTTCCAGTCAGAGTGGCACATCTT
GAGGTCACGGCAGGTGCGGGCGGGGTTCTTGACCTCGGCCGCGACCACGCT

*Fig. 15LL*

46_16491.edit

GTGGGNTTGAACCCNTTTNANCTCCGCTTGGTACCGAGCTCGGATCCACTAGTAACGGCCGCCAGTGTGC
TGGAATTCGGCTTAGCGTGGTCGCGGCCGAGGTCAAGAACCCCGCCCGCACCTGCCGTGACCTCAAGATG
TGCCACTCTGACTGGAAGAGTGGAGAGTACTGGATTGACCCCAACCAAGGCTGCAACCTGGATGCCATCA
AAGTCTTCTGCAACATGGAGACTGGTGAGACCTGCGTGTACCCCACTCAGCCCAGTGTGGCCCAGAAGAA
CTGGTACATCAGCAAGAACCCCAAGGACAAGAGGCATGTCTGGTTCGGCGAGAGCATGACCGATGGATTC
CAGTTCGAGTATGGCGGCCAGGGCTCCGACCCTGCCGATGTGGACCTGCCCGGGCGGCCGCTCGA

47_16492.edit

AGCGTGGTCGCGGCCGAGGTCTGGGATGCTCCTGCTGTCACAGTGAGATATTACAGGATCACTTACGGAG
AAACAGGAGGAAATAGCCCTGTCCAGGAGTTCACTGTGCCTGGGAGCAAGTCTACAGCTACCATCAGCGG
CCTTAAACCTGGAGTTGATTATACCATCACTGTGTATGCTGTCACTGGCCGTGGAGACAGCCCCGCAAGCA
GCAAGCCAATTTCCATTAATTACCGAACAGAAATTGACAAACCATCCCAGATGCAAGTGACCGATGTTCAGG
ACAACAGCATTAGTGTCAAGTGGCTGCCTTCAAGTTCCCCTGTTACTGGTTACAGAGTAACCACCACTCCCA
AAAATGGACCAGGACCAACAAAAACTAAAACTGCAGGTCCAGATCAAACAGAAATGACTATTGAAGGCTTG
CAGCCCACAGTGGAGTATGTGGTTAAGTGTCTATGCTCAGAATCCAAGCGGAGAGAAGTCAGCCTCTGGTT
CAGACTGNAAGTAACCAACATTGATCGCCTAAAGGACTGGCATTCACTGATGNGGATGCCGATTCCATCAA
AATTGNTTGGGAAAACCCACAGGGGCAAGTTTNCANGTCNAGGNGGACCTACTCGAGCCCTGAGGATGGA
ATCCTTGACTNTTCCTTNNCCTGATGGGGAAAAAAAACCTTNAAAACTTGAAGGACCTGCCCGGGCGGCCG
TNCAAAACCCAATTCCACCCCCTTGGGGGCGTTCTATGGGNCCCACTCGGACCAAACTTGGGGTAAN

48_16492.edit

TCGAGCGGCCGCCCGGGCAGGTCCTTGCAGCTCTGCAGTGTCTTCTTCACCATCAGGTGCAGGGAATAGC
TCATGGATTCCATCCTCAGGGCTCGAGTAGGTCACCCTGTACCTGGAAACTTGCCCCTGTGGGCTTTCCCA
AGCAATTTTGATGGAATCGGCATCCACATCAGTGAATGCCAGTCCTTTAGGGCGATCAATGTTGGTTACTGC
AGTCTGAACCAGAGGCTGACTCTCTCCGCTTGGATTCTGAGCATAGACACTAACCACATACTCCACTGTGG
GCTGCAAGCCTTCAATAGTCATTTCTGTTTGATCTGGACCTGCAGTTTTAGTTTTTGTTGGTCCTGGTCCATT
TTTGGGAGTGGTGGTTACTCTGTAACCAGTAACAGGGGAACTTGAAGGCAGCCACTTGACACTAATGCTGT
TGTCCTGAACATCGGTCACTTGCATCTGGGATGGTTTGTCAATTTCTGTTCGGTAATTAATGGAAATTGGCT
TGCTGCTTGCGGGGCTTGTCTCCACGGCCAGTGACAGCATACACAGTGATGGTATAATCAACTCCAGGTTT
AAGCCGCTGATGGTAGCTGAAACTTTGCTCCAGGCACAAGTGAACTCCTGACAGGGCTATTTCCTNCTGTT
CTCCGTAAGTGATCCTGTAATATCTCACTGGGACAGCAGGANGCATTCCAAAACTTCGGGCGNGACCCCCT
AAGCCGAATTNTGCAATATNCATCACACTGGCGGGCGCTCGANCATTCATTAAAAGGCCCAATCNCCCCTA
TAGGGAGTNTANTACAATTNG

*Fig. 15MM*

49_16493.edit

TCGAGCGGCCGCCCGGGCAGGTCACTTTTGGTTTTTGGTCATGTTCGGTTGGTCAAAGATAAAAACTAAGT
TTGAGAGATGAATGCAAAGGAAAAAAATATTTTCCAAAGTCCATGTGAAATTGTCTCCCATTTTTTTGGCTTT
TGAGGGGGTTCAGTTTGGGTTGCTTGTCTGTTTCCGGGTTGGGGGGAAAGTTGGTTGGGTGGGAGGGAGC
CAGGTTGGGATGGAGGGAGTTTACAGGAAGCAGACAGGGCCAACGTCG

55_16496.edit

AGCGTGGTCGCGGCCGAGGTCCTCACCAGAGGTGCCACCTACAACATCATAGTGGAGGCACTGAAAGACC
AGCAGAGGCATAAGGTTCGGGAAGAGGTTGTTACCGTGGGCAACTCTGTCAACGAAGGCTTGAACCAACC
TACGGATGACTCGTGCTTTGACCCCTACACAGTTTCCCATTATGCCGTTGGAGATGAGTGGGAACGAATGT
CTGAATCAGGCTTTAAACTGTTGTGCCAGTGCTTAGGCTTTGGAAGTGGTCATTTCAGATGTGATTCATCTA
GATGGTGCCATGACAATGGTGTGAACTACAAGATTGGAGAGAAGTGGGACCGTCAGGGAGAAAATGGACC
TGCCCGGGCGGCCGCTCGA

56_16496.edit

TCGAGCGGCCGCCCGGGCAGGTCCATTTTCTCCCTGACGGTCCCACTTCTCTCCAATCTTGTAGTTCACAC
CATTGTCATGGCACCATCTAGATGAATCACATCTGAAATGACCACTTCCAAAGCCTAAGCACTGGCACAACA
GTTTAAAGCCTGATTCAGACATTCGTTCCCACTCATCTCCAACGGCATAATGGGAAACTGTGTAGGGGTCAA
AGCACGAGTCATCCGTAGGTTGGTTCAAGCCTTCGTTGACAGAGTTGCCCACGGTAACAACCTCTTCCCGA
ACCTTATGCCTCTGCTGGTCTTTCAGTGCCTCCACTATGATGTTGTAGGTGGCACCTCTGGTGAGGACCTC
GGCCGCGACCACGCT

59_16498.edit

TCGAGCGGCCGCCCGGGCAGGTCCACCATAAGTCCTGATACAACCACGGATGAGCTGTCAGGAGCAAGGT
TGATTTCTTTCATTGGTCCGGTCTTCTCCTTGGGGGTCACCCGCACTCGATATCCAGTGAGCTGAACATTGG
GTGGTGTCCACTGGGCGCTCAGGCTTGTGGGTGTGACCTGAGTGAACTTCAGGTCAGTTGGTGCAGGAAT
AGTGGTTACTGCAGTCTGAACCAGAGGCTGACTCTCTCCGCTTGGATTCTGAGCATAGACACTAACCACAT
ACTCCACTGTGGGCTGCAAGCCTTCAATAGTCATTTCTGTTTGATCTGGACCTGCAGTTTTAGTTTTTGTTG
GTCCTGGTCCATTTTTGGGAGTGGTGGTTACTCTGTAACCAGTAACAGGGGAACTTGAAGGCAGCCACTTG
ACACTAATGCTGTTGTCCTGAACATCGGTCACTTGCATCTGGGATGGTTTGNCAATTTCTGTTCGGTAATTA
ATGGAAATTGGCTTGCTGCTTGCGGGGCTGTCTCCACGGCCAGTGACAGCATACACAGNGATGGNATNAT
CAACTCCAAGTTTAAGGCCCTGATGGTAACTTTAAACTTGCTCCCAGCCAGNGAACTTCCGGACAGGGTAT
TTCTTCTGGTTTTCCGAAAGNGANCCTGGAATNNTCTCCTTGGANCAGAAGGANCNTCCAAAACTTGGGCC
GGAACCCCTT

*Fig. 15NN*

60_16473.edit

AGCGTGGTCGCGGCCGAGGTCCTGTCAGAGTGGCACTGGTAGAAGTTCCAGGAACCCTGAACTGTAAGGG
TTCTTCATCAGTGCCAACAGGATGACATGAAATGATGTACTCAGAAGTGTCCTGGAATGGGGCCCATGAGA
TGGTTGTCTGAGAGAGAGCTTCTTGTCCTACATTCGGCGGGTATGGTCTTGGCCTATGCCTTATGGGGGTG
GCCGTTGTGGGCGGTGTGGTCCGCCTAAAACCATGTTCCTCAAAGATCATTTGTTGCCCAACACTGGGTTG
CTGACCAGAAGTGCCAGGAAGCTGAATACCATTTCCAGTGTCATACCCAGGGTGGGTGACGAAAGGGGTC
TTTTGAACTGTGGAAGGAACATCCAAGATCTCTGGTCCATGAAGATTGGGGTGTGGAAGGGTTACCAGTTG
GGGAAGCTCGTCTGTCTTTTTCCTTCCAATCAGGGGCTCGCTCTTCTGATTATTCTTCAGGGCAATGACATA
AATTGTATATTCGGTTCCCGGTTCCAGGCCAGTAATAGTAGCCTCTTGTGACACCAGGCGGGGCCCANGGA
CCACTTCTCTGGGANGAGACCCAGCTTCTCATACTTGATGATGTAACCCGGTAATCCTGCACGTGGCGGCT
GNCATGATACCANCAAGGAATTGGGTGNGGNGGACCTGCCCGGCGGCCCTCNA

60_16498.edit

AGCGTGGTCGCGGCCGAGGTCTGGGATGCTCCTGCTGTCACAGTGAGATATTACAGGATCACTTACGGAG
AAACAGGAGGAAATAGCCCTGTCCAGGAGTTCACTGTGCCTGGGAGCAAGTCTACAGCTACCATCAGCGG
CCTTAAACCTGGAGTTGATTATACCATCACTGTGTATGCTGTCACTGGCCGTGGAGACAGCCCCGCAAGCA
GCAAGCCAATTTCCATTAATTACCGAACAGAAATTGACAAACCATCCCAGATGCAAGTGACCGATGTTCAGG
ACAACAGCATTAGTGTCAAGTGGCTGCCTTCAAGTTCCCCTGTTACTGGTTACAGAGTAACCACCACTCCCA
AAAATGGACCAGGACCAACAAAAACTAAAACTGCAGGTCCAGATCAAACAGAAATGACTATTGAAGGCTTG
CAGCCCACAGTGGAGTATGTGGTTAGTGTCTATGCTCAGAATCCAAGCGGAGAGAGTCAGCCTCTGGTTCA
GACTGCAGTAACCACTATTCCTGCACCAACTGACCTGAAGTTCACTCAGGTCACACCCACAAGCCTGAGCC
GCCAGTGGACACCACCCAATGTTCACTCACTGGATATCGAGTGCGGGTGACCCCCAAGGAGAAGACCCGG
ACCCATGAAAGAAATCAACCTTGCTCCTGACAGCTCATCCGNGGGTGTATCAGGACTTATGGGGACTGCC
CCGGCNGGCCGNTCGAAANCGAATTNTGAAATTTCCTTCNCACTGGGNGGCGNTTCGAGCTTNCTTNTANA
NGGCCCAATTCNCCTNTAGNGGGTCGTN

61_16499.edit

AGCGTGGTCGCGGCCGAGGTCNAGG

62_16483.edit

TCGAGCGGCCGCCCGGGCAGGTCCACCACACCCAATTCCTTGCTGGTATCATGGCAGCCGCCACGTGCCA
GGATTACCGGCTACATCATCAAGTATGAGAAGCCTGGGTCTCCTCCCAGAGAAGTGGTCCCTCGGCCCCG
CCCTGGTGTCACAGAGGCTACTATTACTGGCCTGGAACCGGGAACCGAATATACAATTTATGTCATTGCCC
TGAAGAATAATCAGAAGAGCGAGCCCCTGATTGGAAGGAAAAAGACAGACGAGCTTCCCCAACTGGTAACC
CTTCCACACCCCAATCTTCATGGACCAGAGATCTTGGATGTTCCTTCCACAGTTCAAAAGACCCCTTTCGTC
ACCCACCCTGGGTATGACACTGGAAATGGTATTCAGCTTCCTGGCACTTCTGGTCAGCAACCCAGTGTTGG
GCAACAAATGATCTTTGAGGAACATGGTTTTAGGCGGACCACACCGCCCACAACGGGCACCCCCATAAGG
NATAGGCCAAGACCATACCCCGCCGAATGTAGGACAAGAAGCTCTNTCTCAACAACCATCTCATGGGCCCC
ATTCCAGGACACTTCTGAGTACATCATTTCATGTCATCCTGGTGGGCACTTGATGAANAACCCTTACAGTTC
AGGGTTCCTGGAACTTCTACCAGNGCCACTTCTGACAGGANCTTGGGCGNGACCACCCT

Fig. 1500

63_16500.edit

AGCGTGGTCGCGGCCGAGGTCCATTTTCTCCCTGACGGTCCCACTTCTCTCCAATCTTGTAGTTCACACCA
TTGTCATGGCACCATCTAGATGAATCACATCTGAAATGACCACTTCCAAAGCCTAAGCACTGGCACAACAGT
TTAAAGCCTGATTCAGACATTCGTTCCCACTCATCTCCAACGGCATAATGGGAAACTGTGTAGGGGTCAAAG
CACGAGTCATCCGTAGGTTGGTTCAAGCCTTCGTTGACAGAGTTGCCCACGGTAACAACCTCTTCCCGAAC
CTTATGCCTCTGCTGGTCTTTCAGTGCCTCCACTATGATGTTGTAGGTGGCACCTCTGGTGAGGACCTGCC
CGGGCGGCCCGCTCGA

64_16493.edit

AGCGTGGTCGCGGCCGAGGTGTGCCCCAGACCAGGAATTCGGCTTCGACGTTGGCCCTGTCTGCTTCCTG
TAAACTCCCTCCATCCCAACCTGGCTCCCTCCCACCCAACCAACTTTCCCCCCAACCCGGAAACAGACAAG
CAACCCAAACTGAACCCCCTCAAAAGCCAAAAAAATGGGAGACAATTTCACATGGACTTTGGAAAATATTTT
TTTCCTTTGCATTCATCTCTCAAACTTAGTTTTTATCTTTGACCAACCGAACATGACCAAAAACCAAAAGTGA
CCTGCCCGGGCGGCCGCTCGA

64_16500.edit

TCGAGCGGCCGCCCGGGCAGGTCCTCACCAGAGGTGCCACCTACAACATCATAGTGGAGGCACTGAAAGA
CCAGCAGAGGCATAAGGTTCGGGAAGAGGTTGTTACCGTGGGCAACTCTGTCAACGAAGGCTTGAACCAA
CCTACGGATGACTCGTGCTTTGACCCCTACACAGTTTCCCATTATGCCGTTGGAGATGAGTGGGAACGAAT
GTCTGAATCAGGCTTTAAACTGTTGTGCCAGTGCTTAGGCTTTGGAAGTGGTCATTTCAGATGTGATTCATC
TAGATGGTGCCATGACAATGGTGTGAACTACAAGATTGGAGAGAAGTGGGACCGTCAGGGAGAAAATGGA
CCTCGGCCGCGACCACGCT

*Fig. 15PP*

16501.edit

TCGAGCGGCCGCCCGGGCAGGTACCGGGGTGGTCAGCGAGGAGCCATTCACACTGAACTTCACCATCAA
CAACCTGCGGTATGAGGAGAACATGCAGCACCCTGGCTCCAGGAAGTTCAACACCACGGAGAGGGTCCTT
CAGGGCCTGCTCAGGTCCCTGTTCAAGAGCACCAGTGTTGGCCCTCTGTACTCTGGCTGCAGACTGACTTT
GCTCAGACCTGAGAAACATGGGGCAGCCACTGGAGTGGACGCCATCTGCACCCTCCGCCTTGATCCCACT
GGTNCTGGACTGGACANANAGCGGCTATACTTGGGAGCTGANCCNAACCTTTGGCGGNGACNCCNCTT

16501.2.edit

GAGGACTGGCTCAGCTCCCAGTATAGCCGCTCTCTGTCCAGTCCAGGACCAGTGGGATCAAGGCGGAGG
GTGCAGATGGCGTCCACTCCAGTGGCTGCCCCATGTTTCTCAAGTCTGAGCAAAGNCAGTCTGCAGCCAG
AGTACAGAGGGCCAACACTGGTGCTCTTGAACAGGGACCTGAGCAGGCCCTGAAGGACCCTCTCCGTGGT
GTTGAACTTCCTGGAGCCAGGGTGCTGCATGTTCTCCTCATACCGCAGGTTGTTGATGGTGAAGTTCAGTG
TGAATGGCTCCTCGCTGACCACCC

16502.1.edit

AGCGTGGTCGCGGCCGAGGTCCACCACACCCAATTCCTTGCTGGTATCATGGCAGCCGCCACGTGCCAGG
ATTACCGGCTACATCATCAAGTATGAGAAGCCTGGGTCTCCTCCCAGAGAAGTGGTCCCTCGGCCCCGCC
CTGGTGTCACAGAGGCTACTATTACTGGCCTGGAACCGGGAACCGAATATACAATTTATGTCATTGCCCTG
AAGAATAATCAGAAGAGCGAGCCCCTGATTGGAAGGAAAAAGACAGACGAGCTTCCCCAACTGGTAACCCT
TCCACACCCCAATCTTCATGGACCANANANCTTGGATNGTCCTTTCACNGGTTNAAAAAACCCTTTTCGCCC
CCCCACCTTGGGGATTAACCTTGGGAAANGGGGATTTNACCNTTCC

16502.2.edit

TCGAGCGGCCGCCCGGGCAGGTCCTGTCAGAGTGGCACTGGTAGAAGTTCCAGGAACCCTGAACTGTAAG
GGTTCTTCATCAGTGCCAACAGGATGACATGAAATGATGTACTCAGAAGTGTCCTGGAATGGGGCCCATGA
GATGGTTGTCTGAGAGAGAGCTTCTTGTCCTACATTCGGCGGGTATGGTCTTGGCCTATGCCTTATGGGGG
TGGCCGTTGTGGGCGGTGTGGTCCGCCTAAAACCATGTTCCTCAAAGATCATTTGTTGCCCAACACTGGGT
TGCTGACCAGAAGTGCCAGGAAGCTGAATACCATTTCCAGTGTCATACCCAGGGNGGGTGACCAAAGGGG
GTCNTTTNGACCTGGNGAAAGGAACCATCCAAAANCTCTGNCCCATG

*Fig. 15QQ*

16503.1.edit

AGCGTGGNCGCGGCCGAGGTCTGAGGATGTAAACTCTTCCCAGGGGAAGGCTGAAGTGCTGACCATGGT
GCTACTGGGTCCTTCTGAGTCAGATATGTGACTGATGNGAACTGAAGTAGGTACTGTAGATGGTGAAGTCT
GGGTGTCCCTAAATGCTGCATCTCCAGAGCCTTCCATCATTACCGTTTCTTCTTTTGCTATGGGATGAGACA
CTGTTGAGTATTCTCTAAAGTCACCACTGAAATCTTCCTCCAAAGGAAAACCTGTGGAAAAGCCCCTTATTT
CTGCCCCATAATTTGGTTCTCCTAATCNCTCTGAAATCACTATTTCCCTGGAANGTTTGGGAAAAANNGGGC
NACCTGNCANTGGAAANTGGATANAAAGATCCCACCATTTTACCCAACNAGCAGAAAGTGGGAANGGTACC
GAAAAGCTCCAAGTAANAAAAAGGAGGGAAGTAAAGGTCAAGTGGGCACCAGTTTCAAACAAAACTTTCCC
CAAACTATANAACCCA

16503.2.edit

AAGCGGCCGCCCGGGCAGGNNCAGNAGTGCCTTCGGGACTGGGNTCACCCCCAGGTCTGCGGCAGTTGT
CACAGCGCCAGCCCCGCTGGCCTCCAAAGCATGTGCAGGAGCAAATGGCACCGAGATATTCCTTCTGCCA
CTGTTCTCCTACGTGGTATGTCTTCCCATCATCGTAACACGTTGCCTCATGAGGGTCACACTTGAATTCTCC
TTTTCCGTTCCCAAGACATGTGCAGCTCATTTGGCTGGCTCTATAGTTTGGGGAAAGTTTGTTGAAACTGTG
CCACTGACCTTTACTTCCTCCTTCTCTACTGGAGCTTTCCGTACCTTCCACTTCTGCTGNTGGNAAAAAGGG
NGGAACNTCTTATCAATTTCATTGGACAGTANCCCNCTTTCTNCCCAAAACATNCAAGGGAAAATATTGATT
NCNAGAGCGGATTAAGGAACAACCCNAATTATGGGGGCCAGAAATAAAGGGGGCTTTTCCACAGGTNTTTT
CCT

16504.1.edit

TCGAGCGGCCGCCCGGGCAGGTCTGCAGGCTATTGTAAGTGTTCTGAGCACATATGAGATAACCTGGGCC
AAGCTATGATGTTCGATACGTTAGGTGTATTAAATGCACTTTTGACTGCCATCTCAGTGGATGACAGCCTTC
TCACTGACAGCAGAGATCTTCCTCACTGTGCCAGTGGGCAGGAGAAAGAGCATGCTGCGACTGGACCTCG
GCCGCGACCACGCT

16504.2.edit

AGCGTGGTCGCGGCCGAGGTCCAGTCGCAGCATGCTCTTTCTCCTGCCCACTGGCACAGTGAGGAAGATC
TCTGCTGTCAGTGAGAAGGCTGTCATCCACTGAGATGGCAGTCAAAAGTGCATTTAATACACCTAACGTATC
GAACATCATAGCTTGGCCCAGGTTATCTCATATGTGCTCAGAACACTTACAATAGCCTGCAGACCTGCCCG
GCGGCCGCTCGA

*Fig. 15RR*

16505.1.edit

```
CGAGCGGCCGCCCGGGCAGGTCCAGACTCCAATCCAGAGAACCACCAAGCCAGATGTCAGAAGCTACAC
CATCACAGGTTTACAACCAGGCACTGACTACAAGATCTACCTGTACACCTTGAATGACAATGCTCGGAGCTC
CCCTGTGGTCATCGACGCCTCCACTGCCATTGATGCACCATCCAACCTGCGTTTCCTGGCCACCACACCCA
ATTCCTTGCTGGTATCATGGCAGCCGCCACGTGCCAGGATTACCGGCTACATCATCAAGTATGAGAAGCCT
GGGTCTCCTCCCAGAGAAGTGGTCCCTCGGCCCCGCCCTGGTGNCACAGAAGCTACTATTACTGGCCTGG
AACCGGGAACCGAATATACAATTTATGTCATTGCCCTGAAGAATAATCANAAGAGCGAGCCCCTGATTGGAA
GG
```

16505.2.edit

```
AGCGTGGTCGCGGCCGAGGTCCTGTCAGAGTGGCACTGGTAGAAGTTCCAGGAACCCTGAACTGTAAGGG
TTCTTCATCAGTGCCAACAGGATGACATGAAATGATGTACTCAGAAGTGTCCTGGAATGGGGCCCATGAGA
TGGTTGTCTGAGAGAGAGCTTCTTGTCCTGTCTTTTTCCTTCCAATCAGGGGCTCGCTCTTCTGATTATTCTT
CAGGGCAATGACATAAATTGTATATTCGGTTCCCGGTTCCAGGCCAGTAATAGTAGCCTCTGTGACACCAG
GGCGGGGCCGAGGGACCACTTCTCTGGGAGGAGACCCAGGCTTCTCATACTTGATGATGTANCCGGTAAT
CCTGGCACCGTGGCGGCTGCCATGATACCAGCAAGGAATTGGGTGTGGTGGCCAAGAAACGCAGGTTGG
ATGGTGCATCAATGGCAGTGGAGGCGTCGATNACCACAGGGGAGCTCCGANCATTGTCATTCAAGGTGGA
CAGGTAGAATCTTGTAATCAGGTGCCTGGTTTGTAAACCTG
```

16506.1.edit

```
TCGAGCGGCCGCCCGGGCAGGTTTCGTGACCGTGACCTCGAGGTGGACACCACCCTCAAGAGCCTGAGC
CAGCAGATCGAGAACATCCGGAGCCCAGAGGGCAGCCGCAAGAACCCCGCCCGCACCTGCCGTGACCTC
AAGATGTGCCACTCTGACTGGAAGAGTGGAGAGTACTGGATTGACCCCAACCAAGGCTGCAACCTGGATG
CCATCAAAGTCTTCTGCAACATGGAGACTGGTGAGACCTGCGTGTACCCCACTCAGCCCAGTGTGGCCCA
GAAGAACTGGTACATCAGCAAGAACCCCAAGGACAAGAAGCATGTCTGGTTCGGCGAAAGCATGACCGAT
GGATTCCAGTTCGAGTATGGCGGCCAGGGCTCCGACCCTGCCGATGTGGACCTCGGCCGCGACCACGCT
AAGCCCGAATTCCAGCACACTGGCGGCCGTTACTAGTGGGATCCGAGCTTCGGTACCAAGCTTGGCGTAA
TCATGGGNCATAGCTGTTTCCTGNGTGAAAATGGTATTCCGCTTCACAATTTCCCAC
```

16506.2.edit

```
AGCGTGGTCGCGGCCGAGGTCCACATCGGCAGGGTCGGAGCCCTGGCCGCCATACTCGAACTGGAATCC
ATCGGTCATGCTCTCGCCGAACCAGACATGCCTCTTGTCCTTGGGGTTCTTGCTGATGTACCAGTTCTTCTG
GGCCACACTGGGCTGAGTGGGGTACACGCAGGTCTCACCAGTCTCCATGTTGCAGAAGACTTTGATGGCA
TCCAGGTTGCAGCCTTGGTTGGGGTCAATCCAGTACTCTCCACTCTTCCAGTCAGAGTGGCACATCTTGAG
GTCACGGCAGGTGCGGGCGGGGTTCTTGCGGCTGCCCTCTGGGCTCCGGATGTTCTCGATCTGCTGGCT
CAAGCTCTTGAAGGGTGGTGTCCACCTCGAGGTCACGGTCACGAAACCTGCCCGGGCGGCCGCTCGA
```

*Fig. 15SS*

16507.1.edit

AGCGTGGTCGCGGCCGAGGTCAAGAACCCCGCCCGCACCTGCCGTGACCTCAAGATGTGCCACTCTGACT
GGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGCCCAGAAGAACTGGTACATCAGCA
AGAACCCCAAGGACAAGAGGCATGTCTGGTTCGGCGAGAGCATGACCGATGGATTCCAGTTCGAGTATGG
CGGCCAGGGCTCCGACCCTGCCGATGTGGACCTGCCCGNGCCGGNCCGCTCGAAAAGCCCNAATTTCCA
GNCACACTTGGCCGGCCGTTACTACTG

16507.2.edit

TCGAGCGGCCGCCCGGGCAGGTCCACATCGGCAGGGTCGGAGCCCTGGCCGCCATACTCGAACTGGAAT
CCATCGGTCATGCTCTCGCCGAACCAGACATGCCTCTTGTCCTTGGGGTTCTTGCTGATGTACCAGTTCTT
CTGGGCCACACTGGGCTGAGTGGGGTACACGCAGGTCTCACCAGTCTCCATGTTGCAGAAGACTTTGATG
GCATCCAGGTTGCAGCCTTGGTTGGGGTCAATCCAGTACTCTCCACTCTTCCAGTCAGAGTGGCACATCTT
GAGGTCACGGCAGGTGCGGGCGGGGTTCTTGACCTCGGCCGCGACCACGCT

16508.1.edit

CGAGCGGCCGCCCGGGCAGGTCCCCCCCCCTTTTTTTTTTTTTTTTTTTTTTTTTTTTTTTTTTTTTTTTT
TTTTTTTTTTTTTTTTTTT

16508.2.edit

AGCGTGGTCGCGGCCGAGGTCTGGCATTCCTTCGACTTCTCTCCAGCCGAGCTTCCCAGAACATCACATAT
CACTGCAAAAATAGCATTGCATACATGGATCAGGCCAGTGGAAATGTAAAGAAGGCCCTGAAGCTGATGGG
GTCAAATGAAGGTGAATTCAAGGCTGAAGGAAATAGCAAATTCACCTACACAGTTCTGGAGGATGGTTGCA
CGAAACACACTGGGGAATGGAGCAAAACAGTCTTTGAATATCGAACACGCAAGGCTGTGAGACTACCTATT
GTAGATATTGCACCCTATGACATTGGTGGTCCTGATCAAGAATTTGGTGTGGACGTTGGCCCTGTTTGCTTT
TTATAAACCAAACTCTATCTGAAATCCCAACAAAAAAAAATTTAACTCCATATGTGNTCCTCTTGTTCTAATCTT
GGCAACCAGTGCAAGTGACCGACAAAATTCCAGTTATTTATTTCCAAAATGTTTGGAAACAGTATAATTTGAC
AAAGAAAAAAGGATACTTCTCTTTTTTTGGCTGGTCCACCAAATACAATTCAAAAGGCTTTTTGGTTTTATTTT
TTTANCCAATTCCAATTTCAAAATGTCTCAATGGNGCTTATAATAAAATAAACTTTCACCCTTNTTTTNTGAT

*Fig. 15TT*

16509.1.edit

AGCGTGGTCGCGGCCGAGGTCTGGGATGCTCCTGCTGTCACAGTGAGATATTACAGGATCACTTACGGAG
AAACAGGAGGAAATAGCCCTGTCCAGGAGTTCACTGTGCCTGGGAGCAAGTCTACAGCTACCATCAGCGG
CCTTAAACCTGGAGTTGATTATACCATCACTGTGTATGCTGTCACTGGCCGTGGAGACAGCCCCGCAAGCA
GCAAGCCAATTTCCATTAATTACCGAACAGAAATTGACAAACCATCCCAGATGCAAGTGACCGATGTTCAGG
ACAACAGCATTAGTGTCAAGTGGCTGCCTTCAAGTTCCCCTGTTACTGGTTACAGAAGTAACCACCACTCCC
AAAAATGGACCAGGACCAACAAAAACTAAAACTGCAGGTCCAGATCAAACAGAAAATGGACTATTGAAGGC
TTGCAGCCCACAGTGGAAGTATGTGGNTAGGNGTCTATGCTCAGAATCCCAAGCCGGAGAAAGTCAGCCTT
CTGGTTTAGACTGCAGTAACCAACATTGATCGCCCTAAAGGACTGGNCATTCACTTGGATGGTGGATGTCC
AATTC

16509.2.edit

TCGAGCGGCCGCCCGGGCAGGTCCTTGCAGCTCTGCAGNGTCTTCTTCACCATCAGGTGCAGGGAATAGC
TCATGGATTCCATCCTCAGGGCTCGAGTAGGTCACCCTGTACCTGGAAACTTGCCCCTGTGGGCTTTCCCA
AGCAATTTTGATGGAATCGACATCCACATCAGNGAATGCCAGTCCTTTAGGGCGATCAATGTTGGTTACTGC
AGTCTGAACCAGAGGCTGACTCTCTCCGCTTGGATTCTGAGCATAGACACTAACCACATACTCCACTGTGG
GCTGCAAGCCTTCAATAGTCATTTCTGTTTGATCTGGACCTGCAGTTTTAAGTTTTTGGTGGTCCTGNCCCA
TTTTTGGGAAGTGGGGGGTTACTCTGTAACCAGTAACAGGGGAACTTGAAGGCAGCCACTTGACACTAATG
CTGTTGTCCTGAACATCGGTCACTTGCATCTGGGGATGGTTTGACAATTTCTGGTTCGGCAAATTAATGGA
AATTGGCTTGCTGCTTGGCGGGGCTGNCTCCACGGGCCAGTGACAGCATAC

16510.1.edit

TCGAGCGGCCGCCCGGGCAGGTCCTTGCAGCTCTGCAGTGTCTTCTTCACCATCAGGTGCAGGGAATAGC
TCATGGATTCCATCCTCAGGGCTCGAGTAGGTCACCCTGTACCTGGAAACTTGCCCCTGTGGGCTTTCCCA
AGCAATTTTGATGGAATCGACATCCACATCAGTGAATGCCAGTCCTTTAGGGCGATCAATGTTGGTTACTGC
AGTCTGAACCAGAGGCTGACTCTCTCCGCTTGGATTCTGAGCATAGACACTAACCACATACTCCACTGTGG
GCTGCAAGCCTTCAATAGTCATTTCTGTTTGATCTGGACCTGCAGTTTTAAGTTTTTGTTGGNCCTGNNCCA
TTTTTGGGGAAGGGGTGGTTACTCTTGTAACCAGTAACAGGGGAACTTGAAGCAGCCACTTGACACTAATG
CTGGTGGCCTGAACATCGGTCACTTGCATCTGGGATGGTTTGGTCAATTTCTGTTCGGTAATTAATGGGAAA
TTGGCTTACTGGCTTGCGGGGGCTGTCTCCACGGNCAGTGACAAGCATACACAGGNGATGGGTATAATCA
ACTCCAGGTTTAAGGCCNCTGATGGTA

16510.2.edit

AGCGTGGTCGCGGCCGAGGTCTGGGATGCTCCTGCTGTCACAGTGAGATATTACAGGATCACTTACGGAG
AAACAGGAGGAAATAGCCCTGTCCAGGAGTTCACTGTGCCTGGGAGCAAGTCTACAGCTACCATCAGCGG
CCTTAAACCTGGAGTTGATTATACCATCACTGTGTATGCTGTCACTGGCCGTGGAGACAGCCCCGCAAGCA
GTAAGCCAATTTCCATTAATTACCGAACAGAAATTGACAAACCATCCCAGATGCAAGTGACCGATGTTCAGG
ACAACAGCATTAGTGTCAAGTGGCTGCCTTCAAGTTCCCCTGTTACTGGTTACAGAGTAACCACCACTCCCA
AAAATGGGACCAGGACCAACAAAAAACTAAAACTGCANGGTCCAGATCAAACAGAAATGACTATTGAAGGC
TTGCAGCCCACAGTGGAGTATGTGGGTTAGTGTCTATGCTCAGAATNCCAAGCGGAGAGAGTCAGCCTCTG
GTTCAGACT

*Fig. 15UU*

16511.1.edit

TCGAGCGGCCGCCCGGGCAGGTCAGCGCTCTCAGGACGTCACCACCATGGCCTGGGCTCTGCTCCTCCT
CACCCTCCTCACTCAGGGCACAGGGTCCTGGGCCCAGTCTGCCCTGACTCAGCCTCCCTCCGCGTCCGG
GTCTCCTGGACAGTCAGTCACCATCTCCTGCACTGGAACCAGCAGTGACGTTGGTGCTTATGAATTTGTCT
CCTGGTACCAACAACACCCAGGCAAGGCCCCCAAACTCATGATTTCTGAGGTCACTAAGCGGCCCTCAGG
GGTCCCTGATCGCTTCTCTGGCTCCAAGTCTGGCAACACGGCCTCCCTGACCGTCTCTGGGCTCCANGCT
GAGGATGANGCTGATTATTACTGGAAGCTCATATGCAGGCAACAACAATTGGGTGTTCGGCGGAAGGGAC
CAAGCTGACCGTNCTAAGGTCAAGCCCAAGGCTTGCCCCCCTCGGTCACTCTGTTCCCACCCTCCTCTGAA
GAAGCTTTCAAGCCAACAANGNCACACTGGGTGTGTCTCATAAGTGGACTTTCTACCC

16511.2.edit

AGCGTGGTCGCGGCCGAGGTCTGTAGCTTCTGTGGGACTTCCACTGCTCAGGCGTCAGGCTCAGGTAGCT
GCTGGCCGCGTACTTGTTGTTGCTTTGNTTGGAGGGTGTGGTGGTCTCCACTCCCGCCTTGACGGGGCTG
CTATCTGCCTTCCAGGCCACTGTCACGGCTCCCGGGTAGAAGTCACTTATGAGACACACCAGTGTGGCCTT
GTTGGCTTGAAGCTCCTCAGAGGAGGGTGGGAACAGAGTGACCGAGGGGGCAGCCTTGGGCTGACCTAG
GACGGTCAGCTTGGTCCCTCCGCCGAACACCCAATTGTTGTTGCCTGCATATGAGCTGCAGTAATAATCAG
CCTCATCCTCAGCCTGGAGCCCAGAGACNGTCAAGGGAGGCCCGTGTTTGCCAAGACTTGGAAGCCAGAN
AAGCGATCAGGGACCCCTGAGGGCCGCTTTACNGACCTCAAAAAATCATGAATTTGGGGGGCCTTTGCCT
GGGNGTTGGTTGGTNACCAGNAAAACAAAATTTCATAAAGCACCAACGTCACTGCTGGTTTCCAGTGCANG
AANATGGTGAACTGAANTGTCC

16512.1.edit

AGCGTGGTCGCGGCCGAGGTCCAGCATCAGGAGCCCCGCCTTGCCGGCTCTGGTCATCGCCTTTCTTTTT
GTGGCCTGAAACGATGTCATCAATTCGCAGTAGCAGAACTGCCGTCTCCACTGCTGTCTTATAAGTCTGCA
GCTTCACAGCCAATGGCTCCCATATGCCCAGTTCCTTCATGTCCACCAAAGTACCCGTCTCACCATTTACAC
CCCAGGTCTCACAGTTCTCCTGGGTGTGCTTGGCCCGAAGGGAGGTAAGTANACGGATGGTGCTGGTCCC
ACAGTTCTGGATCAGGGTACGAGGAATGACCTCTAGGGCCTGGGCNACAAGCCCTGTATGGACCTGCCCG
GGCGGGCCCGCTCGA

16512.2.edit

TCGAGCGGCCGCCCGGGCAGGTCCATACAGGGCTGTTGCCCAGGCCCTAGAGGNCATTCCTTGTACCCT
GATCCAGAACTGTGGGACCAGCACCATCCGTCTACTTACCTCCCTTCGGGCCAAGCACACCCAGGAGAAC
TGTGAGACCTGGGGTGTAAATGGNGAGACGGGTACTTTGGTGGACATGAAGGAACTGGGCATATGGGAGC
CATTGGCTGNGAAGCTGCANACTTATAAGACAGCAGTGGAGACGGCAGTTCTGCTACTGCGAATTGATGAC
ATCGTTTCAGGCCACAAAAAGAAAGGCGATGACCANAGCCGGCAAGGCGGGGCTTCCTGATGCTGGACCT
CGGCCGCCGACCACGCTT

*Fig. 15VV*

16514.1.edit

```
AGCGTGGTCGCGGCCGAGGTCCACTAGAGGTCTGTGTGCCATTGCCCAGGCAGAGTCTCTGCGTTACAAA
CTCCTAGGAGGGCTTGCTGTGCGGAGGGCCTGCTATGGTGTGCTGCGGTTCATCATGGAGAGTGGGGCC
AAAGGCTGCGAGGTTGTGGTGTCTGGGAAACTCCGAGGACAGAGGGCTAAATCCATGAAGTTTGTGGATG
GCCTGATGATCCACAGCGGAGACCCTGTTAACTACTACGTTGACACTGCTGTGCGCCACGTGTTGCTCANA
CAGGGTGTGCTGGGCATCAAGGTGAAGATCATGCTGCCCTGGGACCCANCTGGCAAAAATGGCCCTTAAA
AACCCCTTGCCNTGACCACGTGAACCATTTGTGNGAACCCCAAGATGAANATACTTGCCCACCACCCCCCA
TTC
```

16514.2.edit

```
TCGAGCGGCCGCCCGGGCAGGTCTGCCAAGGAGACCCTGTTATGCTGTGGGGACTGGCTGGGGCATGGC
AGGCGGCTCTGGCTTCCCACCCTTCTGTTCTGAGATGGGGGTGGTGGGCAGTATCTCATCTTTGGGTTCCA
CAATGCTCACGTGGTCAGGCAGGGGCTTCTTAGGGCCAATCTTACCAGTTGGGTCCCAGGGCAGCATGAT
CTTCACCTTGATGCCCAGCACACCCTGTCTGAGCAACACGTGGCGCACAGCAGTGTCAACGTAGTAGTTAA
CAGGGTCTCCGCTGTGGATCATCAGGCCATCCACAAACTTCATGGATTTAGCCCTCTGTCCTCGGAGTTTC
CCAAAACACCACAACCTCGCCAGCCTTTGGGCCCCACTTCTTCATGAATGAAACCGCAGCACACCATTANC
AAGGCCCTTCCGCACAGGNAAGCCCTTCCTAAGGAGTTTTGTAAACGCAAAAAACTCTTGCCTGGGGCAAA
TGGGCACACAGACCTNTANTNGGACCTTGGNCCGCGAACCACCGCTT
```

16515.1.edit

```
AGCGTGGTCGCGGCCGAGGTCTGGCCCTCCTGGCAAGGCTGGTGAAGATGGTCACCCTGGAAAACCCGG
ACGACCTGGTGAGAGAGGAGTTGTTGGACCACAGGGTGCTCGTGGTTTCCCTGGAACTCCTGGACTTCCT
GGCTTCAAAGGCATTAGGGGACACAATGGTCTGGATGGATTGAAGGGACAGCCCGGTGCTCCTGGTGTGA
AGGGTGAACCTGGNGCCCCTGGTGAAAATGGAACTCCAGGTCAAACAGGAGCCCGNGGGCTTCCTGGNG
AGAGAGGACGTGTTGGTGCCCCTGGCCCANACCTGCCCGGGCGGCCGCTCNAAAAGCCGAAATCCAGNA
CACTGGCGGCCGNTACTANTGGAATCCGAACTTCGGTACCAAAGCTTGGCCGTAATCATGGCCATAGCTTG
TTCCCTGGGGNGGAAATTGGTATTCCGCTNCCAATTCCACACAACATACCGAACCCGGAAAGCATTAAAGT
GTAAAAGCCCTGGGGGGGCCTAAATGANGTGAGCNTAACTCNCATTTAATTGGCGTTGCGCTTCACTGCCC
CGCTTTTCCAGTCCGGGNA
```

16515.2.edit

```
TCGAGCGGCCGCCCGGGCAGGTCTGGGCCAGGGGCACCAACACGTCCTCTCTCACCAGGAAGCCCACGG
GCTCCTGTTTGACCTGGAGTTCCATTTTCACCAGGGGCACCAGGTTCACCCTTCACACCAGGAGCACCGG
GCTGTCCCTTCAATCCATCCAGACCATTGTGNCCCCTAATGCCTTTGAAGCCAGGAAGTCCAGGAGTTCCA
GGGAAACCACGAGCACCCTGTGGTCCAACAACTCCTCTCTCACCAGGTCGTCCGGGTTTTCCAGGGTGAC
CATCTTCACCAGCCTTGCCAGGAGGGCCAGACCTCGGCCGCGACCACGCT
```

*Fig. 15WW*

16516.1.edit

ANCGTGGTCGCGGCCGAGGTCCTCACCAGAGGTGNCACCTACAACATCATAGTGGAGGCACTGAAAGACC
ANCAGAGGCATAAGGTTCGGGAAGAGG

16516.2.edit

TCGAGCGGCCGCCCGGGCAGGTCCATTTTCTCCCTGACGGTCCCACTTCTCTCCAATCTTGTAGTTCACAC
CATTGTCATGGCACCATCTAGATGAATCACATCTGAAATGACCACTTCCAAAGCCTAAGCACTGGCACAACA
GTTTAAAGCCTGATTCAGACATTCGTTCCCACTCATCTCCAACGGCATAATGGGAAACTGTGTAGGGGTCAA
AGCACGAGTCATCCGTAGGTTGGTTCAAGCCTTCGTTGACAGAGTTGTCCACGGTAACAACCTCTTCCCGA
ACCTTATGCCTCTGCTGGTCTTTCAGTGCCTCCACTATGATGTTGTAGGTGGCACCTCTGGTGAGGACCTC
NGNCCNGAACAACGCTTAAGCCCGNATTCTGCAGAATAATCCCATCACACTTGGCGGCCGCTTCGANCATG
CATCNTAAAAGGGGCCCCAATTTCCCCCTTATAAGNGAANCCGTATTTNCCAATTTCACTGGNCCCGCCGN
TTTTACAAACGNCGGTGAACTGGGGAAAAACCCTGGCGGTTACCCAACTTTAATCGCCNTTGGCAGCACAA
TCCCCCCTTTTCGNCCANCNTGGGCGTAAATAACCGAAAA

16517.1.edit

ANCGNGGTCGCGGCCGANGTNTTTTTTCTTNTTTTTTT

16518.1.edit

AGCGTGGTCGCGGCCGAGGTCTGAGGTTACATGCGTGGTGGTGGACGTGAGCCACGAAGACCCTGAGGT
CAAGTTCAACTGGTACGTGGACGGCGTGGAGGTGCATAATGCCAAGACAAAGCCGCGGGAGGAGCAGTAC
AACAGCACGTACCGGGNGGTCAGCGTCCTCACCGTCCTGCACCAGAATTGGTTGAATGGCAAGGAGTACA
AGNGCAAGGTTTCCAACAAAGCCNTCCCAGCCCCCNTCGAAAAAACCATTTCCAAAGCCAAAGGGCAGCC
CCGAGAACCACAGGTGTACACCCTGCCCCCATCCCGGGAGGAAAAGANCAANAACCNGGTTCAGCCTTAA
CTTGCTTGGTCNAANGCTTTTTATCCCAACGNACTTCCCCCNTGGAANTGGGAAAAACCAATGGGCCAANC
CGAAAAACAATTACAANAACCCC

16518.2.edit

TCGAGCGGCCGCCCGGGCAGGTGTCGGAGTCCAGCACGGGAGGCGTGGTCTTGTAGTTGTTCTCCGGCT
GCCCATTGCTCTCCCACTCCACGGCGATGTCGCTGGGATAGAAGCCTTTGACCAGGCAGGTCAGGCTGAC
CTGGTTCTTGGTCATCTCCTCCCGGGATGGGGGCAGGGTGAACACCTGGGGTTCTCGGGCTTGCCCTTT
GGTTTTGAANATGGTTTTCTCGATGGGGGCTGGAAGGGCTTTGTTGNAAACCTTGCACTTGACTCCTTGCC
ATTCACCCAGNCCTGGNGCAGGACGGNGAGGACNCTNACCACACGGAACCGGGCTGGTGGACTGCTCC

*Fig. 15XX*

16519.1.edit

AGCGTGGTCGCGGACGANGTCCTGTCAGAGTGGNACTGGTAGAAGTTCCANGAACCCTGAACTGTAAGGG
TTCTTCATCAGTGCCAACAGGATGACATGAAATGATGTACTCAGAAGNGNCCTGGAATGGGGCCCATGANA
TGGTTGCC

16519.2.edit

TCGAGCGGCCGCCCGGGCAGGTCCACCACACCCAATTCCTTGCTGGTATCATGGCAGCCGCCACGTGCCA
GGATTACCGGCTACATCATCAAGTATGAGAAGCCTGGGTCTCCTCCCAGAGAAGTGGTCCCTCGGCCCCG
CCCTGGTGTCACAGAGGCTACTATTACTGGCCTGGAACCGGGAACCGAATATACAATTTATGTCATTGCCC
TGAAGAATAATCAGAAGAGCGAGCCCCTGATTGGAAGGAAAAAGACAGACGAGCTTCCCCAACTGGTAACC
CTTCCACACCCCAATCTTCATGGACCAGAGATCTTGGATGTTCCTTCCACAGTTCAAAAGACCCCTTTCGGC
ACCCCCCCTGGGTATGAACCTGGGAAAANGGNANTTAANCTTTCCTGGCA

16520.1.edit

AGCGTGGTCGCGGCCGAGGTCTGGGATGCTCCTGCTGTCACAGTGAGATATTACAGGATCACTTACGGAG
AAACAGGAGGAAATAGCCCTGTCCAGGAGTTCACTGTGCCTGGGAGCAAGTCTACAGCTACCATCAGCGG
CCTTAAACCTGGAGTTGATTATACCATCACTGTGTATGCTGTCACTGGCCGTGGAGACAGCCCCGCAAGCA
GCAAGCCAATTTCCATTAATTACCGAACAGAAATTGACAAACCATCCCAGATGCAAGTGACCGATGTTCAGG
ACAACAGCATTAGTGTCAAGTGGCTGCCTTCAAGGTNCCCTGGTACTGGGTTACAGANTAACCACCACTCC
CAAAAATGGACCAGGAACCACAAAAACTTAAACTGCAGGGTCCAGATCAAAACAGAAATGACTATTGAANG
CTTGCAGCCCACAGTGGGAGTATGNGGGTAGTGNCTATGCTTCAGAATCCAAGCGGAAAAANGTCAAGCC
TTNTGGGTTCAA

16520.2.edit

TCGAGCGGCCGCCCGGGCAGGTCCTTGCAGCTCTGCAGTGTCTTCTTCACCATCAGGTGCAGGGAATAGC
TCATGGATTCCATCCTCAGGGCTCGAGTAGGTCACCCTGTACCTGGAAACTTGCCCCTGTGGGCTTTCCCA
AGCAATTTTGATGGAATCGACATCCACATCAGTGAATGCCAGTCCTTTAGGGCGATCAATGTTGGTTACTGC
AGNCTGAACCAGAGGCTGACTCTCTCCGCTTGGATTCTGAGCATAGACACTAACCACATACTCCACTGTGG
GCTGCAANCCTTCAATAANNCATTTCTGTTTGATCTGGACC

16521.2.edit

TCGAGCGGCCGCCCGGGCAGGTCTGGTGGGGTCCTGGCACACGCACATGGGGGNGTTGNTCTNATCCAG
CTGCCCAGCCCCCATTGGCGAGTTTGAGAAGGTGTGCAGCAATGACAACAANACCTTCGACTCTTCCTGCC
ACTTCTTTGCCACAAAGTGCACCCTGGAGGGCACCAAGAAGGGCCACAAGCTCCACCTGGACTACATCGG
GCCTTGCAAATACATCCCCCCTTGCCTGGACTCTGAGCTGACCGAATTCCCCCTTGCGCATGCGGGACTG
GCTCAAGAACCGTCCTGGCACCCTTGTATGANAGGGATGAAGACACNACCC

*Fig. 15YY*

16522.1.edit

AGCGTGGTCGCGGCCGAGGTCTGTCCTACAGTCCTCAGGACTCTACTCCCTCAGCAGCGTGGTGACCGTG
CCCTCCAGCAACTTCGGCACCCAGACCTACACCTGCAACGTAGATCACAAGCCCAGCAACACCAAGGTGG
ACAAGAGAGTTGAGCCCAAATCTTGTGACAAAACTCACACATGCCCACCGTGCCCAGCACCTGAACTCCTG
GGGGGACCGTCAGTCTTCCTCTTCCCCCGCATCCCCCTTCCAAACCTGCCCGGGCGGCCGCTCGAAAGCC
GAATTCCAGCACACTGGCGGCCGGTACTAGTGGANCCNAACTTGGNANCCAACCTGGNGGAANTAATGGG
CATAANCTGTTTCTGGGGGGAAATTGGTATCCNGTTTACAATTCCCNCACAACATACGAGCCGGAAGCATA
AAAGNGTAAAAGCCTGGGGGNGGCCTANTGAAGTGAAGCTAAACTCACATTAATTNGCGTTGCCGCTCACT
GGCCCGCTTTTCCAGC

16522.2.edit

TCGAGCGGCCGCCCGGGCAGGTTTGGAAGGGGGATGCGGGGGAAGAGGAAGACTGACGGTCCCCCCAG
GAGTTCAGGTGCTGGGCACGGTGGGCATGTGTGAGTTTTGTCACAAGATTTGGGCTCAACTCTCTTGTCCA
CCTTGGTGTTGCTGGGCTTGTGATCTACGTTGCAGGTGTAGGTCTGGGNGCCGAAGTTGCTGGAGGGCAC
GGTCACCACGCTGCTGAGGGAGTAGAGTCCTGAGGACTGTANGACAGACCTCGGCCGNGACCACGCTAA
GCCGAATTCTGCAGATATCCATCACACTGGCGGCCGCTCCGAGCATGCATTTTAGAGG

16523.1.edit

AGCGTGGNCGCGGACGANGACAACAACCCC

16523.2.edit

TCGAGCGGCCGCCCGGGCAGGNCCACATCGGCAGGGTCGGAGCCCTGGCCGCCATACTCGAACTGGAAT
CCATCGGTCATGCTCTTGCCGAACCAGACATGCCTCTTGTCCTTGGGGTTCTTGCTGATGNACCAGTTCTT
CTGGGCCACACTGGGCTGAGTGGGGTACACGCAGGTCTCACCAGTCTCCATGTTGCAGAAGACTTTGATG
GCATCCAGGTTGCAGCCTTGGTTGGGGTCAATCCAGTACTCTCCACTCTTCCAGTCAGAGTGGCACATCTT
GAGGTCACGGCAGGTGCGGGCGGGGTTCTTGACCT

16524.1.edit

AGCGTGGTCGCGGCCGAGGTCCAGCCTGGAGATAANGGTGAAGGTGGTGCCCCCGGACTTCCAGGTATA
GCTGGACCTCGTGGTAGCCCTGGTGAGAGAGGTGAAACTGGCCCTCCAGGACCTGCTGGTTTCCCTGGTG
CTCCTGGACAGAATGGTGAACCTGGNGGTAAAGGAGAAAGAGGGGCTCCGGNTGANAAAGGTGAAGGAG
GCCCTCCTGNATTGGCAGGGGCCCCANGACTTAGAGGTGGAGCTGGCCCCCCTGGCCCCGAAGGAGGAA
AGGGTGCTGCTGGTCCTCCTGGGCCACCTGG

Fig. 15ZZ

16524.2.edit

TCGAGCGGCCGCCCGGGCAGGTCTGGGCCAGGAGGACCAATAGGACCAGTAGGACCCCTTGGGCCATCT
TTCCCTGGGACACCATCAGCACCTGGACCGCCTGGTTCACCCTTGTCACCCTTTGGACCAGGACTTCCAAG
ACCTCCTCTTTCTCCAGGCATTCCTTGCAGACCAGGAGTACCANCAGCACCAGGTGGCCCAGGAGGACCA
GCAGCACCCTTTCCTCCTTCGGGACCAGGGGGACCAGCTCCACCTCTAAGTCCTGGGGCCCCTGCCAATC
CAGGAGGGCCTCCTTCACCTTTCTCACCCGGAGCCCCTCTTTCT

16526.1.edit

TCGAGCGGCCGCCCGGGCAGGTCCACCGGGATATTCGGGGGTCTGGCAGGAATGGGAGGCATCCAGAAC
GAGAAGGAGACCATGCAAAGCCTGAACGACCGCCTGGCCTCTTACCTGGACAGAGTGAGGAGCCTGGAGA
CCGACAACCGGAGGCTGGAGAGCAAAATCCGGGAGCACTTGGAGAAGAAGGGACCCCAGGTCAGAGACT
GGAGCCATTACTTCAAGATCATCGAGGACCTGAGGGCTCANATCTTCGCAAATACTGCNGACAATGCCCG

16526.2.edit

ATGCGNGGTCGCGGCCGANGACCANCTCTGGCTCATACTTGACTCTAAAGNCNTCACCAGNANTTACGGN
CATTGCCAATCTGCAGAACGATGCGGGCATTGTCCGCANTATTTGCGAAGATCTGAGCCCTCAGGNCCTCG
ATGATCTTGAAGTAANGGCTCCAGTCTCTGACCTGGGGTCCCTTCTTCTCCAAGTGCTCCCGGATTTTGCTC
TCCAGCCTCCGGTTCTCGGTCTCCAAGNCTTCTCACTCTGTCCAGGAAAAGAGGCCAGGCGGNCGATCAG
GGCTTTTGCATGGACT

16527.1.edit

AGCGTGGTCGCGGCCGAGGTTGTACAAGCTTTTTTTTTTTTTTTTTTTTTTTTTTTTTTTTTTTTTTTTTTTTTT
TTTTTTTTTTTTTTTTTTTTTTTTT

16527.2.edit

TCGAGCGGCCGCCCGGGCAGGTCTGCCAACACCAAGATTGGCCCCCGCCGCATCCACACAGTTNGTGTG
CGGGGAGGTAACAAGAAATACCGTGCCCTGAGGNTGGACGNGGGGAATTTCTCCTGGGGCTCAGAGTGTT
GTACTCGTAAAACAAGGATCATCGATGTTGTCTACAATGCATCTAATAACGAGCTGGTTCGTACCAAGACCC
TGGTGAAGAATTGCATCGTGCTCATNGACAGCACACCGTACCGACAGTGGGTACCGAAGTCCCACTATGCN
CCT

*Fig. 15AAA*

16528.1.edit

TCGAGCGGCCGCCCGGGCAGGTCCACCACACCCAATTCCTTGCTGGTATCATGGCAGCCGCCACGTGCCA
GGATTACCGGCTACATCATCAAGTATGAGAAGCCTGGGTCTCCTCCCAGAGAAGTGGTCCCTCGGCCCCG
CCCTGGTGTCACAGAGGCTACTATTACTGGCCTGGAACCGGGAACCGAATATACAATTTATGTCATTGCCC
TGAAG

16528.2.edit

AGCGTGNTCNCGGCCGAGGATGGGGAAGCTCGNCTGTCTTTTTCCTTCCAATCAGGGGCTNNNTCTTCTG
ATTATTCTTCAGGGCAANGACATAAATTGTATATTCGGNTCCCGGTTCCAGNCCAGTAATAGTAGCCTCTGT
GACACCAGGGCGGGGCCGAGGGACCACTTCTCTGGGAGGAGACCCAGGCTTCTCATACTTGATGATGAAG
CCGGTAATCCTGGCACGTGGGCGGCTGCCATGATACCACCAANGAATTGGGTGTGGTGGACCTGCCCGG
GCGGGCCGCTCGAAAANCCGAATTCNTGCAAGAATATCCATCACACTTGGGCGGGCCGNTCGAACCATGC
ATCNTAAAAGGGCCCCAATTTCCCCCCTATTAGGNGAAGCCNCATTTAACAAATTCCACTTGG

16529.1.edit

TCGAGCGGCCGCCCGGGCAGGTCTCGCGGTCGCACTGGTGATGCTGGTCCTGTTGGTCCCCCCGGCCCT
CCTGGACCTCCTGGTCCCCCTGGTCCTCCCAGCGCTGGTTTCGACTTCAGCTTCCTGCCCCAGCCACCTC
AAGAGAAGGCTCACGATGGTGGCCGCTACTACCGGGCTGATGATGCCAATGTGGTTCGTGACCGTGACCT
CGAGGTGGACACCACCCTCAAGAGCCTTGAGCCAGCAGAATCGAAAACATTCGGAACCCAAGAAGGGCAA
GCCCGCAAAGAAACCCCGCCCGCACCTGGCCGNGAACCTCCAAGAANGTGCCCACNTCTTGACTGGGAAA
AAAAGGGAAAANTACTTGGAATTGGAC

16529.2.edit

AGCGTGGTCGCGGCCGAGGTCCACATCGGCAGGGTCGGAGCCCTGGCCGCCATACTCGAACTGGAATCC
ATCGGTCATGCTCTCGCCGAACCAGACATGCCTCTTGTCCTTGGGGTTCTTGCTGATGTACCAGTTCTTCTG
GGCCACACTGGGCTGAGTGGGGTACACGCAGGTCTCACCAGTCTCCATGTTGCAGAAGACTTTGATGGCA
TCCAGGTTGCAGCCTTGGTTGGGGTCAATCCAGTACTCTCCACTCTTCCAGTCAGAAGTGGCACATCTTGA
GGTCACGGCAGGGTGCGGGCGGGGTTCTTGCGGGCTGCCCTTCTGGGCTCCCGGAATGTTCTNNGAACT
TGCTGG

*Fig. 15BBB*

16530.1.edit

AGCGTGGTCGCGGCCGAGGTCCACTAGAGGTCTGTGTGCCATTGCCCAGGCAGAGTCTCTGCGTTACAAA
CTCCTAGGAGGGCTTGCTGTGCGGAGGGCCTGCTATGGTGTGCTGCGGTTCATCATGGAGAGTGGGGCC
AAAGGCTGCGAGGTTGTGGTGTCTGGGAAACTCCGAGGACAGAGGGCTAAATCCATGAAGTTTGTGGATG
GCCTGATGATCCACAGCGGAGACCCTGTTAACTACTACGTTGACACTTGCTTGTGCGCCACGTGTTGCTCA
NACANGGGTGGGCTGGGCATCAAGGNG

16530.2.edit

TCGAGCGGCCGCCCGGGCAGGTCTGCCAAGGAGACCCTGTTATGCTGTGGGGACTGGCTGGGGCATGGC
AGGCGGCTCTGGCTTCCCACCCTTCTGTTCTGAGATGGGGGTGGTGGGCAGTATCTCATCTTTGGGTTCCA
CAATGCTCACGTGGTCAGGCAGGGGCTTCTTAGGGCCAATCTTACCAGTTGGGTCCCAGGGCAGCATGAT
CTTCACCTTGATGCCCAGCACACCCTGTCTGAGCAACACGTGGCGCACAGCAAGTGTCAACGTAAGTAAGT
TAACAGGGTCTCCGCTGTGGATCATCAGGCCATCCACAAACTTCATGGATTTAACCCTCTGTCCTCGGAG

16531.1.edit

TCGAGCGGCCGCCCGGGCAGGTGTTTCAGAGGTTCCAAGGTCCACTGTGGAGGTCCCAGGAGTGCTGGT
GGTGGGCACAGAGGTCCGATGGGTGAAACCATTGACATAGAGACTGTTCCTGTCCAGGGTGTAGGGGCCC
AGCTCTTTGATGCCATTGGCCAGTTGGCTCAGCTCCCAGTACAGCCGCTCTCTGTTGAGTCCAGGGCTTTT
GGGGTCAAGATGATGGATGCAGATGGCATCCACTCCAGTGGCTGCTCCATCCTTCTCGGACCTGAGAGAG
GTCAGTCTGCAGCCAGAGTACAGAGGGCCAACACTGGTGTTCTTTGAATA

16531.2.edit

AGCGTGGTCGCGGCCGAGGTCTGTACTGGGAGCTAAGCAAACTGACCAATGACATTGAAGAGCTGGGCCC
CTACACCCTGGACAGGAACAGTCTCTATGTCAATGGTTTCACCCATCAGAGCTCTGTGNCCACCACCAGCA
CTCCTGGGACCTCCACAGTGGATTTCAGAACCTCAGGGACTCCATCCTCCCTCTCCAGCCCCACAATTATG
GCTGCTGGCCCTCTCCTGGTACCATTCACCCTCAACTTCACCATCACCAACCTGCAGTATGGGGAGGACAT
GGGTCACCCTGNCTCCAGGAAGTTCAACACCACA

16532.1.edit

TCGAGCGGCCGCCCGGACAGGTCTGGGCGGATAGCACCGGGCATATTTTGGAATGGATGAGGTCTGGCA
CCCTGAGCAGTCCAGCGAGGACTTGGTCTTAGTTGAGCAATTTGGCTAGGAGGATAGTATGCAGCACGGN
TCTGAGNCTGTGGGATAGCTGCCATGAAGTAACCTGAAGGAGGTGCTGGCTGGTANGGGTTGATTACAGG
GTTGGGAACAGCTCGTACACTTGCCATTCTCTGCATATACTGGTTAGTGAGGTGAGCCTGGCCCTCTTCTTT
TG

*Fig. 15CCC*

01_16558.3.edit

AGCGTGGTCGCGGCCGAGGTGAGCCACAGGTGACCGGGGCTGAAGCTGGGGCTGCTGGNCCTGCTGGT
CCTG

02_16558.4.edit

CAGCNGCTCCNACGGGGCCTGNGGGACCAACAACACCGTTTTCACCCTTAGGCCCTTTGGCTCCTCTTTCT
CCTTTAGCACCAGGTTGACCAGCAGCNCCANCAGGACCAGCAAATCCATTGGGGCCAGCAGGACCGACCT
CACCACGTTCACCAGGGCTTCCCCGAGGACCAGCAGGACCAGCAGGACCAGCAGCCCCAGCTTCGCCCC
GGTCACCTGTGGCTCACCTCGGCCGCGACCACGCT

03_16535.1.edit

TCGAGCGGTCGCCCGGGCAGGTCCACCGGGATAGCCGGGGGTCTGGCAGGAATGGGAGGCATCCAGAA
CGAGAAGGAGACCATGCAAAGCCTGAACGACCGCCTGGCCTCTTACCTGGACAGAGTGAGGAGCCTGGA
GACCGANAACCGGAGGCTGGANAGCAAAATCCGGGAGCACTTGGAGAAGAAGGGACCCCAGGTCAAGAG
ACTGGAGCCATTACTTCAAGATCATCGAGGGACCTGGAGG

04_16535.2.edit

AGCGNGGTCGCGGCCGAGGTCCAGCTCTGTCTCATACTTGACTCTAAAGTCATCAGCAGCAAGACGGGCA
TTGTCAATCTGCAGAACGATGCGGGCATTGTCCGCAGTATTTGCGAAGATCTGAGCCCTCAGGTCCTCGAT
GATCTTGAAGTAATGGCTCCAGTCTCTGACCTGGGGTCCCTTCTTCTCCAAGTGCTCCCGGATTTTGCTCTC
CAGCCTCCGGTTCTCGGTCTCCAGGCTCCTCACTCTGTCCAGGTAAGAAGGCCCAGGCGGTCGTTCAGGC
TTTGCATGGTCTCCTTCTCGTTCTGGATGCCTCCCATTCCTGCCAGACCC

05_16536.1.edit

TCGAGCGGCCGCCCGGGCAGGTCAGGAAGCACATTGGTCTTAGAGCCACTGCCTCCTGGATTCCACCTGT
GCTGCGGACATCTCCAGGGAGTGCAGAAGGGAAGCAGGTCAAACTGCTCAGATCAGTCAGACTGGCTGTT
CTCAGTTCTCACCTGAGCAAGGTCAGTCTGCAGCCAGAGTACAGAGGGCCAACACTGGTGTTCTTGAACAA
GGGCTTGAGCAGACCCTGCAGAACCCTCTTCCGTGGTGTTGAACTTCCTGGAAACCAGGGTGTTGCATGTT
TTTCCTCATAATGCAAGGTTGGTGATGG

*Fig. 15DDD*

07_16537.1.edit

AGCGTGGTCGCGGCCGAGGTCCACATCGGCAGGGTCGGAGCCCTGGCCGCCATACTCGAACTGGAATCC
ATCGGTCATGCTCTCGCCGAACCAGACATGCCTCTTGTCCTTGGGGTTCTTGCTGATGTACCAGTTCTTCTG
GGCCACACTGGGCTGAGTGGGGTACACCGCAGGTCTCACCAGTCTCCATGTTGCAGAAGACTTTGATGGC
ATCCAGGTTGCAGCCTTGGTTGGGGTCAATCCAGTACTCTCCACTCTTCCAGTCAGAAGTGGGCACATCTT
GAGGTCACCGGCAGGTGCCGGGCCGGGGGTTCTTGCGGCTTGCCCTCTGGGCTCCGGATGTTCTCGATC
TGCTTGGCTCAGGCTCTTGAGGGTGGGTGTCCACCTCGAGGTCACGGTCACCGAAACCTGCCCGGGCGG
CCCGCTCGA

08_16537.2.edit

TCGAGCGGTCGCCCGGGCAGGTTTCGTGACCGTGACCTCGAGGTGGACACCACCCTCAAGAGCCTGAGC
CAGCAGATCGAGAACATCCGGAGCCCAGAGGGCAGCCGCAAGAACCCCGCCCGCACCTGCCGTGACCTC
AAGATGTGCCACTCTGACTGGAAGAGTGGAGAGTACTGGATTGACCCCAACCAAGGCTGCAACCTGGATG
CCATCAAAGTCTTCTGCAACATGGAGACTGGTGAGACCTGCGTGTACCCCACTCAGCCCAGTGTGGGCCC
AGAAGAAACTGGTACATCAGCAAGGAACCCCAAGGACAAGAGGCATTGTCTTGGTTCGGCGAGNAGCATG
ACCCGATGGATTCCAGTTTCGAGTATTGGCGGCCAGGGCTTCCCGACCCTTGCCGATGTGGACCTCGGCC
GCGACCACCGCT

*Fig. 15EEE*

Date:1/21/99

O8E Rabbits 01212000

| Antigen on Plate | Sera Sample | Antibody Dilutions | | | | | | | | | | |
|---|---|---|---|---|---|---|---|---|---|---|---|---|
| | | 1:1000 | 1:2000 | 1:4000 | 1:8000 | 1:16000 | 1:32000 | 1:64000 | 1:128000 | 1:256000 | 1:512000 | 1:1024000 | 1:2048000 |
| O8E (#632-24) | Preimmune sera (#2576L):11/10/99 | 0.13 | 0.09 | 0.08 | 0.07 | 0.07 | 0.07 | 0.07 | 0.06 | 0.07 | 0.07 | 0.07 | 0.07 |
| | | 0.10 | 0.08 | 0.07 | 0.07 | 0.07 | 0.07 | 0.07 | 0.06 | 0.06 | 0.07 | 0.06 | 0.07 |
| | Average | 0.11 | 0.08 | 0.07 | 0.07 | 0.07 | 0.07 | 0.07 | 0.06 | 0.07 | 0.07 | 0.06 | 0.07 |
| | α-O8E (#2576K):1/11/2000 | 2.92 | 2.81 | 2.74 | 2.70 | 2.58 | 2.08 | 1.61 | 1.01 | 0.68 | 0.40 | 0.24 | 0.15 |
| | | 2.93 | 2.77 | 2.74 | 2.69 | 2.48 | 2.08 | 1.57 | 1.00 | 0.66 | 0.40 | 0.23 | 0.16 |
| | Average | 2.93 | 2.79 | 2.74 | 2.69 | 2.53 | 2.08 | 1.59 | 1.00 | 0.67 | 0.40 | 0.23 | 0.16 |
| | Preimmune sera (#2333L):11/10/99 | 0.09 | 0.07 | 0.06 | 0.06 | 0.07 | 0.07 | 0.07 | 0.07 | 0.07 | 0.07 | 0.07 | 0.07 |
| | | 0.08 | 0.07 | 0.06 | 0.06 | 0.10 | 0.07 | 0.07 | 0.07 | 0.07 | 0.07 | 0.07 | 0.07 |
| | Average | 0.08 | 0.07 | 0.06 | 0.06 | 0.08 | 0.07 | 0.07 | 0.07 | 0.07 | 0.07 | 0.07 | 0.07 |
| | α-O8E (#2333L):1/11/2000 | 2.73 | 2.75 | 2.64 | 2.48 | 2.30 | 1.78 | 1.41 | 0.92 | 0.58 | 0.32 | 0.20 | 0.14 |
| | | 2.73 | 2.76 | 2.51 | 2.60 | 2.37 | 1.93 | 1.44 | 0.88 | 0.58 | 0.35 | 0.20 | 0.14 |
| | Average | 2.73 | 2.76 | 2.57 | 2.54 | 2.33 | 1.85 | 1.43 | 0.90 | 0.58 | 0.33 | 0.20 | 0.14 |

Fig. 23 affi-pure O8E #2576L 739.87A&B

| Date: 5/2/2000 | |
|---|---|
| Antibody Name | O8E polyclonal |
| Rabbit #, Bleed Date | 2576L, 1/11/2000 |
| Purification Method | affinity |
| Buffer | PBS |
| Notebook | #705, p150 |

| lot # | 739.87A | 739.87B |
|---|---|---|
| Antibody Concentration | 1.4mg/ml | 1.7mg/ml |
| Initial Amount | 18mg | 3mg |

| Antigen on Plate | Sera Sample | Antibody Dilutions | | | | | | | | | | |
|---|---|---|---|---|---|---|---|---|---|---|---|---|
| | | 1:1000 | 1:2000 | 1:4000 | 1:8000 | 1:16000 | 1:32000 | 1:64000 | 1:128000 | 1:256000 | 1:512000 | 1:1024000 | 1:2048000 |
| O8E #632-24 | preimmune sera (2576L) | 0.15 | 0.11 | 0.09 | 0.08 | 0.08 | 0.07 | 0.07 | 0.07 | 0.07 | 0.08 | 0.07 | 0.08 |
| | | 0.14 | 0.10 | 0.09 | 0.08 | 0.07 | 0.07 | 0.07 | 0.07 | 0.07 | 0.07 | 0.07 | 0.07 |
| | Average | 0.14 | 0.10 | 0.09 | 0.08 | 0.07 | 0.07 | 0.07 | 0.07 | 0.07 | 0.08 | 0.07 | 0.08 |
| | α-O8E (2576K):2/8/2000 | 2.74 | 2.71 | 2.63 | 2.49 | 2.29 | 1.87 | 1.39 | 0.92 | 0.57 | 0.33 | 0.20 | 0.14 |
| | | 2.72 | 2.68 | 2.64 | 2.47 | 2.26 | 1.93 | 1.42 | 0.94 | 0.57 | 0.34 | 0.21 | 0.14 |
| | Average | 2.73 | 2.70 | 2.63 | 2.48 | 2.27 | 1.90 | 1.41 | 0.93 | 0.57 | 0.34 | 0.21 | 0.14 |
| | affinity pure α-O8E poly salt peak 739-87A | 2.69 | 2.60 | 2.50 | 2.21 | 1.83 | 1.34 | 0.99 | 0.64 | 0.38 | 0.22 | 0.15 | 0.11 |
| | | 2.59 | 2.48 | 2.38 | 2.21 | 1.82 | 1.33 | 1.00 | 0.62 | 0.37 | 0.22 | 0.14 | 0.11 |
| | Average | 2.64 | 2.54 | 2.44 | 2.21 | 1.83 | 1.34 | 1.00 | 0.63 | 0.37 | 0.22 | 0.15 | 0.11 |
| | affinity pure α-O8E poly acid peak 739-67B | 2.46 | 2.39 | 2.40 | 2.34 | 2.08 | 1.73 | 1.29 | 0.81 | 0.49 | 0.29 | 0.19 | 0.13 |
| | | 2.65 | 2.66 | 2.61 | 2.45 | 2.14 | 1.76 | 1.30 | 0.82 | 0.48 | 0.29 | 0.19 | 0.13 |
| | Average | 2.56 | 2.53 | 2.51 | 2.39 | 2.11 | 1.74 | 1.30 | 0.81 | 0.49 | 0.29 | 0.19 | 0.13 |

Fig. 24

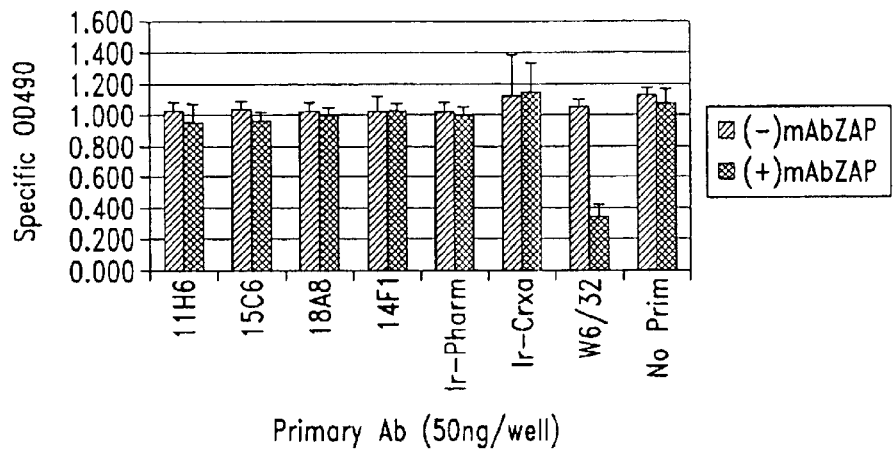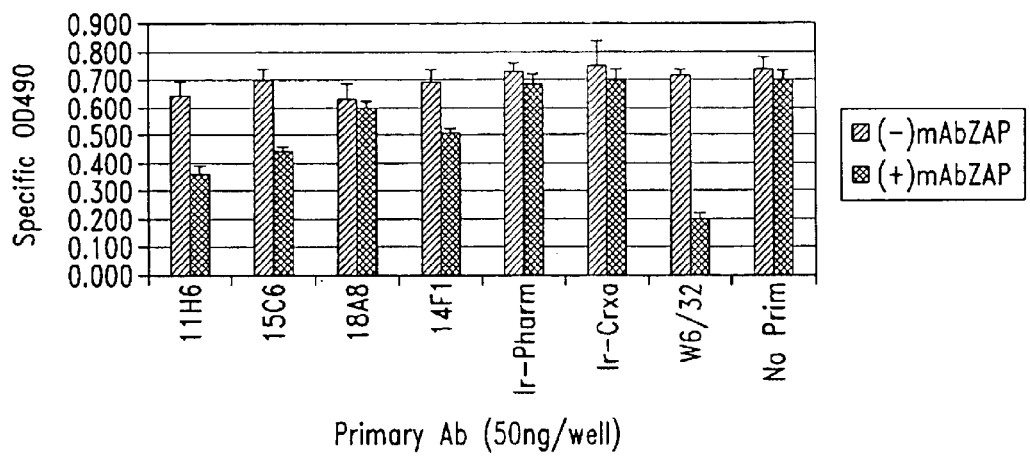
Fig. 25

```
                         SEQUENCE LISTING

<160> NUMBER OF SEQ ID NOS: 461

<210> SEQ ID NO 1
<211> LENGTH: 461
<212> TYPE: DNA
<213> ORGANISM: Homo sapien

<400> SEQUENCE: 1
ttagagaggc acagaaggaa gaagagttaa aagcagcaaa gccgggtttt tttgttttgt      60
tttgttttgt tttgttttga gatggagtct cactctgttg cccaagctgg agtacaacgg     120
catgatctca gctcgctgca acctccgcct cccacgttca agtgattctc ctgcctcagc     180
ctcccaagta gctgggatta caggcgcccg ccaccacgct cagctaattt tttttgtatt     240
tttagtagag acagggtttc accaggttgg ccaggctgct cttgaactcc tgacctcagg     300
tgatccaccc gcctcggcct cccaaagtgc tgggattaca ggcgtgagcc accacgcccg     360
gcccccaaag ctgtttcttt tgtctttagc gtaaagctct cctgccatgc agtatctaca     420
taactgacgt gactgccagc aagctcagtc actccgtggt c                         461

<210> SEQ ID NO 2
<211> LENGTH: 540
<212> TYPE: DNA
<213> ORGANISM: Homo sapien

<400> SEQUENCE: 2
taggatgtgt tggaccctct gtgtcaaaaa aaacctcaca aagaatcccc tgctcattac      60
agaagaagat gcatttaaaa tatgggttat tttcaacttt ttatctgagg acaagtatcc     120
attaattatt gtgtcagaag agattgaata cctgcttaag aagcttacag aagctatggg     180
aggaggttgg cagcaagaac aatttgaaca ttataaaatc aactttgatg acagtaaaaa     240
tggcctttct gcatgggaac ttattgagct tattggaaat ggacagttta gcaaaggcat     300
ggaccggcag actgtgtcta tggcaattaa tgaagtcttt aatgaactta tattagatgt     360
gttaaagcag ggttacatga tgaaaaaggg ccacagacgg aaaaactgga ctgaaagatg     420
gtttgtacta aaacccaaca taatttctta ctatgtgagt gaggatctga aggataagaa     480
aggagacatt ctcttggatg aaaattgctg tgtagagtcc ttgcctgaca aagatggaaa     540

<210> SEQ ID NO 3
<211> LENGTH: 461
<212> TYPE: DNA
<213> ORGANISM: Homo sapien
```

-continued

```
<400> SEQUENCE: 3
ttagagaggc acagaaggaa gaagagttaa aagcagcaaa gccgggtttt tttgttttgt    60
tttgttttgt tttgtttga gatggagtct cactctgttg cccaagctgg agtacaacgg   120
catgatctca gctcgctgca acctccgcct cccacgttca agtgattctc ctgcctcagc   180
ctcccaagta gctgggatta caggcgcccg ccaccacgct cagctaattt ttttgtatt   240 tttagtagag acagggtttc accaggttgg ccaggctgct cttgaactcc tgacctcagg   300
tgatccaccc gcctcggcct cccaaagtgc tgggattaca ggcgtgagcc accacgcccg   360 gccccccaaag ctgtttcttt tgtctttagc gtaaagctct cctgccatgc agtatctaca   420
taactgacgt gactgccagc aagctcagtc actccgtggt c                      461

<210> SEQ ID NO 4
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 4 tcttttctt tcgatttcct tcaatttgtc acgtttgatt ttatgaagtt gttcaagggc    60
taactgctgt gtattatagc tttctctgag ttccttcagc tgattgttaa atgaatccat   120
ttctgagagc ttagatgcag tttcttttc aagagcatct aattgttctt taagtctttg   180
gcataattct tccttttctg atgactttt atgaagtaaa ctgatccctg aatcaggtgt   240
gttactgagc tgcatgtttt taattctttc gtttaatagc tgcttctcag ggaccagata   300
gataagctta ttttgatatt ccttaagctc ttgttgaagt tgtttgattt ccataatttc   360
caggtcacac tgtttatcca aaacttctag ctcagtcttt tgtgtttgct ttctgatttg   420
gacatcttgt agtctgcctg agatctgctg atgntttcca ttcactgctt ccagttccag   480
gtggagactt tnctttctgg agctcagcct gacaatgcct tcttgntccc t            531

<210> SEQ ID NO 5
<211> LENGTH: 531
<212> TYPE: DNA
<213> ORGANISM: Homo sapien

<400> SEQUENCE: 5
agccagatgg ctgagagctg caagaagaag tcaggatcat gatggctcag tttcccacag    60
cgatgaatgg agggccaaat atgtgggcta ttacatctga agaacgtact aagcatgata   120
aacagtttga taacctcaaa ccttcaggag gttacataac aggtgatcaa gcccgtactt   180
ttttcctaca gtcaggtctg ccggccccgg ttttagctga aatatgggcc ttatcagatc   240
tgaacaagga tgggaagatg gaccagcaag agttctctat agctatgaaa ctcatcaagt   300
taaagttgca gggccaacag ctgcctgtag tcctccctcc tatcatgaaa caaccccta    360 tgttctctcc actaatctct gctcgttttg ggatgggaag catgcccaat ctgtccattc   420
atcagccatt gcctccagtt gcacctatag caacacccatt gtcttctgct acttcaggga   480
ccagtattcc tcccctaatg atgcctgctc ccctagtgcc ttctgttagt a            531

<210> SEQ ID NO 6
<211> LENGTH: 531
<212> TYPE: DNA
<213> ORGANISM: Homo sapien
```

<400> SEQUENCE: 6

```
aatagattta atgcagagtg tcaacttcaa ttgattgata gtggctgcct agagtgctgt      60
gttgagtagg tttctgagga tgcaccctgg cttgaagaga aagactggca ggattaacaa     120
tatctaaaat ctcacttgta ggagaaacca caggcaccag agctgccact ggtgctggca     180
ccagctccac caaggccagc gaagagccca aatgtgagag tggcggtcag gctggcacca     240
gcactgaagc caccactggt gctggcactg gcactggcac tgttattggt actggtactg     300
gcaccagtgc tggcactgcc actctcttgg gctttggctt tagcttctgc tcccgcctgg     360
atccgggctt tggcccaggg tccgatatca gcttcgtccc agttgcaggg cccggcagca     420
ttctccgagc cgagcccaat gcccattcga gctctaatct cggccctagc cttggcttca     480
gctgcagcct cagctgcagc cttcaaatcc gcttccatcg cctctcggta c              531
```

<210> SEQ ID NO 7
<211> LENGTH: 531
<212> TYPE: DNA
<213> ORGANISM: Homo sapien

<400> SEQUENCE: 7

```
gccaagaaag cccgaaaggt gaagcatctg gatggggaag aggatggcag cagtgatcag      60
agtcaggctt ctggaaccac aggtggccga agggtctcaa aggccctaat ggcctcaatg     120
gcccgcaggg cttcaagggg tcccatagcc ttttgggccc gcaggcatc aaggactcgg      180
ttggctgctt gggcccggag agccttgctc tccctgagat cacctaaagc ccgtaggggc     240
aaggctcgcc gtagagctgc caagctccag tcatcccaag agcctgaagc accaccacct     300
cgggatgtgg ccctttttgca agggagggca aatgatttgg tgaagtacct tttggctaaa     360
gaccagacga agattcccat caagcgctcg gacatgctga aggacatcat caagaataca     420
actgatgtgt accccgaaat cattgaacga gcaggctatt ccttggagaa ggtatttggg     480
attcaattga aggaaattga taagaatgac cacttgtaca ttcttctcag c              531
```

<210> SEQ ID NO 8
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 8

```
gaggtctcac tatgttgccc aggctgttct tgaactcctg ggatcaagca atccacccat      60
gttggtctcc aaaagtgctg ggatcatagg cgtgagccac ctcacccagc caccaatttt     120
caatcaggaa gactttttcc ttcttcaaga agtgaagggt ttccagagta tagctacact     180
attgcttgcc tgagggtgac tacaaaattg cttgctaaaa ggttaggatg ggtaaagaat     240
tagattttct gaatgcaaaa ataaaatgtg aactaatgaa ctttaggtaa tacatattca     300
taaaataatt attcacatat ttcctgattt atcacagaaa taatgtatga aatgctttga     360
gtttcttgga gtaaactcca ttactcatcc caagaaacca tattataagt atcactgata     420
ataagaacaa caggaccttg tcataaattc tggataagag aaatagtctc tgggtgtttg     480
ntcttaattg ataaaattta cttgtccatc ttttagttca gaatcacaaa a              531
```

<210> SEQ ID NO 9

```
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 9
aagcggaaat gagaaaggag ggaaaatcat gtggtattga gcggaaaact gctggatgac      60
agggctcagt cctgttggag aactctgggt ggtgctgtag aacagggcca ctcacagtgg     120
ggtgcacaga ccagcacggc tctgtgacct gtttgttaca ggtccatgat gaggtaaaca     180
atacactgag tataagggtt ggtttagaaa ctcttacagc aatttgacaa agtaatcttc     240
tgtgcagtga atctaagaaa aaattggggg ctgtatttgt atgttccttt ttttcatttc     300
atgttctgag ttacctattt ttattgcatt ttacaaaagc atccttccat gaaggaccgg     360
aagttaaaaa caaagcaggt cctttatcac agcactgtcg tagaacacag ttcagagtta     420
tccacccaag gagccaggga gctgggctaa accaagaat tttgcttttg gttaatcatc      480
aggtacttga gttggaattg ttttaatccc atcattacca ggctggangt g              531

<210> SEQ ID NO 10
<211> LENGTH: 861
<212> TYPE: DNA
<213> ORGANISM: Homo sapien

<400> SEQUENCE: 10
ccgcggctcc tgtccagacc ctgaccctcc ctcccaaggc tcaaccgtcc cccaacaacc      60
gccagccttg tactgatgtc ggctgcgaga gcctgtgctt aagtaagaat caggccttat     120
tggagacatt caagcaaagg ttggacaact acttttccag aacagaaagg aaactcatgc     180
atcagaaaag gtgactaata aaggtaccag aagaatatgg ctgcacaaat accagaatct     240
gatcagataa aacagtttaa ggaatttctg gggacctaca ataaacttac agagacctgc     300
tttttggact gtgttagaga cttcacaaca agagaagtaa aacctgaaga gaccacctgt     360
tcagaacatt gcttacagaa atatttaaaa atgacacaaa gaatatccat gagatttcag     420
gaatatcata ttcagcagaa tgaagccctg gcagccaaag caggactcct tggccaacca     480
cgatagagaa gtcctgatgg atgaactttt gatgaaagat tgccaacagc tgctttattg     540
gaaatgagga ctcatctgat agaatcccct gaaagcagta gccaccatgt tcaaccatct     600
gtcatgactg tttggcaaat ggaaaccgct ggagaaacaa aattgctatt taccaggaat     660
aatcacaata gaaggtctta ttgttcagtg aaataataag atgcaacatt tgttgaggcc     720
ttatgattca gcagcttggt cacttgatta gaaaaataaa ccattgtttc ttcaattgtg     780
actgttaatt ttaaagcaac ttatgtgttc gatcatgtat gagatagaaa aattttttatt    840
actcaaagta aaataaatgg a                                               861

<210> SEQ ID NO 11
<211> LENGTH: 541
<212> TYPE: DNA
<213> ORGANISM: Homo sapien

<400> SEQUENCE: 11
gaaaaaaaat ataaaacaca cttttgcgaa aacggtggcc ctaaaagagg aaaagaattt      60
caccaatata aatccaattt tatgaaaact gacaatttaa tccaagaatc acttttgtaa     120
atgaagctag caagtgatga tatgataaaa taaacgtgga ggaaataaaa acacaagact     180
```

```
tggcataaga tatatccact tttgatatta aacttgtgaa gcatattctt cgacaaattg    240
tgaaagcgtt cctgatcttg cttgttctcc atttcaaata aggaggcata tcacatccca    300
agagtaacag aaaagaaaa aagacatttt tgcattttga gatgaaccaa agacacaaaa     360
caaaacgaac aaagtgtcat gtctaattct agcctctgaa ataaaccttg aacatctcct    420
acaaggcacc gtgattttg taattctaac ctgaagaaat gtgatgactt ttgtggacat     480
gaaaatcaga tgagaaaact gtggtctttc caaagcctga actcccctga aaacctttgc    540
a                                                                    541

<210> SEQ ID NO 12
<211> LENGTH: 541
<212> TYPE: DNA
<213> ORGANISM: Homo sapien

<400> SEQUENCE: 12
ctgggatcat ttctcttgat gtcataaaag actcttcttc ttcctcttca tcctcttctt     60
catcctcttc tgtacagtgc tgccgggtac aacggctatc tttgtcttta tcctgagatg    120
aagatgatgc ttctgtttct cctaccataa ctgaagaaat ttcgctggaa gtcgtttgac    180
tggctgtttc tctgacttca ccttctttgt caaacctgag tcttttttacc tcatgccct    240 cagcttccac agcatcttca tctggatgtt tattttcaa agggctcact gaggaaactt    300
ctgattcaga ggtcgaagag tcactgtgat ttttctcctc attttgctgc aaatttgcct   360 cttttgctgtc tgtgctctca ggcaacccat tgttgtcat gggggctgac aaagaaacct  420
ttggtcgatt aagtggcctg ggtgtcccag gcccatttat attagacctc tcagtatagc   480
ttggtgaatt tccaggaaac ataacaccat tcattcgatt taaactattg gaattggttt   540
t                                                                    541

<210> SEQ ID NO 13
<211> LENGTH: 441
<212> TYPE: DNA
<213> ORGANISM: Homo sapien

<400> SEQUENCE: 13
gagggttggt ggtagcggct tggggaggtg ctcgctctgt cggtcttgct ctctcgcacg     60
cttcccccgg ctcccttcgt ttccccccc cggtcgcctg cgtgccggag tgtgtgcgag    120
ggagggggag ggcgtcgggg gggtggggg aggcgttccg gtccccaaga gacccgcgga   180
gggaggcgga ggctgtgagg gactccggga agccatggac gtcgagaggc tccaggaggc   240
gctgaaagat tttgagaaga gggggaaaaa ggaagtttgt cctgtcctgg atcagtttct   300
ttgtcatgta gccaagactg gagaaacaat gattcagtgg tcccaattta aaggctattt    360
tattttcaaa ctggagaaag tgatggatga tttcagaact tcagctcctg agccaagagg    420
tcctcccaac cctaatgtcg a                                              441

<210> SEQ ID NO 14
<211> LENGTH: 131
<212> TYPE: DNA
<213> ORGANISM: Homo sapien
<220> FEATURE:
<221> NAME/KEY: misc_feature
<222> LOCATION: (1)...(131)
<223> OTHER INFORMATION: n = A,T,C or G

<400> SEQUENCE: 14
```

```
aagcaggcgg ctcccgcgct cgcagggccg tgccacctgc ccgcccgccc gctcgctcgc    60
tcgcccgccg cgccgcgctg ccgaccgcca gcatgctgcc gagagtgggc tgcccgcgc    120 tgccgntgcc g                                                        131
```

```
<210> SEQ ID NO 15
<211> LENGTH: 692
<212> TYPE: DNA
<213> ORGANISM: Homo sapien

<400> SEQUENCE: 15
atctcttgta tgccaaatat ttaatataaa tctttgaaac aagttcagat gaaataaaaa    60
tcaaagtttg caaaaacgtg aagattaact taattgtcaa atattcctca ttgccccaaa   120
tcagtatttt ttttatttct atgcaaaagt atgccttcaa actgcttaaa tgatatatga   180
tatgatacac aaaccagttt tcaaatagta aagccagtca tcttgcaatt gtaagaaata   240
ggtaaaagat tataagacac cttacacaca cacacacaca cacacgtg tgcacgccaa    300 tgacaaaaaa caatttggcc tctcctaaaa taagaacatg aagacccta attgctgcca   360 ggagggaaca ctgtgtcacc cctccctaca atccaggtag tttcctttaa tccaatagca   420
aatctgggca tatttgagag gagtgattct gacagccacg ttgaaatcct gtggggaacc   480
attcatgtcc acccactggt gccctgaaaa atgccaata attttcgct cccacttctg     540 ctgctgtctc ttccacatcc tcacatagac cccagaccg ctggcccctg gctgggcatc    600
gcattgctgg tagagcaagt cataggtctc gtctttgacg tcacagaagc gatacaccaa   660
attgcctggt cggtcattgt cataaccaga ga                                 692
```

```
<210> SEQ ID NO 16
<211> LENGTH: 728
<212> TYPE: DNA
<213> ORGANISM: Homo sapien

<400> SEQUENCE: 16
cagacggggt ttcactatgt tggctaggct ggtcttgaac tcctgacttc aggtgatctg    60
cctgccttgg cctcccaaag tgctgggatt acaggcataa gccactgcgc ccggctgatc   120
tgatggtttc ataaggcttt tccccctttt gctcagcact tctccttcct gccgccatgt   180
gaagaaggac atgtttgctt cccttccac cacgattgta agttgtttcc tgaggcctcc    240
ccggccatgc tgaactgtga gtcaattaaa cctctttcct ttataaatta tccagttttg   300
ggtatgtctt tattagtaga atgagaacag actaatacaa cccttaaagg agactgacgg   360
agaggattct tcctggatcc cagcacttcc tctgaatgct actgacattc ttcttgagga   420
ctttaaactg ggagatagaa aacagattcc atggctcagc agcctgagag cagggaggga   480
gccaagctat agatgacatg ggcagcctcc cctgaggcca ggtgtggccg aacctgggca   540
gtgctgccac ccaccccacc agggccaagt cctgtccttg gagagccaag cctcaatcac   600
tgctagcctc aagtgtcccc aagccacagt ggctaggggg actcagggaa cagttcccag   660
tctgccctac ttctcttacc tttacccctc atacctccaa agtagaccat gttcatgagg   720
tccaaagg                                                            728
```

```
<210> SEQ ID NO 17
<211> LENGTH: 531
<212> TYPE: DNA
<213> ORGANISM: Homo sapien
<220> FEATURE:
<221> NAME/KEY: misc_feature
```

<222> LOCATION: (1)...(531)
<223> OTHER INFORMATION: n = A,T,C or G

<400> SEQUENCE: 17

| | | | | | |
|---|---|---|---|---|---|
| aagcgaggaa | gccactgcgg | ctcctggctg | aaaagcggcg | ccaggctcgg | gaacagaggg | 60 |
| aacgcgaaga | acaggagcgg | aagctgcagg | ctgaaaggga | caagcgaatg | cgagaggagc | 120 |
| agctggcccg | ggaggctgaa | gcccgggctg | aacgtgaggc | cgaggcgcgg | agacgggagg | 180 |
| agcaggaggc | tcgagagaag | gcgcaggctg | agcaggagga | gcaggagcga | ctgcagaagc | 240 |
| agaaagagga | agccgaagcc | cggtcccggg | aagaagctga | gcgccagcgc | caggagcggg | 300 |
| aaaagcactt | tcagaaggag | gaacaggaga | gacaagagcg | aagaaagcgg | ctggaggaga | 360 |
| taatgaagag | gactcggaaa | tcagaagccg | ccgaaaccaa | gaagcaggat | gcaaaggaga | 420 |
| ccgcagctaa | caattccggc | ccagacccct | tgtgaaagctg | tagagactcg | gccctctggg | 480 |
| cttccagaaa | ggattctatt | gcagaaagga | aggagctngg | ccccccangg | a | 531 |

<210> SEQ ID NO 18
<211> LENGTH: 1041
<212> TYPE: DNA
<213> ORGANISM: Homo sapien
<220> FEATURE:
<221> NAME/KEY: misc_feature
<222> LOCATION: (1)...(1041)
<223> OTHER INFORMATION: n = A,T,C or G

<400> SEQUENCE: 18

| | | | | | |
|---|---|---|---|---|---|
| ctctgtggaa | aactgatgag | gaatgaattt | accattaccc | atgttctcat | ccccaagcaa | 60 |
| agtgctgggt | ctgattactg | caacacagag | aacgaagaag | aacttttcct | catacaggat | 120 |
| cagcagggcc | tcatcacact | gggctggatt | catactcacc | ccacacagac | cgcgtttctc | 180 |
| tccagtgtcg | acctacacac | tcactgctct | taccagatga | tgttgccaga | gtcagtagcc | 240 |
| attgtttgct | cccccaagtt | ccaggaaact | ggattcttta | aactaactga | ccatggacta | 300 |
| gaggagattt | cttcctgtcg | ccagaaagga | tttcatccac | acagcaagga | tccacctctg | 360 |
| ttctgtagct | gcagccacgt | gactgttgtg | gacagagcag | tgaccatcac | agaccttcga | 420 |
| tgagcgtttg | agtccaacac | cttccaagaa | caacaaaacc | atatcagtgt | actgtagccc | 480 |
| cttaatttaa | gctttctaga | aagctttgga | agttttgta | gatagtagaa | agggggggcat | 540 |
| cacntgagaa | agagctgatt | ttgtatttca | ggtttgaaaa | gaaataactg | aacatatttt | 600 |
| ttaggcaagt | cagaaagaga | acatggtcac | ccaaaagcaa | ctgtaactca | gaaattaagt | 660 |
| tactcagaaa | ttaagtagct | cagaaattaa | gaaagaatgg | tataatgaac | ccccatatac | 720 |
| ccttccttct | ggattcacca | attgttaaca | ttttttttcct | ctcagctatc | cttctaattt | 780 |
| ctctctaatt | tcaatttgtt | tatatttacc | tctgggctca | ataagggcat | ctgtgcagaa | 840 |
| atttggaagc | catttagaaa | atcttttgga | ttttcctgtg | gtttatggca | atatgaatgg | 900 |
| agcttattac | tggggtgagg | gacagcttac | tccatttgac | cagattgttt | ggctaacaca | 960 |
| tcccgaagaa | tgattttgtc | aggaattatt | gttatttaat | aaatatttca | ggatatttt | 1020 |
| cctctacaat | aaagtaacaa | t | | | | 1041 |

<210> SEQ ID NO 19
<211> LENGTH: 1043
<212> TYPE: DNA
<213> ORGANISM: Homo sapien

<400> SEQUENCE: 19

-continued

| | |
|---|---|
| ctctgtggaa aactgatgag gaatgaattt accattaccc atgttctcat ccccaagcaa | 60 |
| agtgctgggt ctgattactg caacacagag aacgaagaag aacttttcct catacaggat | 120 |
| cagcagggcc tcatcacact gggctggatt catactcacc ccacacagac cgcgtttctc | 180 |
| tccagtgtcg acctacacac tcactgctct taccagatga tgttgccaga gtcagtagcc | 240 |
| attgtttgct cccccaagtt ccaggaaact ggattcttta aactaactga ccatggacta | 300 |
| gaggagattt cttcctgtcg ccagaaagga tttcatccac acagcaagga tccacctctg | 360 |
| ttctgtagct gcagccacgt gactgttgtg gacagagcag tgaccatcac agaccttcga | 420 |
| tgagcgtttg agtccaacac cttccaagaa caacaaaacc atatcagtgt actgtagccc | 480 |
| cttaatttaa gctttctaga aagctttgga agttttgta gatagtagaa aggggggcat | 540 |
| cacctgagaa agagctgatt ttgtatttca ggtttgaaaa gaataactg aacatatttt | 600 |
| ttaggcaagt cagaaagaga acatggtcac ccaaaagcaa ctgtaactca gaaattaagt | 660 |
| tactcagaaa ttaagtagct cagaaattaa gaaagaatgg tataatgaac ccccatatac | 720 |
| ccttccttct ggattcacca attgttaaca tttttttcct ctcagctatc cttctaattt | 780 |
| ctctctaatt tcaatttgtt tatatttacc tctgggctca ataagggcat ctgtgcagaa | 840 |
| atttggaagc catttagaaa atcttttgga ttttcctgtg gtttatggca atatgaatgg | 900 |
| agcttattac tggggtgagg gacagcttac tccatttgac cagattgttt ggctaacaca | 960 |
| tcccgaagaa tgattttgtc aggaattatt gttatttaat aaatatttca ggatattttt | 1020 |
| cctctacaat aaagtaacaa tta | 1043 |

<210> SEQ ID NO 20
<211> LENGTH: 448
<212> TYPE: DNA
<213> ORGANISM: Homo sapien

<400> SEQUENCE: 20

| | |
|---|---|
| ggacgacaag gccatggcga tatcggatcc gaattcaagc ctttggaatt aaataaacct | 60 |
| ggaacaggga aggtgaaagt tggagtgaga tgtcttccat atctataccet ttgtgcacag | 120 |
| ttgaatggga actgtttggg tttagggcat cttagagttg attgatggaa aaagcagaca | 180 |
| ggaactggtg ggaggtcaag tggggaagtt ggtgaatgtg gaataactta cctttgtgct | 240 |
| ccacttaaac cagatgtgtt gcagctttcc tgacatgcaa ggatctactt taattccaca | 300 |
| ctctcattaa taaattgaat aaaagggaat gttttggcac ctgatataat ctgccaggct | 360 |
| atgtgacagt aggaaggaat ggtttcccct aacaagccca atgcactggt ctgactttat | 420 |
| aaattattta ataaaatgaa ctattatc | 448 |

<210> SEQ ID NO 21
<211> LENGTH: 411
<212> TYPE: DNA
<213> ORGANISM: Homo sapien

<400> SEQUENCE: 21

| | |
|---|---|
| ggcagtgaca ttcaccatca tgggaaccac cttcccttt cttcaggatt ctctgtagtg | 60 |
| gaagagagca cccagtgttg ggctgaaaac atctgaaagt agggagaaga acctaaaata | 120 |
| atcagtatct cagagggctc taaggtgcca agaagtctca ctggacattt aagtgccaac | 180 |
| aaaggcatac tttcggaatc gccaagtcaa aactttctaa cttctgtctc tctcagagac | 240 |
| aagtgagact caagagtcta ctgctttagt ggcaactaca gaaaactggt gttacccaga | 300 |
| aaaacaggag caattagaaa tggttccaat atttcaaagc tccgcaaaca ggatgtgctt | 360 |

```
tcctttgccc atttagggtt tcttctcttt cctttctctt tattaaccac t            411
```

<210> SEQ ID NO 22
<211> LENGTH: 896
<212> TYPE: DNA
<213> ORGANISM: Homo sapien
<220> FEATURE:
<221> NAME/KEY: misc_feature
<222> LOCATION: (1)...(896)
<223> OTHER INFORMATION: n = A,T,C or G

<400> SEQUENCE: 22

```
tgcgctgaaa acaacggcct cctttactgt taaaatgcag ccacaggtgc ttagccgtgg    60
gcatctcaac caccagcctc tgtgggggc aggtgggcgt ccctgtgggc ctctgggccc    120
acgtccagcc tctgtcctct gccttccgtt cttcgacagt gttcccggca tccctggtca   180
cttggtactt ggcgtgggcc tcctgtgctg ctccagcagc cctccaggn ggtcggcccg    240
cttcaccgca gcctcatgtt gtgtccggag gctgctcacg gcctcctcct tcctcgcgag   300
ggctgtcttc accctccggn gcacctcctc cagctccagc tgctggcggg cctgcagcgt   360
ggccagctcg gccttggcct gccgcgtctc ctcctcarag gctgccagcc ggtcctcgaa   420
ctcctggcgg atcacctggg ccaggttgct gcgctcgcta gaaagctgct cgttcaccgc   480
ctgcgcatcc tccagcgccc gctccttctg ccgcacaagg ccctgcagac gcagattctc   540
gccctcggcc tccccaagct ggcccttcag ctccgagcac cgctcctgaa gcttccgctc   600
cgactgctcc agctcggaga gctcggcctc gtacttgtcc cgtaagcgct tgatgcggct   660
ctcggcagcc ttctcactct cctccttggc cagcgccatg tcggcctcca gccggtgaat   720
gaccagctca atctccttgt cccggccttt ccggatttct tccctcagct cctgttcccg   780
gttcagcagc cacgcctcct ccttcctggt gcggccggcc tcccacgcct gcctctccag   840
ctccagctgc tgcttcaggg tattcagctc catctggcgg gcctgcagcg tggcca        896
```

<210> SEQ ID NO 23
<211> LENGTH: 111
<212> TYPE: DNA
<213> ORGANISM: Homo sapien

<400> SEQUENCE: 23

```
caacttatta cttgaaatta taatatagcc tgtccgtttg ctgtttccag gctgtgatat    60
attttcctag tggtttgact ttaaaaataa ataaggttta attttctccc c             111
```

<210> SEQ ID NO 24
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 24

```
tgcaagtcac gggagtttat ttatttaatt ttttccccca gatggagact ctgtcgccca    60
ggctggagtg caatggtgtg atcttggctc actgcaacct ccacctcctg ggttcaagcg   120
attctcctgc cacagcctcc cgagtagctg ggattacagg tgcccgccac cacacccagc   180
taatttttat attttagta aagacagggg ttccccatgt tggccaggct ggtcttgaac    240
ttctgacctc aggtgatcca cctgcctcgg cctcccaaag tgttgggatt acaggcgtga   300
```

```
gctacccgtg cctggccagc cactggagtt taaaggacag tcatgttggc tccagcctaa    360
ggcggcattt tccccccatca gaaagcccgc ggctcctgta cctcaaaata gggcacctgt   420
aaagtcagtc agtgaagtct ctgctctaac tggccacccg gggccattgg cntctgacac    480
agccttgcca ggangcctgc atctgcaaaa gaaaagttca cttcctttcc g             531
```

<210> SEQ ID NO 25
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 25

```
cagagaatct kagaaagatg tcgcgttttc ttttaatgaa tgagagaagc ccatttgtat     60
ccctgaatca ttgagaaaag gcggcggtgg cgacagcggc gacctaggga tcgatctgga   120
gggacttggg gagcgtgcag agacctctag ctcgagcgcg agggacctcc cgccgggatg   180
cctggggagc agatggaccc tactggaagt cagttggatt cagatttctc tcagcaagat   240
actccttgcc tgataattga agattctcag cctgaaagcc aggttctaga ggatgattct   300
ggttctcact tcagtatgct atctcgacac cttcctaatc tccagacgca aaagaaaat    360 cctgtgttgg atgttgngtc caatccttga acaaacagct ggagaagaac gaggagaccg   420
gtaatagtgg gttcaatgaa catttgaaag aaaaccaggt tgcagaccct g            471
```

<210> SEQ ID NO 26
<211> LENGTH: 541
<212> TYPE: DNA
<213> ORGANISM: Homo sapien

<400> SEQUENCE: 26

```
gactgtcctg aacaagggac tctgaccag agagctgcag gagatgcaga gtggtggcag     60
gagtggaagc caaagaacac ccaccttcct cccttgaagg agtagagcaa ccatcagaag   120
atactgtttt attgctctgg tcaaacaagt cttcctgagt tgacaaaacc tcaggctctg   180
gtgacttctg aatctgcagt ccactttcca taagttcttg tgcagacaac tgttctttg    240 cttccatagc agcaacagat gctttggggc taaaaggcat gtcctctgac cttgcaggtg   300
gtggattttg ctcttttaca acatgtacat ccttactggg ctgtgctgtc acagggatgt   360
ccttgctgga ctgttctgct atggggatat cttcgttgga ctgttcttca tgcttaattg   420
cagtattagc atccacatca gacagcctgg tataaccaga gttggtggtt actgattgta   480
gctgctcttt gtccacttca tatggcacaa gtatttcct caacatcctg gctctgggaa    540
g                                                                   541
```

<210> SEQ ID NO 27
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 27

```
gaaatgtata tttaatcatt ctcttgaacg atcagaactc traaatcagt tttctataac     60
arcatgtaat acagtcaccg tggctccaag gtccaggaag gcagtggtta acacatgaag   120
```

```
agtgtgggaa gggggctgga aacaaagtat tcttttcctt caaagcttca ttcctcaagg      180
cctcaattca agcagtcatt gtccttgctt tcaaaagtct gtgtgtgctt catggaaggt      240
atatgtttgt tgccttaatt tgaattgtgg ccaggaaggg tctggagatc taaattcaga      300
gtaagaaaac ctgagctaga actcaggcat ttctcttaca gaacttggct tgcagggtag      360
aatgaangga aagaaactta gaagctcaac aagctgaaga taatcccatc aggcatttcc      420
cataggcctt gcaactctgt tcactgagag atgttatcct g                          461

<210> SEQ ID NO 28
<211> LENGTH: 541
<212> TYPE: DNA
<213> ORGANISM: Homo sapien

<400> SEQUENCE: 28
agtctggagt gagcaaacaa gagcaagaaa caarragaag ccaaaagcag aaggctccaa      60
tatgaacaag ataaatctat cttcaaagac atattagaag ttgggaaaat aattcatgtg      120
aactagacaa gtgtgttaag agtgataagt aaaatgcacg tggagacaag tgcatcccca      180
gatctcaggg acctcccccct gcctgtcacc tggggagtga aggacagga tagtgcatgt      240 tctttgtctc tgaattttta gttatatgtg ctgtaatgtt gctctgagga agccctggaa      300
aagtctatcc caacatatcc acatcttata ttccacaaat taagctgtag tatgtacccct     360 aagacgctgc taattgactg ccacttcgca actcaggggc ggctgcattt tagtaatggg      420
tcaaatgatt cactttttat gatgcttccc aaggtgcctt ggcttctctt cccaactgac      480
aaatgcccaa gttgagaaaa atgatcataa ttttagcata aaccgagcaa tcggcgaccc      540
c                                                                      541

<210> SEQ ID NO 29
<211> LENGTH: 411
<212> TYPE: DNA
<213> ORGANISM: Homo sapien

<400> SEQUENCE: 29
tagctgtctt cctcactctt atggcaatga ccccatatct taatggatta agataatgaa      60
agtgtatttc ttacactctg tatctatcac cagaagctga ggtgatagcc cgcttgtcat      120
tgtcatccat attctgggac tcaggcggga actttctgga atattgccag ggagcatggc      180
agaggggcac agtgcattct gggggaatgc acattggctc agcctgggta atgagtgata      240
tacattacct ctgttcacaa ctcattgccc agcaccagtc acaaggcccc accaaatacc      300
agagcccaag aaatgtagtc ctgttgatat ggttttgctg tgtcccaacc caaatctcat      360
cttgaattgt aagctcccat aattcccatg tgttgtggga gggacctggt g              411

<210> SEQ ID NO 30
<211> LENGTH: 511
<212> TYPE: DNA
<213> ORGANISM: Homo sapien

<400> SEQUENCE: 30
atcatgagga tgttaccaaa gggatggtac taaaccattt gtattcgtct gttttcacac      60
tgctttgaag atactacctg agactgggta atttataaac aaaagagatt taattgactc      120
acagttctgc atggctgaag aggcctcagg aaacttacag tcatggtgga aggcaaagga      180
ggagcaaggc atgtcttaca tgtcagtagg agagagagcg agagcaggag aacctgccac      240
```

| | |
|---|---:|
| ttataaacca ttcagatctc ataactccct atcatgagaa aaacatggag gaaaccaccc | 300 |
| tcatgatcca atcacctccc gccaggtccc tccctcgaca cgtggggatt ataattcagg | 360 |
| attagaggga cacagagaca aaccatatca tcattcatga gaaatccacc ctcatagtcc | 420 |
| aatcagctcc taccaggccc cacctccaac actggggatt gcaattcaac atgagatttg | 480 |
| gatggggaca cagattcaaa ccatatcata c | 511 |

<210> SEQ ID NO 31
<211> LENGTH: 827
<212> TYPE: DNA
<213> ORGANISM: Homo sapien

<400> SEQUENCE: 31

| | |
|---|---:|
| catggccttt ctccttagag gccagaggtg ctgccctggc tgggagtgaa gctccaggca | 60 |
| ctaccagctt tcctgatttt cccgtttggt ccatgtgaag agctaccacg agccccagcc | 120 |
| tcacagtgtc cactcaaggg cagcttggtc ctcttgtcct gcagaggcag gctggtgtga | 180 |
| ccctgggaac ttgacccggg aacaacaggt ggcccagagt gagtgtggcc tggcccctca | 240 |
| acctagtgtc cgtcctcctc tctcctggag ccagtcttga gtttaaaggc attaagtgtt | 300 |
| agatacaagc tccttgtggc tggaaaaaca cccctctgct gataaagctc aggggcact | 360 |
| gaggaagcag aggccccttg ggggtgccct cctgaagaga cgtcaggcc atcagctctg | 420 |
| tccctctggt gctcccacgt ctgttcctca ccctccatct ctgggagcag ctgcacctga | 480 |
| ctggccacgc gggggcagtg gaggcacagg ctcaggtgg ccgggctacc tggcaccta | 540 |
| tggcttacaa agtagagttg gcccagtttc cttccacctg aggggagcac tctgactcct | 600 |
| aacagtcttc cttgccctgc catcatctgg ggtggctggc tgtcaagaaa ggccgggcat | 660 |
| gctttctaaa cacagccaca ggaggcttgt agggcatctt ccaggtgggg aaacagtctt | 720 |
| agataagtaa ggtgacttgc ctaaggcctc ccagcaccct tgatcttgga gtctcacagc | 780 |
| agactgcatg tsaacaactg gaaccgaaaa catgcctcag tataaaa | 827 |

<210> SEQ ID NO 32
<211> LENGTH: 291
<212> TYPE: DNA
<213> ORGANISM: Homo sapien

<400> SEQUENCE: 32

| | |
|---|---:|
| ccagaacctc cttctctttg gagaatgggg aggcctcttg gagacacaga gggtttcacc | 60 |
| ttggatgacc tctagagaaa ttgcccaaga agcccacctt ctggtcccaa cctgcagacc | 120 |
| ccacagcagt cagttggtca ggccctgctg tagaaggtca cttggctcca ttgcctgctt | 180 |
| ccaaccaatg ggcaggagag aaggccttta tttctcgccc acccattctc ctgtaccagc | 240 |
| acctccgttt tcagtcagyg ttgtccagca acggtaccgt ttacacagtc a | 291 |

<210> SEQ ID NO 33
<211> LENGTH: 491
<212> TYPE: DNA
<213> ORGANISM: Homo sapien

<400> SEQUENCE: 33

| | |
|---|---:|
| tgcatgtagt tttatttatg tgttttsgtc tggaaaacca agtgtcccag cagcatgact | 60 |
| gaacatcact cacttcccct acttgatcta caaggccaac gccgagagcc cagaccagga | 120 |
| ttccaaacac actgcacgag aatattgtgg atccgctgtc aggtaagtgt ccgtcactga | 180 |
| cccaracgct gttacgtggc acatgactgt acagtgccac gtaacagcac tgtacttttc | 240 |

```
tcccatgaac agttacctgc catgtatcta catgattcag acatttttga acagttaatt      300
ctgacacttg aataatccca tcaaaaaccg taaaatcact ttgatgtttg taacgacaac      360
atagcatcac tttacgacag aatcatctgg aaaaacagaa caacgaatac atacatctta     420
aaaaatgctg gggtgggcca ggcacagctt cacgcctgta atcccagcac tttgggaggc     480
ttaagcgggt g                                                          491
```

<210> SEQ ID NO 34
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 34

```
tggggcggaa agaagccaag gccaaggagc tggtgcggca gctgcagctg gaggccgagg      60
agcagaggaa gcagaagaag cggcagagtg tgtcgggcct gcacagatac cttcacttgc     120
tggatggaaa tgaaaattac ccgtgtcttg tggatgcaga cggtgatgtg atttccttcc     180
caccaataac caacagtgag aagacaaagg ttaagaaaac gacttctgat ttgttttttgg    240 aagtaacaag tgccaccagt ctgcagattt gcaaggatgt catggatgcc ctcattctga     300
aaatggcaag aaatgaaaaa gtacacttta gaaaataaag aggaaggatc actctcagat     360
actgaagccg atgcagtctc tggacaactt ccagatccca caacgaatcc cagtgctgga     420
aaggacgggc ccttccttct ggtggtggaa cangtcccgg tggtggatct tggaanggaa     480
cctgaangtg gtgtaccccg tccaaggccg accttggcca c                         521
```

<210> SEQ ID NO 35
<211> LENGTH: 161
<212> TYPE: DNA
<213> ORGANISM: Homo sapien
<220> FEATURE:
<221> NAME/KEY: misc_feature
<222> LOCATION: (1)...(161)
<223> OTHER INFORMATION: n = A,T,C or G

<400> SEQUENCE: 35

```
tcccgcgctc gcagggcncg tgccacctgc cygtccgccc gctcgctcgc tcgcccgccg      60
cgccgcgctg ccgaccgyca gcatgctgcc gagagtgggc tgccccgcgc tgccgctgcc     120
gccgccgccg ctgctgccgc tgctgccgct gctgctgctg c                         161
```

<210> SEQ ID NO 36
<211> LENGTH: 341
<212> TYPE: DNA
<213> ORGANISM: Homo sapien

<400> SEQUENCE: 36

```
ggcgggtagg catggaactg agaagaacga agaagctttc agactacgtg gggaagaatg      60
aaaaaaccaa aattatcgcc aagattcagc aaaggggaca gggagctcca gcccgagagc     120
ctattattag cagtgaggag cagaagcagc tgatgctgta ctatcacaga agacaagagg     180
agctcaagag attggaagaa aatgatgatg atgcctattt aaactcacca tgggcggata     240
acactgcttt gaaagacat tttcatggag tgaaagacat aaagtggaga ccaagatgaa      300
gttcaccagc tgatgacact tccaaagaga ttagctcacc t                         341
```

```
<210> SEQ ID NO 37
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 37
tctgaaggtt aaatgtttca tctaaatagg gataatgrta aacacctata gcatagagtt      60
gtttgagatt aaatgagata atacatgtaa aattatgtgc ctggcataca gcaagattgt     120
tgttgttgtt gatgatgatg atgatgatga taatatttt ctatcccag tgcacaactg      180
cttgaaccta ttagataatc aatacatgtt tcttgaactg agatcaattt ccccatgttg     240
tctgactgat gaagccctac attttcttct agaggagatg acatttgagc aagatcttaa     300
agaaaatcag atgccttcac ctgaccactg cttggtgatc ccatggcact ttgtacatct     360
ctccattagc tctcatctca ccagcccatc attattgtat gtgctgcctt ctgaagcttg     420
cagctggcta ccatcmggta gaataaaaat catccttttca taaatagtg accctccttt     480
tttatttgca tttcccaaag ccaagcaccg tgggaggta g                         521

<210> SEQ ID NO 38
<211> LENGTH: 461
<212> TYPE: DNA
<213> ORGANISM: Homo sapien

<400> SEQUENCE: 38
tatgaagaag ggaaaagaag ataatttgtg aaagaaatgg gtccagttac tagtctttga      60
aaagggtcag tctgtagctc ttcttaatga gaataggcag ctttcagttg ctcagggtca     120
gatttcctta gtggtgtatc taatcacagg aaacatctgt ggttccctcc agtctctttc     180
tgggggactt gggcccactt ctcatttcat ttaattagag gaaatagaac tcaaagtaca     240
atttactgtt gtttaacaat gccacaaaga catggttggg agctattct tgatttgtgt      300
aaaatgctgt ttttgtgtgc tcataatggt tccaaaaatt gggtgctggc aaagagaga     360
tactgttaca gaagccagca agaagacctc tgttcattca cacccccggg gatatcagga     420
attgactcca gtgtgtgcaa atccagtttg gcctatcttc t                         461

<210> SEQ ID NO 39
<211> LENGTH: 769
<212> TYPE: DNA
<213> ORGANISM: Homo sapien

<400> SEQUENCE: 39
tgagggactg attggtttgc tctctgctat tcaattcccc aagcccactt gttcctgcag      60
cgtcctcctt ctcattccct ttagttgtac cctctctttc atctgagacc tttccttctt     120
gatgtcgcct tttcttcttc ttgcttttc tgatgttctg ctcagcatgt tctgggtgct     180
tctcatctgc atcattcctt tcagatgctg tagcttcttc ctcctctttc tgcctccttt     240
tcttttcctt ttttttgggg ggcttgctct ctgactgcag ttgaggggcc ccagggtcct     300
ggcctttgag acgagccagg aaggcctgct cctgggcctc taggcgagca gcttggcct     360
tcattgtgat cccaagacgg gcagccttgt gtgctgttcg cccctcacag gcttggagca     420
gcatctcatc agtcagaatc tttggggact tggaccctg gttgtcgtca tcactgcagc      480
tctccaagtc tttgtttggc ttctctccac ctgaagtcaa tgtagccatc ttcacaaact     540
```

```
tctgatacag caagttgggc ttgggatgat tataacgggt ggtctcctta gaaaggctcc    600
ttatctgtac tccatcctgc ccagtttcca ctaccaagtt ggccgcagtc ttgttgaaga    660
gctcattcca ccagtggttt gtgaactcct tgcagggtc  atgtcctacc ccatgagtgt    720
cttgcttcag ygtcaccctg agagcctgag tgataccatt ctccttccg               769
```

<210> SEQ ID NO 40
<211> LENGTH: 292
<212> TYPE: DNA
<213> ORGANISM: Homo sapien

<400> SEQUENCE: 40

```
gacaacatga aataaatcct agaggacaaa attaaactca atagagtgta gtctagttaa     60
aaactcgaaa aatgagcaag tctggtggga gtggaggaag ggctatacta taaatccaag    120
tgggcctcct gatcttaaca agccatgctc attatacaca tctctgaact ggacatacca    180
cctttacgca ggaaacaggg cttggaactt ctaagggaaa ttaacatgca ccacccacat    240
ctaacctacc tgccgggtag gtaccatccc tgcttcgctg aaatcagtgc tc            292
```

<210> SEQ ID NO 41
<211> LENGTH: 406
<212> TYPE: DNA
<213> ORGANISM: Homo sapien

<400> SEQUENCE: 41

```
ttggaattaa ataaacctgg aacagggaag gtgaaagttg gagtgagatg tcttccatat     60 ctatacctttt gtgcacagtt gaatgggaac tgtttgggtt tagggcatct tagagttgat   120
tgatggaaaa agcagacagg aactggtggg aggtcaagtg gggaagttgg tgaatgtgga   180
ataacttacc tttgtgctcc acttaaacca gatgtgttgc agctttcctg acatgcaagg   240
atctacttta attccacact ctcattaata aattgaataa aagggaatgt tttggcacct   300
gatataatct gccaggctat gtgacagtag gaaggaatgg tttcccctaa caagcccaat   360
gcactggtct gactttataa attatttaat aaaatgaact attatc                  406
```

<210> SEQ ID NO 42
<211> LENGTH: 381
<212> TYPE: DNA
<213> ORGANISM: Homo sapien

<400> SEQUENCE: 42

```
aaactggacc tgcaacaggg acatgaattt actgcarggt ctgagcaagc tcagcccctc     60
tacctcaggg ccccacagcc atgactacct cccccaggag cggagggtg  aagggggcct   120 gtctctgcaa gtggagccag agtggaggaa tgagctctga agacacagca cccagccttc   180
tcgcaccagc caagccttaa ctgcctgcct gaccctgaac cagaacccag ctgaactgcc   240
cctccaaggg acaggaaggc tgggggaggg agtttacaac ccaagccatt ccaccccctc   300
ccctgctggg gagaatgaca catcaagctg ctaacaattg ggggaagggg aaggaagaaa   360
actctgaaaa caaaatcttg t                                             381
```

<210> SEQ ID NO 43
<211> LENGTH: 451
<212> TYPE: DNA
<213> ORGANISM: Homo sapien

<400> SEQUENCE: 43

```
catgcgtttc accactgttg gccaggctgg tctcgaactc ctggcctcaa gcaatccacc     60
cgcctcagcc tccaaaagtg ctgggattac agatgtgagc catggcacca tgccaaaagg    120
ctatattcct ggctctgtgt ttccgagact gcttttaatc ccaacttctc tacatttaga    180
ttaaaaaata ttttattcat ggtcaatctg aacataatt actgcatctt aagtttccac     240
tgatgtatat agaaggctaa aggcacaatt tttatcaaat ctagtagagt aaccaaacat    300
aaaatcatta attactttca acttaataac taattgacat tcctcaaaag agctgttttc    360
aatcctgata ggttctttat tttttcaaaa tatatttgcc atgggatgct aatttgcaat    420
aaggcgcata atgagaatac cccaaactgg a                                   451

<210> SEQ ID NO 44
<211> LENGTH: 521
<212> TYPE: DNA
<213> ORGANISM: Homo sapien

<400> SEQUENCE: 44
gttggacccc cagggactgg aaagacactt cttgcccgag ctgtggcggg agaagctgat     60 gttcctttt attatgcttc tggatccgaa tttgatgaga tgtttgtggg tgtgggagcc    120
agccgtatca gaaatctttt tagggaagca aaggcgaatg ctccttgtgt tatatttatt    180
gatgaattag attctgttgg tgggaagaga attgaatctc caatgcatcc atattcaagg    240
cagaccataa atcaacttct tgctgaaatg gatggtttta aacccaatga aggagttatc    300
ataataggag ccacaaactt cccagaggca ttagataatg ccttaatacc gtcctggtcg    360
ttttgacatg caagttacag ttccaaggcc agatgtaaaa ggtcgaacag aaatttttgaa    420 atggtatctc aataaaataa agtttgatca atcccgttga tccagaaatt atagcctcga    480
ggtactggtg gcttttccgg aagcagagtt gggagaatct t                        521

<210> SEQ ID NO 45
<211> LENGTH: 585
<212> TYPE: DNA
<213> ORGANISM: Homo sapien

<400> SEQUENCE: 45
gcctacaaca tccagaaaga gtctaccctg cacctggtgc tscgtctcag aggtgggatg     60
cagatcttcg tgaagaccct gactggtaag accatcactc tcgaagtgga gccgagtgac    120
accatygaga acgtcaaagc aaagatccar gacaaggaag gcrtycctcc tgaccagcag    180
aggttgatct ttgccggaaa gcagctggaa gatggdcgca ccctgtctga ctacaacatc    240
cagaaagagt cyaccctgca cctggtgctc cgtctcagag gtgggatgca ratcttcgtg    300
aagaccctga ctggtaagac catcaccctc gaggtggagc ccagtgacac catcgagaat    360
gtcaaggcaa agatccaaga taaggaaggc atccctcctg atcagcagag gttgatcttt    420
gctgggaaac agctggaaga tggacgcacc ctgtctgact acaacatcca gaaagagtcc    480
actctgcact ggtcctgcg cttgaggggg ggtgtctaag tttccccttt taaggtttcm    540
acaaatttca ttgcactttc ctttcaataa agttgttgca ttccc                    585

<210> SEQ ID NO 46
<211> LENGTH: 481
<212> TYPE: DNA
<213> ORGANISM: Homo sapien

<400> SEQUENCE: 46
gaactgggcc ctgagcccaa gtcatgcctt gtgtccgcat ctgccgtgtc acctctgtkc     60
```

```
ctgccootca ccootccctc ctggtcttct gagccagcac catctccaaa tagcctattc    120
cttcctgcaa atcacacaca catgcgggcc acacatacct gctgccctgg agatggggaa    180
gtaggagaga tgaatagagg cccatacatt gtacagaagg aggggcaggt gcagataaaa    240
gcagcagacc cagcggcagc tgaggtgcat ggagcacggt tggggccggc attgggctga    300
gcacctgatg ggcctcatct cgtgaatcct cgaggcagcg ccacagcaga ggagttaagt    360
ggcacctggg ccgagcagag caggagactg agggtcagag tggaggctaa gctgccctgg    420
aactcctcaa tcttgcctgc ccctagtat gaagcccoct tcctgcccct acaattcctg     480
a                                                                    481
```

<210> SEQ ID NO 47
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 47

```
atggatctta ctttgccacc caggttggag tgcagtgctg caatcttggc tcactgcagc    60
cttaacctcc caggctcaag ctatcctcct gccaaagcct tccacatagc tgggactaca    120
ggtacacngc caccacaccc agctaaaatt tttgtatttt ttgtagagac gggatctcgc    180
cacgttgccc aggctggtcc catcctgacc tcaagcagat ctgcccacct cagcccccca    240
acgtgctagg attacaggcg tgagccaccg cacccagcct tgttttgct tttaatggaa     300 tcaccagttc ccctccgtgt ctcagcagca gctgtgagaa atgctttgca tctgtgacct    360
ttatgaaggg gaacttccat gctgaatgag ggtaggatta catgctcctg tttcccgggg    420
gtcaagaaag cctcagactc cagcatgata agcagggtga g                        461
```

<210> SEQ ID NO 48
<211> LENGTH: 571
<212> TYPE: DNA
<213> ORGANISM: Homo sapien

<400> SEQUENCE: 48

```
atagggctt taaggaggga attcaggttc aatgaggtcg taaggccagg gctcttatcc     60
agtaagactg gggtccttag atgagaaaga gacacccgag gtccttctct ctgccgtgtg    120
aggatgcatc aagaaggcgg ccgtctgcaa gcgaaggaga ggccgcacca gaaaccgaca    180
ccttcatctt ggacttgcag cctctagaac tgagaaaata actgtctgtt ggttaagcca    240
cccagtttgt agtattctct tatggcttcc taagcagact aacaaacaaa cacccaaaat    300
taactgatgg cttcgctgtc ttctgtaaaa attgctatga gagaacttttt cactcactgt    360 tttgcagttt ctccctcagt ccctggttct ttcttctcac ataatcccaa tttcaattta    420
tagttcatgg cccaggcaga gtcattcatc acggcatctc ctgagctaaa ccagcacctg    480
ctctgctcac ttcttgactg gctgctcatc atcagccctc ttgcagagat ttcatttcct    540
cccgtgccag gtacttcacg caccaagctc a                                    571
```

<210> SEQ ID NO 49
<211> LENGTH: 511
<212> TYPE: DNA
<213> ORGANISM: Homo sapien

<400> SEQUENCE: 49

```
ggataatgaa gttgttttat ttagcttgga caaaaaggca tattcctcta ttttcttata      60
caacaaatat ccccaaaata aagcaagcat atatatcttg aatgtgtaat aatccagtga     120
taaacaagag cagtacttta aagaaaaaa aaatatgtat ttctgtcagg ttaaaatgag      180
aatcaaaacc atttactctg ctaactcatt attttttgct ttcttttttgg ttaagagagg    240
caatgcaata cactgaaaaa ggttttatc ttatctggca ttggaattag acatattcaa      300
accccagccc ccatttccaa actttaagac cacaaacaag taatttactt ttctgaacat     360
tggtttttc tggaaaatgg gaattataaa atagactttg cagactctta tgagattaaa      420
taagataatg tatgaaattc tttcttcttt tttacttctt tttcctttt gagatggagt      480
ctcacccgt cacccaggct ggagtacagt g                                     511
```

<210> SEQ ID NO 50
<211> LENGTH: 561
<212> TYPE: DNA
<213> ORGANISM: Homo sapien

<400> SEQUENCE: 50

```
ccactgcact ccagcctggg tgacggagtg agactctgtc tcaaaaaaac aaacaaacaa      60
acaaacaaaa aactgaaaag gaaatagagt tcctctttcc tcatatatga atatattatt    120
tcaacagatt gttgatcacc taccatatgc ttggtattgt tctaattgct ggggatacag    180
caagaggttc tgcagaactt catggagcat gaaagtaaat aaacaaagtt aatttcaagg    240
ccaggcatgg ttgctcacac ctttagtccc agcactttgg gaggctgagg caggtggatc    300
acttgggccc aggagttcaa ggctgcagtg agccaagatt gtgccactac tctccaggct    360
gggcaacaga gcaagaccct gtctcagggg gaacaaaag ttaatttcag attttgttaa     420
gtgctgtaaa ggaagtaaat aggttgatat tcaagagagc acctgaaggc caggcgtggt    480
ggctcacgcc tgtggtctaa cgctttggga agcccgagcg ggcggatcac aaggtcagga    540
gaattttggc caggcatggt g                                              561
```

<210> SEQ ID NO 51
<211> LENGTH: 451
<212> TYPE: DNA
<213> ORGANISM: Homo sapien

<400> SEQUENCE: 51

```
agaatccatt tattgggttt taaactagtt acacaactga atcagtttg gcactacttt       60
atacagggat tacgcctgtg tatgccgaca cttaaatact gtaccaggac cactgctgtg     120
cttaggtctg tattcagtca ttcagcatgt agatactaaa aatatactgt agtgttcctt     180
taaggaagac tgtacagggt gtgttgcaag atgacattca ccaatttgtg aattatttca     240
acccagaaga taccttttcac tctataaact tgtcataggc aaacatgtgg tgttagcatt    300
gagagatgca cacaaaaatg ttacataaaa gttcagacat tctaatgata agtgaactga    360
aaaaaaaaa aaccccacat ctcaattttt gtaacaagat aaagaaaata atttaaaaac     420
acaaaaaatg gcattcagtg ggtacaaagc c                                   451
```

<210> SEQ ID NO 52
<211> LENGTH: 682
<212> TYPE: DNA
<213> ORGANISM: Homo sapien

<400> SEQUENCE: 52

```
caaatattta atataaatct ttgaaacaag ttcagakgaa ataaaaatca aagtttgcaa      60
aaacgtgaag attaacttaa ttgtcaaata ttcctcattg ccccaaatca gtatttttt      120 tatttctatg caaagtatg ccttcaaact gcttaaatga tatatgatat gatacacaaa     180
ccagttttca aatagtaaag ccagtcatct tgcaattgta agaaataggt aaaagattat     240
aagacacctt acacacacac acacacacac acacacgt gtgcaccgcc aatgacaaaa      300
aacaatttgg cctctcctaa aataagaaca tgaagaccct taattgctgc caggagggaa     360
cactgtgtca ccctccccta caatccaggt agtttccttt aatccaatag caaatctggg     420
catatttgag aggagtgatt ctgacagcca csgttgaaat cctgtgggga accattcatg     480
tccacccact ggtgccctga aaaaatgcca ataattttc gctcccactt ctgctgctgt      540
ctcttccaca tcctcacata gaccccagac ccgctggccc ctggctgggc atcgcattgc     600
tggtagagca agtcataggt ctcgtctttg acgtcacaga agcgatacac caaattgcct     660
ggtcggtcat tgtcataacc ag                                              682

<210> SEQ ID NO 53
<211> LENGTH: 311
<212> TYPE: DNA
<213> ORGANISM: Homo sapien
<220> FEATURE:
<221> NAME/KEY: misc_feature
<222> LOCATION: (1)...(311)
<223> OTHER INFORMATION: n = A,T,C or G

<400> SEQUENCE: 53 tttgactta gtagggtct gaactattta ttttactttg ccmgtaatat ttaraccyta      60 tatatcttc attatgccat cttatcttct aatgbcaagg gaacagwtgc taamctggct     120
tctgcattwa tcacattaaa aatggctttc ttggaaaatc ttcttgatat gaataaagga     180
tcttttavag ccatcattta aagcmggntt ctctccaaca cgagtctgct sasgggggk      240 gagctgtgaa ctctggctga aggctttccc atacacactg caatgacmtg gtttctgacc    300
agbgtgagtt a                                                          311

<210> SEQ ID NO 54
<211> LENGTH: 561
<212> TYPE: DNA
<213> ORGANISM: Homo sapien

<400> SEQUENCE: 54
agagaagccc cataaatgca atcagtgtgg gaaggccttc agtcagagct caagcctttt     60
cctccatcat cgggttcata ctggagagaa accctatgta tgtaatgaat gcggcagagc    120
ctttggtttt aactctcatc ttactgaaca cgtaaggatt cacacaggag aaaaacccta    180
tgtttgtaat gagtgcggca aagcctttcg tcggagttcc actcttgttc agcatcgaag     240
agttcacact ggggagaagc cctaccagtg cgttgaatgt gggaaagctt tcagccagag     300 ctccagctc accctacatc agccgagttc acactggaga aagccctat gactgtggtg     360 actgtgggaa ggccttcagc cggaggtcaa ccctcattca gcatcagaaa gttcacagcg     420
gagagactcg taagtgcaga aaacatggtc cagccttgt tcatggctcc agcctcacag     480
cagatggaca gattcccact ggagagaagc acggcagaac ctttaaccat ggtgcaaatc     540
tcattctgcg ctggacagtt c                                              561

<210> SEQ ID NO 55
```

<211> LENGTH: 811
<212> TYPE: DNA
<213> ORGANISM: Homo sapien

<400> SEQUENCE: 55

```
gagacagggt ctcactttgt cacccaggct ggaatgcagt ggtgcgatct tacgtagctc    60
actgcagccc tgacctcctg gactcaaaca attctcctgc ctcagccctg caagtagctg   120
ggactgtggg tgcatgccac catgcctggc taacttttgt agttttttgta aagatggggt   180
tttgccatgt tgcacatgct ggtcttgaac tcctgagctc aaacgatctg cccacctcgg   240
cctcccagaa tgttgggatt acaggggtaa accaccacgc ctggccccat tagggtattc   300
ttagcatcca cttgctcact gagattaatc ataagagatg ataagcactg gaagaaaaaa   360
atttttacta ggctttggat attttttttcc tttttcagct ttatacagag gattggatct   420
ttagttttcc tttaactgat aataaaacat tgaaggaaa taagtttacc tgagattcac    480
agagataacc ggcatcactc ccttgctcaa ttccagtctt taccacatca attattttca   540
gaggtgcagg ataaaggcct ttagtctgct ttcgcacttt ttcttccact ttttttgtaaa  600
cctgttgcct gacaaatgga attgacagcg tatgccatga ctattccatt tgtcaggcat   660
acgctgtcaa tttttccacc aatcccttgt ctctctttgg agagatcttc ttatcagcta   720
gtcctttggc aaaagtaatt gcaacttctt ctaggtattc tattgtccgt tccactggtg   780
gaaccctggg gaccaggact aaaacctcca g                                  811
```

<210> SEQ ID NO 56
<211> LENGTH: 591
<212> TYPE: DNA
<213> ORGANISM: Homo sapien
<220> FEATURE:
<221> NAME/KEY: misc_feature
<222> LOCATION: (1)...(591)
<223> OTHER INFORMATION: n = A,T,C or G

<400> SEQUENCE: 56

```
atctcatata tatatttctt cctgactttta tttgcttgct tctgncacgc atttaaaata    60
tcacagagac caaaatagag cggctttctg gtggaacgca tggcagtcac aggacaaaat   120
acaaaactag ggggctctgt cttctcatac atcatacaat tttcaagtat tttttttatg   180
tacaaagagc tactctatct gaaaaaaaat taaaaaataa atgagacaag atagtttatg   240
catcctagga agaaagaatg ggaagaaaga acggggcagt tgggtacaga ttcctgtccc   300
ctgttcccag ggaccactac cttcctgcca ctgagttccc ccacagcctc acccatcatg   360
tcacagggca agtgccaggg taggtgggga ccagtggaga caggaaccag caacatactt   420
tggcctggaa gataaggaga aagtctcaga aacacactgg tgggaagcaa tcccacnggc   480
cgtgccccan gagcttccca cctgctgctg gctccctggg tggctttggg aacagcttgg   540
gcaggccctt tgggtgggg nccaactggg cctttgggcc cgtgtggaaa g             591
```

<210> SEQ ID NO 57
<211> LENGTH: 481
<212> TYPE: DNA
<213> ORGANISM: Homo sapien

<400> SEQUENCE: 57

```
aaacattgag atggaatgat agggtttccc agaatcaggt ccatatttta actaaatgaa    60
aattatgatt tatagccttc tcaaatacct gccatacttg atatctcaac cagagctaat   120
tttacctctt tacaaattaa ataagcaagt aactggatcc acaatttata atacctgtca   180
```

```
attttttctg tattaaacct ctatcatagt ttaagcctat tagggtactt aatccttaca     240
aataaacagg tttaaaatca cctcaatagg caactgccct tctggttttc ttctttgact     300
aaacaatctg aatgcttaag attttccact ttgggtgcta gcagtacaca gtgttacact     360
ctgtattcca gacttcttaa attatagaaa aaggaatgta cacttttgt attctttctg      420 agcagggccg ggaggcaaca tcatctacca tggtagggac ttgtatgcat ggactacttt     480
a                                                                    481
```

<210> SEQ ID NO 58
<211> LENGTH: 141
<212> TYPE: DNA
<213> ORGANISM: Homo sapien

<400> SEQUENCE: 58

```
actctgtcgc ccaggctgga gcccabtggm gcgatctcga ctccctgcaa gctmcgcctc     60
acaggwtcat gccattctcc tgcctcagca tctggagtag ctgggactac aggcgccagc    120
caccatgccc agctaatttt t                                              141
```

<210> SEQ ID NO 59
<211> LENGTH: 191
<212> TYPE: DNA
<213> ORGANISM: Homo sapien

<400> SEQUENCE: 59

```
accttaaaga cataggagaa tttatactgg gagagaaagc ttacaaatgt aaggtttctg     60
acaagacttg ggagtgattc acacctggaa caacatactg gacttcacac tggabagaaa    120
ccttacaagt gtaatgagtg tggcaaagcc tttggcaagc agtcaacact tattcaccat    180
caggcaattc a                                                         191
```

<210> SEQ ID NO 60
<211> LENGTH: 480
<212> TYPE: DNA
<213> ORGANISM: Homo sapien

<400> SEQUENCE: 60

```
agtcaggatc atgatggctc agtttcccac agcgatgaat ggagggccaa atatgtgggc     60
tattacatct gaagaacgta ctaagcatga taaacagttt gataacctca aaccttcagg    120
aggttacata acaggtgatc aagcccgtac ttttttccta cagtcaggtc tgccggcccc    180
ggttttagct gaaatatggg ccttatcaga tctgaacaag gatgggaaga tggaccagca    240
agagttctct atagctatga aactcatcaa gttaaagttg cagggccaac agctgcctgt    300
agtcctccct cctatcatga acaaccccc tatgttctct ccactaatct ctgctcgttt     360
tgggatggga agcatgccca atctgtccat tcatcagcca ttgcctccag ttgcacctat    420
agcaacaccc ttgtcttctg ctacttcagg gaccagtatt cctccctaat gatgcctgct    480
```

<210> SEQ ID NO 61
<211> LENGTH: 381
<212> TYPE: DNA
<213> ORGANISM: Homo sapien

<400> SEQUENCE: 61

```
ctttcgattt ccttcaattt gtcacgtttg attttatgaa gttgttcaag ggctaactgc      60
tgtgtattat agctttctct gagttccttc agctgattgt taaatgaatc catttctgag    120
```

```
agcttagatg cagtttctttt tcaagagca tctaattgtt ctttaagtct ttggcataat      180
tcttcctttt ctgatgactt tctatgaagt aaactgatcc ctgaatcagg tgtgttactg      240
agctgcatgt ttttaattct ttcgtttaat agctgcttct cagggaccag atagataagc      300
ttattttgat attccttaag ctcttggtga agttgttcga tttccataat ttccaggtca      360
cactggttat cccaaacttc t                                                381
```

<210> SEQ ID NO 62
<211> LENGTH: 906
<212> TYPE: DNA
<213> ORGANISM: Homo sapien

<400> SEQUENCE: 62

```
gtggaggtga acggaggca agaaagggg ctacctcagg agcgagggac aaaggggcg         60 tgaggcacct aggccgcggc accccggcga caggaagccg tcctgaaccg ggctaccggg     120
taggggaagg gcccgcgtag tcctcgcagg gccccagagc tggagtcggc tccacagccc     180
cgggccgtcg gcttctcact tcctggacct ccccggcgcc cgggcctgag gactggctcg     240
gcggagggag aagaggaaac agacttgagc agctccccgt tgtctcgcaa ctccactgcc     300
gaggaactct catttcttcc ctcgctcctt cacccccac ctcatgtaga aaggtgctga      360
agcgtccgga gggaagaaga acctgggcta ccgtcctggc cttcccmccc ccttcccggg     420
gcgctttggt gggcgtggag ttgggggttgg ggggtgggt ggggggttctt ttttggagtg    480 ctggggaact ttttccctt cttcaggtca ggggaaaggg aatgcccaat tcagagagac     540
atgggggcaa gaaggacggg agtggaggag cttctggaac tttgcagccg tcatcgggag     600
gcggcagctc taacagcaga gagcgtcacc gcttggtatc gaagcacaag cggcataagt     660
ccaaacactc caaagacatg gggttggtga ccccgaagc agcatccctg ggcacagtta      720
tcaaaccttt ggtggagtat gatgatatca gctctgattc cgacaccttc tccgatgaca     780
tggccttcaa actagaccga agggagaacg acgaacgtcg tggatcagat cggagcgacc     840
gcctgcacaa acatcgtcac caccagcaca ggcgttcccg ggacttacta aaagctaaac     900
agaccg                                                                906
```

<210> SEQ ID NO 63
<211> LENGTH: 491
<212> TYPE: DNA
<213> ORGANISM: Homo sapien

<400> SEQUENCE: 63

```
gacatgtttg cctgcagggg accagagaca atgggattag ccagtgctca ctgttctta      60 tgcttccaga gaggatgggg acagctctca ggtcagaatc caggctgaga aggccatgct    120
ggttgggggc cccggaagc acggtccgga tcctccctgg catcagcgta gacccgctgc     180
tcaggcttgg ggtaccaaac tcatgctctg tactgttttg gccccatgcg gtgagaggaa     240
aacctagaaa aagattggtc gtgctaagga atcagctgcc ccctcatcct ccgcatccaa     300
tgctggtgac aacatattcc ctctcccagg acacagactc ggtgactcca cactgggctg     360
agtggcctct ggaggctcgt ggcctaaggc agggctccgt aaggctgatc ggctgaactg     420 ggtgggtga ggtttctga cccttcgctt cccatcccat aaccgctgtc aatgagctca      480
cactgtggtc a                                                          491
```

<210> SEQ ID NO 64
<211> LENGTH: 511

<212> TYPE: DNA
<213> ORGANISM: Homo sapien

<400> SEQUENCE: 64

| | | | | | |
|---|---|---|---|---|---|
| gatggcatgg | tcgttgctaa | tgtgcctgct | gggatggagc | acttcctcct | gtgagcccag | 60 |
| gggacccgcc | tgtccctgga | gcttggggca | aggagggaag | agtgatacca | ggaaggtggg | 120 |
| gctgcagcca | ggggcagag | tcagttcagg | gagtggtcct | cggccctcaa | agctcctccg | 180 |
| gggactgctc | aggagtgatg | gtgccctgga | gtttgcccca | acttccctgg | ccaccctgga | 240 |
| aggtgcctgg | ctgctccagg | cctctaggct | gggctgatgg | gtttctccag | gacacaagta | 300 |
| tcattaaagc | caccctctcc | tcagcttgtc | aggccgcaca | tgtgggacag | gctgtgctca | 360 |
| caacccctc | gcctgccctg | ccctccatca | ggaggagcca | gtggaacctt | cggaaagctc | 420 |
| ccagcatctc | agcagccctc | aaaagtcgtc | ctggggcaag | ctctggttct | cctgactgga | 480 |
| ggtcatctgg | gcttggcctg | ctctctctcg | c | | | 511 |

<210> SEQ ID NO 65
<211> LENGTH: 394
<212> TYPE: DNA
<213> ORGANISM: Homo sapien

<400> SEQUENCE: 65

| | | | | | |
|---|---|---|---|---|---|
| taaaaaagtg | taacaaaggt | ttatttagac | tttcttcatg | cccccagatc | caggatgtct | 60 |
| atgtaaaccg | ttatcttaca | aagaaagcac | aatatttggt | ataaactaag | tcagtgactt | 120 |
| gcttaactga | aatagcgtcc | atccaaaagt | gggtttaagg | taaaactacc | tgacgatatt | 180 |
| ggcggggatc | ctgcagtttg | gactgcttgc | cgggtttgtc | cagggttccg | ggtctgttct | 240 |
| tggcactcat | ggggacaggc | atcctgctcg | tctgtggggc | cccgctggag | cccttacgtg | 300 |
| aagctgaagg | tatcgaccst | aggggggtct | agggcagtgg | gaccttcatc | cggaactaac | 360 |
| aagggtcggg | gagaggcctc | ttgggctatg | tggg | | | 394 |

<210> SEQ ID NO 66
<211> LENGTH: 359
<212> TYPE: DNA
<213> ORGANISM: Homo sapien

<400> SEQUENCE: 66

| | | | | | |
|---|---|---|---|---|---|
| caagcgttcc | tttatggatg | taaattcaaa | cagtcatgct | gagccatccc | gggctgacag | 60 |
| tcacgttwaa | gacactaggt | cgggcgccac | agtgccaccc | aaggagaaga | agaatttgga | 120 |
| attttttccat | gaagatgtac | ggaaatctga | tgttgaatat | gaaaatggcc | cccaaatgga | 180 |
| attccaaaag | gttaccacag | gggctgtaag | acctagtgac | cctcctaagt | gggaaagagg | 240 |
| aatggagaat | agtatttctg | atgcatcaag | aacatcagaa | tataaaactg | agatcataat | 300 |
| gaaggaaaat | tccatatcca | atatgagttt | actcagagac | agtagaaact | attcccagg | 359 |

<210> SEQ ID NO 67
<211> LENGTH: 450
<212> TYPE: DNA
<213> ORGANISM: Homo sapien
<220> FEATURE:
<221> NAME/KEY: misc_feature
<222> LOCATION: (1)...(450)
<223> OTHER INFORMATION: n = A,T,C or G

<400> SEQUENCE: 67

| | | | | | |
|---|---|---|---|---|---|
| taggaataac | aaatgttttat | tcagaaatgg | ataagtaata | cataatcacc | cttcatctct | 60 |

| | |
|---|---:|
| taatgcccct tcctctcctt ctgcacagga gacacagatg ggtaacatag aggcatggga | 120 |
| agtggaggag gacacaggac tagcccacca ccttctcttc ccggtctccc aagatgactg | 180 |
| cttatagagt ggaggaggca aacaggtccc ctcaatgtac cagatggtca cctatagcac | 240 |
| cagctccaga tggccacgtg gttgcagctg gactcaatga aactctgtga caaccagaag | 300 |
| atacctgctt tgggatgaga gggaggataa agccatgcag ggaggatatt taccatccct | 360 |
| accctaagca cagtgcaagc agtgagcccc cggctcccag tacctgaaaa accaaggcct | 420 |
| actgncttttt ggatgctctc ttgggccacg | 450 |

<210> SEQ ID NO 68
<211> LENGTH: 511
<212> TYPE: DNA
<213> ORGANISM: Homo sapien

<400> SEQUENCE: 68

| | |
|---|---:|
| aagcctcctg ccctggaaat ctggagcccc ttggagctga gctggacggg gcagggaggg | 60 |
| gctgagaggc aagaccgtct ccctcctgct gcagctgctt ccccagcagc cactgctggg | 120 |
| cacagcagaa acgccagcag agaaaatggg agccgagagt ccttagccct ggagctgagg | 180 |
| ctgcctctgg gctgacccgc tggctgtacg tggccagaac tggggttggc atctggcatc | 240 |
| catttgaggc caggatggag gaaagggagg ccaacagagg aaaacctatt cctgctgtga | 300 |
| caacacagcc cttgtcccac gcagcctaag tgcagggagc gtgatgaagt caggcagcca | 360 |
| gtcggggagg acgaggtaac tcagcagcaa tgtcaccttg tagcctatgc gctcaatggc | 420 |
| ccggaggggc agcaaccccc cgcacacgtc agccaacagc agtgcctctg caggcaccaa | 480 |
| gagagcgatg atggacttga gcgccgtgtt c | 511 |

<210> SEQ ID NO 69
<211> LENGTH: 511
<212> TYPE: DNA
<213> ORGANISM: Homo sapien

<400> SEQUENCE: 69

| | |
|---|---:|
| gtttggcaga agacatgttt aataacattt tcatatttaa aaaatacagc aacaattctc | 60 |
| tatctgtcca ccatcttgcc ttgcccttcc tggggctgag gcagacaaag gaaaggtaat | 120 |
| gaggttaggg cccccaggcg ggctaagtgc tattggcctg ctcctgctca aagagagcca | 180 |
| tagccagctg ggcacggccc cctagcccct ccaggttgct gaggcggcag cggtggtaga | 240 |
| gttcttcact gagccgtggg ctgcagtctc gcagggagaa cttctgcacc agccctggct | 300 |
| ctacggcccg aaagaggtgg agccctgaga accggaggaa aacatccatc acctccagcc | 360 |
| cctccagggc ttcctcctct tcctggcctg ccagttcacc tgccagccgg gctcgggccg | 420 |
| ccaggtagtc agcgttgtag aagcagccct ccgcagaagc ctgccggtca atctccccg | 480 |
| ctataggagc cccccgggag gggtcagcac c | 511 |

<210> SEQ ID NO 70
<211> LENGTH: 511
<212> TYPE: DNA
<213> ORGANISM: Homo sapien

<400> SEQUENCE: 70

| | |
|---|---:|
| caagttgaac gtcaggcttg gcagaggtgg agtgtagatg aaaacaaagg tgtgattatg | 60 |
| aagaggatgt gagtcctttg ggtgtaggag agaaaggctg ttgagcttct atttcaagat | 120 |
| acttttacct gtgcaaaaag cacattttcc acctccttct catggcattt gtgtaaggtg | 180 |

```
agtatgattc ctattccatc tgcattttag aggtgaagaa taacgtacaa gggattcagt      240
gattagcaag ggacccctca ctaagtgttg atggagttag dacagagctc agctgtttga      300
atctcagagc ccaggcagct ggagctgggt aggatcctgg agctggcact aatgtgaggt      360
gcattccctc caacccaggc tcagatccgg aacctgaccg tgctgacccc cgaaggggag      420
gcagggctga gctggcccgt tgggctccct gctcctttca caccacactc tcgctttgag      480
gtgctgggct gggactactt cacagagcag c                                    511

<210> SEQ ID NO 71
<211> LENGTH: 511
<212> TYPE: DNA
<213> ORGANISM: Homo sapien

<400> SEQUENCE: 71
tggcctgggc aggattggga gagaggtagc tacccggatg cagtcctttg ggatgaagac       60
tatagggtat gaccccatca tttccccaga ggtctcggcc tcctttggtg ttcagcagct      120 gccccctggag gagatctggc ctctctgtga tttcatcact gtgcacactc ctctcctgcc     180
ctccacgaca ggcttgctga atgacaacac ctttgcccag tgcaagaagg gggtgcgtgt      240
ggtgaactgt gcccgtggag ggatcgtgga cgaaggcgcc ctgctccggg ccctgcagtc      300
tggccagtgt gccggggctg cactggacgt gtttacggaa gagccgccac gggaccgggc      360
cttggtggac catgagaatg tcatcagctg tccccacctg ggtgccagca ccaaggaggc      420
tcagagccgc tgtggggagg aaattgctgt tcagttcgtg acatggtgaa agggaaatc       480 tctcacgggg gttgtgaatg cccaggccct t                                    511

<210> SEQ ID NO 72
<211> LENGTH: 2017
<212> TYPE: DNA
<213> ORGANISM: Homo sapien

<400> SEQUENCE: 72
agccagatgg ctgagagctg caagaagaag tcaggatcat gatggctcag tttcccacag       60
cgatgaatgg agggccaaat atgtgggcta ttacatctga gaacgtact aagcatgata      120 aacagtttga taacctcaaa ccttcaggag gttacataac aggtgatcaa gcccgtactt      180
ttttcctaca gtcaggtctg ccggccccgg ttttagctga aatatgggcc ttatcagatc      240
tgaacaagga tggaagatg gaccagcaag agttctctat agctatgaaa ctcatcaagt       300
taaagttgca gggccaacag ctgcctgtag tcctccctcc tatcatgaaa caacccccta      360
tgttctctcc actaatctct gctcgttttg ggatgggaag catgcccaat ctgtccattc      420
atcagccatt gcctccagtt gcacctatag caacacccct gtcttctgct acttcaggga     480
ccagtattcc tcccctaatg atgcctgctc ccctagtgcc ttctgttagt acatcctcat      540
taccaaatgg aactgccagt ctcattcagc ctttatccat tccttattct tcttcaacat      600
tgcctcatgc atcatcttac agcctgatga tgggaggatt tggtggtgct agtatccaga      660
aggcccagtc tctgattgat ttaggatcta gtagctcaac ttcctcaact gcttccctct      720
cagggaactc acctaagaca gggacctcag agtgggcagt tcctcagcct tcaagattaa      780
agtatcggca aaatttaat agtctagaca aaggcatgag cggataccctc tcaggttttc      840 aagctagaaa tgcccttctt cagtcaaatc tctctcaaac tcagctagct actatttgga     900
ctctggctga catcgatggt gacggacagt tgaaagctga agaatttatt ctggcgatgc      960
```

-continued

```
acctcactga catggccaaa gctggacagc cactaccact gacgttgcct cccgagcttg    1020
tccctccatc tttcagaggg ggaaagcaag ttgattctgt taatggaact ctgccttcat    1080
atcagaaaac acaagaagaa gagcctcaga gaaactgcc agttactttt gaggacaaac     1140
ggaaagccaa ctatgaacga ggaaacatgg agctggagaa gcgacgccaa gtgttgatgg    1200
agcagcagca gagggaggct gaacgcaaag cccagaaaga gaaggaagag tgggagcgga    1260
aacagagaga actgcaagag caagaatgga gaagcagct ggagttggag aaacgcttgg     1320
agaaacagag agagctggag agacagcggg aggaagagag gagaaaggag atagaaagac    1380
gagaggcagc aaaacaggag cttgagagac aacgccgttt agaatgggaa agactccgtc    1440
ggcaggagct gctcagtcag aagaccaggg aacaagaaga cattgtcagg ctgagctcca    1500
gaaagaaaag tctccacctg gaactggaag cagtgaatgg aaaacatcag cagatctcag    1560
gcagactaca agatgtccaa atcagaaagc aaacacaaaa gactgagcta aagttttgg    1620 ataaacagtg tgacctggaa attatggaaa tcaaacaact tcaacaagag cttaaggaat    1680
atcaaaataa gcttatctat ctggtccctg agaagcagct attaaacgaa gaattaaaa     1740 acatgcagct cagtaacaca cctgattcag ggatcagttt acttcataaa aagtcatcag    1800
aaaaggaaga attatgccaa agacttaaag aacaattaga tgctcttgaa aagaaactg     1860 catctaagct ctcagaaatg gattcattta caatcagct gaaggaactc agagaaagct     1920
ataatacaca gcagttagcc cttgaacaac ttcataaaat caaacgtgac aaattgaagg    1980
aaatcgaaag aaaaagatta gagcaaaaaa aaaaaaa                              2017
```

<210> SEQ ID NO 73
<211> LENGTH: 414
<212> TYPE: DNA
<213> ORGANISM: Homo sapien

<400> SEQUENCE: 73

```
atggcagtga cattcaccat catgggaacc accttccctt tcttcagga ttctctgtag      60 tggaagagag cacccagtgt tgggctgaaa acatctgaaa gtagggagaa gaacctaaaa    120
taatcagtat ctcagagggc tctaaggtgc caagaagtct cactggacat ttaagtgcca    180
acaaaggcat actttcggaa tcgccaagtc aaaactttct aacttctgtc tctctcagag    240
acaagtgaga ctcaagagtc tactgcttta gtggcaacta cagaaaactg gtgttaccca    300 gaaaacagg agcaattaga aatggttcca atatttcaaa gctccgcaaa caggatgtgc     360
tttcctttgc ccatttaggg tttcttctct ttcctttctc tttattaacc acta          414
```

<210> SEQ ID NO 74
<211> LENGTH: 1567
<212> TYPE: DNA
<213> ORGANISM: Homo sapien

<400> SEQUENCE: 74

```
atatctagaa gtctggagtg agcaaacaag agcaagaaac aaaaagaagc caaaagcaga     60
aggctccaat atgaacaaga taatctatc ttcaaagaca tattagaagt tgggaaaata    120
attcatgtga actagacaag tgtgttaaga gtgataagta aaatgcacgt ggagacaagt    180
gcatccccag atctcaggga cctccccctg cctgtcacct ggggagtgag aggacaggat    240
agtgcatgtt ctttgtctct gaattttag ttatatgtgc tgtaatgttg ctctgaggaa     300 gccctggaa agtctatccc aacatatcca catcttatat tccacaaatt aagctgtagt     360
atgtacccta agacgctgct aattgactgc cacttcgcaa ctcaggggcg gctgcatttt    420
```

```
agtaatgggt caaatgattc acttttatg atgcttccaa aggtgccttg gcttctcttc    480
ccaactgaca aatgccaaag ttgagaaaaa tgatcataat tttagcataa acagagcagt    540
cggcgacacc gattttataa ataaactgag caccttcttt ttaaacaaac aaatgcgggt    600
ttatttctca gatgatgttc atccgtgaat ggtccaggga aggacctttc accttgacta    660
tatggcatta tgtcatcaca agctctgagg cttctccttt ccatcctgcg tggacagcta    720
agacctcagt tttcaatagc atctagagca gtgggactca gctgggtga tttcgccccc    780 catctccggg ggaatgtctg aagacaattt tgttacctca atgagggagt ggaggaggat    840
acagtgctac taccaactag tggataaagg ccagggatgc tgctcaacct cctaccatgt    900
acaggacgtc tccccattac aactacccaa tccgaagtgt caactgtgtc aggactaaga    960
aaccctggtt ttgagtagaa aagggcctgg aaagagggga gccaacaaat ctgtctgctt   1020
cctcacatta gtcattggca ataagcatt ctgtctcttt ggctgctgcc tcagcacaga   1080
gagccagaac tctatcgggc accaggataa catctctcag tgaacagagt tgacaaggcc   1140
tatgggaaat gcctgatggg attatcttca gcttgttgag cttctaagtt tctttcccttt  1200 cattctaccc tgcaagccaa gttctgtaag agaaatgcct gagttctagc tcaggttttc   1260
ttactctgaa tttagatctc cagacccttc ctggccacaa ttcaaattaa ggcaacaaac   1320
atataccttc catgaagcac acacagactt ttgaaagcaa ggacaatgac tgcttgaatt   1380
gaggccttga ggaatgaagc tttgaaggaa aagaatactt tgtttccagc cccttccca   1440 cactcttcat gtgttaacca ctgccttcct ggaccttgga gccacggtga ctgtattaca   1500
tgttgttata gaaaactgat tttagagttc tgatcgttca agagaatgat taaatataca   1560
tttccta                                                              1567

<210> SEQ ID NO 75
<211> LENGTH: 240
<212> TYPE: DNA
<213> ORGANISM: Homo sapien

<400> SEQUENCE: 75
tcgagcggcc gcccgggcag gtccttcaga cttggactgt gtcacactgc caggcttcca     60
gggctccaac ttgcagacgg cctgttgtgg gacagtctct gtaatcgcga aagcaaccat    120
ggaagacctg ggggaaaaca ccatggtttt atccaccctg agatctttga acaacttcat    180
ctctcagcgt gcggagggag gctctggact ggatatttct acctcggccg cgaccacgct    240

<210> SEQ ID NO 76
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 76
tagcgyggtc gcggccgagg yctgcttytc tgtccagccc agggcctgtg gggtcagggc     60
ggtgggtgca gatggcatcc actccggtgg cttccccatc tttctctggc ctgagcaagg    120
tcagcctgca gccagagtac agagggccaa cactggtgtt cttgaacaag ggccttagca    180
ggccctgaag grccctctct gtagtgttga acttcctgga gccaggccac atgttctcct    240
cataccgcag gytagygatg gtgaagttga gggtgaaata gtattmangr agatggctgg    300
```
caracctgcc cgggcggccg ctcsaaatcc                                    330

<210> SEQ ID NO 77
<211> LENGTH: 361
<212> TYPE: DNA
<213> ORGANISM: Homo sapien

<400> SEQUENCE: 77
agcgtggtcg cggccgaggt gtccttcagg gtctgcttat gcccttgttc aagaacacca    60
gtgtcagctc tctgtactct ggttgcagac tgaccttgct caggcctgag aaggatgggg   120
cagccaccag agtggatgct gtctgcaccc atcgtcctga ccccaaaagc cctggactgg   180
acagagagcg gctgtactgg aagctgagcc agctgaccca cggcatcact gagctgggcc   240
cctacaccct ggacagggac agtctctatg tcaatggttt cacccatcgg agctctgtac   300
ccaccaccag caccggggtg gtcagcgagg agccattcaa cctgcccggg cggccgctcg   360
a                                                                   361

<210> SEQ ID NO 78
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 78
ttggggnttt mgagcggccg cccgggcagg taccggggtg gtcagcgagg agccattcac    60
actgaacttc accatcaaca acctgcggta tgaggagaac atgcagcacc ctggctccag   120
gaagttcaac accacggaga gggtccttca gggcctgctc aggtccctgt tcaagagcac   180
cagtgttggc cctctgtact ctggctgcag actgactttg ctcagacttg agaaacatgg   240
ggcagccact ggagtggacg ccatctgcac cctccgcctt gatcccactg gtcctggact   300
ggacagagag cggctatact gggagctgag ccagtcctct ggcggngacn ccnctt       356

<210> SEQ ID NO 79
<211> LENGTH: 226
<212> TYPE: DNA
<213> ORGANISM: Homo sapien

<400> SEQUENCE: 79
agcgtggtcg cggccgaggt ccagtcgcag catgctcttt ctcctgccca ctggcacagt    60
gaggaagatc tctgctgtca gtgagaaggc tgtcatccac tgagatggca gtcaaaagtg   120
catttaatac acctaacgta tcgaacatca tagcttggcc caggttatct catatgtgct   180
cagaacactt acaatagcct gcagacctgc ccgggcggcc gctcga                  226

<210> SEQ ID NO 80
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 80
tgtggtgttg aacttcctgg agncagggtg acccatgtcc tccccatact gcaggttggt    60
gatggtgaag ttgagggtga atggtaccag gagagggcca gcagccataa ttgtsgrgck   120

```
gsmgmssgag gmwggwgtyy cwgaggttcy rarrtccact gtggaggtcc caggagtgct    180
ggtggtgggc acagagstcy gatgggtgaa accattgaca tagagactgt tcctgtccag    240
ggtgtagggg cccagctctt yratgycatt ggycagttkg ctyagctccc agtacagccr    300
ctctckgyyg mgwccagsgc ttttggggtc aagatgatgg atgcagatgg catccactcc    360
agtggctgct ccatccttct cggacctgag agaggtcagt ctgcagccag agtacagagg    420
gccaacactg gtgttctttg aata                                          444
```

<210> SEQ ID NO 81
<211> LENGTH: 310
<212> TYPE: DNA
<213> ORGANISM: Homo sapien

<400> SEQUENCE: 81

```
tcgagcggcc gcccgggcag gtcaggaagc acattggtct tagagccact gcctcctgga     60
ttccacctgt gctgcggaca tctccaggga gtgcagaagg gaagcaggtc aaactgctca    120
gatcagtcag actggctgtt ctcagttctc acctgagcaa ggtcagtctg cagccagagt    180
acagagggcc aacactggtg ttcttgaaca agggcttgag cagaccctgc agaaccctct    240
tccgtggtgt tgaacttcct ggaaaccagg gtgttgcatg ttttcctca taatgcaagg    300 ttggtgatgg                                                          310
```

<210> SEQ ID NO 82
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 82

```
acggtttcaa tggacacttt tattgtttac ttaatggatc atcaattttg tctcactacc     60
tacaaatgga atttcatctt gtttccatgc tgagtagtga acagtgaca aagctaatca    120 taataaccta catcaaaaga gaactaagct aacactgctc actttctttt taacaggcaa    180
aatataaata tatgcactct anaatgcaca atggtttagt cactaaaaaa ttcaaatggg    240
atcttgaaga atgtatgcaa atccagggtg cagtgaagat gagctgagat gctgtgcaac    300
tgtttaaggg ttcctggcac tgcatctctt ggccactagc tgaatcttga catgaaggt    360 tttagctaat gccaagtgga gatgcagaaa atgctaagtt gacttagggg ctgtgcacag    420
gaactaaaag gcaggaaagt actaaatatt gctgagagca tccacccag gaaggactt    480 accttccagg agctccaaac tggcaccacc cccagtgctc acatggctga ctttatcctc    540
cgtgttccat ttggcacagc aagtggcagt g                                  571
```

<210> SEQ ID NO 83
<211> LENGTH: 551
<212> TYPE: DNA
<213> ORGANISM: Homo sapien

<400> SEQUENCE: 83

```
aaggctggtg ggtttttgat cctgctggag aacctccgct tcatgtgga ggaagaaggg     60 aagggaaaag atgcttctgg gaacaaggtt aaagccgagc cagccaaaat agaagctttc    120
cgagcttcac tttccaagct aggggatgtc tatgtcaatg atgcttttgg cactgctcac    180
```

```
agagcccaca gctccatggt aggagtcaat ctgccacaga aggctggtgg gttttttgatg      240 aagaaggagc tgaactactt tgcaaaggcc ttggagagcc cagagcgacc cttcctggcc      300
atcctgggcg gagctaaagt tgcagacaag atccagctca tcaataatat gctggacaaa      360
gtcaatgaga tgattattgg tggtggaatg gcttttacct tccttaaggt gctcaacaac      420
atggagattg gcacttctct gtttgatgaa gagggagcca agattgtcaa agacctaatg      480
tccaaagctg agaagaatgg tgtgaagatt accttgcctg ttgactttgt cactgctgac      540
aagtttgatg a                                                          551

<210> SEQ ID NO 84
<211> LENGTH: 571
<212> TYPE: DNA
<213> ORGANISM: Homo sapien

<400> SEQUENCE: 84
tttgttcctt acattttcct aaagagttac ttaaatcagt caactggtct ttgagactct       60
taagttctga ttccaactta gctaattcat tctgagaact gtggtatagg tggcgtgtct      120
cttctagctg ggacaaaagt tctttgtttt cccctgtag agtatcacag accttctgct      180
gaagctggac ctctgtctgg gccttggact cccaaatctg cttgtcatgt tcaagcctgg      240
aaatgttaat ctttaattct tccatatgga tggacatctg tctaagttga tcctttagaa      300
cactgcaatt atcttctttg agtctaattt cttcttcttt gctttgaatc gcatcactaa      360
acttcctctc ccatttctta gcttcatcta tcaccctgtc acgatcatcc tggagggaag      420
acatgctctt agtaaaggct gcaagctggg tcacagtact gtccaagttt tcctgaagtt      480
gctgaacttc cttgtctttc ttgttcaaag taacctgaat ctctccaatt gtctcttcca      540
agtggacttt ttctctgcgc aaagcatcca g                                    571

<210> SEQ ID NO 85
<211> LENGTH: 561
<212> TYPE: DNA
<213> ORGANISM: Homo sapien

<400> SEQUENCE: 85
tcattgcctg tgatggcatc tggaatgtga tgagcagcca ggaagttgta gatttcattc       60
aatcaaagga ttcagcatgt ggtggaagct gtgaggcaag agaaacaaga actgtatggc      120
aagttaagaa gcacagaggc aaacaagaag gagacagaaa agcagttgca ggaagctgag      180
caagaaatgg aggaaatgaa agaaagatg agaaagtttg ctaaatctaa acagcagaaa      240
atcctagagc tggaagaaga gaatgaccgg cttagggcag aggtgcaccc tgcaggagat      300
acagctaaag agtgtatgga aacacttctt tcttccaatg ccagcatgaa ggaagaactt      360
gaaagggtca aaatggagta tgaaacccctt tctaagaagt ttcagtcttt aatgtctgag      420
aaagactctc taagtgaaga ggttcaagat ttaaagcatc agatagaagg taatgtatct      480
aaacaagcta acctagaggc caccgagaaa catgataacc aaacgaatgt cactgaagag      540
ggaacacagt ctataccagg t                                               561

<210> SEQ ID NO 86
<211> LENGTH: 795
<212> TYPE: DNA
<213> ORGANISM: Homo sapien

<400> SEQUENCE: 86
aagccaataa tcaccatttta ttacttaata tatgccaacc actgtacttg gcagttcaca       60
```

```
aattctcacc gttacaacaa ccccatgagg tatttattcc cattctatag atagggaaac      120
cacagctcaa gtaagttagg aaactgagcc aagtatacac agaatacgaa gtggcaaaac      180
tagaaggaaa gactgacact gctatctgct ggcctccagt gtcctggctc ttttcacacg      240
ggttcaatgt ctccagcgct gctgctgctg ctgcattacc atgccctcat tgttttcctt      300
cctctggtgt tcaactgcat ccttcaaaga atctaactca ttccagagac cacttatttc      360
tttctctctt tctgaaatta cttttaataa ttcttcatga gggggaaaag aagatgcctg      420
ttggtagttt tgttgtttaa gctgctcaat ttgggactta acaaatttgt tttcatcttg      480
tacatcctgt aacagctgtg ttttgctaga agatcactc tccctctctt ttagcatggc       540
ttctaacctc ttcaattcat tttccttttc tttcaacaca atctcaagtt cttcaaactg      600
tgatgcagaa gaggcctctt tcaagttatg ttgtgctact tcctgaacat gtgcttttaa      660
agattcattt tcttcttgaa gatcctgtaa ccacttccct gtattggcta ggtctttctc      720
tttctcttcc aaaacagcct tcatggtatt catctgttcc tcttttcctt ttaataagtt      780
caggagcttc agaac                                                      795

<210> SEQ ID NO 87
<211> LENGTH: 594
<212> TYPE: DNA
<213> ORGANISM: Homo sapien

<400> SEQUENCE: 87
caagcttttt ttttttttt aaaaagtgtt agcattaatg ttttattgtc acgcagatgg        60
caactgggtt tatgtcttca tattttatat ttttgtaaat taaaaaaatt acaagtttta      120
aatagccaat ggctggttat attttcagaa acatgattga gactaattca ttaatggtgg      180
cttcaagctt ttccttattg gctccagaaa attcacccac cttttgtccc ttcttaaaaa      240
actggaatgt tggcatgcat ttgacttcac actctgaagc aacatcctga cagtcatcca      300
catctacttc aaggaatatc acgttggaat acttttcaga gagggaatga agaaaggct       360 tgatcatttt gcaaggccca caccacgtgg ctgagaagtc aactactaca agtttatcac      420
ctgcagcgtc caaggcttcc tgaaaagcag tcttgctctc gatctgcttc accatcttgg      480
ctgctggagt ctgacgagcg gctgtaagga ccgatggaaa tggatccaaa gcaccaaaca      540
gagcttcaag actcgctgct tggcttgaat tcggatccga tatcgccatg gcct           594

<210> SEQ ID NO 88
<211> LENGTH: 557
<212> TYPE: DNA
<213> ORGANISM: Homo sapien

<400> SEQUENCE: 88
aagtgttagc attaatgttt tattgtcacg cagatggcaa ctgggtttat gtcttcatat       60
tttatatttt tgtaaattaa aaaaattmca agttttaaat agccaatggc tggttatatt      120
ttcagaaaac atgattagac taattcatta atggtggctt caagcttttc cttattggct      180
ccagaaaatt cacccaccttt tgtcccttc ttaaaaaact ggaatgttgg catgcatttg      240
acttcacact ctgaagcaac atcctgacag tcatccacat ctacttcaag gaatatcacg      300
ttggaatact tttcagagag ggaatgaaag aaaggcttga tcattttgca aggcccacac      360
cacgtggctg agaagtcaac tactacaagt ttatcacctg cagcgtccaa ggcttcctga      420
aaagcagtct tgctctcgat ctgcttcacc atcttggctg ctggagtctg acgagcggct      480
```

```
gtaaggaccg atggaaatgg atccaaagca ccaaacagag cttcaagact cgctgcttgg    540
catgaattcg gatccga                                                   557

<210> SEQ ID NO 89
<211> LENGTH: 561
<212> TYPE: DNA
<213> ORGANISM: Homo sapien
<220> FEATURE:
<221> NAME/KEY: misc_feature
<222> LOCATION: (1)...(561)
<223> OTHER INFORMATION: n = A,T,C or G

<400> SEQUENCE: 89
tacaaacttt attgaaacgc acacgcgcac acacacaaac acccctgtgg atagggaaaa     60
gcacctggcc acaggtccca ctgaaacggg gagggatgg cagcttgtaa tgtggctttt    120
gccacaaccc ccttctgaca gggaaggcct tagattgagg ccccacctcc catggtgatg    180
gggagctcag aatggggtcc aggagaatt tggttagggg gaggtgctag ggaggcatga    240
gcagagggca ccctccgagt ggggtcccga gggctgcaga gtcttcagta ctgtccctca    300
cagcagctgt ctcaaggctg gtccctcaa aggggcgtcc cagcgcgggg cctccctgcg    360
caaacacttg gtaccctgg ctgcgcagcg gaagccagca ggacagcagt ggcgccgatc    420
agcacaacag acgccctggc ggtagggaca gcaggcccag ccctgtcggt tgtctcggca    480
gcaggtctgg ttatcatggc agaagtgtcc ttcccacact tcacgtcctt cacacccacg    540
tganggctac nggccaggaa g                                             561

<210> SEQ ID NO 90
<211> LENGTH: 561
<212> TYPE: DNA
<213> ORGANISM: Homo sapien

<400> SEQUENCE: 90
cccgtgggtg ccatccacgg agttgttacc tgatctttgg aagcaggatc gcccgtctgc     60
actgcagtgg aagccccgtg ggcagcagtg atggccatcc ccgcatgcca cggcctctgg    120 gaagggcag caactggaag tccctgagac ggtaaagatg caggagtggc cggcagagca    180
gtgggcatca acctggcagg ggccacccag atgcctgctc agtgttgtgg gccatttgtc    240 cagaaggga cggcagcagc tgtagctggc tcctccgggg tccaggcagc aggccacagg    300
gcagaactga ccatctgggc accgcgttcc agccaccagc cctgctgtta aggccaccca    360
gctcaccagg gtccacatgg tctgcctgcg tccgactccg cggtccttgg gccctgatgg    420
ttctacctgc tgtgagctgc ccagtgggaa gtatggctgc tgccaatgcc caacgccacc    480
tgctgctccg atcacctgca ctgctgcccc aagacactgt gtgtgacctg atccagagta    540
agtgcctctc caaggagaac g                                             561

<210> SEQ ID NO 91
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 91
gaatcacctt tctggtttag ctagtacttt gtacagaaca atgaggtttc ccacagcgga     60
gtctccctgg gctctgtttg gctctcggta aggcaggcct acacctttc ctctcctcta    120
```

```
tggagagggg aatatgcatt aaggtgaaaa gtcaccttcc aaaagtgaga aagggattcg      180
attgctgctt caggactgtg gaattatttg gaatgtttta caaatggttg ctacaaaaca      240
acaaaaaagg taattacaaa atgtgtacat cacaacatgc tttttaaaga cattatgcat      300
tgtgctcaca ttcccttaaa tgttgtttcc aaaggtgctc agcctctagc ccagctggat      360
tctccgggaa gaggcagaga cagtttggcg aaaaagacac agggaaggag ggggtggtga      420
aaggagaaag cagccttcca gttaaagatc agccctcagt taaaggtcag cttcccgcan      480
gctggcctca ncggagtct gggtcagagg gaggagcagc agcagggtgg gactggggcg      540
t                                                                     541

<210> SEQ ID NO 92
<211> LENGTH: 551
<212> TYPE: DNA
<213> ORGANISM: Homo sapien

<400> SEQUENCE: 92
aaccggagcg cgagcagtag ctgggtgggc accatggctg ggatcaccac catcgaggcg      60
gtgaagcgca agatccaggt tctgcagcag caggcagatg atgcagagga gcgagctgag     120
cgcctccagc gagaagttga gggagaaagg cgggcccggg aacaggctga ggctgaggtg     180
gcctccttga accgtaggat ccagctggtt gaagaagagc tggaccgtgc tcaggagcgc     240
ctggccactg ccctgcaaaa gctggaagaa gctgaaaaag ctgctgatga gagtgagaga     300
ggtatgaagg ttattgaaaa ccgggcctta aaagatgaag aaaagatgga actccaggaa     360
atccaactca aagaagctaa gcacattgca gaagaggcag ataggaagta tgaagaggtg     420
gctcgtaagt tggtgatcat tgaaggagac ttggaacgca cagaggaacg agctgagctg     480
gcagagtccc gttgccgaga gatggatgag cagattagac tgatggacca gaacctgaag     540
tgtctgagtg c                                                         551

<210> SEQ ID NO 93
<211> LENGTH: 531
<212> TYPE: DNA
<213> ORGANISM: Homo sapien

<400> SEQUENCE: 93
gagaacttgg cctttattgt gggcccagga gggcacaaag gtcaggaggc ccaagggagg      60
gatctggttt tctggatagc caggtcatag catgggtatc agtaggaatc cgctgtagct     120
gcacaggcct cacttgctgc agttccgggg agaacacctg cactgcatgg cgttgatgac     180
ctcgtggtac acgacagagc cattggtgca gtgcaagggc acgcgcatgg gctccgtcct     240
cgagggcagg cagcaggagc attgctcctg cacatcctcg atgtcaatgg agtacacagc     300
tttgctggca cactttccct ggcagtaatg aatgtccact tcctcttggg acttacaatc     360
tcccactttg atgtactgca ccttggctgt gatgtctttg caatcaggct cctcacatgt     420
gtcacagcag gtgcctggaa ttttcacgat tttgcctcct tcagccagac acttgtgttc     480
atcaaatggt gggcagcccg tgaccctctt ctcccagatg tactctcctc t              531

<210> SEQ ID NO 94
<211> LENGTH: 531
<212> TYPE: DNA
<213> ORGANISM: Homo sapien
<220> FEATURE:
<221> NAME/KEY: misc_feature
<222> LOCATION: (1)...(531)
```

<223> OTHER INFORMATION: n = A,T,C or G

<400> SEQUENCE: 94

| | | | | | |
|---|---|---|---|---|---|
| gcctggacct | tgccggatca | gtgccacaca | gtgacttgct | tggcaaatgg | ccagaccttg | 60 |
| ctgcagagtc | atcgtgtcaa | ttgtgaccat | ggaccccggc | cttcatgtgc | caacagccag | 120 |
| tctcctgttc | gggtggagga | gacgtgtggc | tgccgctgga | cctgcccttg | tgtgtgcacg | 180 |
| ggcagttcca | ctcggcacat | cgtcaccttc | gatgggcaga | atttcaagct | tactggtagc | 240 |
| tgctcctatg | tcatctttca | aaacaaggag | caggacctgg | aagtgctcct | ccacaatggg | 300 |
| gcctgcagcc | ccggggcaaa | acaagcctgc | atgaagtcca | ttgagattaa | gcatgctggc | 360 |
| gtctctgctg | agctgcacag | taacatggag | atggcagtgg | atgggagact | ggtccttgcc | 420 |
| ccgtacgttg | gtgaaaacat | ggaagtcagc | atctacggcg | ctatcatgta | tgaagtcagg | 480 |
| tttacccatc | ttggccacat | cctcacatac | accgccncaa | aacaacgagt | t | 531 |

<210> SEQ ID NO 95
<211> LENGTH: 605
<212> TYPE: DNA
<213> ORGANISM: Homo sapien

<400> SEQUENCE: 95

| | | | | | |
|---|---|---|---|---|---|
| agatcaacct | ctgctggtca | ggaggaatgc | cttccttgtc | ttggatcttt | gctttgacgt | 60 |
| tctcgatagt | rwcaactkkr | ytsramskma | agkgyratgr | wmttksywgw | rasyktmwwm | 120 |
| rsgraraytt | agacayccm | cctcwgagac | gsagkaccar | gtgcagaggt | ggactctttc | 180 |
| tggatgttgt | agtcagacag | ggtgcgtcca | tcttccagct | gtttcccagc | aaagatcaac | 240 |
| ctctgctgat | caggagggat | gccttcctta | tcttggatct | tgccttgac | attctcgatg | 300 |
| gtgtcactgg | gctccacctc | gagggtgatg | gtcttaccag | tcagggtctt | cacgaagaty | 360 |
| tgcatcccac | ctctgagacg | gagcaccagg | tgcagggtrg | actctttctg | gatgttgtag | 420 |
| tcagacaggg | tgcgyccatc | ttccagctgc | tttccsagca | aagatcaacc | tctgctggtc | 480 |
| aggaggratg | ccttccttgt | cytggatctt | tgcyttgacr | ttctcratgg | tgtcactcgg | 540 |
| ctccacttcg | agagtgatgg | tcttaccagt | cagggtcttc | acgaagatct | gcatcccacc | 600 |
| tctaa | | | | | | 605 |

<210> SEQ ID NO 96
<211> LENGTH: 531
<212> TYPE: DNA
<213> ORGANISM: Homo sapien

<400> SEQUENCE: 96

| | | | | | |
|---|---|---|---|---|---|
| aagtcacaaa | cagacaaaga | ttattaccag | ctgcaagcta | tattagaagc | tgaacgaaga | 60 |
| gacagaggtc | atgattctga | gatgattgga | gaccttcaag | ctcgaattac | atctttacaa | 120 |
| gaggaggtga | agcatctcaa | acataatctc | gaaaagtgg | aaggagaaag | aaaagaggct | 180 |
| caagacatgc | ttaatcactc | agaaaaggaa | aagaataatt | tagagataga | tttaaactac | 240 |
| aaacttaaat | cattacaaca | acggttagaa | caagaggtaa | atgaacacaa | agtaaccaaa | 300 |
| gctcgtttaa | ctgacaaaca | tcaatctatt | gaagagcaa | agtctgtggc | aatgtgtgag | 360 |
| atggaaaaaa | agctgaaaga | agaaagagaa | gctcgagaga | aggctgaaaa | tcgggttgtt | 420 |
| cagattgaga | aacagtgttc | catgctagac | gttgatctga | agcaatctca | gcagaaacta | 480 |
| gaacatttga | ctggaaataa | agaaaggatg | gaggatgaag | ttaagaatct | a | 531 |

<210> SEQ ID NO 97
<211> LENGTH: 1017
<212> TYPE: DNA
<213> ORGANISM: Homo sapien
<220> FEATURE:
<221> NAME/KEY: misc_feature
<222> LOCATION: (1)...(1017)
<223> OTHER INFORMATION: n = A,T,C or G

<400> SEQUENCE: 97

| | | | | | |
|---|---|---|---|---|---|
| cgcctccacc | atgtccatca | gggtgaccca | gaagtcctac | aaggtgtcca | cctctggccc | 60 |
| ccgggccttc | agcagccgct | cctacacgag | tgggcccggt | tcccgcatca | gctcctcgag | 120 |
| cttctcccga | gtgggcagca | gcaactttcg | cggtggcctg | ggcggcggct | atggtggggc | 180 |
| cagcggcatg | ggaggcatca | ccgcagttac | ggtcaaccag | agcctgctga | ccccccttgt | 240 |
| cctggaggtg | gaccccaaca | tccaggccgt | gcgcacccag | gagaaggagc | agatcaagac | 300 |
| cctcaacaac | aagtttgcct | ccttcataga | caaggtacgg | ttcctggagc | agcagaacaa | 360 |
| gatgctggag | accaagtgga | gcctcctgca | gcagcagaag | acggctcgaa | gcaacatgga | 420 |
| caacatgttc | gagagctaca | tcaacarcct | taggcggcag | ctggagactc | tgggccagga | 480 |
| gaagctgaag | ctggaggcgg | agcttggcaa | catgcagggg | ctggtggagg | acttcaagaa | 540 |
| caagtatgag | gatgagatca | ataagcgtac | agagatggaa | aacgaatttg | tcctcatcaa | 600 |
| gaaggatgtg | gatgaagctt | acatgaacaa | ggtagagctg | gagtctcgcc | tggaagggct | 660 |
| gaccgacgag | atcaacttcc | tcaggcagct | gtatgaagag | gagatccggg | agctgcagtc | 720 |
| ccagatctcg | gacacatctg | tggtgctgtc | catggacaac | agccgctccc | tggacatgga | 780 |
| cagcatcatt | gctgaggtca | aggcacagta | cgaggatatt | gccaaccgca | gccgggctga | 840 |
| ggctgagagc | atgtaccagg | tcaagtatga | ggagctgcag | agcctggctg | gaagcacgg | 900 |
| ggatgacctg | cggcgcacaa | agactgagat | ctctgagatg | aacccggaac | atcagcccgg | 960 |
| ctncaggctg | agattgaggg | cctcaaaggc | cagangggctt | ncctggangn | ccgccat | 1017 |

<210> SEQ ID NO 98
<211> LENGTH: 561
<212> TYPE: DNA
<213> ORGANISM: Homo sapien

<400> SEQUENCE: 98

| | | | | | |
|---|---|---|---|---|---|
| cccggagcca | gccaacgagc | ggaaaatggc | agacaatttt | tcgctccatg | atgcgttatc | 60 |
| tgggtctgga | aacccaaacc | ctcaaggatg | gcctggcgca | tggggaacc | agcctgctgg | 120 |
| ggcaggggc | tacccagggg | cttcctatcc | tggggcctac | cccgggcagg | cacccccagg | 180 |
| ggcttatcct | ggacaggcac | ctccaggcgc | ctaccctgga | gcacctggag | cttatcccgg | 240 |
| agcacctgca | cctggagtct | acccagggcc | acccagcggc | cctggggcct | acccatcttc | 300 |
| tggacagcca | agtgccaccg | gagcctaccc | tgccactggc | ccctatggcg | ccctgctgg | 360 |
| gccactgatt | gtgcccttata | acctgccttt | gcctggggga | gtggtgcctc | gcatgctgat | 420 |
| aacaattctg | ggcacggtga | agcccaatgc | aaacagaatt | gctttagatt | tccaaagagg | 480 |
| gaatgatgtt | gccttccact | ttaacccacg | cttcaatgag | aacaacagga | gagtcattgg | 540 |
| ttgcaataca | aagctggata | a | | | | 561 |

<210> SEQ ID NO 99
<211> LENGTH: 636
<212> TYPE: DNA
<213> ORGANISM: Homo sapien

```
<400> SEQUENCE: 99
gggaatgcaa caactttatt gaaaggaaag tgcaatgaaa tttgttgaaa ccttaaaagg      60
ggaaacttag acaccccccc tcragcgmag kaccargtgc araggtggac tctttctgga     120
tgttgtagtc agacagggtr cgwccatctt ccagctgttt yccrgcaaag atcaacctct     180
gctgatcagg aggratgcct tccttatctt ggatctttgc cttgacattc tcgatggtgt     240
cactgggctc cacctcgagg gtgatggtct taccagtcag ggtcttcacg aagatytgca     300
tcccacctct gagacggagc accaggtgca gggtrgactc tttctggatg ttgtagtcag     360 acaggggtgcg yccatcttcc agctgctttc csagcaaaga tcaacctctg ctggtcagga    420
ggratgcctt ccttgtcytg gatctttgcy ttgacrttct caatggtgtc actcggctcc    480
acttcgagag tgatggtctt accagtcagg gtcttcacga agatctgcat cccacctcta    540
agacggagca ccaggtgcag ggtggactct ttctggatgg ttgtagtcag acagggtgcg    600
tccatcttcc agctgtttcc cagcaaagat caacct                              636

<210> SEQ ID NO 100
<211> LENGTH: 697
<212> TYPE: DNA
<213> ORGANISM: Homo sapien

<400> SEQUENCE: 100
aggttgatct ttgctgggaa acagctggaa gatggacgca ccctgtctga ctacaaccat      60
ccagaaagag tccaccctgc acctggtgct ccgtcttaga ggtgggatgc agatcttcgt     120
gaagaccctg actggtaaga ccatcactct cgaagtggag ccgagtgaca ccattgagaa     180
ygtcaargca aagatccarg acaaggaagg catycctcct gaccagcaga ggttgatctt     240
tgctsggaaa gcagctggaa gatggrcgca ccctgtctga ctacaacatc cagaaagagt     300
cyaccctgca cctggtgctc cgtctcagag gtgggatgca ratcttcgtg aagaccctga     360
ctggtaagac catcaccctc gaggtggagc ccagtgacac catcgagaat gtcaaggcaa     420
agatccaaga taaggaaggc atccctcctg atcagcagag gttgatcttt gctgggaaac     480
agctggaaga tggacgcacc ctgtctgact acaacatcca gaaagagtcc acctytgcac    540
ytggtmctbc gtctyagagg kgggrtgcaa atctwmgtkw agacactcac tkkyaagryy    600
atcamcmwtg akktcgakys castkwcact wtcrakaamg tyrwwgcawa gatccmagac    660
aaggaaggca ttcctcctga ccagcagagg ttgatct                              697

<210> SEQ ID NO 101
<211> LENGTH: 451
<212> TYPE: DNA
<213> ORGANISM: Homo sapien

<400> SEQUENCE: 101
atggagtctc actctgtcga ccaggctgga gcgctgtggt gcgatatcgg ctcactgcag      60
tctccacttc ctgggttcaa gcgatcctcc tgcctcagcc tcccgagtag ctgggactac     120
aggcaggcgt caccataatt tttgtatttt tagtagagac atggttttcgc catgttggct    180 gggctggtct cgaactcctg acctcaagtg atctgtcctg gcctcccaaa gtgttgggat     240
tacaggcgaa agccaacgct cccggccagg gaacaacttt agaatgaagg aaatatgcaa     300 agaacatca catcaaggat caattaatta ccatctatta attactatat gtgggtaatt      360
atgactattt cccaagcatt ctacgttgac tgcttgagaa gatgtttgtc ctgcatggtg     420
gagagtggag aagggccagg attcttaggt t                                    451
```

<210> SEQ ID NO 102
<211> LENGTH: 571
<212> TYPE: DNA
<213> ORGANISM: Homo sapien

<400> SEQUENCE: 102

| | | | | | |
|---|---|---|---|---|---|
| agcgcggtct | tccggcgcga | gaaagctgaa | ggtgatgtgg | ccgccctcaa | ccgacgcatc | 60 |
| cagctcgttg | aggaggagtt | ggacagggct | caggaacgac | tggccacggc | cctgcagaag | 120 |
| ctggaggagg | cagaaaaagc | tgcagatgag | agtgagagag | gaatgaaggt | gatagaaaac | 180 |
| cgggccatga | aggatgagga | gaagatggag | attcaggaga | tgcagctcaa | agaggccaag | 240 |
| cacattgcgg | aagaggctga | ccgcaaatac | gaggaggtag | ctcgtaagct | ggtcatcctg | 300 |
| gagggtgagc | tggagagggc | agaggagcgt | gcggaggtgt | ctgaactaaa | atgtggtgac | 360 |
| ctggaagaag | aactcaagaa | tgttactaac | aatctgaaat | ctctggaggc | tgcatctgaa | 420 |
| aagtattctg | aaaaggagga | caaatatgaa | gaagaaatta | aacttctgtc | tgacaaactg | 480 |
| aaagaggctg | agacccgtgc | tgaatttgca | gagagaacgg | ttgcaaaact | ggaaaagaca | 540 |
| attgatgacc | tggaagagaa | acttgcccag | c | | | 571 |

<210> SEQ ID NO 103
<211> LENGTH: 451
<212> TYPE: DNA
<213> ORGANISM: Homo sapien

<400> SEQUENCE: 103

| | | | | | |
|---|---|---|---|---|---|
| gtgcacaggt | cccatttatt | gtagaaaata | ataataatta | cagtgatgaa | tagctcttct | 60 |
| taaattacaa | aacagaaacc | acaaagaagg | aagaggaaaa | accccaggac | ttccaagggt | 120 |
| gaagctgtcc | cctcctccct | gccaccctcc | caggctcatt | agtgtccttg | gaaggggcag | 180 |
| aggactcaga | ggggatcagt | ctccaggggc | cctgggctga | agcgggtgag | gcagagagtc | 240 |
| ctgaggccac | agagctgggc | aacctgagcc | gcctctctgg | ccccctcccc | caccactgcc | 300 |
| caaacctgtt | tacagcacct | tcgcccctcc | cctctaaacc | cgtccatcca | ctctgcactt | 360 |
| cccaggcagg | tgggtgggcc | aggcctcagc | catactcctg | ggcgcgggtt | tcggtgagca | 420 |
| aggcacagtc | ccagaggtga | tatcaaggcc | t | | | 451 |

<210> SEQ ID NO 104
<211> LENGTH: 441
<212> TYPE: DNA
<213> ORGANISM: Homo sapien

<400> SEQUENCE: 104

| | | | | | |
|---|---|---|---|---|---|
| gcaaggaact | ggtctgctca | cacttgctgg | cttgcgcatc | aggactggct | ttatctcctg | 60 |
| actcacggtg | caaaggtgca | ctctgcgaac | gttaagtccg | tccccagcgc | ttggaatcct | 120 |
| acggccccca | cagccggatc | ccctcagcct | tccaggtcct | caactcccgt | ggacgctgaa | 180 |
| caatggcctc | catggggcta | caggtaatgg | gcatcgcgct | ggccgtcctg | ggctggctgg | 240 |
| ccgtcatgct | gtgctgcgcg | ctgcccatgt | ggcgcgtgac | ggccttcatc | ggcagcaaca | 300 |
| ttgtcacctc | gcagaccatc | tgggagggc | tatggatgaa | ctgcgtggtg | cagagcaccg | 360 |
| gccagatgca | gtgcaaggtg | tacgactcgc | tgctggcact | gccgcaggac | ctgcaggcgc | 420 |
| cccgcgccct | cgtcatcatc | a | | | | 441 |

<210> SEQ ID NO 105

```
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 105
tgcaaaaggg acacagggt tcaaaaataa aatttctct tccccctccc caaacctgta      60
ccccagctcc ccgaccacaa ccccttcct cccccgggga aagcaagaag gagcaggtgt     120
ggcatctgca gctgggaaga gagaggccgg ggaggtgccg agctcggtgc tggtctcttt    180
ccaaatataa atacntgtgt cagaactgga aaatcctcca gcacccacca cccaagcact    240
ctccgttttc tgccggtgtt tggagagggg cgggggggcag gggcgccagg caccggctgg   300
ctgcggtcta ctgcatccgc tgggtgtgca ccccgcgagc ctcctgctgc tcattgtaga    360
agagatgaca ctcggggtcc ccccggatgg tgggggctcc ctggatcagc ttcccggtgt    420
tggggttcac acaccagcac tccccacgct gcccgttcag agacatcttg cactgtttga    480
ggttgtacag gccatgcttg tcacagttg                                      509

<210> SEQ ID NO 106
<211> LENGTH: 571
<212> TYPE: DNA
<213> ORGANISM: Homo sapien

<400> SEQUENCE: 106
gggttggagg gactggttct ttatttcaaa aagcacttg tcaatattca gtatcaaaac     60
agttgcacta ttgatttctc tttctcccaa tcggccccaa agagaccaca taaaaggaga    120
gtacatttta agccaataag ctgcaggatg tacacctaac agacctccta gaaaccttac    180
cagaaaatgg ggactgggta gggaaggaaa cttaaaagat caacaaactg ccagcccacg    240
gactgcagag gctgtcacag ccagatgggg tggccagggt gccacaaacc caaagcaaag    300
tttcaaaata atataaaatt taaaagtttt tgtacataag ctattcaaga tttctccagc    360
actgactgat acaaagcaca attgagatgg cacttctaga gacagcagct tcaaacccag    420
aaaagggtga tgagatgagt ttcacatggc taaatcagtg gcaaaaacac agtcttcttt    480
cttctttct ttcaaggagg caggaaagca attaagtggt cacctcaaca taaggggac      540
atgatccatt ctgtaagcag ttgtgaaggg g                                   571

<210> SEQ ID NO 107
<211> LENGTH: 555
<212> TYPE: DNA
<213> ORGANISM: Homo sapien

<400> SEQUENCE: 107
caggaaccgg agcgcgagca gtagctgggt gggcaccatg gctgggatca ccaccatcga    60
ggcggtgaag cgcaagatcc aggttctgca gcagcaggca gatgatgcag aggagcgagc    120
tgagcgcctc cagcgagaag ttgagggaga aggcgggcc cggaacagg ctgaggctga     180
ggtggcctcc ttgaaccgta ggatccagct ggttgaagaa gagctggacc gtgctcagga    240
gcgcctggcc actgccctgc aaaagctgga agaagctgaa aaagctgctg atgagagtga    300
gagaggtatg aaggttattg aaaaccgggc cttaaaagat gaagaaaaga tggaactcca    360
ggaaatccaa ctcaaagaag ctaagcacat tgcagaagag gcagataggga agtatgaaga    420
ggtggctcgt aagttggtga tcattgaagg agacttggaa cgcacagagg aacgagctga    480
```

```
gctggcagag tcccgttgcc gagagatgga tgagcagatt agactgatgg accagaacct    540
gaagtgtctg agtgc                                                    555

<210> SEQ ID NO 108
<211> LENGTH: 541
<212> TYPE: DNA
<213> ORGANISM: Homo sapien

<400> SEQUENCE: 108
atctacgtca tcaatcaggc tggagacacc atgttcaatc gagctaagct gctcaatatt     60
ggctttcaag aggccttgaa ggactatgat tacaactgct ttgtgttcag tgatgtggac    120
ctcattccga tggacgaccg taatgcctac aggtgttttt cgcagccacg gcacatttct    180
gttgcaatgg acaagttcgg gtttagcctg ccatatgttc agtattttgg aggtgtctct    240
gctctcagta acaacagtt tcttgccatc aatggattcc ctaataatta ttggggttgg    300
ggaggagaag atgacgacat ttttaacaga ttagttcata aaggcatgtc tatatcacgt    360
ccaaatgctg tagtagggag gtgtcgaatg atccggcatt caagagacaa gaaaaatgag    420
cccaatcctc agaggtttga ccggatcgca catacaaagg aaacgatgcg cttcgatggt    480
ttgaactcac ttacctacaa ggtgttggat gtcagagata cccgttatat acccaaatca    540
c                                                                   541

<210> SEQ ID NO 109
<211> LENGTH: 411
<212> TYPE: DNA
<213> ORGANISM: Homo sapien

<400> SEQUENCE: 109
ctagacctct aattaaaagg cacaatcatg ctggagaatg aacagtctga ccccgagggc     60
cacagcgaat tttagggaag gaggcaaaga ggtgagaagg gaaaggaaag aaggaaggaa    120
ggagaacaat aagaactgga gacgttgggt gggtcaggga gtgtggtgga ggctcggaga    180
gatggtaaac aaacctgact gctatgagtt ttcaaccccca tagtctaggg ccatgagggc    240
gtcagttctt ggtggctgag ggtccttcca cccagcccac ctgggggagt ggagtgggga    300
gttctgccag gtaagcagat gttgtctccc aagttcctga cccagatgtc tgcaggata    360 acgctgacct gttccctcaa caagggacct gaaagtaatt ttgctctttta c           411

<210> SEQ ID NO 110
<211> LENGTH: 451
<212> TYPE: DNA
<213> ORGANISM: Homo sapien

<400> SEQUENCE: 110
ccgaattcaa gcgtcaacga tccytcccct accatcaaat caattggcca ccaatggtac     60
tgaacctacg agtacaccga ctacgggcgg actaatcttc aactcctaca tacttccccc    120
attattccta gaaccaggcg acctgcgact ccttgacgtt gacaatcgag tagtactccc    180
gattgaagcc cccattcgta taataattac atcacaagac gtcttgcact catgagctgt    240
ccccacatta ggcttaaaaa cagatgcaat tcccggacgt ctaagccaaa ccactttcac    300
cgctacacga ccgggggtat actacggtca atgctctgaa atctgtggag caaaccacag    360
tttcatgccc atcgtcctag aattaattcc cctaaaaatc tttgaaatag ggcccgtatt    420
taccctatag cacccctctc accccctcta g                                   451
```

<210> SEQ ID NO 111
<211> LENGTH: 541
<212> TYPE: DNA
<213> ORGANISM: Homo sapien

<400> SEQUENCE: 111

| | | | | | |
|---|---|---|---|---|---|
| gctcttcaca | cttttattgt | taattctctt | cacatggcag | atacagagct | gtcgtcttga | 60 |
| agaccaccac | tgaccaggaa | atgccacttt | tacaaaatca | tcccccettt | tcatgattgg | 120 |
| aacagttttc | ctgaccgtct | gggagcgttg | aagggtgacc | agcacatttg | cacatgcaaa | 180 |
| aaaggagtga | ccccaaggcc | tcaaccacac | ttcccagagc | tcaccatggg | ctgcaggtga | 240 |
| cttgccaggt | tgggggttcg | tgagctttcc | ttgctgctgc | ggtggggagg | ccctcaagaa | 300 |
| ctgagaggcc | ggggtatgct | tcatgagtgt | taacatttac | gggacaaaag | cgcatcatta | 360 |
| ggataaggaa | cagccacagc | acttcatgct | tgtgagggtt | agctgtagga | gcgggtgaaa | 420 |
| ggattccagt | ttatgaaaat | ttaaagcaaa | caacggtttt | tagctgggtg | gaaacagga | 480 |
| aaactgtgat | gtcggccaat | gaccaccatt | tttctgccca | tgtgaaggtc | cccatgaaac | 540 |
| c | | | | | | 541 |

<210> SEQ ID NO 112
<211> LENGTH: 521
<212> TYPE: DNA
<213> ORGANISM: Homo sapien

<400> SEQUENCE: 112

| | | | | | |
|---|---|---|---|---|---|
| caagcgcttg | gcgtttggac | ccagttcagt | gaggttcttg | ggttttgtgc | ctttggggat | 60 |
| tttggtttga | cccagggggtc | agccttagga | aggtcttcag | gaggaggccg | agttccccctt | 120 |
| cagtaccacc | cctctctccc | cactttccct | ctcccggcaa | catctctggg | aatcaacagc | 180 |
| atattgacac | gttggagccg | agcctgaaca | tgccctcgg | ccccagcaca | tggaaaaccc | 240 |
| ccttccttgc | ctaaggtgtc | tgagtttctg | gctcttgagg | catttccaga | cttgaaattc | 300 |
| tcatcagtcc | attgctcttg | agtctttgca | gagaacctca | gatcaggtgc | acctgggaga | 360 |
| aagactttgt | ccccacttac | agatctatct | cctcccttgg | gaagggcagg | gaatggggac | 420 |
| ggtgtatgga | ggggaaggga | tctcctgcgc | ccttcattgc | cacacttggt | gggaccatga | 480 |
| acatctttag | tgtctgagct | tctcaaatta | ctgcaatagg | a | | 521 |

<210> SEQ ID NO 113
<211> LENGTH: 568
<212> TYPE: DNA
<213> ORGANISM: Homo sapien

<400> SEQUENCE: 113

| | | | | | |
|---|---|---|---|---|---|
| agcgtcaaat | cagaatggaa | aagactcaaa | accatcatca | acaccaagat | caaaaggaca | 60 |
| agratccttc | aagaaacagg | aaaaaactcc | taaaacacca | aaaggaccta | gttctgtaga | 120 |
| agacattaaa | gcaaaaatgc | aagcaagtat | agaaaaaggt | ggttctcttc | ccaaagtgga | 180 |
| agccaaattc | atcaattatg | tgaagaattg | cttccggatg | actgaccaag | aggctattca | 240 |
| agatctctgg | cagtggagga | agtctcttta | agaaaatagt | ttaaacaatt | tgttaaaaaa | 300 |
| ttttccgtct | tatttcattt | ctgtaacagt | tgatatctgg | ctgtccttttt | tataatgcag | 360 |
| agtgagaact | ttccctaccg | tgtttgataa | atgttgtcca | ggttctattg | ccaagaatgt | 420 |
| gttgtccaaa | atgcctgttt | agttttttaaa | gatggaactc | cacccttttgc | ttggttttaa | 480 |
| gtatgtatgg | aatgttatga | taggacatag | tagtagcggt | ggtcagacat | ggaaatggtg | 540 |

```
ggsmgacaaa aatatacatg tgaaataa                                        568

<210> SEQ ID NO 114
<211> LENGTH: 483
<212> TYPE: DNA
<213> ORGANISM: Homo sapien

<400> SEQUENCE: 114
tccgaattcc aagcgaatta tggacaaacg attccttta gaggattact ttttcaatt      60 tcggttttag taatctaggc tttgcctgta aagaatacaa cgatggattt taaatactgt   120
ttgtggaatg tgtttaaagg attgattcta gaacctttgt atatttgata gtatttctaa   180 cttcattc tttactgttt gcagttaatg ttcatgttct gctatgcaat cgtttatatg     240
cacgtttctt taatttttt agattttcct ggatgtatag tttaaacaac aaaaagtcta    300
tttaaaactg tagcagtagt ttacagttct agcaaagagg aaagttgtgg ggttaaactt   360
tgtattttct ttcttataga ggcttctaaa aaggtatttt tatatgttct ttttaacaaa   420
tattgtgtac aacctttaaa acatcaatgt ttggatcaaa acaagaccca gcttattttc   480
tgc                                                                  483

<210> SEQ ID NO 115
<211> LENGTH: 521
<212> TYPE: DNA
<213> ORGANISM: Homo sapien

<400> SEQUENCE: 115
tgtggtggcg cgggctgagg tggaggccca ggactctgac cctgcccctg ccttcagcaa    60
ggcccccggc agcgccggcc actacgaact gccgtgggtt gaaaaatata ggccagtaaa   120
gctgaatgaa attgtcggga atgaagacac cgtgagcagg ctagaggtct ttgcaaggga   180
aggaaatgtg cccaacatca tcattgcggg ccctccagga accggcaaga ccacaagcat   240
tctgtgcttg gcccgggccc tgctgggccc agcactcaaa gatgccatgt ggaactcaa    300 tgcttcaaat gacaggggca ttgacgttgt gaggaataaa attaaaatgt ttgctcaaca   360
aaaagtcact cttcccaaag gccgacataa gatcatcatt ctggatgaag cagacagcat   420
gaccgacgga gcccagcaag ccttgaggag aaccatggaa atctactcta aaaccactcg   480 ttcgccttg cttgtaatgc ttcggataag atcatcgagc c                        521

<210> SEQ ID NO 116
<211> LENGTH: 501
<212> TYPE: DNA
<213> ORGANISM: Homo sapien

<400> SEQUENCE: 116 cttttgcaaag cttttatttc atgtctgcgg catggaatcc acctgcacat ggcatcttag    60
ctgtgaagga gaaagcagtg cacgagaagg aatgagtggg cggaaccaac ggcctccaca   120
agctgccttc cagcagcctg ccaaggccat ggcagagaga gactgcaaac aaacacaagc   180
aaacagagtc tcttcacagc tggagtctga agctcatag tggcatgtgt gaatctgaca    240
aaattaaaag tgtgcatagt ccattacatg cataaaacac taataataat cctgtttaca   300
cgtgactgca gcaggcaggt ccagctccac cactgccctc ctgccacatc acatcaagtg   360
ccatggttta gagggttttt catatgtaat tctttattc tgtaaaaggt aacaaaaatat   420 acagaacaaa actttcccctt tttaaaacta atgttacaaa tctgtattat cacttggata   480
```

```
taaatagtat ataagctgat c                                              501
```

<210> SEQ ID NO 117
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 117

```
caagggatat atgttgaggg tacrgrgtga cactgaacag atcacaaagc acgagaaaca     60
ttagttctct ccctccccag cgtctccttc gtctccctgg ttttccgatg tccacagagt    120
gagattgtcc ctaagtaact gcatgatcag agtgctgkct ttataagact cttcattcag    180
cgtatccaat tcagcaattg cttcatcaaa tgccgttttt gccaggctac aggccttttc    240
aggagagttt agaatctcat agtaaaagac tgagaaattt agtgccagac caagacgaat    300
tgggtgtgta ggctgcattn ctttcttact aatttcaaat gcttcctggt aagcctgctg    360
ggagttcgac acaagtggtt tgtttgttgc tccagatgcc acttcagaaa gatacctaaa    420
ataatctcct ttcattttca aagtagaaca c                                   451
```

<210> SEQ ID NO 118
<211> LENGTH: 501
<212> TYPE: DNA
<213> ORGANISM: Homo sapien

<400> SEQUENCE: 118

```
tccggagccg gggtagtcgc cgccgccgcc gccggtgcag ccactgcagg caccgctgcc     60
gccgcctgag tagtgggctt aggaaggaag aggtcatctc gctcggagct tcgctcggaa    120
gggtctttgt tccctgcagc cctcccacgg gaatgacaat ggataaaagt gagctggtac    180
agaaagccaa actcgctgag caggctgagc gatatgatga tatggctgca gccatgaagg    240
cagtcacaga acaggggcat gaactctcca acgaagagag aaatctgctc tctgttgcct    300
acaagaatgt ggtaaggccg cccgccgctc ttcctggcgt gtcatctcca gcattgagca    360
gaaaacagag aggaatgaga agaagcagca gatgggcaaa gagtaccgtg agaagataga    420
ggcagaactg caggacatct gcaatgatgt tctggagctt gttggacaaa tatcttattc    480
caatgctaca caacccagaa a                                              501
```

<210> SEQ ID NO 119
<211> LENGTH: 391
<212> TYPE: DNA
<213> ORGANISM: Homo sapien

<400> SEQUENCE: 119

```
aaaaagcagc argttcaaca caaatagaa atctcaaatg taggatagaa caaaaccaag      60
tgtgtgaggg gggaagcaac agcaaaagga agaaatgaga tgttgcaaaa agatggagg     120
agggttcccc tctcctctgg ggactgactc aaacactgat gtggcagtat acaccattcc    180
agagtcaggg gtgttcattc ttttttggga gtaagaaaag gtggggatta agaagacgtt    240
tctggaggct tagggaccaa ggctggtctc tttccccct cccaaccccc ttgatccctt     300
tctctgatca ggggaaagga gctcgaatga gggaggtaga gttggaaagg gaaaggattc    360
cacttgacag aatgggacag actccttccc a                                   391
```

<210> SEQ ID NO 120
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 120
tggcaatagc acagccatcc aggagctctt cargcgcatc tcggagcagt tcactgccat    60
gttccgccgg aaggccttcc tccactggta cacaggcgag ggcatggacg agatggagtt   120
caccgaggct gagagcaaca tgaacgacct cgtctctgag tatcaagcag taccaggatg   180
ccaccgcaga agaggaggag gatttcggtg aggaggccga agaggaggcc taaggcagag   240
cccccatcac ctcaggcttc tcagttccct tagccgtctt actcaactgc ccctttcctc   300
tccctcagaa tttgtgtttg ctgcctctat cttgttttt gttttttctt ctggggggt    360 ctagaacagt gcctggcaca tagtaggcgc tcaataaata cttggttgnt gaatgtctcc   420
t                                                                  421

<210> SEQ ID NO 121
<211> LENGTH: 206
<212> TYPE: DNA
<213> ORGANISM: Homo sapien

<400> SEQUENCE: 121
agctggcgct agggctcggt tgtgaaatac agcgtrgtca gcccttgcgc tcagtgtaga    60
aacccacgcc tgtaaggtcg gtcttcgtcc atctgctttt ttctgaaata cactaagagc   120
agccacaaaa ctgtaacctc aaggaaacca taaagcttgg agtgccttaa tttttaacca   180
gtttccaata aaacggttta ctacct                                       206

<210> SEQ ID NO 122
<211> LENGTH: 131
<212> TYPE: DNA
<213> ORGANISM: Homo sapien

<400> SEQUENCE: 122
ggagatgaag atgaggaagc tgagtcagct acgggcargc gggcagctga agatgatgag    60
gatgacgatg tcgataccaa gaagcagaag accgacgagg atgactagac agcaaaaaag   120
gaaaagttaa a                                                       131

<210> SEQ ID NO 123
<211> LENGTH: 231
<212> TYPE: DNA
<213> ORGANISM: Homo sapien
<220> FEATURE:
<221> NAME/KEY: misc_feature
<222> LOCATION: (1)...(231)
<223> OTHER INFORMATION: n = A,T,C or G

<400> SEQUENCE: 123
gatgaaaatt aaatacttaa attaatcaaa aggcactacg ataccaccta aaacctactg    60
cctcagtggc agtakgctaa kgaagatcaa gctacagsac atyatctaat atgaatgtta   120
gcaattacat akcargaagc atgtttgctt tccagaagac tatggnacaa tggtcattwg   180
ggcccaagag gatatttggc cnggaaagga tcaagataga tnaangtaaa g           231

<210> SEQ ID NO 124

```
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 124
gagtagcaac gcaaagcgct tggtattgag tctgtgggsg acttcggttc cggtctctgc      60
agcagccgtg atcgcttagt ggagtgctta gggtagttgg ccaggatgcc gaatatcaaa     120
atcttcagca ggcagctccc accaggactt atctcasaaa attgctgacc gcctgggcct    180
ggagctaggc aaggtggtga ctaagaaatt cagcaaccag agacctgtg tggaaattgg      240
tgaaagtgta ccgtggagag gatgtctaca ttgttcagag tggntgtggc gaaatcaatg     300
acaatttaat ggagcttttg atcatgatta atgcctgcaa gattgcttca gccagccggg     360
ttactgcagt catcccatgc ttcccttatg ccccggcagg ataagaaaga tnagagccgg    420
gccgccaatc tcagccaagc ttggtgcaaa tatgctatct gtagcagtgc agatcatatt   480
atcaccatgg acctacatgc ttctcaaatt canggcttttt t                        521

<210> SEQ ID NO 125
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 125
atgcaaaagg ggacacaggg ggttcaaaaa taaaaatttc tcttcccct ccccaaacct      60
gtaccccagc tccccgacca aaccccctt cctcccccgg ggaaagcaag aaggagcagg    120
tgtggcatct gcagctggga agagagaggc cggggaggtg ccgagctcgg tgctggtctc    180
tttccaaata taaatacgtg tgtcagaact ggaaaatcct ccagcaccca ccacccaagc   240
actctccgtt ttctgccggt gttttggagag gggcggnggg caggggcgcc aggcaccggc   300
tggctgcggt ctactgcatc cgctgggtgt gcaccccgcg a                        341

<210> SEQ ID NO 126
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 126
aggttggaga aggtcatgca ggtgcagatt gtccaggskc agccacaggg tcaagcccaa     60
caggcccaga gtggcactgg acagaccatg caggtgatgc agcagatcat cactaacaca    120
ggagagatcc agcagatccc ggtgcagctg aatgccggcc agctgcagta tatccgctta    180
gcccagcctg tatcaggcac tcaagttgtg cagggacaga tccagacact tgccaccaat   240
gctcaacaga ttacacagac agaggtccag caaggacagc agcagttcaa gccagttcac   300
aagatggaca gcagctctac cagatccagc aagtcaccat gcctgcgggc cangacctcg   360
ccagcccatg ttcatccagt caagccaacc agccttcna cgggcaggcc ccccaggtga   420
ccggcgactg aagggcctga gctggcaagg ccaangacac ccaacacaat ttttgccata   480
```

-continued cagcccccag gcaatgggca cagcctttct tcccagagga c     521

<210> SEQ ID NO 127
<211> LENGTH: 351
<212> TYPE: DNA
<213> ORGANISM: Homo sapien

<400> SEQUENCE: 127
tgagatttat tgcatttcat gcagcttgaa gtccatgcaa aggrgactag cacagttttt     60
aatgcattta aaaataaaa gggaggtggg cagcaaacac acaaagtcct agtttcctgg     120
gtccctggga gaaagagtg tggcaatgaa tccacccact ctccacaggg aataaatctg     180
tctcttaaat gcaaagaatg tttccatggc ctctggatgc aaatacacag agctctgggg     240
tcagagcaag ggatggggag aggaccacga gtgaaaaagc agctacacac attcacctaa     300
ttccatctga gggcaagaac aacgtggcaa gtcttggggg tagcagctgt t     351

<210> SEQ ID NO 128
<211> LENGTH: 521
<212> TYPE: DNA
<213> ORGANISM: Homo sapien

<400> SEQUENCE: 128
tccagacatg ctcctgtcct aggcggggag caggaaccag acctgctatg ggaagcagaa     60
agagttaagg gaaggtttcc tttcattcct gttccttctc ttttgctttt gaacagtttt     120
taaatatact aatagctaag tcatttgcca gccaggtccc ggtgaacagt agagaacaag     180
gagcttgcta agaattaatt ttgctgtttt tcaccccatt caaacagagc tgccctgttc     240
cctgatggag ttccattcct gccagggcac ggctgagtaa cacgaagcca ttcaagaaag     300
gcgggtgtga atcactgcc accccatgga cagacccctc actcttcctt cttagccgca     360
gcgctactta ataaatatat ttatactttg aaattatgat aaccgatttt tcccatgcgg     420
catcctaagg gcacttgcca gctcttatcc ggacagtcaa gcactgttgt tggacaacag     480
ataaaggaaa agaaaagaa gaaaacaacc gcaacttctg t     521

<210> SEQ ID NO 129
<211> LENGTH: 521
<212> TYPE: DNA
<213> ORGANISM: Homo sapien

<400> SEQUENCE: 129
tgagacggac cactggcctg gtccccctc atktgctgtc gtaggacctg acatgaaacg     60
cagatctagt ggcagagagg aagatgatga ggaacttctg agacgtcggc agcttcaaga     120
agagcaatta atgaagctta actcaggcct gggacagttg atcttgaaag aagagatgga     180
gaaagagagc cggaaaggt catctctgtt agccagtcgc tacgattctc ccatcaactc     240
agcttcacat attccatcat ctaaaactgc atctctccct ggctatggaa gaaatgggct     300
tcaccggcct gtttctaccg acttcgctca gtataacagc tatggggatg tcagcggggg     360
agtgcgagat taccagacac ttccagatgg ccacatgcct gcaatgagaa tggaccgagg     420
agtgtctatg cccaacatgt tggaaccaaa gatatttcca tatgaaatgc tcatggtgac     480
caacagaggg ccgaaaccaa atctcagaga ggtggacaga a     521

<210> SEQ ID NO 130
<211> LENGTH: 270
<212> TYPE: DNA

<213> ORGANISM: Homo sapien

<400> SEQUENCE: 130

| tcactttatt tttcttgtat aaaaaccta tgttgtagcc acagctggag cctgagtccg | 60 |
| ctgcacggag actctggtgt gggtcttgac gaggtggtca gtgaactcct gatagggaga | 120 |
| cttggtgaat acagtctcct tccagaggtc gggggtcagg tagctgtagg tcttagaaat | 180 |
| ggcatcaaag gtggccttgg cgaagttgcc caggtggca gtgcagcccc gggctgaggt | 240 |
| gtagcagtca tcgataccag ccatcatgag | 270 |

<210> SEQ ID NO 131
<211> LENGTH: 341
<212> TYPE: DNA
<213> ORGANISM: Homo sapien

<400> SEQUENCE: 131

| ctggaatata gacccgtgat cgacaaaact ttgaacgagg ctgactgtgc caccgtcccg | 60 |
| ccagccattc gctcctactg atgagacaag atgtggtgat gacagaatca gcttttgtaa | 120 |
| ttatgtataa tagctcatgc atgtgtccat gtcataactg tcttcatacg cttctgcact | 180 |
| ctggggaaga aggagtacat tgaagggaga ttggcaccta gtggctggga gcttgccagg | 240 |
| aacccagtgg ccagggagcg tggcacttac ctttgtccct tgcttcattc ttgtgagatg | 300 |
| ataaaactgg gcacagctct taaataaaat ataaatgaac a | 341 |

<210> SEQ ID NO 132
<211> LENGTH: 844
<212> TYPE: DNA
<213> ORGANISM: Homo sapien
<220> FEATURE:
<221> NAME/KEY: misc_feature
<222> LOCATION: (1)...(844)
<223> OTHER INFORMATION: n = A,T,C or G

<400> SEQUENCE: 132

| tgaatgggga ggagctgacc caggaaatgg agcttgngga gaccaggcct gcagggatg | 60 |
| gaaccttcca gaagtgggca tctgtggtgg tgcctcttgg gaaggagcag aagtacacat | 120 |
| gccatgtgga acatgagggg ctgcctgagc ccctcaccct gagatggggc aaggaggagc | 180 |
| ctccttcatc caccaagact aacacagtaa tcattgctgt tccggttgtc cttggagctg | 240 |
| tggtcatcct tggagctgtg atggcttttg tgatgaagag gaggagaaac acaggtggaa | 300 |
| aaggaggga ctatgctctg gctccaggct cccagagctc tgatatgtct ctcccagatt | 360 |
| gtaaagtgtg aagacagctg cctggtgtgg acttggtgac agacaatgtc ttcacacatc | 420 |
| tcctgtgaca tccagagacc tcagttctct ttagtcaagt gtctgatgtt ccctgtgagt | 480 |
| ctgcgggctc aaagtgaaga actgtggagc ccagtccacc cctgcacacc aggaccctat | 540 |
| ccctgcactg ccctgtgttc ccttccacag ccaaccttgc tgctccagcc aaacattggt | 600 |
| ggacatctgc agcctgtcag ctccatgcta ccctgacctt caactcctca cttccacact | 660 |
| gagaataata atttgaatgt gggtggctgg agagatggct cagcgctgac tgctcttcca | 720 |
| aaggtcctga gttcaaatcc cagcaaccac atggtggctc acaaccatct gtaatgggat | 780 |
| ctaataccct cttctgcagt gtctgaagac asctacagtg tacttacata taataataaa | 840 |
| taag | 844 |

<210> SEQ ID NO 133
<211> LENGTH: 601

```
<212> TYPE: DNA
<213> ORGANISM: Homo sapien

<400> SEQUENCE: 133
ggccgggcgc gcgcgccccc gccacacgca cgccgggcgt gccagtttat aaagggagag      60
agcaagcagc gagtcttgaa gctctgtttg gtgctttgga tccatttcca tcggtcctta     120
cagccgctcg tcagactcca gcagccaaga tggtgaagca gatcgagagc aagactgctt     180
ttcaggaagc cttggacgct gcaggtgata aacttgtagt agttgacttc tcagccacgt     240
ggtgtgggcc ttgcaaaatg atcaagcctt tctttcattc cctctctgaa aagtattcca     300
acgtgatatt ccttgaagta gatgtggatg actgtcagga tgttgcttca gagtgtgaag     360
tcaaatgcat gccaacattc cagtttttta agaagggaca aaaggtgggt gaattttctg     420
gagccaataa ggaaaagctt gaagccacca ttaatgaatt agtctaatca tgttttctga     480
aaatataacc agccattggc tatttaaaac ttgtaatttt tttaatttac aaaaatataa     540
aatatgaaga cataaacccm gttgccatct gcgtgacaat aaaacattaa tgctaacact     600
t                                                                     601

<210> SEQ ID NO 134
<211> LENGTH: 421
<212> TYPE: DNA
<213> ORGANISM: Homo sapien

<400> SEQUENCE: 134
tcacataaga aatttaagca agttacrcta tcttaaaaaa cacaacgaat gcattttaat      60
agagaaaccc ttccctccct ccacctccct cccccaccct cctcatgaat taagaatcta     120
agagaagaag taaccataaa accaagtttt gtggaatcca tcatccagag tgcttacatg     180
gtgattaggt taatattgcc ttcttacaaa atttctattt taaaaaaaat tataaccttg     240
attgcttatt acaaaaaaat tcagtacaaa agttcaatat attgaaaaat gcttttcccc     300
tccctcacag caccgtttta tatatagcag agaataatga agagattgct agtctagatg     360
gggcaatctt caaattacac caagacgcac agtggtttat ttaccctccc cttctcataa     420
g                                                                     421

<210> SEQ ID NO 135
<211> LENGTH: 511
<212> TYPE: DNA
<213> ORGANISM: Homo sapien

<400> SEQUENCE: 135
ggaaaggatt caagaattag aggacttgct tgctrragaa aaagacaact ctcgtcgcat      60
gctgacagac aaagagagag agatggcgga ataagggat caaatgcagc aacagctgaa     120
tgactatgaa cagcttcttg atgtaaagtt agccctggac atggaaatca gtgcttacag     180
gaaactctta gaaggcgaag aagagaggtt gaagctgtct ccaagccctt cttccgtgt      240
gacagtatcc cgagcatcct caagtcgtag tgtaccgtac aactagagga agcggaaga     300
gggttgatgt ggaagaatca gaggcgaagt agtagtgtta gcatctctca ttccgcctca     360
accactggaa atgtttgcat cgaagaaatt gatgttgatg ggaaatttat cccgcttgaa     420
gaacacttct gaacaggatc aaccaatggg aaggcttggg agatgatcag aaaaattgga     480
gacacatcag tcagttataa atatacctca a                                    511

<210> SEQ ID NO 136
```

<211> LENGTH: 341
<212> TYPE: DNA
<213> ORGANISM: Homo sapien

<400> SEQUENCE: 136

```
catgggtttc accaggttgg ccaggctgct cttgaactsc tgacctcagg tgatccaccc      60
gcctcggcct cccaaagtgc tgggattaca ggcgtgagcc accacgcccg gcccccaaag     120
ctgtttcttt tgtctttagc gtaaagctct cctgccatgc agtatctaca taactgacgt     180
gactgccagc aagctcagtc actccgtggt cttttctct  ttccagttct tctctctctc     240
ttcaagttct gcctcagtga aagctgcagg tccccagtta agtgatcagg tgagggttct     300
ttgaacctgg ttctatcagt cgaattaatc cttcatgatg g                         341
```

<210> SEQ ID NO 137
<211> LENGTH: 551
<212> TYPE: DNA
<213> ORGANISM: Homo sapien

<400> SEQUENCE: 137

```
gatgtgttgg accctctgtg tcaaaaaaaa cctcacaaag aatcccctgc tcattacaga      60
agaagatgca tttaaaatat gggttatttt caacttttta tctgaggaca agtatccatt     120
aattattgtg tcagaagaga ttgaatacct gcttaagaag cttacagaag ctatgggagg     180
aggttggcag caagaacaat tgaacatta  taaaatcaac tttgatgaca gtaaaaatgg     240
cctttctgca tgggaactta ttgagcttat tggaaatgga cagtttagca aaggcatgga     300
ccggcagact gtgtctatgg caattaatga agtctttaat gaacttatat tagatgtgtt     360
aaagcagggt tacatgatga aaaagggcca cagacgaaaa aactggactg aaagatggtt     420
tgtactaaaa cccaacataa tttcttacta tgtgagtgag gatctgaagg ataagaaagg     480
agacattctc ttggatgaaa attgctgtgt agaagtcctt gcctgacaaa agatggaaag     540
aaatgccttt t                                                          551
```

<210> SEQ ID NO 138
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 138

```
gactggttct ttatttcaaa aagacacttg tcaatattca gtrtcaaaac agttgcacta      60
ttgatttctc tttctcccaa tcggcccaa  agagaccaca taaaggaga  gtacatttta     120
agccaataag ctgcaggatg tacacctaac agacctccta gaaaccttac cagaaaatgg     180
ggactgggta gggaaggaaa cttaaaagat caacaaactg ccagcccacg gactgcagag     240
gctgtcacag ccagatgggg tggccagggt gccacaaacc caaagcaaag tttcaaaata     300
atataaaatt taaaaagttt tgtacataag ctattcaaga tttctccagc actgactgat     360
acaaagcaca attgagatgg cacttctaga gacagcagct tcaaacccag aaaagggtga     420
tgagatgaag tttcacatgg ctaaatcagt ggcaaaaaca cagtcttctt tctttctttc     480
tttcaaggan gcaggaaagc aattaagtgg tcaccttaac ataaggggga c              531
```

<210> SEQ ID NO 139
<211> LENGTH: 521

```
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 139
tgggtgggca ccatggctgg gatcaccacc atcgaggcgg tgaagcgcaa gatccaggtt      60
ctgcagcagc aggcagatga tgcagaggag cgagctgagc gcctccagcg agaagttgag     120
ggagaaaggc gggcccggga acaggctgag gctgaggtgg cctccttgaa ccgtaggatc     180
cagctggttg aagaagagct ggaccgtgct caggagcgcc tggccactgc cctgcaaaag     240
ctggaagaag ctgaaaaagc tgctgatgag agtgagagag tatgaaggt tattgaaaac      300 cgggccttaa aagatgaaga aaagatggaa ctccaggaaa tccaactcaa agaagctaag     360
cacattgcag aagaggcaga taggaagtat gaagaggtgg ctcgtaagtt ggtgatcatt     420
gaaggagact tggaaccgca cagaaggaac gagcttgagc ttggcaaaag tcccgttgcc     480
cagagatggg atgaaccaga ttagactgat ggaccanaac c                         521

<210> SEQ ID NO 140
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 140
aggggcngcg ggtgcgtggg ccactgggtg accgacttag cctggccaga ctctcagcac      60
ctggaagcgc cccgagagtg acagcgtgag gctgggaggg aggacttggc ttgagcttgt     120
taaactctgc tctgagcctc cttgtcgcct gcatttagat ggctcccgca agaagggtg      180 gcgagaagaa aaagggccgt tctgccatca acgaagtggt aacccgagaa tacaccatca     240
acattcacaa gcgcatccat ggagtgggct tcaagaagcg tgcacctcgg gcactcaaag     300
agattcggaa atttgccatg aaggagatgg gaactccaga tgtgcgcatt gacaccaggc     360
tcaacaaagc tgtctgggcc aaaggaataa ggaatgtgcc ataccgaatc cggtgtgcgg     420
ctgtccagaa aacgtaatga ggatgaagat tcaccaaata agctatatac tttggttacc     480
tatgtacctg ttaccacttt caaaaatcta cagacagtca atgtggatga aactaatcg      540 ctgatcgtca gatcaaataa agttataaaa t                                    571

<210> SEQ ID NO 141
<211> LENGTH: 531
<212> TYPE: DNA
<213> ORGANISM: Homo sapien

<400> SEQUENCE: 141
tcgggagcca cacttggccc tcttcctctc caaagsgcca gaacctcctt ctctttggag      60
aatggggagg cctcttggag acacagaggg tttcaccttg gatgacctct agagaaattg     120
cccaagaagc ccaccttctg gtcccaacct gcagacccca cagcagtcag ttggtcaggc     180
cctgctgtag aaggtcactt ggctccattg cctgcttcca accaatgggc aggagagaag     240
gcctttattt ctcgcccacc cattcctcct gtaccagcac ctcgttttc agtcagtgtt      300 gtccagcaac ggtaccgttt acacagtcac ctcagacaca ccatttcacc tcccttgcca     360
```

```
agctgttagc cttagagtga ttgcagtgaa cactgtttac acaccgtgaa tccattccca    420
tcagtccatt ccagttggca ccagcctgaa ccatttggta cctggtgtta actggagtcc    480
tgtttacaag gtggagtcgg ggcttgctga cttctcttca tttgagggca c             531
```

<210> SEQ ID NO 142
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 142

```
acctagacag aaggtgggtg agggaggact ggtaggaggc tgaggcaatt ccttggtagt     60
ttgtcctgaa accctactgg agaagtcagc atgaggcacc tactgagaga agtgcccaga    120
aactgctgac tgcatctgtt aagagttaac agtaaagagg tagaagtgtg tttctgaatc    180
agagtggaag cgtctcaagg gtcccacagt ggaggtccct gagctacctc ccttccgtga    240
gtgggaagag tgaagcccat gaagaactga gatgaagcaa ggatgggtt  cctgggctcc    300 aggcaagggc tgtgctctct gcagcaggga gccccacgag tcagaagaaa agaactaatc    360
atttgttgca agaaaccttg cccggatact agccgaaaac tggaggcggn ggtgggggca    420
caggaaagtg gaagtgattt gatggagagc agagaagcct atgcacagtg gccgagtcca    480
cttgtaaagt g                                                         491
```

<210> SEQ ID NO 143
<211> LENGTH: 515
<212> TYPE: DNA
<213> ORGANISM: Homo sapien

<400> SEQUENCE: 143

```
ttcaagcaat tgtaacaagt atatgtagat tagagtgagc aaaatcatat acaattttca     60
tttccagttg ctattttcca aattgttctg taatgtcgtt aaaattactt aaaaattaac    120
aaagccaaaa attatattta tgacaagaaa gccatcccta cattaatctt acttttccac    180
tcaccggccc atctccttcc tcttttttcct aactatgcca ttaaaactgt tctactgggc    240
cgggcgtgtg gctcatgcct gtaatcccag catttggga  ggccaaggca ggcggatcat    300
gaggtcaaga gattgagacc atcctggcca acatggtgaa accccgcctc gactaagaat    360
acaaaaatta gctgggcatg gtggcgcatg cctgtagtct cagctactcg ggaggctgag    420
gcagaagaat cgcttgaacc cgggaggcag aggatgcagt gagccccgat cgcgccactg    480
cactctagcc tgggcgacag actgagactc tgctc                               515
```

<210> SEQ ID NO 144
<211> LENGTH: 340
<212> TYPE: DNA
<213> ORGANISM: Homo sapien

<400> SEQUENCE: 144

```
tgtgccagtc tacaggccta tcagcagcga ctccttcagc aacagatggg gtcccctgtt     60
cagcccaacc ccatgagccc ccagcagcat atgctcccaa atcaggccca gtccccacac    120
ctacaaggcc agcagatccc taattctctc tccaatcaag tgcgctctcc ccagcctgtc    180
ccttctccac ggccacagtc ccagccccce cactccagtc cttccccaag gatgcagcct    240
cagccttctc cacaccacgt ttccccacag acaagttccc cacatcctgg actggtagtt    300
```

```
gcccaggcca accccatgga acaagggcat tttgccagcc                    340
```

<210> SEQ ID NO 145
<211> LENGTH: 630
<212> TYPE: DNA
<213> ORGANISM: Homo sapien

<400> SEQUENCE: 145

```
tgtaaaaact tgtttttaat tttgtataaa ataaaggtgg tccatgccca cggggctgt    60
aggaaatcca agcagaccag ctgggtgggg gggatgtagc ctacctcggg ggactgtctg   120
tcctcaaaac gggctgagaa ggcccgtcag gggcccaggt cccacagaga ggcctgggat   180
actcccccaa cccgaggggc agactgggca gtggggagcc cccatcgtgc cccagaggtg   240
gccacaggct gaaggagggg cctgaggcac cgcagcctgc aaccccagg gctgcagtcc    300
actaactttt tacagaataa aggaacatg gggatgggga aaaaagcacc aggtcaggca    360
gggcccgagg gccccagatc ccaggagggc caggactcag gatgccagca ccaccctagc   420
agctcccaca gctcctggca caggaggccg ccacggattg gcacaggccg ctgctggcca   480
tcacgccaca tttggagaac ttgtcccgac agaggtcagc tcggaggagc tcctcgtggg   540
cacacactgt acgaacacag atctccttgt taatgacgta cacacggcgg aggctgcggg   600
gacagggcac gggaggtctc agccccactt                                    630
```

<210> SEQ ID NO 146
<211> LENGTH: 521
<212> TYPE: DNA
<213> ORGANISM: Homo sapien

<400> SEQUENCE: 146

```
atggctgctg gatttaggtg gtaatagggg ctgtgggcca taaatctgaa gccttgagaa    60
ccttgggtct ggagagccat gaagagggaa ggaaaagagg gcaagtcctg aacctaacca   120
atgacctgat ggattgctcg accaagacac agaagtgaag tctgtgtctg tgcacttccc   180
acagactgga gttttttggtg ctgaatagag ccagttgcta aaaaattggg ggtttggtga   240
agaaatctga ttgttgtgtg tattcaatgt gtgattttaa aaataaacag caacaacaat   300
aaaaaccctg actggctgtt ttttccctgt attctttaca actattttttt gaccctctga   360
aaattattat acttcaccta aatggaagac tgctgtgttt gtggaaattt tgtaattttt   420
taatttattt tattctctct ccttttttatt ttgcctgcag aatccgttga gagactaata   480
aggcttaata tttaattgat ttgtttaata tgtatataaa t                        521
```

<210> SEQ ID NO 147
<211> LENGTH: 562
<212> TYPE: DNA
<213> ORGANISM: Homo sapien

<400> SEQUENCE: 147

```
ggcatgcgag cgcactcggc ggacgcaagg gcggcgggga gcacacggag cactgcaggc    60
gccgggttgg gacagcgtct tcgctgctgc tggatagtcg tgttttcggg gatcgaggat   120
actcaccaga aaccgaaaat gccgaaacca atcaatgtcc gagttaccac catggatgca   180
gagctggagt ttgcaatcca gccaaataca actggaaaac agcttttttga tcaggtggta   240
aagactatcg gcctccggga agtgtggtac tttggcctcc actatgtgga taataaagga   300
tttcctacct ggctgaagct ggataagaag gtgtctgccc aggaggtcag gaaggagaat   360
```

| | |
|---|---|
| cccctccagt tcaagttccg ggccaaagtt ctaccctgaa gatgtggctg aggagctcat | 420 |
| ccaggacatc acccagaaac ttttcttcct tcaagtgaag gaaggaatcc ttagcgatga | 480 |
| gatctactgc cccccttgar actgccgtgc tcttggggtc ctacgcttgt gcatgccaag | 540 |
| tttggggact accaccaaga ag | 562 |

<210> SEQ ID NO 148
<211> LENGTH: 820
<212> TYPE: DNA
<213> ORGANISM: Homo sapien

<400> SEQUENCE: 148

| | |
|---|---|
| gaaggagtcg ggatactcag cattgatgca ccccaatttc aaagcggcat tcttcggcag | 60 |
| gtctctggga caatctctag ggtcactacc tggaaactcg ttagggtaca actgaatgct | 120 |
| gaaaggaaag aacacctgca gaaccggaca gaaattcacc ccggcgatca gctgattgat | 180 |
| ctcggtcgac cagaagtcat ggctaaagat gacgaggacg ttgtcaattc cctgggcttt | 240 |
| tcgaagtgag tccagcagca gtctgaggta ttcgggccgg ttatgcacct ggaccaccag | 300 |
| caccagctcc cggggggccc aggtgccagc cttatctaca ttcctcaggg tctgatcaaa | 360 |
| gttcagctgg tacaccaggg accggtaccg cagcgtcagg ttgtccgctc gggctggggg | 420 |
| accgccggga ccagggaagc cgccgacacg ttggagaccc tgcggatgcc acagccaca | 480 |
| gagggtggt ccccaccgcg gccgccggca ccccgcgcgg gttcggcgtc cagcaacggt | 540 |
| ggggcgaggg cctcgttctt cctttgtcgc ccattgctgc tccagaggac gaagccgcag | 600 |
| gcggccacca cgagcgtcag gattagcacc ttccgtttgt agatgcggaa cctcatggtc | 660 |
| tccaggccg ggagcgcagc tacagctcga gcgtcggcgc cgccgctagg agccgcggct | 720 |
| cggcttcgtc tccgtcctct ccattcagca ccacgggtcc cggaaaaagc tcagccscgg | 780 |
| tcccaaccgc accctagctt cgttacctgc gcctcgcttg | 820 |

<210> SEQ ID NO 149
<211> LENGTH: 501
<212> TYPE: DNA
<213> ORGANISM: Homo sapien

<400> SEQUENCE: 149

| | |
|---|---|
| cagatttta tttgcagtcg tcactggggc cgtttcttgc tgcttatttg tctgctagcc | 60 |
| tgctcttcca gctgcatggc caggcgcaag gccttgatga catctcgcag ggctgagaaa | 120 |
| tgcttggctt gctgggccag agcagattcc gctttgttca caaaggtctc caggtcatag | 180 |
| tctggctgct cggtcatctc agagagctca agccagtctg gtccttgctg tatgatctcc | 240 |
| ttgagctctt ccatagcctt ctcctccagc tccctgatct gagtcatggc ttcgttaaag | 300 |
| ctggacatct gggaagacag ttcctcctct tccttggata aattgcctgg aatcagcgcc | 360 |
| ccgttagagc aggcttccat ctcttctgtt tccatttgaa tcaactgctc tccactgggc | 420 |
| ccactgtggg ggctcagctc cttgaccctg ctgcatatct taagggtgtt taaaggatat | 480 |
| tcacaggagc ttatgcctgg t | 501 |

<210> SEQ ID NO 150
<211> LENGTH: 511
<212> TYPE: DNA
<213> ORGANISM: Homo sapien
<220> FEATURE:
<221> NAME/KEY: misc_feature
<222> LOCATION: (1)...(511)
<223> OTHER INFORMATION: n = A,T,C or G -continued

<400> SEQUENCE: 150

```
ctcctcttgg tacatgaacc caagttgaaa gtggacttaa caaagtatct ggagaaccaa      60
gcattctgct ttgactttgc atttgatgaa acagcttcga atgaagttgt ctacaggttc     120
acagcaaggc cactggtaca gacaatcttt gaaggtggaa aagcaacttg ttttgcatat     180
ggccagacag gaagtggcaa gacacatact atgggcggag acctctctgg gaaagcccag     240
aatgcatcca agggatcta tgccatggcc ttccgggacg tcttcttctg aagaatcaac     300
cctgctaccg gaagttgggc ctggaagtct atgtgacatt cttcgagatc tacaatggga     360
agctgtttga cctgctcaac aagaaggcca agcttgcgcg tgctggaaga cggcaagcaa     420
caggtgcaag tggtgggggc ttgcaggaac atcggntaa ctctgcttga tgatggcant     480
caagatgatc gacatgggca gcgcctgcag a                                    511
```

<210> SEQ ID NO 151
<211> LENGTH: 566
<212> TYPE: DNA
<213> ORGANISM: Homo sapien

<400> SEQUENCE: 151

```
tcccgaattc aagcgacaaa ttggawagtg aaatggaaga tgcctatcat gaacatcagg      60
caaatctttt gcgccaagat ctgatgagac acaggaaga attaagacgc atggaagaac     120
ttcacaatca gaaatgcag aaacgtaaag aaatgcaatt gaggcaagag gaggaacgac     180
gtagaagaga ggaagagatg atgattcgtc aacgtgagat ggaagaacaa atgaggcgcc     240
aaagagagga aagttacagc cgaatgggct acatggatcc acgggaaaga gacatgcgaa     300
tgggtggcgg aggagcaatg aacatggag atccctatgg ttcaggaggc cagaaatttc     360
cacctctagg aggtggtggt ggcataggtt atgaagctaa tcctggcgtt ccaccagcaa     420
ccatgagtgg ttccatgatg ggaagtgaca tgcgtactga gcgctttggg cagggaggtg     480
cggggcctgt gggtggacag ggtcctagag aatgggcc tggaactcca gcaggatatg     540
gtagagggag agaagagtac gaaggc                                          566
```

<210> SEQ ID NO 152
<211> LENGTH: 518
<212> TYPE: DNA
<213> ORGANISM: Homo sapien

<400> SEQUENCE: 152

```
ttcgtgaaga ccctgactgg taagaccatc actctcgaag tggagcccga gtgacaccat      60
tgagaatgtc aaggcaaaga tccaagacaa ggaaggcatc cctcctgacc agcakaggtt     120
gatctttgct gggaaacagc tggaagatgg acgcaccctg tctgactaca acatccagaa     180
agagtccacc ctgcacctgg tgctccgtct cagaggtggg atgcaaatct tcgtgaagac     240
cctgactggt aagaccatca ccctcgaggt ggagcccagt gacaccatcg agaatgtcaa     300
ggcaaagatc caagataagg aaggcatccc tcctgatcag cagaggttga tctttgctgg     360
gaaacagctg gaagatggac gcaccctgtc tgactacaac atccagaaag agtccactct     420
gcacttggtc ctgcgcttga ggggggggtgt ctaagtttcc ccttttaagg tttcaacaaa     480
tttcattgca ctttcctttc aataaagttg ttgcattc                             518
```

<210> SEQ ID NO 153
<211> LENGTH: 542
<212> TYPE: DNA

<213> ORGANISM: Homo sapien

<400> SEQUENCE: 153

```
gcgcgggtgc gtgggccact gggtgaccga cttagcctgg ccagactctc agcacctgga    60
agcgccccga gagtgacagc gtgaggctgg gagggaggac ttggcttgag cttgttaaac   120
tctgctctga gcctccttgt cgcctgcatt tagatggctc ccgcaaagaa gggtggcgag   180
aagaaaaagg gccgttctgc catcaacgaa gtggtaaccc gagaatacac catcaacatt   240
cacaagcgca tccatggagt gggcttcaag aagcgtgcac ctcgggcact caaagagatt   300
cggaaatttg ccatgaagga gatgggaact ccagatgtgc gcattgacac caggctcaac   360
aaagctgtct gggccaaagg aataaggaat gtgccatacc gaatccgtgt gcggctgtcc   420
agaaaacgta atgaggatga agattcacca aataagctat atactttggt tacctatgta   480
cctgttacca ctttcaaaaa tctacagaca gtcaatgtgg atgagaacta atcgctgatc   540
gt                                                                  542
```

<210> SEQ ID NO 154
<211> LENGTH: 411
<212> TYPE: DNA
<213> ORGANISM: Homo sapien

<400> SEQUENCE: 154

```
aattctttat ttaaatcaac aaactcatct tcctcaagcc ccagaccatg gtaggcagcc    60
ctccctctcc atcccctcac ccaccccctt agccacagtg aagggaatgg aaaatgagaa   120
gccacgaggg cccctgccag ggaaggctgc cccagatgtg tggtgagcac agtcagtgca   180
gctgtggctg gggcagcagc tgccacaggc tcctccctat aaattaagtt cctgcagcca   240
cagctgtggg agaagcatac ttgtagaagc aaggccagtc cagcatcaga aggcagaggc   300
agcatcagtg actcccagcc atggaatgaa cggaggacac agagctcaga gacagaacag   360
gccaggggga agaaggagag acagaatagg ccagggcatg gcggtgaggg a            411
```

<210> SEQ ID NO 155
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 155

```
tgatgaatct gggtgggctg gcagtagccc gagatgatgg gctcttctct ggggatccca    60
actggttccc taagaaatcc aaggagaatc ctcggaactt ctcggataac cagctgcaag   120
agggcaagaa cgtgatcggg ttacagatgg gcaccaaccg cggggcgtct cangcaggca   180
tgactggcta cgggatgcca cgccagatcc tctgatccca ccccaggcct tgcccctgcc   240
ctcccacgaa tggttaatat atatgtagat atatatttta gcagtgacat tcccagagag   300
ccccagagct ctcaagctcc tttctgtcag ggtgggggt tcaagcctgt cctgtcacct   360
ctgaagtgcc tgctggcatc ctctccccca tgcttactaa tacattccct tccccatagc   420
c                                                                   421
```

<210> SEQ ID NO 156
<211> LENGTH: 670
<212> TYPE: DNA
<213> ORGANISM: Homo sapien

<400> SEQUENCE: 156

```
agcggagctc cctcccctgg tggctacaac ccacacacgc caggctcagg catcgagcag      60
aactccagcg actgggtaac cactgacatt caggtgaagg tgcgggacac ctacctggat     120
acacaggtgg tgggacagac aggtgtcatc cgcagtgtca cgggggggcat gtgctctgtg     180
tacctgaagg acagtgagaa ggttgtcagc atttccagtg agcacctgga gcctatcacc     240
cccaccaaga caacaaggt gaaagtgatc ctgggcgagg atcgggaagc cacgggcgtc       300
ctactgagca ttgatggtga ggatggcatt gtccgtatgg accttgatga gcagctcaag     360
atcctcaacc tccgcttcct ggggaagctc ctggaagcct gaagcaggca gggccggtgg     420
acttcgtcgg atgaagagtg atcctccttc cttccctggc ccttggctgt gacacaagat     480
cctcctgcag ggctaggcgg attgttctgg atttccttt gttttccctt ttaggtttcc     540
atcttttccc tccctggtgc tcattggaat ctgagtagag tctgggggag ggtccccacc     600
ttcctgtacc tcctccccac agcttgcttt tgttgtaccg tctttcaata aaagaagct     660
gtttggtcta                                                             670
```

<210> SEQ ID NO 157
<211> LENGTH: 421
<212> TYPE: DNA
<213> ORGANISM: Homo sapien

<400> SEQUENCE: 157

```
ggttcacagc actgctgctt gtgtgttgcc ggccaggaat tccaggctca caaggctatc      60
ttagcagctc gttctccggt ttttagtgcc atgtttgaac atgaaatgga ggagagcaaa     120
aagaatcgag ttgaaatcaa tgatgtggag cctgaagttt ttaaggaaat gatgtgcttc     180
atttacacgg ggaaggctcc aaacctcgac aaaatggctg atgatttgct ggcagctgct     240
gacaagtatg ccctggagcg cttaaaggtc atgtgtgagg atgccctctg cagtaacctg     300
tccgtggaga acgctgcaga aattctcatc ctggccgacc tccacagtgc agatcagttg     360
aaaactcagg cagtggattt catcaactat catgcttcgg atgtcttgga gacctcttgg     420
g                                                                      421
```

<210> SEQ ID NO 158
<211> LENGTH: 321
<212> TYPE: DNA
<213> ORGANISM: Homo sapien

<400> SEQUENCE: 158

```
tcgtagccat ttttctgctt ctttggagaa tgacgccaca ctgactgctc attgtcgttg      60
gttccatgcc aattggtgaa atagaacctc atccggtagt ggagccggag ggacatcttg     120
tcatcaacgg tgatggtgcg atttggagca taccagagct tggtgttctc gccatacagg     180
gcaaagaggt tgtgacaaag aggagagata cggcatgcct gtgcagccct gatgcacagt     240
tcctctgctg tgtactctcc actgcccagc cggaggggct ccctgtccga cagatagaag     300
atcacttcca cccctggctt g                                                321
```

<210> SEQ ID NO 159
<211> LENGTH: 596
<212> TYPE: DNA
<213> ORGANISM: Homo sapien

<400> SEQUENCE: 159

| | | | | |
|---|---|---|---|---|
| tggcacactg | ctcttaagaa | actatgawga | tctgagattt | tttgtgtat gttttgact | 60
| cttttgagtg | gtaatcatat | gtgtctttat | agatgtacat | acctccttgc acaaatggag | 120
| gggaattcat | tttcatcact | gggagtgtcc | ttagtgtata | aaaaccatgc tggtatatgg | 180
| cttcaagttg | taaaaatgaa | agtgacttta | aagaaaata | ggggatggtc caggatctcc | 240
| actgataaga | ctgtttttaa | gtaacttaag | gacctttggg | tctacaagta tatgtgaaaa | 300
| aaatgagact | tactgggtga | ggaaattcat | tgtttaaaga | tggtcgtgtg tgtgtgtgtg | 360
| tgtgtgtgtg | ttgtgttgtg | tttgttttt | taagggaggg | aatttattat ttaccgttgc | 420
| ttgaaattac | tgkgtaaaata | tatgtytgat | aatgatttgc | tytttgvcma ctaaaattag | 480
| gvctgtataa | gtwctaratg | cmtccctggg | kgttgatytt | ccmagatatt gatgatamcc | 540
| cttaaaattg | taaccygcct | tttcccttt | gctytcmatt | aaagtctatt cmaaag | 596

<210> SEQ ID NO 160
<211> LENGTH: 515
<212> TYPE: DNA
<213> ORGANISM: Homo sapien

<400> SEQUENCE: 160

| | | | | |
|---|---|---|---|---|
| gggggtaggc | tctttattag | acggttattg | ctgtactaca | gggtcagagt gcagtgtaag | 60
| cagtgtcaga | ggcccgcgtt | cagcccaaga | atgtggattt | tctctcccta ttgatcacag | 120
| tgggtgggtt | tcttcagaaa | agcccagag | gcagggacca | gtgagctcca aggttagaag | 180
| tggaactgga | aggcttcagt | cacatgctgc | ttccacgctt | ccaggctggg cagcaaggag | 240
| gagatgccca | tgacgtgcca | ggtctcccca | tctgacacca | gtgaagtctg gtaggacagc | 300
| agccgcacgc | ctgcctctgc | caggaggcca | atcatggtag | gcagcattgc agggtcagag | 360
| gtctgagtcc | ggaataggag | caggggcagg | tccctgcgga | gaggcacttc tggcctgaag | 420
| acagctccat | tgagcccctg | cagtacaggy | gtagtgcctt | ggaccaagcc cacagcctgg | 480
| taagggcgc | ctgccagggc | cacggccagg | aggca | | 515

<210> SEQ ID NO 161
<211> LENGTH: 936
<212> TYPE: DNA
<213> ORGANISM: Homo sapien

<400> SEQUENCE: 161

| | | | | |
|---|---|---|---|---|
| taatttctta | gtcgtttgga | atccttaagc | atgcaaaagc | tttgaacaga agggttcaca | 60
| aaggaaccag | ggttgtctta | tggcatccag | ttaagccaga | gctgggaatg cctctgggtc | 120
| atccacatca | ggagcagaag | cacttgactt | gtcggtcctg | ctgccacggt ttgggcgccc | 180
| accacgccca | cgtccacctc | gtcctcccct | gccgccacgt | cctgggcggc caaggtctcc | 240
| aaaattgatc | tccagctgag | acgttatatc | atttgctggc | ttccggaaat gatggtccat | 300
| aaccgaatct | tcagcatgag | cctcttcact | cttgattta | tgaagaacaa atcccttctt | 360
| ccactgccca | tcagcacctt | catttggttt | tcggatatta | aattctactt ttgcccggtc | 420
| cttattttga | atagccttcc | actcatccaa | agtcatctct | tttggaccct cctcttttac | 480
| ctcttcaact | tcattctcct | tattttcagt | gtctgccact | ggatgatgtt cttcaccttc | 540
| aggtgtttcc | tcagtcacat | ttgattgatc | caagtcagtt | aattcgtctt tgacagttcc | 600
| ccagttgtga | gatccgctac | ctccacgttt | gtcctcgtgc | ttcaggccag atctatcact | 660
| tccactatgc | ctatcaaatt | cacgtttgcc | acgagaatca | aatccatctc ctcggcccat | 720
| tccacgtcca | cggccccctc | gacctcttcc | aagaccacca | cgacctcgaa taggtcggtc | 780

```
aataatcggt ctatcaactg aaaattcgcc tccttcaccc ttttcttcaa gtggcttttc      840
gaatcttcgt tcacgaggtg gtcgcctttc tggtcttcta tcaattattt tcccttcacc      900
ctgaagttgt tgatcaggtc ttcttccaac tcgtgc                                936
```

<210> SEQ ID NO 162
<211> LENGTH: 950
<212> TYPE: DNA
<213> ORGANISM: Homo sapien

<400> SEQUENCE: 162

```
aagcggatgg acctgagtca gccgaatcct agcccttcc cttgggcctg ctgtggtgct       60
cgacatcagt gacagacgga agcagcagac catcaaggct acgggaggcc cggggcgctt     120
gcgaagatga agtttggctg cctctccttc cggcagcctt atgctggctt tgtcttaaat     180
ggaatcaaga ctgtggagac gcgctggcgt cctctgctga gcagccagcg gaactgtacc     240
atcgccgtcc acattgctca cagggactgg gaaggcgatg cctgtcggga gctgctggtg     300
gagagactcg ggatgactcc tgctcagatt caggccttgc tcaggaaagg ggaaaagttt     360
ggtcgaggag tgatagcggg actcgttgac attggggaaa ctttgcaatg ccccgaagac     420
ttaactcccg atgaggttgt ggaactagaa aatcaagctg cactgaccaa cctgaagcag     480
aagtacctga ctgtgatttc aaaccccagg tggttactgg agcccatacc taggaaagga     540
ggcaaggatg tattccaggt agacatccca gagcacctga tccctttggg gcatgaagtg     600
tgacaagtgt gggctcctga aaggaatgtt ccrgagaaac cagctaaatc atggcacctt     660
caatttgcca tcgtgacgca gacctgtata aattaggtta aagatgaatt tccactgctt     720
tggagagtcc cacccactaa gcactgtgca tgtaaacagg ttccttgct cagatgaagg     780 aagtaggggg tggggctttc cttgtgtgat gcctccttag gcacacaggc aatgtctcaa     840
gtactttgac cttagggtag aaggcaaagc tgccagtaaa tgtctcagca ttgctgctaa     900
ttttggtcct gctagtttct ggattgtaca aataaatgtg ttgtagatga                950
```

<210> SEQ ID NO 163
<211> LENGTH: 475
<212> TYPE: DNA
<213> ORGANISM: Homo sapien
<220> FEATURE:
<221> NAME/KEY: misc_feature
<222> LOCATION: (1)...(475)
<223> OTHER INFORMATION: n = A,T,C or G

<400> SEQUENCE: 163

```
tcgagcggcc gcccgggcag gtgtcggagt ccagcacggg aggcgtggtc ttgtagttgt       60
tctccggctg cccattgctc tcccactcca cggcgatgtc gctgggatag aagcctttga     120
ccaggcaggt caggctgacc tggttcttgg tcatctcctc ccgggatggg ggcagggtgt     180
acacctgtgg ttctcggggc tgccctttgg ctttggagat ggttttctcg atgggggctg     240
ggagggcttt gttggagacc ttgcacttgt actccttgcc attcaaccag tcctggtgca     300
ngacggtgag gacgctnacc acacggtacg ngctggtgta ctgctcctcc cgcggctttg     360
tcttggcatt atgcacctcc acgccgtcca cgtaccaatt gaacttgacc tcagggtctt     420
cgtggctcac gtccaccacc acgcatgtaa cctcaaanct cggncgcgan cacgc           475
```

<210> SEQ ID NO 164
<211> LENGTH: 476
<212> TYPE: DNA

<213> ORGANISM: Homo sapien

<400> SEQUENCE: 164

| | | | | | |
|---|---|---|---|---|---|
| agcgtggtcg | cggccgaggt | ctgaggttac | atgcgtggtg | gtggacgtga | gccacgaaga | 60 |
| ccctgaggtc | aagttcaact | ggtacgtgga | cggcgtggag | gtgcataatg | ccaagacaaa | 120 |
| gccgcgggag | gagcagtaca | acagcacgta | ccgtgtggtc | agcgtcctca | ccgtcctgca | 180 |
| ccaggactgg | ctgaatggca | aggagtacaa | gtgcaaggtc | tccaacaaag | ccctcccagc | 240 |
| ccccatcgag | aaaaccatct | ccaaagccaa | agggcagccc | cgagaaccac | aggtgtacac | 300 |
| cctgccccca | tcccgggagg | agatgaccaa | gaaccaggtc | agcctgacct | gcctggtcaa | 360 |
| aggcttctat | cccagcgaca | tcgcccgtgg | agtgggagag | caatgggcag | ccggagaaca | 420 |
| actacaagac | cacgcctccc | gtgctggact | ccgacacctg | ccgggcggcc | gctcga | 476 |

<210> SEQ ID NO 165
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 165

| | | | | | |
|---|---|---|---|---|---|
| agcgtggttn | cggccgaggt | cccaaccaag | gctgcancct | ggatgccatc | aaagtcttct | 60 |
| gcaacatgga | gactggtgag | acctgcgtgt | accccactca | gcccagtgtg | cccagaaga | 120 |
| actggtacat | cagcaagaac | cccaaggaca | agaggcatgt | ctggttcggc | gagagcatga | 180 |
| ccgatggatt | ccagttcgag | tatggcggcc | agggctccga | ccctgccgat | gtggacctgc | 240 |
| ccgggcggnc | gctcga | | | | | 256 |

<210> SEQ ID NO 166
<211> LENGTH: 332
<212> TYPE: DNA
<213> ORGANISM: Homo sapien

<400> SEQUENCE: 166

| | | | | | |
|---|---|---|---|---|---|
| agcgtggtcg | cggccgaggt | caagaacccc | gcccgcacct | gccgtgacct | caagatgtgc | 60 |
| cactctgact | ggaagagtgg | agagtactgg | attgacccca | accaaggctg | caacctggat | 120 |
| gccatcaaag | tcttctgcaa | catggagact | ggtgagacct | gcgtgtaccc | cactcagccc | 180 |
| agtgtggccc | agaagaactg | gtacatcagc | aagaacccca | aggacaagag | gcatgtctgg | 240 |
| ttcggcgaga | gcatgaccga | tggattccag | ttcgagtatg | cggccaggg | ctccgaccct | 300 |
| gccgatgtgg | acctgcccgg | gcggccgctc | ga | | | 332 |

<210> SEQ ID NO 167
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 167

| | | | | | |
|---|---|---|---|---|---|
| tcgagcggtc | gcccgggcag | gtccacatcg | gcagggtcgg | agccctggcc | gccatactcg | 60 |
| aactggaatc | catcggncat | gctctcgccg | aaccagacat | gcctcttgnc | cttgggttc | 120 |
| ttgctgatgt | accagntctt | ctgggccaca | ctgggctgag | tggggtacac | gcaggtctca | 180 |

```
ccantctcca tgttgcanaa gactttgatg gcatccaggt tgcagccttg gttggggtca    240
atccagtact ctccactctt ccagacagag tggcacatct tgaggtcacg gcaggtgcgg    300
gcggggttct tgacctcggt cgcgaccacg ct                                  332
```

<210> SEQ ID NO 168
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 168

```
tcgagcggcc gcccgggcag gtcctcctca gagcggtagc tgttcttatt gccccggcag    60
cctccataga tnaagttatt gcangagttc ctctccacgt caaagtacca gcgtgggaag   120
gatgcacggc aaggcccagt gactgcgttg gcggtgcagt attcttcata gttgaacata   180
tcgctggagt ggacttcaga atcctgcctt ctgggagcac ttgggacaga ggaatccgct   240
gcattcctgc tggtggacct cggccgcgac cacgct                             276
```

<210> SEQ ID NO 169
<211> LENGTH: 276
<212> TYPE: DNA
<213> ORGANISM: Homo sapien

<400> SEQUENCE: 169

```
agcgtggtcg cggccgaggt ccaccagcag gaatgcagcg gattcctctg tcccaagtgc    60
tcccagaagg caggattctg aagaccactc cagcgatatg ttcaactatg aagaatactg   120
caccgccaac gcagtcactg ggccttgccg tgcatccttc ccacgctggt actttgacgt   180
ggagaggaac tcctgcaata acttcatcta tggaggctgc cggggcaata agaacagcta   240
ccgctctgag gaggacctgc ccgggcggcc gctcga                             276
```

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170

```
tcgagcggcc gcccgggcag gtccacatcg gcagggtcgg agccctggcc gccatactcg    60
aactggaatc catcggtcat gctctcgccg aaccagacat gcctcttgtc cttggggttc   120
ttgctgatgt accagttctt ctgggccaca ctgggctgag tggggtacac gcaggtctca   180
ccagtctcca tgttgcagaa gactttgatg gcatccaggt tgcagccttg gttggggtca   240
atccagtact ctccactctt ccagccagaa tggcacatct tgaggtcacg gcangtgcgg   300
gcggggttct tgacctcggc cgcgaccacg ct                                 332
```

<210> SEQ ID NO 171
<211> LENGTH: 333
<212> TYPE: DNA
<213> ORGANISM: Homo sapien

<400> SEQUENCE: 171

```
agcgtggtcg cggccgaggt caagaaaccc cgcccgcacc tgccgtgacc tcaagatgtg    60
ccactctggc tggaagagtg gagagtactg gattgacccc aaccaaggct gcaacctgga   120
tgccatcaaa gtcttctgca acatggagac tggtgagacc tgcgtgtacc ccactcagcc   180
cagtgtggcc cagaagaact ggtacatcag caagaacccc aaggacaaga ggcatgtctg   240
gctcggcgag agcatgaccg atggattcca gttcgagtat ggcggccagg gctccgaccc   300
tgccgatgtg gacctgcccg gcggccgct cga                                  333

<210> SEQ ID NO 172
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 172
agcgtggtcg cggccgaggt cctgtcagag tggcactggt agaagntcca ggaaccctga    60
actgtaaggg ttcttcatca gtgccaacag gatgacatga aatgatgtac tcagaagtgt   120
cctgnaatgg ggcccatgan atggttgnct gagagagagc ttcttgtcct acattcggcg   180
ggtatggtct tggcctatgc cttatggggg tggccgttgn gggcggtgng gtccgcctaa   240
aaccatgttc ctcaaagatc atttgttgcc caacactggg ttgctgacca naagtgccag   300
gaagctgaat accatttcca gtgtcatacc cagggtgggt gacgaaaggg gtcttttgaa   360
ctgtggaagg aacatccaag atctctgntc catgaagatt ggggtgtgga agggttacca   420
gttggggaag ctcgctgtct ttttccttcc aatcanggge tcgctcttct gaatattctt   480
cagggcaatg acataaattg tatattcggt tcccggttcc aggccag                 527

<210> SEQ ID NO 173
<211> LENGTH: 635
<212> TYPE: DNA
<213> ORGANISM: Homo sapien
<220> FEATURE:
<221> NAME/KEY: misc_feature
<222> LOCATION: (1)...(635)
<223> OTHER INFORMATION: n = A,T,C or G

<400> SEQUENCE: 173
tcgagcggcc gcccgggcag gtccaccaca cccaattcct tgctggtatc atggcagccg    60
ccacgtgcca ggattaccgg ctacatcatc aagtatgaga agcctgggtc tcctcccaga   120
gaagtggtcc ctcggccccg ccctggtgtc acagaggcta ctattactgg cctggaaccg   180
ggaaccgaat atacaattta tgtcattgcc ctgaagaata atcagaagag cgagcccctg   240
attggaagga aaaagacaga cgagcttccc caactggtaa cccttccaca ccccaatctt   300 catgaccag agatcttgga tgttccttcc acagttcaaa agacccctt cgtcacccac    360 cctgggtatg acactggaaa tggtattcag cttcctggca cttctggtca gcaacccagt   420
gttgggcaac aaatgatctt tgangaacat ggntttaggc ggaccacacc ggccacaacg   480
ggcaccccca taaggcatag gccaagaaca tacccgncga atgtaggaca agaagctctn   540
tctcanacaa ncatctcatg ggccccattc cangacactt ctgagtacat canttcatgg   600
catcctggtg gcactgataa aaaccttac agtta                               635

<210> SEQ ID NO 174
<211> LENGTH: 572
```

```
<212> TYPE: DNA
<213> ORGANISM: Homo sapien
<220> FEATURE:
<221> NAME/KEY: misc_feature
<222> LOCATION: (1)...(572)
<223> OTHER INFORMATION: n = A,T,C or G

<400> SEQUENCE: 174
agcgtggtcg cgggcgaggt cctgtcagag tggcactggt agaagttcca ggaaccctga      60
actgtaaggg ttcttcatca gtgccaacag gatgacatga aatgatgtac tcagaagtgt     120
cctggaatgg ggcccatgag atggttgtct gagagagagc ttcttgtcct acattcggcg     180
ggtatggtct tggcctatgc cttatggggg tggccgttgt gggcggtgtg gtccgcctaa     240
aaccatgttc ctcaaagatc atttgttgcc caacactggg ttgctgacca gaagtgccag     300
gaagctgaat accatttcca gtgtcatacc cagggtgggt gacgaaaggg gtcttttgaa     360
ctgtggaagg aacatccaag atctctggtc catgaagatt ggggtgtgga agggttacca     420
gttggggaag ctcgtctgtc tttttccttc caatcanggg ctcgctcttc tgattattct     480
tcagggcaat gacataaatt gtatattcgg ntcccgggtn cagccaataa taataaccct     540
ctgtgacacc anggcggggc cgaagganca ct                                   572

<210> SEQ ID NO 175
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 175
agcgtggtcg cggccgaggt cctcaccaga ggtaccacct acaacatcat agtggaggca      60
ctgaaagacc agcagaggca taaggttcgg gaagaggttg ttaccgtggg caactctgtc     120
aacgaaggct tgaaccaacc tacggatgac tcgtgctttg accctacac agtttcccat     180 tatgccgttg gagatgagtg ggaacgaatg tctgaatcag gctttaaact gttgtgccag     240
tgcttangct ttggaagtgg tcatttcaga tgtgattcat ctagatggtg ccatgacaat     300
ggtgtgaact acaagattgg agagaagtgg gaccgtcagg gagaaaatgg acctgcccgg     360
gcggccgctc ga                                                         372

<210> SEQ ID NO 176
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 176
tcgagcggcc gcccgggcag gtccattttc tccctgacgg tcccacttct ctccaatctt      60
gtagttcaca ccattgtcat ggcaccatct agatgaatca catctgaaat gaccacttcc     120
aaagcctaag cactggcaca acagtttaaa gcctgattca gacattcgtt cccactcatc     180
tccaacggca taatgggaaa ctgtgtaggg gtcaaagcac gagtcatccg taggttggtt     240
caagccttcg ntgacagagt tgcccacggt acaacctct tccgaacct tatgcctctg     300 ctggtctttc agtgcctcca ctatgatgtt gtaggtggta cctctggtga ggacctcggc     360
```

```
cgcgaccacg ct                                                         372
```

<210> SEQ ID NO 177
<211> LENGTH: 269
<212> TYPE: DNA
<213> ORGANISM: Homo sapien
<220> FEATURE:
<221> NAME/KEY: misc_feature
<222> LOCATION: (1)...(269)
<223> OTHER INFORMATION: n = A,T,C or G

<400> SEQUENCE: 177

```
agcgtggccg cggccgaggt ccattggctg gaacggcatc aacttggaag ccagtgatcg     60
tctcagcctt ggttctccag ctaatggtga tggnggtctc agtagcatct gtcacacgag    120
cccttcttgg tgggctgaca ttctccagag tggtgacaac accctgagct ggtctgcttg    180
tcaaagtgtc cttaagagca tagacactca cttcatattt ggcgnccacc ataagtcctg    240
atacaaccac ggaatgacct gtcaggaac                                      269
```

<210> SEQ ID NO 178
<211> LENGTH: 529
<212> TYPE: DNA
<213> ORGANISM: Homo sapien

<400> SEQUENCE: 178

```
tcgagcggcc gcccgggcag gtcctcagac cgggttctga gtacacagtc agtgtggttg     60
ccttgcacga tgatatggag agccagcccc tgattggaac ccagtccaca gctattcctg    120
caccaactga cctgaagttc actcaggtca cacccacaag cctgagcgcc cagtggacac    180
cacccaatgt tcagctcact ggatatcgag tgcgggtgac ccccaaggag aagaccggac    240
caatgaaaga aatcaacctt gctcctgaca gctcatccgt ggttgtatca ggacttatgg    300
cggccaccaa atatgaagtg agtgtctatg ctcttaagga cactttgaca agcagaccag    360
ctcagggtgt tgtcaccact ctggagaatg tcagcccacc aagaagggct cgtgtgacag    420
atgctactga gaccaccatc accattagct ggagaaccaa gactgagacg atcactggct    480
tccaagttga tgccgttcca gccaatggac ctcggccgcg accacgctt                529
```

<210> SEQ ID NO 179
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 179

```
agcgtggtcg cggccgaggt ctggccgaac tgccagtgta cagggaagat gtacatgtta     60
tagntcttct cgaagtcccg ggccagcagc tccacgggt ggtctcctgc ctccaggcgc     120
ttctcattct catggatctt cttcacccgc agcttctgct tctcagtcag aaggttgttg    180
tcctcatccc tctcatacag ggtgaccagg acgttcttga gccagtcccg catgcgcagg    240 ggaattcgg tcagctcaga gtccaggcaa gggggatgt atttgcaagg cccgatgtag     300
tccaagtgga gcttgtggcc cttcttggtg ccctccaagg tgcactttgt ggcaaagaag    360
tggcaggaag agtcgaaggt cttgttgtca ttgctgcaca ccttctcaaa ctcgccaatg    420
ggggctgggc agacctgccc gggcggccgc tcga                                454
```

<210> SEQ ID NO 180
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 180

```
tcgagcggcc gcccgggcag gtctgcccag cccccattgg cgagtttgag aaggngtgca    60
gcaatgacaa caagaccttc gactcttcct gccacttctt tgccacaaag tgcaccctgg   120
agggcaccaa gaagggccac aagctccacc tggactacat cgggccttgc aaatacatcc   180
cccccttgcct ggactctgag ctgaccgaat tccccctgcg catgcgggac tggctcaaga   240
acgtcctggt caccctgtat gagagggatg aggacaacaa ccttctgact gagaagcana   300
agctgcgggt gaagaanatc catgagaatg anaagcgcct gnaggcanga gaccaccccg   360
tggagctgct ggcccgggac ttcgagaaga actataacat gtacatcttc cctgtacact   420
ggcagttcgg ccagacctcg gccgcgacca cgct                               454
```

<210> SEQ ID NO 181
<211> LENGTH: 102
<212> TYPE: DNA
<213> ORGANISM: Homo sapien
<220> FEATURE:
<221> NAME/KEY: misc_feature
<222> LOCATION: (1)...(102)
<223> OTHER INFORMATION: n = A,T,C or G

<400> SEQUENCE: 181

```
agcgtggntg cggacgacgc ccacaaagcc attgtatgta gttttanttc agctgcaaan    60
aataccncca gcatccacct tactaaccag catatgcaga ca                      102
```

<210> SEQ ID NO 182
<211> LENGTH: 337
<212> TYPE: DNA
<213> ORGANISM: Homo sapien
<220> FEATURE:
<221> NAME/KEY: misc_feature
<222> LOCATION: (1)...(337)
<223> OTHER INFORMATION: n = A,T,C or G

<400> SEQUENCE: 182

```
tcgagcggtc gcccgggcag gtctgggcgg atagcaccgg gcatattttg gaatggatga    60
ggtctggcac cctgagcagc ccagcgagga cttggtctta gttgagcaat ttggctagga   120
ggatagtatg cagcacggtt ctgagtctgt gggatagctg ccatgaagna acctgaagga   180
ggcgctggct ggtangggtt gattacaggg ctgggaacag ctcgtacact tgccattctc   240
tgcatatact ggntagtgag gcgagcctgg cgctcttctt tgcgctgagc taaagctaca   300
tacaatggct ttgnggacct cggccgcgac cacgctt                            337
```

<210> SEQ ID NO 183
<211> LENGTH: 374
<212> TYPE: DNA
<213> ORGANISM: Homo sapien

<400> SEQUENCE: 183

```
tcgagcggcc gcccgggcag gtccattttc tccctgacgg tcccacttct ctccaatctt    60
gtagttcaca ccattgtcat gacaccatct agatgaatca catctgaaat gaccacttcc   120
```

```
aaagcctaag cactggcaca acagtttaaa gcctgattca gacattcgtt cccactcatc      180
tccaacggca taatgggaaa ctgtgtaggg gtcaaagcac gagtcatccg taggttggtt      240
caagccttcg ttgacagaag ttgcccacgg taacaacctc ttcccgaacc ttatgcctct      300
gctggtcttt caagtgcctc cactatgatg ttgtaggtgg cacctctggt gaggacctcg      360
gccgcgacca cgct                                                        374
```

<210> SEQ ID NO 184
<211> LENGTH: 375
<212> TYPE: DNA
<213> ORGANISM: Homo sapien
<220> FEATURE:
<221> NAME/KEY: misc_feature
<222> LOCATION: (1)...(375)
<223> OTHER INFORMATION: n = A,T,C or G

<400> SEQUENCE: 184

```
agcgtggttt gcggccgagg tcctcaccan aggtgccacc tacaacatca tagtggaggc      60
actgaaagac cagcagaggc ataaggttcg ggaagaggtt gttaccgtgg gcaactctgt      120
caacgaaggc ttgaaccaac ctacggatga ctcgtgcttt gaccectaca cagnttccca    180 ttatgccgtt ggagatgagt gggaacgaat gtctgaatca ggctttaaac tgttgtgcca      240
gtgcttangc tttggaagtg gtcatttcag atgtgattca tctanatggt gtcatgacaa      300
tggtgngaac tacaagattg gagagaagtg gnaccgtcag ggganaaaat ggacctgccc      360
gggcggcncg ctcga                                                       375
```

<210> SEQ ID NO 185
<211> LENGTH: 148
<212> TYPE: DNA
<213> ORGANISM: Homo sapien
<220> FEATURE:
<221> NAME/KEY: misc_feature
<222> LOCATION: (1)...(148)
<223> OTHER INFORMATION: n = A,T,C or G

<400> SEQUENCE: 185

```
agcgtggtcg cggccgaggt ctggcttnct gctcangtga ttatcctgaa ccatccaggc      60
caaataagcg ccggctatgc ccctgnattg gattgccaca cggctcacat tgcatgcaag      120
tttgctgagc tgaaggaaaa gattgatc                                         148
```

<210> SEQ ID NO 186
<211> LENGTH: 397
<212> TYPE: DNA
<213> ORGANISM: Homo sapien
<220> FEATURE:
<221> NAME/KEY: misc_feature
<222> LOCATION: (1)...(397)
<223> OTHER INFORMATION: n = A,T,C or G

<400> SEQUENCE: 186

```
tcgagcggcc gcccgggcag gtccaattga acaaacagt tctgagaccg ttcttccacc       60
actgattaag agtgggnggg cgggtattag ggataatatt catttagcct tctgagcttt      120
ctgggcagac ttggtgacct tgccagctcc agcagccttc tggtccactg ctttgatgac      180
acccaccgca actgtctgtc tcatatcacg aacagcaaag cgacccaaag gtggatagtc      240
tgagaagctc tcaacacaca tgggcttgcc aggaaccata tcaacaatgg gcagcatcac      300
cagacttcaa gaatttaagg gccatcttcc agctttttac cagaacggcg atcaatcttt      360
tccttcagct cagcaaactt gcatgcaatg tgagccg                               397
```

<210> SEQ ID NO 187
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 187

```
tcgagcggcc gcccgggcag gtccagaggg ctgtgctgaa gtttgctgct gccactggag    60
ccactccaat tgctggccgc ttcactcctg gaaccttcac taaccagatc caggcagcct   120
tccgggagcc acggcttctt gtggntactg accccagggc tgaccaccag cctctcacgg   180
aggcatctta tgttaaccta cctaccattg cgctgtgtaa cacagattct cctctgcgct   240
atgtggacat tgccatccca tgcaacaaca agggagctca ctcagngggg tttgatgtgg   300
tggatgctgg ctcgggaagt tctgcgcatg cgtggcacca tttcccgtga cacccatgg    360
gangncatgc ctgatctgga cttctacaga gatcctgaag agattgaaaa agaagaacag   420
gctgnttgct ganaaagcaa gtgaccaagg angaaatttc angggtgaaa nggactgctc   480
ccgctcctga attcactgct actcaacctg angntgcaga ctggtcttga aggngnacan   540
gggccctctg ggcctattta agcancttcg gtcgcgaaca cgnt                    584
```

<210> SEQ ID NO 188
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 188

```
agcgtgngtc gcggccgagg tgctgaatag gcacagaggg cacctgtaca ccttcagacc    60
agtctgcaac ctcaggctga gtagcagtga actcaggagc gggagcagtc cattcaccct   120
gaaattcctc cttggncact gccttctcag cagcagcctg ctcttctttt tcaatctctt   180
caggatctct gtagaagtac agatcaggca tgacctccca tgggtgttca cgggaaatgg   240
tgccacgcat gcgcagaact tcccgagcca gcatccacca catcaaaccc actgagtgag   300
ctcccttgtt gttgcatggg atgggcaatg tccacatagc gcagaggaga atctgtgtta   360
cacagcgcaa tggtaggtag gttaacataa gatgcctccg cgagaagctg gtggtcagcc   420
ctggggtcaa gtaaccacaa gaagccgtgg ctcccggaag gctgcctgga tctggttagt   480
gaaggntcca ggagtgaagc ggccaacaat tggagtggct tcagtggcaa gcagcaaact   540
tcagcacaag ccctctggac ctgcccggcg gccgctcga                          579
```

<210> SEQ ID NO 189
<211> LENGTH: 374
<212> TYPE: DNA
<213> ORGANISM: Homo sapien
<220> FEATURE:
<221> NAME/KEY: misc_feature
<222> LOCATION: (1)...(374)
<223> OTHER INFORMATION: n = A,T,C or G

<400> SEQUENCE: 189

```
tcgagcggcc gcccgggcag gtccattttc tccctgacgg ncccacttct ctccaatctt    60
```

```
gtagttcaca ccattgtcat ggcaccatct agatgaatca catctgaaat gaccacttcc     120
aaagcctaag cactggcaca acagtttaaa gcctgattca gacattcgtt cccactcatc     180
tccaacggca taatgggaaa ctgtgtaggg gtcaaagcac gagtcatccg taggttggtt     240
caagccttcg ttgacagagt tgcccacggt aacaacctcn tccccgaacc ttatgcctct     300
gctgggcttt cagngcctcc actatgatgn tgtagggggg cacctctggn gangacctcg     360
gccgcgacca cgct                                                       374

<210> SEQ ID NO 190
<211> LENGTH: 373
<212> TYPE: DNA
<213> ORGANISM: Homo sapien
<220> FEATURE:
<221> NAME/KEY: misc_feature
<222> LOCATION: (1)...(373)
<223> OTHER INFORMATION: n = A,T,C or G

<400> SEQUENCE: 190
agcgtggtcg cggccgaggt cctcaccaga ggtgccacct acaacatcat agtggaggca      60
ctgaaagacc agcagaggca taaggctcgg gaagaggttg ttaccgtggg caactctgtc     120
aacgaaggct tgaaccaacc tacggatgac tcgtgctttg accccacaca gtttcccat     180 tatgccgttg gagatgagtg ggaacgaatg tctgaatcag gctttaaaact gttgtgccag    240 tgcttangct ttggaagtgg gtcatttcag atgtgattca tctagatggt gccatgacaa    300
tggngngaac tacaagattg gagagaagtg gnaccgncag ggagaaaatg gacctgcccg    360
ggcggccgct cga                                                       373

<210> SEQ ID NO 191
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 191
agcgtggtcg cggccgaggt ccacatcggc agggtcggag ccctggccgc catactcgaa      60
ctggaatcca tcggtcatgc tctcgccgaa ccagacatgc ctcttgtcct tggggttctt    120
gctgatgtac cagttcttct gggccacact gggctgagtg gggtacacgc aggtctcacc    180
agtctccatg ttgcagaaga ctttgatggc atccaggntg caaccttggt tggggtcaat    240
ccagtactct ccactcttcc agccagagtg gcacatcttg aggtcacggc aggtgcggnc    300 gggggnttt gcggctgccc tctggncttc ggntgtnctc natctgctgg ctca            354

<210> SEQ ID NO 192
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 192
tcgagcggcc gcccgggcag gtctcgcggt cgcactggtg atgctggtcc tgttggtccc      60
cccggccctc ctggacctcc tggcccccct ggtcctccca gcgctggttt cgacttcagc    120
ttcctgcccc agccacctca agagaaggct cacgatggtg gccgctacta ccgggctgat    180
```

```
gatgccaatg tggttcgtga ccgtgacctc gaggtggaca ccaccctcaa gagcctgagc      240
cagcagatcg agaacatccg gagcccagag ggcagncgca agaacccgc ccgcacctgc       300 cgtgacctca agatgtgcca ctctgactgg aagagtggag agtactggat tgaccccaac     360
caagctgcaa cctggatgcc atcaaagtct tctgcaacat ggagactggt gagacctgcg     420
tgtaccccac tcagcccagt gtggcccaaa agaactggta catcagcaag aaccccaagg     480
acaagaagca tgtctggttc ggcgagaaca tgaccgatgg attccagttc gagtatggcg     540
ggcagggctc cgaccctgcc gatggggacc ttggccgcga acacgct                   587
```

<210> SEQ ID NO 193
<211> LENGTH: 98
<212> TYPE: DNA
<213> ORGANISM: Homo sapien
<220> FEATURE:
<221> NAME/KEY: misc_feature
<222> LOCATION: (1)...(98)
<223> OTHER INFORMATION: n = A,T,C or G

<400> SEQUENCE: 193

```
agcgtggnng cggccgaggt ataaatatcc agnccatatc ctccctccac acgctganag      60
atgaagctgt ncaaagatct cagggtggan aaaaccat                              98
```

<210> SEQ ID NO 194
<211> LENGTH: 240
<212> TYPE: DNA
<213> ORGANISM: Homo sapien

<400> SEQUENCE: 194

```
tcgagcggcc gcccgggcag gtccttcaga cttggactgt gtcacactgc caggcttcca     60
gggctccaac ttgcagacgg cctgttgtgg gacagtctct gtaatcgcga aagcaaccat    120
ggaagacctg ggggaaaaca ccatggtttt atccaccctg agatctttga acaacttcat    180
ctctcagcgt gcggagggag gctctggact ggatatttct acctcggccg cgaccacgct    240
```

<210> SEQ ID NO 195
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 195

```
cgagcgggcg accgggcagg tncagactcc aatccanana accatcaagc cagatgtcag      60
aagctacacc atcacaggtt tacaaccagg cactgactac aaganctacc tgcacacctt    120
gaatgacaat gctcggagct cccctgtggt catcgacgcc tccactgcca ttgatgcacc    180
atccaacctg cgtttcctgg ccaccacacc caattccttg ctggtatcat ggcagccgcc    240
acgtgccagg attaccggta catcatcnag tatganaagc ctgggcctcc tcccagagaa    300
gnggtccctc ggccccgccc tgntgtccca naggntacta ttactgngcc ngcaaccggc    360
aaccgatatc nattttgnca ttggccttca acaataatta                           400
```

<210> SEQ ID NO 196
<211> LENGTH: 494
<212> TYPE: DNA
<213> ORGANISM: Homo sapien
<220> FEATURE:

<221> NAME/KEY: misc_feature
<222> LOCATION: (1)...(494)
<223> OTHER INFORMATION: n = A,T,C or G

<400> SEQUENCE: 196

```
agcgtggttc gcggccgang tcctgtcaga gtggcactgg tagaagttcc aggaaccctg      60
aactgtaagg gttcttcatc agngccaaca ggatgacatg aaatgatgta ctcagaagtg     120
tcctggaatg gggcccatga gatggttgtc tgagagagag cttcttgncc tgtcttttc      180
cttccaatca ggggctcgct cttctgatta ttcttcaggg caatgacata aattgtatat     240
tcgggtcccg gntccaggcc agtaatagta ncctctgtga caccagggcg gngccgaggg     300
accacttctc tgggaggaga cccaggcttc tcatacttga tgatgtaacc ggtaatcctg     360
gcacgtggcg gctgccatga taccagcaag gaattgggt gtggtggcca ggaaacgcag      420
gttggatggn gcatcaatgg cagtggaggc cgtcgatgac cacaggggga gctccgacat     480
tgtcattcaa ggtg                                                       494
```

<210> SEQ ID NO 197
<211> LENGTH: 118
<212> TYPE: DNA
<213> ORGANISM: Homo sapien
<220> FEATURE:
<221> NAME/KEY: misc_feature
<222> LOCATION: (1)...(118)
<223> OTHER INFORMATION: n = A,T,C or G

<400> SEQUENCE: 197

```
agcgtggncg cggccgaggt gcagcgcggg ctgtgccacc ttctgctctc tgcccaacga      60
taaggagggt ncctgccccc aggagaacat taactntccc cagctcggcc tctgccgg      118
```

<210> SEQ ID NO 198
<211> LENGTH: 403
<212> TYPE: DNA
<213> ORGANISM: Homo sapien
<220> FEATURE:
<221> NAME/KEY: misc_feature
<222> LOCATION: (1)...(403)
<223> OTHER INFORMATION: n = A,T,C or G

<400> SEQUENCE: 198

```
tcgagcggcc gcccgggcag gttttttttg ctgaaagtgg ntactttatt ggntgggaaa      60
gggagaagct gtggtcagcc caagagggaa tacagagncc cgaaaaaggg gagggcaggt     120
gggctggaac cagacgcagg gccaggcaga aactttctct cctcactgct cagcctggtg     180
gtggctggag ctcanaaatt gggagtgaca caggacacct tcccacagcc attgcggcgg     240
catttcatct ggccaggaca ctggctgtcc acctggcact ggtcccgaca gaagcccgag     300
ctggggaaag ttaatgttca cctgggggca ggaaccctcc ttatcattgn gcagagagca     360
gaaggtggca cagcccgcgc tgcacctcgg ccgcgaccac gct                       403
```

<210> SEQ ID NO 199
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G

<400> SEQUENCE: 199

```
tcgagcggcc gcccgggcag gtccaccata agtcctgata caaccacgga tgagctgtca      60
```

```
ggagcaaggt tgatttcttt cattggtccg gncttctcct tgggggncac ccgcactcga    120
tatccagtga gctgaacatt gggtggcgtc cactgggcgc tcaggct                  167
```

<210> SEQ ID NO 200
<211> LENGTH: 252
<212> TYPE: DNA
<213> ORGANISM: Homo sapien
<220> FEATURE:
<221> NAME/KEY: misc_feature
<222> LOCATION: (1)...(252)
<223> OTHER INFORMATION: n = A,T,C or G

<400> SEQUENCE: 200

```
tcgagcggtt cgcccgggca ggtccaccac acccaattcc ttgctggtat catggcagcc    60
gccacgtgcc aggattaccg gctacatcat caagtatgag aagcctgggt ctcctcccag   120
agaagcggtc cctcggcccc gccctggtgt cacagaggct actattactg gcctggaacc   180
gggaaccgaa tatacaattt atgtcattgn cctgaagaat aatcannaan agcgancccc   240
tgattggaag ga                                                       252
```

<210> SEQ ID NO 201
<211> LENGTH: 91
<212> TYPE: DNA
<213> ORGANISM: Homo sapien

<400> SEQUENCE: 201

```
agcgtggtcg cggccgaggt tgtacaagct tttttttttt tttttttttt tttttttttt    60
tttttttttt tttttttttt tttttttttt t                                   91
```

<210> SEQ ID NO 202
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 202

```
tcgagcggnc gcccgggcag gtctgccaac accaagattg gccccgccg catccacaca    60 gtccgtgtgc ggggaggtaa caagaaatac cgtgccctga ggttggacgt ggggaatttc   120
tcctggggct cagagtgttg tactcgtaaa acaaggatca tcgatgttgt ctacaatgca   180
tctaataacg agctggttcg taccaagacc ctggtgaaga attgcatcgt gctcatcgac   240
agcacaccgt accgacagtg gtacgagtcc cactatgcgc tgccctggg ccgcaagaag   300 ggagccaagc tgactcctga ggaagaagag atttaaaca aaaacgatc taanaaaaaa   360 aaaacaat                                                             368
```

<210> SEQ ID NO 203
<211> LENGTH: 340
<212> TYPE: DNA
<213> ORGANISM: Homo sapien

<400> SEQUENCE: 203

```
agcgtggtcg cggccgaggt gaatggtat tcagcttcct ggcacttctg gtcagcaacc    60
cagtgttggg caacaaatga tctttgagga acatggtttt aggcggacca caccgcccac   120
aacggccacc cccataaggc ataggccaag accatacccg ccgaatgtag gacaagaagc   180
```

```
tctctctcag acaaccatct catgggcccc attccaggac acttctgagt acatcatttc    240
atgtcatcct gttggcactg atgaagaacc cttacagttc agggttcctg gaacttctac    300
cagtgccact ctgacaggac ctgcccgggc ggccgctcga                          340
```

<210> SEQ ID NO 204
<211> LENGTH: 341
<212> TYPE: DNA
<213> ORGANISM: Homo sapien

<400> SEQUENCE: 204

```
tcgagcggcc gcccgggcag gtcctgtcag agtggcactg gtagaagttc caggaaccct    60
gaactgtaag ggttcttcat cagtgccaac aggatgacat gaaatgatgt actcagaagt    120
gtcctggaat gggcccatg agatggttgt ctgagagaga gcttcttgtc ctacattcgg     180
cgggtatggt cttggcctat gccttatggg ggtggccgtt gtgggcggtg tggtccgcct    240
aaaaccatgt tcctcaaaga tcatttgttg cccaacactg ggttgctgac cagaagtgcc    300
aggaagctga ataccatttc acctcggccg cgaccacgct a                        341
```

<210> SEQ ID NO 205
<211> LENGTH: 770
<212> TYPE: DNA
<213> ORGANISM: Homo sapien
<220> FEATURE:
<221> NAME/KEY: misc_feature
<222> LOCATION: (1)...(770)
<223> OTHER INFORMATION: n = A,T,C or G

<400> SEQUENCE: 205

```
tcgagcggcc gcccgggcag gtctcccttc ttgcggccca ggggcagcgc atagtgggac    60
tcgtaccact gtcggtacgg tgtgctgtcg atgagcacga tgcaattctt caccagggtc    120
ttggtacgaa ccagctcgtt attagatgca ttgtagacaa catcgatgat ccttgtttta    180
cgagtacaac actctgagcc ccaggagaaa ttccccacgt ccaacctcag ggcacggtat    240
ttcttgttac ctccccgcac acggactgtg tggatgcggc gggggccaag ctgactcctg    300
aggaagaaga gattttaaac aaaaaacgat ctaaaaaaat tcagaagaaa tatgatgaaa    360
ggaaaaagaa tgccaaaatc agcagtctcc tggaggagca gttccagcag ggcaagcttc    420
ttgcgtgcat cgcttcaagg ccgggacagt gtgaccgagc agatggctat gtgctagagg    480
gcaaagaagt ggagttctat cttaagaaaa tcagggccca gaatggtgng tcttcaacta    540
atccaaaggg gagtttcaga ccagtgcaat cagcaaaaac attgatactg ntggccaaat    600
ttattggtgc agggcttgca cantangann ggctgggtct tggggcttgg attggnacaa    660
gctttggcag cctttcttt ggttttgcca aaaacctttt gntgaagang anacctnggg     720
cggacccctt aaccgattcc acnccnggng gcgttctang gncccncttg               770
```

<210> SEQ ID NO 206
<211> LENGTH: 810
<212> TYPE: DNA
<213> ORGANISM: Homo sapien
<220> FEATURE:
<221> NAME/KEY: misc_feature
<222> LOCATION: (1)...(810)
<223> OTHER INFORMATION: n = A,T,C or G

<400> SEQUENCE: 206

```
agcgtggtcg cggccgaggt ctgctgcttc agcgaagggt ttctggcata accaatgata    60
aggctgccaa agactgttcc aataccagca ccagaaccag ccactcctac tgttgcagca    120
cctgcaccaa taaatttggc agcagtatca atgtctctgc tgattgcact ggtctgaaac    180
```

```
tcccttttgga ttagctgaga cacaccattc tgggccctga ttttcctaag atagaactcc      240
aactctttgc cctctagcac atagccatct gctcggtcac actgtcccgg ccttgaagcg      300
atgcacgcaa gaagcttgcc ctgctggaac tgctcctcca ggagactgct gattttggca      360
ttcttttttcc tttcatcata tttcttctga attttttttag atcgtttttt gtttaaaatc    420
tcttcttcct caggagtcag cttggccccc gccgcatcca cacagtccgt gtgcggggag      480
gtaacaagaa ataccgtgcc ctgaggttgg acgtggggaa tttctcctgg ggctcagagt      540
ggtgtactcg taaaacaagg atcatcgatg gtgnctacaa tgcatctaat aacgagctgg      600
gtcggaccca aagaacctgg ngaanaaatg gatcgnctca tcgacaggac accgtacccg      660
acagggggnac gantcccact atgcgcttgc ccctgggccg caanaaagga aaactgcccg      720
ggcggccntc gaaagcccaa ttntggaaaa aatccatcac actgggnggc cngtcgagca      780
tgcatntana ggggcccatt ccccctnann                                       810

<210> SEQ ID NO 207
<211> LENGTH: 257
<212> TYPE: DNA
<213> ORGANISM: Homo sapien

<400> SEQUENCE: 207
tcgagcggcc gcccgggcag gtccccaacc aaggctgcaa cctggatgcc atcaaagtct       60
tctgcaacat ggagactggt gagacctgcg tgtaccccac tcagcccagt gtggcccaga      120
agaactggta catcagcaag aaccccaagg acaagaggca tgtctggttc ggcgagagca      180
tgaccgatgg attccagttc gagtatggcg gccagggctc cgaccctgcc gatgtggacc      240
tcggccgcga ccacgct                                                     257

<210> SEQ ID NO 208
<211> LENGTH: 257
<212> TYPE: DNA
<213> ORGANISM: Homo sapien

<400> SEQUENCE: 208
agcgtggtcg cggccgaggt ccacatcggc agggtcggag ccctggccgc catactcgaa       60
ctggaatcca tcggtcatgc tctcgccgaa ccagacatgc ctcttgtcct tggggttctt      120
gctgatgtac cagttcttct gggccacact gggctgagtg gggtacacgc aggtctcacc      180
agtctccatg ttgcagaaga cttttgatgg catccaggtt cagccttggt tggggacctg      240
cccgggcggc cgctcga                                                     257

<210> SEQ ID NO 209
<211> LENGTH: 747
<212> TYPE: DNA
<213> ORGANISM: Homo sapien
<220> FEATURE:
<221> NAME/KEY: misc_feature
<222> LOCATION: (1)...(747)
<223> OTHER INFORMATION: n = A,T,C or G

<400> SEQUENCE: 209
tcgagcggcc gcccgggcag gtccaccaca cccaattcct tgctggtatc atggcagccg       60
ccacgtgcca ggattaccgg ctacatcatc aagtatgaga agcctgggtc tcctcccaga      120
gaagtggtcc ctcggccccg ccctggtgtc acagaggcta ctattactgg cctggaaccg      180
ggaaccgaat atacaattta tgtcattgcc ctgaagaata atcagaagag cgagcccctg      240
attggaagga aaaagacaga cgagcttccc caactggtaa cccttccaca ccccaatctt      300
catggaccag agatcttgga tgttccttcc acagttcaaa agaccccttt cgtcacccac      360
cctgggtatg acactggaaa tggtattcag cttcctggca cttctggtca gcaacccagt      420
gttgggcaac aaatgatctt tgaggaacat ggntttaggc ggaccacacc gcccacaacg      480 gccacccccca taaggcatag gccaagacca taccgccgga atgtaggaca agaagctntn      540
tntcanacac catntnatgg gccccattcc aggacacttc tgagtacatc atttatgnca      600
```

```
tctgtggcac ttgatgaaaa cccttacagt tcagggttct ggaacttta  ccaggcctnt      660 tacaggactn ggccggacnc cttaagccna ttncaccctg gggcgttcta nggtcccact      720
cgnncactgg ngaaaatggc tactgtn                                         747
```

<210> SEQ ID NO 210
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 210

```
agcgtggtcg cggccgaggt ccactagagg tctgtgtgcc attgcccagg cagagtctct       60
gcgttacaaa ctcctaggag ggcttgctgt gcggagggcc tgctatggtg tgctgcggtt      120
catcatggag agtggggcca aaggctgcga ggttgtggtg tctgngaaac tccnaggaca      180
ngagggctaa attccatgaa gtttgtggat ggcctgatga tccacaatcg gagaccctgt      240
taactactac cgtctnaccn cctgctgtnc nccccntttt ctgctnaana catngggntn      300
ntncttgncc ntccttgggt ngaanatnna atngcctncc cnttcntanc nctactngt      360 ccananttgg cctttaaana atccncttg ccttnncac tgttcannt ntttnntcgta       420 aaccctatna nttnnattan atnntnnnnn nctcaccccc ctcntcattn anccnatang     480
ctnnnaantc cttnanncct cccncccnnt ncnctctac tnantncttc tnncccatta      540
cnnagctctt tcntttaana taatgnngcc nngctctnca tntctacnat ntgnnnaatn     600
cccccncccc cnancgnntt tttgacctnn naacctcctt tcctcttccc tncnnaaatt     660
ncnnanttcc ncnttccnnc ntttcggntn ntcccatnct ttccannnct tcantctanc     720
ncnctncaac ttattttcct ntcatcccttt nttcttaca nncccccctnn tctactcnnc    780 nnttncatta natttgaaac tnccacnnct anttncctcn ctctacnntt ttattttncg     840
ntcnctctac ntaatanttt aatnanttnt cn                                    872
```

<210> SEQ ID NO 211
<211> LENGTH: 517
<212> TYPE: DNA
<213> ORGANISM: Homo sapien
<220> FEATURE:
<221> NAME/KEY: misc_feature
<222> LOCATION: (1)...(517)
<223> OTHER INFORMATION: n = A,T,C or G

<400> SEQUENCE: 211

```
tcgagcggcc gcccgggcag gtctgccaag gagaccctgt tatgctgtgg ggactggctg       60
gggcatggca gcggctctg gcttcccacc cttctgttct gagatggggg tggtgggcag      120
tatctcatct ttgggttcca caatgctcac gtggtcaggc aggggcttct tagggccaat     180
cttaccagtt gggtcccagg gcagcatgat cttcaccttg atgcccagca cccctgtct     240 gagcaacacg tggcgcacaa gcagtgtcaa cgtagtaagt taacagggtc tccgctgtgg     300
atcatcaggc catccacaaa cttcatggat ttagccctct gtcctcggag tttcccagac     360
accacaacct cgcagccttt ggccccactc tccatgatga accgcagcac accatagcag    420
gccctccgca caagcaagcc ctcctaagaa tttgtaacgc ananactctg ctggcaatgg     480
cacacaaacc tctagtggac ctcggncgcg accacgc                              517
```

<210> SEQ ID NO 212
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 212

```
tcgagcggcc gcccgggcag gtctggtcca ggatagcctg cgagtcctcc tactgctact      60
ccagacttga catcatatga atcatactgg ggagaatagt tctgaggacc agtagggcat     120
gattcacaga ttccaggggg gccaggagaa ccagggacc ctggttgtcc tggaatacca     180
gggtcaccat ttctcccagg aataccagga gggcctggat ctcccttggg gccttgaggt     240
ccttgaccat taggagggcg agtaggagca gttggaggct gtgggcaaac tgcacaacat     300
tctccaaatg gaatttctgg gttggggcag tctaattctt gatccgtcac atattatgtc     360
atcgcagaga acggatcctg agtcacagac acatatttgg catggttctg cttccagac     420
atctctatcc gncataggac tgaccaagat gggaacatcc tccttcaaca agcttnctgt     480
tgtgccaaaa ataatagtgg gatgaagcag accgagaagt anccagctcc ccttttttgca    540
caaagcntca tcatgtctaa atatcagaca tgagacttct ttgggcaaaa aaggagaaaa     600
agaaaaagca gttcaaagta nccnccatca agttggttcc ttgcccnttc agcacccggg     660
ccccgttata aaacacctng ggccggaccc ccctt                                695
```

<210> SEQ ID NO 213
<211> LENGTH: 804
<212> TYPE: DNA
<213> ORGANISM: Homo sapien
<220> FEATURE:
<221> NAME/KEY: misc_feature
<222> LOCATION: (1)...(804)
<223> OTHER INFORMATION: n = A,T,C or G

<400> SEQUENCE: 213

```
agcgtggtcg cggccgaggt gttttatgac gggcccggtg ctgaagggca gggaacaact      60
tgatggtgct actttgaact gcttttcttt tctccttttt gcacaaagag tctcatgtct     120
gatatttaga catgatgagc tttgtgcaaa aggggagctg gctacttctc gctctgcttc     180
atcccactat tattttggca acaggaag ctgttgaagg aggatgttcc catcttggtc        240
agtcctatgc ggatagagat gtctggaagc cagaaccatg ccaaatatgt gtctgtgact     300
caggatccgt tctctgcgat gacataatat gtgacgatca agaattagac tgccccaacc     360
cagaaattcc atttggagaa tgttgtgcag tttgcccaca gcctccaact gctcctactc     420
gccctcctaa tggtcaagga cctcaaggcc caagggaga tccaggccct cctggtattc      480
ctgggagaaa tggtgaccct ggtattccag acaaccagg gtcccctggt tctcctggcc      540
cccctggaat cnggngaatc atgccctact ggtcctcaaa ctattctccc anatgattca     600
tatgatgtca agtctgggat agcnagtang ganggactcg caggctattc tggaccanac    660
ctgccggggg ggcgttcgaa agcccgaatc tgcananntn cnttcacact ggcggccgtc    720
gagctgcttt aaaagggcca ttccnccttt agngngggg antacaatta ctnggcggcg    780
ttttananancg cgngnctggg aaat                                          804
```

<210> SEQ ID NO 214
<211> LENGTH: 594

```
<212> TYPE: DNA
<213> ORGANISM: Homo sapien
<220> FEATURE:
<221> NAME/KEY: misc_feature
<222> LOCATION: (1)...(594)
<223> OTHER INFORMATION: n = A,T,C or G

<400> SEQUENCE: 214
agcgtggtcg cggccgaggt ccacatcggc agggtcggag ccctggccgc catactcgaa      60
ctggaatcca tcggtcatgc tctcgccgaa ccagacatgc ctcttgtcct tggggttctt     120
gctgatgtac cagttcttct gggccacact gggctgagtg gggtacacgc aggtctcacc     180
agtctccatg ttgcagaaga ctttgatggc atccaggttg cagccttggt tggggtcaat     240
ccagtactct ccactcttcc agtcagagtg gcacatcttg aggtcacggc aggtgcgggc     300
ggggttcttg cggctgccct ctgggctccg gatgttctcg atctgctggc tcaggctctt     360
gagggtggtg tccacctcga ggtcacggtc acgaaccaca ttggcatcat cagcccggta     420
gtagcggcca ccatcgtgag ccttctcttg angtggctgg ggcaggaact gaagtcgaaa     480
ccagcgctgg gaggaccagg gggaccaana ggtccaggaa gggcccgggg gggaccaaca     540
ggaccagcat caccaagtgc gacccgcgag aacctgcccg ccgnccgct cgaa            594

<210> SEQ ID NO 215
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 215
tcgagcgnnc gcccgggcag gtctcgcggt cgcactggtg atgctggtcc tgttggtccc      60
cccggccctc ctggacctcc tggtccccct ggtcctccca gcgctggttt cgacttcagc     120
ttcctgcccc agccacctca agagaaggct cacgatggtg gccgctacta ccgggctgat     180
gatgccaatg tggttcgtga ccgtgacctc gaggtggaca ccaccctcaa gagcctgagc     240
cagcagatcg agaacatccg gagcccagag ggcagccgca agaacccgc ccgcacctgc      300
cgtgacctca agatgtgcca ctctgactgg aagagtggag agtactggat tgaccccaac     360
caaggctgca acctggatgc catcaaagtc ttctgcaaca tggagactgg tgagacctgc     420
gtgtaccccca ctcagcccag tgtggcccag aagaactggt acatcagcaa gaaccccaag     480
gacaagaggc atgtctggtt cggcgagagc atgaccgatg gattccagtt cgagtatggc     540
ggccagggct cccacctgc cgatgtggac ctccggccgc gaccacctt                   590

<210> SEQ ID NO 216
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 216
tngagcggcc gcccgggcag gntgnnaacg ctggtcctgc tggtcctcct ggcaaggctg      60
gtgaagatgg tcaccctgga aaacccggac gacctggtga gaggagtt gttggaccac      120
agggtgctcg tggtttccct ggaactcctg gacttcctgg cttcaaggc attaggggac     180
```

```
acaatggtct ggatggattg aagggacagc ccgtgctcc tggtgtgaag ggtgaacctg      240
gtgcccctgg tgaaaatgga actccaggtc aaacaggagc ccgtgggctt cctggtgaga      300
gaggaccgtg ttggtgcccc tggcccanac ctcggccgcg accacgctaa gcccgaattt      360
ccagcacact ggnggccgtt actantggat ccgagctcgg taccaagctt ggcgtaatca      420
tggtcatagc tgtttcctgn gtgaaattgt tatccgctca caatttcaca cancatacga      480
agccggaaag cataaagtgt aaagccttgg ggtgctaatg agtgagctaa ctcncattaa      540
attgcgttgc gctcactgcc cgcttttcca nnngggaaac cntggcntng ccngcttgcn      600
ttaantgaaa tccgccnacc cccggggaaa agncggtttg cngtattggg gcncttttc       660 cctttcctcg gnttacttga nttantgggc tttggncgnt tcggttgng gcgancnggt       720 tcaacntcac nccaaggng gnaanacggt tttcccanaa tccgggggnt ancccaangn       780
aaaacatnng ncnaangggc t                                                801

<210> SEQ ID NO 217
<211> LENGTH: 349
<212> TYPE: DNA
<213> ORGANISM: Homo sapien
<220> FEATURE:
<221> NAME/KEY: misc_feature
<222> LOCATION: (1)...(349)
<223> OTHER INFORMATION: n = A,T,C or G

<400> SEQUENCE: 217
agcgtggttn gcggccgagg tctgggccag gggcaccaac acgtcctctc tcaccaggaa      60
gcccacgggc tcctgtttga cctggagttc cattttcacc aggggcacca ggttcaccct      120
tcacaccagg agcaccgggc tgtcccttca atccatncag accattgtgn ccctaatgc      180 ctttgaagcc aggaagtcca ggagttccag ggaaaccacc gagcaccctg tggtccaaca      240
actcctctct caccaggtcg tccgggtttt ccagggtgac catcttcacc agccttgcca      300
ggaggaccag caggaccagc gttaccaacc tgcccgggcg gccgctcga              349

<210> SEQ ID NO 218
<211> LENGTH: 372
<212> TYPE: DNA
<213> ORGANISM: Homo sapien

<400> SEQUENCE: 218
tcgagcggcc gccgggcag gtccattttc tccctgacgg tcccacttct ctccaatctt      60
gtagttcaca ccattgtcat ggcaccatct agatgaatca catctgaaat gaccacttcc      120
aaagcctaag cactggcaca acagtttaaa gcctgattca gacattcgtt cccactcatc      180
tccaacggca taatgggaaa ctgtgtaggg gtcaaagcac gagtcatccg taggttggtt      240
caagccttcg ttgacagagt tgcccacggt aacaacctct tcccgaacct tatgcctctg      300
ctggtctttc agtgcctcca ctatgatgtt gtaggtggca cctctggtga ggacctcggc      360
cgcgaccacg ct                                                         372

<210> SEQ ID NO 219
<211> LENGTH: 374
<212> TYPE: DNA
<213> ORGANISM: Homo sapien

<400> SEQUENCE: 219
agcgtggtcg cggccgaggt cctcaccaga ggtgccacct acaacatcat agtggaggca      60
ctgaaagacc agcagaggca taaggttcgg gaagaggttg ttaccgtggg caactctgtc      120
```

```
aacgaaggct tgaaccaacc tacggatgac tcgtgctttg acccctacac agtttcccat    180
tatgccgttg gagatgagtg ggaacgaatg tctgaatcag gctttaaact gttgtgccag    240
tgcttaggct ttggaagtgg tcatttcaag atgtgattca tctagatggt gccatgacaa    300
tggtgtgaac tacaagattg gagagaagtg ggaccgtcag ggagaaaatg gacctgcccg    360
ggccggccgc tcga                                                      374
```

<210> SEQ ID NO 220
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 220

```
tcgagcgnnc gcccgggcag gtccagtagt gccttcggga ctgggttcac ccccaggtct     60
gcggcagttg tcacagcgcc agcccgctg gcctccaaag catgtgcagg agcaaatggc    120
accgagatat tccttctgcc actgttctcc tacgtggtat gtcttcccat catcgtaaca    180
cgttgcctca tgagggtcac acttgaattc ccttttccg ttcccaagac atgtgcagct    240
catttggctg gctctatagt ttggggaaag tttgttgaaa ctgtgccact gacctttact    300
tcctccttct ctactggagc tttcgtacct tccacttctg ctgttggtaa atggtggat    360 cttctatcaa tttcattgac agtacccact tctcccaaac atccagggaa atagtgattt    420
cagagcgatt aggagaacca aattatgggg cagaaataag gggcttttcc acaggttttc    480
ctttggagga agatttcagt ggtgactta aagaatact caacagtgtc ttcatcccca    540
tagcaaaaga agaaacngta aatgatggaa ngcttctgga gatgccnnca tttaagggac    600
ncccagaact tcaccatcta caggacctac ttcagtttac annaagncac atantctgac    660
tcanaaagga cccaagtagc nccatggnca gcactttnag cctttcccct ggggaaaann    720
ttacnttctt aaanncctngg ccnngacccc cttaagncca aatntgaa aanttccntn     780 cnnctggggg gcngttcnac atgcntttna agggcccaat tncccccnt                 828
```

<210> SEQ ID NO 221
<211> LENGTH: 476
<212> TYPE: DNA
<213> ORGANISM: Homo sapien

<400> SEQUENCE: 221

```
tcgagcggcc gcccgggcag gtgtcggagt ccagcacggg aggcgtggtc ttgtagttgt     60
tctccggctg cccattgctc tcccactcca cggcgatgtc gctgggatag aagcctttga    120
ccaggcaggt caggctgacc tggttcttgg tcatctcctc ccgggatggg ggcagggtgt    180
acacctgtgg ttctcggggc tgccctttgg ctttggagat ggttttctcg atggggctg    240 ggagggcttt gttggagacc ttgcacttgt actccttgcc attcagccag tcctggtgca    300
ggacggtgag gacgctgacc acacggtacg tgctgttgta ctgctcctcc cgcggctttg    360
tcttggcatt atgcacctcc acgccgtcca cgtaccagtt gaacttgacc tcagggtctt    420
cgtggctcac gtccaccacc acgcatgtaa cctcagacct cggccgcgac cacgct         476
```

<210> SEQ ID NO 222
<211> LENGTH: 477
<212> TYPE: DNA

<213> ORGANISM: Homo sapien

<400> SEQUENCE: 222

| | | | | | |
|---|---|---|---|---|---|
| agcgtggtcg | cggccgaggt | ctgaggttac | atgcgtggtg | gtggacgtga | gccacgaaga | 60 |
| ccctgaggtc | aagttcaact | ggtacgtgga | cggcgtggag | gtgcataatg | ccaagacaaa | 120 |
| gccgcgggag | gagcagtaca | acagcacgta | ccgtgtggtc | agcgtcctca | ccgtcctgca | 180 |
| ccaggactgg | ctgaatggca | aggagtacaa | gtgcaaggtc | tccaacaaag | ccctcccagc | 240 |
| ccccatcgag | aaaaccatct | ccaaagccaa | agggcaagcc | cgagaacca | caggtgtaca | 300 |
| ccctgccccc | atcccgggag | gagatgacca | agaaccaggt | cagcctgacc | tgcctggtca | 360 |
| aaggcttcta | tcccagcgac | atcgccgtgg | agtgggagag | caatgggcag | ccggagaaca | 420 |
| actacaagac | cacgcctccc | gtgctggact | ccgacacctg | cccgggcggc | cgctcga | 477 |

<210> SEQ ID NO 223
<211> LENGTH: 361
<212> TYPE: DNA
<213> ORGANISM: Homo sapien

<400> SEQUENCE: 223

| | | | | | |
|---|---|---|---|---|---|
| tcgagcggcc | gcccgggcag | gttgaatggc | tcctcgctga | ccaccccggt | gctggtggtg | 60 |
| ggtacagagc | tccgatgggt | gaaaccattg | acatagagac | tgtccctgtc | cagggtgtag | 120 |
| gggcccagct | cagtgatgcc | gtgggtcagc | tggctcagct | tccagtacag | ccgctctctg | 180 |
| tccagtccag | ggcttttggg | gtcaggacga | tgggtgcaga | cagcatccac | tctggtggct | 240 |
| gccccatcct | tctcaggcct | gagcaaggtc | agtctgcaac | cagagtacag | agagctgaca | 300 |
| ctggtgttct | tgaacaaggg | cataagcaga | ccctgaagga | cacctcggcc | gcgaccacgc | 360 |
| t | | | | | | 361 |

<210> SEQ ID NO 224
<211> LENGTH: 361
<212> TYPE: DNA
<213> ORGANISM: Homo sapien

<400> SEQUENCE: 224

| | | | | | |
|---|---|---|---|---|---|
| agcgtggtcg | cggccgaggt | gtccttcagg | gtctgcttat | gcccttgttc | aagaacacca | 60 |
| gtgtcagctc | tctgtactct | ggttgcagac | tgaccttgct | caggcctgag | aaggatgggg | 120 |
| cagccaccag | agtggatgct | gtctgcaccc | atcgtcctga | ccccaaaagc | cctggactgg | 180 |
| acagagagcg | gctgtactgg | aagctgagcc | agctgaccca | cggcatcact | gagctgggcc | 240 |
| cctacaccct | ggacagggac | agtctctatg | tcaatggttt | cacccatcgg | agctctgtac | 300 |
| ccaccaccag | caccggggtg | gtcagcgagg | agccattcaa | cctgcccggg | cggccgctcg | 360 |
| a | | | | | | 361 |

<210> SEQ ID NO 225
<211> LENGTH: 766
<212> TYPE: DNA
<213> ORGANISM: Homo sapien
<220> FEATURE:
<221> NAME/KEY: misc_feature
<222> LOCATION: (1)...(766)
<223> OTHER INFORMATION: n = A,T,C or G

<400> SEQUENCE: 225

| | | | | | |
|---|---|---|---|---|---|
| agcgtggtcg | cggccgaggt | cctgtcagag | tggcactggt | agaagttcca | ggaaccctga | 60 |
| actgtaaggg | ttcttcatca | gtgccaacag | gatgacatga | aatgatgtac | tcagaagtgt | 120 |

-continued

```
cctggaatgg ggcccatgag atggttgtct gagagagagc ttcttgtcct acattcggcg    180
ggtatggtct tggcctatgc cttatggggg tggccgttgt gggcggtgtg gtccgcctaa    240
aaccatgttc ctcaaagatc atttgttgcc caacactggg ttgctgacca gaagtgccag    300
gaagctgaat accatttcca gtgtcatacc cagggtgggt gacgaaaggg gtcttttgaa    360
ctgtggaagg aacatccaag atctctggtc catgaagatt ggggtgtgga agggttacca    420
gttggggaag ctcgtctgtc ttttccttc caatcagggg ctcgctcttc tgattattct     480
tcagggcaat gacataaatt gtatattcgg tcccggttcc aggccagtaa tagtagcctc    540
tgtgacacca gggcggggcc gagggaccct tctnttggaa gagaccagct tctcatactt    600
gatgatgagn ccggtaatcc tggcacgtgg nggttgcatg atnccaccaa ggaaatnggn    660
gggggnggac ctgcccggcg gccgttcnaa agcccaattc cacacacttg gnggccgtac    720
tatggatccc actcngtcca acttggngga atatggcata actttt                   766
```

<210> SEQ ID NO 226
<211> LENGTH: 364
<212> TYPE: DNA
<213> ORGANISM: Homo sapien

<400> SEQUENCE: 226

```
tcgagcggcc gcccgggcag gtccttgacc ttttcagcaa gtgggaaggt gtaatccgtc    60
tccacagaca aggccaggac tcgtttgtac ccgttgatga tagaatgggg tactgatgca    120
acagttgggt agccaatctg cagacagaca ctggcaacat tgcggacacc ctccaggaag    180
cgagaatgca gagtttcctc tgtgatatca agcacttcag ggttgtagat gctgccattg    240
tcgaacacct gctggatgac cagcccaaag gagaagggg agatgttgag catgttcagc    300
agcgtggctt cgctggctcc cactttgtct ccagtcttga tcagacctcg ccgcgacca    360 cgct                                                                  364
```

<210> SEQ ID NO 227
<211> LENGTH: 275
<212> TYPE: DNA
<213> ORGANISM: Homo sapien

<400> SEQUENCE: 227

```
agcgtggtcg cggccgaggt ctgtcctaca gtcctcagga ctctactccc tcagcagcgt    60
ggtgaccgtg ccctccagca acttcggcac ccagacctac acctgcaacg tagatcacaa    120
gcccagcaac accaaggtgg acaagagagt tgagcccaaa tcttgtgaca aaactcacac    180
atgcccaccg tgcccagcac ctgaactcct gggggaccg tcagtcttcc tcttccccg     240 catcccctt ccaaacctgc ccgggcggcc gctcg                                 275
```

<210> SEQ ID NO 228
<211> LENGTH: 275
<212> TYPE: DNA
<213> ORGANISM: Homo sapien

<400> SEQUENCE: 228

```
cgagcggccg cccgggcagg tttggaaggg ggatgcgggg gaagaggaag actgacggtc    60
cccccaggag ttcaggtgct gggcacggtg ggcatgtgtg agttttgtca caagatttgg    120
gctcaactct cttgtccacc ttggtgttgc tgggcttgtg atctacgttg caggtgtagg    180
tctgggtgcc gaagttgctg gagggcacgg tcaccacgct gctgagggag tagagtcctg    240
```
aggactgtag gacagacctc ggccgcgacc acgct 275

<210> SEQ ID NO 229
<211> LENGTH: 40
<212> TYPE: DNA
<213> ORGANISM: Homo sapien
<220> FEATURE:
<221> NAME/KEY: misc_feature
<222> LOCATION: (1)...(40)
<223> OTHER INFORMATION: n = A,T,C or G

<400> SEQUENCE: 229
nggnnggtcc ggncngncag gaccactcnt cttcgaaata 40

<210> SEQ ID NO 230
<211> LENGTH: 208
<212> TYPE: DNA
<213> ORGANISM: Homo sapien

<400> SEQUENCE: 230
agcgtggtcg cggccgaggt cctcacttgc ctcctgcaaa gcaccgatag ctgcgctctg 60
gaagcgcaga tctgttttaa agtcctgagc aatttctcgc accagacgct ggaagggaag 120
tttgcgaatc agaagttcag tggacttctg ataacgtcta atttcacgga gcgccacagt 180
accaggacct gcccgggcgg ccgctcga 208

<210> SEQ ID NO 231
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 231
tcgagcggcc gcccgggcag gtcctggtac tgnggcgctc cgtgaaatta gacgttatca 60
gaagtccact gaacttctga ttcgcaaact tcccttccag cgtctggtgc gagaaattgc 120
tcaggacttt aaaacagatc tgcgcttcca gagcgcagct atcggtgctt tgcaggaggc 180
aagtgaggac ctcggccgcg accacgct 208

<210> SEQ ID NO 232
<211> LENGTH: 332
<212> TYPE: DNA
<213> ORGANISM: Homo sapien

<400> SEQUENCE: 232
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacctcggc cgcgaccacg ct 332

<210> SEQ ID NO 233
<211> LENGTH: 415
<212> TYPE: DNA
<213> ORGANISM: Homo sapien
<220> FEATURE:
<221> NAME/KEY: misc_feature

```
<222> LOCATION: (1)...(415)
<223> OTHER INFORMATION: n = A,T,C or G

<400> SEQUENCE: 233
gtgggnttga acccntttna nctccgcttg gtaccgagct cggatccact agtaacggcc    60
gccagtgtgc tggaattcgg cttagcgtgg tcgcggccga ggtcaagaac cccgcccgca   120
cctgccgtga cctcaagatg tgccactctg actggaagag tggagagtac tggattgacc   180
ccaaccaagg ctgcaacctg gatgccatca agtcttctg caacatggag actggtgaga   240
cctgcgtgta ccccactcag cccagtgtgg cccagaagaa ctggtacatc agcaagaacc   300
ccaaggacaa gaggcatgtc tggttcggcg agagcatgac cgatggattc cagttcgagt   360
atggcggcca gggctccgac cctgccgatg tggacctgcc cgggcggccg ctcga        415

<210> SEQ ID NO 234
<211> LENGTH: 776
<212> TYPE: DNA
<213> ORGANISM: Homo sapien
<220> FEATURE:
<221> NAME/KEY: misc_feature
<222> LOCATION: (1)...(776)
<223> OTHER INFORMATION: n = A,T,C or G

<400> SEQUENCE: 234
agcgtggtcg cggccgaggt ctgggatgct cctgctgtca cagtgagata ttacaggatc    60
acttacggag aaacaggagg aaatagccct gtccaggagt tcactgtgcc tgggagcaag   120
tctacagcta ccatcagcgg ccttaaacct ggagttgatt ataccatcac tgtgtatgct   180
gtcactggcc gtggagacag ccccgcaagc agcaagccaa tttccattaa ttaccgaaca   240
gaaattgaca aaccatccca gatgcaagtg accgatgttc aggacaacag cattagtgtc   300
aagtggctgc cttcaagttc ccctgttact ggttacagag taaccaccac tcccaaaaat   360
ggaccaggac caacaaaaac taaaactgca ggtccagatc aaacagaaat gactattgaa   420
ggcttgcagc ccacagtgga gtatgtggtt aagtgtctat gctcagaatc caagcggaga   480
gaagtcagcc tctggttcag actgnaagta accaacattg atcgcctaaa ggactggcat   540
tcactgatgn ggatgccgat tccatcaaaa ttgnttggga aaacccacag gggcaagttt   600
ncangtcnag gnggacctac tcgagccctg aggatgnaat ccttgactnt tccttnncct   660
gatggggaaa aaaaaccttn aaaacttgaa ggacctgccc gggcggccgt ncaaaaccca   720
attccacccc cttgggggcg ttctatgggn cccactcgga ccaaacttgg ggtaan       776

<210> SEQ ID NO 235
<211> LENGTH: 805
<212> TYPE: DNA
<213> ORGANISM: Homo sapien
<220> FEATURE:
<221> NAME/KEY: misc_feature
<222> LOCATION: (1)...(805)
<223> OTHER INFORMATION: n = A,T,C or G

<400> SEQUENCE: 235
tcgagcggcc gcccgggcag gtccttgcag ctctgcagtg tcttcttcac catcaggtgc    60
agggaatagc tcatggattc catcctcagg gtcgagtag gtcaccctgt acctggaaac   120
ttgcccctgt gggctttccc aagcaatttt gatggaatcg gcatccacat cagtgaatgc   180
cagtccttta gggcgatcaa tgttggttac tgcagtctga accagaggct gactctctcc   240
gcttggattc tgagcataga cactaaccac atactccact gtgggctgca agccttcaat   300
```

```
agtcatttct gtttgatctg gacctgcagt tttagttttt gttggtcctg gtccattttt      360
gggagtggtg gttactctgt aaccagtaac aggggaactt gaaggcagcc acttgacact      420
aatgctgttg tcctgaacat cggtcacttg catctgggat ggtttgtcaa tttctgttcg      480
gtaattaatg gaaattggct tgctgcttgc ggggcttgtc tccacggcca gtgacagcat      540
acacagtgat ggtataatca actccaggtt taagccgctg atggtagctg aaactttgct      600
ccaggcacaa gtgaactcct gacagggcta tttcctnctg ttctccgtaa gtgatcctgt      660
aatatctcac tgggacagca ggangcattc caaaacttcg ggcgngaccc cctaagccga      720
attntgcaat atncatcaca ctggcgggcg ctcgancatt cattaaaagg cccaatcncc      780
cctataggga gtntantaca attng                                            805
```

<210> SEQ ID NO 236
<211> LENGTH: 262
<212> TYPE: DNA
<213> ORGANISM: Homo sapien

<400> SEQUENCE: 236

```
tcgagcggcc gcccgggcag gtcactttg gttttggtc atgttcggtt ggtcaaagat        60
aaaaactaag tttgagagat gaatgcaaag gaaaaaaata ttttccaaag tccatgtgaa     120
attgtctccc atttttttgg cttttgaggg ggttcagttt gggttgcttg tctgtttccg     180
ggttgggggg aaagttggtt gggtgggagg gagccaggtt gggatggagg gagtttacag     240
gaagcagaca gggccaacgt cg                                              262
```

<210> SEQ ID NO 237
<211> LENGTH: 372
<212> TYPE: DNA
<213> ORGANISM: Homo sapien

<400> SEQUENCE: 237

```
agcgtggtcg cggccgaggt cctcaccaga ggtgccacct acaacatcat agtggaggca       60
ctgaaagacc agcagaggca taaggttcgg gaagaggttg ttaccgtggg caactctgtc     120
aacgaaggct tgaaccaacc tacggatgac tcgtgctttg accctacac agtttcccat      180 tatgccgttg gagatgagtg ggaacgaatg tctgaatcag gctttaaact gttgtgccag     240
tgcttaggct ttggaagtgg tcatttcaga tgtgattcat ctagatggtg ccatgacaat     300
ggtgtgaact acaagattgg agagaagtgg gaccgtcagg gagaaaatgg acctgcccgg     360
gcggccgctc ga                                                          372
```

<210> SEQ ID NO 238
<211> LENGTH: 372
<212> TYPE: DNA
<213> ORGANISM: Homo sapien

<400> SEQUENCE: 238

```
tcgagcggcc gcccgggcag gtccatttc tccctgacgg tcccacttct ctccaatctt       60
gtagttcaca ccattgtcat ggcaccatct agatgaatca catctgaaat gaccacttcc     120
aaagcctaag cactggcaca acagtttaaa gcctgattca gacattcgtt cccactcatc     180
tccaacggca taatgggaaa ctgtgtaggg gtcaaagcac gagtcatccg taggttggtt     240
caagccttcg ttgacagagt tgcccacggt aacaacctct tcccgaacct tatgcctctg     300
ctggtctttc agtgcctcca ctatgatgtt gtaggtggca cctctggtga ggacctcggc     360
cgcgaccacg ct                                                          372
```

<210> SEQ ID NO 239
<211> LENGTH: 720
<212> TYPE: DNA
<213> ORGANISM: Homo sapien
<220> FEATURE:
<221> NAME/KEY: misc_feature
<222> LOCATION: (1)...(720)
<223> OTHER INFORMATION: n = A,T,C or G

<400> SEQUENCE: 239

| | | | | | |
|---|---|---|---|---|---|
| tcgagcggcc | gcccgggcag | gtccaccata | agtcctgata | caaccacgga | tgagctgtca | 60 |
| ggagcaaggt | tgatttcttt | cattggtccg | gtcttctcct | tgggggtcac | ccgcactcga | 120 |
| tatccagtga | gctgaacatt | gggtggtgtc | cactgggcgc | tcaggcttgt | gggtgtgacc | 180 |
| tgagtgaact | tcaggtcagt | tggtgcagga | atagtggtta | ctgcagtctg | aaccagaggc | 240 |
| tgactctctc | cgcttggatt | ctgagcatag | acactaacca | catactccac | tgtgggctgc | 300 |
| aagccttcaa | tagtcatttc | tgtttgatct | ggacctgcag | ttttagtttt | tgttggtcct | 360 |
| ggtccatttt | tgggagtggt | ggttactctg | taaccagtaa | caggggaact | tgaaggcagc | 420 |
| cacttgacac | taatgctgtt | gtcctgaaca | tcggtcactt | gcatctggga | tggtttgnca | 480 |
| atttctgttc | ggtaattaat | ggaaattggc | ttgctgcttg | cggggctgtc | tccacggcca | 540 |
| gtgacagcat | acacagngat | ggnatnatca | actccaagtt | taaggccctg | atggtaactt | 600 |
| taaacttgct | cccagccagn | gaacttccgg | acagggtatt | tcttctggtt | ttccgaaagn | 660 |
| gancctggaa | tnntctcctt | ggancagaag | gancntccaa | aacttgggcc | ggaaccccctt | 720 |

<210> SEQ ID NO 240
<211> LENGTH: 691
<212> TYPE: DNA
<213> ORGANISM: Homo sapien
<220> FEATURE:
<221> NAME/KEY: misc_feature
<222> LOCATION: (1)...(691)
<223> OTHER INFORMATION: n = A,T,C or G

<400> SEQUENCE: 240

| | | | | | |
|---|---|---|---|---|---|
| agcgtggtcg | cggccgaggt | cctgtcagag | tggcactggt | agaagttcca | ggaaccctga | 60 |
| actgtaaggg | ttcttcatca | gtgccaacag | gatgacatga | aatgatgtac | tcagaagtgt | 120 |
| cctggaatgg | ggcccatgag | atggttgtct | gagagagagc | ttcttgtcct | acattcggcg | 180 |
| ggtatggtct | tggcctatgc | cttatggggg | tggccgttgt | gggcggtgtg | gtccgcctaa | 240 |
| aaccatgttc | ctcaaagatc | atttgttgcc | caacactggg | ttgctgacca | gaagtgccag | 300 |
| gaagctgaat | accatttcca | gtgtcatacc | caggtgggt | gacgaaaggg | gtcttttgaa | 360 |
| ctgtggaagg | aacatccaag | atctctggtc | catgaagatt | ggggtgtgga | agggttacca | 420 |
| gttggggaag | ctcgtctgtc | tttttccttc | caatcagggg | ctcgctcttc | tgattattct | 480 |
| tcagggcaat | gacataaatt | gtatattcgg | ttcccggttc | caggccagta | atagtagcct | 540 |
| cttgtgacac | caggcggggc | ccanggacca | cttctctggg | angagaccca | gcttctcata | 600 |
| cttgatgatg | taacccggta | atcctgcacg | tggcggctgn | catgatacca | ncaaggaatt | 660 |
| gggtgnggng | gacctgcccg | gcggccctcn | a | | | 691 |

<210> SEQ ID NO 241
<211> LENGTH: 808
<212> TYPE: DNA
<213> ORGANISM: Homo sapien
<220> FEATURE:

<220> FEATURE:
<221> NAME/KEY: misc_feature
<222> LOCATION: (1)...(808)
<223> OTHER INFORMATION: n = A,T,C or G

<400> SEQUENCE: 241

```
agcgtggtcg cggccgaggt ctgggatgct cctgctgtca cagtgagata ttacaggatc    60
acttacggag aaacaggagg aaatagccct gtccaggagt tcactgtgcc tgggagcaag   120
tctacagcta ccatcagcgg ccttaaacct ggagttgatt ataccatcac tgtgtatgct   180
gtcactggcc gtggagacag ccccgcaagc agcaagccaa tttccattaa ttaccgaaca   240
gaaattgaca aaccatccca gatgcaagtg accgatgttc aggacaacag cattagtgtc   300
aagtggctgc cttcaagttc ccctgttact ggttacagag taaccaccac tcccaaaaat   360
ggaccaggac caacaaaaac taaaactgca ggtccagatc aaacagaaat gactattgaa   420
ggcttgcagc ccacagtgga gtatgtggtt agtgtctatg ctcagaatcc aagcggagag   480
agtcagcctc tggttcagac tgcagtaacc actattcctg caccaactga cctgaagttc   540
actcaggtca cacccacaag cctgagccgc cagtggacac cacccaatgt tcactcactg   600
gatatcgagt gcgggtgacc cccaaggaga agacccggac ccatgaaaga aatcaacctt   660
gctcctgaca gctcatccgn gggtgtatca ggacttatgg gggactgccc cggcnggccg   720
ntcgaaancg aattntgaaa tttccttcnc actgggnggc gnttcgagct tncttntana   780
nggcccaatt cncctntagn gggtcgtn                                       808
```

<210> SEQ ID NO 242
<211> LENGTH: 26
<212> TYPE: DNA
<213> ORGANISM: Homo sapien
<220> FEATURE:
<221> NAME/KEY: misc_feature
<222> LOCATION: (1)...(26)
<223> OTHER INFORMATION: n = A,T,C or G

<400> SEQUENCE: 242

```
agcgtggtcg cggccgaggt cnagga                                          26
```

<210> SEQ ID NO 243
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 243

```
tcgagcggcc gcccgggcag gtccaccaca cccaattcct tgctggtatc atggcagccg    60
ccacgtgcca ggattaccgg ctacatcatc aagtatgaga agcctgggtc tcctcccaga   120
gaagtggtcc ctcggccccg ccctggtgtc acagaggcta ctattactgg cctggaaccg   180
ggaaccgaat atacaattta tgtcattgcc ctgaagaata tcagaagag cgagcccctg   240
attggaagga aaaagacaga cgagcttccc caactggtaa cccttccaca ccccaatctt   300
catggaccag agatcttgga tgttccttcc acagttcaaa gaccccttt cgtcacccac   360
cctgggtatg acactggaaa tggtattcag cttcctggca cttctggtca gcaacccagt   420
gttgggcaac aaatgatctt tgaggaacat ggttttaggc ggaccacacc gcccacaacg   480
ggcaccccca taaggnatag gccaagacca taccccgccg aatgtaggac aagaagctct   540
ntctcaacaa ccatctcatg ggccccattc caggacactt ctgagtacat catttcatgt   600
```

```
catcctggtg ggcacttgat gaanaaccct tacagttcag ggttcctgga acttctacca    660
gngccacttc tgacagganc ttgggcgnga ccaccct                              697

<210> SEQ ID NO 244
<211> LENGTH: 373
<212> TYPE: DNA
<213> ORGANISM: Homo sapien

<400> SEQUENCE: 244
agcgtggtcg cggccgaggt ccatttctc cctgacggtc ccacttctct ccaatcttgt      60
agttcacacc attgtcatgg caccatctag atgaatcaca tctgaaatga ccacttccaa    120
agcctaagca ctggcacaac agtttaaagc ctgattcaga cattcgttcc cactcatctc    180
caacggcata atgggaaact gtgtagggt caaagcacga gtcatccgta ggttggttca    240
agccttcgtt gacagagttg cccacggtaa caacctcttc ccgaacctta tgcctctgct    300
ggtctttcag tgcctccact atgatgttgt aggtggcacc tctggtgagg acctgcccgg    360
gcggcccgct cga                                                       373

<210> SEQ ID NO 245
<211> LENGTH: 307
<212> TYPE: DNA
<213> ORGANISM: Homo sapien

<400> SEQUENCE: 245
agcgtggtcg cggccgaggt gtgccccaga ccaggaattc ggcttcgacg ttggccctgt     60
ctgcttcctg taaactccct ccatcccaac ctggctccct cccacccaac caactttccc    120 cccaaccccgg aaacagacaa gcaacccaaa ctgaaccccc tcaaaagcca aaaaaatggg   180
agacaatttc acatggactt tggaaaatat tttttttcctt tgcattcatc tctcaaactt    240 agttttatc tttgaccaac cgaacatgac caaaaaccaa aagtgacctg cccgggcggc    300
cgctcga                                                              307

<210> SEQ ID NO 246
<211> LENGTH: 372
<212> TYPE: DNA
<213> ORGANISM: Homo sapien

<400> SEQUENCE: 246
tcgagcggcc gcccgggcag gtcctcacca gaggtgccac ctacaacatc atagtggagg     60
cactgaaaga ccagcagagg cataaggttc gggaagaggt tgttaccgtg ggcaactctg    120
tcaacgaagg cttgaaccaa cctacggatg actcgtgctt tgaccctac acagtttccc     180 attatgccgt tggagatgag tgggaacgaa tgtctgaatc aggctttaaa ctgttgtgcc    240
agtgcttagg ctttggaagt ggtcatttca gatgtgattc atctagatgg tgccatgaca    300
atggtgtgaa ctacaagatt gggagagaagt gggaccgtca gggagaaaat ggacctcggc    360
cgcgaccacg ct                                                       372

<210> SEQ ID NO 247
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G
```

```
<400> SEQUENCE: 247
tcgagcggcc gcccgggcag gtaccggggt ggtcagcgag gagccattca cactgaactt      60
caccatcaac aacctgcggt atgaggagaa catgcagcac cctggctcca ggaagttcaa     120
caccacggag agggtccttc agggcctgct caggtccctg ttcaagagca ccagtgttgg     180
ccctctgtac tctggctgca gactgacttt gctcagacct gagaaacatg gggcagccac     240
tggagtggac gccatctgca ccctccgcct tgatcccact ggtnctggac tggacanana     300
gcggctatac ttgggagctg anccnaacct ttggcggnga cnccnctt                  348

<210> SEQ ID NO 248
<211> LENGTH: 304
<212> TYPE: DNA
<213> ORGANISM: Homo sapien
<220> FEATURE:
<221> NAME/KEY: misc_feature
<222> LOCATION: (1)...(304)
<223> OTHER INFORMATION: n = A,T,C or G

<400> SEQUENCE: 248
gaggactggc tcagctccca gtatagccgc tctctgtcca gtccaggacc agtgggatca      60
aggcggaggg tgcagatggc gtccactcca gtggctgccc catgtttctc aagtctgagc     120
aaagncagtc tgcagccaga gtacagaggg ccaacactgg tgctcttgaa cagggacctg     180
agcaggccct gaaggaccct ctccgtggtg ttgaacttcc tggagccagg gtgctgcatg     240
ttctcctcat accgcaggtt gttgatggtg aagttcagtg tgaatggctc ctcgctgacc     300
accc                                                                  304

<210> SEQ ID NO 249
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 249
agcgtggtcg cggccgaggt ccaccacacc caattccttg ctggtatcat ggcagccgcc      60
acgtgccagg attaccggct acatcatcaa gtatgagaag cctgggtctc ctcccagaga     120
agtggtccct cggccccgcc ctggtgtcac agaggctact attactgcc tggaaccggg      180 aaccgaatat acaatttatg tcattgccct gaagaataat cagaagagcg agcccctgat     240
tggaaggaaa aagacagacg agcttcccca actggtaacc cttccacacc ccaatcttca     300
tggaccanan ancttggatn gtcctttcac nggttnaaaa aacccttttc gcccccccac     360 cttgggggatt aaccttggga aanggggatt tnaccnttcc                          400

<210> SEQ ID NO 250
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 250
tcgagcggcc gcccgggcag gtcctgtcag agtggcactg gtagaagttc caggaaccct      60
gaactgtaag ggttcttcat cagtgccaac aggatgacat gaaatgatgt actcagaagt     120
```

```
gtcctggaat ggggcccatg agatggttgt ctgagagaga gcttcttgtc ctacattcgg      180
cgggtatggt cttggcctat gccttatggg ggtggccgtt gtgggcggtg tggtccgcct      240
aaaaccatgt tcctcaaaga tcatttgttg cccaacactg ggttgctgac cagaagtgcc      300
aggaagctga ataccatttc cagtgtcata cccagggngg gtgaccaaag ggggtcnttt      360
ngacctggng aaaggaacca tccaaaanct ctgncccatg                            400
```

<210> SEQ ID NO 251
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 251

```
agcgtggncg cggccgaggt ctgaggatgt aaactcttcc caggggaagg ctgaagtgct       60
gaccatggtg ctactgggtc cttctgagtc agatatgtga ctgatgngaa ctgaagtagg      120
tactgtagat ggtgaagtct gggtgtccct aaatgctgca tctccagagc cttccatcat      180
taccgtttct tcttttgcta tgggatgaga cactgttgag tattctctaa agtcaccact      240
gaaatcttcc tccaaaggaa aacctgtgga aaagccccctt atttctgccc cataatttgg      300
ttctcctaat cnctctgaaa tcactatttc cctggaangt ttgggaaaaa nngggcnacc      360
tgncantgga aantggatan aaagatccca ccatttttacc caacnagcag aaagtgggaa      420
nggtaccgaa aagctccaag taanaaaaag gagggaagta aaggtcaagt gggcaccagt      480
ttcaaacaaa actttcccca aactatanaa ccca                                 514
```

<210> SEQ ID NO 252
<211> LENGTH: 501
<212> TYPE: DNA
<213> ORGANISM: Homo sapien
<220> FEATURE:
<221> NAME/KEY: misc_feature
<222> LOCATION: (1)...(501)
<223> OTHER INFORMATION: n = A,T,C or G

<400> SEQUENCE: 252

```
aagcggccgc ccgggcaggn ncagnagtgc cttcgggact gggntcaccc ccaggtctgc       60
ggcagttgtc acagcgccag ccccgctggc ctccaaagca tgtgcaggag caaatggcac      120
cgagatattc cttctgccac tgttctccta cgtggtatgt cttcccatca tcgtaacacg      180
ttgcctcatg agggtcacac ttgaattctc cttttccgtt cccaagacat gtgcagctca      240
tttggctggc tctatagttt ggggaaagtt tgttgaaact gtgccactga cctttacttc      300
ctccttctct actggagctt tccgtacctt ccacttctgc tgntggnaaa aagggnggaa      360
cntcttatca atttcattgg acagtancccc nctttctncc caaaacatnc aagggaaaat      420
attgattncn agagcggatt aaggaacaac ccnaattatg ggggccagaa ataaagggg      480 cttttccaca ggtnttttcc t                                               501
```

<210> SEQ ID NO 253
<211> LENGTH: 226
<212> TYPE: DNA
<213> ORGANISM: Homo sapien

<400> SEQUENCE: 253

-continued

```
tcgagcggcc gcccgggcag gtctgcaggc tattgtaagt gttctgagca catatgagat      60
aacctgggcc aagctatgat gttcgatacg ttaggtgtat taaatgcact tttgactgcc     120
atctcagtgg atgacagcct tctcactgac agcagagatc ttcctcactg tgccagtggg     180
caggagaaag agcatgctgc gactggacct cggccgcgac cacgct                    226
```

<210> SEQ ID NO 254
<211> LENGTH: 226
<212> TYPE: DNA
<213> ORGANISM: Homo sapien

<400> SEQUENCE: 254

```
agcgtggtcg cggccgaggt ccagtcgcag catgctcttt ctcctgccca ctggcacagt      60
gaggaagatc tctgctgtca gtgagaaggc tgtcatccac tgagatggca gtcaaaagtg     120
catttaatac acctaacgta tcgaacatca tagcttggcc caggttatct catatgtgct     180
cagaacactt acaatagcct gcagacctgc ccgggcggcc gctcga                    226
```

<210> SEQ ID NO 255
<211> LENGTH: 427
<212> TYPE: DNA
<213> ORGANISM: Homo sapien
<220> FEATURE:
<221> NAME/KEY: misc_feature
<222> LOCATION: (1)...(427)
<223> OTHER INFORMATION: n = A,T,C or G

<400> SEQUENCE: 255

```
cgagcggccg cccgggcagg tccagactcc aatccagaga accaccaagc cagatgtcag      60
aagctacacc atcacaggtt tacaaccagg cactgactac aagatctacc tgtacacctt     120
gaatgacaat gctcggagct cccctgtggt catcgacgcc tccactgcca ttgatgcacc     180
atccaacctg cgtttcctgg ccaccacacc caattccttg ctggtatcat ggcagccgcc     240
acgtgccagg attaccggct acatcatcaa gtatgagaag cctgggtctc ctcccagaga     300
agtggtccct cggccccgcc ctggtgncac agaagctact attactgcc tggaaccggg      360 aaccgaatat acaatttatg tcattgccct gaagaataat canaagagcg agcccctgat     420
tggaagg                                                               427
```

<210> SEQ ID NO 256
<211> LENGTH: 535
<212> TYPE: DNA
<213> ORGANISM: Homo sapien
<220> FEATURE:
<221> NAME/KEY: misc_feature
<222> LOCATION: (1)...(535)
<223> OTHER INFORMATION: n = A,T,C or G

<400> SEQUENCE: 256

```
agcgtggtcg cggccgaggt cctgtcagag tggcactggt agaagttcca ggaaccctga      60
actgtaaggg ttcttcatca gtgccaacag gatgacatga aatgatgtac tcagaagtgt     120
cctggaatgg ggcccatgag atggttgtct gagagagagc ttcttgtcct gtctttttcc     180
ttccaatcag gggctcgctc ttctgattat tcttcagggc aatgacataa attgtatatt     240
cggttccccg ttcaggcca gtaatagtag cctctgtgac accagggcgg ggccgaggga     300
ccacttctct gggaggagac ccaggcttct catacttgat gatgtancgg gtaatcctgg     360
caccgtggcg gctgccatga taccagcaag gaattgggtg tggtggccaa gaaacgcagg     420
ttggatggtg catcaatggc agtggaggcg tcgatnacca caggggagct ccgancattg     480
```

```
tcattcaagg tggacaggta gaatcttgta atcaggtgcc tggtttgtaa acctg        535
```

<210> SEQ ID NO 257
<211> LENGTH: 544
<212> TYPE: DNA
<213> ORGANISM: Homo sapien
<220> FEATURE:
<221> NAME/KEY: misc_feature
<222> LOCATION: (1)...(544)
<223> OTHER INFORMATION: n = A,T,C or G

<400> SEQUENCE: 257

```
tcgagcggcc gcccgggcag gtttcgtgac cgtgacctcg aggtggacac caccctcaag    60
agcctgagcc agcagatcga gaacatccgg agcccagagg gcagccgcaa gaaccccgcc   120
cgcacctgcc gtgacctcaa gatgtgccac tctgactgga gagtggaga gtactggatt    180
gaccccaacc aaggctgcaa cctggatgcc atcaaagtct tctgcaacat ggagactggt   240
gagacctgcg tgtaccccac tcagcccagt gtggcccaga gaactggta catcagcaag    300
aaccccaagg acaagaagca tgtctggttc ggcgaaagca tgaccgatgg attccagttc   360
gagtatggcg ccagggctc cgaccctgcc gatgtggacc tcgccgcga ccacgctaag     420
cccgaattcc agcacactgg cggccgttac tagtgggatc cgagcttcgg taccaagctt   480
ggcgtaatca tgggncatag ctgtttcctg ngtgaaaatg gtattccgct tcacaatttc   540
ccac                                                                544
```

<210> SEQ ID NO 258
<211> LENGTH: 418
<212> TYPE: DNA
<213> ORGANISM: Homo sapien

<400> SEQUENCE: 258

```
agcgtggtcg cggccgaggt ccacatcggc agggtcggag ccctggccgc catactcgaa    60
ctggaatcca tcggtcatgc tctcgccgaa ccagacatgc ctcttgtcct tggggttctt   120
gctgatgtac cagttcttct gggccacact gggctgagtg gggtacacgc aggtctcacc   180
agtctccatg ttgcagaaga cttttgatggc atccaggttg cagccttggt tggggtcaat   240
ccagtactct ccactcttcc agtcagagtg gcacatcttg aggtcacggc aggtgcgggc   300
ggggttcttg cggctgccct ctgggctccg gatgttctcg atctgctggc tcaagctctt   360
gaagggtggt gtccacctcg aggtcacggt cacgaaacct gcccgggcgg ccgctcga     418
```

<210> SEQ ID NO 259
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 259

```
agcgtggtcg cggccgaggt caagaacccc gcccgcacct gccgtgacct caagatgtgc    60
cactctgact ggaagagtgg agagtactgg attgacccca accaaggctg caacctggat   120
gccatcaaag tcttctgcaa catggagact ggtgagacct gcgtgtaccc cactcagccc   180
agtgtggccc agaagaactg gtacatcagc aagaacccca aggacaagag gcatgtctgg   240
ttcggcgaga gcatgaccga tggattccag ttcgagtatg gcggccaggg ctccgaccct   300
```

```
gccgatgtgg acctgcccgn gccggnccgc tcgaaaagcc cnaatttcca gncacacttg    360
gccggccgtt actactg                                                  377
```

<210> SEQ ID NO 260
<211> LENGTH: 332
<212> TYPE: DNA
<213> ORGANISM: Homo sapien

<400> SEQUENCE: 260

```
tcgagcggcc gcccgggcag gtccacatcg gcagggtcgg agccctggcc gccatactcg    60
aactggaatc catcggtcat gctctcgccg aaccagacat gcctcttgtc cttggggttc   120
ttgctgatgt accagttctt ctgggccaca ctgggctgag tggggtacac gcaggtctca   180
ccagtctcca tgttgcagaa gactttgatg gcatccaggt tgcagccttg gttggggtca   240
atccagtact ctccactctt ccagtcagag tggcacatct tgaggtcacg gcaggtgcgg   300
gcggggttct tgacctcggc cgcgaccacg ct                                 332
```

<210> SEQ ID NO 261
<211> LENGTH: 94
<212> TYPE: DNA
<213> ORGANISM: Homo sapien

<400> SEQUENCE: 261

```
cgagcggccg cccgggcagg tccccccccct tttttttttt tttttttttt tttttttttt    60
tttttttttt tttttttttt tttttttttt tttt                                94
```

<210> SEQ ID NO 262
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 262

```
agcgtggtcg cggccgaggt ctggcattcc ttcgacttct ctccagccga gcttcccaga    60
acatcacata tcactgcaaa aatagcattg catacatgga tcaggccagt ggaaatgtaa   120
agaaggccct gaagctgatg gggtcaaatg aaggtgaatt caaggctgaa ggaaatagca   180
aattcaccta cacagttctg gaggatggtt gcacgaaaca cactgggaa tggagcaaaa   240 cagtctttga atatcgaaca cgcaaggctg tgagactacc tattgtagat attgcaccct   300
atgacattgg tggtcctgat caagaatttg gtgtggacgt tggccctgtt tgcttttat    360 aaaccaaact ctatctgaaa tcccaacaaa aaaaatttaa ctccatatgt gntcctcttg   420
ttctaatctt ggcaaccagt gcaagtgacc gacaaaattc cagttattta tttccaaaat   480
gtttggaaac agtataattt gacaaagaaa aaaggatact tctctttttt tggctggtcc   540
accaaataca attcaaaagg cttttttggtt ttatttttt anccaattcc aatttcaaaa   600
tgtctcaatg gngcttataa taaaataaac tttcaccctt nttttntgat               650
```

<210> SEQ ID NO 263
<211> LENGTH: 573
<212> TYPE: DNA
<213> ORGANISM: Homo sapien
<220> FEATURE:
<221> NAME/KEY: misc_feature
<222> LOCATION: (1)...(573)
<223> OTHER INFORMATION: n = A,T,C or G

<400> SEQUENCE: 263

| | | | | | |
|---|---|---|---|---|---|
| agcgtggtcg | cggccgaggt | ctgggatgct | cctgctgtca | cagtgagata | ttacaggatc | 60 |
| acttacggag | aaacaggagg | aaatagccct | gtccaggagt | tcactgtgcc | tgggagcaag | 120 |
| tctacagcta | ccatcagcgg | ccttaaacct | ggagttgatt | ataccatcac | tgtgtatgct | 180 |
| gtcactggcc | gtggagacag | ccccgcaagc | agcaagccaa | tttccattaa | ttaccgaaca | 240 |
| gaaattgaca | aaccatccca | gatgcaagtg | accgatgttc | aggacaacag | cattagtgtc | 300 |
| aagtggctgc | cttcaagttc | ccctgttact | ggttacagaa | gtaaccacca | ctcccaaaaa | 360 |
| tggaccagga | ccaacaaaaa | ctaaaactgc | aggtccagat | caaacagaaa | atggactatt | 420 |
| gaaggcttgc | agcccacagt | ggaagtatgt | ggntaggngt | ctatgctcag | aatcccaagc | 480 |
| cggagaaagt | cagccttctg | gtttagactg | cagtaaccaa | cattgatcgc | cctaaaggac | 540 |
| tggncattca | cttggatggt | ggatgtccaa | ttc | | | 573 |

```
<210> SEQ ID NO 264
<211> LENGTH: 550
<212> TYPE: DNA
<213> ORGANISM: Homo sapien
<220> FEATURE:
<221> NAME/KEY: misc_feature
<222> LOCATION: (1)...(550)
<223> OTHER INFORMATION: n = A,T,C or G
```

<400> SEQUENCE: 264

| | | | | | |
|---|---|---|---|---|---|
| tcgagcggcc | gcccgggcag | gtccttgcag | ctctgcagng | tcttcttcac | catcaggtgc | 60 |
| agggaatagc | tcatggattc | catcctcagg | gctcgagtag | gtcaccctgt | acctggaaac | 120 |
| ttgcccctgt | gggctttccc | aagcaatttt | gatggaatcg | acatccacat | cagngaatgc | 180 |
| cagtccttta | gggcgatcaa | tgttggttac | tgcagtctga | accagaggct | gactctctcc | 240 |
| gcttggattc | tgagcataga | cactaaccac | atactccact | gtgggctgca | agccttcaat | 300 |
| agtcatttct | gtttgatctg | gacctgcagt | tttaagtttt | tggtggtcct | gnccatttt | 360 |
| tgggaagtgg | ggggttactc | tgtaaccagt | aacaggggaa | cttgaaggca | gccacttgac | 420 |
| actaatgctg | ttgtcctgaa | catcggtcac | ttgcatctgg | ggatggtttt | gacaatttct | 480 |
| ggttcggcaa | attaatggaa | attggcttgc | tgcttggcgg | ggctgnctcc | acgggccagt | 540 |
| gacagcatac | | | | | | 550 |

```
<210> SEQ ID NO 265
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G
```

<400> SEQUENCE: 265

| | | | | | |
|---|---|---|---|---|---|
| tcgagcggcc | gcccgggcag | gtccttgcag | ctctgcagtg | tcttcttcac | catcaggtgc | 60 |
| agggaatagc | tcatggattc | catcctcagg | gctcgagtag | gtcaccctgt | acctggaaac | 120 |
| ttgcccctgt | gggctttccc | aagcaatttt | gatggaatcg | acatccacat | cagtgaatgc | 180 |
| cagtccttta | gggcgatcaa | tgttggttac | tgcagtctga | accagaggct | gactctctcc | 240 |
| gcttggattc | tgagcataga | cactaaccac | atactccact | gtgggctgca | agccttcaat | 300 |
| agtcatttct | gtttgatctg | gacctgcagt | tttaagtttt | tgttggncct | gnncatttt | 360 |

```
tggggaaggg gtggttactc ttgtaaccag taacagggga acttgaagca gccacttgac      420
actaatgctg gtggcctgaa catcggtcac ttgcatctgg gatggtttgg tcaatttctg      480
ttcggtaatt aatgggaaat tggcttactg gcttgcgggg gctgtctcca cggncagtga      540
caagcataca caggngatgg gtataatcaa ctccaggttt aaggccnctg atggta          596

<210> SEQ ID NO 266
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 266
agcgtggtcg cggccgaggt ctgggatgct cctgctgtca cagtgagata ttacaggatc      60
acttacggag aaacaggagg aaatagccct gtccaggagt tcactgtgcc tgggagcaag      120
tctacagcta ccatcagcgg ccttaaacct ggagttgatt ataccatcac tgtgtatgct      180
gtcactggcc gtggagacag ccccgcaagc agtaagccaa tttccattaa ttaccgaaca      240
gaaattgaca aaccatccca gatgcaagtg accgatgttc aggacaacag cattagtgtc      300
aagtggctgc cttcaagttc ccctgttact ggttacagag taaccaccac tcccaaaaat      360
gggaccagga ccaacaaaaa actaaaactg canggtccag atcaaacaga aatgactatt      420
gaaggcttgc agcccacagt ggagtatgtg ggttagtgtc tatgctcaga atnccaagcg      480
gagagagtca gcctctggtt cagact                                          506

<210> SEQ ID NO 267
<211> LENGTH: 548
<212> TYPE: DNA
<213> ORGANISM: Homo sapien
<220> FEATURE:
<221> NAME/KEY: misc_feature
<222> LOCATION: (1)...(548)
<223> OTHER INFORMATION: n = A,T,C or G

<400> SEQUENCE: 267
tcgagcggcc gcccgggcag gtcagcgctc tcaggacgtc accaccatgg cctgggctct      60
gctcctcctc accctcctca ctcagggcac agggtcctgg gcccagtctg ccctgactca      120
gcctccctcc gcgtccgggt ctcctggaca gtcagtcacc atctcctgca ctggaaccag      180
cagtgacgtt ggtgcttatg aatttgtctc ctggtaccaa caacacccag gcaaggcccc      240
caaactcatg atttctgagg tcactaagcg gccctcaggg gtccctgatc gcttctctgg      300
ctccaagtct ggcaacacgg cctccctgac cgtctctggg ctccangctg aggatgangc      360
tgattattac tggaagctca tatgcaggca acaacaattg ggtgttcggc ggaagggacc      420
aagctgaccg tnctaaggtc aagcccaagg cttgcccccc tcggtcactc tgttcccacc      480
ctcctctgaa gaagctttca agccaacaan gncacactgg gtgtgtctca taagtggact      540
ttctaccc                                                              548

<210> SEQ ID NO 268
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G
```

<400> SEQUENCE: 268

```
agcgtggtcg cggccgaggt ctgtagcttc tgtgggactt ccactgctca ggcgtcaggc      60
tcaggtagct gctggccgcg tacttgttgt tgctttgntt ggagggtgtg gtggtctcca     120
ctcccgcctt gacggggctg ctatctgcct tccaggccac tgtcacggct cccgggtaga    180
agtcacttat gagacacacc agtgtggcct tgttggcttg aagctcctca gaggagggtg    240
ggaacagagt gaccgagggg gcagccttgg gctgacctag gacggtcagc ttggtccctc    300
cgccgaacac ccaattgttg ttgcctgcat atgagctgca gtaataatca gcctcatcct    360
cagcctggag cccagagacn gtcaagggag gcccgtgttt gccaagactt ggaagccaga    420
naagcgatca gggacccctg agggccgctt tacngacctc aaaaaatcat gaatttgggg    480
ggcctttgcc tgggngttgg ttggtnacca gnaaaacaaa atttcataaa gcaccaacgt    540
cactgctggt ttccagtgca ngaanatggt gaactgaant gtcc                     584
```

<210> SEQ ID NO 269
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 269

```
agcgtggtcg cggccgaggt ccagcatcag gagccccgcc ttgccggctc tggtcatcgc      60
ctttcttttt gtggcctgaa acgatgtcat caattcgcag tagcagaact gccgtctcca    120
ctgctgtctt ataagtctgc agcttcacag ccaatggctc ccatatgccc agttccttca    180
tgtccaccaa agtaccgtc tcaccattta caccccaggt ctcacagttc tctgggtgt      240
gcttggcccg aagggaggta agtanacgga tggtgctggc cccacagttc tggatcaggg    300
tacgaggaat gacctctagg gcctgggcna caagccctgt atggacctgc ccgggcgggc    360
ccgctcga                                                             368
```

<210> SEQ ID NO 270
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 270

```
tcgagcggcc gcccgggcag gtccatacag ggctgttgcc caggccctag aggncattcc      60
ttgtaccctg atccagaact gtgggaccag caccatccgt ctacttacct cccttcgggc    120
caagcacacc caggagaact gtgagacctg gggtgtaaat ggngagacgg gtactttggt    180
ggacatgaag gaactgggca tatgggagcc attggctgng aagctgcana cttataagac    240
agcagtggag acggcagttc tgctactgcg aattgatgac atcgtttcag gccacaaaaa    300
gaaaggcgat gaccanagcc ggcaaggcgg ggcttcctga tgctggacct cggccgccga    360
ccacgctt                                                             368
```

<210> SEQ ID NO 271
<211> LENGTH: 424
<212> TYPE: DNA

```
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 271
agcgtggtcg cggccgaggt ccactagagg tctgtgtgcc attgcccagg cagagtctct      60
gcgttacaaa ctcctaggag ggcttgctgt gcggagggcc tgctatggtg tgctgcggtt     120
catcatggag agtggggcca aaggctgcga ggttgtggtg tctgggaaac tccgaggaca     180
gagggctaaa tccatgaagt ttgtggatgg cctgatgatc cacagcggag accctgttaa     240
ctactacgtt gacactgctg tgcgccacgt gttgctcana caggtgtgtgc tgggcatcaa     300 ggtgaagatc atgctgccct gggacccanc tggcaaaaat ggcccttaaa aaccccttgc     360
cntgaccacg tgaaccattt gtgngaaccc caagatgaan atacttgccc accaccccccc    420 attc                                                                  424

<210> SEQ ID NO 272
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 272
tcgagcggcc gcccgggcag gtctgccaag gagaccctgt tatgctgtgg ggactggctg      60
gggcatggca gcggctctg gcttcccacc cttctgttct gagatggggg tggtgggcag     120
tatctcatct ttgggttcca caatgctcac gtggtcaggc aggggcttct tagggccaat    180
cttaccagtt gggtcccagg gcagcatgat cttcaccttg atgcccagca caccctgtct    240
gagcaacacg tggcgcacag cagtgtcaac gtagtagtta acagggtctc cgctgtggat    300
catcaggcca tccacaaact tcatggattt agccctctgt cctcggagtt tcccaaaaca    360
ccacaacctc gccagccttt gggccccact tcttcatgaa tgaaaccgca gcacaccatt    420
ancaaggccc ttccgcacag gnaagcccct cctaaggagt tttgtaaacg caaaaaactc    480
ttgcctgggg caaatgggca cacagacctn tantnggacc ttggnccgcg aaccaccgct    540
t                                                                    541

<210> SEQ ID NO 273
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 273
agcgtggtcg cggccgaggt ctggccctcc tggcaaggct ggtgaagatg gtcaccctgg      60
aaaacccgga cgacctggtg agagaggagt tgttggacca cagggtgctc gtggtttccc     120
tggaactcct ggacttcctg gcttcaaagg cattagggga cacaatggtc tggatggatt    180
gaagggacag cccggtgctc ctggtgtgaa gggtgaacct ggngcccctg gtgaaaatgg    240
aactccaggt caaacaggag cccgngggct tcctggngag agaggacgtg ttggtgcccc    300
tggcccanac ctgcccgggc ggccgctcna aaagccgaaa tccagnacac tggcggccgn    360
```

```
tactantgga atccgaactt cggtaccaaa gcttggccgt aatcatggcc atagcttgtt      420
ccctggggng gaaattggta ttccgctncc aattccacac aacataccga acccggaaag      480
cattaaagtg taaaagccct ggggggggcct aaatgangtg agcntaactc ncatttaatt     540
ggcgttgcgc ttcactgccc cgcttttcca gtccgggna                             579
```

<210> SEQ ID NO 274
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 274

```
tcgagcggcc gcccgggcag gtctgggcca ggggcaccaa cacgtcctct ctcaccagga      60
agcccacggg ctcctgtttg acctggagtt ccatttttcac caggggcacc aggttcaccc    120
ttcacaccag gagcaccggg ctgtcccttc aatccatcca gaccattgtg nccctaatg     180 cctttgaagc caggaagtcc aggagttcca gggaaaccac gagcaccctg tggtccaaca    240
actcctctct caccaggtcg tccgggtttt ccagggtgac catcttcacc agccttgcca    300
ggagggccag acctcggccg cgaccacgct                                      330
```

<210> SEQ ID NO 275
<211> LENGTH: 97
<212> TYPE: DNA
<213> ORGANISM: Homo sapien
<220> FEATURE:
<221> NAME/KEY: misc_feature
<222> LOCATION: (1)...(97)
<223> OTHER INFORMATION: n = A,T,C or G

<400> SEQUENCE: 275

```
ancgtggtcg cggccgaggt cctcaccaga ggtgncacct acaacatcat agtggaggca      60
ctgaaagacc ancagaggca taaggttcgg gaagagg                               97
```

<210> SEQ ID NO 276
<211> LENGTH: 610
<212> TYPE: DNA
<213> ORGANISM: Homo sapien
<220> FEATURE:
<221> NAME/KEY: misc_feature
<222> LOCATION: (1)...(610)
<223> OTHER INFORMATION: n = A,T,C or G

<400> SEQUENCE: 276

```
tcgagcggcc gcccgggcag gtccattttc tccctgacgg tcccacttct ctccaatctt      60
gtagttcaca ccattgtcat ggcaccatct agatgaatca catctgaaat gaccacttcc    120
aaagcctaag cactggcaca acagtttaaa gcctgattca gacattcgtt cccactcatc    180
tccaacggca taatgggaaa ctgtgtaggg gtcaaagcac gagtcatccg taggttggtt    240
caagccttcg ttgacagagt tgtccacggt aacaacctct tcccgaacct tatgcctctg    300
ctggtctttc agtgcctcca ctatgatgtt gtaggtggca cctctggtga ggacctcngn    360
ccngaacaac gcttaagccc gnattctgca gaataatccc atcacacttg gcggccgctt    420
cgancatgca tcntaaaagg ggccccaatt tcccccttat aagngaaacc gtatttncca    480
atttcactgg ncccgccgnt tttacaaacg ncggtgaact ggggaaaaac cctggcggtt    540
```

| | | |
|---|---|---|
| acccaacttt aatcgccntt ggcagcacaa tccccccttt tcgnccancn tgggcgtaaa | 600 | |
| taaccgaaaa | 610 | |

<210> SEQ ID NO 277
<211> LENGTH: 38
<212> TYPE: DNA
<213> ORGANISM: Homo sapien
<220> FEATURE:
<221> NAME/KEY: misc_feature
<222> LOCATION: (1)...(38)
<223> OTHER INFORMATION: n = A,T,C or G

<400> SEQUENCE: 277

| | | |
|---|---|---|
| ancgnggtcg cggccgangt nttttttctt nttttttt | 38 | |

<210> SEQ ID NO 278
<211> LENGTH: 443
<212> TYPE: DNA
<213> ORGANISM: Homo sapien
<220> FEATURE:
<221> NAME/KEY: misc_feature
<222> LOCATION: (1)...(443)
<223> OTHER INFORMATION: n = A,T,C or G

<400> SEQUENCE: 278

| | | |
|---|---|---|
| agcgtggtcg cggccgaggt ctgaggttac atgcgtggtg gtggacgtga gccacgaaga | 60 | |
| ccctgaggtc aagttcaact ggtacgtgga cggcgtggag gtgcataatg ccaagacaaa | 120 | |
| gccgcgggag gagcagtaca acagcacgta ccgggnggtc agcgtcctca ccgtcctgca | 180 | |
| ccagaattgg ttgaatggca aggagtacaa gngcaaggtt tccaacaaag ccntcccagc | 240 | |
| ccccntcgaa aaaccatttt ccaaagccaa agggcagccc cgagaaccac aggtgtacac | 300 | |
| cctgccccca tcccgggagg aaaagancaa naaccnggtt cagccttaac ttgcttggtc | 360 | |
| naangctttt tatcccaacg nacttccccc ntggaantgg gaaaaaccaa tgggccaanc | 420 | |
| cgaaaaacaa ttacaanaac ccc | 443 | |

<210> SEQ ID NO 279
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G

<400> SEQUENCE: 279

| | | |
|---|---|---|
| tcgagcggcc gcccgggcag gtgtcggagt ccagcacggg aggcgtggtc ttgtagttgt | 60 | |
| tctccggctg cccattgctc tcccactcca cggcgatgtc gctgggatag aagcctttga | 120 | |
| ccaggcaggt caggctgacc tggttcttgg tcatctcctc ccgggatggg ggcagggtga | 180 | |
| acacctgggg ttctcggggc ttgcccttg gttttgaana tggttttctc gatggggct | 240 | |
| ggaagggctt tgttgnaaac cttgcacttg actccttgcc attcacccag ncctggngca | 300 | |
| ggacggngag gacnctnacc acacggaacc gggctggtgg actgctcc | 348 | |

<210> SEQ ID NO 280
<211> LENGTH: 149
<212> TYPE: DNA
<213> ORGANISM: Homo sapien
<220> FEATURE:
<221> NAME/KEY: misc_feature
<222> LOCATION: (1)...(149)
<223> OTHER INFORMATION: n = A,T,C or G

```
<400> SEQUENCE: 280
agcgtggtcg cggacgangt cctgtcagag tggnactggt agaagttcca ngaaccctga      60
actgtaaggg ttcttcatca gtgccaacag gatgacatga aatgatgtac tcagaagngn     120
cctggaatgg ggcccatgan atggttgcc                                        149

<210> SEQ ID NO 281
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 281
tcgagcggcc gcccgggcag gtccaccaca cccaattcct tgctggtatc atggcagccg      60
ccacgtgcca ggattaccgg ctacatcatc aagtatgaga agcctgggtc tcctcccaga     120
gaagtggtcc ctcggccccg ccctggtgtc acagaggcta ctattactgg cctggaaccg     180
ggaaccgaat atacaattta tgtcattgcc ctgaagaata atcagaagag cgagcccctg     240
attggaagga aaaagacaga cgagcttccc caactggtaa cccttccaca ccccaatctt     300 catgaccag agatcttgga tgttccttcc acagttcaaa agaccccttt cggcaccccc      360
cctgggtatg aacctgggaa aanggnantt aanctttcct ggca                      404

<210> SEQ ID NO 282
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 282
agcgtggtcg cggccgaggt ctgggatgct cctgctgtca cagtgagata ttacaggatc      60
acttacggag aaacaggagg aaatagccct gtccaggagt tcactgtgcc tgggagcaag     120
tctacagcta ccatcagcgg ccttaaacct ggagttgatt ataccatcac tgtgtatgct     180
gtcactggcc gtggagacag ccccgcaagc agcaagccaa tttccattaa ttaccgaaca     240
gaaattgaca aaccatccca gatgcaagtg accgatgttc aggacaacag cattagtgtc     300
aagtggctgc cttcaaggtn ccctggtact gggttacaga ntaaccacca ctcccaaaaa     360
tggaccagga accacaaaaa cttaaactgc agggtccaga tcaaaacaga aatgactatt     420
gaangcttgc agcccacagt gggagtatgn gggtagtgnc tatgcttcag aatccaagcg     480
gaaaaangtc aagccttntg ggttcaa                                         507

<210> SEQ ID NO 283
<211> LENGTH: 325
<212> TYPE: DNA
<213> ORGANISM: Homo sapien
<220> FEATURE:
<221> NAME/KEY: misc_feature
<222> LOCATION: (1)...(325)
<223> OTHER INFORMATION: n = A,T,C or G

<400> SEQUENCE: 283
tcgagcggcc gcccgggcag gtccttgcag ctctgcagtg tcttcttcac catcaggtgc      60
```

-continued

```
agggaatagc tcatggattc catcctcagg gctcgagtag gtcaccctgt acctggaaac    120
ttgcccctgt gggctttccc aagcaatttt gatggaatcg acatccacat cagtgaatgc    180
cagtccttta gggcgatcaa tgttggttac tgcagnctga accagaggct gactctctcc    240
gcttggattc tgagcataga cactaaccac atactccact gtgggctgca anccttcaat    300
aanncatttc tgtttgatct ggacc                                          325
```

<210> SEQ ID NO 284
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 284

```
tcgagcggcc gcccgggcag gtctggtggg gtcctggcac acgcacatgg gggngttgnt    60
ctnatccagc tgcccagccc ccattggcga gtttgagaag gtgtgcagca atgacaacaa    120
naccttcgac tcttcctgcc acttctttgc cacaaagtgc accctggagg gcaccaagaa    180
gggccacaag ctccacctgg actacatcgg gccttgcaaa tacatccccc cttgcctgga    240
ctctgagctg accgaattcc cccttgcgca tgcgggactg gctcaagaac cgtcctggca    300
cccttgtatg anagggatga agacacnacc c                                  331
```

<210> SEQ ID NO 285
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 285

```
agcgtggtcg cggccgaggt ctgtcctaca gtcctcagga ctctactccc tcagcagcgt    60
ggtgaccgtg ccctccagca acttcggcac ccagacctac acctgcaacg tagatcacaa    120
gcccagcaac accaaggtgg acaagagagt tgagcccaaa tcttgtgaca aaactcacac    180
atgcccaccg tgcccagcac ctgaactcct gggggaccg tcagtcttcc tcttccccg    240 catccccctt ccaaacctgc ccgggcggcc gctcgaaagc cgaattccag cacactggcg    300
gccggtacta gtggancena acttggnanc caacctggng gaantaatgg gcataanctg    360 tttctgggggg gaaattggta tccngtttac aattcccnca caacatacga gccggaagca    420
taaaagngta aaagcctggg ggnggcctan tgaagtgaag ctaaactcac attaattngc    480
gttgccgctc actggcccgc ttttccagc                                      509
```

<210> SEQ ID NO 286
<211> LENGTH: 336
<212> TYPE: DNA
<213> ORGANISM: Homo sapien
<220> FEATURE:
<221> NAME/KEY: misc_feature
<222> LOCATION: (1)...(336)
<223> OTHER INFORMATION: n = A,T,C or G

<400> SEQUENCE: 286

```
tcgagcggcc gcccgggcag gtttggaagg gggatgcggg ggaagaggaa gactgacggt    60 cccccccagga gttcaggtgc tgggcacggt gggcatgtgt gagttttgtc acaagatttg    120
```

```
ggctcaactc tcttgtccac cttggtgttg ctgggcttgt gatctacgtt gcaggtgtag    180
gtctgggngc cgaagttgct ggagggcacg gtcaccacgc tgctgaggga gtagagtcct    240
gaggactgta ngacagacct cggccgngac cacgctaagc cgaattctgc agatatccat    300
cacactggcg gccgctccga gcatgcattt tagagg                              336
```

<210> SEQ ID NO 287
<211> LENGTH: 30
<212> TYPE: DNA
<213> ORGANISM: Homo sapien
<220> FEATURE:
<221> NAME/KEY: misc_feature
<222> LOCATION: (1)...(30)
<223> OTHER INFORMATION: n = A,T,C or G

<400> SEQUENCE: 287

```
agcgtggncg cggacganga caacaacccc                                      30
```

<210> SEQ ID NO 288
<211> LENGTH: 316
<212> TYPE: DNA
<213> ORGANISM: Homo sapien
<220> FEATURE:
<221> NAME/KEY: misc_feature
<222> LOCATION: (1)...(316)
<223> OTHER INFORMATION: n = A,T,C or G

<400> SEQUENCE: 288

```
tcgagcggcc gcccgggcag gnccacatcg gcagggtcgg agccctggcc gccatactcg     60
aactggaatc catcggtcat gctcttgccg aaccagacat gcctcttgtc cttggggttc    120
ttgctgatgn accagttctt ctgggccaca ctgggctgag tggggtacac gcaggtctca    180
ccagtctcca tgttgcagaa gactttgatg gcatccaggt tgcagccttg gttggggtca    240
atccagtact ctccactctt ccagtcagag tggcacatct tgaggtcacg gcaggtgcgg    300
gcggggttct tgacct                                                    316
```

<210> SEQ ID NO 289
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 289

```
agcgtggtcg cggccgaggt ccagcctgga gataaggtg aaggtggtgc ccccggactt      60
ccaggtatag ctggacctcg tggtagccct ggtgagagag gtgaaactgg ccctccagga    120
cctgctggtt tccctggtgc tcctggacag aatggtgaac ctggnggtaa aggagaaaga    180
ggggctccgg ntganaaagg tgaaggaggc cctcctgnat tggcaggggc cccangactt    240
agaggtggag ctggcccccc tggccccgaa ggaggaaagg gtgctgctgg tcctcctggg    300
ccacctgg                                                             308
```

<210> SEQ ID NO 290
<211> LENGTH: 324
<212> TYPE: DNA
<213> ORGANISM: Homo sapien
<220> FEATURE:
<221> NAME/KEY: misc_feature
<222> LOCATION: (1)...(324)

<223> OTHER INFORMATION: n = A,T,C or G

<400> SEQUENCE: 290

```
tcgagcggcc gcccgggcag gtctgggcca ggaggaccaa taggaccagt aggacccctt      60
gggccatctt tccctgggac accatcagca cctggaccgc ctggttcacc cttgtcaccc     120
tttggaccag gacttccaag acctcctctt tctccaggca ttccttgcag accaggagta     180
ccancagcac caggtggccc aggaggacca gcagcaccct ttcctccttc gggaccaggg     240
ggaccagctc cacctctaag tcctgggcc cctgccaatc caggagggcc tccttcacct      300
ttctcacccg agcccctct ttct                                              324
```

<210> SEQ ID NO 291
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 291

```
tcgagcggcc gcccgggcag gtccaccggg atattcgggg gtctggcagg aatgggaggc      60
atccagaacg agaaggagac catgcaaagc ctgaacgacc gcctggcctc ttacctggac     120
agagtgagga gcctggagac cgacaaccgg aggctggaga gcaaaatccg ggagcacttg     180
gagaagaagg acccccaggt cagagactgg agccattact tcaagatcat cgaggacctg     240
agggctcana tcttcgcaaa tactgcngac aatgcccg                             278
```

<210> SEQ ID NO 292
<211> LENGTH: 299
<212> TYPE: DNA
<213> ORGANISM: Homo sapien
<220> FEATURE:
<221> NAME/KEY: misc_feature
<222> LOCATION: (1)...(299)
<223> OTHER INFORMATION: n = A,T,C or G

<400> SEQUENCE: 292

```
atgcgnggtc gcggccgang accanctctg gctcatactt gactctaaag ncntcaccag      60
nanttacggn cattgccaat ctgcagaacg atgcgggcat tgtccgcant atttgcgaag     120
atctgagccc tcaggnccctc gatgatcttg aagtaanggc tccagtctct gacctggggt    180
cccttcttct ccaagtgctc ccggattttg ctctccagcc tccggttctc ggtctccaag     240
ncttctcact ctgtccagga aaagaggcca ggcggncgat cagggctttt gcatggact     299
```

<210> SEQ ID NO 293
<211> LENGTH: 101
<212> TYPE: DNA
<213> ORGANISM: Homo sapien

<400> SEQUENCE: 293

```
agcgtggtcg cggccgaggt tgtacaagct tttttttttt tttttttttt tttttttttt      60
tttttttttt tttttttttt tttttttttt tttttttttt t                         101
```

<210> SEQ ID NO 294
<211> LENGTH: 285
<212> TYPE: DNA
<213> ORGANISM: Homo sapien
<220> FEATURE:
<221> NAME/KEY: misc_feature

```
<222> LOCATION: (1)...(285)
<223> OTHER INFORMATION: n = A,T,C or G

<400> SEQUENCE: 294
tcgagcggcc gcccgggcag gtctgccaac accaagattg gcccccgccg catccacaca      60
gttngtgtgc ggggaggtaa caagaaatac cgtgccctga ggntggacgn ggggaatttc     120
tcctggggct cagagtgttg tactcgtaaa acaaggatca tcgatgttgt ctacaatgca     180
tctaataacg agctggttcg taccaagacc ctggtgaaga attgcatcgt gctcatngac     240
agcacaccgt accgacagtg ggtaccgaag tcccactatg cncct                     285

<210> SEQ ID NO 295
<211> LENGTH: 216
<212> TYPE: DNA
<213> ORGANISM: Homo sapien

<400> SEQUENCE: 295
tcgagcggcc gcccgggcag gtccaccaca cccaattcct tgctggtatc atggcagccg      60
ccacgtgcca ggattaccgg ctacatcatc aagtatgaga agcctgggtc tcctcccaga     120
gaagtggtcc ctcggccccg ccctggtgtc acagaggcta ctattactgg cctggaaccg     180
ggaaccgaat atacaattta tgtcattgcc ctgaag                               216

<210> SEQ ID NO 296
<211> LENGTH: 414
<212> TYPE: DNA
<213> ORGANISM: Homo sapien
<220> FEATURE:
<221> NAME/KEY: misc_feature
<222> LOCATION: (1)...(414)
<223> OTHER INFORMATION: n = A,T,C or G

<400> SEQUENCE: 296
agcgtgntcn cggccgagga tggggaagct cgnctgtctt tttccttcca atcagggggct     60 nnntcttctg attattcttc agggcaanga cataaattgt atattcggnt cccggttcca    120
gnccagtaat agtagcctct gtgacaccag ggcggggccg agggaccact tctctgggag    180
gagacccagg cttctcatac ttgatgatga agccggtaat cctggcacgt gggcggctgc    240
catgatacca ccaangaatt gggtgtggtg gacctgcccg ggcgggccgc tcgaaaancc    300
gaattcntgc aagaatatcc atcacacttg ggcgggccgn tcgaaccatg catcntaaaa    360 gggcccaat ttcccccta ttaggngaag ccncatttaa caaattccac ttgg            414

<210> SEQ ID NO 297
<211> LENGTH: 376
<212> TYPE: DNA
<213> ORGANISM: Homo sapien
<220> FEATURE:
<221> NAME/KEY: misc_feature
<222> LOCATION: (1)...(376)
<223> OTHER INFORMATION: n = A,T,C or G

<400> SEQUENCE: 297
tcgagcggcc gcccgggcag gtctcgcggt cgcactggtg atgctggtcc tgttggtccc      60
cccggccctc ctggacctcc tggtccccct ggtcctccca gcgctggttt cgacttcagc    120
ttcctgcccc agccacctca agagaaggct cacgatggtg gccgctacta ccgggctgat    180
gatgccaatg tggttcgtga ccgtgacctc gaggtggaca ccaccctcaa gagccttgag    240
ccagcagaat cgaaaacatt cggaacccaa gaagggcaag cccgcaaaga aacccgcccc    300
```

-continued

| gcacctggcc gngaacctcc aagaangtgc ccacntcttg actgggaaaa aaagggaaaa | 360 |
| ntacttggaa ttggac | 376 |

<210> SEQ ID NO 298
<211> LENGTH: 357
<212> TYPE: DNA
<213> ORGANISM: Homo sapien
<220> FEATURE:
<221> NAME/KEY: misc_feature
<222> LOCATION: (1)...(357)
<223> OTHER INFORMATION: n = A,T,C or G

<400> SEQUENCE: 298

| agcgtggtcg cggccgaggt ccacatcggc agggtcggag ccctggccgc catactcgaa | 60 |
| ctggaatcca tcggtcatgc tctcgccgaa ccagacatgc tcttgtcct tggggttctt | 120 |
| gctgatgtac cagttcttct gggccacact gggctgagtg gggtacacgc aggtctcacc | 180 |
| agtctccatg ttgcagaaga ctttgatggc atccaggttg cagccttggt tggggtcaat | 240 |
| ccagtactct ccactcttcc agtcagaagt ggcacatctt gaggtcacgg cagggtgcgg | 300 |
| gcggggttct tgcgggctgc ccttctgggc tcccggaatg ttctnngaac ttgctgg | 357 |

<210> SEQ ID NO 299
<211> LENGTH: 307
<212> TYPE: DNA
<213> ORGANISM: Homo sapien
<220> FEATURE:
<221> NAME/KEY: misc_feature
<222> LOCATION: (1)...(307)
<223> OTHER INFORMATION: n = A,T,C or G

<400> SEQUENCE: 299

| agcgtggtcg cggccgaggt ccactagagg tctgtgtgcc attgcccagg cagagtctct | 60 |
| gcgttacaaa ctcctaggag ggcttgctgt gcggagggcc tgctatggtg tgctgcggtt | 120 |
| catcatggag agtggggcca aggctgcga ggttgtggtg tctgggaaac tccgaggaca | 180 |
| gagggctaaa tccatgaagt ttgtggatgg cctgatgatc cacagcggag accctgttaa | 240 |
| ctactacgtt gacacttgct tgtgcgccac gtgttgctca nacangggtg ggctgggcat | 300 |
| caaggng | 307 |

<210> SEQ ID NO 300
<211> LENGTH: 351
<212> TYPE: DNA
<213> ORGANISM: Homo sapien

<400> SEQUENCE: 300

| tcgagcggcc gcccgggcag gtctgccaag gagaccctgt tatgctgtgg ggactggctg | 60 |
| gggcatggca ggcggctctg gcttcccacc cttctgttct gagatggggg tggtgggcag | 120 |
| tatctcatct ttgggttcca caatgctcac gtggtcaggc aggggcttct tagggccaat | 180 |
| cttaccagtt gggtcccagg gcagcatgat cttcaccttg atgcccagca caccctgtct | 240 |
| gagcaacacg tggcgcacag caagtgtcaa cgtaagtaag ttaacagggt ctccgctgtg | 300 |
| gatcatcagg ccatccacaa acttcatgga tttaaccctc tgtcctcgga g | 351 |

<210> SEQ ID NO 301
<211> LENGTH: 330
<212> TYPE: DNA
<213> ORGANISM: Homo sapien

<400> SEQUENCE: 301

-continued

```
tcgagcggcc gcccgggcag gtgtttcaga ggttccaagg tccactgtgg aggtcccagg        60
agtgctggtg gtgggcacag aggtccgatg ggtgaaacca ttgacataga gactgttcct       120
gtccagggtg taggggccca gctctttgat gccattggcc agttggctca gctcccagta       180
cagccgctct ctgttgagtc cagggctttt ggggtcaaga tgatggatgc agatggcatc       240
cactccagtg gctgctccat ccttctcgga cctgagagag gtcagtctgc agccagagta       300
cagagggcca acactggtgt tctttgaata                                        330
```

<210> SEQ ID NO 302
<211> LENGTH: 317
<212> TYPE: DNA
<213> ORGANISM: Homo sapien
<220> FEATURE:
<221> NAME/KEY: misc_feature
<222> LOCATION: (1)...(317)
<223> OTHER INFORMATION: n = A,T,C or G

<400> SEQUENCE: 302

```
agcgtggtcg cggccgaggt ctgtactggg agctaagcaa actgaccaat gacattgaag        60
agctgggccc ctacaccctg gacaggaaca gtctctatgt caatggtttc acccatcaga       120
gctctgtgnc caccaccagc actcctggga cctccacagt ggatttcaga acctcaggga       180
ctccatcctc cctctccagc cccacaatta tggctgctgg ccctctcctg gtaccattca       240
ccctcaactt caccatcacc aacctgcagt atggggagga catgggtcac cctgnctcca       300
ggaagttcaa caccaca                                                      317
```

<210> SEQ ID NO 303
<211> LENGTH: 283
<212> TYPE: DNA
<213> ORGANISM: Homo sapien
<220> FEATURE:
<221> NAME/KEY: misc_feature
<222> LOCATION: (1)...(283)
<223> OTHER INFORMATION: n = A,T,C or G

<400> SEQUENCE: 303

```
tcgagcggcc gcccggacag gtctgggcgg atagcaccgg gcatattttg gaatggatga        60
ggtctggcac cctgagcagt ccagcgagga cttggtctta gttgagcaat ttggctagga       120
ggatagtatg cagcacggnt ctgagnctgt gggatagctg ccatgaagta acctgaagga       180
ggtgctggct ggtangggtt gattacaggg ttgggaacag ctcgtacact tgccattctc       240
tgcatatact ggttagtgag gtgagcctgg ccctcttctt ttg                         283
```

<210> SEQ ID NO 304
<211> LENGTH: 72
<212> TYPE: DNA
<213> ORGANISM: Homo sapien
<220> FEATURE:
<221> NAME/KEY: misc_feature
<222> LOCATION: (1)...(72)
<223> OTHER INFORMATION: n = A,T,C or G

<400> SEQUENCE: 304

```
agcgtggtcg cggccgaggt gagccacagg tgaccggggc tgaagctggg gctgctggnc        60
ctgctggtcc tg                                                            72
```

<210> SEQ ID NO 305
<211> LENGTH: 245
<212> TYPE: DNA

<213> ORGANISM: Homo sapien
<220> FEATURE:
<221> NAME/KEY: misc_feature
<222> LOCATION: (1)...(245)
<223> OTHER INFORMATION: n = A,T,C or G

<400> SEQUENCE: 305

| | |
|---|---|
| cagcngctcc nacggggcct gngggaccaa caacaccgtt ttcaccctta ggcccttttgg | 60 |
| ctcctctttc tcctttagca ccaggttgac cagcagcncc ancaggacca gcaaatccat | 120 |
| tggggccagc aggaccgacc tcaccacgtt caccagggct tccccgagga ccagcaggac | 180 |
| cagcaggacc agcagcccca gcttcgcccc ggtcacctgt ggctcacctc ggccgcgacc | 240 |
| acgct | 245 |

<210> SEQ ID NO 306
<211> LENGTH: 246
<212> TYPE: DNA
<213> ORGANISM: Homo sapien
<220> FEATURE:
<221> NAME/KEY: misc_feature
<222> LOCATION: (1)...(246)
<223> OTHER INFORMATION: n = A,T,C or G

<400> SEQUENCE: 306

| | |
|---|---|
| tcgagcggtc gcccgggcag gtccaccggg atagccgggg gtctggcagg aatgggaggc | 60 |
| atccagaacg agaaggagac catgcaaagc ctgaacgacc gcctggcctc ttacctggac | 120 |
| agagtgagga gcctggagac cganaaccgg aggctggana gcaaaatccg ggagcacttg | 180 |
| gagaagaagg accccaggt caagagactg gagccattac ttcaagatca tcgagggacc | 240 |
| tggagg | 246 |

<210> SEQ ID NO 307
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 307

| | |
|---|---|
| agcgnggtcg cggccgaggt ccagctctgt ctcatacttg actctaaagt catcagcagc | 60 |
| aagacgggca ttgtcaatct gcagaacgat gcgggcattg tccgcagtat ttgcgaagat | 120 |
| ctgagccctc aggtcctcga tgatcttgaa gtaatggctc cagtctctga cctggggtcc | 180 |
| cttcttctcc aagtgctccc ggattttgct ctccagcctc cggttctcgg tctccaggct | 240 |
| cctcactctg tccaggtaag aaggcccagg cggtcgttca ggctttgcat ggtctccttc | 300 |
| tcgttctgga tgcctcccat tcctgccaga ccc | 333 |

<210> SEQ ID NO 308
<211> LENGTH: 310
<212> TYPE: DNA
<213> ORGANISM: Homo sapien

<400> SEQUENCE: 308

| | |
|---|---|
| tcgagcggcc gcccgggcag gtcaggaagc acattggtct tagagccact gcctcctgga | 60 |
| ttccacctgt gctgcggaca tctccaggga gtgcagaagg gaagcaggtc aaactgctca | 120 |
| gatcagtcag actggctgtt ctcagttctc acctgagcaa ggtcagtctg cagccagagt | 180 |
| acagagggcc aacactggtg ttcttgaaca agggcttgag cagaccctgc agaaccctct | 240 |

```
tccgtggtgt tgaacttcct ggaaaccagg gtgttgcatg tttttcctca taatgcaagg      300
ttggtgatgg                                                              310
```

<210> SEQ ID NO 309
<211> LENGTH: 429
<212> TYPE: DNA
<213> ORGANISM: Homo sapien

<400> SEQUENCE: 309

```
agcgtggtcg cggccgaggt ccacatcggc agggtcggag ccctggccgc catactcgaa       60
ctggaatcca tcggtcatgc tctcgccgaa ccagacatgc ctcttgtcct tggggttctt      120
gctgatgtac cagttcttct gggccacact gggctgagtg gggtacaccg caggtctcac      180
cagtctccat gttgcagaag actttgatgg catccaggtt gcagccttgg ttggggtcaa      240
tccagtactc tccactcttc cagtcagaag tgggcacatc ttgaggtcac ggcaggtgc       300 cgggccgggg gttcttgcgg cttgccctct gggctccgga tgttctcgat ctgcttggct      360
caggctcttg agggtgggtg tccacctcga ggtcacggtc accgaaacct gcccgggcgg      420
cccgctcga                                                              429
```

<210> SEQ ID NO 310
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 310

```
tcgagcggtc gcccgggcag gtttcgtgac cgtgacctcg aggtggacac caccctcaag       60
agcctgagcc agcagatcga gaacatccgg agcccagagg gcagccgcaa gaaccccgcc      120
cgcacctgcc gtgacctcaa gatgtgccac tctgactgga gagtggaga gtactggatt       180 gaccccaacc aaggctgcaa cctggatgcc atcaaagtct tctgcaacat ggagactggt      240
gagacctgcg tgtaccccac tcagcccagt gtgggcccag aagaaactgg tacatcagca      300
aggaacccca aggacaagag gcattgtctt ggttcggcga gnagcatgac ccgatggatt      360
ccagtttcga gtattggcgg ccagggcttc ccgacccttg ccgatgtgga cctcggccgc      420
gaccaccgct                                                              430
```

<210> SEQ ID NO 311
<211> LENGTH: 2996
<212> TYPE: DNA
<213> ORGANISM: Homo sapien

<400> SEQUENCE: 311

```
cagccaccgg agtggatgcc atctgcaccc accgcctga ccccacaggc cctgggctgg        60
acagagagca gctgtatttg gagctgagcc agctgaccca cagcatcact gagctgggcc      120
cctacaccct ggacagggac agtctctatg tcaatggttt cacacagcgg agctctgtgc      180
ccaccactag cattcctggg accccacag tggacctggg aacatctggg actccagttt      240
ctaaacctgg tccctcggct gccagccctc tcctggtgct attcactctc aacttccacca     300 tcaccaacct gcggtatgag gagaacatgc agcaccctgg ctccaggaag ttcaacacca     360
cggagagggt ccttcagggc ctggtccctg ttcaagagca ccagtgttgg ccctctgtac     420
```

```
tctggctgca gactgacttt gctcaggcct gaaaaggatg ggacagccac tggagtggat    480
gccatctgca cccaccaccc tgaccccaaa agccctaggc tggacagaga gcagctgtat    540
tgggagctga gccagctgac ccacaatatc actgagctgg ccccctatgc cctggacaac    600
gacagcctct ttgtcaatgg tttcactcat cggagctctg tgtccaccac cagcactcct    660
gggaccccca cagtgtatct gggagcatct aagactccag cctcgatatt tggcccttca    720
gctgccagcc atctcctgat actattcacc ctcaacttca ccatcactaa cctgcggtat    780
gaggagaaca tgtggcctgg ctccaggaag ttcaacacta cagagagggt ccttcagggc    840
ctgctaaggc ccttgttcaa gaacaccagt gttggccctc tgtactctgg ctgcaggctg    900
accttgctca ggccagagaa agatggggaa gccaccggag tggatgccat ctgcacccac    960
cgccctgacc ccacaggccc tgggctggac agagagcagc tgtatttgga gctgagccag   1020
ctgacccaca gcatcactga gctgggcccc tacacactgg acagggacag tctctatgtc   1080
aatggtttca cccatcggag ctctgtaccc accaccagca ccgggtggt cagcgaggag    1140 ccattcacac tgaacttcac catcaacaac ctgcgctaca tggcggacat gggccaaccc   1200
ggctccctca gttcaacat cacagacaac gtcatgaagc acctgctcag tcctttgttc    1260
cagaggagca gcctgggtgc acggtacaca ggctgcaggg tcatcgcact aaggtctgtg   1320
aagaacggtg ctgagacacg ggtggacctc ctctgcacct acctgcagcc cctcagcggc   1380
ccaggtctgc ctatcaagca ggtgttccat gagctgagcc agcagaccca tggcatcacc   1440
cggctgggcc cctactctct ggacaaagac agcctctacc ttaacggtta caatgaacct   1500
ggtccagatg agcctcctac aactcccaag ccagccacca cattcctgcc tcctctgtca   1560
gaagccacaa cagccatggg gtaccacctg aagaccctca cactcaactt caccatctcc   1620
aatctccagt attcaccaga tatgggcaag ggctcagcta cattcaactc caccgagggg   1680
gtccttcagc acctgctcag acccttgttc cagaagagca gcatgggccc cttctacttg   1740
ggttgccaac tgatctccct caggcctgag aaggatgggg cagccactgg tgtggacacc   1800
acctgcacct accaccctga ccctgtgggc ccgggctgg acatacagca gctttactgg   1860
gagctgagtc agctgaccca tggtgtcacc caactgggct tctatgtcct ggacagggat   1920
agcctcttca tcaatggcta tgcaccccag aatttatcaa tccggggcga gtaccagata   1980
aatttccaca ttgtcaactg gaacctcagt aatccagacc ccacatcctc agagtacatc   2040
accctgctga gggacatcca ggacaaggtc accacactct acaaaggcag tcaactacat   2100
gacacattcc gcttctgcct ggtcaccaac ttgacgatga ctccgtgtt ggtcactgtc    2160 aaggcattgt tctcctccaa tttggacccc agcctggtgg agcaagtctt tctagataag   2220
accctgaatg cctcattcca ttggctgggc tccacctacc agttggtgga catccatgtg   2280
acagaaatgg agtcatcagt ttatcaacca caagcagct ccagcaccca gcacttctac    2340
ctgaatttca ccatcaccaa ctaccatat tcccaggaca agcccagcc aggcaccacc    2400 aattaccaga ggaacaaaag gaatattgag gatgcgctca accaactctt ccgaaacagc   2460
agcatcaaga gttatttttc tgactgtcaa gtttcaacat tcaggtctgt ccccaacagg   2520
caccacaccg gggtggactc cctgtgtaac ttctcgccac tggctcggag agtagacaga   2580
gttgccatct atgaggaatt tctgcggatg acccggaatg gtacccagct gcagaacttc   2640
accctggaca ggagcagtgt ccttgtggat gggtattttc ccaacagaaa tgagcccttg   2700
actgggaatt ctgaccttcc cttctgggct gtcatcctca tcggcttggc aggactcctg   2760
ggactcatca catgcctgat ctgcggtgtc ctggtgacca cccgccggcg gaagaaggaa   2820
```

```
ggagaataca acgtccagca acagtgccca ggctactacc agtcacacct agacctggag   2880
gatctgcaat gactggaact tgccggtgcc tggggtgcct ttcccccagc cagggtccaa   2940
agaagcttgg ctggggcaga aataaaccat attggtcgga cacaaaaaaa aaaaaa       2996
```

<210> SEQ ID NO 312
<211> LENGTH: 914
<212> TYPE: PRT
<213> ORGANISM: Homo sapien

<400> SEQUENCE: 312

```
Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
```

-continued

```
                340                 345                 350
Ser Leu Lys Phe Asn Ile Thr Asp Asn Val Met Lys His Leu Leu Ser
            355                 360                 365
Pro Leu Phe Gln Arg Ser Ser Leu Gly Ala Arg Tyr Thr Gly Cys Arg
        370                 375                 380
Val Ile Ala Leu Arg Ser Val Lys Asn Gly Ala Glu Thr Arg Val Asp
385                 390                 395                 400
Leu Leu Cys Thr Tyr Leu Gln Pro Leu Ser Gly Pro Gly Leu Pro Ile
                405                 410                 415
Lys Gln Val Phe His Glu Leu Ser Gln Gln Thr His Gly Ile Thr Arg
            420                 425                 430
Leu Gly Pro Tyr Ser Leu Asp Lys Asp Ser Leu Tyr Leu Asn Gly Tyr
        435                 440                 445
Asn Glu Pro Gly Pro Asp Glu Pro Thr Thr Pro Lys Pro Ala Thr
    450                 455                 460
Thr Phe Leu Pro Pro Leu Ser Glu Ala Thr Thr Ala Met Gly Tyr His
465                 470                 475                 480
Leu Lys Thr Leu Thr Leu Asn Phe Thr Ile Ser Asn Leu Gln Tyr Ser
                485                 490                 495
Pro Asp Met Gly Lys Gly Ser Ala Thr Phe Asn Ser Thr Glu Gly Val
            500                 505                 510
Leu Gln His Leu Leu Arg Pro Leu Phe Gln Lys Ser Ser Met Gly Pro
        515                 520                 525
Phe Tyr Leu Gly Cys Gln Leu Ile Ser Leu Arg Pro Glu Lys Asp Gly
    530                 535                 540
Ala Ala Thr Gly Val Asp Thr Thr Cys Thr Tyr His Pro Asp Pro Val
545                 550                 555                 560
Gly Pro Gly Leu Asp Ile Gln Gln Leu Tyr Trp Glu Leu Ser Gln Leu
                565                 570                 575
Thr His Gly Val Thr Gln Leu Gly Phe Tyr Val Leu Asp Arg Asp Ser
            580                 585                 590
Leu Phe Ile Asn Gly Tyr Ala Pro Gln Asn Leu Ser Ile Arg Gly Glu
        595                 600                 605
Tyr Gln Ile Asn Phe His Ile Val Asn Trp Asn Leu Ser Asn Pro Asp
    610                 615                 620
Pro Thr Ser Ser Glu Tyr Ile Thr Leu Leu Arg Asp Ile Gln Asp Lys
625                 630                 635                 640
Val Thr Thr Leu Tyr Lys Gly Ser Gln Leu His Asp Thr Phe Arg Phe
                645                 650                 655
Cys Leu Val Thr Asn Leu Thr Met Asp Ser Val Leu Val Thr Val Lys
            660                 665                 670
Ala Leu Phe Ser Ser Asn Leu Asp Pro Ser Leu Val Glu Gln Val Phe
        675                 680                 685
Leu Asp Lys Thr Leu Asn Ala Ser Phe His Trp Leu Gly Ser Thr Tyr
    690                 695                 700
Gln Leu Val Asp Ile His Val Thr Glu Met Glu Ser Ser Val Tyr Gln
705                 710                 715                 720
Pro Thr Ser Ser Ser Thr Gln His Phe Tyr Leu Asn Phe Thr Ile
                725                 730                 735
Thr Asn Leu Pro Tyr Ser Gln Asp Lys Ala Gln Pro Gly Thr Thr Asn
            740                 745                 750
Tyr Gln Arg Asn Lys Arg Asn Ile Glu Asp Ala Leu Asn Gln Leu Phe
        755                 760                 765
```

```
Arg Asn Ser Ser Ile Lys Ser Tyr Phe Ser Asp Cys Gln Val Ser Thr
    770                 775                 780

Phe Arg Ser Val Pro Asn Arg His His Thr Gly Val Asp Ser Leu Cys
785                 790                 795                 800

Asn Phe Ser Pro Leu Ala Arg Arg Val Asp Arg Val Ala Ile Tyr Glu
                805                 810                 815

Glu Phe Leu Arg Met Thr Arg Asn Gly Thr Gln Leu Gly Asn Phe Thr
            820                 825                 830

Leu Asp Arg Ser Ser Val Leu Val Asp Gly Tyr Phe Pro Asn Arg Asn
        835                 840                 845

Glu Pro Leu Thr Gly Asn Ser Asp Leu Pro Phe Trp Ala Val Ile Leu
850                 855                 860

Ile Gly Leu Ala Gly Leu Leu Gly Leu Ile Thr Cys Leu Ile Cys Gly
865                 870                 875                 880

Val Leu Val Thr Thr Arg Arg Lys Lys Glu Gly Glu Tyr Asn Val
                885                 890                 895

Gln Gln Gln Cys Pro Gly Tyr Tyr Gln Ser His Leu Asp Leu Glu Asp
            900                 905                 910

Leu Gln

<210> SEQ ID NO 313
<211> LENGTH: 656
<212> TYPE: DNA
<213> ORGANISM: Homo sapiens

<400> SEQUENCE: 313
acagccagtc ggagctgcaa gtgttctggg tggatcgcgy atatgcactc aaaatgctct      60
ttgtaaagga aagccacaac atgtccaagg gacctgaggc gacttggagg ctgagcaaag     120
tgcagtttgt ctacgactcc tcggagaaaa cccacttcaa agacgcagtc agtgctggga     180
agcacacagc caactcgcac cacctctctg ccttggtcac ccccgctggg aagtcctatg     240
agtgtcaagc tcaacaaacc atttcactgg cctctagtga tccgcagaag acggtcacca     300
tgatcctgtc tgcggtccac atccaacctt ttgacattat ctcagatttt gtcttcagtg     360
aagagcataa atgcccagtg gatgagcggg agcaactgga agaaaccttg cccctgattt     420
tggggctcat cttgggcctc gtcatcatgg taacactcgc gatttaccac gtccaccaca     480
aaatgactgc caaccaggtg cagatccctc gggacagatc ccagtataag cacatgggct     540
agaggccgtt aggcaggcac cccctattcc tgctccccca actggatcag gtagaacaac     600
aaaagcactt ttccatcttg tacacgagat acaccaacat agctacaatc aaacag        656

<210> SEQ ID NO 314
<211> LENGTH: 519
<212> TYPE: DNA
<213> ORGANISM: Homo sapiens

<400> SEQUENCE: 314
tgtgcgtgga ccagtcagct tccgggtgtg actggagcag ggcttgtcgt cttcttcaga      60
gtcactttgc aggggttggt gaagctgctc ccatccatgt acagctccca gtctactgat     120
gtttaaggat ggtctcggtg gttaggccca ctagaataaa ctgagtccaa tacctctaca     180
cagttatgtt taactgggct ctctgacacc gggaggaagg tggcgggggtt taggtgttgc     240 aaacttcaat ggttatgcgg ggatgttcac agagcaagct ttggtatcta gctagtctag     300
cattcattag ctaatggtgt cctttggtat ttattaaaat caccacagca tagggggact     360
```

```
ttatgtttag gttttgtcta agagttagct tatctgcttc ttgtgctaac agggctattg      420
ctaccaggga ctttggacat ggggccagc gtttggaaac ctcatctagt tttttgaga       480 gataggccac tggccttgga cctcggccgc gaccacgct                             519
```

<210> SEQ ID NO 315
<211> LENGTH: 441
<212> TYPE: DNA
<213> ORGANISM: Homo sapiens

<400> SEQUENCE: 315

```
cacagagcgt ttattgacac caccactcct gaaaattggg atttcttatt aggttcccct     60
aaaagttccc atgttgatta catgtaaata gtcacatata caatgaag gcagtttctt       120 cagaggcaac cagggtttat agtgctaggt aaatgtcatc tcttttgtgc tactgactca    180
ttgtcaaacg tctctgcact gttttcagcc tctccacgtt gcctctgtcc tgcttcttag    240
ttccttcttt gtgacaaacc aaaagaataa gaggatttag aacaggactg ctttccctcct   300 atgatttaaa aattccaatg actttcgccc ttgggagaaa tttccaagga aatctctctc    360
gctcgctctc tccgttttcc tttgtgagct tctgggggag ggttagtggt gactttttga    420
tacgaaaaaa tgcattttgt g                                               441
```

<210> SEQ ID NO 316
<211> LENGTH: 247
<212> TYPE: DNA
<213> ORGANISM: Homo sapiens

<400> SEQUENCE: 316

```
tggcgcggct gctggatttc accttcttgc acctgccggt gagcgcctgg ggtctaaagg    60
ggcgggatac tccattatgg cccctcgccc tgtagggctg gaatagttag aaaaggcaac    120
ccagtctagc ttggtaagaa gagagacatg ccccaacct cggcgccctt ttccctcacg     180
atctgctgtc cttacttcag cgactgcagg agcttcacct gcaagaaaac agcattgagc    240
tgctgac                                                               247
```

<210> SEQ ID NO 317
<211> LENGTH: 409
<212> TYPE: DNA
<213> ORGANISM: Homo sapiens

<400> SEQUENCE: 317

```
tgacagggct cctggagttg ttaagtcacc aagtagctgc aggggatgga cactgcccca    60
cacgatgtgg gatgaacagc agccttggtt tgtagcccag ggtgtccatg gatttgaccc   120
gaatgctccc tggaggccct gtggcgagga caggcactgg atggtccaga ccctctggct   180
ggaggagtgg tggagccagg actgggcctt cagccatgag ggctagaata acctgacctc   240
ttgcattcta acactgggtc attaatgaca cctttccagt ggatgttgca aaaccaaca    300 ctgtcaggaa cctggccctg ggagggctca ggtgagctca caaggagagg tcaagccaag   360
ccaaagggta ggkaacacac aacaccaggg gaaaccagcc cccaaacca                409
```

<210> SEQ ID NO 318
<211> LENGTH: 320
<212> TYPE: DNA
<213> ORGANISM: Homo sapiens
<220> FEATURE:
<221> NAME/KEY: misc_feature
<222> LOCATION: (1)...(320)

<223> OTHER INFORMATION: n = A,T,C or G

<400> SEQUENCE: 318

```
caaggnagat cttaagnggg gtcntatgta agtgtgctcc tggctccagg gttcctggag      60
cctcacgagg tcagggaac ccttgtagaa ctccaccagc agcatcatct cgtgaaggat     120
gtcattggtc aggaagctgt cctggacgta ggccatctcc acatccatgg ggatgccata    180
gtcactgggc ctttgctcgg gaggaggcat cacccagaaa ggcgagatct tggactcggg    240
gcctgggttg ccagaatagt aaggggagca nagcagggcg aggcagggct ggaagccatt    300
gctggagccc tgcagccgca                                                320
```

<210> SEQ ID NO 319
<211> LENGTH: 212
<212> TYPE: DNA
<213> ORGANISM: Homo sapiens
<220> FEATURE:
<221> NAME/KEY: misc_feature
<222> LOCATION: (1)...(212)
<223> OTHER INFORMATION: n = A,T,C or G

<400> SEQUENCE: 319

```
tgaagcaata gcgcccccat tttacaggcg gagcatggaa gccagagagg tgggtggggg      60
aggggtcct tccctggctc aggcagatgg gaagatgagg aagccgctga agacgctgtc     120
ggcctcagag ccctggtaaa tgtgacccct tttggggtct ttttcaaccc anacctggtc    180
accctgctgc agacctcggc cgcgaccacg ct                                  212
```

<210> SEQ ID NO 320
<211> LENGTH: 769
<212> TYPE: DNA
<213> ORGANISM: Homo sapiens

<400> SEQUENCE: 320

```
tggaggtgta gcagtgagag gagatytcag gcaagagtgt cacagcagag ccctaaascc      60
tccaactcac cagtgagaga tgagactgcc cagtactcag ccttcatctc ctgggccacc    120
tggagggcgt cttttctccat cagcgcatac tgagcagggg tactcagatc cttcttggaa    180
cctacaagga agagaagcac actggaaggg tcattctcct tcagggcatc ggccagccac    240
tgcctgccat gggaggtgga agtaaggga tgagtgagtc tgcagggccc ctcccactga     300
cattcatagg cccaattacc ccctctctgg tcctacatgc attcttcttc ttcctgacca    360
cccctctgtt ctgaaccctc tcttcccgga gcctcccatt atattgcagg atgctcactt    420
acttggtatg ttccagagat gccacatcat tcaggttgaa gacaatgatg atggcttgga    480
agagtggcag aaacagcccc aggttgacag gaagacact actgctcatt tccccaatcc     540
ttccagctcc atatgagaaa gccatgtgca ctctgagacc cacctacccc acttcaccca    600
gcccttacc ttgagctcct ctatagtagg ttgatgcaat gcatttgaac ctctcctgcc     660
cagcggtatc ccaactggaa ggaaggaaga gtgaagcaca ggtatgtatc ttgggggtg    720
tgggtgctgg ggagaaggga tagctggaag gggtgtggaa gcactcaca                769
```

<210> SEQ ID NO 321
<211> LENGTH: 690
<212> TYPE: DNA
<213> ORGANISM: Homo sapiens
<220> FEATURE:
<221> NAME/KEY: misc_feature
<222> LOCATION: (1)...(690)
<223> OTHER INFORMATION: n = A,T,C or G

<400> SEQUENCE: 321

```
tgggctgtgg gcggcacctg tgctctgcag gccagacagc gatagaagcc tttgtctgtg      60
cctactcccc cggaggcaac tgggaggtca acgggaagac aatcatcccc tataagaagg     120
gtgcctggtg ttcgctctgc acagccagtg tctcaggctg cttcaaagcc tgggaccatg     180
caggggggct ctgtgaggtc cccaggaatc cttgtcgcat gagctgccag aaccatggac     240
gtctcaacat cagcacctgc cactgccact gtcccctgg ctacacgggc agatactgcc      300
aagtgaggtg cagcctgcag tgtgtgcacg gccggttccg ggaggaggag tgctcgtgcg     360
tctgtgacat cggctacggg ggagcccagt gtgccaccaa ggtgcatttt cccttccaca     420
cctgtgacct gaggatcgac ggagactgct tcatggtgtc ttcagaggca gacacctatt     480
acagaagcca ggatgaaatg tcagaggaat ggcggggtgc tggcccagat caagagccag     540
aaagtgcagg acatcctcgc cttctatctg ggccgcctgg agaccaccaa cgaggtgact     600
gacagtgact ttgagaccag gaacttctgg atngggctca cctacaagac cgccaaggac     660
tccttncgct gggccacagg ggagcaccag                                      690
```

<210> SEQ ID NO 322
<211> LENGTH: 104
<212> TYPE: DNA
<213> ORGANISM: Homo sapiens

<400> SEQUENCE: 322

```
gtcgcaagcc ggagcaccac catgtagcct ttcccgaagt accggacctt ctcctcctcc      60
acgctcacat cacggacatc atggagcagg accaccacct ggtc                      104
```

<210> SEQ ID NO 323
<211> LENGTH: 118
<212> TYPE: DNA
<213> ORGANISM: Homo sapiens

<400> SEQUENCE: 323

```
gggccctggg cgcttccaaa tgacccagga ggtggtctgc gacgaatgcc ctaatgtcaa      60
actagtgaat gaagaacgaa cactggaagt agaaatagag cctggggtga gagacgga     118
```

<210> SEQ ID NO 324
<211> LENGTH: 354
<212> TYPE: DNA
<213> ORGANISM: Homo sapiens

<400> SEQUENCE: 324

```
tgctctccgg gagcttgaag aagaaactgg ctacaaaggg gacattgccg aatgttctcc      60
agcggtctgt atggacccag gcttgtcaaa ctgtactata cacatcgtga cagtcaccat     120
taacggagat gatgccgaaa acgcaaggcc gaagccaaag ccaggggatg gagagtttgt     180
ggaagtcatt tctttaccca gaatgacct gctgcagaga cttgatgctc tggtagctga     240
agaacatctc acagtggacg ccagggtcta ttcctacgct ctagcgctga acatgcaaa      300
tgcaaagcca tttgaagtgc ccttcttgaa attttaagcc caaatatgac actg           354
```

<210> SEQ ID NO 325
<211> LENGTH: 642
<212> TYPE: DNA
<213> ORGANISM: Homo sapiens
<220> FEATURE:
<221> NAME/KEY: misc_feature
<222> LOCATION: (1)...(642)

<223> OTHER INFORMATION: n = A,T,C or G

<400> SEQUENCE: 325

```
ncatgcttga atgggctcct ggtgagagat tgccccctgg tggtgaaaca atcgtgtgtg      60
cccactgata ccaagaccaa tgaaagagac acagttaagc agcaatccat ctcatttcca     120
ggcacttcaa taggtcgctg attggtcctt gcaccagcag tggtagtcgt acctatttca     180
gagaggtctg aaattcaggt tcttagtttg ccagggacag gccctacctt atatttttt     240
ccatcttcat catccacttc tgcttacagt ttgctgctta caataactta atgatggatt     300
gagttatctg ggtggtctct agccatctgg gcagtgtggt tctgtctaac caaagggcat     360
tggcctcaaa ccctgcattt ggtttagggg ctaacagagc tcctcagata atcttcacac     420
acatgtaact gctggagatc ttattctatt atgaataaga aacgagaagt ttttccaaag     480
tgttagtcag gatctgaagg ctgtcattca gataacccag cttttccttt ggcttttag     540
cccattcaga ctttgccaga gtcaagccaa ggattgcttt tttgctacag ttttctgcca     600
aatggcctag ttcctgagta cctggaaacc agagagaaag ag                        642
```

<210> SEQ ID NO 326
<211> LENGTH: 455
<212> TYPE: DNA
<213> ORGANISM: Homo sapiens

<400> SEQUENCE: 326

```
tccgtgagga tgagcttcga gtccttcacc aggcactgca ggggcacagt cacgtcaatc      60
accttcacct tctcgctctt cctgctcttg tcattgacaa acttcccgta ccaggcattg     120
acgatgatga ggcccattct ggactcttct gcctcaatta tccttcggac agattcctgc     180
atcagccgga cagcggactc cgcctcttgc ttcttctgca gcacatcggt ggcggcgctt     240
tccctctgct tctccaattc cttctctttc tgagccctga ggtatggttt gatgatcaga     300
cggtgcatgg caaagtagac cactagaggc cccacggtgg catagaacat ggcgctgggc     360
agaagctggt ccgtcaagtg aatagggaag aagtatgtct gactggccct gttgagcttg     420
actttgagag aaacgccctg tggaactcca acgct                                455
```

<210> SEQ ID NO 327
<211> LENGTH: 321
<212> TYPE: DNA
<213> ORGANISM: Homo sapiens

<400> SEQUENCE: 327

```
ttcactgtga actcgcagtc ctcgatgaac tcgcacagat gtgacagccc tgtctccttg      60
ctctctgagt tctcttcaat gatgctgatg atgcagtcca cgatagcgcg cttatactca     120
aagccaccct cttcccgcag catggtgaac aggaagttca taaggacggc gtgtttgcga     180
ggatatttct gacacagggc actgatggcc tggacaacca ccaccttgaa ttcatccgag     240
atttctgaca tgaaggagga gatctgcttc atgaggcggt cgatgctgct ctcgctgccc     300
gtcttaagga gggtggtgat g                                               321
```

<210> SEQ ID NO 328
<211> LENGTH: 476
<212> TYPE: DNA
<213> ORGANISM: Homo sapiens
<220> FEATURE:
<221> NAME/KEY: misc_feature
<222> LOCATION: (1)...(476)
<223> OTHER INFORMATION: n = A,T,C or G

<400> SEQUENCE: 328

```
tgcaggaggg gccatggggg ctgtgaatgg gatgcagccc catggtgtcc ctgataaatc      60
cagtgtgcag tctgatgaag tctggtgggg tgtggtctac gggctggcag ctaccatgat     120
ccaagaggta atgcactcct tttcccatct ctccaccatc tgtatcctgg ccmagaaaaa     180
cttcccttca aaccaaccaa aatttccttt caaaggcata acccaaatgc catccttggt     240
ccggtctaat aaagcctccc ccattttttcc cctggtatgc attcccaggc tccctggcct     300
tncagggctt nctgtctgtg ggtcatagtt tatctcctcc cacttgctgg gagctccttg     360
aaggcaaaga ctctactgcc tccatctatc cagtggaagt ggctcttcag agggtgccaa     420
gttagtatgt atgactgtca tctctcccaa cagggcctga cttggsaggg cttcca         476
```

<210> SEQ ID NO 329
<211> LENGTH: 340
<212> TYPE: DNA
<213> ORGANISM: Homo sapiens

<400> SEQUENCE: 329

```
cgagggagat tgccagcacc ctgatggaga gtgagatgat ggagatcttg tcagtgctag      60
ctaagggtga ccacagccct gtcacaaggg ctgctgcagc ctgcctggac aaagcagtgg     120
aatatgggct tatccaaccc aaccaagatg agagtgagg gggttgtccc tgggcccaag     180
gctcatgcac acgctaccta ttgtggcacg gagagtaagg acggaagcag ctttggctgg     240
tggtggctgg catgcccaat actcttgccc atcctcgctt gctgcccag gatgtcctct     300
gttctgagtc agcggccacg ttcagtcaca cagccctgct                            340
```

<210> SEQ ID NO 330
<211> LENGTH: 277
<212> TYPE: DNA
<213> ORGANISM: Homo sapiens

<400> SEQUENCE: 330

```
tgtcaccatc acattggtgc caaatacccca gaagacatcg tagatgaaga gtccgcccag      60
caggatgcag ccagtgctga cattgttgag gtgcaggagc tctactccat taagggagaa     120
ggccaggcca aaaaggttgt tggcaatcca gtgcttcctc agcaggtacc agacgccaac     180
gatgctgctc aggcccaggc acaccaggtc cttggtgtca aattcataat tgatgatctc     240
ctccttgttt tcccagaacc ctgtgtgaag agcagac                               277
```

<210> SEQ ID NO 331
<211> LENGTH: 136
<212> TYPE: DNA
<213> ORGANISM: Homo sapiens

<400> SEQUENCE: 331

```
ttgcttccca cctcctttct ctgtcctctc ctgaggttct gccttacaat ggggacactg      60
atacaaacca cacacacaat gaggatgaaa acagataaca ggtaaaatga cctcacctgc     120
ccgggcggcc gctcga                                                     136
```

<210> SEQ ID NO 332
<211> LENGTH: 184
<212> TYPE: DNA
<213> ORGANISM: Homo sapiens

<400> SEQUENCE: 332

```
ttgtgagata aacgcagata ctgcaatgca ttaaaacgct tgaaatactc atcagggatg      60
ttgctgatct tattgttgtc taagtagaga gttagaagag agacagggag accagaaggc     120
agtctggcta tctgattgaa gctcaagtca aggtattcga gtgatttaag accttta aaa    180 gcag                                                                  184

<210> SEQ ID NO 333
<211> LENGTH: 384
<212> TYPE: DNA
<213> ORGANISM: Homo sapiens

<400> SEQUENCE: 333
cggaaaactt cgaggaattg ctcaaagtgc tgggggtgaa tgtgatgctg aggaagattg      60
ctgtggctgc agcgtccaag ccagcagtgg agatcaaaca ggaggagac actttctaca     120 tcaaaacctc caccaccgtg cgcaccacag agattaactt caaggttggg gaggagtttg     180
aggagcagac tgtggatggg aggccctgta agagcctggt gaaatgggag agtgagaata     240
aaatggtctg tgagcagaag ctcctgaagg gagagggccc caagacctcg tggaccagag     300
aactgaccaa cgatggggaa ctgatcctga ccatgacggc ggatgacgtt gtgtgcacca     360
gggtctacgt ccgagagtga gcgg                                            384

<210> SEQ ID NO 334
<211> LENGTH: 169
<212> TYPE: DNA
<213> ORGANISM: Homo sapiens
<220> FEATURE:
<221> NAME/KEY: misc_feature
<222> LOCATION: (1)...(169)
<223> OTHER INFORMATION: n = A,T,C or G

<400> SEQUENCE: 334
cnacaaacag agcagacacc ctggatccgg tcctgctact ggccaggacg gctggaccgt      60
aaaattgaat ttccacttcc tgaccgccgc cagaagagat tgattttctc cactatcact     120
agcaagatga acctctctga ggaggttgac ttggaagact atgtngccc                 169

<210> SEQ ID NO 335
<211> LENGTH: 185
<212> TYPE: DNA
<213> ORGANISM: Homo sapiens

<400> SEQUENCE: 335
ccaggtttgc agcccaggct gcacatcagg ggactgcctc gcaatacttc atgctgttgc      60
tgctgactga tggtgctgtg acggatgtgg aagccacacg tgaggctgtg gtgcgtgcct     120
cgaacctgcc catgtcagtg atcattgtgg gtgtgggtgg tgctgacttt gaggccatgg     180
agcag                                                                 185

<210> SEQ ID NO 336
<211> LENGTH: 358
<212> TYPE: DNA
<213> ORGANISM: Homo sapiens
<220> FEATURE:
<221> NAME/KEY: misc_feature
<222> LOCATION: (1)...(358)
<223> OTHER INFORMATION: n = A,T,C or G

<400> SEQUENCE: 336
ctgcccctgc cttacggcgg ccaganacac acccaggatg gcattggccc caaacttgga      60
tttgttctca gtcccatcca actccagcat caggttgtcc agtttctctt gctccaccac     120
```

```
agagagacct gagctgatga gggctggcgc gatggtggag ttgatgtggt ccactgcctt    180
caggacacct ttgcctaagt aacgctgttt gtctccatcc ctcagctcca gggcctcata    240
gatgcccgta gaggctccac tgggcactgc agcccggaaa agacctttgg cagtatagag    300
atccacctcc actgtggggt tcccgcggga gtccaggatc tcccgggccc agatcttc     358
```

<210> SEQ ID NO 337
<211> LENGTH: 271
<212> TYPE: DNA
<213> ORGANISM: Homo sapiens
<220> FEATURE:
<221> NAME/KEY: misc_feature
<222> LOCATION: (1)...(271)
<223> OTHER INFORMATION: n = A,T,C or G

<400> SEQUENCE: 337

```
cacaaagcca ccagccnggg aaatcagaat ttacttgatg caactgactt gtaatagcca    60
gaaatcctgc ccagcatggg attcagaacc tggtctgcaa ccaaatccac cgtcaaagtt   120
catacaggat aaaacaaatt caattgcctt ttccacatta atagcatcaa gcttccccaa   180
caaagccaaa gttgccaccg cacaaaaaga gaatcttgtg tcaatttctc cctactttat   240
aaaagtagat ttttcacatc ccatgaagca g                                  271
```

<210> SEQ ID NO 338
<211> LENGTH: 326
<212> TYPE: DNA
<213> ORGANISM: Homo sapiens
<220> FEATURE:
<221> NAME/KEY: misc_feature
<222> LOCATION: (1)...(326)
<223> OTHER INFORMATION: n = A,T,C or G

<400> SEQUENCE: 338

```
ctgtgctccc gactngnnca tctcaggtac caccgactgc actgggcggg gccctctggg    60
gggaaaggct ccacggggca gggatacatc tcgaggccag tcatcctctg gaggcagccc   120
aatcaggtca agattttgc ccaactggtc ggcttcagag tttccacaga agagaggctt    180
tcgacgaaac atctctgcaa agatacagcc aacactccac atgtccacag gtgttgcata   240
tgtggactgc agaagaactt cgggagctcg gtaccagagt gtaacaacca cgggtgtaag   300
tgccatctgg tagctgtaga ttctgg                                        326
```

<210> SEQ ID NO 339
<211> LENGTH: 260
<212> TYPE: DNA
<213> ORGANISM: Homo sapiens
<220> FEATURE:
<221> NAME/KEY: misc_feature
<222> LOCATION: (1)...(260)
<223> OTHER INFORMATION: n = A,T,C or G

<400> SEQUENCE: 339

```
ttcacctgag gactcatttc gtgccctttg ttgacttcaa gcaaagncct tcanggtctn    60
caaggacgnc acatttccac ttgcgaatgn nctcanggct catcttgaag aanaagnanc   120
ccaagtgctg gatcccagac tcgggggtaa ccttgtgggt aagagctcat ccagtttatg   180
ctttaggacg tccanctact cggggagct ggaagcctgc gtggatgcgg ccctgctgga    240
cctcggccgc gaccacgcta                                               260
```

<210> SEQ ID NO 340

```
<211> LENGTH: 220
<212> TYPE: DNA
<213> ORGANISM: Homo sapiens
<220> FEATURE:
<221> NAME/KEY: misc_feature
<222> LOCATION: (1)...(220)
<223> OTHER INFORMATION: n = A,T,C or G

<400> SEQUENCE: 340
ctggaagccc ggctnggnct ggcagcggaa ggagccaggc aggttcacgc agcggtgctg      60
gcagtagcgg tagcggcact cgtctatgtc cacacactcg ggcccgatct tgcggtaacc     120
atcagggcag gtgcactgat aggagccagg caagttatgg cagtcctggc tggggcgaca     180
gtcgtgcagg gcctgggcac actcgtccac atccacacag                           220

<210> SEQ ID NO 341
<211> LENGTH: 384
<212> TYPE: DNA
<213> ORGANISM: Homo sapiens

<400> SEQUENCE: 341
ctgctaccag gggagcgaga gctgactatc ccagcctcgg ctaatgtatt ctacgccatg      60
gatggagctt cacacgattt cctcctgcgg cagcggcgaa ggtcctctac tgctacaccg     120
ggcgtcacca gtgcccgtc tgcctcagga actcctccga gtgagggagg aggggctcc      180 tttcccagga tcaaggccac aggaggaag attgcacggg cactgttctg aggaggaagc     240
cccgttggct tacagaagtc atggtgttca taccagatgt gggtagccat cctgaatggt    300
ggcaattata tcacattgag acagaaattc agaaagggag ccagccaccc tggggcagtg    360
aagtgccact ggtttaccag acag                                           384

<210> SEQ ID NO 342
<211> LENGTH: 245
<212> TYPE: DNA
<213> ORGANISM: Homo sapiens

<400> SEQUENCE: 342
ctggctaagc tcatcattgt tactggtggg caccatgtcc ttgaagcttc aggcaagcaa      60
tgtaaccaac aagaatgacc ccaagtccat caactctcga gtcttcattg gaaacctcaa    120
cacagctctg gtgaagaaat cagatgtgga gaccatcttc tctaagtatg ccgtgtggc     180 cggctgttct gtgcacaagg gctatgcctt tgttcagtac tccaatgagc gccatgcccg    240
ggcag                                                                245

<210> SEQ ID NO 343
<211> LENGTH: 611
<212> TYPE: DNA
<213> ORGANISM: Homo sapiens

<400> SEQUENCE: 343
ccaaaaaaat caagatttaa tttttttatt tgcactgaaa aactaatcat aactgttaat      60
tctcagccat ctttgaagct tgaaagaaga gtctttggta ttttgtaaac gttagcagac    120
tttcctgcca gtgtcagaaa atcctattta tgaatcctgt cggtattcct tggtatctga    180 aaaaatacc aaatagtacc atacatgagt tatttctaag tttgaaaaat aaaaagaaat     240
tgcatcacac taattacaaa atacaagttc tggaaaaaat attttctc attttaaaac      300 ttttttaac taataatggc tttgaaagaa gaggcttaat ttggggtgg taactaaaat      360 caaaagaaat gattgacttg agggtctctg tttggtaaga atacatcatt agcttaaata    420
```

```
agcagcagaa ggttagtttt aattatgtag cttctgttaa tattaagtgt tttttgtctg    480
ttttacctca atttgaacag ataagtttgc ctgcatgctg acatgcctc agaaccatga    540 atagcccgta ctagatcttg gaacatgga tcttagagtc ctttggaata agttcttata    600
taaatacccc c                                                         611
```

```
<210> SEQ ID NO 344
<211> LENGTH: 311
<212> TYPE: DNA
<213> ORGANISM: Homo sapiens
<220> FEATURE:
<221> NAME/KEY: misc_feature
<222> LOCATION: (1)...(311)
<223> OTHER INFORMATION: n = A,T,C or G

<400> SEQUENCE: 344
nctcgaaaaa gcccaagaca gcagaagcag acacctccag tgaactagca aagaaaagca    60
aagaagtatt cagaaaagag atgtcccagt tcatcgtcca gtgcctgaac ccttaccgga   120
aacctgactg caaagtggga agaattacca caactgaaga ctttaaacat ctggctcgca   180
agctgactca cggtgttatg aataaggagc tgaagtactg taagaatcct gaggacctgg   240
agtgcaatga gaatgtgaaa cacaaaacca aggantacat taanaagtac atgcannaan   300
tttggggctt g                                                         311
```

```
<210> SEQ ID NO 345
<211> LENGTH: 201
<212> TYPE: DNA
<213> ORGANISM: Homo sapiens

<400> SEQUENCE: 345
cacacggtca tcccgactgc caacctggag gcccaggccc tgtggaagga gccgggcagc    60
aatgtcacca tgagtgtgga tgctgagtgt gtgcccatgg tcaggaccct tctcaggtac   120
ttctactccc gaaggattga catcaccctg tcgtcagtca agtgcttcca caagctggcc   180
tctgcctatg gggccaggca g                                              201
```

```
<210> SEQ ID NO 346
<211> LENGTH: 370
<212> TYPE: DNA
<213> ORGANISM: Homo sapiens

<400> SEQUENCE: 346
ctgctccagg gcgtggtgtg ccttcgtggc ctctgcctcc tccgaggagc caggctgtgt    60
tctcttcaga atgttctgga gcagcagttt gaggcgggtg atgcgttgga agggcagaat   120
cagaaaggac ttgagggaaa ggcgctggca gacgggtcg ctctccagct tctccaagac   180
ctcccggaaa ttgctgttgc tattcatcag gctctggaag gtgcgttcct gataggtctg   240
gttggtgaca taaggcaggt agacccggcg gaagtctggg gcgtggttca ggactacgtc   300
acatacttgg aaggagaaga tattgttctc aaagttctct tccaggtctg aaaggaacgt   360
ggcgctgacg                                                           370
```

```
<210> SEQ ID NO 347
<211> LENGTH: 416
<212> TYPE: DNA
<213> ORGANISM: Homo sapiens
<220> FEATURE:
<221> NAME/KEY: misc_feature
<222> LOCATION: (1)...(416)
```

<223> OTHER INFORMATION: n = A,T,C or G

<400> SEQUENCE: 347

```
ctgttgtgct gtgtatggac gtgggcttta ccatgagtaa ctccattcct ggtatagaat      60
ccccatttga acaagcaaag aaggtgataa ccatgtttgt acagcgacag gtgtttgctg     120
agaacaagga tgagattgct ttagtcctgt ttggtacaga tggcactgac aatccccttt     180
ctggtgggga tcagtatcag aacatcacag tgcacagaca tctgatgcta ccagattttg     240
atttgctgga ggacattgaa agcaaaatcc aaccaggttc tcaacaggct gacttcctgg     300
atgcactaat cgtgagcatg gatgtgattc aacatgaaac aataggaaag aagtttggag     360
aagaggcata ttgaaatatt cactgacctc aagcagcccg attcagcaaa agtcan        416
```

<210> SEQ ID NO 348
<211> LENGTH: 351
<212> TYPE: DNA
<213> ORGANISM: Homo sapiens

<400> SEQUENCE: 348

```
gtacaggaga ggatggcagg tgcagagcgg gcactgagct ctgcaggtga aagggctcgg      60
cagttggatg ctctcctgga ggctctgaaa ttgaaacggg caggaaatag tctggcagcc     120
tctacagcag aagaaacggc aggcagtgcc cagggacgag caggagacag atgccttcct     180
cttgtctcaa ctgcaaagag gcgttccttc ctctttcact aatcctcctc agcacagacc     240
ctttacgggt gtcaggctgg gggacagtaa ggtctttccc ttcccacaag gccatatctc     300
aggctgtctc agtgggggga aaccttggac aatacccggg ctttcttggg c              351
```

<210> SEQ ID NO 349
<211> LENGTH: 207
<212> TYPE: DNA
<213> ORGANISM: Homo sapiens
<220> FEATURE:
<221> NAME/KEY: misc_feature
<222> LOCATION: (1)...(207)
<223> OTHER INFORMATION: n = A,T,C or G

<400> SEQUENCE: 349

```
nccgggacat ctccaccctc aacagtggca agaagagcct ggagactgaa cacaaggcct      60
tgaccagtga gattgcactg ctgcagtcca ggctgaagac agaggctct gatctgtgcg      120
acagagtgag cgaaatgcag aagctggatg cacaggtcaa ggagctggtg ctgaagtcgg     180
cggtggaggc tgagcgcctg gtggctg                                         207
```

<210> SEQ ID NO 350
<211> LENGTH: 323
<212> TYPE: DNA
<213> ORGANISM: Homo sapiens

<400> SEQUENCE: 350

```
ccatacaggg ctgttgccca ggccctagag gtcattcctc gtaccctgat ccagaactgt      60
ggggccagca ccatccgtct acttacctcc cttcgggcca agcacaccca ggagaactgt     120
gagacctggg gtgtaaatgg tgagacgggt actttggtgg acatgaagga actgggcata     180
tgggagccat ggctgtgaa gctgcagact tataagacag cagtgagac ggcagttctg       240
ctactgcgaa ttgatgacat cgtttcaggc cacgaaaaga aggcgatga ccagagccgg      300
caaggcgggg ctcctgatgc tgg                                             323
```

<210> SEQ ID NO 351
<211> LENGTH: 353
<212> TYPE: DNA
<213> ORGANISM: Homo sapiens
<220> FEATURE:
<221> NAME/KEY: misc_feature
<222> LOCATION: (1)...(353)
<223> OTHER INFORMATION: n = A,T,C or G

<400> SEQUENCE: 351

| | | | | | |
|---|---|---|---|---|---|
| cgccgcatcc | cntggtccct | tccantccct | tttcctttnt | cngggaacgt | gtatgcggtt | 60 |
| tgttttttgtt | ttgtagggtt | tttttccttc | tccacctctc | cctgtctctt | ttgctccatg | 120 |
| ttgtccgttt | ctgtggggtt | aggtttatgt | ttttaatcat | ctgaggtcac | gtctatttcc | 180 |
| tccggactcg | cctgcttggt | ggcgattctc | caccggttaa | tatggtgcgt | ccctttttc | 240 |
| ttttgttgcg | aatctgagcc | ttcttcctcc | agcttctgcc | ttttgaactt | tgttcttcgg | 300 |
| ttctgaaacc | atacttttac | ctgagtttcc | gtgaggctga | ggctgtgtgc | caa | 353 |

<210> SEQ ID NO 352
<211> LENGTH: 467
<212> TYPE: DNA
<213> ORGANISM: Homo sapiens

<400> SEQUENCE: 352

| | | | | | |
|---|---|---|---|---|---|
| ctgcccacac | tgatcacttg | cgagatgtcc | ttagggtaca | agaacaggaa | ttgaagtctg | 60 |
| aatttgagca | gaacctgtct | gagaaactct | ctgaacaaga | attacaattt | cgtcgtctca | 120 |
| gtcaagagca | agttgacaac | tttactctgg | atataaatac | tgcctatgcc | agactcagag | 180 |
| gaatcgaaca | ggctgttcag | agccatgcag | ttgctgaaga | ggaagccaga | aaagcccacc | 240 |
| aactctggct | ttcagtggag | gcattaaagt | acagcatgaa | gacctcatct | gcagaaacac | 300 |
| ctactatccc | gctgggtagt | gcagttgagg | ccatcaaagc | caactgttct | gataatgaat | 360 |
| tcacccaagc | tttaaccgca | gctatccctc | cagagtccct | gacccgtggg | gtgtacagtg | 420 |
| aagagaccct | tagagcccgt | tctatgctg | ttcaaaaact | ggcccga | | 467 |

<210> SEQ ID NO 353
<211> LENGTH: 350
<212> TYPE: DNA
<213> ORGANISM: Homo sapiens

<400> SEQUENCE: 353

| | | | | | |
|---|---|---|---|---|---|
| ctgctgcagc | cacagtagtt | cctcccatgg | tgggtggccc | tcctggtcct | gctgcccag | 60 |
| gaaatctgtc | cccaccagga | acagcccctg | gaaaacggcc | ccgtcctcta | ccaccttgtg | 120 |
| gaaatgctgc | acgggaactg | cctcctggag | gaccagcttt | accttcccca | gacatttgtc | 180 |
| ctgattgtgt | agttttcctg | gactgcattt | caaattgact | caggaactgt | ttattgcatg | 240 |
| gagttacaac | aggattctga | ccatgaagtt | ctcttttagg | taacagatcc | attaactttt | 300 |
| ttgaagatgc | ttcagatcca | acaccaacaa | gggcaaaccc | ctttgactgg | | 350 |

<210> SEQ ID NO 354
<211> LENGTH: 351
<212> TYPE: DNA
<213> ORGANISM: Homo sapiens

<400> SEQUENCE: 354

| | | | | | |
|---|---|---|---|---|---|
| atttagatga | gatctgaggc | atggagacat | ggagacagta | tacagactcc | tagatttaag | 60 |
| ttttaggttt | tttgcttttc | taatcaccaa | ttcttatata | caatgtatat | tttagactcg | 120 |

| | |
|---|---|
| agcagatgat catcttcatc ttaagtcatt cctttgact gagtatggca ggattagagg | 180 |
| gaatggcagt atagatcaat gtcttttct gtaaagtata ggaaaaacca gagaggaaaa | 240 |
| aaagagctga caattggaag gtagtagaaa attgacgata atttcttctt aacaaataat | 300 |
| agttgtatat acaaggaggc tagtcaacca gattttattt gttgagggcg a | 351 |

<210> SEQ ID NO 355
<211> LENGTH: 308
<212> TYPE: DNA
<213> ORGANISM: Homo sapiens

<400> SEQUENCE: 355

| | |
|---|---|
| ttttggcgca agttttacag attttattaa agtcgaagct attggtcttg gaagatgaaa | 60 |
| atgcaaatgt tgatgaggtg gaattgaagc cagatacctt aataaaatta tatcttggtt | 120 |
| ataaaaataa gaaattaagg gttaacatca atgtgccaat gaaaaccgaa cagaagcagg | 180 |
| aacaagaaac cacacacaaa acatcgagg aagaccgcaa actactgatt caggcggcca | 240 |
| tcgtgagaat catgaagatg aggaaggttc tgaaacacca gcagttactt ggcgaggtcc | 300 |
| tcactcag | 308 |

<210> SEQ ID NO 356
<211> LENGTH: 207
<212> TYPE: DNA
<213> ORGANISM: Homo sapiens

<400> SEQUENCE: 356

| | |
|---|---|
| ctgtcccaag tgctcccaga aggcaggatt ctgaagacca ctccagcgat atgttcaact | 60 |
| atgaagaata ctgcaccgcc aacgcagtca ctgggccttg ccgtgcatcc ttcccacgct | 120 |
| ggtactttga cgtggagagg aactcctgca ataacttcat ctatggaggc tgccggggca | 180 |
| ataagaacag ctaccgctct gaggagg | 207 |

<210> SEQ ID NO 357
<211> LENGTH: 188
<212> TYPE: DNA
<213> ORGANISM: Homo sapiens
<220> FEATURE:
<221> NAME/KEY: misc_feature
<222> LOCATION: (1)...(188)
<223> OTHER INFORMATION: n = A,T,C or G

<400> SEQUENCE: 357

| | |
|---|---|
| tcgaccacgc cctcgtagcg catgngctnc aggacgatgc tcagagtgat gaacaccccg | 60 |
| gtgcggccca cgccagcact gcagtgcacc gtgataggcc catcctgtcc aaactgctcc | 120 |
| ttggtcttat gcacctgccc gatgaagtca atgaatccct cgcctgtctt gggcacgccc | 180 |
| tgctctgg | 188 |

<210> SEQ ID NO 358
<211> LENGTH: 291
<212> TYPE: DNA
<213> ORGANISM: Homo sapiens

<400> SEQUENCE: 358

| | |
|---|---|
| ctgggagcat cggcaagcta ctgccttaaa atccgatctc cccgagtgca caatttctgt | 60 |
| ccctttaag ggttcacaac actaaagatt tcacatgaaa gggttgtgat tgatttgagc | 120 |
| aggcaggcgg tacgtgacag gggctgcatg caccggtggt cagagagaaa cagaacaggg | 180 |
| cagggaattt cacaatgttc ttctatacaa tggctggaat ctatgaataa catcagtttc | 240 | taagttatgg gttgattttt aactactggg tttaggccag gcaggcccag g          291

<210> SEQ ID NO 359
<211> LENGTH: 117
<212> TYPE: DNA
<213> ORGANISM: Homo sapiens
<220> FEATURE:
<221> NAME/KEY: misc_feature
<222> LOCATION: (1)...(117)
<223> OTHER INFORMATION: n = A,T,C or G

<400> SEQUENCE: 359
gccaccacac tccagcctgg gcaatacagc aagactgtct caaaaaaaaa aaaaaaaaa   60 cccaaaaaaa ctcaaaaang taatgaatga tacccaangn gccttttcta gaaaaag     117

<210> SEQ ID NO 360
<211> LENGTH: 394
<212> TYPE: DNA
<213> ORGANISM: Homo sapiens

<400> SEQUENCE: 360
ctgttcctct ggggtggtcc agttctagag tgggagaaag ggagtcaggc gcattgggaa   60
tcgtggttcc agtctggttg cagaatctgc acatttgcca agaaattttc cctgtttgga  120
aagtttgccc cagctttccc gggcacacca ccttttgtcc caagtgtctg ccggtcgacc  180
aatctgcctg ccacacattg accaagccaa acccggttca cccagctcga ggatcccagg  240
ttgaagagtg gccccttgag gccctggaaa gaccaatcac tggacttctt cccttgagag  300
tcagaggtca cccgtgattc tgcctgcacc ttatcattga tctgcagtga tttctgcaaa  360
tcaagagaaa ctctgcaggg cactcccctg tttc                             394

<210> SEQ ID NO 361
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 361
ctgggcggat agcaccgggc atattttntt natggatgag gtctggcacc ctgagcagtc   60
cagcgaggac ttggtcttag ttgagcaatt tggctaggag gatagtatgc agcacggttc  120
tgagtctgtg ggatagctgc catgaagtaa cctgaaggag gtgctggctg gtaggggttg  180
attacagggt tgggaacagc tcgtacactt gccattctct gcatatactg gttagtgagg  240
tgagcctggc gctcttcttt gcgctgagct aaagctacat acaatggctt tgtggacctc  300
ggccgcgacc acgctaagcc gaattccagc acactggcgg ccgttactag tggatccgag  360
ctcggtacca agcttggcgt aatcatggtc atag                             394

<210> SEQ ID NO 362
<211> LENGTH: 268
<212> TYPE: DNA
<213> ORGANISM: Homo sapiens

<400> SEQUENCE: 362
ctgcgcgtgg accagtcagc ttccgggtgt gactggagca gggcttgtcg tcttcttcag   60
agtcactttg caggggttgg tgaagctgct cccatccatg tacagctccc agtctactga  120

```
tgtttaagga tggtctcggt ggttaggccc actagaataa actgagtcca atacctctac      180
acagttatgt ttaactgggc tctctgacac cgggaggaag gtggcgggt ttaggtgttg       240 caaacttcaa tggttatgcg gggatgtt                                         268

<210> SEQ ID NO 363
<211> LENGTH: 323
<212> TYPE: DNA
<213> ORGANISM: Homo sapiens

<400> SEQUENCE: 363
ccttgacctt ttcagcaagt gggaaggtgt aatccgtctc cacagacaag gccaggactc       60
gtttgtaccc gttgatgata gaatgggta ctgatgcaac agttgggtag ccaatctgca      120
gacagacact ggcaacattg cggacaccct ccaggaagcg agaatgcaga gtttcctctg      180
tgatatcaag cacttcaggg ttgtagatgc tgccattgtc gaacacctgc tggatgacca      240
gcccaaagga gaaggggag atgttgagca tgttcagcag cgtggcttcg ctggctccca      300
ctttgtctcc agtcttgatc aga                                              323

<210> SEQ ID NO 364
<211> LENGTH: 393
<212> TYPE: DNA
<213> ORGANISM: Homo sapiens
<220> FEATURE:
<221> NAME/KEY: misc_feature
<222> LOCATION: (1)...(393)
<223> OTHER INFORMATION: n = A,T,C or G

<400> SEQUENCE: 364
ccaagctctc catcgtcccc gtgcgcagng gctactgggg gaacaagatc ggcaagcccc       60
acactgtccc ttgcaaggtg acaggccgct gcggctctgt gctggtacgc ctcatcactg      120
cacccagggg cactggcatc gtctccgcac ctgtgcctaa gaagctgctc atgatggctg      180
gcatcgatga ctgctacacc tcagcccggg gctgcactgc caccctgggc aacttcgcca      240
aggccacctt tgatgccatt tctaagacct acagctacct gaccccccgac ctctggaagg      300 agactgtatt caccaagtct ccctatcagg agttcactga ccacctcgtc aagacccaca      360
ccagagtctc cgtgcagcgg actcaggctc cag                                   393

<210> SEQ ID NO 365
<211> LENGTH: 371
<212> TYPE: DNA
<213> ORGANISM: Homo sapiens

<400> SEQUENCE: 365
cctcctcaga gcggtagctg ttcttattgc cccggcagcc tccatagatg aagttattgc       60
aggagttcct ctccacgtca aagtaccagc gtgggaagga tgcacggcaa ggcccagtga      120
ctgcgttggc ggtgcagtat tcttcatagt tgaacatatc gctggagtgg tcttcagaat      180
cctgccttct gggagcactt gggacagagg aatccgctgc attcctgctg gtggacctcg      240
gccgcgacca cgctaagccg aattccagca cactggcggc cgttactagt ggatccgagc      300
tcggtaccaa gcttggcgta atcatggtca tagctgtttc ctgtgtgaaa ttgttatccg      360
ctcacaattc c                                                           371

<210> SEQ ID NO 366
<211> LENGTH: 393
<212> TYPE: DNA
<213> ORGANISM: Homo sapiens
```

<400> SEQUENCE: 366

```
atttcttgcc agatgggagc tctttggtga agactccttt cgggaaaagt ttttttggctt    60
cttcttcagg gatggttgga aggaccatca cactatcccc atccttccaa tcaactgggg   120
tggcaaccct ttttctgct gtcagctgga gagagatgac taccctgaga atctcatcaa    180
agttcctgcc agtggtagct gggtagagga tagacagctt cagcttctta tcaggaccaa   240
aaacaaacac cacacgagct gccacaggca tgcccttttc atccttctct gctggatcca   300
gcatgcccaa caggatggca agctcccgat tcctatcatc gatgatggga aaggtaact    360
tttctgtggg ctcttcacaa ttgtaagcat tga                                393
```

<210> SEQ ID NO 367
<211> LENGTH: 327
<212> TYPE: DNA
<213> ORGANISM: Homo sapiens
<220> FEATURE:
<221> NAME/KEY: misc_feature
<222> LOCATION: (1)...(327)
<223> OTHER INFORMATION: n = A,T,C or G

<400> SEQUENCE: 367

```
ccagctctgt ctcatacttg actctaaagt cttnagcagc aagacgggca ttgnnaatct    60
gcagaacgat gcgggcattg tccacagtat ttgcgaagat ctgagccctc aggtcctcga   120
tgatcttgaa gtaatggctc cagtctctga cctggggtcc cttcttctcc aagtgctccc   180
ggattttgct ctccagcctc cggttctcgg tctccaggct cctcactctg tccaggtaag   240
aggccaggcg gtcgttcagg ctttgcatgg tctccttctc gttctggatg cctcccattc   300
ctgccagacc cccggctatc ccggtgg                                       327
```

<210> SEQ ID NO 368
<211> LENGTH: 306
<212> TYPE: DNA
<213> ORGANISM: Homo sapiens
<220> FEATURE:
<221> NAME/KEY: misc_feature
<222> LOCATION: (1)...(306)
<223> OTHER INFORMATION: n = A,T,C or G

<400> SEQUENCE: 368

```
ctggagaagg acttcagcag tttnaagaag tactgccaag tcatccgtgt cattgcccac    60
acccagatgc gcctgcttcc tctgcgccag aagaaggccc acctgatgga gatccaggtg   120
aacggaggca ctgtggccga aagctggac tgggcccgcg agaggcttga gcagcaggta    180
cctgtgaacc aagtgtttgg gcaggatgag atgatcgacg tcatcggggt gaccaagggc   240
aaaggctaca aggggtcac cagtcgttgg cacaccaaga agctgccccg caagacccac   300
cgagga                                                              306
```

<210> SEQ ID NO 369
<211> LENGTH: 394
<212> TYPE: DNA
<213> ORGANISM: Homo sapiens

<400> SEQUENCE: 369

```
tcgacccaca ccggaacacg gagagctggg ccagcattgg cacttgatag gatttcccgt    60
cggctgccac gaaagtgcgt ttctttgtgt tctcggggttg aaccgtgat ttccacagac   120
ccttgaaata cactgcgttg acgaggacca gtctggtgag cacaccatca ataagatctg   180
```

| | |
|---|---|
| gggacagcag attgtcaatc atatccctgg tttcattttt aacccatgca ttgatggaat | 240 |
| cacaggcaga ggctggatcc tcaaagttca cattccggac ctcacactgg aacacatctt | 300 |
| tgttccttgt aacaaaaggc acttcaattt cagaggcatt cttaacaaac acggcgttag | 360 |
| ccactgtcac aatgtcttta ttcttcttgg agac | 394 |

<210> SEQ ID NO 370
<211> LENGTH: 653
<212> TYPE: DNA
<213> ORGANISM: Homo sapiens

<400> SEQUENCE: 370

| | |
|---|---|
| ccaccacacc caattccttg ctggtatcat ggcagccgcc acgtgccagg attaccggct | 60 |
| acatcatcaa gtatgagaag cctgggtctc ctcccagaga gtggtccct cggcccgcc | 120 |
| ctggtgtcac agaggctact attactggcc tggaaccggg aaccgaatat acaatttatg | 180 |
| tcattgccct gaagaataat cagaagagcg agccctgat tggaaggaaa aagacagacg | 240 |
| agcttcccca actggtaacc cttccacacc ccaatcttca tggaccagag atcttggatg | 300 |
| ttccttccac agttcaaaag acccctttcg tcacccaccc tgggtatgac actggaaatg | 360 |
| gtattcagct tcctggcact tctggtcagc aacccagtgt tgggcaacaa atgatctttg | 420 |
| aggaacatgg ttttaggcgg accacaccgc ccacaacggc cacccccata aggcataggc | 480 |
| caagaccata cccgccgaat gtaggacaag aagctctctc tcagacaacc atctcatggg | 540 |
| ccccattcca ggacacttct gagtacatca tttcatgtca tcctgttggc actgatgaag | 600 |
| aacccttaca gttcagggtt cctggaactt ctaccagtgc cactctgaca gga | 653 |

<210> SEQ ID NO 371
<211> LENGTH: 268
<212> TYPE: DNA
<213> ORGANISM: Homo sapiens

<400> SEQUENCE: 371

| | |
|---|---|
| ctgcccagcc cccattggcg agtttgagaa ggtgtgcagc aatgacaaca agaccttcga | 60 |
| ctcttcctgc cacttctttg ccacaaagtg caccctggag ggcaccaaga agggccacaa | 120 |
| gctccacctg gactacatcg ggccttgcaa atacatcccc ccttgcctgg actctgagct | 180 |
| gaccgaattc cccctgcgca tgcgggactg gctcaagaac gtcctggtca ccctgtatga | 240 |
| gagggatgag acaacaacc ttctgact | 268 |

<210> SEQ ID NO 372
<211> LENGTH: 392
<212> TYPE: DNA
<213> ORGANISM: Homo sapiens

<400> SEQUENCE: 372

| | |
|---|---|
| gctggtgccc ctggtgaacg tggacctcct ggattggcag gggccccagg acttagaggt | 60 |
| ggaactggtc ccctggtcc cgaaggagga agggtgctg ctggtcctcc tgggccacct | 120 |
| ggtgctgctg gtactcctgg tctgcaagga atgcctggag aaagaggagg tcttggaagt | 180 |
| cctggtccaa aggtgacaa gggtgaacca ggcggtccag gtgctgatgg tgtcccaggg | 240 |
| aaagatggcc caagggtcc tactggtcct attggtcctc ctggcccagc tggccagcct | 300 |
| ggagataagg gtgaaggtgg tgcccccgga cttccaggta tagctggacc tcgtggtagc | 360 |
| cctggtgaga gaggtgaaac ctcggccgcg ac | 392 |

<210> SEQ ID NO 373
<211> LENGTH: 388
<212> TYPE: DNA
<213> ORGANISM: Homo sapiens
<220> FEATURE:
<221> NAME/KEY: misc_feature
<222> LOCATION: (1)...(388)
<223> OTHER INFORMATION: n = A,T,C or G

<400> SEQUENCE: 373

```
ccaagcgctc agatcggcaa ggggcaccan ttttgatctg cccagtgcac agccccacaa      60
ccaggtcagc gatgaaggta tcttcagtct cccccgaacg atgagacacc atgacgcccc    120
aaccattggc ctgggccagc ttgcacgcct gaagagactc ggtcacggag ccaatctggt    180
tgactttgag caggaggcag ttgcaggact tctcgttcac ggccttggcg atcctctttg    240
ggttggtcac tgtgagatca tcccccacta cctggattcc tgcactggct gtgaacttct    300
gccaagctcc ccagtcatcc tggtcaaagg gatcttcgat agacaccact gggtagtcct    360
tgatgaagga cttgtacagg tcagccag                                       388
```

<210> SEQ ID NO 374
<211> LENGTH: 393
<212> TYPE: DNA
<213> ORGANISM: Homo sapiens

<400> SEQUENCE: 374

```
ctgacgaccg cgtgaacccc tgcattgggg gtgtcatcct cttccatgag acactctacc      60
agaaggcgga tgatgggcgt cccttccccc aagttatcaa atccaagggc ggtgttgtgg    120
gcatcaaggt agacaagggc gtggtccccc tggcagggac aaatggcgag actaccaccc    180
aagggttgga tgggctgtct gagcgctgtg cccagtacaa gaaggacgga gctgacttcg    240
ccaagtggcg ttgtgtgctg aagattgggg aacacacccc ctcagccctc gccatcatgg    300
aaaatgccaa tgttctggcc cgttatgcca gtatctgcca gcagaatggc attgtgccca    360
tcgtggagcc tgagatcctc cctgatgggg acc                                 393
```

<210> SEQ ID NO 375
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 375

```
ccacaaatgg cgtggtccat gtcatcaccn ttnttctgca gcctccagcc aacagacctc      60
aggaaagagg ggatgaactt gcagactctg cgcttgagat cttcaaacaa gcatcagcgt    120
tttccagggc ttcccagagg tctgtgcgac tagcccctgt ctatcaaaag ttattagaga    180
ggatgaagca ttagcttgaa gcactacagg aggaatgcac cacggcagct ctccgccaat    240
ttctctcaga tttccacaga gactgtttga atgttttcaa aaccaagtat cacactttaa    300
tgtacatggg ccgcaccata atgagatgtg agccttgtgc atgtggggga ggagggagag    360
agatgtactt tttaaatcat gttcccccta aaca                                394
```

<210> SEQ ID NO 376
<211> LENGTH: 392
<212> TYPE: DNA
<213> ORGANISM: Homo sapiens
<220> FEATURE:

-continued

```
<221> NAME/KEY: misc_feature
<222> LOCATION: (1)...(392)
<223> OTHER INFORMATION: n = A,T,C or G

<400> SEQUENCE: 376
ctgcccagcc cccattggcg agtttgattn ggtgtgcagc aatgacaaca agaccttcga      60
ctcttcctgc cacttctttg ccacaaagtg caccctggag ggcaccaaga agggccacaa     120
gctccacctg gactacatcg ggccttgcaa atacatcccc ccttgcctgg actctgagct     180
gaccgaattc cccctgcgca tgcgggactg gctcaagaac gtcctggtca ccctgtatga     240
gagggatgag gacaacaacc ttctgactga gaagcagaag ctgcgggtga agaagatcca     300
tgagaatgag aagcgcctgg aggcaggaga ccaccccgtg gagctgctgg cccgggactt     360
cgagaagaac tataacatgt acatcttccc tg                                   392

<210> SEQ ID NO 377
<211> LENGTH: 292
<212> TYPE: DNA
<213> ORGANISM: Homo sapiens

<400> SEQUENCE: 377
caatgtttga tgcttaaccc ccccaatttc tgtgagatgg atggccagtg caagcgtgac      60
ttgaagtgtt gcatgggcat gtgtgggaaa tcctgcgttt ccctgtgaa agcttgattc     120 ctgccatatg gaggaggctc tggagtcctg ctctgtgtgg tccaggtcct ttccaccctg     180
agacttggct ccaccactga tatcctcctt tggggaaagg cttggcacac agcaggcttt     240
caagaagtgc cagttgatca atgaataaat aaacgagcct atttctcttt gc             292

<210> SEQ ID NO 378
<211> LENGTH: 395
<212> TYPE: DNA
<213> ORGANISM: Homo sapiens

<400> SEQUENCE: 378
ctgctgcttc agcgaagggt ttctggcata tccaatgata aggctgccaa agactgttcc      60
aataccagca ccagaaccag ccactcctac tgttgcagca cctgcaccaa taaatttggc     120
agcagtatca atgtctctgc tgattgcact ggtctgaaac tccctttgga ttagctgaga     180
cacaccattc tgggccctga ttttcctaag atagaactcc aactctttgc cctctagcac     240
atagccatct gctcggccac actgtcccgg ccttgaagcg atgcacgcaa gaagcttgcc     300
ctgctggaac tgctcctcca ggagactgct gattttggca ttcttttttcc tttcatcata     360 tttcttctga attttttaga tcgttttttg tttaa                                395

<210> SEQ ID NO 379
<211> LENGTH: 223
<212> TYPE: DNA
<213> ORGANISM: Homo sapiens

<400> SEQUENCE: 379
ccagatgaaa tgctgccgca atggctgtgg gaaggtgtcc tgtgtcactc ccaatttctg      60
agctccagcc accaccaggc tgagcagtga ggagagaaag tttctgcctg gccctgcatc     120
tggttccagc ccacctgccc tcccttttt cgggactctg tattccctct tgggctgacc     180
acagcttctc ccttccccaa ccaataaagt aaccactttc agc                       223

<210> SEQ ID NO 380
<211> LENGTH: 317
```

```
<212> TYPE: DNA
<213> ORGANISM: Homo sapiens
<220> FEATURE:
<221> NAME/KEY: misc_feature
<222> LOCATION: (1)...(317)
<223> OTHER INFORMATION: n = A,T,C or G

<400> SEQUENCE: 380
tcgaccacag tattccaacc ctcctgtgcn tngagaagtg atggagggtg ctgacaacca      60
gggtgcagga gaacaaggta gaccagtgag gcagaatatg tatcgggat atagaccacg     120 attccgcagg ggccctcctc gccaaagaca gcctagagag gacggcaatg aagaagataa     180
agaaaatcaa ggagatgaga cccaaggtca gcagccacct caacgtcggt accgccgcaa     240
cttcaattac cgacgcagac gcccagaaaa ccctaaacca caagatggca aagagacaaa     300
agcagccgat ccaccag                                                     317

<210> SEQ ID NO 381
<211> LENGTH: 392
<212> TYPE: DNA
<213> ORGANISM: Homo sapiens
<220> FEATURE:
<221> NAME/KEY: misc_feature
<222> LOCATION: (1)...(392)
<223> OTHER INFORMATION: n = A,T,C or G

<400> SEQUENCE: 381
cctgaaggaa gagctggcct acctgaatnn naaccatgag gaggaaatca gtacgctgag      60
gggccaagtg ggaggccagg tcagtgtgga ggtggattcc gctccgggca ccgatctcgc     120
caagatcctg agtgacatgc gaagccaata tgaggtcatg gccgagcaga accggaagga     180
tgctgaagcc tggttcacca gccggactga agaattgaac cggaggtcg ctggccacac      240 ggagcagctc cagatgagca ggtccgaggt tactgacctg cggcgcaccc ttcagggtct     300
tgagattgag ctgcagtcac agacctcggc cgcgaccacg ctaagccgaa ttccagcaca     360
ctggcggccg ttactagtgg atccgagctc gg                                    392

<210> SEQ ID NO 382
<211> LENGTH: 234
<212> TYPE: DNA
<213> ORGANISM: Homo sapiens

<400> SEQUENCE: 382
cctcgatgtc taaatgagcg tggtaaagga tggtgcctgc tggggtctcg tagatacctc      60
gggacttcat tccaatgaag cggttctcca cgatgtcaat acggcccacg ccatgcttgc     120
ccgcgacttc gttcaggtac atgaagagct ccaaggaggt ctggtgggtg gtgccatcct     180
tgacgttggt caccttcaca gggacccctt ttttgaactc catctccaga atgt            234

<210> SEQ ID NO 383
<211> LENGTH: 396
<212> TYPE: DNA
<213> ORGANISM: Homo sapiens
<220> FEATURE:
<221> NAME/KEY: misc_feature
<222> LOCATION: (1)...(396)
<223> OTHER INFORMATION: n = A,T,C or G

<400> SEQUENCE: 383
ccttgacctt tcagcaagt gggaaggtgt tttccgtctc cacagacaag gccaggactc       60
gtttgnaccc gttgatgata gaatgggta ctgatgcaac agttgggtag ccaatctgca      120
```

| | |
|---|---|
| gacagacact ggcaacattg cggacaccca ggatttcaat ggtgccctg gagattttag | 180 |
| tggtgatacc taaagcctgg aaaaggagg tcttctcggg cccgagacca gtgttctggg | 240 |
| ctggcacagt gacttcacat ggggcaatgg caccagcacg ggcagcagac ctgcccgggc | 300 |
| ggccgctcga aagccgaatt ccagcacact ggcggccgtt actagtggat ccgagctcgg | 360 |
| taccaagctt ggcgtaatca tggtcatagc tgtttc | 396 |

<210> SEQ ID NO 384
<211> LENGTH: 396
<212> TYPE: DNA
<213> ORGANISM: Homo sapiens

<400> SEQUENCE: 384

| | |
|---|---|
| gctgaatagg cacagagggc acctgtacac cttcagacca gtctgcaacc tcaggctgag | 60 |
| tagcagtgaa ctcaggagcg ggagcagtcc attcaccctg aaattcctcc ttggtcactg | 120 |
| ccttctcagc agcagcctgc tcttcttttt caatctcttc aggatctctg tagaagtaca | 180 |
| gatcaggcat gacctcccat gggtgttcac gggaaatggt gccacgcatg cgcagaactt | 240 |
| cccgagccag catccaccac atcaaaccca ctgagtgagc tcccttgttg ttgcatggga | 300 |
| tggcaatgtc cacatagcgc agaggagaat ctgtgttaca cagcgcaatg gtaggtaggt | 360 |
| taacataaga tgcctccgtg agaggctggt ggtcag | 396 |

<210> SEQ ID NO 385
<211> LENGTH: 2943
<212> TYPE: DNA
<213> ORGANISM: Homo sapiens

<400> SEQUENCE: 385

| | |
|---|---|
| cagccaccgg agtggatgcc atctgcaccc accgccctga ccccacaggc cctgggctgg | 60 |
| acagagagca gctgtatttg gagctgagcc agctgaccca cagcatcact gagctgggcc | 120 |
| cctacaccct ggacagggac agtctctatg tcaatggttt cacacagcgg agctctgtgc | 180 |
| ccaccactag cattcctggg acccccacag tggacctggg aacatctggg actccagttt | 240 |
| ctaaacctgg tccctcggct gccagccctc tcctggtgct attcactctc aacttcacca | 300 |
| tcaccaacct gcggtatgag gagaacatgc agcaccctgg ctccaggaag ttcaacacca | 360 |
| cggagagggt ccttcagggc ctggtccctg ttcaagagca ccagtgttgg ccctctgtac | 420 |
| tctggctgca gactgacttt gctcaggcct gaaaaggatg ggacagccac tggagtggat | 480 |
| gccatctgca cccaccaccc tgaccccaaa agccctaggc tggacagaga gcagctgtat | 540 |
| tgggagctga gccagctgac ccacaatatc actgagctgg gcccctatgc cctggacaac | 600 |
| gacagcctct ttgtcaatgg tttcactcat cggagctctg tgtccaccac cagcactcct | 660 |
| gggacccca cagtgtatct gggagcatct aagactccag cctcgatatt tggcccttca | 720 |
| gctgccagcc atcctgat actattcacc ctcaacttca ccatcactaa cctgcggtat | 780 |
| gaggagaaca tgtggcctgg ctccaggaag ttcaacacta cagagagggt ccttcagggc | 840 |
| ctgctaaggc ccttgttcaa gaacaccagt gttggccctc tgtactctgg ctgcaggctg | 900 |
| accttgctca ggccagagaa agatggggaa gccaccggag tggatgccat ctgcacccac | 960 |
| cgccctgacc ccacaggccc tgggctggac agagagcagc tgtatttgga gctgagccag | 1020 |
| ctgaccccaca gcatcactga gctgggcccc tacacactgg acagggacag tctctatgtc | 1080 |
| aatggtttca cccatcggag ctctgtaccc accaccagca ccgggtggt cagcgaggag | 1140 |
| ccattcacac tgaacttcac catcaacaac ctgcgctaca tggcggacat gggccaaccc | 1200 |

-continued

```
ggctccctca agttcaacat cacagacaac gtcatgaagc acctgctcag tcctttgttc    1260
cagaggagca gcctgggtgc acggtacaca ggctgcaggg tcatcgcact aaggtctgtg    1320
aagaacggtg ctgagacacg ggtggacctc ctctgcacct acctgcagcc cctcagcggc    1380
ccaggtctgc ctatcaagca ggtgttccat gagctgagcc agcagaccca tggcatcacc    1440
cggctgggcc cctactctct ggacaaagac agcctctacc ttaacggtta caatgaacct    1500
ggtccagatg agcctcctac aactcccaag ccagccacca cattcctgcc tcctctgtca    1560
gaagccacaa cagccatggg gtaccaccctg aagaccctca cactcaactt caccatctcc    1620
aatctccagt attcaccaga tatgggcaag ggctcagcta cattcaactc caccgagggg    1680
gtccttcagc acctgctcag acccttgttc cagaagagca gcatgggccc cttctacttg    1740
ggttgccaac tgatctccct caggcctgag aaggatgggg cagccactgg tgtggacacc    1800
acctgcacct accaccctga ccctgtgggc cccgggctgg acatacagca gctttactgg    1860
gagctgagtc agctgaccca tggtgtcacc caactgggct tctatgtcct ggacagggat    1920
agcctcttca tcaatggcta tgcaccccag aatttatcaa tccggggcga gtaccagata    1980
aatttccaca ttgtcaactg gaacctcagt aatccagacc ccacatcctc agagtacatc    2040
accctgctga gggacatcca ggacaaggtc accacactct acaaaggcag tcaactacat    2100
gacacattcc gcttctgcct ggtcaccaac ttgacgatgg actccgtgtt ggtcactgtc    2160
aaggcattgt tctcctccaa tttggacccc agcctggtgg agcaagtctt tctagataag    2220
accctgaatg cctcattcca ttggctgggc tccacctacc agttggtgga catccatgtg    2280
acagaaatgg agtcatcagt ttatcaacca caagcagct ccagcaccca gcacttctac    2340
ctgaatttca ccatcaccaa cctaccatat tcccaggaca aagcccagcc aggcaccacc    2400
aattaccaga ggaacaaaag gaatattgag gatgcggcac cacccggggg tggactccct    2460
gtgtaacttc tcgccactgg ctcggagagt agacagagtt gccatctatg aggaatttct    2520
gcggatgacc cggaatggta cccagctgca gaacttcacc ctggacagga gcagtgtcct    2580
tgtggatggg tattttccca acagaaatga gcccttaact gggaattctg accttccctt    2640
ctgggctgtc atcctcatcg gcttggcagg actcctggga ctcatcacat gcctgatctg    2700
cggtgtcctg gtgaccaccc gccggcggaa gaaggaagga gaatcaacg tccagcaaca    2760 gtgcccaggc tactaccagt cacacctaga cctggaggat ctgcaatgac tggaacttgc    2820
cggtgcctgg ggtgccttc ccccagccag ggtccaaaga agcttggctg gggcagaaat    2880
aaaccatatt ggtcggaaaa aaaaaaaaaa aaaaaaaaa aaaaaaaaaa aaaaaaaaa    2940 aaa                                                                2943
```

<210> SEQ ID NO 386
<211> LENGTH: 2608
<212> TYPE: DNA
<213> ORGANISM: Homo sapiens

<400> SEQUENCE: 386

```
gttcaagagc accagtgttg gccctctgta ctctggctgc agactgactt tgctcaggcc     60
tgaaaaggat gggacagcca ctggagtgga tgccatctgc acccaccacc ctgaccccaa    120
aagccctagg ctggacagag agcagctgta ttgggagctg agccagctga cccacaatat    180
cactgagctg ggcccctatg ccctggacaa cgacagcctc tttgtcaatg gtttcactca    240
tcggagctct gtgtccacca ccagcactcc tgggaccccc acagtgtatc tgggagcatc    300
```

-continued

```
taagactcca gcctcgatat ttggcccttc agctgccagc catctcctga tactattcac     360
cctcaacttc accatcacta acctgcggta tgaggagaac atgtggcctg gctccaggaa     420
gttcaacact acagagaggg tccttcaggg cctgctaagg cccttgttca agaacaccag     480
tgttggccct ctgtactctg gctgcaggct gaccttgctc aggccagaga agatggggaa     540
agccaccgga gtggatgcca tctgcaccca ccgccctgac ccacaggcc ctgggctgga     600 cagagagcag ctgtatttgg agctgagcca gctgacccac agcatcactg agctgggccc     660
ctacacactg gacagggaca gtctctatgt caatggtttc acccatcgga gctctgtacc     720
caccaccagc accggggtgg tcagcgagga gccattcaca ctgaacttca ccatcaacaa     780
cctgcgctac atggcggaca tgggccaacc cggctccctc aagttcaaca tcacagacaa     840
cgtcatgaag cacctgctca gtcctttgtt ccagaggagc agcctgggtg cacggtacac     900
aggctgcagg gtcatcgcac taaggtctgt gaagaacggt gctgagacac gggtggacct     960
cctctgcacc tacctgcagc ccctcagcgg cccaggtctg cctatcaagc aggtgttcca    1020
tgagctgagc cagcagaccc atggcatcac ccggctgggc ccctactctc tggacaaaga    1080
cagcctctac cttaacggtt acaatgaacc tggtccagat gagcctccta caactcccaa    1140
gccagccacc acattcctgc ctcctctgtc agaagccaca acagccatgg ggtaccacct    1200
gaagaccctc acactcaact tcaccatctc caatctccag tattcaccag atatgggcaa    1260
gggctcagct acattcaact ccaccgaggg ggtccttcag cacctgctca gacccttgtt    1320
ccagaagagc agcatgggcc ccttctactt gggttgccaa ctgatctccc tcaggcctga    1380
gaaggatggg gcagccactg gtgtggacac cacctgcacc taccaccctg accctgtggg    1440
ccccgggctg gacatacagc agctttactg ggagctgagt cagctgaccc atggtgtcac    1500
ccaactgggc ttctatgtcc tggacaggga tagcctcttc atcaatggct atgcacccca    1560
gaatttatca atccggggcg agtaccagat aaatttccac attgtcaact ggaacctcag    1620
taatccagac cccacatcct cagagtacat caccctgctg agggacatcc aggacaaggt    1680
caccacactc tacaaaggca gtcaactaca tgacacattc cgcttctgcc tggtcaccaa    1740
cttgacgatg gactccgtgt tggtcactgt caaggcattg ttctcctcca atttggaccc    1800
cagcctggtg gagcaagtct ttctagataa gaccctgaat gcctcattcc attggctggg    1860
ctccacctac cagttggtgg acatccatgt gacagaaatg gagtcatcag tttatcaacc    1920
aacaagcagc tccagcaccc agcacttcta cctgaatttc accatcacca acctaccata    1980
ttcccaggac aaagcccagc caggcaccac caattaccag aggaacaaaa ggaatattga    2040
ggatgcgctc aaccaactct tccgaaacag cagcatcaag agttatttttt ctgactgtca    2100 agtttcaaca ttcaggtctg tccccaacag gcaccacacc ggggtggact ccctgtgtaa    2160
cttctcgcca ctggctcgga gagtagacag agttgccatc tatgaggaat ttctgcggat    2220
gacccggaat ggtacccagc tgcagaactt caccctggca aggagcagtg tccttgtgga    2280
tgggtatttt cccaacagaa atgagccctt aactgggaat tctgaccttc ccttctgggc    2340
tgtcatcctc atcggcttgg caggactcct gggactcatc acatgcctga tctgcggtgt    2400
cctggtgacc acccgccggc ggaagaagga aggagaatac aacgtccagc aacagtgccc    2460
aggctactac cagtcacacc tagacctgga ggatctgcaa tgactggaac ttgccggtgc    2520
ctggggtgcc tttccccag ccagggtcca agaagcttg gctggggcag aaataaacca    2580
tattggtcgg acacaaaaaa aaaaaaaa                                       2608
```

<210> SEQ ID NO 387
<211> LENGTH: 1761
<212> TYPE: DNA
<213> ORGANISM: Homo sapiens

<400> SEQUENCE: 387

```
ctgaacttca ccatcaacaa cctgcgctac atggcggaca tgggccaacc cggctccctc      60
aagttcaaca tcacagacaa cgtcatgaag cacctgctca gtcctttgtt ccagaggagc     120
agcctgggtg cacggtacac aggctgcagg gtcatcgcac taaggtctgt gaagaacggt     180
gctgagacac gggtggacct cctctgcagg taggtgcaga ggaggtccac ggcatcaccc     240
ggctgggccc ctactctctg gacaaagaca gcctctacct taacgctccc aagccagcca     300
ccacattcct gcctcctctg tcagaagcca acagccat ggggtaccac ctgaagaccc       360
tcacactcaa cttcaccatc tccaatctcc agtattcacc agatatgggc aagggctcag     420
ctacattcaa ctccaccgag ggggtccttc agcacctgct cagacccttg ttccagaaga     480
gcagcatggg ccccttctac ttgggttgcc aactgatctc cctcaggcct gagaaggatg     540
gggcagccac tggtgtggac accacctgca cctaccaccc tgaccctgtg gcccccgggc     600
tggacataca gcagctttac tgggagctga gtcagctgac ccatggtgtc acccaactgg     660
gcttctatgt cctggacagg gatagcctct tcatcaatgg ctatgcaccc cagaatttat     720
caatccgggg cgagtaccag ataaatttcc acattgtcaa ctggaacctc agtaatccag     780
accccacatc ctcagagtac atcaccctgc tgagggacat ccaggacaag gtcaccacac     840
tctacaaagg cagtcaacta catgacacat tccgcttctg cctggtcacc aacttgacga     900
tggactccgt gttggtcact gtcaaggcat tgttctcctc caatttggac cccagcctgg     960
tggagcaagt ctttctagat aagaccctga atgcctcatt ccattggctg ggctccacct    1020
accagttggt ggacatccat gtgacagaaa tggagtcatc agtttatcaa ccaacaagca    1080
gctccagcac ccagcacttc tacctgaatt tcaccatcac caacctacca tattcccagg    1140
acaaagccca gccaggcacc accaattacc agaggaacaa aaggaatatt gaggatgcgc    1200
tcaaccaact cttccgaaac agcagcatca agagttattt ttctgactgt caagtttcaa    1260
cattcaggtc tgtccccaac aggcaccaca ccggggtgga ctccctgtgt aacttctcgc    1320
cactggctcg gagagtagac agagttgcca tctatgagga atttctgcgg atgacccgga    1380
atggtacccca gctgcagaac ttcaccctgg acaggagcag tgtccttgtg gatgggtatt    1440
ttcccaacag aaatgagccc ttaactggga attctgacct tcccttctgg gctgtcatcc    1500
tcatcggctt ggcaggactc ctgggactca tcacatgcct gatctgcggt gtcctggtga    1560
ccaccccgcg gcggaagaag gaaggagaat acaacgtcca gcaacagtgc ccaggctact    1620
accagtcaca cctagacctg gaggatctgc aatgactgga acttgccggt gcctggggtg    1680
cctttccccc agccagggtc caaagaagct tggctggggc agaaataaac catattggtc    1740
ggacacaaaa aaaaaaaaaa a                                              1761
```

<210> SEQ ID NO 388
<211> LENGTH: 772
<212> TYPE: PRT
<213> ORGANISM: Homo sapiens

<400> SEQUENCE: 388

```
Met Ser Met Val Ser His Ser Gly Ala Leu Cys Pro Pro Leu Ala Phe
             5                  10                  15

Leu Gly Pro Pro Gln Trp Thr Trp Glu His Leu Gly Leu Gln Phe Leu
```

-continued

```
                20                  25                  30
Asn Leu Val Pro Arg Leu Pro Ala Leu Ser Trp Cys Tyr Ser Leu Ser
             35                  40                  45

Thr Ser Pro Ser Pro Thr Cys Gly Met Arg Arg Thr Cys Ser Thr Leu
 50                  55                  60

Ala Pro Gly Ser Ser Thr Pro Arg Arg Gly Ser Phe Arg Ala Trp Ser
 65                  70                  75                  80

Leu Phe Lys Ser Thr Ser Val Gly Pro Leu Tyr Ser Gly Cys Arg Leu
             85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
            115                 120                 125

Gln Leu Tyr Trp Glu Leu Ser Gln Leu Thr His Asn Ile Thr Glu Leu
            130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
            195                 200                 205

Leu Arg Tyr Glu Glu Asn Met Trp Pro Gly Ser Arg Lys Phe Asn Thr
            210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
            275                 280                 285

Leu Ser Gln Leu Thr His Ser Ile Thr Glu Leu Gly Pro Tyr Thr Leu
            290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
            355                 360                 365

Pro Leu Phe Gln Arg Ser Ser Leu Gly Ala Arg Tyr Thr Gly Cys Arg
            370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
            435                 440                 445
```

```
Asn Glu Pro Gly Pro Asp Glu Pro Pro Thr Thr Pro Lys Pro Ala Thr
    450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
        515                 520                 525

Phe Tyr Leu Gly Cys Gln Leu Ile Ser Leu Arg Pro Glu Lys Asp Gly
    530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
                565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
        595                 600                 605

Tyr Gln Ile Asn Phe His Ile Val Asn Trp Asn Leu Ser Asn Pro Asp
    610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
                645                 650                 655

Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
        675                 680                 685

Leu Asp Lys Thr Leu Asn Ala Ser Phe His Trp Leu Gly Ser Thr Tyr
    690                 695                 700

Gln Leu Val Asp Ile His Val Thr Glu Met Glu Ser Ser Val Tyr Gln
705                 710                 715                 720

Pro Thr Ser Ser Ser Thr Gln His Phe Tyr Leu Asn Phe Thr Ile
                725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Ala Pro His Arg Gly
        755                 760                 765

Gly Leu Pro Val
    770

<210> SEQ ID NO 389
<211> LENGTH: 833
<212> TYPE: PRT
<213> ORGANISM: Homo sapiens

<400> SEQUENCE: 389

Phe Lys Ser Thr Ser Val Gly Pro Leu Tyr Ser Gly Cys Arg Leu Thr
                5                   10                  15

Leu Leu Arg Pro Glu Lys Asp Gly Thr Ala Thr Gly Val Asp Ala Ile
            20                  25                  30

Cys Thr His His Pro Asp Pro Lys Ser Pro Arg Leu Asp Arg Glu Gln
```

-continued

```
            35                  40                  45
Leu Tyr Trp Glu Leu Ser Gln Leu Thr His Asn Ile Thr Glu Leu Gly
 50                  55                  60

Pro Tyr Ala Leu Asp Asn Asp Ser Leu Phe Val Asn Gly Phe Thr His
 65                  70                  75                  80

Arg Ser Ser Val Ser Thr Thr Ser Thr Pro Gly Thr Pro Thr Val Tyr
                 85                  90                  95

Leu Gly Ala Ser Lys Thr Pro Ala Ser Ile Phe Gly Pro Ser Ala Ala
                100                 105                 110

Ser His Leu Leu Ile Leu Phe Thr Leu Asn Phe Thr Ile Thr Asn Leu
                115                 120                 125

Arg Tyr Glu Glu Asn Met Trp Pro Gly Ser Arg Lys Phe Asn Thr Thr
130                 135                 140

Glu Arg Val Leu Gln Gly Leu Leu Arg Pro Leu Phe Lys Asn Thr Ser
145                 150                 155                 160

Val Gly Pro Leu Tyr Ser Gly Cys Arg Leu Thr Leu Leu Arg Pro Glu
                165                 170                 175

Lys Asp Gly Glu Ala Thr Gly Val Asp Ala Ile Cys Thr His Arg Pro
                180                 185                 190

Asp Pro Thr Gly Pro Gly Leu Asp Arg Glu Gln Leu Tyr Leu Glu Leu
                195                 200                 205

Ser Gln Leu Thr His Ser Ile Thr Glu Leu Gly Pro Tyr Thr Leu Asp
                210                 215                 220

Arg Asp Ser Leu Tyr Val Asn Gly Phe Thr His Arg Ser Ser Val Pro
225                 230                 235                 240

Thr Thr Ser Thr Gly Val Val Ser Glu Pro Phe Thr Leu Asn Phe
                245                 250                 255

Thr Ile Asn Asn Leu Arg Tyr Met Ala Asp Met Gly Gln Pro Gly Ser
                260                 265                 270

Leu Lys Phe Asn Ile Thr Asp Asn Val Met Lys His Leu Leu Ser Pro
                275                 280                 285

Leu Phe Gln Arg Ser Ser Leu Gly Ala Arg Tyr Thr Gly Cys Arg Val
                290                 295                 300

Ile Ala Leu Arg Ser Val Lys Asn Gly Ala Glu Thr Arg Val Asp Leu
305                 310                 315                 320

Leu Cys Thr Tyr Leu Gln Pro Leu Ser Gly Pro Gly Leu Pro Ile Lys
                325                 330                 335

Gln Val Phe His Glu Leu Ser Gln Gln Thr His Gly Ile Thr Arg Leu
                340                 345                 350

Gly Pro Tyr Ser Leu Asp Lys Asp Ser Leu Tyr Leu Asn Gly Tyr Asn
                355                 360                 365

Glu Pro Gly Pro Asp Glu Pro Thr Thr Pro Lys Pro Ala Thr Thr
                370                 375                 380

Phe Leu Pro Pro Leu Ser Glu Ala Thr Thr Ala Met Gly Tyr His Leu
385                 390                 395                 400

Lys Thr Leu Thr Leu Asn Phe Thr Ile Ser Asn Leu Gln Tyr Ser Pro
                405                 410                 415

Asp Met Gly Lys Gly Ser Ala Thr Phe Asn Ser Thr Glu Gly Val Leu
                420                 425                 430

Gln His Leu Leu Arg Pro Leu Phe Gln Lys Ser Ser Met Gly Pro Phe
                435                 440                 445

Tyr Leu Gly Cys Gln Leu Ile Ser Leu Arg Pro Glu Lys Asp Gly Ala
                450                 455                 460
```

```
Ala Thr Gly Val Asp Thr Thr Cys Thr Tyr His Pro Asp Pro Val Gly
465                 470                 475                 480

Pro Gly Leu Asp Ile Gln Gln Leu Tyr Trp Glu Leu Ser Gln Leu Thr
            485                 490                 495

His Gly Val Thr Gln Leu Gly Phe Tyr Val Leu Asp Arg Asp Ser Leu
        500                 505                 510

Phe Ile Asn Gly Tyr Ala Pro Gln Asn Leu Ser Ile Arg Gly Glu Tyr
    515                 520                 525

Gln Ile Asn Phe His Ile Val Asn Trp Asn Leu Ser Asn Pro Asp Pro
530                 535                 540

Thr Ser Ser Glu Tyr Ile Thr Leu Leu Arg Asp Ile Gln Asp Lys Val
545                 550                 555                 560

Thr Thr Leu Tyr Lys Gly Ser Gln Leu His Asp Thr Phe Arg Phe Cys
            565                 570                 575

Leu Val Thr Asn Leu Thr Met Asp Ser Val Leu Val Thr Val Lys Ala
                580                 585                 590

Leu Phe Ser Ser Asn Leu Asp Pro Ser Leu Val Glu Gln Val Phe Leu
        595                 600                 605

Asp Lys Thr Leu Asn Ala Ser Phe His Trp Leu Gly Ser Thr Tyr Gln
    610                 615                 620

Leu Val Asp Ile His Val Thr Glu Met Glu Ser Ser Val Tyr Gln Pro
625                 630                 635                 640

Thr Ser Ser Ser Thr Gln His Phe Tyr Leu Asn Phe Thr Ile Thr
            645                 650                 655

Asn Leu Pro Tyr Ser Gln Asp Lys Ala Gln Pro Gly Thr Thr Asn Tyr
                660                 665                 670

Gln Arg Asn Lys Arg Asn Ile Glu Asp Ala Leu Asn Gln Leu Phe Arg
        675                 680                 685

Asn Ser Ser Ile Lys Ser Tyr Phe Ser Asp Cys Gln Val Ser Thr Phe
    690                 695                 700

Arg Ser Val Pro Asn Arg His His Thr Gly Val Asp Ser Leu Cys Asn
705                 710                 715                 720

Phe Ser Pro Leu Ala Arg Val Asp Arg Val Ala Ile Tyr Glu Glu
            725                 730                 735

Phe Leu Arg Met Thr Arg Asn Gly Thr Gln Leu Gln Asn Phe Thr Leu
                740                 745                 750

Asp Arg Ser Ser Val Leu Val Asp Gly Tyr Phe Pro Asn Arg Asn Glu
        755                 760                 765

Pro Leu Thr Gly Asn Ser Asp Leu Pro Phe Trp Ala Val Ile Leu Ile
    770                 775                 780

Gly Leu Ala Gly Leu Leu Gly Leu Ile Thr Cys Leu Ile Cys Gly Val
785                 790                 795                 800

Leu Val Thr Arg Arg Arg Lys Lys Glu Gly Glu Tyr Asn Val Gln
            805                 810                 815

Gln Gln Cys Pro Gly Tyr Tyr Gln Ser His Leu Asp Leu Glu Asp Leu
                820                 825                 830

Gln
```

<210> SEQ ID NO 390
<211> LENGTH: 438
<212> TYPE: PRT
<213> ORGANISM: Homo sapiens

<400> SEQUENCE: 390

```
Met Gly Tyr His Leu Lys Thr Leu Thr Leu Asn Phe Thr Ile Ser Asn
              5                   10                  15

Leu Gln Tyr Ser Pro Asp Met Gly Lys Gly Ser Ala Thr Phe Asn Ser
             20                  25                  30

Thr Glu Gly Val Leu Gln His Leu Leu Arg Pro Leu Phe Gln Lys Ser
         35                  40                  45

Ser Met Gly Pro Phe Tyr Leu Gly Cys Gln Leu Ile Ser Leu Arg Pro
     50                  55                  60

Glu Lys Asp Gly Ala Ala Thr Gly Val Asp Thr Thr Cys Thr Tyr His
 65              70                  75                      80

Pro Asp Pro Val Gly Pro Gly Leu Asp Ile Gln Gln Leu Tyr Trp Glu
                 85                  90                  95

Leu Ser Gln Leu Thr His Gly Val Thr Gln Leu Gly Phe Tyr Val Leu
             100                 105                 110

Asp Arg Asp Ser Leu Phe Ile Asn Gly Tyr Ala Pro Gln Asn Leu Ser
             115                 120                 125

Ile Arg Gly Glu Tyr Gln Ile Asn Phe His Ile Val Asn Trp Asn Leu
         130                 135                 140

Ser Asn Pro Asp Pro Thr Ser Ser Glu Tyr Ile Thr Leu Leu Arg Asp
145                 150                 155                 160

Ile Gln Asp Lys Val Thr Thr Leu Tyr Lys Gly Ser Gln Leu His Asp
             165                 170                 175

Thr Phe Arg Phe Cys Leu Val Thr Asn Leu Thr Met Asp Ser Val Leu
             180                 185                 190

Val Thr Val Lys Ala Leu Phe Ser Ser Asn Leu Asp Pro Ser Leu Val
         195                 200                 205

Glu Gln Val Phe Leu Asp Lys Thr Leu Asn Ala Ser Phe His Trp Leu
         210                 215                 220

Gly Ser Thr Tyr Gln Leu Val Asp Ile His Val Thr Glu Met Glu Ser
225                 230                 235                 240

Ser Val Tyr Gln Pro Thr Ser Ser Ser Thr Gln His Phe Tyr Leu
             245                 250                 255

Asn Phe Thr Ile Thr Asn Leu Pro Tyr Ser Gln Asp Lys Ala Gln Pro
             260                 265                 270

Gly Thr Thr Asn Tyr Gln Arg Asn Lys Arg Asn Ile Glu Asp Ala Leu
             275                 280                 285

Asn Gln Leu Phe Arg Asn Ser Ser Ile Lys Ser Tyr Phe Ser Asp Cys
         290                 295                 300

Gln Val Ser Thr Phe Arg Ser Val Pro Asn Arg His His Thr Gly Val
305                 310                 315                 320

Asp Ser Leu Cys Asn Phe Ser Pro Leu Ala Arg Val Asp Arg Val
             325                 330                 335

Ala Ile Tyr Glu Glu Phe Leu Arg Met Thr Arg Asn Gly Thr Gln Leu
             340                 345                 350

Gln Asn Phe Thr Leu Asp Arg Ser Ser Val Leu Val Asp Gly Tyr Phe
         355                 360                 365

Pro Asn Arg Asn Glu Pro Leu Thr Gly Asn Ser Asp Leu Pro Phe Trp
         370                 375                 380

Ala Val Ile Leu Ile Gly Leu Ala Gly Leu Leu Gly Leu Ile Thr Cys
385                 390                 395                 400

Leu Ile Cys Gly Val Leu Val Thr Thr Arg Arg Arg Lys Lys Glu Gly
                 405                 410                 415
```

-continued

Glu Tyr Asn Val Gln Gln Gln Cys Pro Gly Tyr Tyr Gln Ser His Leu
        420                 425                 430
Asp Leu Glu Asp Leu Gln
        435

<210> SEQ ID NO 391
<211> LENGTH: 2627
<212> TYPE: DNA
<213> ORGANISM: Homo sapiens

<400> SEQUENCE: 391

| | | | | | |
|---|---|---|---|---|---|
| ccacgcgtcc | gcccacgcgt | ccggaaggca | gcggcagctc | cactcagcca | gtacccagat | 60 |
| acgctgggaa | ccttccccag | ccatggcttc | cctggggcag | atcctcttct | ggagcataat | 120 |
| tagcatcatc | attattctgg | ctggagcaat | tgcactcatc | attggctttg | gtatttcagg | 180 |
| gagacactcc | atcacagtca | ctactgtcgc | ctcagctggg | aacattgggg | aggatggaat | 240 |
| cctgagctgc | acttttgaac | tgacatcaa | actttctgat | atcgtgatac | aatggctgaa | 300 |
| ggaaggtgtt | ttaggcttgg | tccatgagtt | caaagaaggc | aaagatgagc | tgtcggagca | 360 |
| ggatgaaatg | ttcagaggcc | ggacagcagt | gtttgctgat | caagtgatag | ttggcaatgc | 420 |
| ctctttgcgg | ctgaaaaacg | tgcaactcac | agatgctggc | acctacaaat | gttatatcat | 480 |
| cacttctaaa | ggcaagggga | atgctaacct | tgagtataaa | actggagcct | tcagcatgcc | 540 |
| ggaagtgaat | gtggactata | atgccagctc | agagaccttg | cggtgtgagg | ctccccgatg | 600 |
| gttcccccag | cccacagtgg | tctgggcatc | ccaagttgac | cagggagcca | acttctcgga | 660 |
| agtctccaat | accagctttg | agctgaactc | tgagaatgtg | accatgaagg | ttgtgtctgt | 720 |
| gctctacaat | gttacgatca | caacacata | ctcctgtatg | attgaaaatg | acattgccaa | 780 |
| agcaacaggg | gatatcaaag | tgacagaatc | ggagatcaaa | aggcggagtc | acctacagct | 840 |
| gctaaactca | aaggcttctc | tgtgtgtctc | ttctttcttt | gccatcagct | gggcacttct | 900 |
| gcctctcagc | ccttacctga | tgctaaaata | atgtgccttg | gccacaaaaa | agcatgcaaa | 960 |
| gtcattgtta | caacagggat | ctacagaact | atttcaccac | cagatatgac | ctagtttat | 1020 |
| atttctggga | ggaaatgaat | tcatatctag | aagtctggag | tgagcaaaca | agagcaagaa | 1080 |
| acaaaaagaa | gccaaaagca | gaaggctcca | atatgaacaa | gataaatcta | tcttcaaaga | 1140 |
| catattagaa | gttgggaaaa | taattcatgt | gaactagaca | agtgtgttaa | gagtgataag | 1200 |
| taaaatgcac | gtggagacaa | gtgcatcccc | agatctcagg | gacctccccc | tgcctgtcac | 1260 |
| ctggggagtg | agaggacagg | atagtgcatg | ttctttgtct | ctgaattttt | agttatatgt | 1320 |
| gctgtaatgt | tgctctgagg | aagccctgg | aaagtctatc | ccaacatatc | cacatcttat | 1380 |
| attccacaaa | ttaagctgta | gtatgtaccc | taagacgctg | ctaattgact | gccacttcgc | 1440 |
| aactcagggg | cggctgcatt | ttagtaatgg | gtcaaatgat | tcacttttta | tgatgcttcc | 1500 |
| aaaggtgcct | tggcttctct | tcccaactga | caaatgccaa | agttgagaaa | aatgatcata | 1560 |
| atttagcat | aaacagagca | gtcggcgaca | ccgattttat | aaataaactg | agcaccttct | 1620 |
| ttttaaacaa | acaaatgcgg | gtttatttct | cagatgatgt | tcatccgtga | atggtccagg | 1680 |
| gaaggacctt | tcaccttgac | tatatggcat | tatgtcatca | caagctctga | ggcttctcct | 1740 |
| ttccatcctg | cgtggacagc | taagacctca | gttttcaata | gcatctagag | cagtgggact | 1800 |
| cagctgggt | gatttcgccc | ccatctccg | ggggaatgtc | tgaagacaat | tttggttacc | 1860 |
| tcaatgaggg | agtggaggag | gatacagtgc | tactaccaac | tagtggataa | aggccaggga | 1920 |
| tgctgctcaa | cctcctacca | tgtacaggac | gtctccccat | tacaactacc | caatccgaag | 1980 |

-continued

```
tgtcaactgt gtcaggacta agaaaccctg gttttgagta gaaaagggcc tggaaagagg    2040
ggagccaaca aatctgtctg cttcctcaca ttagtcattg gcaaataagc attctgtctc    2100
tttggctgct gcctcagcac agagagccag aactctatcg ggcaccagga taacatctct    2160
cagtgaacag agttgacaag gcctatggga aatgcctgat gggattatct tcagcttgtt    2220
gagcttctaa gtttctttcc cttcattcta ccctgcaagc caagttctgt aagagaaatg    2280
cctgagttct agctcaggtt ttcttactct gaatttagat ctccagaccc ttcctggcca    2340
caattcaaat taaggcaaca aacatatacc ttccatgaag cacacacaga cttttgaaag    2400
caaggacaat gactgcttga attgaggcct tgaggaatga agctttgaag gaaaagaata    2460
ctttgtttcc agcccccttc ccacactctt catgtgttaa ccactgcctt cctggacctt    2520
ggagccacgg tgactgtatt acatgttgtt atagaaaact gattttagag ttctgatcgt    2580
tcaagagaat gattaaatat acatttccta caccaaaaaa aaaaaaa               2627
```

<210> SEQ ID NO 392
<211> LENGTH: 309
<212> TYPE: PRT
<213> ORGANISM: Homo sapiens

<400> SEQUENCE: 392

```
His Ala Ser Ala His Ala Ser Gly Arg Gln Arg Gln Leu His Ser Ala
                 5                  10                  15

Ser Thr Gln Ile Arg Trp Glu Pro Ser Pro Ala Met Ala Ser Leu Gly
             20                  25                  30

Gln Ile Leu Phe Trp Ser Ile Ser Ile Ile Ile Leu Ala Gly
         35                  40                  45

Ala Ile Ala Leu Ile Ile Gly Phe Gly Ile Ser Gly Arg His Ser Ile
     50                  55                  60

Thr Val Thr Thr Val Ala Ser Ala Gly Asn Ile Gly Glu Asp Gly Ile
 65                  70                  75                  80

Leu Ser Cys Thr Phe Glu Pro Asp Ile Lys Leu Ser Asp Ile Val Ile
                 85                  90                  95

Gln Trp Leu Lys Glu Gly Val Leu Gly Leu Val His Glu Phe Lys Glu
            100                 105                 110

Gly Lys Asp Glu Leu Ser Glu Gln Asp Glu Met Phe Arg Gly Arg Thr
        115                 120                 125

Ala Val Phe Ala Asp Gln Val Ile Val Gly Asn Ala Ser Leu Arg Leu
    130                 135                 140

Lys Asn Val Gln Leu Thr Asp Ala Gly Thr Tyr Lys Cys Tyr Ile Ile
145                 150                 155                 160

Thr Ser Lys Gly Lys Gly Asn Ala Asn Leu Glu Tyr Lys Thr Gly Ala
                165                 170                 175

Phe Ser Met Pro Glu Val Asn Val Asp Tyr Asn Ala Ser Ser Glu Thr
            180                 185                 190

Leu Arg Cys Glu Ala Pro Arg Trp Phe Pro Gln Pro Thr Val Val Trp
        195                 200                 205

Ala Ser Gln Val Asp Gln Gly Ala Asn Phe Ser Glu Val Ser Asn Thr
    210                 215                 220

Ser Phe Glu Leu Asn Ser Glu Asn Val Thr Met Lys Val Val Ser Val
225                 230                 235                 240

Leu Tyr Asn Val Thr Ile Asn Asn Thr Tyr Ser Cys Met Ile Glu Asn
                245                 250                 255
```

-continued

Asp Ile Ala Lys Ala Thr Gly Asp Ile Lys Val Thr Glu Ser Glu Ile
        260                 265                 270

Lys Arg Arg Ser His Leu Gln Leu Leu Asn Ser Lys Ala Ser Leu Cys
        275                 280                 285

Val Ser Ser Phe Phe Ala Ile Ser Trp Ala Leu Leu Pro Leu Ser Pro
        290                 295                 300

Tyr Leu Met Leu Lys
305

<210> SEQ ID NO 393
<211> LENGTH: 282
<212> TYPE: PRT
<213> ORGANISM: Homo sapiens

<400> SEQUENCE: 393

Met Ala Ser Leu Gly Gln Ile Leu Phe Trp Ser Ile Ser Ile Ile
                 5                  10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280

<210> SEQ ID NO 394
<211> LENGTH: 20
<212> TYPE: PRT
<213> ORGANISM: Homo sapiens

```
<400> SEQUENCE: 394

Met Ala Ser Leu Gly Gln Ile Leu Phe Trp Ser Ile Ile Ser Ile Ile
 1               5                  10                  15

Ile Ile Leu Ala
            20

<210> SEQ ID NO 395
<211> LENGTH: 20
<212> TYPE: PRT
<213> ORGANISM: Homo sapiens

<400> SEQUENCE: 395

Ile Ile Ile Leu Ala Gly Ala Ile Ala Leu Ile Ile Gly Phe Gly Ile
 1               5                  10                  15

Ser Gly Arg His
            20

<210> SEQ ID NO 396
<211> LENGTH: 20
<212> TYPE: PRT
<213> ORGANISM: Homo sapiens

<400> SEQUENCE: 396

Ile Ser Gly Arg His Ser Ile Thr Val Thr Thr Val Ala Ser Ala Gly
 1               5                  10                  15

Asn Ile Gly Glu
            20

<210> SEQ ID NO 397
<211> LENGTH: 20
<212> TYPE: PRT
<213> ORGANISM: Homo sapiens

<400> SEQUENCE: 397

Gly Asn Ile Gly Glu Asp Gly Ile Leu Ser Cys Thr Phe Glu Pro Asp
 1               5                  10                  15

Ile Lys Leu Ser
            20

<210> SEQ ID NO 398
<211> LENGTH: 20
<212> TYPE: PRT
<213> ORGANISM: Homo sapiens

<400> SEQUENCE: 398

Asp Ile Lys Leu Ser Asp Ile Val Ile Gln Trp Leu Lys Glu Gly Val
 1               5                  10                  15

Leu Gly Leu Val
            20

<210> SEQ ID NO 399
<211> LENGTH: 20
<212> TYPE: PRT
<213> ORGANISM: Homo sapiens

<400> SEQUENCE: 399

Val Leu Gly Leu Val His Glu Phe Lys Glu Gly Lys Asp Glu Leu Ser
 1               5                  10                  15

Glu Gln Asp Glu
            20
```

-continued

```
<210> SEQ ID NO 400
<211> LENGTH: 20
<212> TYPE: PRT
<213> ORGANISM: Homo sapiens

<400> SEQUENCE: 400

Ser Glu Gln Asp Glu Met Phe Arg Gly Arg Thr Ala Val Phe Ala Asp
 1               5                  10                  15

Gln Val Ile Val
            20

<210> SEQ ID NO 401
<211> LENGTH: 20
<212> TYPE: PRT
<213> ORGANISM: Homo sapiens

<400> SEQUENCE: 401

Asp Gln Val Ile Val Gly Asn Ala Ser Leu Arg Leu Lys Asn Val Gln
 1               5                  10                  15

Leu Thr Asp Ala
            20

<210> SEQ ID NO 402
<211> LENGTH: 21
<212> TYPE: PRT
<213> ORGANISM: Homo sapiens

<400> SEQUENCE: 402

Val Gln Leu Thr Asp Ala Gly Thr Tyr Lys Cys Tyr Ile Ile Thr Ser
 1               5                  10                  15

Lys Gly Lys Gly Asn
            20

<210> SEQ ID NO 403
<211> LENGTH: 20
<212> TYPE: PRT
<213> ORGANISM: Homo sapiens

<400> SEQUENCE: 403

Lys Gly Lys Gly Asn Ala Asn Leu Glu Tyr Lys Thr Gly Ala Phe Ser
 1               5                  10                  15

Met Pro Glu Val
            20

<210> SEQ ID NO 404
<211> LENGTH: 20
<212> TYPE: PRT
<213> ORGANISM: Homo sapiens

<400> SEQUENCE: 404

Ser Met Pro Glu Val Asn Val Asp Tyr Asn Ala Ser Ser Glu Thr Leu
 1               5                  10                  15

Arg Cys Glu Ala
            20

<210> SEQ ID NO 405
<211> LENGTH: 20
<212> TYPE: PRT
<213> ORGANISM: Homo sapiens

<400> SEQUENCE: 405

Leu Arg Cys Glu Ala Pro Arg Trp Phe Pro Gln Pro Thr Val Val Trp
```

```
                1               5                  10                 15
Ala Ser Gln Val
            20

<210> SEQ ID NO 406
<211> LENGTH: 20
<212> TYPE: PRT
<213> ORGANISM: Homo sapiens

<400> SEQUENCE: 406

Trp Ala Ser Gln Val Asp Gln Gly Ala Asn Phe Ser Glu Val Ser Asn
1               5                  10                 15
Thr Ser Phe Glu
            20

<210> SEQ ID NO 407
<211> LENGTH: 20
<212> TYPE: PRT
<213> ORGANISM: Homo sapiens

<400> SEQUENCE: 407

Asn Thr Ser Phe Glu Leu Asn Ser Glu Asn Val Thr Met Lys Val Val
1               5                  10                 15
Ser Val Leu Tyr
            20

<210> SEQ ID NO 408
<211> LENGTH: 20
<212> TYPE: PRT
<213> ORGANISM: Homo sapiens

<400> SEQUENCE: 408

Val Ser Val Leu Tyr Asn Val Thr Ile Asn Asn Thr Tyr Ser Cys Met
1               5                  10                 15
Ile Glu Asn Asp
            20

<210> SEQ ID NO 409
<211> LENGTH: 20
<212> TYPE: PRT
<213> ORGANISM: Homo sapiens

<400> SEQUENCE: 409

Met Ile Glu Asn Asp Ile Ala Lys Ala Thr Gly Asp Ile Lys Val Thr
1               5                  10                 15
Glu Ser Glu Ile
            20

<210> SEQ ID NO 410
<211> LENGTH: 20
<212> TYPE: PRT
<213> ORGANISM: Homo sapiens

<400> SEQUENCE: 410

Thr Glu Ser Glu Ile Lys Arg Arg Ser His Leu Gln Leu Leu Asn Ser
1               5                  10                 15
Lys Ala Ser Leu
            20

<210> SEQ ID NO 411
<211> LENGTH: 20
<212> TYPE: PRT
<213> ORGANISM: Homo sapiens
```

<400> SEQUENCE: 411

Ser Lys Ala Ser Leu Cys Val Ser Ser Phe Ala Ile Ser Trp Ala
1               5                   10                  15

Leu Leu Pro Leu
            20

<210> SEQ ID NO 412
<211> LENGTH: 20
<212> TYPE: PRT
<213> ORGANISM: Homo sapiens

<400> SEQUENCE: 412

Ser Ser Phe Phe Ala Ile Ser Trp Ala Leu Leu Pro Leu Ser Pro Tyr
1               5                   10                  15

Leu Met Leu Lys
            20

<210> SEQ ID NO 413
<211> LENGTH: 35
<212> TYPE: PRT
<213> ORGANISM: Homo sapiens

<400> SEQUENCE: 413

Ile Ser Gly Arg His Ser Ile Thr Val Thr Val Ala Ser Ala Gly
1               5                   10                  15

Asn Ile Gly Glu Asp Gly Ile Leu Ser Cys Thr Phe Glu Pro Asp Ile
                20                  25                  30

Lys Leu Ser
        35

<210> SEQ ID NO 414
<211> LENGTH: 35
<212> TYPE: PRT
<213> ORGANISM: Homo sapiens

<400> SEQUENCE: 414

Val Leu Gly Leu Val His Glu Phe Lys Glu Gly Lys Asp Glu Leu Ser
1               5                   10                  15

Glu Gln Asp Glu Met Phe Arg Gly Arg Thr Ala Val Phe Ala Asp Gln
                20                  25                  30

Val Ile Val
        35

<210> SEQ ID NO 415
<211> LENGTH: 65
<212> TYPE: PRT
<213> ORGANISM: Homo sapiens

<400> SEQUENCE: 415

Lys Gly Lys Gly Asn Ala Asn Leu Glu Tyr Lys Thr Gly Ala Phe Ser
1               5                   10                  15

Met Pro Glu Val Asn Val Asp Tyr Asn Ala Ser Ser Glu Thr Leu Arg
                20                  25                  30

Cys Glu Ala Pro Arg Trp Phe Pro Gln Pro Thr Val Val Trp Ala Ser
            35                  40                  45

Gln Val Asp Gln Gly Ala Asn Phe Ser Glu Val Ser Asn Thr Ser Phe
        50                  55                  60

Glu
65

```
<210> SEQ ID NO 416
<211> LENGTH: 10
<212> TYPE: PRT
<213> ORGANISM: Homo sapiens

<400> SEQUENCE: 416

Lys Leu Ser Asp Ile Val Ile Gln Trp Leu
1               5                   10

<210> SEQ ID NO 417
<211> LENGTH: 10
<212> TYPE: PRT
<213> ORGANISM: Homo sapiens

<400> SEQUENCE: 417

Ser Leu Gly Gln Ile Leu Phe Trp Ser Ile
1               5                   10

<210> SEQ ID NO 418
<211> LENGTH: 10
<212> TYPE: PRT
<213> ORGANISM: Homo sapiens

<400> SEQUENCE: 418

Leu Leu Asn Ser Lys Ala Ser Leu Cys Val
1               5                   10

<210> SEQ ID NO 419
<211> LENGTH: 10
<212> TYPE: PRT
<213> ORGANISM: Homo sapiens

<400> SEQUENCE: 419

Ser Leu Cys Val Ser Ser Phe Phe Ala Ile
1               5                   10

<210> SEQ ID NO 420
<211> LENGTH: 10
<212> TYPE: PRT
<213> ORGANISM: Homo sapiens

<400> SEQUENCE: 420

Val Leu Tyr Asn Val Thr Ile Asn Asn Thr
1               5                   10

<210> SEQ ID NO 421
<211> LENGTH: 10
<212> TYPE: PRT
<213> ORGANISM: Homo sapiens

<400> SEQUENCE: 421

Ile Leu Phe Trp Ser Ile Ile Ser Ile Ile
1               5                   10

<210> SEQ ID NO 422
<211> LENGTH: 10
<212> TYPE: PRT
<213> ORGANISM: Homo sapiens

<400> SEQUENCE: 422

Leu Leu Pro Leu Ser Pro Tyr Leu Met Leu
1               5                   10
```

-continued

```
<210> SEQ ID NO 423
<211> LENGTH: 10
<212> TYPE: PRT
<213> ORGANISM: Homo sapiens

<400> SEQUENCE: 423

Cys Met Ile Glu Asn Asp Ile Ala Lys Ala
 1               5                  10

<210> SEQ ID NO 424
<211> LENGTH: 10
<212> TYPE: PRT
<213> ORGANISM: Homo sapiens

<400> SEQUENCE: 424

Lys Thr Gly Ala Phe Ser Met Pro Glu Val
 1               5                  10

<210> SEQ ID NO 425
<211> LENGTH: 10
<212> TYPE: PRT
<213> ORGANISM: Homo sapiens

<400> SEQUENCE: 425

Trp Ala Leu Leu Pro Leu Ser Pro Tyr Leu
 1               5                  10

<210> SEQ ID NO 426
<211> LENGTH: 10
<212> TYPE: PRT
<213> ORGANISM: Homo sapiens

<400> SEQUENCE: 426

Ile Ile Leu Ala Gly Ala Ile Ala Leu Ile
 1               5                  10

<210> SEQ ID NO 427
<211> LENGTH: 10
<212> TYPE: PRT
<213> ORGANISM: Homo sapiens

<400> SEQUENCE: 427

Gln Leu Thr Asp Ala Gly Thr Tyr Lys Cys
 1               5                  10

<210> SEQ ID NO 428
<211> LENGTH: 10
<212> TYPE: PRT
<213> ORGANISM: Homo sapiens

<400> SEQUENCE: 428

Ala Leu Leu Pro Leu Ser Pro Tyr Leu Met
 1               5                  10

<210> SEQ ID NO 429
<211> LENGTH: 10
<212> TYPE: PRT
<213> ORGANISM: Homo sapiens

<400> SEQUENCE: 429

Gln Leu Leu Asn Ser Lys Ala Ser Leu Cys
 1               5                  10

<210> SEQ ID NO 430
<211> LENGTH: 10
```

```
<212> TYPE: PRT
<213> ORGANISM: Homo sapiens

<400> SEQUENCE: 430

Ile Leu Ser Cys Thr Phe Glu Pro Asp Ile
 1               5                  10

<210> SEQ ID NO 431
<211> LENGTH: 10
<212> TYPE: PRT
<213> ORGANISM: Homo sapiens

<400> SEQUENCE: 431

Trp Leu Lys Glu Gly Val Leu Gly Leu Val
 1               5                  10

<210> SEQ ID NO 432
<211> LENGTH: 10
<212> TYPE: PRT
<213> ORGANISM: Homo sapiens

<400> SEQUENCE: 432

Leu Gln Leu Leu Asn Ser Lys Ala Ser Leu
 1               5                  10

<210> SEQ ID NO 433
<211> LENGTH: 10
<212> TYPE: PRT
<213> ORGANISM: Homo sapiens

<400> SEQUENCE: 433

Gln Ile Leu Phe Trp Ser Ile Ile Ser Ile
 1               5                  10

<210> SEQ ID NO 434
<211> LENGTH: 10
<212> TYPE: PRT
<213> ORGANISM: Homo sapiens

<400> SEQUENCE: 434

Gly Ile Ser Gly Arg His Ser Ile Thr Val
 1               5                  10

<210> SEQ ID NO 435
<211> LENGTH: 10
<212> TYPE: PRT
<213> ORGANISM: Homo sapiens

<400> SEQUENCE: 435

Phe Glu Pro Asp Ile Lys Leu Ser Asp Ile
 1               5                  10

<210> SEQ ID NO 436
<211> LENGTH: 9
<212> TYPE: PRT
<213> ORGANISM: Homo sapiens

<400> SEQUENCE: 436

Ala Leu Leu Pro Leu Ser Pro Tyr Leu
 1               5

<210> SEQ ID NO 437
<211> LENGTH: 9
<212> TYPE: PRT
<213> ORGANISM: Homo sapiens
```

<400> SEQUENCE: 437

Ser Leu Cys Val Ser Ser Phe Phe Ala
1               5

<210> SEQ ID NO 438
<211> LENGTH: 9
<212> TYPE: PRT
<213> ORGANISM: Homo sapiens

<400> SEQUENCE: 438

Ile Leu Phe Trp Ser Ile Ile Ser Ile
1               5

<210> SEQ ID NO 439
<211> LENGTH: 9
<212> TYPE: PRT
<213> ORGANISM: Homo sapiens

<400> SEQUENCE: 439

Gln Leu Leu Asn Ser Lys Ala Ser Leu
1               5

<210> SEQ ID NO 440
<211> LENGTH: 9
<212> TYPE: PRT
<213> ORGANISM: Homo sapiens

<400> SEQUENCE: 440

Lys Val Val Ser Val Leu Tyr Asn Val
1               5

<210> SEQ ID NO 441
<211> LENGTH: 9
<212> TYPE: PRT
<213> ORGANISM: Homo sapiens

<400> SEQUENCE: 441

Ile Leu Ala Gly Ala Ile Ala Leu Ile
1               5

<210> SEQ ID NO 442
<211> LENGTH: 9
<212> TYPE: PRT
<213> ORGANISM: Homo sapiens

<400> SEQUENCE: 442

Trp Leu Lys Glu Gly Val Leu Gly Leu
1               5

<210> SEQ ID NO 443
<211> LENGTH: 9
<212> TYPE: PRT
<213> ORGANISM: Homo sapiens

<400> SEQUENCE: 443

Ile Ile Leu Ala Gly Ala Ile Ala Leu
1               5

<210> SEQ ID NO 444
<211> LENGTH: 9
<212> TYPE: PRT
<213> ORGANISM: Homo sapiens

<400> SEQUENCE: 444

Asn Val Thr Met Lys Val Val Ser Val
1               5

<210> SEQ ID NO 445
<211> LENGTH: 9
<212> TYPE: PRT
<213> ORGANISM: Homo sapiens

<400> SEQUENCE: 445

Glu Met Phe Arg Gly Arg Thr Ala Val
1               5

<210> SEQ ID NO 446
<211> LENGTH: 9
<212> TYPE: PRT
<213> ORGANISM: Homo sapiens

<400> SEQUENCE: 446

Ala Val Phe Ala Asp Gln Val Ile Val
1               5

<210> SEQ ID NO 447
<211> LENGTH: 9
<212> TYPE: PRT
<213> ORGANISM: Homo sapiens

<400> SEQUENCE: 447

Leu Leu Pro Leu Ser Pro Tyr Leu Met
1               5

<210> SEQ ID NO 448
<211> LENGTH: 9
<212> TYPE: PRT
<213> ORGANISM: Homo sapiens

<400> SEQUENCE: 448

Leu Leu Asn Ser Lys Ala Ser Leu Cys
1               5

<210> SEQ ID NO 449
<211> LENGTH: 9
<212> TYPE: PRT
<213> ORGANISM: Homo sapiens

<400> SEQUENCE: 449

Val Ile Gln Trp Leu Lys Glu Gly Val
1               5

<210> SEQ ID NO 450
<211> LENGTH: 9
<212> TYPE: PRT
<213> ORGANISM: Homo sapiens

<400> SEQUENCE: 450

Ala Ile Ser Trp Ala Leu Leu Pro Leu
1               5

<210> SEQ ID NO 451
<211> LENGTH: 9
<212> TYPE: PRT
<213> ORGANISM: Homo sapiens

<400> SEQUENCE: 451

Ser Leu Gly Gln Ile Leu Phe Trp Ser

<210> SEQ ID NO 452
<211> LENGTH: 9
<212> TYPE: PRT
<213> ORGANISM: Homo sapiens

<400> SEQUENCE: 452

Ile Ala Leu Ile Ile Gly Phe Gly Ile
 1               5

<210> SEQ ID NO 453
<211> LENGTH: 9
<212> TYPE: PRT
<213> ORGANISM: Homo sapiens

<400> SEQUENCE: 453

Cys Thr Phe Glu Pro Asp Ile Lys Leu
 1               5

<210> SEQ ID NO 454
<211> LENGTH: 9
<212> TYPE: PRT
<213> ORGANISM: Homo sapiens

<400> SEQUENCE: 454

Ile Val Gly Asn Ala Ser Leu Arg Leu
 1               5

<210> SEQ ID NO 455
<211> LENGTH: 9
<212> TYPE: PRT
<213> ORGANISM: Homo sapiens

<400> SEQUENCE: 455

Gly Gln Ile Leu Phe Trp Ser Ile Ile
 1               5

<210> SEQ ID NO 456
<211> LENGTH: 3447
<212> TYPE: DNA
<213> ORGANISM: Homo sapiens

<400> SEQUENCE: 456
atgcccttgt tcaagaacac cagtgtcagc tctctgtact ctggttgcag actgaccttg      60
ctcaggcctg agaaggatgg ggcagccacc agagtggatg ctgtctgcac ccatcgtcct     120
gaccccaaaa gccctggact ggacagagag cggctgtact ggaagctgag ccagctgacc     180
cacggcatca ctgagctggg ccctacaccc tggacaggc acagtctcta tgtcaatggt      240
ttcacccatc agagctctat gacgaccacc agaactcctg atacctccac aatgcacctg     300
gcaacctcga gaactccagc ctccctgtct ggacctacga ccgccagccc tctcctggtg     360
ctattcacaa ttaacttcac catcactaac ctgcggtatg aggagaacat gcatcaccct     420
ggctctagaa agtttaacac cacggagaga gtccttcagg gtctgctcag gcctgtgttc     480
aagaacacca gtgttggccc tctgtactct ggctgcagac tgaccttgct caggcccaag     540
aaggatgggg cagccaccaa agtggatgcc atctgcacct accgcctga tcccaaaagc      600 cctggactgg acagagagca gctatactgg agctgagcc agctaaccca cagcatcact      660
gagctgggcc cctacaccct ggacagggac agtctctatg tcaatggttt cacacagcgg     720
agctctgtgc ccaccactag cattcctggg acccccacag tggacctggg aacatctggg     780

```
actccagttt ctaaacctgg tccctcggct gccagccctc tcctggtgct attcactctc    840
aacttcacca tcaccaacct gcggtatgag agaacatgc agcaccctgg ctccaggaag     900
ttcaacacca cggagagggt ccttcagggc ctgctcaggt ccctgttcaa gagcaccagt    960
gttggccctc tgtactctgg ctgcagactg actttgctca ggcctgaaaa ggatgggaca   1020
gccactggag tggatgccat ctgcacccac caccctgacc ccaaaagccc taggctggac   1080
agagagcagc tgtattggga gctgagccag ctgacccaca atatcactga gctgggccac   1140
tatgccctgg acaacgacag cctctttgtc aatggtttca ctcatcggag ctctgtgtcc   1200
accaccagca ctcctgggac ccccacagtg tatctgggag catctaagac tccagcctcg   1260
atatttggcc cttcagctgc cagccatctc ctgatactat tcaccctcaa cttcaccatc   1320
actaacctgc ggtatgagga acatgtgtgg cctggctcca ggaagttcaa cactacagag   1380
aggtccttc agggcctgct aaggcccttg ttcaagaaca ccagtgttgg ccctctgtac    1440
tctggctcca ggctgacctt gctcaggcca gagaaagatg gggaagccac cggagtggat   1500
gccatctgca cccaccgccc tgaccccaca ggccctgggc tggacagaga gcagctgtat   1560
ttggagctga gccagctgac ccacagcatc actgagctgg gccctacac actggacagg    1620
gacagtctct atgtcaatgg tttcacccat cggagctctg tacccaccac cagcaccggg   1680
gtggtcagcg aggagccatt cacactgaac ttcaccatca caacctgcg ctacatggcg    1740
gacatgggcc aacccggctc cctcaagttc aacatcacag acaacgtcat gaagcacctg   1800
ctcagtcctt tgttccagag gagcagcctg ggtgcacggt acacaggctg cagggtcatc   1860
gcactaaggt ctgtgaagaa cggtgctgag acacgggtgg acctcctctg cacctacctg   1920
cagcccctca gcggcccagg tctgcctatc aagcaggtgt ccatgagct gagccagcag    1980
acccatggca tcacccggct gggcccctac tctctggaca agacagcct ctaccttaac    2040
ggttacaatg aacctggtct agatgagcct cctacaactc ccaagccagc caccacattc   2100
ctgcctcctc tgtcagaagc cacaacagcc atggggtacc acctgaagac cctcacactc   2160
aacttcacca tctccaatct ccagtattca ccagatatgg gcaagggctc agctacattc   2220
aactccaccg aggggtcct tcagcacctg ctcagaccct tgttccagaa gagcagcatg    2280
ggcccccttct acttggggttg ccaactgatc tccctcaggc ctgagaagga tgggcagcc   2340
actggtgtgg acaccacctg cacctaccac cctgaccctg tgggcccgg gctggacata    2400
cagcagcttt actgggagct gagtcagctg acccatggtg tcacccaact gggcttctat   2460
gtcctggaca gggatagcct cttcatcaat ggctatgcac cccagaattt atcaatccgg   2520
ggcgagtacc agataaattt ccacattgtc aactggaacc tcagtaatcc agaccccaca   2580
tcctcagagt acatcaccct gctgagggac atccaggaca aggtcaccac actctacaaa   2640
ggcagtcaac tacatgacac attccgcttc tgcctggtca ccaacttgac gatggactcc   2700
gtgttggtca ctgtcaaggc attgttctcc tccaatttgg accccagcct ggtggagcaa   2760
gtctttctag ataagaccct gaatgcctca ttccattggc tgggctccac ctaccagttg   2820
gtggacatcc atgtgacaga atggagtca tcagtttatc aaccaacaag cagctccagc    2880
acccagcact tctacccgaa tttcaccatc accaacctac catattccca ggacaaagcc   2940
cagccaggca ccaccaatta ccagaggaac aaaaggaata ttgaggatgc gctcaaccaa   3000
ctcttccgaa acagcagcat caagagttat ttttctgact gtcaagtttc aacattcagg   3060
tctgtcccca acaggcacca caccggggtg gactccctgt gtaacttctc gccactggct   3120
```

-continued

```
cggagagtag acagagttgc catctatgag gaatttctgc ggatgacccg gaatggtacc    3180
cagctgcaga acttcaccct ggacaggagc agtgtccttg tggatgggta ttctcccaac    3240
agaaatgagc ccttaactgg gaattctgac cttcccttct gggctgtcat cttcatcggc    3300
ttggcaggac tcctgggact catcacatgc ctgatctgcg gtgtcctggt gaccacccgc    3360
cggcggaaga aggaaggaga atacaacgtc cagcaacagt gcccaggcta ctaccagtca    3420
cacctagacc tggaggatct gcaatga                                        3447

<210> SEQ ID NO 457
<211> LENGTH: 3557
<212> TYPE: DNA
<213> ORGANISM: Homo sapiens

<400> SEQUENCE: 457
gagagggtcc ttcagggtct gcttatgccc ttgttcaaga acaccagtgt cagctctctg      60
tactctggtt gcagactgac cttgctcagg cctgagaagg atggggcagc caccagagtg     120
gatgctgtct gcacccatcg tcctgacccc aaaagccctg gactggacag agagcggctg     180
tactggaagc tgagccagct gacccacggc atcactgagc tgggcccta caccctggac      240 aggcacagtc tctatgtcaa tggtttcacc catcagagct ctatgacgac caccagaact     300
cctgatacct ccacaatgca cctggcaacc tcgagaactc cagcctccct gtctggacct     360
acgaccgcca gccctctcct ggtgctattc acaattaact tcaccatcac taacctgcgg     420
tatgaggaga acatgcatca ccctggctct agaaagttta acaccacgga gagagtcctt     480
cagggtctgc tcaggcctgt gttcaagaac accagtgttg gccctctgta ctctggctgc     540
agactgacct tgctcaggcc caagaaggat ggggcagcca ccaaagtgga tgccatctgc     600
acctaccgcc ctgatcccaa agccctgga ctggacagag agcagctata ctgggagctg      660
agccagctaa cccacagcat cactgagctg gccccctaca ccctggacag ggacagtctc     720
tatgtcaatg gtttcacaca gcggagctct gtgcccacca ctagcattcc tgggaccccc    780
acagtggacc tgggaacatc tgggactcca gtttctaaac ctggtccctc ggctgccagc     840
cctctcctgg tgctattcac tctcaacttc accatcacca acctgcggta tgaggagaac      900
atgcagcacc ctggctccag gaagttcaac accacggaga gggtccttca gggcctgctc     960
aggtccctgt tcaagagcac cagtgttggc cctctgtact ctggctgcag actgactttg    1020
ctcaggcctg aaaaggatgg gacagccact ggagtggatg ccatctgcac ccaccaccct    1080
gaccccaaaa gccctaggct ggacagagag cagctgtatt gggagctgag ccagctgacc    1140
cacaatatca ctgagctggg ccactatgcc ctggacaacg acagcctctt tgtcaatggt    1200
ttcactcatc ggagctctgt gtccaccacc agcactcctg gacccccac agtgtatctg      1260 ggagcatcta agactccagc ctcgatattt ggcccttcag ctgccagcca tctcctgata    1320
ctattcaccc tcaacttcac catcactaac ctgcggtatg aggagaacat gtggcctggc    1380
tccaggaagt tcaacactac agagagggtc cttcagggcc tgctaaggcc cttgttcaag    1440
aacaccagtg ttggccctct gtactctggc tccaggctga ccttgctcag gccagagaaa    1500
gatggggaag ccaccggagt ggatgccatc tgcacccacc gccctgaccc cacaggccct    1560
gggctggaca gagagcagct gtatttggag ctgagccagc tgacccacag catcactgag    1620
ctgggcccct acacactgga cagggacagt ctctatgtca atggtttcac ccatcggagc    1680
tctgtaccca ccaccagcac cggggtggtc agcgaggagc cattcacact gaacttcacc    1740
atcaacaacc tgcgctacat ggcggacatg ggccaacccg gctccctcaa gttcaacatc    1800
```

-continued

```
acagacaacg tcatgaagca cctgctcagt cctttgttcc agaggagcag cctgggtgca    1860
cggtacacag gctgcagggt catcgcacta aggtctgtga agaacggtgc tgagacacgg    1920
gtggacctcc tctgcaccta cctgcagccc ctcagcggcc aggtctgcc tatcaagcag     1980
gtgttccatg agctgagcca gcagacccat ggcatcaccc ggctgggccc ctactctctg    2040
gacaaagaca gcctctacct taacggttac aatgaacctg tctagatga gcctcctaca     2100
actcccaagc cagccaccac attcctgcct cctctgtcag aagccacaac agccatgggg    2160
taccacctga agaccctcac actcaacttc accatctcca atctccagta ttcaccagat    2220
atgggcaagg gctcagctac attcaactcc accgaggggg tccttcagca cctgctcaga    2280
cccttgttcc agaagagcag catgggcccc ttctacttgg gttgccaact gatctccctc    2340
aggcctgaga aggatggggc agccactggt gtggacacca cctgcaccta ccaccctgac    2400
cctgtgggcc ccgggctgga catacagcag ctttactggg agctgagtca gctgacccat    2460
ggtgtcaccc aactgggctt ctatgtcctg gacagggata gcctcttcat caatggctat    2520
gcaccccaga atttatcaat ccggggcgag taccagataa atttccacat tgtcaactgg    2580
aacctcagta atccagaccc cacatcctca gagtacatca ccctgctgag ggacatccag    2640
gacaaggtca ccacactcta caaaggcagt caactacatg acacattccg cttctgcctg    2700
gtcaccaact tgacgatgga ctccgtgttg gtcactgtca aggcattgtt ctcctccaat    2760
ttggacccca gctggtgga gcaagtcttt ctagataaga ccctgaatgc ctcattccat    2820
tggctgggct ccacctacca gttggtggac atccatgtga cagaaatgga gtcatcagtt    2880
tatcaaccaa caagcagctc cagcacccag cacttctacc cgaatttcac catcaccaac    2940
ctaccatatt cccaggacaa agcccagcca ggcaccacca attaccagag gaacaaaagg    3000
aatattgagg atgcgctcaa ccaactcttc cgaaacagca gcatcaagag ttattttct    3060
gactgtcaag tttcaacatt caggtctgtc cccaacaggc accacccgg ggtggactcc    3120
ctgtgtaact tctcgccact ggctcggaga gtagacagag ttgccatcta tgaggaattt    3180
ctgcggatga cccggaatgg tacccagctg cagaacttca ccctggacag gagcagtgtc    3240
cttgtggatg ggtattctcc caacagaaat gagcccttaa ctgggaattc tgaccttccc    3300
ttctgggctg tcatcttcat cggcttggca ggactcctgg gactcatcac atgcctgatc    3360
tgcggtgtcc tggtgaccac ccgccggcgg aagaaggaag agaatacaa cgtccagcaa    3420
cagtgcccag gctactacca gtcacaccta gacctggagg atctgcaatg actggaactt    3480
gccggtgcct ggggtgcctt tcccccagcc agggtccaaa gaagcttggc tggggcagaa    3540
ataaaccata ttggtcg                                                   3557
```

<210> SEQ ID NO 458
<211> LENGTH: 1148
<212> TYPE: PRT
<213> ORGANISM: Homo sapiens

<400> SEQUENCE: 458

```
Met Pro Leu Phe Lys Asn Thr Ser Val Ser Ser Leu Tyr Ser Gly Cys
                 5                  10                  15

Arg Leu Thr Leu Leu Arg Pro Glu Lys Asp Gly Ala Ala Thr Arg Val
            20                  25                  30

Asp Ala Val Cys Thr His Arg Pro Asp Pro Lys Ser Pro Gly Leu Asp
        35                  40                  45

Arg Glu Arg Leu Tyr Trp Lys Leu Ser Gln Leu Thr His Gly Ile Thr
```

-continued

```
                50                      55                      60
Glu Leu Gly Pro Tyr Thr Leu Asp Arg His Ser Leu Tyr Val Asn Gly
 65                      70                      75                      80

Phe Thr His Gln Ser Ser Met Thr Thr Arg Thr Pro Asp Thr Ser
                 85                      90                      95

Thr Met His Leu Ala Thr Ser Arg Thr Pro Ala Ser Leu Ser Gly Pro
                100                     105                     110

Thr Thr Ala Ser Pro Leu Leu Val Leu Phe Thr Ile Asn Phe Thr Ile
                115                     120                     125

Thr Asn Leu Arg Tyr Glu Glu Asn Met His His Pro Gly Ser Arg Lys
                130                     135                     140

Phe Asn Thr Thr Glu Arg Val Leu Gln Gly Leu Leu Arg Pro Val Phe
145                     150                     155                     160

Lys Asn Thr Ser Val Gly Pro Leu Tyr Ser Gly Cys Arg Leu Thr Leu
                165                     170                     175

Leu Arg Pro Lys Lys Asp Gly Ala Ala Thr Lys Val Asp Ala Ile Cys
                180                     185                     190

Thr Tyr Arg Pro Asp Pro Lys Ser Pro Gly Leu Asp Arg Glu Gln Leu
                195                     200                     205

Tyr Trp Glu Leu Ser Gln Leu Thr His Ser Ile Thr Glu Leu Gly Pro
210                     215                     220

Tyr Thr Leu Asp Arg Asp Ser Leu Tyr Val Asn Gly Phe Thr Gln Arg
225                     230                     235                     240

Ser Ser Val Pro Thr Thr Ser Ile Pro Gly Thr Pro Thr Val Asp Leu
                245                     250                     255

Gly Thr Ser Gly Thr Pro Val Ser Lys Pro Gly Pro Ser Ala Ala Ser
                260                     265                     270

Pro Leu Leu Val Leu Phe Thr Leu Asn Phe Thr Ile Thr Asn Leu Arg
                275                     280                     285

Tyr Glu Glu Asn Met Gln His Pro Gly Ser Arg Lys Phe Asn Thr Thr
                290                     295                     300

Glu Arg Val Leu Gln Gly Leu Leu Arg Ser Leu Phe Lys Ser Thr Ser
305                     310                     315                     320

Val Gly Pro Leu Tyr Ser Gly Cys Arg Leu Thr Leu Leu Arg Pro Glu
                325                     330                     335

Lys Asp Gly Thr Ala Thr Gly Val Asp Ala Ile Cys Thr His His Pro
                340                     345                     350

Asp Pro Lys Ser Pro Arg Leu Asp Arg Glu Gln Leu Tyr Trp Glu Leu
                355                     360                     365

Ser Gln Leu Thr His Asn Ile Thr Glu Leu Gly His Tyr Ala Leu Asp
                370                     375                     380

Asn Asp Ser Leu Phe Val Asn Gly Phe Thr His Arg Ser Ser Val Ser
385                     390                     395                     400

Thr Thr Ser Thr Pro Gly Thr Pro Thr Val Tyr Leu Gly Ala Ser Lys
                405                     410                     415

Thr Pro Ala Ser Ile Phe Gly Pro Ser Ala Ala Ser His Leu Leu Ile
                420                     425                     430

Leu Phe Thr Leu Asn Phe Thr Ile Thr Asn Leu Arg Tyr Glu Glu Asn
                435                     440                     445

Met Trp Pro Gly Ser Arg Lys Phe Asn Thr Thr Glu Arg Val Leu Gln
                450                     455                     460

Gly Leu Leu Arg Pro Leu Phe Lys Asn Thr Ser Val Gly Pro Leu Tyr
465                     470                     475                     480
```

```
Ser Gly Ser Arg Leu Thr Leu Leu Arg Pro Glu Lys Asp Gly Glu Ala
            485                 490                 495
Thr Gly Val Asp Ala Ile Cys Thr His Arg Pro Asp Pro Thr Gly Pro
        500                 505                 510
Gly Leu Asp Arg Glu Gln Leu Tyr Leu Glu Leu Ser Gln Leu Thr His
        515                 520                 525
Ser Ile Thr Glu Leu Gly Pro Tyr Thr Leu Asp Arg Asp Ser Leu Tyr
    530                 535                 540
Val Asn Gly Phe Thr His Arg Ser Ser Val Pro Thr Thr Ser Thr Gly
545                 550                 555                 560
Val Val Ser Glu Glu Pro Phe Thr Leu Asn Phe Thr Ile Asn Asn Leu
            565                 570                 575
Arg Tyr Met Ala Asp Met Gly Gln Pro Gly Ser Leu Lys Phe Asn Ile
            580                 585                 590
Thr Asp Asn Val Met Lys His Leu Leu Ser Pro Leu Phe Gln Arg Ser
        595                 600                 605
Ser Leu Gly Ala Arg Tyr Thr Gly Cys Arg Val Ile Ala Leu Arg Ser
    610                 615                 620
Val Lys Asn Gly Ala Glu Thr Arg Val Asp Leu Leu Cys Thr Tyr Leu
625                 630                 635                 640
Gln Pro Leu Ser Gly Pro Gly Leu Pro Ile Lys Gln Val Phe His Glu
            645                 650                 655
Leu Ser Gln Gln Thr His Gly Ile Thr Arg Leu Gly Pro Tyr Ser Leu
            660                 665                 670
Asp Lys Asp Ser Leu Tyr Leu Asn Gly Tyr Asn Glu Pro Gly Leu Asp
        675                 680                 685
Glu Pro Pro Thr Thr Pro Lys Pro Ala Thr Thr Phe Leu Pro Pro Leu
    690                 695                 700
Ser Glu Ala Thr Thr Ala Met Gly Tyr His Leu Lys Thr Leu Thr Leu
705                 710                 715                 720
Asn Phe Thr Ile Ser Asn Leu Gln Tyr Ser Pro Asp Met Gly Lys Gly
            725                 730                 735
Ser Ala Thr Phe Asn Ser Thr Glu Gly Val Leu Gln His Leu Leu Arg
            740                 745                 750
Pro Leu Phe Gln Lys Ser Ser Met Gly Pro Phe Tyr Leu Gly Cys Gln
        755                 760                 765
Leu Ile Ser Leu Arg Pro Glu Lys Asp Gly Ala Ala Thr Gly Val Asp
    770                 775                 780
Thr Thr Cys Thr Tyr His Pro Asp Pro Val Gly Pro Gly Leu Asp Ile
785                 790                 795                 800
Gln Gln Leu Tyr Trp Glu Leu Ser Gln Leu Thr His Gly Val Thr Gln
            805                 810                 815
Leu Gly Phe Tyr Val Leu Asp Arg Asp Ser Leu Phe Ile Asn Gly Tyr
            820                 825                 830
Ala Pro Gln Asn Leu Ser Ile Arg Gly Glu Tyr Gln Ile Asn Phe His
        835                 840                 845
Ile Val Asn Trp Asn Leu Ser Asn Pro Asp Pro Thr Ser Ser Glu Tyr
    850                 855                 860
Ile Thr Leu Leu Arg Asp Ile Gln Asp Lys Val Thr Thr Leu Tyr Lys
865                 870                 875                 880
Gly Ser Gln Leu His Asp Thr Phe Arg Phe Cys Leu Val Thr Asn Leu
            885                 890                 895
```

```
Thr Met Asp Ser Val Leu Val Thr Val Lys Ala Leu Phe Ser Ser Asn
            900                 905                 910

Leu Asp Pro Ser Leu Val Glu Gln Val Phe Leu Asp Lys Thr Leu Asn
            915                 920                 925

Ala Ser Phe His Trp Leu Gly Ser Thr Tyr Gln Leu Val Asp Ile His
            930                 935                 940

Val Thr Glu Met Glu Ser Ser Val Tyr Gln Pro Thr Ser Ser Ser Ser
945                 950                 955                 960

Thr Gln His Phe Tyr Pro Asn Phe Thr Ile Thr Asn Leu Pro Tyr Ser
            965                 970                 975

Gln Asp Lys Ala Gln Pro Gly Thr Thr Asn Tyr Gln Arg Asn Lys Arg
            980                 985                 990

Asn Ile Glu Asp Ala Leu Asn Gln Leu Phe Arg Asn Ser Ser Ile Lys
            995                 1000                1005

Ser Tyr Phe Ser Asp Cys Gln Val Ser Thr Phe Arg Ser Val Pro Asn
        1010                1015                1020

Arg His His Thr Gly Val Asp Ser Leu Cys Asn Phe Ser Pro Leu Ala
1025                1030                1035                1040

Arg Arg Val Asp Arg Val Ala Ile Tyr Glu Glu Phe Leu Arg Met Thr
                1045                1050                1055

Arg Asn Gly Thr Gln Leu Gln Asn Phe Thr Leu Asp Arg Ser Ser Val
                1060                1065                1070

Leu Val Asp Gly Tyr Ser Pro Asn Arg Asn Glu Pro Leu Thr Gly Asn
            1075                1080                1085

Ser Asp Leu Pro Phe Trp Ala Val Ile Phe Ile Gly Leu Ala Gly Leu
    1090                1095                1100

Leu Gly Leu Ile Thr Cys Leu Ile Cys Gly Val Leu Val Thr Thr Arg
1105                1110                1115                1120

Arg Arg Lys Lys Glu Gly Glu Tyr Asn Val Gln Gln Gln Cys Pro Gly
                1125                1130                1135

Tyr Tyr Gln Ser His Leu Asp Leu Glu Asp Leu Gln
            1140                1145

<210> SEQ ID NO 459
<211> LENGTH: 1156
<212> TYPE: PRT
<213> ORGANISM: Homo sapiens

<400> SEQUENCE: 459

Glu Arg Val Leu Gln Gly Leu Leu Met Pro Leu Phe Lys Asn Thr Ser
                5                   10                  15

Val Ser Ser Leu Tyr Ser Gly Cys Arg Leu Thr Leu Leu Arg Pro Glu
            20                  25                  30

Lys Asp Gly Ala Ala Thr Arg Val Asp Ala Val Cys Thr His Arg Pro
        35                  40                  45

Asp Pro Lys Ser Pro Gly Leu Asp Arg Glu Arg Leu Tyr Trp Lys Leu
    50                  55                  60

Ser Gln Leu Thr His Gly Ile Thr Glu Leu Gly Pro Tyr Thr Leu Asp
65                  70                  75                  80

Arg His Ser Leu Tyr Val Asn Gly Phe Thr His Gln Ser Ser Met Thr
                85                  90                  95

Thr Thr Arg Thr Pro Asp Thr Ser Met His Leu Ala Thr Ser Arg
            100                 105                 110

Thr Pro Ala Ser Leu Ser Gly Pro Thr Thr Ala Ser Pro Leu Leu Val
        115                 120                 125
```

```
Leu Phe Thr Ile Asn Phe Thr Ile Thr Asn Leu Arg Tyr Glu Glu Asn
    130                 135                 140

Met His His Pro Gly Ser Arg Lys Phe Asn Thr Thr Glu Arg Val Leu
145                 150                 155                 160

Gln Gly Leu Leu Arg Pro Val Phe Lys Asn Thr Ser Val Gly Pro Leu
                165                 170                 175

Tyr Ser Gly Cys Arg Leu Thr Leu Leu Arg Pro Lys Lys Asp Gly Ala
            180                 185                 190

Ala Thr Lys Val Asp Ala Ile Cys Thr Tyr Arg Pro Asp Pro Lys Ser
        195                 200                 205

Pro Gly Leu Asp Arg Glu Gln Leu Tyr Trp Glu Leu Ser Gln Leu Thr
    210                 215                 220

His Ser Ile Thr Glu Leu Gly Pro Tyr Thr Leu Asp Arg Asp Ser Leu
225                 230                 235                 240

Tyr Val Asn Gly Phe Thr Gln Arg Ser Ser Val Pro Thr Thr Ser Ile
                245                 250                 255

Pro Gly Thr Pro Thr Val Asp Leu Gly Thr Ser Gly Thr Pro Val Ser
            260                 265                 270

Lys Pro Gly Pro Ser Ala Ala Ser Pro Leu Leu Val Leu Phe Thr Leu
        275                 280                 285

Asn Phe Thr Ile Thr Asn Leu Arg Tyr Glu Glu Asn Met Gln His Pro
    290                 295                 300

Gly Ser Arg Lys Phe Asn Thr Thr Glu Arg Val Leu Gln Gly Leu Leu
305                 310                 315                 320

Arg Ser Leu Phe Lys Ser Thr Ser Val Gly Pro Leu Tyr Ser Gly Cys
                325                 330                 335

Arg Leu Thr Leu Leu Arg Pro Glu Lys Asp Gly Thr Ala Thr Gly Val
            340                 345                 350

Asp Ala Ile Cys Thr His His Pro Asp Pro Lys Ser Pro Arg Leu Asp
        355                 360                 365

Arg Glu Gln Leu Tyr Trp Glu Leu Ser Gln Leu Thr His Asn Ile Thr
    370                 375                 380

Glu Leu Gly His Tyr Ala Leu Asp Asn Asp Ser Leu Phe Val Asn Gly
385                 390                 395                 400

Phe Thr His Arg Ser Ser Val Ser Thr Thr Ser Thr Pro Gly Thr Pro
                405                 410                 415

Thr Val Tyr Leu Gly Ala Ser Lys Thr Pro Ala Ser Ile Phe Gly Pro
            420                 425                 430

Ser Ala Ala Ser His Leu Leu Ile Leu Phe Thr Leu Asn Phe Thr Ile
        435                 440                 445

Thr Asn Leu Arg Tyr Glu Glu Asn Met Trp Pro Gly Ser Arg Lys Phe
    450                 455                 460

Asn Thr Thr Glu Arg Val Leu Gln Gly Leu Leu Arg Pro Leu Phe Lys
465                 470                 475                 480

Asn Thr Ser Val Gly Pro Leu Tyr Ser Gly Ser Arg Leu Thr Leu Leu
                485                 490                 495

Arg Pro Glu Lys Asp Gly Glu Ala Thr Gly Val Asp Ala Ile Cys Thr
            500                 505                 510

His Arg Pro Asp Pro Thr Gly Pro Gly Leu Asp Arg Glu Gln Leu Tyr
        515                 520                 525

Leu Glu Leu Ser Gln Leu Thr His Ser Ile Thr Glu Leu Gly Pro Tyr
    530                 535                 540
```

```
Thr Leu Asp Arg Asp Ser Leu Tyr Val Asn Gly Phe Thr His Arg Ser
545                 550                 555                 560

Ser Val Pro Thr Thr Ser Thr Gly Val Val Ser Glu Glu Pro Phe Thr
                565                 570                 575

Leu Asn Phe Thr Ile Asn Asn Leu Arg Tyr Met Ala Asp Met Gly Gln
            580                 585                 590

Pro Gly Ser Leu Lys Phe Asn Ile Thr Asp Asn Val Met Lys His Leu
            595                 600                 605

Leu Ser Pro Leu Phe Gln Arg Ser Ser Leu Gly Ala Arg Tyr Thr Gly
            610                 615                 620

Cys Arg Val Ile Ala Leu Arg Ser Val Lys Asn Gly Ala Glu Thr Arg
625                 630                 635                 640

Val Asp Leu Leu Cys Thr Tyr Leu Gln Pro Leu Ser Gly Pro Gly Leu
                645                 650                 655

Pro Ile Lys Gln Val Phe His Glu Leu Ser Gln Gln Thr His Gly Ile
                660                 665                 670

Thr Arg Leu Gly Pro Tyr Ser Leu Asp Lys Asp Ser Leu Tyr Leu Asn
            675                 680                 685

Gly Tyr Asn Glu Pro Gly Leu Asp Glu Pro Pro Thr Thr Pro Lys Pro
            690                 695                 700

Ala Thr Thr Phe Leu Pro Pro Leu Ser Glu Ala Thr Thr Ala Met Gly
705                 710                 715                 720

Tyr His Leu Lys Thr Leu Thr Leu Asn Phe Thr Ile Ser Asn Leu Gln
                725                 730                 735

Tyr Ser Pro Asp Met Gly Lys Gly Ser Ala Thr Phe Asn Ser Thr Glu
                740                 745                 750

Gly Val Leu Gln His Leu Leu Arg Pro Leu Phe Gln Lys Ser Ser Met
            755                 760                 765

Gly Pro Phe Tyr Leu Gly Cys Gln Leu Ile Ser Leu Arg Pro Glu Lys
            770                 775                 780

Asp Gly Ala Ala Thr Gly Val Asp Thr Thr Cys Thr Tyr His Pro Asp
785                 790                 795                 800

Pro Val Gly Pro Gly Leu Asp Ile Gln Gln Leu Tyr Trp Glu Leu Ser
                805                 810                 815

Gln Leu Thr His Gly Val Thr Gln Leu Gly Phe Tyr Val Leu Asp Arg
                820                 825                 830

Asp Ser Leu Phe Ile Asn Gly Tyr Ala Pro Gln Asn Leu Ser Ile Arg
            835                 840                 845

Gly Glu Tyr Gln Ile Asn Phe His Ile Val Asn Trp Asn Leu Ser Asn
            850                 855                 860

Pro Asp Pro Thr Ser Ser Glu Tyr Ile Thr Leu Leu Arg Asp Ile Gln
865                 870                 875                 880

Asp Lys Val Thr Thr Leu Tyr Lys Gly Ser Gln Leu His Asp Thr Phe
                885                 890                 895

Arg Phe Cys Leu Val Thr Asn Leu Thr Met Asp Ser Val Leu Val Thr
                900                 905                 910

Val Lys Ala Leu Phe Ser Ser Asn Leu Asp Pro Ser Leu Val Glu Gln
            915                 920                 925

Val Phe Leu Asp Lys Thr Leu Asn Ala Ser Phe His Trp Leu Gly Ser
            930                 935                 940

Thr Tyr Gln Leu Val Asp Ile His Val Thr Glu Met Glu Ser Ser Val
945                 950                 955                 960

Tyr Gln Pro Thr Ser Ser Ser Ser Thr Gln His Phe Tyr Pro Asn Phe
```

```
                       965                 970                 975
Thr Ile Thr Asn Leu Pro Tyr Ser Gln Asp Lys Ala Gln Pro Gly Thr
                980                 985                 990
Thr Asn Tyr Gln Arg Asn Lys Arg Asn Ile Glu Asp Ala Leu Asn Gln
            995                1000                1005
Leu Phe Arg Asn Ser Ser Ile Lys Ser Tyr Phe Ser Asp Cys Gln Val
       1010                1015                1020
Ser Thr Phe Arg Ser Val Pro Asn Arg His His Thr Gly Val Asp Ser
1025                1030                1035                1040
Leu Cys Asn Phe Ser Pro Leu Ala Arg Arg Val Asp Arg Val Ala Ile
                1045                1050                1055
Tyr Glu Glu Phe Leu Arg Met Thr Arg Asn Gly Thr Gln Leu Gln Asn
                1060                1065                1070
Phe Thr Leu Asp Arg Ser Ser Val Leu Val Asp Gly Tyr Ser Pro Asn
            1075                1080                1085
Arg Asn Glu Pro Leu Thr Gly Asn Ser Asp Leu Pro Phe Trp Ala Val
       1090                1095                1100
Ile Phe Ile Gly Leu Ala Gly Leu Leu Gly Leu Ile Thr Cys Leu Ile
1105                1110                1115                1120
Cys Gly Val Leu Val Thr Thr Arg Arg Arg Lys Lys Glu Gly Glu Tyr
                1125                1130                1135
Asn Val Gln Gln Gln Cys Pro Gly Tyr Tyr Gln Ser His Leu Asp Leu
                1140                1145                1150
Glu Asp Leu Gln
        1155

<210> SEQ ID NO 460
<211> LENGTH: 79
<212> TYPE: PRT
<213> ORGANISM: Homo sapiens

<400> SEQUENCE: 460

Met Ser Met Val Ser His Ser Gly Ala Leu Cys Pro Pro Leu Ala Phe
                 5                  10                  15
Leu Gly Pro Pro Gln Trp Thr Trp Glu His Leu Gly Leu Gln Phe Leu
            20                  25                  30
Asn Leu Val Pro Arg Leu Pro Ala Leu Ser Trp Cys Tyr Ser Leu Ser
        35                  40                  45
Thr Ser Pro Ser Pro Thr Cys Gly Met Arg Arg Thr Cys Ser Thr Leu
    50                  55                  60
Ala Pro Gly Ser Ser Thr Pro Arg Arg Gly Ser Phe Arg Ala Trp
65                  70                  75

<210> SEQ ID NO 461
<211> LENGTH: 313
<212> TYPE: PRT
<213> ORGANISM: Homo sapiens

<400> SEQUENCE: 461

Met Pro Leu Phe Lys Asn Thr Ser Val Ser Ser Leu Tyr Ser Gly Cys
                 5                  10                  15
Arg Leu Thr Leu Leu Arg Pro Glu Lys Asp Gly Ala Ala Thr Arg Val
            20                  25                  30
Asp Ala Val Cys Thr His Arg Pro Asp Pro Lys Ser Pro Gly Leu Asp
        35                  40                  45
Arg Glu Arg Leu Tyr Trp Lys Leu Ser Gln Leu Thr His Gly Ile Thr
```

-continued

```
                50                      55                      60
Glu Leu Gly Pro Tyr Thr Leu Asp Arg His Ser Leu Tyr Val Asn Gly
 65                      70                      75                      80

Phe Thr His Gln Ser Ser Met Thr Thr Thr Arg Thr Pro Asp Thr Ser
                 85                      90                      95

Thr Met His Leu Ala Thr Ser Arg Thr Pro Ala Ser Leu Ser Gly Pro
                100                     105                     110

Thr Thr Ala Ser Pro Leu Leu Val Leu Phe Thr Ile Asn Phe Thr Ile
                115                     120                     125

Thr Asn Leu Arg Tyr Glu Glu Asn Met His His Pro Gly Ser Arg Lys
                130                     135                     140

Phe Asn Thr Thr Glu Arg Val Leu Gln Gly Leu Leu Arg Pro Val Phe
145                     150                     155                     160

Lys Asn Thr Ser Val Gly Pro Leu Tyr Ser Gly Cys Arg Leu Thr Leu
                165                     170                     175

Leu Arg Pro Lys Lys Asp Gly Ala Ala Thr Lys Val Asp Ala Ile Cys
                180                     185                     190

Thr Tyr Arg Pro Asp Pro Lys Ser Pro Gly Leu Asp Arg Glu Gln Leu
                195                     200                     205

Tyr Trp Glu Leu Ser Gln Leu Thr His Ser Ile Thr Glu Leu Gly Pro
    210                     215                     220

Tyr Thr Leu Asp Arg Asp Ser Leu Tyr Val Asn Gly Phe Thr Gln Arg
225                     230                     235                     240

Ser Ser Val Pro Thr Thr Ser Ile Pro Gly Thr Pro Thr Val Asp Leu
                245                     250                     255

Gly Thr Ser Gly Thr Pro Val Ser Lys Pro Gly Pro Ser Ala Ala Ser
                260                     265                     270

Pro Leu Leu Val Leu Phe Thr Leu Asn Phe Thr Ile Thr Asn Leu Arg
                275                     280                     285

Tyr Glu Glu Asn Met Gln His Pro Gly Ser Arg Lys Phe Asn Thr Thr
    290                     295                     300

Glu Arg Val Leu Gln Gly Leu Leu Arg
305                     310
```

COMPOSITIONS AND METHODS FOR THE THERAPY AND DIAGNOSIS OF OVARIAN CANCER

CROSS REFERENCE TO RELATED APPLICATIONS

This application is a continuation-in-part of U.S. application Ser. No. 09/667,857, filed Sep. 20, 2000, now U.S. Pat. No. 6,699,664, which is a continuation in part of U.S. application Ser. No. 09/636,801, filed Aug. 10, 2000, which is a continuation-in part of U.S. application Ser. No. 09/617,747, filed Jul. 17, 2000, now abandoned, which is a continuation-in-part of U.S. application Ser. No. 09/404,879, filed Sep. 24, 1999, now U.S. Pat. No. 6,468,546.

TECHNICAL FIELD

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides, antibodies and cells may be used in vaccines and pharmaceutical compositions for treatment of ovarian cancer.

BACKGROUND OF THE INVENTION

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

SUMMARY OF THE INVENTION

Briefly stated, this invention provides compositions and methods for the therapy of cancer, such as ovarian cancer. In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished.

Within certain embodiments, the ovarian carcinoma protein comprises a sequence that is encoded by a polynucleotide sequence selected from the group consisting of SEQ ID NOs:1–81, 313–331, 359, 366, 379, 385–387, 391 and complements of such polynucleotides.

The present invention further provides polynucleotides that encode a polypeptide as described above or a portion thereof, expression vectors comprising such polynucleotides and host cells transformed or transfected with such expression vectors.

Within other aspects, the present invention provides pharmaceutical compositions and vaccines. Pharmaceutical compositions may comprise a physiologically acceptable carrier or excipient in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–81, 313–331, 359, 366, 379, 385–387 or 391; (ii) a polynucleotide encoding such a polypeptide; (iii) an antibody that specifically binds to such a polypeptide; (iv) an antigen-presenting cell that expresses such a polypeptide and/or (v) a T cell that specifically reacts with such a polypeptide. Vaccines may comprise a non-specific immune response enhancer in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–81, 313–331, 359, 366, 379, 385–387 or 391; (ii) a polynucleotide encoding such a polypeptide; (iii) an anti-idiotypic antibody that is specifically bound by an antibody that specifically binds to such a polypeptide; (iv) an antigen-presenting cell that expresses such a polypeptide and/or (v) a T cell that specifically reacts with such a polypeptide.

The present invention further provides, in other aspects, fusion proteins that comprise at least one polypeptide as described above, as well as polynucleotides encoding such fusion proteins.

Within related aspects, pharmaceutical compositions comprising a fusion protein or polynucleotide encoding a fusion protein in combination with a physiologically acceptable carrier are provided.

Vaccines are further provided, within other aspects, comprising a fusion protein or polynucleotide encoding a fusion protein in combination with a non-specific immune response enhancer.

Within further aspects, the present invention provides methods for inhibiting the development of a cancer in a patient, comprising administering to a patient a pharmaceutical composition or vaccine as recited above.

The present invention further provides, within other aspects, methods for stimulating and/or expanding T cells, comprising contacting T cells with (a) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–387 or 391; (b) a polynucleotide encoding such a polypeptide and/or (c) an antigen presenting cell that expresses such a polypeptide under conditions and for a time sufficient to permit the stimulation and/or expansion of T cells. Such polypeptide, polynucleotide and/or antigen presenting cell(s) may be present within a pharmaceutical composition or vaccine, for use in stimulating and/or expanding T cells in a mammal.

Within other aspects, the present invention provides methods for inhibiting the development of ovarian cancer in a patient, comprising administering to a patient T cells prepared as described above.

Within further aspects, the present invention provides methods for inhibiting the development of ovarian cancer in a patient, comprising the steps of: (a) incubating CD4+ and/or CD8+ T cells isolated from a patient with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs: 1–387 or 391; (ii) a polynucleotide encoding such a polypeptide; or (iii) an antigen-presenting cell that expresses such a polypeptide; such that T cells proliferate; and (b) administering to the patient an effective amount of the proliferated T cells, and thereby inhibiting the development of ovarian cancer in the patient. The proliferated cells may be cloned prior to administration to the patient.

The present invention also provides, within other aspects, methods for identifying secreted tumor antigens. Such methods comprise the steps of: (a) implanting tumor cells in an immunodeficient mammal; (b) obtaining serum from the immunodeficient mammal after a time sufficient to permit secretion of tumor antigens into the serum; (c) immunizing an immunocompetent mammal with the serum; (d) obtaining antiserum from the immunocompetent mammal; and (e) screening a tumor expression library with the antiserum, and therefrom identifying a secreted tumor antigen. A preferred method for identifying a secreted ovarian carcinoma antigen comprises the steps of: (a) implanting ovarian carcinoma cells in a SCID mouse; (b) obtaining serum from the SCID mouse after a time sufficient to permit secretion of ovarian carcinoma antigens into the serum; (c) immunizing an immunocompetent mouse with the serum; (d) obtaining antiserum from the immunocompetent mouse; and (e) screening an ovarian carcinoma expression library with the antiserum, and therefrom identifying a secreted ovarian carcinoma antigen.

The present invention also discloses antibody epitopes recognized by the O8E polyclonal anti-sera which epitopes are presented herein as SEQ ID NOs: 394–415.

Further disclosed by the present invention are 10-mer and 9-mer peptides predicted to bind HLA-0201 which peptides are disclosed herein as SEQ ID NOs: 416–435 and SEQ ID NOs: 436–455, respectively.

These and other aspects of the present invention will become apparent upon reference to the following detailed description and attached drawings. All references disclosed herein are hereby incorporated by reference in their entirety as if each was incorporated individually.

BRIEF DESCRIPTION OF THE SEQUENCE IDENTIFIERS AND DRAWINGS

SEQ ID NOs:1–71 are ovarian carcinoma antigen polynucleotides shown in FIGS. 1A–1S.

SEQ ID NOs:72–74 are ovarian carcinoma antigen polynucleotides shown in FIGS. 2A–2C.

SEQ ID NO:75 is the ovarian carcinoma polynucleotide 3g (FIG. 4).

SEQ ID NO:76 is the ovarian carcinoma polynucleotide 3f (FIG. 5).

SEQ ID NO:77 is the ovarian carcinoma polynucleotide 6b (FIG. 6).

SEQ ID NO:78 is the ovarian carcinoma polynucleotide 8e (FIG. 7A).

SEQ ID NO:79 is the ovarian carcinoma polynucleotide 8h (FIG. 7B).

SEQ ID NO:80 is the ovarian carcinoma polynucleotide 12e (FIG. 8).

SEQ ID NO:81 is the ovarian carcinoma polynucleotide 12h (FIG. 9).

SEQ ID NOs:82–310 are ovarian carcinoma antigen polynucleotides shown in FIGS. 15A–15EEE.

SEQ ID NO:311 is a full length sequence of ovarian carcinoma polynucleotide O772P.

SEQ ID NO:312 is the O772P amino acid sequence.

SEQ ID NOs:313–384 are ovarian carcinoma antigen polynucleotides.

SEQ ID NOs:385–390 present sequences of O772P forms.

SEQ ID NO:391 is a full length sequence of ovarian carcinoma polynucleotide O8E.

SEQ ID NOs:392–393 are protein sequences encoded by O8E.

SEQ ID NOs:394–415 are peptide sequences corresponding to the OE8 antibody epitopes.

SEQ ID NOs:416–435 are potential HLA-A2 10-mer binding peptides predicted using the full length open-reading frame from OE8.

SEQ ID NOs:436–455 are potential HLA-A2 9-mer binding peptides predicted using the full length open-reading frame from OE8.

SEQ ID NO:456 is a truncated nucleotide sequence of the full length Genbank sequence showing homology to O772P SEQ ID NO:457 is the full length Genbank sequence showing significant homology to O772P SEQ ID NO:458 is a protein encoding a truncated version of the full length Genbank sequence showing homology to O772P SEQ ID NO:459 is the full length protein sequence from Genbank showing significant homology to the protein sequence for O772P SEQ ID NO:460 encodes a unique N-terminal portion of O772P contained in residues 1–70.

SEQ ID NO:461 contains unique sequence and encodes residues 1–313 of SEQ ID NO: 456.

FIGS. 1A–1S (SEQ ID NOs:1–71) depict partial sequences of polynucleotides encoding representative secreted ovarian carcinoma antigens.

FIGS. 2A–2C depict full insert sequences for three of the clones of FIG. 1. FIG. 2A shows the sequence designated O7E (11731; SEQ ID NO:72), FIG. 2B shows the sequence designated O9E (11785; SEQ ID NO:73) and FIG. 2C shows the sequence designated O8E (13695; SEQ ID NO:74).

FIG. 3 presents results of microarray expression analysis of the ovarian carcinoma sequence designated O8E.

FIG. 4 presents a partial sequence of a polynucleotide (designated 3g; SEQ ID NO:75) encoding an ovarian carcinoma sequence that is a splice fusion between the human T-cell leukemia virus type I oncoprotein TAX and osteonectin.

FIG. 5 presents the ovarian carcinoma polynucleotide designated 3f (SEQ ID NO:76).

FIG. 6 presents the ovarian carcinoma polynucleotide designated 6b (SEQ ID NO:77).

FIGS. 7A and 7B present the ovarian carcinoma polynucleotides designated 8e (SEQ ID NO:78) and 8h (SEQ ID NO:79).

FIG. 8 presents the ovarian carcinoma polynucleotide designated 12c (SEQ ID NO:80).

FIG. 9 presents the ovarian carcinoma polynucleotide designated 12h (SEQ ID NO:81).

FIG. 10 depicts results of microarray expression analysis of the ovarian carcinoma sequence designated 3f.

FIG. 11 depicts results of microarray expression analysis of the ovarian carcinoma sequence designated 6b.

FIG. 12 depicts results of microarray expression analysis of the ovarian carcinoma sequence designated 8e.

FIG. 13 depicts results of microarray expression analysis of the ovarian carcinoma sequence designated 12c.

FIG. 14 depicts results of microarray expression analysis of the ovarian carcinoma sequence designated 12h.

FIGS. 15A–15EEE depict partial sequences of additional polynucleotides encoding representative secreted ovarian carcinoma antigens (SEQ ID NOs:82–310).

Figure 16:
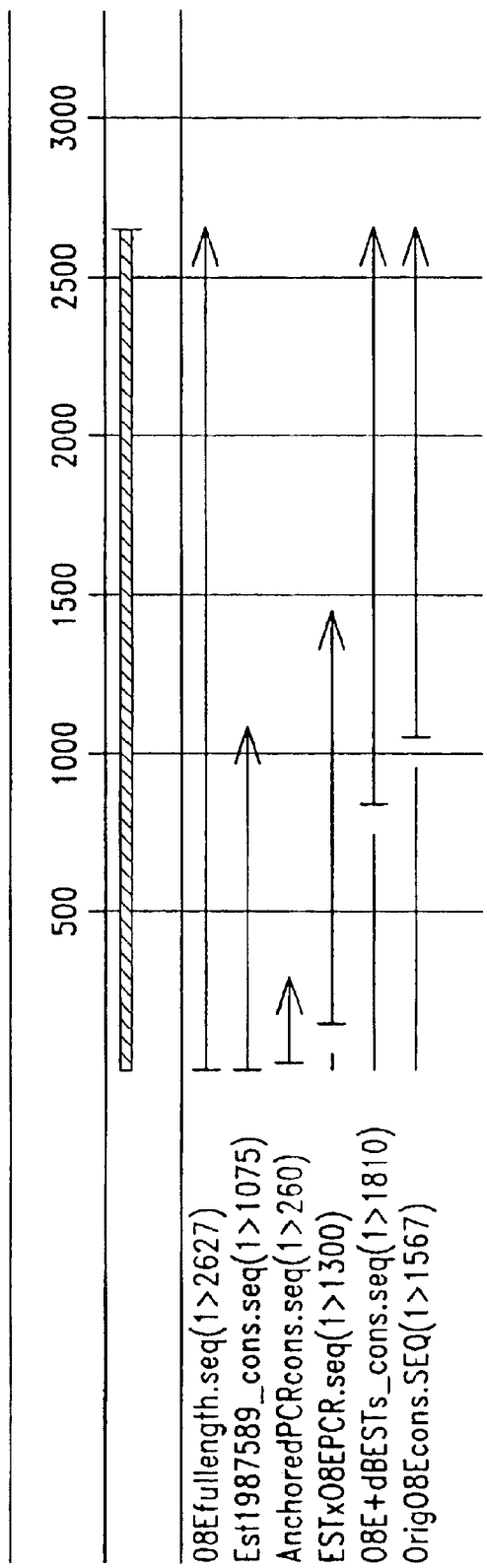

FIG. 16 is a diagram illustrating the location of various partial O8E sequences within the full length sequence.

Figure 17:
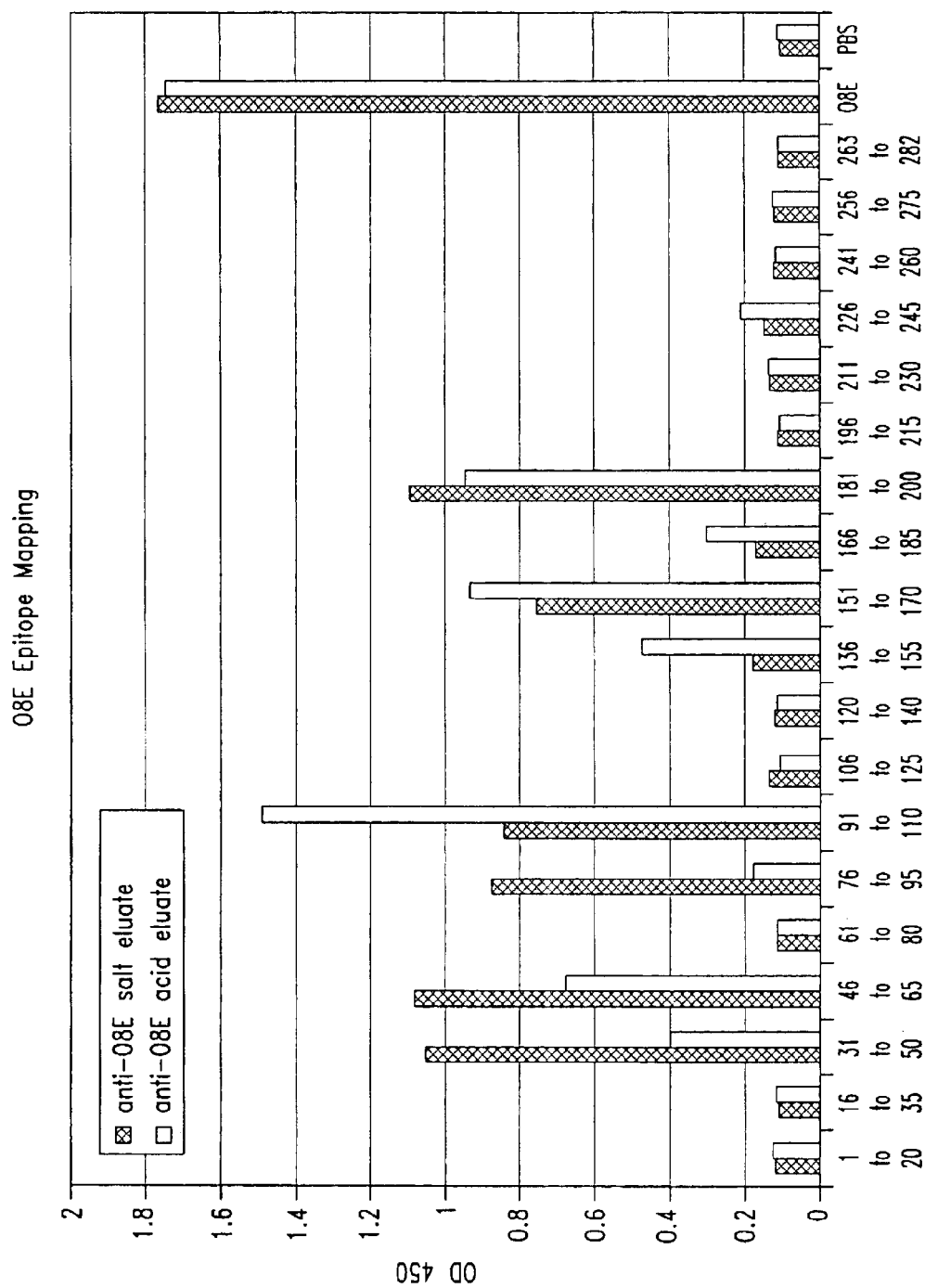

FIG. 17 is a graph illustrating the results of epitope mapping studies on O8E protein.

Figure 18:
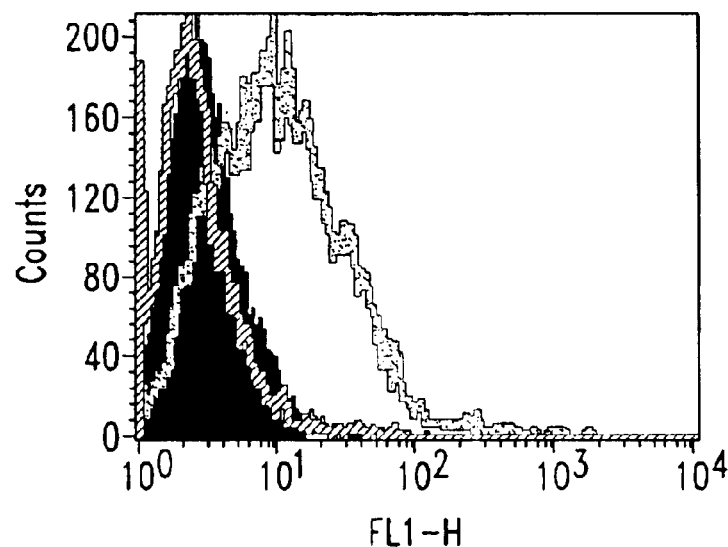

FIG. 18 is graph of a fluorescence activated cell sorting (FACS) analysis of O8E cell surface expression.

Figure 19:
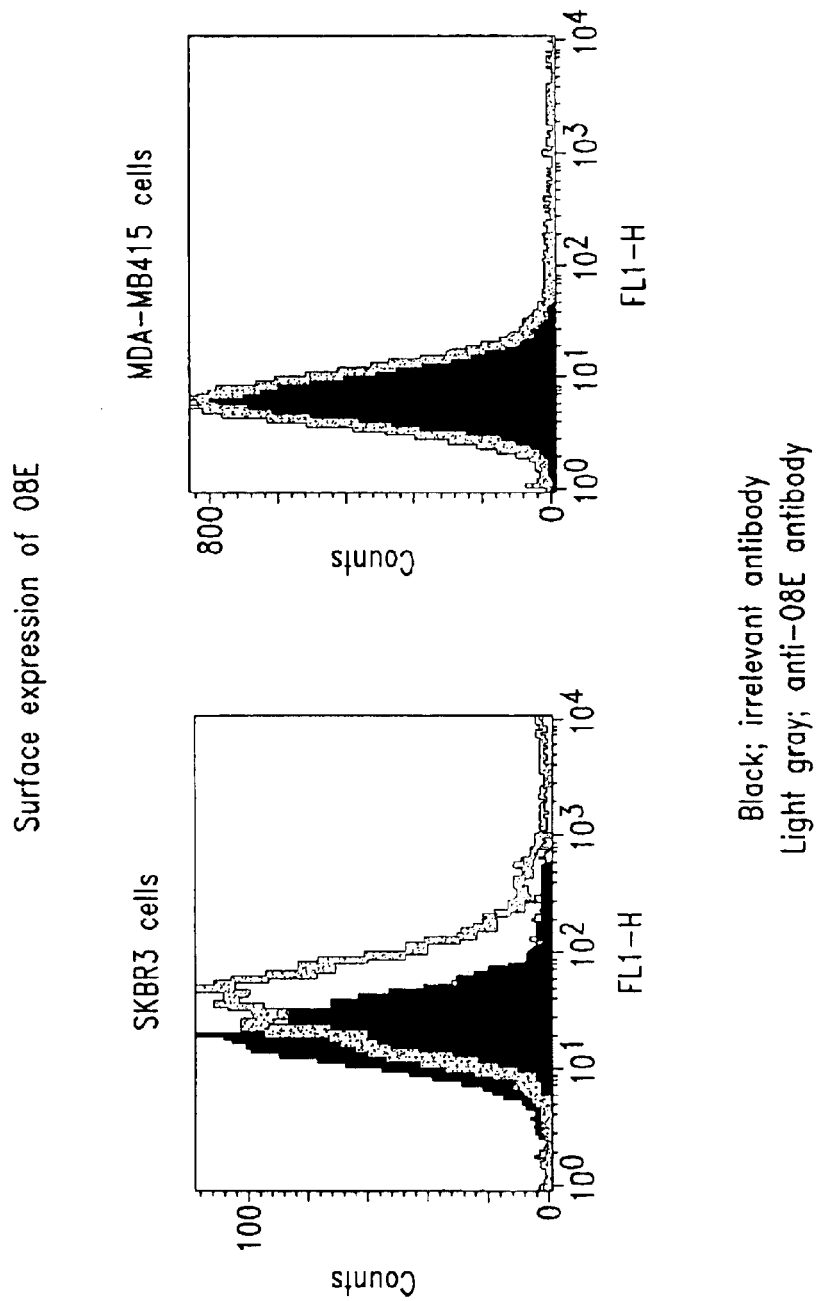

FIG. 19 is graph of a FACS analysis of O8E cell surface expression.

Figure 20:
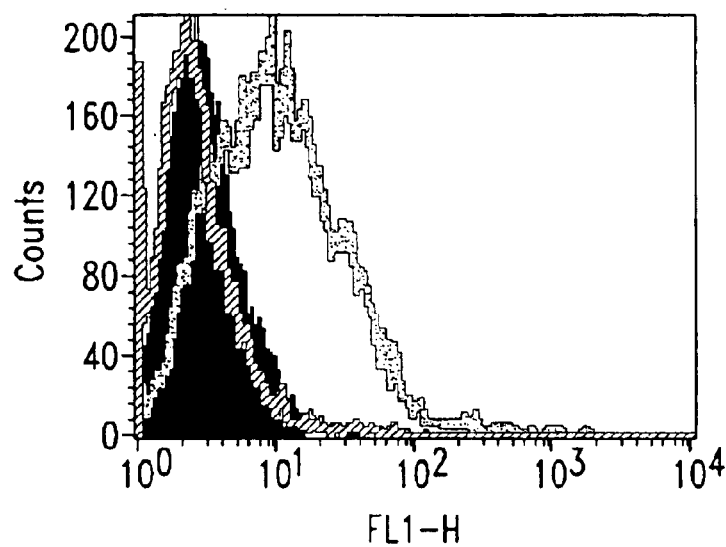

FIG. 20 shows FACS analysis results for O8E transfected HEK293 cells demonstrating cell surface expression of O8E.

Figure 21:
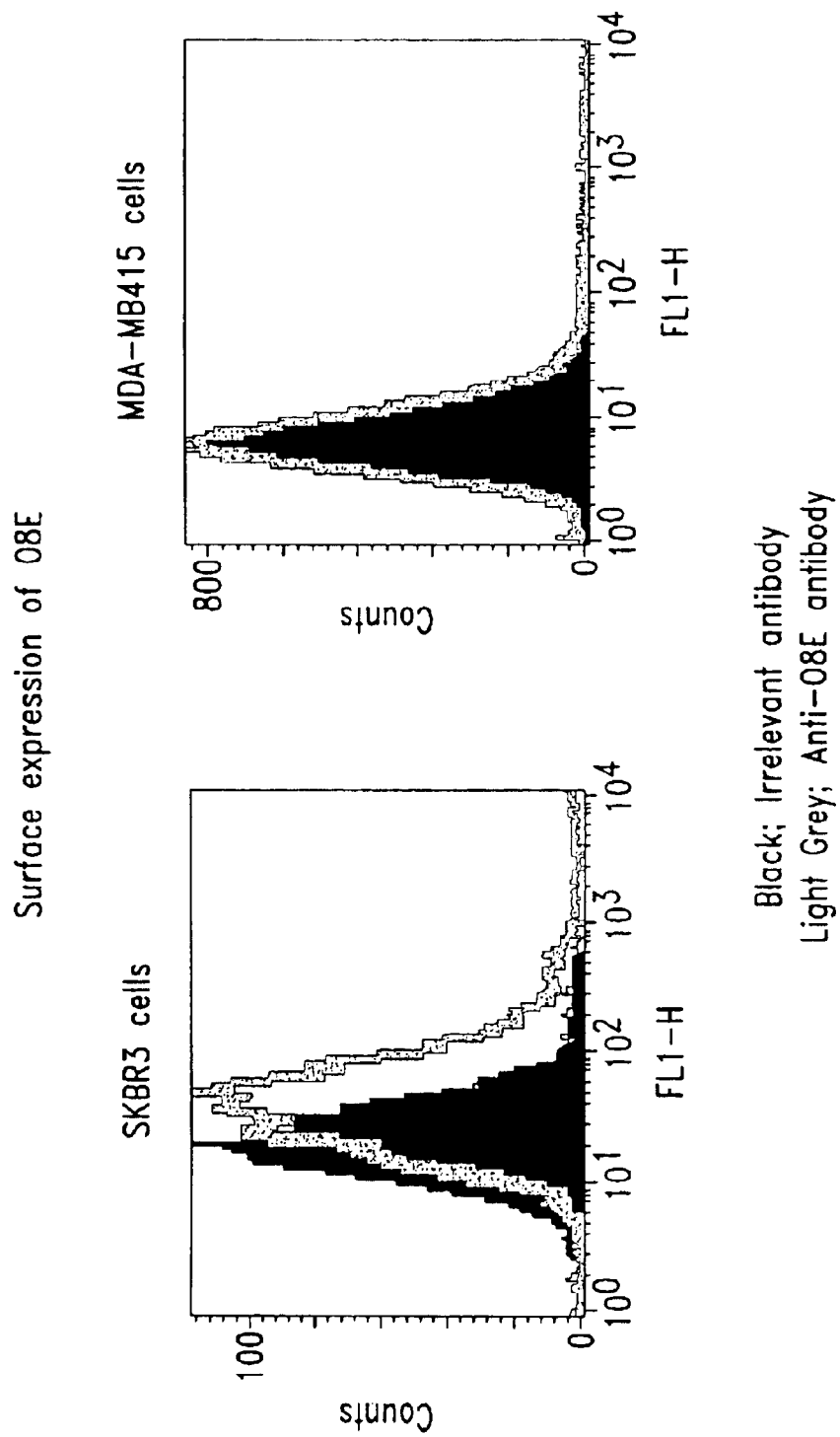

FIG. 21 shows FACS analysis results for SKBR3 breast tumor cells demonstrating cell surface expression of O8E.

Figure 22:
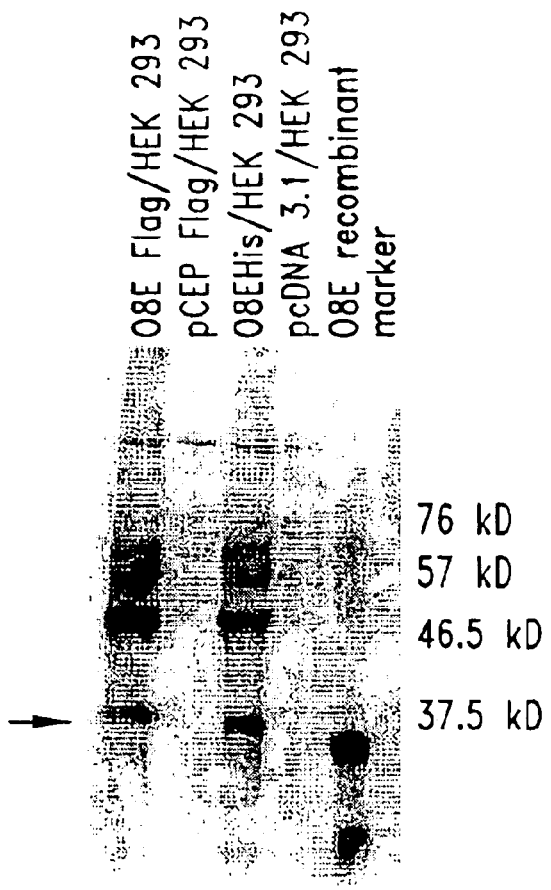

FIG. 22 shows 08E expression in HEK 293 cells. The cells were probed with anti-O8E rabbit polyclonal antisera #2333L.

FIG. 23 shows the ELISA analysis of anti-08E rabbit sera.

FIG. 24 shows the ELISA analysis of affinity purified rabbit anti-08E polyclonal antibody.

FIG. 25 is a graph determining antibody internalization of anti-O8E mAb showing that mAbs against amino acids 61–80 induces ligand internalization.

DETAILED DESCRIPTION OF THE INVENTION

As noted above, the present invention is generally directed to compositions and methods for the therapy of cancer, such as ovarian cancer. The compositions described herein may include immunogenic polypeptides, polynucleotides encoding such polypeptides, binding agents such as antibodies that bind to a polypeptide, antigen presenting cells (APCs) and/or immune system cells (e.g., T cells).

Polypeptides of the present invention generally comprise at least an immunogenic portion of an ovarian carcinoma protein or a variant thereof. Certain ovarian carcinoma proteins have been identified using an immunoassay technique, and are referred to herein as ovarian carcinoma antigens. An "ovarian carcinoma antigen" is a protein that is expressed by ovarian tumor cells (preferably human cells) at a level that is at least two fold higher than the level in normal ovarian cells. Certain ovarian carcinoma antigens react detectably (within an immunoassay, such as an ELISA or Western blot) with antisera generated against serum from an immunodeficient animal implanted with a human ovarian tumor. Such ovarian carcinoma antigens are shed or secreted from an ovarian tumor into the sera of the immunodeficient animal. Accordingly, certain ovarian carcinoma antigens provided herein are secreted antigens. Certain nucleic acid sequences of the subject invention generally comprise a DNA or RNA sequence that encodes all or a portion of such a polypeptide, or that is complementary to such a sequence.

The present invention further provides ovarian carcinoma sequences that are identified using techniques to evaluate altered expression within an ovarian tumor. Such sequences may be polynucleotide or protein sequences. Ovarian carcinoma sequences are generally expressed in an ovarian tumor at a level that is at least two fold, and preferably at least five fold, greater than the level of expression in normal ovarian tissue, as determined using a representative assay provided herein. Certain partial ovarian carcinoma polynucleotide sequences are presented herein. Proteins encoded by genes comprising such polynucleotide sequences (or complements thereof) are also considered ovarian carcinoma proteins.

Antibodies are generally immune system proteins, or antigen-binding fragments thereof, that are capable of binding to at least a portion of an ovarian carcinoma polypeptide as described herein. T cells that may be employed within the compositions provided herein are generally T cells (e.g., CD4$^+$ and/or CD8$^+$) that are specific for such a polypeptide. Certain methods described herein further employ antigen-presenting cells (such as dendritic cells or macrophages) that express an ovarian carcinoma polypeptide as provided herein.

Ovarian Carcinoma Polynucleotides

Any polynucleotide that encodes an ovarian carcinoma protein or a portion or other variant thereof as described herein is encompassed by the present invention. Preferred polynucleotides comprise at least 15 consecutive nucleotides, preferably at least 30 consecutive nucleotides, and more preferably at least 45 consecutive nucleotides, that encode a portion of an ovarian carcinoma protein. More preferably, a polynucleotide encodes an immunogenic portion of an ovarian carcinoma protein, such as an ovarian carcinoma antigen. Polynucleotides complementary to any such sequences are also encompassed by the present invention. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an ovarian carcinoma protein or a portion thereof) or may comprise a variant of such a sequence. Polynucleotide variants may contain one or more substitutions, additions, deletions and/or insertions such that the immunogenicity of the encoded polypeptide is not diminished, relative to a native ovarian carcinoma protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native ovarian carcinoma protein or a portion thereof.

The percent identity for two polynucleotide or polypeptide sequences may be readily determined by comparing sequences using computer algorithms well known to those of ordinary skill in the art, such as Megalign, using default parameters. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned. Optimal alignment of sequences for comparison may be conducted, for example, using the Megalign program in the Lasergene suite of bioinformatics software (DNASTAR, Inc., Madison, Wis.), using default parameters. Preferably, the percentage of sequence identity is determined by comparing two optimally aligned sequences over a window of comparison of at least 20 positions, wherein the portion of the polynucleotide or polypeptide sequence in the window may comprise additions or deletions (i.e., gaps) of 20% or less, usually 5 to 15%, or 10 to 12%, relative to the reference sequence (which does not contain additions or deletions). The percent identity may be calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native ovarian carcinoma protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, an ovarian carcinoma polynucleotide may be identified, as described in more detail below, by screening a late passage ovarian tumor expression library with antisera generated against sera of immunocompetent mice after injection of such mice with sera from SCID mice implanted with late passage ovarian tumors. Ovarian carcinoma polynucleotides may also be identified using any of a variety of techniques designed to evaluate differential gene expression. Alternatively, polynucleotides may be amplified from cDNA prepared from ovarian tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., an ovarian carcinoma cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial CDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of ovarian carcinoma antigens are provided in FIGS. 1A–1S (SEQ ID NOS:1 to 71) and FIGS. 15A to 15EEE (SEQ ID NOs:82 to 310). The sequences provided in FIGS. 1A–1S appear to be novel. For sequences in FIGS. 15A–15EEE, database searches revealed matches having substantial identity. These polynucleotides were isolated by serological screening of an ovarian tumor cDNA expression library, using a technique designed to identify secreted tumor antigens. Briefly, a late passage ovarian tumor expression library was prepared from a SCID-derived human ovarian tumor (OV9334) in the vector λ-screen (Novagen). The sera used for screening were obtained by injecting immunocompetent mice with sera from SCID mice implanted with one late passage ovarian tumors. This technique permits the identification of cDNA molecules that encode immunogenic portions of secreted tumor antigens.

The polynucleotides recited herein, as well as full length polynucleotides comprising such sequences, other portions of such full length polynucleotides, and sequences complementary to all or a portion of such full length molecules, are specifically encompassed by the present invention. It will be apparent to those of ordinary skill in the art that this technique can also be applied to the identification of antigens that are secreted from other types of tumors.

Other nucleic acid sequences of cDNA molecules encoding portions of ovarian carcinoma proteins are provided in FIGS. 4–9 (SEQ ID NOs:75–81), as well as SEQ ID NOs:313–384. These sequences were identified by screening a microarray of cDNAs for tumor-associated expression (i.e., expression that is at least five fold greater in an ovarian tumor than in normal ovarian tissue, as determined using a representative assay provided herein). Such screens were performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). SEQ ID NOs:311 and 391 provide full length sequences incorporating certain of these nucleic acid sequences.

Any of a variety of well known techniques may be used to evaluate tumor-associated expression of a cDNA. For example, hybridization techniques using labeled polynucleotide probes may be employed. Alternatively, or in addition, amplification techniques such as real-time PCR may be used (see Gibson et al., *Genome Research* 6:995–1001, 1996; Heid et al., *Genome Research* 6:986–994, 1996). Real-time PCR is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR may be performed, for example, using a Perkin Elmer/Applied Biosystems (Foster City, Calif.) 7700 Prism instrument. Matching primers and fluorescent probes may be designed for genes of interest using, for example, the primer express program provided by Perkin Elmer/Applied Biosystems (Foster City, Calif.). Optimal concentrations of primers and probes may be initially determined by those of ordinary skill in the art, and control (e.g., β-actin) primers and probes may be obtained commercially from, for example, Perkin Elmer/Applied Biosystems (Foster City, Calif.). To quantitate the amount of specific RNA in a sample, a standard curve is generated alongside using a plasmid containing the gene of interest. Standard curves may be generated using the Ct values determined in the real-time PCR, which are related to the initial cDNA concentration used in the assay. Standard dilutions ranging from $10-10^6$ copies of the gene of interest are generally sufficient. In addition, a standard curve is generated for the control sequence. This permits standardization of initial RNA content of a tissue sample to the amount of control for comparison purposes.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding an ovarian carcinoma antigen, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (i.e., an antisense polynucleotide) may also be used as a probe or to modulate gene expression. cDNA constructs that can be transcribed into antisense RNA may also be introduced into cells or tissues to facilitate the production of antisense RNA. An antisense polynucleotide may be used, as described herein, to inhibit expression of an ovarian carcinoma protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994). Alternatively, an antisense molecule may be designed to hybridize with a control region of a gene (e.g., promoter, enhancer or transcription initiation site), and block transcription of the gene; or to block translation by inhibiting binding of a transcript to ribosomes.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Ovarian Carcinoma Polypeptides

Within the context of the present invention, polypeptides may comprise at least an immunogenic portion of an ovarian carcinoma protein or a variant thereof, as described herein. As noted above, certain ovarian carcinoma proteins are ovarian carcinoma antigens that are expressed by ovarian tumor cells and react detectably within an immunoassay (such as an ELISA) with antisera generated against serum from an immunodeficient animal implanted with an ovarian tumor. Other ovarian carcinoma proteins are encoded by ovarian carcinoma polynucleotides recited herein. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of an ovarian carcinoma protein or a variant thereof. Preferred immunogenic portions are encoded by cDNA molecules isolated as described herein. Further immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with ovarian carcinoma protein-specific antibodies, antisera and/or T-cell lines or clones. As used herein, antisera and antibodies are "ovarian carcinoma protein-specific" if they specifically bind to an ovarian carcinoma protein (i.e., they react with the ovarian carcinoma protein in an ELISA or other immunoassay, and do not react detectably with unrelated proteins). Such antisera, antibodies and T cells may be prepared as described herein, and using well known techniques. An immunogenic portion of a native ovarian carcinoma protein is a portion that reacts with such antisera, antibodies and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length protein. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native ovarian carcinoma protein. A polypeptide "variant," as used herein, is a polypeptide that differs from a native ovarian carcinoma protein in one or more substitutions, deletions, additions and/or insertions, such that the immunogenicity of the polypeptide is not substantially diminished. In other words, the ability of a variant to react with ovarian carcinoma protein-specific antisera may be enhanced or unchanged, relative to the native ovarian carcinoma protein, or may be diminished by less than 50%, and preferably less than 20%, relative to the native ovarian carcinoma protein. Such variants may generally be identified by modifying one of the above polypeptide sequences and evaluating the reactivity of the modified polypeptide with ovarian carcinoma protein-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity to the native polypeptide. Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are $E.$ $coli$, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, $J.$ $Am.$ $Chem.$ $Soc.$ 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known tumor antigen, such as an ovarian carcinoma protein or a variant of such a protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., $Gene$ 40:39–46, 1985; Murphy et al., $Proc.$ $Natl.$ $Acad.$ $Sci.$ $USA$ 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. $New$ $Engl.$ $J.$ $Med.$, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in $E.$ $coli$ (thus functioning as an expression enhancer). The lipid tail ensures optimal presentation of the antigen to antigen present cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to an ovarian carcinoma protein. As used herein, an antibody, or antigen-binding fragment thereof, is said to "specifically bind" to an ovarian carcinoma protein if it reacts at a detectable level (within, for example, an ELISA) with an ovarian carcinoma protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant maybe determined using methods well known in the art.

Binding agents may be further capable of differentiating between patients with and without a cancer, such as ovarian cancer, using the representative assays provided herein. In other words, antibodies or other binding agents that bind to a ovarian carcinoma antigen will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, leukophoresis, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of an ovarian carcinoma protein. Such antibodies may be raised against an antibody, or antigen-binding fragment thereof, that specifically binds to an immunogenic portion of an ovarian carcinoma protein, using well known techniques. Anti-idiotypic antibodies that mimic an immunogenic portion of an ovarian carcinoma protein are those antibodies that bind to an antibody, or antigen-binding fragment thereof, that specifically binds to an immunogenic portion of an ovarian carcinoma protein, as described herein.

T Cells

Immunotherapeutic compositions may also, or alternatively, comprise T cells specific for an ovarian carcinoma protein. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CEPRATE™ system, available from CellPro Inc., Bothell Wash. (see also U.S. Pat. No. 5,240,856; U.S. Pat. No. 5,215,926; WO 89/06280; WO 91/16116 and WO 92/07243). Alternatively, T cells may be derived from related or unrelated humans, non-human animals, cell lines or cultures.

T cells may be stimulated with an ovarian carcinoma polypeptide, polynucleotide encoding an ovarian carcinoma polypeptide and/or an antigen presenting cell (APC) that expresses such a polypeptide. Such stimulation is performed under conditions and for a time sufficient to permit the generation of T cells that are specific for the polypeptide. Preferably, an ovarian carcinoma polypeptide or polynucleotide is present within a delivery vehicle, such as a microsphere, to facilitate the generation of specific T cells.

T cells are considered to be specific for an ovarian carcinoma polypeptide if the T cells kill target cells coated with an ovarian carcinoma polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with an ovarian carcinoma polypeptide (200 ng/ml–100 µg/ml, preferably 100 ng/ml–25 µg/ml) for 3–7 days should result in at least a two fold increase in proliferation of the T cells and/or contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998). T cells that have been activated in response to an ovarian carcinoma polypeptide, polynucleotide or ovarian carcinoma polypeptide-expressing APC may be $CD4^+$ and/or $CD8^+$. Ovarian carcinoma polypeptide-specific T cells may be expanded using standard techniques. Within preferred embodiments, the T cells are derived from a patient or a related or unrelated donor and are administered to the patient following stimulation and expansion.

For therapeutic purposes, $CD4^+$ or $CD8^+$ T cells that proliferate in response to an ovarian carcinoma polypeptide, polynucleotide or APC can be expanded in number either in vitro or in vivo. Proliferation of such T cells in vitro may be accomplished in a variety of ways. For example, the T cells can be re-exposed to an ovarian carcinoma polypeptide, with or without the addition of T cell growth factors, such as interleukin-2, and/or stimulator cells that synthesize an ovarian carcinoma polypeptide. Alternatively, one or more T cells that proliferate in the presence of an ovarian carcinoma polypeptide can be expanded in number by cloning. Methods for cloning cells are well known in the art, and include limiting dilution. Following expansion, the cells may be administered back to the patient as described, for example, by Chang et al., *Crit. Rev. Oncol. Hematol.* 22:213, 1996.

Pharmaceutical Compositions and Vaccines

Within certain aspects, polypeptides, polynucleotides, binding agents and/or immune system cells as described herein may be incorporated into pharmaceutical compositions or vaccines. Pharmaceutical compositions comprise one or more such compounds or cells and a physiologically acceptable carrier. Vaccines may comprise one or more such compounds or cells and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (New York, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, Bortadella pertussis or Mycobacterium tuberculosis derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, M T.; see U.S. Pat. Nos. 4,436,727; 4,877,611; 4,866,034 and 4,912,094). Also preferred is AS-2 (SmithKline Beecham). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic antitumor immunity (see Timmerman and Levy, Ann. Rev. Med. 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a ovarian carcinoma antigen (or portion or other variant thereof) such that the antigen, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as ovarian cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. Within certain preferred embodiments, a patient is afflicted with ovarian cancer. Such cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immuno response-modifying agents (such as tumor vaccines, bacterial adjuvants and/or cytokines).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T lymphocytes (such as CD8$^+$ cytotoxic T lymphocytes and CD4$^+$T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into stem cells taken from a patient and clonally propagated in vitro for autologous transplant back into the same patient.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration), orally or in the bed of a resected tumor. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to an ovarian carcinoma antigen generally correlate with an improved clinical outcome. Such immune responses may generally be evaluated using standard proliferation, cytotoxicity or cytokine assays, which may be performed using samples obtained from a patient before and after treatment.

Screens for Identifying Secreted Ovarian Carcinoma Antigens

The present invention provides methods for identifying secreted tumor antigens. Within such methods, tumors are implanted into immunodeficient animals such as SCID mice and maintained for a time sufficient to permit secretion of tumor antigens into serum. In general, tumors may be implanted subcutaneously or within the gonadal fat pad of an immunodeficient animal and maintained for 1–9 months, preferably 1–4 months. Implantation may generally be performed as described in WO 97/18300. The serum containing secreted antigens is then used to prepare antisera in immunocompetent mice, using standard techniques and as described herein. Briefly, 50–100 µL of sera (pooled from three sets of immunodeficient mice, each set bearing a different SCID-derived human ovarian tumor) may be mixed 1:1 (vol:vol) with an appropriate adjuvant, such as RIBI-MPL or MPL+TDM (Sigma Chemical Co., St. Louis, Mo.) and injected intraperitoneally into syngeneic immunocompetent animals at monthly intervals for a total of 5 months. Antisera from animals immunized in such a manner may be obtained by drawing blood after the third, fourth and fifth immunizations. The resulting antiserum is generally precleared of E. coli and phage antigens and used (generally following dilution, such as 1:200) in a serological expression screen.

The library is typically an expression library containing cDNAs from one or more tumors of the type that was implanted into SCID mice. This expression library may be prepared in any suitable vector, such as λ-screen (Novagen). cDNAs that encode a polypeptide that reacts with the antiserum may be identified using standard techniques, and sequenced. Such cDNA molecules may be further characterized to evaluate expression in tumor and normal tissue, and to evaluate antigen secretion in patients.

The methods provided herein have advantages over other methods for tumor antigen discovery. In particular, all antigens identified by such methods should be secreted or released through necrosis of the tumor cells. Such antigens may be present on the surface of tumor cells for an amount of time sufficient to permit targeting and killing by the immune system, following vaccination.

Methods for Detecting Cancer

In general, a cancer may be detected in a patient based on the presence of one or more ovarian carcinoma proteins and/or polynucleotides encoding such proteins in a biological sample (such as blood, sera, urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of protein that binds to the agent in the biological sample. Polynucleotide primers and probes may be used to detect the level of mRNA encoding a tumor protein, which is also indicative of the presence or absence of a cancer. In general, an ovarian carcinoma-associated sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian carcinoma proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use ovarian carcinoma polypeptides to detect antibodies that bind to such polypeptides in a biological sample. The detection of such ovarian carcinoma protein specific antibodies may correlate with the presence of a cancer.

A cancer may also, or alternatively, be detected based on the presence of T cells that specifically react with an ovarian carcinoma protein in a biological sample. Within certain methods, a biological sample comprising $CD4^+$ and/or $CD8^+$ T cells isolated from a patient is incubated with an ovarian carcinoma protein, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with an ovarian carcinoma protein (e.g., 5–25 µg/ml). It may be desirable to incubate another aliquot of a T cell sample in the absence of ovarian carcinoma protein to serve as a control. For CD4$^+$ T cells, activation is preferably detected by evaluating proliferation of the T cells. For CD8$^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding an ovarian carcinoma protein in a biological sample. For example, at least two oligonucleotide primers may be employed in a polymerase chain reaction (PCR) based assay to amplify a portion of an ovarian carcinoma protein cDNA derived from a biological sample, wherein at least one of the oligonucleotide primers is specific for (i.e., hybridizes to) a polynucleotide encoding the ovarian carcinoma protein. The amplified cDNA is then separated and detected using techniques well known in the art, such as gel electrophoresis. Similarly, oligonucleotide probes that specifically hybridize to a polynucleotide encoding an ovarian carcinoma protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding an ovarian carcinoma protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence provided herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, New York, 1989).

One preferred assay employs RT-PCR, in which PCR is applied in conjunction with reverse transcription. Typically, RNA is extracted from a biological sample such as a biopsy tissue and is reverse transcribed to produce cDNA molecules. PCR amplification using at least one specific primer generates a CDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, ovarian carcinoma proteins and polynucleotides encoding such proteins may be used as markers for monitoring the progression of cancer. In this embodiment, assays as described above for the diagnosis of a cancer may be performed over time, and the change in the level of reactive polypeptide(s) evaluated. For example, the assays may be performed every 24–72 hours for a period of 6 months to 1 year, and thereafter performed as needed. In general, a cancer is progressing in those patients in whom the level of polypeptide detected by the binding agent increases over time. In contrast, the cancer is not progressing when the level of reactive polypeptide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple ovarian carcinoma protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to an ovarian carcinoma protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding an ovarian carcinoma protein in a biological sample. Such kits generally comprise at least one oligonucleotide probe or primer, as described above, that hybridizes to a polynucleotide encoding an ovarian carcinoma protein. Such an oligonucleotide may be used, for example, within a PCR or hybridization assay. Additional components that may be present within such kits include a second oligonucleotide and/or a diagnostic reagent or container to facilitate the detection of a polynucleotide encoding an ovarian carcinoma protein.

The following Examples are offered by way of illustration and not by way of limitation.

EXAMPLES

Example 1

Identification of Representative Ovarian Carcinoma Protein cDNAs

This Example illustrates the identification of cDNA molecules encoding ovarian carcinoma proteins.

Anti-SCID mouse sera (generated against sera from SCID mice carrying late passage ovarian carcinoma) was precleared of E. coli and phage antigens and used at a 1:200 dilution in a serological expression screen. The library screened was made from a SCID-derived human ovarian tumor (OV9334) using a directional RH oligo(dT) priming cDNA library construction kit and the λScreen vector (Novagen). A bacteriophage lambda screen was employed. Approximately 400,000 pfu of the amplified OV9334 library were screened.

196 positive clones were isolated. Certain sequences that appear to be novel are provided in FIGS. 1A–1S and SEQ ID NOs:1 to 71. Three complete insert sequences are shown in FIGS. 2A–2C (SEQ ID NOs:72 to 74). Other clones having known sequences are presented in FIGS. 15A–15EEE (SEQ ID NOs:82 to 310). Database searches identified the following sequences that were substantially identical to the sequences presented in FIGS. 15A–15EEE.

These clones were further characterized using microarray technology to determine mRNA expression levels in a variety of tumor and normal tissues. Such analyses were performed using a Synteni (Palo Alto, Calif.) microarray, according to the manufacturer's instructions. PCR amplification products were arrayed on slides, with each product occupying a unique location in the array. mRNA was extracted from the tissue sample to be tested, reverse transcribed and fluorescent-labeled cDNA probes were generated. The microarrays were probed with the labeled cDNA probes and the slides were scanned to measure fluorescence intensity. Data was analyzed using Synteni's provided GEMtools software. The results for one clone (13695, also referred to as O8E) are shown in FIG. 3.

Example 2

Identification of Ovarian Carcinoma cDNAs Using Microarray Technology

This Example illustrates the identification of ovarian carcinoma polynucleotides by PCR subtraction and microarray analysis. Microarrays of cDNAs were analyzed for ovarian tumor-specific expression using a Synteni (Palo Alto, Calif.) microarray, according to the manufacturer's instructions (and essentially as described by Schena et al., Proc. Natl. Acad. Sci. USA 93:10614–10619, 1996 and Heller et al., Proc. Natl. Acad. Sci. USA 94:2150–2155, 1997).

A PCR subtraction was performed using a tester comprising cDNA of four ovarian tumors (three of which were metastatic tumors) and a driver of cDNA form five normal tissues (adrenal gland, lung, pancreas, spleen and brain). cDNA fragments recovered from this subtraction were subjected to DNA microarray analysis where the fragments were PCR amplified, adhered to chips and hybridized with fluorescently labeled probes derived from mRNAs of human ovarian tumors and a variety of normal human tissues. In this analysis, the slides were scanned and the fluorescence intensity was measured, and the data were analyzed using Synteni's GEMtools software. In general, sequences showing at least a 5-fold increase in expression in tumor cells (relative to normal cells) were considered ovarian tumor antigens. The fluorescent results were analyzed and clones that displayed increased expression in ovarian tumors were further characterized by DNA sequencing and database searches to determine the novelty of the sequences.

Using such assays, an ovarian tumor antigen was identified that is a splice fusion between the human T-cell leukemia virus type I oncoprotein TAX (see Jin et al., Cell 93:81–91, 1998) and an extracellular matrix protein called osteonectin. A splice junction sequence exists at the fusion point. The sequence of this clone is presented in FIG. 4 and SEQ ID NO:75. Osteonectin, unspliced and unaltered, was also identified from such assays independently.

Further clones identified by this method are referred to herein as 3f, 6b, 8e, 8h, 12c and 12h. Sequences of these clones are shown in FIGS. 5 to 9 and SEQ ID NOs:76 to 81. Microarray analyses were performed as described above, and are presented in FIGS. 10 to 14. A full length sequence encompassing clones 3f, 6b, 8e and 12h was obtained by screening an ovarian tumor (SCID-derived) cDNA library. This 2996 base pair sequence (designated O772P) is presented in SEQ ID NO:311, and the encoded 914 amino acid protein sequence is shown in SEQ ID NO:312. PSORT analysis indicates a Type 1a transmembrane protein localized to the plasma membrane.

In addition to certain of the sequences described above, this screen identified the following sequences:

| Sequence | Comments |
| --- | --- |
| OV4vG11 (SEQ ID NO:313) | human clone 1119D9 on chromosome 20p12 |
| OV4vB11 (SEQ ID NO:314) | human UWGC:y14c094 from chromosome 6p21 |
| OV4vD9 (SEQ ID NO:315) | human clone 1049G16 chromosome 20q12-13.2 |
| OV4vD5 (SEQ ID NO:316) | human KIAA0014 gene |
| OV4vC2 (SEQ ID NO:317) | human KIAA0084 gene |
| OV4vF3 (SEQ ID NO:318) | human chromosome 19 cosmid R31167 |
| OV4VC1 (SEQ ID NO:319) | novel |
| OV4vH3 (SEQ ID NO:320) | novel |
| OV4vD2 (SEQ ID NO:321) | novel |
| O815P (SEQ ID NO:322) | novel |
| OV4vC12 (SEQ ID NO:323) | novel |
| OV4vA4 (SEQ ID NO:324) | novel |
| OV4vA3 (SEQ ID NO:325) | novel |
| OV4v2A5 (SEQ ID NO:326) | novel |
| O819P (SEQ ID NO:327) | novel |
| O818P (SEQ ID NO:328) | novel |
| O817P (SEQ ID NO:329) | novel |
| O816P (SEQ ID NO:330) | novel |
| Ov4vC5 (SEQ ID NO:331) | novel |
| 21721 (SEQ ID NO:332) | human lumican |
| 21719 (SEQ ID NO:333) | human retinoic acid-binding protein II |
| 21717 (SEQ ID NO:334) | human26S proteasome ATPase subunit |
| 21654 (SEQ ID NO:335) | human copine I |
| 21627 (SEQ ID NO:336) | human neuron specific gamma-2 enolase |
| 21623 (SEQ ID NO:337) | human geranylgeranyl transferase II |
| 21621 (SEQ ID NO:338) | human cyclin-dependent protein kinase |
| 21616 (SEQ ID NO:339) | human prepro-megakaryocyte potentiating factor |
| 21612 (SEQ ID NO:340) | human UPH1 |
| 21558 (SEQ ID NO:341) | human RalGDS-like 2 (RGL2) |
| 21555 (SEQ ID NO:342) | human autoantigen P542 |
| 21548 (SEQ ID NO:343) | human actin-related protein (ARP2) |
| 21462 (SEQ ID NO:344) | human huntingtin interacting protein |
| 21441 (SEQ ID NO:345) | human 90K product (tumor associated antigen) |
| 21439 (SEQ ID NO:346) | human guanine nucleotide regulator protein (tim1) |
| 21438 (SEQ ID NO:347) | human Ku autoimmune (p70/p80) antigen |
| 21237 (SEQ ID NO:348) | human S-laminin |
| 21436 (SEQ ID NO:349) | human ribophorin I |
| 21435 (SEQ ID NO:350) | human cytoplasmic chaperonin hTRiC5 |
| 21425 (SEQ ID NO:351) | humanEMX2 |
| 21423 (SEQ ID NO:352) | human p87/p89 gene |
| 21419 (SEQ ID NO:353) | human HPBRII-7 |
| 21252 (SEQ ID NO:354) | human T1-227H |
| 21251 (SEQ ID NO:355) | human cullin I |

-continued

| Sequence | Comments |
| --- | --- |
| 21247 (SEQ ID NO:356) | kunitz type protease inhibitor (KOP) |
| 21244-1 (SEQ ID NO:357) | human protein tyrosine phosphatase receptor F (PTPRF) |
| 21718 (SEQ ID NO:358) | human LTR repeat |
| OV2-90 (SEQ ID NO:359) | novel |
| Human zinc finger (SEQ ID NO:360) | |
| Human polyA binding protein (SEQ ID NO:361) | |
| Human pleitrophin (SEQ ID NO:362) | |
| Human PAC clone 278C19 (SEQ ID NO:363) | |
| Human LLRep3 (SEQ ID NO:364) | |
| Human Kunitz type protease inhib (SEQ ID NO:365) | |
| Human KIAA0106 gene (SEQ ID NO:366) | |
| Human keratin (SEQ ID NO:367) | |
| Human HIV-1TAR (SEQ ID NO:368) | |
| Human glia derived nexin (SEQ ID NO:369) | |
| Human fibronectin (SEQ ID NO:370) | |
| Human ECMproBM40 (SEQ ID NO:371) | |
| Human collagen (SEQ ID NO:372) | |
| Human alpha enolase (SEQ ID NO:373) | |
| Human aldolase (SEQ ID NO:374) | |
| Human transf growth factor BIG H3 (SEQ ID NO:375) | |
| Human SPARC osteonectin (SEQ ID NO:376) | |
| Human SLP1 leucocyte protease (SEQ ID NO:377) | |
| Human mitochondrial ATP synth (SEQ ID NO:378) | |
| Human DNA seq clone 461P17 (SEQ ID NO:379) | |
| Human dbpB pro Y box (SEQ ID NO:380) | |
| Human 40 kDa keratin (SEQ ID NO:381) | |
| Human arginosuccinate synth (SEQ ID NO:382) | |
| Human acidic ribosomal phosphoprotein (SEQ ID NO:383) | |
| Human colon carcinoma laminin binding pro (SEQ ID NO:384) | |

This screen further identified multiple forms of the clone O772P, referred to herein as 21013, 21003 and 21008. PSORT analysis indicates that 21003 (SEQ ID NO:386; translated as SEQ ID NO:389) and 21008 (SEQ ID NO:387; translated as SEQ ID NO:390) represent Type 1a transmembrane protein forms of O772P. 21013 (SEQ ID NO:385; translated as SEQ ID NO:388) appears to be a truncated form of the protein and is predicted by PSORT analysis to be a secreted protein.

Additional sequence analysis resulted in a full length clone for O8E (2627 bp, which agrees with the message size observed by Northern analysis; SEQ ID NO:391). This nucleotide sequence was obtained as follows: the original O8E sequence (OrigO8Econs) was found to overlap by 33 nucleotides with a sequence from an EST clone (IMAGE#1987589). This clone provided 1042 additional nucleotides upstream of the original O8E sequence. The link between the EST and O8E was confirmed by sequencing multiple PCR fragments generated from an ovary primary tumor library using primers to the unique EST and the O8E sequence (ESTxO8EPCR). Full length status was further indicated when anchored PCR from the ovary tumor library gave several clones (AnchoredPCR cons) that all terminated upstream of the putative start methionine, but failed to yield any additional sequence information. FIG. 16 presents a diagram that illustrates the location of each partial sequence within the full length O8E sequence.

Two protein sequences may be translated from the full length O8E. For "a" (SEQ ID NO:393) begins with a putative start methionine. A second form "b" (SEQ ID NO:392) includes 27 additional upstream residues to the 5' end of the nucleotide sequence.

Example 3

This example discloses the identification and characterization of antibody epitopes recognized by the O8E polyclonal anti-sera.

Rabbit anti-sera was raised against E. coli derived O8E recombinant protein and tested for antibody epitope recognition against 20 or 21 mer peptides that correspond to the O8E amino acid sequence. Peptides spanning amino acid regions 31 to 65, 76 to 110, 136 to 200 and 226 to 245 of the full length O8E protein were recognized by an acid eluted peak and/or a salt eluted peak from affinity purified anti-O8E sera. Thus, the corresponding amino acid sequences of the above peptides constitute the antibody epitopes recognized by affinity purified anti-O8E antibodies.

ELISA analysis of anti-O8E rabbit sera is shown in FIG. 23, and ELISA analysis of affinity purified rabbit anti-O8E polyclonal antibody is shown in FIG. 24.

For epitope mapping, 20 or 21 mer peptides corresponding to the O8E protein were synthesized. For antibody affinity purification, rabbit anti-O8E sera was run over an O8E-sepharose column, then antibody was eluted with a salt buffer containing 0.5 M NaCl and 20 mM $PO_4$, followed by an acid elution step using 0.2 M Glycine, pH 2.3. Purified antibody was neutralized by the addition of 1M Tris, pH 8 and buffer exchanged into phosphate buffered saline (PBS). For enzyme linked immunosorbant assay (ELISA) analysis, O8E peptides and O8E recombinant protein were coated onto 96 well flat bottom plates at 2 µg/ml for 2 hours at room temperature (RT). Plates were then washed 5 times with PBS+0.1% Tween 20 and blocked with PBS+1% bovine serum albumin (BSA) for 1 hour. Affinity purified anti-O8E antibody, either an acid or salt eluted fraction, was then added to the wells at 1 µg/ml and incubated at RT for 1 hr. Plates were again washed, followed by the addition of donkey anti-rabbit-Ig-horseradish peroxidase (HRP) antibody for 1 hour at RT. Plates were washed, then developed by the addition of the chromagenic substrate 3,3',5,5'-tetramethylbenzidine (TMB) (described by Bos et al., *J. of Immunoassay* 2:187–204 (1981); available from Sigma (St. Louis, Mo.)). The reaction was incubated 15 minutes at RT and then stopped by the addition of 1 N $H_2SO_4$. Plates were read at an optical density of 450 (OD450) in an automated plate reader. The sequences of peptides corresponding to the OE8 antibody epitopes are disclosed herein as SEQ ID NOs: 394–415. Antibody epitopes recognized by the O8E polyclonal anti-sera are disclosed herein in FIG. 17.

Example 4

This example discloses IHC analysis of O8E expression in ovarian cancer tissue samples.

For immunohistochemistry studies, paraffin-embedded formalin fixed ovarian cancer tissue was sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody (anti-O8E rabbit affinity purified polyclonal antibody) was added to each section for 25 min followed by a 25 min incubation with an anti-rabbit biotinylated antibody. Endogenous peroxidase activity was blocked by three 1.5 min incubations with hydrogen peroxidase. The avidin biotin complex/horse radish peroxidase system was used along with DAB chromogen to visualize antigen expression. Slides were counterstained with hematoxylin. One (papillary serous carcinoma) of six ovarian cancer tissue sections displayed O8E immunoreactivity. O8E expression was localized to the plasma membrane.

Six ovarian cancer tissues were analyzed with the anti-O8E rabbit polyclonal antibody. One (papillary serous carcinoma) of six ovarian cancer tissue samples stained positive for O8E expression. O8E expression was localized to the surface membrane.

Example 5

This example discloses O8E peptides that are predicted to bind HLA-A2 and to be immunogenic for CD8 T cell responses in humans.

Potential HLA-A2 binding peptides of O8E were predicted by using the full-length open-reading frame (ORF) from O8E and running it through "Episeek," a program used to predict MHC binding peptides. The program used is based on the algorithm published by Parker, K. C. et al., *J. Immunol.* 152(1):163–175 (1994) (incorporated by reference herein in its entirety). 10-mer and 9-mer peptides predicted to bind HLA-0201 are disclosed herein as SEQ ID NOs: 416–435 and SEQ ID NOs: 436–455, respectively.

Example 6

This example discloses O8E cell surface expression measured by fluoresence activated cell sorting.

For FACS analysis, cells were washed with ice cold staining buffer (PBS/1% BSA/azide). Next, the cells were incubated for 30 minutes on ice with 10 micrograms/ml of affinity purified rabbit anti-B305D polyclonal antibody. The cells were washed 3 times with staining buffer and then incubated with a 1:100 dilution of a goat anti-rabbit Ig (H+L)-FITC reagent (Southern Biotechnology) for 30 minutes on ice. Following 3 washes, the cells were resuspended in staining buffer containing prodium iodide, a vital stain that allows for identification of permeable cells, and analyzed by FACS. O8E surface expression was confirmed on SKBR3 breast cancer cells and HEK293 cells that stably overexpress the cDNA for O8E. Neither MB415 cells nor HEK293 cells stably transfected with a control irrelevant plasmid DNA showed surface expression of O8E (FIGS. 18 and 19).

Example 7

This example further evaluates the expression and surface localization of O8E.

For expression and purification of antigen used for immunization, O8E expressed in an *E. coli* recombinant expression system was grown overnight in LB Broth with the appropriate antibiotics at 37° C. in a shaking incubator. The next morning, 10 ml of the overnight culture was added to 500 ml of 2×YT plus appropriate antibiotics in a 2L-baffled Erlenmeyer flask. When the Optical Density (at 560 nanometers) of the culture reached 0.4–0.6 the cells were induced with IPTG (1 mM). 4 hours after induction with IPTG the cells were harvested by centrifugation. The cells were then washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For protein that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. This material was then evaluated for acceptable purity as determined by SDS-PAGE or HPLC, concentration as determined by Lowry assay or Amino Acid Analysis, identity as determined by amino terminal protein sequence, and endotoxin level as determined by the Limulus (LAL) assay. The proteins were then vialed after filtration through a 0.22 micron filter and the antigens were frozen until needed for immunization.

For generation of polyclonal anti-sera, 400 micrograms of each prostate antigen was combined with 100 micrograms of muramyldipeptide (MDP). Equal volume of Incomplete Freund's Adjuvant (IFA) was added and then mixed. Every four weeks animals were boosted with 100 micrograms of antigen mixed with an equal volume of IFA. Seven days following each boost the animal was bled. Sera was generated by incubating the blood at 4° C. for 12–24 hours followed by centrifugation.

For characterization of polyclonal antisera, 96 well plates were coated with antigen by incubating with 50 microliters (typically 1 microgram)at 4 C for 20 hrs. 250 microliters of BSA blocking buffer was added to the wells and incubated at RT for 2 hrs. Plates were washed 6 times with PBS/0.01% tween. Anti-O8E rabbit sera or affinity purified anti-O8e antibody was diluted in PBS. Fifty microliters of diluted antibody was added to each well and incubated at RT for 30 min. Plates were washed as described above before 50 microliters of goat anti-rabbit horse radish peroxidase (HRP) at a 1:10000 dilution was added and incubated at RT for 30 min. Plates were washed as described above and 100 microliters of TMB microwell Peroxidase Substrate was added to each well. Following a 15 minute incubation in the dark at room temperature the calorimetric reaction was stopped with 100 microliters of 1N H2SO4 and read immediately at 450 nm. All polyclonal antibodies showed immunoreactivity to the O8E antigen.

For recombinant expression in mammalian HEK293 cells, full length O8E cDNA was subcloned into the mammalian expression vectors pcDNA3.1+ and pCEP4 (Invitrogen) which were modified to contain His and FLAG epitope tags, respectively. These constructs were transfected into HEK293 cells (ATCC) using Fugene 6 reagent (Roche). Briefly, HEK293 cells were plated at a density of 100,000 cells/ml in DMEM (Gibco) containing 10% FBS (Hyclone) and grown overnight. The following day, 2 ul of Fugene6 was added to 100 ul of DMEM containing no FBS and incubated for 15 minutes at room temperature. The Fugene6/ DMEM mixture was then added to 1ug of O8E/pCEP4 or O8E/pcDNA3.1 plasmid DNA and incubated for 15 minutes at room temperature. The Fugene/DNA mix was then added to the HEK293 cells and incubated for 48–72 hrs at 37oC with 7% CO2. Cells were rinsed with PBS then collected and pelleted by centrifugation. For Western blot analysis, whole cell lysates were generated by incubating the cells in Triton-X100 containing lysis buffer for 30 minutes on ice. Lysates were then cleared by centrifugation at 10,000 rpm for 5 minutes at 4 C. Samples were diluted with SDS-PAGE loading buffer containing beta-mercaptoethanol, then boiled for 10 minutes prior to loading the SDS-PAGE gel. Protein was transferred to nitrocellulose and probed using anti-O8E rabbit polyclonal sera #2333L at a dilution of 1:750. The blot was revealed with a goat anti-rabbit Ig coupled to HRP followed by incubation in ECL substrate.

For FACS analysis, cells were washed further with ice cold staining buffer (PBS+1%BSA+Azide). Next, the cells were incubated for 30 minutes on ice with 10 ug/ml of Protein A purified anti-O8E polyclonal sera. The cells were washed 3 times with staining buffer and then incubated with a 1:100 dilution of a goat anti-rabbit Ig(H+L)-FITC reagent (Southern Biotechnology) for 30 minutes on ice. Following 3 washes, the cells were resuspended in staining buffer containing Propidium Iodide (PI), a vital stain that allows for the identification of permeable cells, and analyzed by FACS.

From these experiments, the results of which are illustrated in FIGS. 20–21, O8E expression was detected on the surface of transfected HEK293 cells and SKBR3 cells by FACS analysis using rabbit anti-O8E sera. Expression was also detected in transfected HEK293 cell lysates by Western blot analysis (FIG. 22).

Example 8

Generation and Characterization of Anti-O8E mAbs

Mouse monoclonal antibodies were raised against *E. coli* derived O8E proteins as follows. A/J mice were immunized intraperitoneally (IP) with Complete Freund's Adjuvant (CFA) containing 50 μg recombinant O8E, followed by a subsequent IP boost with Incomplete Freund's Adjuvant (IFA) containing 10 μg recombinant O8E protein. Three days prior to removal of the spleens, the mice were immunized intravenously with approximately 50 μg of soluble O8E recombinant protein. The spleen of a mouse with a positive titer to O8E was removed, and a single-cell suspension made and used for fusion to SP2/0 myeloma cells to generate B cell hybridomas. The supernatants from the hybrid clones were tested by ELISA for specificity to recombinant O8E, and epitope mapped using peptides that spanned the entire O8E sequence. The mAbs were also tested by flow cytometry for their ability to detect O8E on the surface of cells stably transfected with O8E and on the surface of a breast tumor cell line.

For ELISA analysis, 96 well plates were coated with either recombinant O8E protein or overlapping 20-mer peptides spanning the entire O8E molecule at a concentration of either 1–2 μg/ml or 10 μg/ml, respectively. After coating, the plates were washed 5 times with washing buffer (PBS+0.1% Tween-20) and blocked with PBS containing 0.5% BSA, 0.4% Tween-20. Hybrid supernatants or purified mAbs were then added and the plates incubated for 60 minutes at room temperature. The plates were washed 5 times with washing buffer and the secondary antibody, donkey-anti mouse Ig linked to horseradish peroxidase (HRP) (Jackson ImmunoResearch), was added for 60 minutes. The plates were again washed 5 times in washing buffer, followed by the addition of the peroxidase substrate.

Of the hybridoma clones generated, 15 secreted mAbs that recognized the entire O8E protein. Epitope mapping revealed that of these 15 clones, 14 secreted mAbs that recognized the O8E amino acid residues 61–80 and one clone secreted a mAb that recognized amino acid residues 151–170.

For flow cytometric analysis, HEK293 cells which had been stably transfected with O8E and SKBR3 cells which express O8E mRNA, were harvested and washed in flow staining buffer (PBS+1% BSA+Azide). The cells were incubated with the supernatant from the mAb hybrids for 30 minutes on ice followed by 3 washes with staining buffer. The cells were incubated with goat-anti mouse Ig-FITC for 30 minutes on ice, followed by three washes with staining buffer before being resuspended in wash buffer containing propidium iodide. Flow cytometric analysis revealed that 15/15 mAbs were able to detect O8E protein expressed on the surface of O8E-transfected HEK293 cells. 6/6 mAbs tested on SKBR3 cells were able to recognize surface expressed O8E.

Example 9

Extended DNA and Protein Sequence Analysis of Sequence O772P

A full-length sequence encompassing clones 3f, 6b, 8e, and 12 was obtained by screening an ovarian tumor (SCID-derived) cDNA library described in detail in Example 2. This 2996 base pair sequence, designated O772P, is presented in SEQ ID NO: 311, and the encoded 914 amino acid protein sequence is shown in SEQ ID NO: 312. The DNA sequence O772P was searched against public databases including Genbank and showed a significant hit to Genbank Accession number AK024365 (SEQ ID NO: 457). This Genbank sequence was found to be 3557 base pairs in length and encodes a protein 1156 amino acids in length (SEQ ID NO: 459). A truncated version of this sequence, residues 25–3471, in which residue 25 corresponds to the first ATG initiation codon in the Genbank sequence, (SEQ ID NO: 456), encodes a protein that is 1148 amino acids in length (SEQ ID NO: 458). The published DNA sequence (SEQ ID NO: 457) differs from O772P in that it has a 5 base pair insertion corresponding to bases 958–962 of SEQ ID NO: 457. This insertion results in a frame shift such that SEQ ID NO: 457 encodes an additional N-terminal protein sequence relative to O772P (SEQ ID NO: 312). In addition, O772P encodes a unique N-terminal portion contained in residues 1–79 (SEQ ID NO: 460). The N-terminal portion of SEQ ID NO: 456, residues 1–313, also contains unique sequence and is listed as SEQ ID NO: 461.

Example 10

The Generation of Polyclonal Antibodies for Immunohistochemistry and Flow Cytometric Analysis of the Cell Associated Expression Pattern of Molecule O772P The O772P molecule was identified in Examples 2 and 9 of this application. To evaluate the subcellular localization and specificity of antigen expression in various tissues, polyclonal antibodies were generated against O772P. To produce these antibodies, O772P-1 (amino acids 44–772 of SEQ ID NO:312) and O772P-2 (477–914 of SEQ ID NO:312) were expressed in an *E. coli* recombinant expression system and grown overnight at 37° C. in LB Broth. The following day, 10 ml of the overnight culture was added to 500 ml of 2×YT containing the appropriate antibiotics. When the optical density of the cultures (560 nanometers) reached 0.4–0.6 the cells were induced with IPTG. Following induction, the cells were harvested, washed, lysed and run through a French Press at a pressure of 16000 psi. The cells were then centrifuged and the pellet checked by SDS-PAGE for the partitioning of the recombinant protein. For proteins that localize to the cell pellet, the pellet was resuspended in 10 mM Tris, pH 8.0, 1% CHAPS and the inclusion body pellet washed and centrifuged. The washed inclusion body was solubilized with either 8M urea or 6M guanidine HCL containing 10 mM Tris, pH 8.0, plus 10 mM imidazole. The solubilized protein was then added to 5 ml of nickel-chelate resin (Qiagen) and incubated for 45 minutes at room temperature.

Following the incubation, the resin and protein mixture was poured through a column and the flow through collected. The column was washed with 10–20 column volumes of buffer and the antigen eluted using 8M urea, 10 mM Tris, pH 8.0, and 300 mM imidazole and collected in 3 ml fractions. SDS-PAGE was run to determine which fractions to pool for further purification. As a final purification step, a strong anion exchange resin was equilibrated with the appropriate buffer and the pooled fractions were loaded onto the column. Each antigen was eluted from the column with an increasing salt gradient. Fractions were collected and analyzed by a SDS-PAGE to determine which fractions from the column to pool. The pooled fractions were dialyzed against 10 mM Tris, pH 8.0, and the resulting protein was submitted for quality control for final release. The release criteria were: (a) purity as determined by SDS-PAGE or HPLC, (b) concentration as determined by Lowry assay or Amino Acid Analysis, (c) identity as determined by amino terminal protein, and (d) endotoxin levels as determined by the Limulus (LAL) assay. The proteins were then filtered through a 0.22 $\mu$M filter and frozen until needed for immunizations.

To generate polyclonal antisera, 400 $\mu$g of O772P-1 or O772P-2 was combined with 100 $\mu$g of muramyldipeptide (MDP). The rabbits were immunized every 4 weeks with 100 $\mu$g of antigen mixed with an equal volume of Incomplete Freund's Adjuvant (IFA). Seven days following each boost, the animals were bled and sera was generated by incubating the blood at 4° C. for 12–24 hours followed by centrifugation.

To characterize the antisera, 96 well plates were coated with antigen followed by blocking with BSA. Rabbit sera was diluted in PBS and added to each well. The plates were then washed, and goat anti-rabbit horseradish peroxidase (HRP). The plates were again washed and TMB microwell Peroxidase Substrate was added. Following this incubation, the colormetric reaction was stopped and the plates read immediately at 450 nm. All polyclonal antibodies showed immunoreactivity to the appropriate antigen.

Immunohistochemistry analysis of O772P expression was performed on paraffin-embedded formalin fixed tissue. O772P was found to be expressed in normal ovary and ovarian tumor, but not in normal heart, kidney, colon, lung or liver. Additionally, immunohistochemistry and flow cytometric analysis indicates that O772P is a plasma membrane-associated molecule. O772P contains 1 plasma transmembrane domain predicted to be encoded by amino acids 859–880. The N-terminus of O772P is extracellular and is encoded by amino acids 1–859, while the C-terminus is intracellular. Sequence analysis shows that there are 17 potential N-linked glycosylation sites.

Example 11

O772P is Expressed on the Surface of Primary Ovarian Tumor Cells

For recombinant expression in mammalian cells, the O772P-21008 (SEQ ID NO:387) and O772P full length cDNA (SEQ ID NO:311 encoding the protein of SEQ ID NO:312) were subcloned into mammalian expression vectors pBIB or pCEP4 respectively. These constructs were transfected into HEK293 cells using Fugene 6 (Roche). The HEK cells were then plated at a density of 100,000 cells/ml in DMEM containing fetal bovine serum (FBS) and grown overnight. The following day, 2 $\mu$l of Fugene 6 was added to 100 $\mu$l of DMEM, which contained no FBS, and incubated for 15 minutes at room temperature. The Fugene 6/DMEM mixture was then added to 1 $\mu$g of O772P/pBIB or O772P/pCEP4 plasmid DNA and incubated for an additional 15 minutes at room temperature. The Fugene 6/DNA mix was then added to the HEK293 cells and incubated for 48–72 hours at 37° C. with 7% $CO_2$. The cells were rinsed and pelleted by centrifugation.

For Western Blot analysis, whole cell lysates were generated by incubating the cells in lysis buffer followed by clarification by centrifugation. The samples were diluted and run on SDS-PAGE. The gel was then transferred to nitrocellulose and probed using purified anti-O772P-2 rabbit polyclonal antibody. The blot was revealed with a goat anti-rabbit Ig coupled to HRP followed by incubation in ECL substrate. Western Blot analysis revealed that O772P-21008 could be detected in HEK293 cells that had been transfected with O772P.

To determine the cell expression profile of O772P in cells, primary ovarian tumor cells were grown in SCID mice. The cells were retrieved from the mice and analyzed by flow cytometry. Briefly, cells washed in cold staining buffer containing PBS, 1% BSA, and Na Azide. The cells were incubated for 30 minutes with 10 $\mu$g/ml of purified anti-O772P-1 and O772P-2 polyclonal sera. Following this incubation, the cells were washed three times in staining buffer and incubated with goat anti-rabbit Ig (H+L) conjugated to FITC (Southern Biotechnology). The cells were washed and resuspended in staining buffer containing Propidium Iodide (PI), a vital stain that identifies non-viable cells. The cells were then analyzed using Fluorescence Activated Cell Sorting (FACS). FACS analysis revealed that O772P was present on the cells surface. Surface expression of O772P on tumor cells allows for immune targeting by therapeutic antibodies.

Example 12

Functional Characterization of Anti-O8E Monoclonal Antibodies

Mouse monoclonal antibodies (mAb) raised against *E. coli* derived O8E, as described in Example 8, were tested for their ability to promote O8E antigen internalization. Internalization of the antibody was determined using an in vitro cytotoxicity assay. Briefly, HEK293 and O8E/HEK transfected cells were plated into 96 well plates containing DME plus 10% heat-inactivated FBS in the presence of 50 ng/well of purified anti-O8E or control antibodies. The isotype of the anti-O8E mAbs are as follows: 11A6-IgG1/kappa, 15C6-IgG2b/kappa, 18A8-IgG2b/kappa, and 14F1-IgG2a/kappa. W6/32 is a pan anti-human MHC class I mouse monoclonal antibody that serves as a positive control, and two irrelevant mAbs, Ir-Pharm and Ir-Crxa were included as negative controls. Following incubation with the O8E specific antibodies or the relevant controls antibodies, the mAb-zap, a goat anti-mouse Ig-saporin conjugated secondary antibody (Advanced Targeting Systems) was added at a concentration of 100 ng/ml to half of the wells, and the plates were incubated for 48 to 72 hours at 37° C. in a 7% $CO_2$ incubator. This assay takes advantage of the toxic nature of saporin, a ribozyme inactivating protein, which when internalized has a cytotoxic effect. Following incubation with the mAb-zap, internalization was quantitated by the addition of MTS reagent, followed by reading the OD490 of the plate on a microplate ELISA reader. FIG. 25 depicts the results from these assays. The top panel represents HEK cells that have not been transfected with O8E and therefore O8E antibody should not bind and be internalized. Levels of proliferation were the same in all samples whether they were incubated with or without the mAb-zap, with the exception of the positive control Ab, W6/32. The lower panel represents cells that have been transfected with O8E and therefore should bind O8E specific antibodies. Antibodies from the hybridomas 11H6, 14F1, and 15C6, which recognize the amino acids 61–80 of O8E were able to promote internalization of the O8E surface protein as measured by decreased levels of proliferation due to the toxic nature of the mAb-zap (See FIG. 25). The antibody generated by the hybridoma 18A8, which recognizes amino acids 151–170 of O8E, was unable to promote internalization as determined by normal levels of proliferation either in the absence or presence of the mAb-zap.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated antibody or antigen-binding fragment thereof that specifically binds to the polypeptide of SEQ ID NO: 392.

2. An antibody according to claim 1, wherein the antibody is a monoclonal antibody.

3. A composition comprising a first component selected from the group consisting of physiologically acceptable carriers and immunostimulants, and a second component selected from the group consisting of an antibody or antigen-binding fragment according to claim 1.

* * * * *

UNITED STATES PATENT AND TRADEMARK OFFICE
CERTIFICATE OF CORRECTION

PATENT NO.        : 6,962,980 B2                                      Page 1 of 1
APPLICATION NO. : 09/827271
DATED             : November 8, 2005
INVENTOR(S)       : Jennifer L. Mitcham et al.

It is certified that error appears in the above-identified patent and that said Letters Patent is hereby corrected as shown below:

On the title page Item (63)
"(63) Continuation-in-part of application No. 09/667,857, filed on Sep. 20, 2000, now Pat. No. 6,699,664, which is a continuation-in-part of application No. 09/636,801, filed on Aug. 10, 2000, now abandoned, which is a continuation-in-part of application No. 09/617,747, filed on Jul. 17, 2000, now abandoned, which is a continuation-in-part of application No. 09/404,879, filed on Sep. 24, 1999, now Pat. No. 6,468,546, which is a continuation-in-part of application No. 09/338,933, filed on Jun. 23, 1999, now Pat. No. 6,488,931, which is a continuation-in-part of application No. 09/216,003, filed on Dec. 17, 1998, now Pat. No. 6,670,463, and a continuation-in-part of application No. 09/215,681, filed on Dec. 17, 1998, now Pat. No. 6,528,253."

should read:

--(63) Continuation-in-part of application No. 09/667,857, filed on Sep. 20, 2000, now Pat. No. 6,699,664, which is a continuation-in-part of application No. 09/636,801, filed on Aug. 10, 2000, which is a continuation-in-part of application No. 09/617,747, filed on Jul. 17, 2000, now abandoned, which is a continuation-in-part of application No. 09/404,879, filed on Sep. 24, 1999, now Pat. No. 6,468,546.--

Signed and Sealed this

Twenty-eighth Day of September, 2010

David J. Kappos
*Director of the United States Patent and Trademark Office*